US009133158B2

(12) United States Patent
Aebi et al.

(10) Patent No.: US 9,133,158 B2
(45) Date of Patent: Sep. 15, 2015

(54) BICYCLIC DIHYDROISOQUINOLINE-1-ONE DERIVATIVES

(71) Applicant: Hoffmann-La Roche Inc., Nutley, NJ (US)

(72) Inventors: Johannes Aebi, Binningen (CH); Kurt Amrein, Itingen (CH); Wenming Chen, Shanghai (CN); Benoit Hornsperger, Altkirch (FR); Bernd Kuhn, Reinach (CH); Yongfu Liu, Shanghai (CN); Hans P. Maerki, Basel (CH); Alexander V. Mayweg, Shanghai (CN); Peter Mohr, Basel (CH); Xuefei Tan, Shanghai (CN); Zhanguo Wang, Shanghai (CN); Mingwei Zhou, Shanghai (CN)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/688,373

(22) Filed: Nov. 29, 2012

(65) Prior Publication Data
US 2013/0143863 A1 Jun. 6, 2013

(30) Foreign Application Priority Data
Nov. 30, 2011 (WO) ................ PCT/CN2011/083229

(51) Int. Cl.
| C07D 471/04 | (2006.01) |
| C07D 217/22 | (2006.01) |
| C07D 405/14 | (2006.01) |
| C07D 401/04 | (2006.01) |
| C07D 401/14 | (2006.01) |
| C07D 413/14 | (2006.01) |
| C07D 417/14 | (2006.01) |
| C07D 491/107 | (2006.01) |
| C07D 491/113 | (2006.01) |

(52) U.S. Cl.
CPC ............ C07D 401/04 (2013.01); C07D 217/22 (2013.01); C07D 401/14 (2013.01); C07D 405/14 (2013.01); C07D 413/14 (2013.01); C07D 417/14 (2013.01); C07D 471/04 (2013.01); C07D 491/107 (2013.01); C07D 491/113 (2013.01)

(58) Field of Classification Search
USPC ............... 546/158, 113, 277.1, 119; 544/128, 544/238, 405; 514/210.18, 312, 303, 514/255.05, 300, 339
See application file for complete search history.

(56) References Cited

U.S. PATENT DOCUMENTS

| 4,710,507 A | 12/1987 | Campbell et al. |
| 2009/0069370 A1* | 3/2009 | Zhou et al. ................... 514/308 |
| 2011/0118241 A1 | 5/2011 | Hartmann et al. |

FOREIGN PATENT DOCUMENTS

| WO | WO 02/068414 | * | 7/2002 |
| WO | 2012/035078 | | 3/2012 |

OTHER PUBLICATIONS

Lippard .The Art of Chemistry, Nature 2002, vol. 416, pp. 587.*
Roy et al. Exploring QSAR for CYP11B2 binding affinity and CYP11B2/CYP11B1 selectivity of diverse functional compounds using GFA and G/PLS techniques 2010, vol. 25, pp. 354-369.*
International Search Report for PCT/EP2012/072563 dated Jan. 24, 2013.
The English translation of he Colombian Office Action, issued on Mar. 27, 2015, in the corresponding Colombian Application No. 14-068.498.

* cited by examiner

*Primary Examiner* — Melenie McCormick
*Assistant Examiner* — Taina D Matos Negron

(57) ABSTRACT

The invention provides novel compounds having the general formula (I)

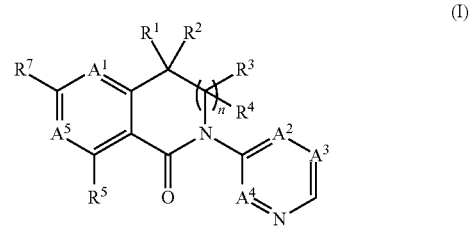

wherein $R^1, R^2, R^3, R^4, R^5, R^6, A^1, A^2, A^3, A^4, A^5$ and n are as described herein, compositions including the compounds and methods of using the compounds. The compounds are useful, for example, as aldosterone synthase (CYP11B2 or CYP11B1) inhibitors for the treatment or prophylaxis of chronic kidney disease, congestive heart failure, hypertension, primary aldosteronism and Cushing syndrome.

56 Claims, No Drawings

BICYCLIC DIHYDROISOQUINOLINE-1-ONE DERIVATIVES

PRIORITY TO RELATED APPLICATION(S)

This application claims the benefit of International Patent Application No. PCT/CN2011/083229, filed Nov. 30, 2011, which is hereby incorporated by reference in its entirety.

FIELD OF THE INVENTION

The present invention relates to organic compounds useful for therapy or prophylaxis in a mammal, and in particular to aldosterone synthase (CYP11B2 or CYP11B1) inhibitors for the treatment or prophylaxis of chronic kidney disease, congestive heart failure, hypertension, primary aldosteronism and Cushing syndrome.

BACKGROUND OF THE INVENTION

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

SUMMARY OF THE INVENTION

The present invention relates to compounds according to formula (I),

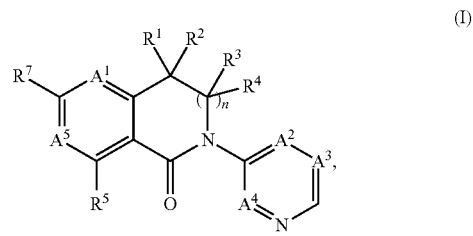

wherein
$R^1$, $R^2$, $R^3$ and $R^4$ are independently selected from the group consisting of H, alkyl, cycloalkyl, cycloalkylalkyl, haloalkyl, halocycloalkyl, hydroxyalkyl, alkoxyalkyl, haloalkoxyalkyl, halocycloalkylalkyl, substituted heterocycloalkyl, substituted heterocycloalkylalkyl, substituted arylalkyl and substituted heteroarylalkyl, wherein substituted heterocycloalkyl, substituted heterocycloalkylalkyl, substituted arylalkyl and substituted heteroarylalkyl are substituted with $R^{12}$, $R^{13}$ and $R^{14}$;

or $R^2$ and $R^4$ together form a double bond, wherein in case $R^2$ and $R^4$ together form a double bond, then $R^5$ is H;

or $R^1$ and $R^2$ together with the carbon atom to which they are attached form a substituted cycloalkyl or a substituted heterocycloalkyl, wherein substituted cycloalkyl and substituted heterocycloalkyl are substituted with $R^{22}$, $R^{23}$ and $R^{24}$;

or $R^3$ and $R^4$ together with the carbon atom to which they are attached form a substituted cycloalkyl or a substituted heterocycloalkyl, wherein substituted cycloalkyl and substituted heterocycloalkyl are substituted with $R^{29}$, $R^{30}$ and $R^{31}$;

or $R^1$ and $R^3$ together with the carbon atom to which they are attached form a substituted cycloalkyl or a substituted heterocycloalkyl, wherein substituted cycloalkyl and substituted heterocycloalkyl are substituted with $R^{44}$, $R^{45}$ and $R^{46}$;

$A^1$ is $CR^8$ or N;
$A^2$ is $CR^9$ or N;
$A^3$ is $CR^{10}$ or N;
$A^4$ is $CR^{11}$ or N;
$A^5$ is $CR^6$ or N;

one of $R^5$, $R^6$, $R^7$ and $R^8$ is selected from the group consisting of halogen, cyano, alkoxy, hydroxyalkoxy, haloalkyl, haloalkoxy and hydroxy and the others are each independently selected from the group consisting of H, halogen, cyano, alkoxy, hydroxyalkoxy, haloalkoxy and hydroxy;

$R^9$ is selected from the group consisting of H, halogen, hydroxy, cyano, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, alkoxycycloalkylalkyl, dialkoxyalkyl, haloalkoxy, haloalkoxyalkyl, alkoxyalkoxy, alkoxyalkoxyalkyl, haloalkoxyalkoxy, haloalkoxyalkoxyalkyl, substituted arylalkyl, substituted arylhydroxyalkyl, substituted heterocycloalkylalkyl and substituted heteroarylalkyl, wherein substituted arylalkyl, substituted arylhydroxyalkyl, substituted heterocycloalkylalkyl and substituted heteroarylalkyl are substituted with $R^{32}$, $R^{33}$ and $R^{34}$;

$R^{10}$ is $-O_m-(CR^{15}R^{16})_p-(CR^{17}R^{18})_q-(CR^{19}R^{20})_r-R^{21}$;

or $R^9$ and $R^{10}$ together with the carbon atoms to which they are attached form a substituted cycloalkyl, a substituted heterocycloalkyl, a substituted aryl or a substituted heteroaryl, wherein substituted cycloalkyl, substituted heterocycloalkyl, substituted aryl and substituted heteroaryl are substituted with $R^{35}$, $R^{36}$ and $R^{37}$;

$R^{11}$ is H;

$R^{15}$, $R^{17}$ and $R^{19}$ are each independently selected from the group consisting of H, alkyl, cycloalkyl, haloalkyl and halocycloalkyl;

$R^{16}$, $R^{18}$ and $R^{20}$ are each independently selected from the group consisting of H, hydroxy, halogen and alkyl;

or $R^{15}$ and $R^{16}$ together with the carbon atom to which they are attached form a cycloalkyl;

or $R^{17}$ and $R^{18}$ together with the carbon atom to which they are attached form a cycloalkyl;

or $R^{19}$ and $R^{20}$ together with the carbon atom to which they are attached form a cycloalkyl;

or $R^{15}$ and $R^{17}$ together form $-(CH_2)_v-$;
or $R^{15}$ and $R^{19}$ together form $-(CH_2)_w-$;
or $R^{17}$ and $R^{19}$ together form $-(CH_2)_x-$;

$R^{21}$ is selected from the group consisting of H, halogen, cyano, $-OR^{25}$, $-SR^{25}$, $-S(O)R^{25}$, $-S(O)_2R^{25}$, $-NR^{25}R^{26}$, $-NR^{26}SO_2R^{25}$, $-NR^{26}SO_2NR^{25}R^{27}$, $-NR^{26}C(O)R^{25}$, $-NR^{26}C(O)NR^{25}R^{27}$, $-C(O)R^{28}$, $-C(O)NR^{25}R^{26}$, cycloalkyl, substituted heterocycloalkyl, substituted heteroaryl and substituted aryl, wherein substituted heterocycloalkyl, substituted heteroaryl, substituted heteroarylalkyl and substituted aryl are substituted with $R^{38}$, $R^{39}$ and $R^{40}$;

$R^{25}$ is selected from the group consisting of H, alkyl, hydroxyalkyl, carboxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxyalkyl, cycloalkoxyalkyl, halocycloalkoxyalkyl, alkylcycloalkoxyalkyl, alkoxyalkyl, haloalkoxyalkyl, alkoxyalkoxyalkyl, haloalkoxyalkoxyalkyl, substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{41}$, $R^{42}$ and $R^{43}$;

$R^{26}$ and $R^{27}$ are each independently selected from the group consisting of H, alkyl, cycloalkyl, haloalkyl and halocycloalkyl;

or $R^{15}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

or $R^{17}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

or $R^{19}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

$R^{28}$ is selected from the group consisting of H, hydroxy, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, haloalkoxy, haloalkoxyalkyl, alkoxyalkoxy, alkoxyalkoxyalkyl, haloalkoxyalkoxy, haloalkoxyalkoxyalkyl substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{50}$, $R^{51}$ and $R^{52}$;

$R^{12}$, $R^{13}$, $R^{14}$, $R^{22}$, $R^{23}$, $R^{24}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$ and $R^{52}$ are each independently selected from the group consisting of H, halogen, hydroxy, amino, nitro, cyano, oxo, alkyl, alkylcarbonyl, alkylsulfonyl, hydroxyalkyl, haloalkyl, cycloalkyl, cycloalkylalkyl, alkylcycloalkyl, halocycloalkyl, alkylcycloalkylalkyl, alkylcarbonylamino, alkylsulfonyl, alkylsulfonylamino, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxycarbonyl, alkoxyalkyl, haloalkoxy, haloalkoxyalkyl, alkoxyalkoxy, alkoxyalkoxyalkyl, haloalkoxyalkyl, haloalkoxyalkoxyalkyl, chloropyridinylcarbonyl and heterocycloalkyl;

n is zero or 1;
m zero or 1;
p, q and r are independently selected from zero and 1;
v and x are independently 1, 2, 3 or 4; and
w is zero, 1, 2 or 3;

with the proviso that no more than two of $A^2$, $A^3$ and $A^4$ are N.

The present invention also relates to pharmaceutically acceptable salts and esters of the aforementioned compounds.

DETAILED DESCRIPTION OF THE INVENTION

The present invention relates to compounds according to formula (I), $$\text{(I)}$$

wherein
$R^1$, $R^2$, $R^3$ and $R^4$ are independently selected from the group consisting of H, alkyl, cycloalkyl, cycloalkylalkyl, haloalkyl, halocycloalkyl, hydroxyalkyl, alkoxyalkyl, haloalkoxyalkyl, halocycloalkylalkyl, substituted heterocycloalkyl, substituted heterocycloalkylalkyl, substituted arylalkyl and substituted heteroarylalkyl, wherein substituted heterocycloalkyl, substituted heterocycloalkylalkyl, substituted arylalkyl and substituted heteroarylalkyl are substituted with $R^{12}$, $R^{13}$ and $R^{14}$;

or $R^2$ and $R^4$ together form a double bond, wherein in case $R^2$ and $R^4$ together form a double bond, then $R^5$ is H;

or $R^1$ and $R^2$ together with the carbon atom to which they are attached form a substituted cycloalkyl or a substituted heterocycloalkyl, wherein substituted cycloalkyl and substituted heterocycloalkyl are substituted with $R^{22}$, $R^{23}$ and $R^{24}$;

or $R^3$ and $R^4$ together with the carbon atom to which they are attached form a substituted cycloalkyl or a substituted heterocycloalkyl, wherein substituted cycloalkyl and substituted heterocycloalkyl are substituted with $R^{29}$, $R^{30}$ and $R^{31}$;

or $R^1$ and $R^3$ together with the carbon atom to which they are attached form a substituted cycloalkyl or a substituted heterocycloalkyl, wherein substituted cycloalkyl and substituted heterocycloalkyl are substituted with $R^{44}$, $R^{45}$ and $R^{46}$;

$A^1$ is $CR^8$ or N;
$A^2$ is $CR^9$ or N;
$A^3$ is $CR^{10}$ or N;
$A^4$ is $CR^{11}$ or N;
$A^5$ is $CR^6$ or N;

one of $R^5$, $R^6$, $R^7$ and $R^8$ is selected from the group consisting of halogen, cyano, alkoxy, hydroxyalkoxy, haloalkyl, haloalkoxy and hydroxy and the others are each independently selected from the group consisting of H, halogen, cyano, alkoxy, hydroxyalkoxy, haloalkoxy and hydroxy;

$R^9$ is selected from the group consisting of H, halogen, hydroxy, cyano, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, alkoxycycloalkylalkyl, dialkoxyalkyl, haloalkoxy, haloalkoxyalkyl, alkoxyalkoxy, alkoxyalkoxyalkyl, haloalkoxyalkyl, haloalkoxyalkoxyalkyl, substituted arylalkyl, substituted arylhydroxyalkyl, substituted heterocycloalkylalkyl and substituted heteroarylalkyl, wherein substituted arylalkyl, substituted arylhydroxyalkyl, substituted heterocycloalkylalkyl and substituted heteroarylalkyl are substituted with $R^{32}$, $R^{33}$ and $R^{34}$;

$R^{10}$ is —$O_m$—$(CR^{15}R^{16})_p$—$(CR^{17}R^{18})_q$—$(CR^{19}R^{20})_r$—$R^{21}$;

or $R^9$ and $R^{10}$ together with the carbon atoms to which they are attached form a substituted cycloalkyl, a substituted heterocycloalkyl, a substituted aryl or a substituted heteroaryl, wherein substituted cycloalkyl, substituted heterocycloalkyl, substituted aryl and substituted heteroaryl are substituted with $R^{35}$, $R^{36}$ and $R^{37}$;

$R^{11}$ is H;

$R^{15}$, $R^{17}$ and $R^{19}$ are each independently selected from the group consisting of H, alkyl, cycloalkyl, haloalkyl and halocycloalkyl;

$R^{16}$, $R^{18}$ and $R^{20}$ are each independently selected from the group consisting of H, hydroxy, halogen and alkyl;

or $R^{15}$ and $R^{16}$ together with the carbon atom to which they are attached form a cycloalkyl;

or $R^{17}$ and $R^{18}$ together with the carbon atom to which they are attached form a cycloalkyl;

or $R^{19}$ and $R^{20}$ together with the carbon atom to which they are attached form a cycloalkyl;

or $R^{15}$ and $R^{17}$ together form —$(CH_2)_v$—;
or $R^{15}$ and $R^{19}$ together form —$(CH_2)_w$—;
or $R^{17}$ and $R^{19}$ together form —$(CH_2)_x$—;

$R^{21}$ is selected from the group consisting of H, halogen, cyano, —$OR^{25}$, —$SR^{25}$, —$S(O)R^{25}$, —$S(O)_2R^{25}$, —$NR^{25}R^{26}$, —$NR^{26}SO_2R^{25}$, —$NR^{26}SO_2NR^{25}R^{27}$, —$NR^{26}C(O)R^{25}$, —$NR^{26}C(O)NR^{25}R^{27}$, —$C(O)R^{28}$, —$C(O)NR^{25}R^{26}$, cycloalkyl, substituted heterocycloalkyl, substituted heteroaryl and substituted aryl, wherein substituted heterocycloalkyl, substituted heteroaryl, substituted heteroarylalkyl and substituted aryl are substituted with $R^{38}$, $R^{39}$ and $R^{40}$;

$R^{25}$ is selected from the group consisting of H, alkyl, hydroxyalkyl, carboxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxyalkyl, cycloalkoxyalkyl, halocycloalkoxyalkyl, alkylcycloalkoxyalkyl, alkoxyalkyl, haloalkoxyalkyl, alkoxyalkoxyalkyl, haloalkoxyalkoxyalkyl, substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{41}$, $R^{42}$ and $R^{43}$;

$R^{26}$ and $R^{27}$ are each independently selected from the group consisting of H, alkyl, cycloalkyl, haloalkyl and halocycloalkyl;

or $R^{15}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

or $R^{17}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

or $R^{19}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

$R^{28}$ is selected from the group consisting of H, hydroxy, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, haloalkoxy, haloalkoxyalkyl, alkoxyalkoxy, alkoxyalkoxyalkyl, haloalkoxyalkoxy, haloalkoxyalkoxyalkyl substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{50}$, $R^{51}$ and $R^{52}$;

$R^{12}$, $R^{13}$, $R^{14}$, $R^{22}$, $R^{23}$, $R^{24}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$ and $R^{52}$ are each independently selected from the group consisting of H, halogen, hydroxy, amino, nitro, cyano, oxo, alkyl, alkylcarbonyl, alkylsulfonyl, hydroxyalkyl, haloalkyl, cycloalkyl, cycloalkylalkyl, alkylcycloalkyl, halocycloalkyl, alkylcycloalkylalkyl, alkylcarbonylamino, alkylsulfonyl, alkylsulfonylamino, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxycarbonyl, alkoxyalkyl, haloalkoxy, haloalkoxyalkyl, alkoxyalkoxy, alkoxyalkoxyalkyl, haloalkoxyalkoxy, haloalkoxyalkoxyalkyl, chloropyridinylcarbonyl and heterocycloalkyl;

n is zero or 1;

m zero or 1;

p, q and r are independently selected from zero and 1;

v and x are independently 1, 2, 3 or 4; and w is zero, 1, 2 or 3;

with the proviso that no more than two of $A^2$, $A^3$ and $A^4$ are N.

The present invention also relates to pharmaceutically acceptable salts and esters of the aforementioned compounds.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl, ethoxypropyl and isopropoxymethyl. Particular alkoxyalkyl group include methoxymethyl, methoxyethyl and isopropoxymethyl.

The term "alkoxycarbonyl" denotes a group of the formula —C(O)—R', wherein R' is an alkoxy group. Examples of alkoxycarbonyl groups include groups of the formula —C(O)—R', wherein R' is methoxy, ethoxy, n-propoxy, isopropoxy, n-butoxy, isobutoxy and tert-butoxy. Particular alkoxycarbonyl group is a group of the formula —C(O)—R', wherein R' is methoxy.

The term "alkoxycycloalkylalkyl" denotes a cycloalkylalkyl group wherein at least one of the hydrogen atoms of the cycloalkyl group is replaced by an alkoxy group. An example of alkoxycycloalkylalkyl group is cyclopropylmethoxymethyl.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, and. Particular alkyl groups include methyl, ethyl, propyl and isopropyl. More particular alkyl groups are methyl, isopropyl and ethyl.

The term "alkylcarbonyl" of the formula —C(O)—R', wherein R' is an alkyl group. Examples of alkylcarbonyl groups include groups of the formula —C(O)—R', wherein R' is methyl or ethyl.

The term "alkylcarbonylamino" denotes an amino group wherein one of the hydrogen atoms of the —NH$_2$ group is replaced by an alkylcarbonyl group. Examples of alkylcarbonylamino groups include groups wherein R' is methyl or ethyl. Particular alkylcarbonylamino groups include groups wherein R' is ethyl.

The term "alkylcarbonylaminoalkyl" denotes an aminoalkyl group wherein one of the hydrogen atoms of the —NH$_2$ group is replaced by an alkylcarbonyl group. Examples of alkylcarbonylaminoalkyl groups include groups wherein R' is methyl or ethyl.

The term "alkylcycloalkoxy" denotes a cycloalkoxy group wherein at least one of the hydrogen atoms of the cycloalkoxy group is replaced by an alkyl group. Examples of alkylcycloalkyl include methyl-cyclopropoxy, dimethyl-cyclopropoxy, methyl-cyclobutoxy, dimethyl-cyclobutoxy, methyl-cyclopentoxy, dimethyl-cyclopentoxy, methyl-cyclohexyloxy and dimethyl-cyclohexyloxy.

The term "alkylcycloalkoxyalkyl" denotes a cycloalkoxyalkyl group wherein at least one of the hydrogen atoms of the cycloalkoxyalkyl group is replaced by an alkyl group. Examples of alkylcycloalkyl include methyl-cyclopropoxymethyl, dimethyl-cyclopropoxymethyl, methyl-cyclobutoxymethyl, dimethyl-cyclobutoxymethyl, methyl-cyclopentoxymethyl, dimethyl-cyclopentoxymethyl, methyl-cyclohexyloxymethyl and dimethyl-cyclohexyloxymethyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "alkylsulfonyl" denotes a group of the formula —S(O)$_2$—R', wherein R' is an alkyl group. Examples of alkylsulfonyl groups include groups of the formula —S(O)$_2$—R', wherein R' is methyl, ethyl, n-propyl, isopropyl, n-butyl, isobutyl and tert-butyl.

The term "alkylsulfonylamino" denotes a group of the formula —NH$_2$—S(O)$_2$—R', wherein R' is an alkyl group. Examples of alkylsulfonyl groups include groups of the formula —NH$_2$—S(O)$_2$—R', wherein R' is methyl, ethyl, n-propyl, isopropyl, n-butyl, isobutyl and tert-butyl.

The term "amino" denotes a —NH$_2$ group.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "arylalkyl" denotes an alkyl group wherein at least one of the hydrogen atoms of the alkyl group has been replaced an aryl group. Particular arylalkyl group is phenylalkyl. More particular arylalkyl group is benzyl.

The term "arylhydroxyalkyl" denotes a hydroxyalkyl group wherein at least one of the hydrogen atoms of the hydroxyalkyl group has been replaced an aryl group. Particular arylalkyl group is phenylhydroxymethyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carbonyl" denotes a —C(O)— group.

The term "carboxyl" denotes a —C(O)OH group.

The term "carboxyalkyl" denotes an alkyl group wherein at least one of the hydrogen atoms of the alkyl group has been replaced by a carboxy group. Examples are carboxymethyl, carboxyethyl, carboxypropyl and 1-carboxy-2-methylpropyl. Particular example is 1-carboxy-2-methylpropyl.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More particular monocyclic cycloalkyl group is cyclopropyl. In particular, the cycloalkyl formed by $R^9$ and $R^{10}$ together with the carbon atoms to which they are attached is cyclohexyl and cyclopentyl. Further particular the cycloalkyl formed by $R^9$ and $R^{10}$ together with the carbon atoms to which they attached is cyclohexyl.

In particular the cycloalkyl formed by $R^1$ and $R^2$ together with the carbon atoms to which they attached is cyclopropyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclopropylbutyl, cyclobutylpropyl, 2-cyclopropylbutyl and cyclopentylbutyl. Particular examples of cycloalkylalkyl groups are cyclopropylmethyl, cyclopropylbutyl and 2-cyclopropylbutyl.

The term "cycloalkylcarbonyl" of the formula —C(O)—R', wherein R' is a cycloalkyl group. Examples of cycloalkylcarbonyl groups include groups of the formula —C(O)—R', wherein R' is cyclopropyl.

The term "cycloalkylcarbonylamino" denotes an amino group wherein one of the hydrogen atoms of the —NH$_2$ group is replaced by a cycloalkylcarbonyl group. Examples of alkylcarbonylamino groups include groups wherein R' is cyclopropyl.

The term "cycloalkylcarbonylaminoalkyl" denotes an aminoalkyl group wherein one of the hydrogen atoms of the —NH$_2$ group is replaced by a cycloalkylcarbonyl group.

Examples of alkylcarbonylaminoalkyl groups include groups wherein R' is cyclopropyl.

The term "dialkoxyalkyl" denotes an alkyl group wherein two of the hydrogen atoms of the alkyl group have been replaced by two alkoxy group. Exemplary dialkoxyalkyl groups include dimethoxymethyl, diethoxymethyl, dimethoxyethyl, diethoxyethyl, dimethoxypropyl, diethoxypropyl and diisopropoxymethyl. Particular dialkoxyalkyl group is dimethoxymethyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and 2,2-difluoroethoxy.

The term "haloalkoxyalkoxy" denotes an alkoxy group wherein at least one of the hydrogen atoms of the alkoxy group has been replaced by a haloalkoxy group. Examples of haloalkoxyalkyl include fluoromethoxymethoxy, difluoromethoxymethoxy, trifluoromethoxymethoxy, fluoroethoxymethoxy, difluoroethoxymethoxy, trifluoroethoxymethyoxy, fluoromethoxyethoxy, difluoromethoxyethoxy, trifluoromethoxyethoxy, fluoroethoxyethoxy, difluoroethoxyethoxy, trifluoroethoxyethoxy, fluoromethoxypropoxy, difluoromethoxypropoxy, trifluoromethoxypropoxy, fluoroethoxypropoxy, difluoroethoxypropoxy and trifluoroethoxypropoxy.

The term "haloalkoxyalkoxyalkyl" denotes an alkyl group wherein at least one of the hydrogen atoms of the alkyl group has been replaced by a haloalkoxyalkoxy group. Examples of haloalkoxyalkyl include fluoromethoxymethoxymethyl, difluoromethoxymethoxymethyl, trifluoromethoxymethoxymethyl, fluoroethoxymethoxymethyl, difluoroethoxymethoxymethyl, trifluoroethoxymethyoxymethyl, fluoromethoxyethoxymethyl, difluoromethoxyethoxymethyl, trifluoromethoxyethoxymethyl, fluoroethoxyethoxymethyl, difluoroethoxyethoxymethyl, trifluoroethoxyethoxymethyl, fluoromethoxypropoxymethyl, difluoromethoxypropoxymethyl, trifluoromethoxypropoxymethyl, fluoroethoxypropoxymethyl, difluoroethoxypropoxymethyl and trifluoroethoxypropoxymethyl.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2-difluoroethoxyethyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl. Also particular groups are difluoromethyl.

The term "halocycloalkoxy" denotes a cycloalkoxy group wherein at least one of the hydrogen atoms of the cycloalkoxy group has been replaced by same or different halogen atoms, particularly fluoro atoms. Examples of halocycloalkoxy groups include fluorocyclopropoxy, difluorocyclopropoxy, fluorocyclobutoxy and difluorocyclobutoxy.

The term "halocycloalkoxyalkyl" denotes an alkyl group wherein at least one of the hydrogen atoms of the alkyl group has been replaced by a halocycloalkoxy group, particularly fluoro atoms. Examples of halocycloalkoxyalkyl groups include fluorocyclopropoxymethyl, difluorocyclopropoxymethyl, fluorocyclobutoxymethyl and difluorocyclobutoxymethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include pyrrolyl, pyrazolyl, imidazolyl, triazolyl, benzoimidazolyl, indazolyl, indolyl, pyridinyl, isooxazolyl and oxazolyl.

In particular, the heteroaryl groups formed by $R^9$ and $R^{10}$ together with the carbon atoms to which they are attached are pyrrolyl and pyrazolyl. In particular, in the case of $R^{21}$, the term "heteroaryl" denotes the imidazolyl, pyrazolyl, triazolyl, benzoimidazolyl, indazolyl, indolyl, pyridinyl and izooxazolyl groups. More particularly the pyrazolyl group.

In particular, in the case of $R^{25}$, the term "heteroaryl" denotes the pyridinyl, pyrazolyl and oxazolyl groups. In particular, in the case of $R^{25}$, the term "heteroaryl" denotes the pyrazolyl and oxazolyl groups. Further particular heteroaryl in the case of $R^{25}$ is pyrazolyl and pyridinyl. More particular is pyrazolyl.

The term "heteroarylalkyl" denotes an alkyl group wherein at least one of the hydrogen atoms of the alkyl group has been replaced a heteroaryl group. Examples are pyrazolylalkyl and imidazolylalkyl. More particular examples are pyrazolylmethyl and imidazolylmethyl.

In particular, in the case of $R^{25}$, the term "heteroarylalkyl" denotes the pyrazolylmethyl and imidazolylmethyl groups. In particular the pyrazolylmethyl group.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl and thiazinanyl. Examples for bicyclic saturated heterocycloalkyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, 3-thia-9-aza-bicyclo[3.3.1]nonyl and 2,6-diaza-spiro[3.3]heptanyl. Examples for partly unsaturated heterocycloalkyl are dihydrofuryl, imidazolinyl, dihydro-oxazolyl, tetrahydro-pyridinyl, or dihydropyranyl. More particular examples of heterocycloalkyl group are pyrrolidinyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, thiazinanyl and 2,6-diaza-spiro[3.3]heptanyl. More particular examples of a heterocycloalkyl are pyrrolydinyl, piperidinyl, thiomorpholinyl, thiazinanyl and 2,6-diaza-spiro[3.3]heptanyl.

In particular, in the case of $R^{21}$, the term "heterocycloalkyl" denotes the pyrrolidinyl, thiazinan-2-yl, isothiazolidin-2-yl, piperidinyl, morphonlinyl, thiomorphonlinyl, oxazolidinyl, imidazolidinyl, piperazinyl, 2-oxa-6-aza-spiro[3.4]heptanyl and 2-oxa-6-aza-spiro[3.4]octanyl groups. Further particularly the piperazinyl and 2-oxa-6-aza-spiro[3.4]octanyl groups More particularly the 2-oxa-6-aza-spiro[3.4]octanyl group. Also more particularly the piperazinyl group.

In particular, in the case of $R^{25}$, the term "heterocycloalkyl" denotes the oxetanyl group.

In particular, in the case of $R^{28}$, the term "heterocycloalkyl" denotes the morpholinyl, pyrrolidinyl and piperidinyl groups.

In particular the heterocycloalkyl formed by $R^{15}$ and $R^{26}$ together with the nitrogen atom and carbon atom to which they are attached are azetanyl, pyrrolidinyl and piperidinyl.

The term "heterocycloalkylalkyl" denotes an alkyl group wherein at least one of the hydrogen atoms of the alkyl group has been replaced a heterocycloalkyl group. Examples are tetrahydrofuranylalkyl, pyrrolidinylalkyl and piperazin-1-ylalkyl. More particularly, tetrahydrofuranylethyl, pyrrolidinylmethyl and piperazin-1-ylmethyl.

In particular, in the case of $R^9$, the term "heterocycloalkylalkyl" denotes the piperazin-1-ylalkyl group. More particularly, the piperazin-1-ylalkyl group.

In particular, in the case of $R^{25}$, the term "heterocycloalkylalkyl" denotes the tetrahydrofuranylalkyl and pyrrolidinylalkyl groups. More particularly, the tetrahydrofuranylethyl and pyrrolidinylmethyl groups.

The term "hydroxy" denotes a —OH group.

The term "hydroxyalkoxy" denotes an alkoxy group wherein at least one of the hydrogen atoms of the alkoxy group has been replaced by a hydroxy group. Examples of hydroxyalkyl include hydroxyethethoxy, hydroxypropoxy and hydroxymethylpropoxy.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxy-1-methylethyl, hydroxypropyl, hydroxymethylpropyl and dihydroxypropyl. Particular examples are hydroxymethyl and hydroxyethyl.

The term "oxo" denotes a divalent oxygen atom =O.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol μM.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H ("T"), $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as 15O, $^{13}$N, $^{11}$C, and $^{18}$F are useful for positron emission tomography (PET) studies to examine substrate receptor occupancy. Isotopically labeled compounds of the present inventions can generally be prepared by following procedures analogous to those disclosed in the Schemes and/ or in the Examples herein below, by substituting a non-isotopically labeled reagent with a isotopically labeled reagent. In particular, compounds of formula (I) wherein one or more H atom have been replaced by a $^2$H atom are also an embodiment of this invention.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

In a particular embodiment, the present invention relates to compounds according to formula (I) as described herein and pharmaceutically acceptable salts thereof, more particularly compounds according to formula (I) as described herein.

A further embodiment of the present invention are compounds according to formula (I) as described herein, wherein $R^1$, $R^2$, $R^3$ and $R^4$ are independently selected from the group consisting of H, alkyl, cycloalkyl, cycloalkylalkyl, haloalkyl, halocycloalkyl, hydroxyalkyl, alkoxyalkyl, haloalkoxyalkyl, halocycloalkylalkyl, substituted heterocycloalkyl, substituted heterocycloalkylalkyl, substituted arylalkyl and substituted heteroarylalkyl, wherein substituted heterocycloalkyl, substituted heterocycloalkylalkyl, substituted arylalkyl and substituted heteroarylalkyl are substituted with $R^{12}$, $R^{13}$ and $R^{14}$.

A particular embodiment of the present invention are compounds according to formula (I) as described herein, wherein $R^2$ and $R^4$ together form a double bond, wherein in case $R^2$ and $R^4$ together form a double bond, then $R^5$ is H.

In a further embodiment of the present invention are compounds according to formula (I) as described herein, wherein $R^1$ and $R^2$ together with the carbon atom to which they are attached form a substituted cycloalkyl or a substituted heterocycloalkyl, wherein substituted cycloalkyl and substituted heterocycloalkyl are substituted with $R^{22}$, $R^{23}$ and $R^{24}$ Another further embodiment of the present invention are compounds according to formula (I) as described herein, wherein $R^3$ and $R^4$ together with the carbon atom to which they are attached form a substituted cycloalkyl or a substituted heterocycloalkyl, wherein substituted cycloalkyl and substituted heterocycloalkyl are substituted with $R^{29}$, $R^{30}$ and $R^{31}$.

Another embodiment of the present invention are compounds according to formula (I) as described herein, wherein $R^1$ and $R^3$ together with the carbon atom to which they are attached form a substituted cycloalkyl or a substituted heterocycloalkyl, wherein substituted cycloalkyl and substituted heterocycloalkyl are substituted with $R^{44}$, $R^{45}$ and $R^{46}$.

The present invention also relates to compounds according to formula (I) as described herein, wherein $R^1$ is H, alkyl or arylalkyl substituted with $R^{12}$, $R^{13}$ and $R^{14}$.

A further particular embodiment of the present invention are compounds according to formula (I) as described herein, wherein $R^1$ is H or alkyl.

A more particular embodiment of the present invention are compounds according to formula (I) as described herein, wherein $R^1$ is H.

Also an embodiment of the present invention are compounds according to formula (I) as described herein, wherein $R^1$ is alkyl.

The present invention also relates to compounds according to formula (I) as described herein, wherein $R^1$ is methyl or ethyl.

Another embodiment of the present invention are compounds according to formula (I) as described herein, wherein $R^1$, $R^2$, $R^3$ and $R^4$ are independently selected from the group consisting of H, alkyl and arylalkyl substituted with $R^{12}$, $R^{13}$ and $R^{14}$.

A further particular embodiment of the present invention are compounds according to formula (I) as described herein, wherein is $R^1$, $R^2$, $R^3$ and $R^4$ are independently selected from H or alkyl.

A particular embodiment of the present invention are compounds according to formula (I) as described herein, wherein $R^1$ is selected from the group consisting of H, alkyl or arylalkyl substituted with $R^{12}$, $R^{13}$ and $R^{14}$ and wherein $R^{12}$, $R^{13}$ and $R^{14}$ are H.

Also an embodiment of the present invention are compounds according to formula (I) as described herein, wherein $R^2$ is H or alkyl.

The present invention also relates to compounds according to formula (I) as described herein, wherein $R^2$ is H.

Another embodiment of the present invention are compounds according to formula (I) as described herein, wherein $R^2$ is alkyl.

The present invention also relates to compounds according to formula (I) as described herein, wherein $R^2$ is methyl.

Another embodiment of the present invention are compounds according to formula (I) as described herein, wherein $R^1$ and $R^2$ together with the carbon atom to which they are attached form a substituted cycloalkyl or a substituted heterocycloalkyl, wherein substituted cycloalkyl and substituted heterocycloalkyl are substituted with $R^{22}$, $R^{23}$ and $R^{24}$.

The present invention also relates to compounds according to formula (I) as described herein, wherein $R^1$ and $R^2$ together with the carbon atom to which they are attached form a cycloalkyl substituted with $R^{22}$, $R^{23}$ and $R^{24}$.

Also an embodiment of the present invention are compounds according to formula (I) as described herein, wherein $R^1$ and $R^2$ together with the carbon atom to which they are attached form a cyclopropyl.

Also an embodiment of the present invention are compounds according to formula (I) as described herein, wherein $R^3$ is H or alkyl.

Another embodiment of the present invention are compounds according to formula (I) as described herein, wherein $R^3$ is H.

Also an embodiment of the present invention are compounds according to formula (I) as described herein, wherein $R^4$ is H.

A particular embodiment of the present invention are compounds according to formula (I) as described herein, wherein $A^1$ is $CR^8$.

A further particular embodiment of the present invention are compounds according to formula (I) as described herein, wherein $A^1$ is N.

A more particular embodiment of the present invention are compounds according to formula (I) as described herein, wherein $A^2$ is $CR^9$.

Also a particular embodiment of the present invention are compounds according to formula (I) as described herein, wherein $A^2$ is N.

Also a particular embodiment of the present invention are compounds according to formula (I) as described herein, wherein $A^3$ is $CR^{10}$.

Another embodiment of the present invention are compounds according to formula (I) as described herein, wherein $A^3$ is N.

Another embodiment of the present invention are compounds according to formula (I) as described herein, wherein $A^4$ is $CR^{11}$.

Also an embodiment of the present invention are compounds according to formula (I) as described herein, wherein $A^4$ is N.

Also an embodiment of the present invention are compounds according to formula (I) as described herein, wherein $A^5$ is $CR^6$.

Also an embodiment of the present invention are compounds according to formula (I) as described herein, wherein $A^5$ is N.

Also an embodiment of the present invention are compounds according to formula (I) as described herein, wherein one of $R^5$, $R^6$, $R^7$ and $R^8$ is selected from the group consisting of halogen, alkoxy and hydroxy and the others are each independently selected from H and halogen.

A further embodiment of the present invention are compounds according to formula (I) as described herein, wherein one of $R^5$, $R^6$ and $R^8$ are H.

Also an embodiment of the present invention are compounds according to formula (I) as described herein, wherein one of $R^5$, $R^6$ and $R^8$ are H and $R^7$ is halogen or alkoxy.

Another embodiment of the present invention are compounds according to formula (I) as described herein, wherein at least one of $R^5$, $R^6$, $R^7$ and $R^8$ is different from H.

A further embodiment of the present invention are compounds according to formula (I) as described herein, wherein $R^5$ is H or halogen and wherein at least one of $R^5$, $R^6$, $R^7$ and $R^8$ is different from H.

A particular embodiment of the present invention are compounds according to formula (I) as described herein, wherein $R^6$ is H or halogen and wherein at least one of $R^5$, $R^6$, $R^7$ and $R^8$ is different from H.

A further particular embodiment of the present invention are compounds according to formula (I) as described herein, wherein $R^7$ is selected from the group consisting of H, halogen, alkoxy and hydroxy and wherein at least one of $R^5$, $R^6$, $R^7$ and $R^8$ is different from H.

A more particular embodiment of the present invention are compounds according to formula (I) as described herein, wherein $R^7$ is halogen or alkoxy.

Another embodiment of the present invention are compounds according to formula (I) as described herein, wherein $R^7$ is halogen.

Another particular embodiment of the present invention are compounds according to formula (I) as described herein, wherein $R^7$ is chloro.

A particular embodiment of the present invention are compounds according to formula (I) as described herein, wherein $R^8$ is H or halogen and wherein at least one of $R^5$, $R^6$, $R^7$ and $R^8$ is different from H.

Also an embodiment of the present invention are compounds according to formula (I) as described herein, wherein $R^9$ is selected from the group consisting of H, halogen, hydroxy, cyano, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, alkoxycycloalkylalkyl, dialkoxyalkyl, haloalkoxy, haloalkoxyalkyl, alkoxyalkoxy, alkoxyalkoxyalkyl, haloalkoxyalkyl, haloalkoxyalkoxyalkyl, substituted arylalkyl, substituted arylhydroxyalkyl, substituted heterocycloalkylalkyl and substituted heteroarylalkyl, wherein substituted arylalkyl, substituted arylhydroxyalkyl, substituted heterocycloalkylalkyl and substituted heteroarylalkyl are substituted with $R^{32}$, $R^{33}$ and $R^{34}$.

Another embodiment of the present invention are compounds according to formula (I) as described herein, wherein $R^9$ is selected from the group consisting of H, halogen, cyano, alkyl, hydroxyalkyl, haloalkyl, alkoxyalkyl, alkoxycycloalkylalkyl, dialkoxyalkyl, substituted arylhydroxyalkyl and substituted heterocycloalkylalkyl, wherein substituted arylhydroxyalkyl and substituted heterocycloalkylalkyl are substituted with $R^{32}$, $R^{33}$ and $R^{34}$.

The present invention also relates to compounds according to formula (I) as described herein, wherein $R^9$ is H or halogen.

A further embodiment of the present invention are compounds according to formula (I) as described herein, wherein $R^9$ is H.

A embodiment of the present invention are compounds according to formula (I) as described herein, wherein $R^9$ and $R^{10}$ together with the carbon atoms to which they are attached form a substituted cycloalkyl, a substituted heterocycloalkyl, a substituted aryl or a substituted heteroaryl, wherein substituted cycloalkyl, substituted heterocycloalkyl, substituted aryl and substituted heteroaryl are substituted with $R^{35}$, $R^{36}$ and $R^{37}$.

A embodiment of the present invention are compounds according to formula (I) as described herein, wherein $R^9$ and $R^{10}$ together with the carbon atoms to which they are attached form a substituted cycloalkyl, a substituted aryl or a substituted heteroaryl, wherein substituted cycloalkyl, substituted aryl and substituted heteroaryl are substituted with $R^{35}$, $R^{36}$ and $R^{37}$.

A embodiment of the present invention are compounds according to formula (I) as described herein, wherein $R^9$ and $R^{10}$ together with the carbon atoms to which they are attached form a substituted cycloalkyl or a substituted aryl, wherein substituted cycloalkyl and substituted aryl are substituted with $R^{35}$, $R^{36}$ and $R^{37}$.

Also an embodiment of the present invention are compounds according to formula (I) as described herein, wherein $R^9$ and $R^{10}$ together with the carbon atoms to which they are attached form a cycloalkyl substituted with $R^{35}$, $R^{36}$ and $R^{37}$.

The present invention also relates to compounds according to formula (I) as described herein, wherein $R^9$ and $R^{10}$ together with the carbon atoms to which they are attached form a cycloalkyl substituted with $R^{35}$, $R^{36}$ and $R^{37}$.

A embodiment of the present invention are compounds according to formula (I) as described herein, wherein $R^{15}$, $R^{17}$ and $R^{19}$ are each independently selected from the group consisting of H, alkyl, cycloalkyl, haloalkyl and halocycloalkyl.

Also an embodiment of the present invention are compounds according to formula (I) as described herein, wherein $R^{15}$, $R^{17}$ and $R^{19}$ are each independently selected from the group consisting of H, alkyl, cycloalkyl and haloalkyl.

The present invention also relates to compounds according to formula (I) as described herein, wherein $R^{17}$ is H.

The present invention also relates to compounds according to formula (I) as described herein, wherein $R^{19}$ is selected from the group consisting of H, alkyl, cycloalkyl and haloalkyl.

Also an embodiment of the present invention are compounds according to formula (I) as described herein, wherein $R^{19}$ is H or alkyl.

A further embodiment of the present invention are compounds according to formula (I) as described herein, wherein $R^{19}$ is H.

The present invention also relates to compounds according to formula (I) as described herein, wherein $R^{19}$ is alkyl.

The present invention also relates to compounds according to formula (I) as described herein, wherein $R^{19}$ is methyl.

The present invention also relates to compounds according to formula (I) as described herein, wherein $R^{16}$, $R^{18}$ and $R^{20}$ are each independently selected from the group consisting of H, hydroxy, halogen and alkyl.

The present invention also relates to compounds according to formula (I) as described herein, wherein $R^{16}$, $R^{18}$ and $R^{20}$ are each independently selected from the group consisting of H, hydroxy and alkyl.

The present invention also relates to compounds according to formula (I) as described herein, wherein $R^{18}$ is H.

A further particular embodiment of the present invention are compounds according to formula (I) as described herein, wherein $R^{20}$ is selected from the group consisting of H, hydroxy and alkyl.

A more particular embodiment of the present invention are compounds according to formula (I) as described herein, wherein $R^{20}$ is H.

Also an embodiment of the present invention are compounds according to formula (I) as described herein, wherein $R^{19}$ and $R^{20}$ together with the carbon atom to which they are attached form a cycloalkyl.

The present invention also relates to compounds according to formula (I) as described herein, wherein $R^{19}$ and $R^{20}$ together with the carbon atom to which they are attached form a cyclopropyl.

Another embodiment of the present invention are compounds according to formula (I) as described herein, wherein $R^{21}$ is selected from the group consisting of H, halogen, cyano, $-OR^{25}$, $-SR^{25}$, $-S(O)R^{25}$, $-NR^{25}R^{26}$, $NR^{26}SO_2R^{25}$, $-NR^{26}C(O)R^{25}$, $-NR^{26}C(O)NR^{25}R^{27}$, $-C(O)R^{28}$, $-C(O)NR^{25}R^{26}$, cycloalkyl, substituted heterocycloalkyl, substituted heteroaryl and substituted aryl, wherein substituted heterocycloalkyl, substituted heteroaryl and substituted aryl are substituted with $R^{38}$, $R^{39}$ and $R^{40}$.

A further particular embodiment of the present invention are compounds according to formula (I) as described herein, wherein $R^{21}$ is selected from the group consisting of H, halogen, $-OR^{25}$, $-NR^{25}R^{26}$, $-NR^{26}SO_2R^{25}$, $-NR^{26}C(O)R^{25}$, substituted heterocycloalkyl and substituted heteroaryl, wherein substituted heterocycloalkyl and substituted heteroaryl are substituted with $R^{38}$, $R^{39}$ and $R^{40}$.

A further particular embodiment of the present invention are compounds according to formula (I) as described herein, wherein $R^{21}$ is selected from the group consisting of H, halogen, $-OR^{25}$, $-NR^{25}R^{26}$, substituted heterocycloalkyl and substituted heteroaryl, wherein substituted heterocycloalkyl and substituted heteroaryl are substituted with $R^{38}$, $R^{39}$ and $R^{40}$.

A particular embodiment of the present invention are compounds according to formula (I) as described herein, wherein $R^{21}$ is selected from the group consisting of $-OR^{25}$, $-NR^{25}R^{26}$, $-NR^{26}SO_2R^{25}$ and $-NR^{26}C(O)R^{25}$.

A further particular embodiment of the present invention are compounds according to formula (I) as described herein, wherein $R^{21}$ is selected from the group consisting of $-NR^{25}R^{26}$, $-NR^{26}SO_2R^{25}$ and $-NR^{26}C(O)R^{25}$.

An embodiment of the present invention are compounds according to formula (I) as described herein, wherein $R^{21}$ is $-OR^{25}$.

A particular embodiment of the present invention are compounds according to formula (I) as described herein, wherein $R^{25}$ is selected from the group consisting of H, alkyl, hydroxyalkyl, carboxyalkyl, haloalkyl, cycloalkyl, cycloalkylalkyl, substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{41}$, $R^{42}$ and $R^{43}$.

Also an embodiment of the present invention are compounds according to formula (I) as described herein, wherein $R^{25}$ is selected from the group consisting of H, alkyl, haloalkyl, cycloalkyl, substituted heteroaryl and substituted heteroarylalkyl, wherein substituted heteroaryl and substituted heteroarylalkyl are substituted with $R^{41}$, $R^{42}$ and $R^{43}$.

The present invention also relates to compounds according to formula (I) as described herein, wherein $R^{21}$ is $-NR^{25}R^{26}$ and $R^{25}$ is substituted heteroaryl or substituted heteroarylalkyl.

Another embodiment of the present invention are compounds according to formula (I) as described herein, wherein $R^{25}$ is selected from the group consisting of H, alkyl, haloalkyl, cycloalkyl, substituted heterocycloalkyl, substituted heterocycloalkylalkyl, substituted heteroaryl and substituted heteroarylalkyl, wherein substituted heteroaryl and substituted heteroarylalkyl are substituted with $R^{41}$, $R^{42}$ and $R^{43}$.

The present invention also relates to compounds according to formula (I) as described herein, wherein $R^{26}$ and $R^{27}$ are each independently selected from the group consisting of H, alkyl, cycloalkyl, haloalkyl and halocycloalkyl.

Also an embodiment of the present invention are compounds according to formula (I) as described herein, wherein $R^{26}$ and $R^{27}$ are each independently selected from H and alkyl.

Another embodiment of the present invention are compounds according to formula (I) as described herein, wherein $R^{26}$ is H.

Also an embodiment of the present invention are compounds according to formula (I) as described herein, wherein $R^{12}$, $R^{13}$, $R^{14}$, $R^{22}$, $R^{23}$, $R^{24}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$ and $R^{52}$ are each independently selected from the group consisting of H, halogen, hydroxy, amino, nitro, cyano, oxo, alkyl, alkylcarbonyl, alkylsulfonyl, hydroxyalkyl, haloalkyl, cycloalkyl, alkylcarbonylamino, alkoxycarbonyl, alkoxyalkyl, haloalkoxy, chloropyridinylcarbonyl and heterocycloalkyl.

Also an embodiment of the present invention are compounds according to formula (I) as described herein, wherein $R^{12}$, $R^{13}$, $R^{14}$, $R^{22}$, $R^{23}$, $R^{24}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$ and $R^{52}$ are each independently selected from the group consisting of H, halogen, hydroxy, amino, nitro, cyano, oxo, alkyl, hydroxyalkyl, haloalkyl, cycloalkyl, alkylcarbonylamino, alkoxycarbonyl, alkoxyalkyl, haloalkoxy and heterocycloalkyl.

A particular embodiment of the present invention are compounds according to formula (I) as described herein, wherein $R^{12}$, $R^{13}$, $R^{14}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{50}$, $R^{51}$ and $R^{52}$ are each independently selected from the group consisting of H, halogen, hydroxy, amino, nitro, cyano, oxo, alkyl, alkylcarbonyl, alkylsulfonyl, hydroxyalkyl, haloalkyl, cycloalkyl, alkylcarbonylamino, alkoxycarbonyl, alkoxyalkyl, haloalkoxy and heterocycloalkyl.

A particular embodiment of the present invention are compounds according to formula (I) as described herein, wherein $R^{12}$, $R^{13}$, $R^{14}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{50}$, $R^{51}$ and $R^{52}$ are each independently selected from the group consisting of H, halogen, hydroxy, amino, nitro, cyano, oxo, alkyl, hydroxyalkyl, haloalkyl, cycloalkyl, alkylcarbonylamino, alkoxycarbonyl, alkoxyalkyl, haloalkoxy and heterocycloalkyl.

A further particular embodiment of the present invention are compounds according to formula (I) as described herein, wherein $R^{12}$, $R^{13}$ and $R^{14}$ are H.

A more particular embodiment of the present invention are compounds according to formula (I) as described herein, wherein $R^{32}$ is alkyl or halogen, and $R^{33}$ and $R^{34}$ are H.

Also a particular embodiment of the present invention are compounds according to formula (I) as described herein, wherein $R^{35}$ is selected from the group consisting of H, halogen, hydroxy, alkyl, haloalkyl and alkylcarbonylamino, and $R^{36}$ and $R^{37}$ are H.

Also a particular embodiment of the present invention are compounds according to formula (I) as described herein, wherein $R^{35}$ is H or alkyl, and $R^{36}$ and $R^{37}$ are H.

Another embodiment of the present invention are compounds according to formula (I) as described herein, wherein $R^{38}$ is selected from the group consisting of H, halogen, hydroxy, cyano, oxo, alkyl, alkylcarbonyl, alkylsulfonyl, hydroxyalkyl, haloalkyl, cycloalkyl, alkoxycarbonyl and alkoxyalkyl, $R^{39}$ is selected from the group consisting of H, halogen, oxo, alkyl and hydroxyalkyl, and $R^{40}$ is H.

Another embodiment of the present invention are compounds according to formula (I) as described herein, wherein $R^{38}$ is selected from the group consisting of H, halogen, hydroxy, cyano, oxo, alkyl, hydroxyalkyl, haloalkyl, cycloalkyl, alkoxycarbonyl and alkoxyalkyl, $R^{39}$ is selected from the group consisting of H, halogen, oxo, alkyl and hydroxyalkyl, and $R^{40}$ is H.

Another embodiment of the present invention are compounds according to formula (I) as described herein, wherein $R^{38}$ is selected from the group consisting of H, alkyl alkylcarbonyl and alkylsulfonyl, and $R^{39}$ and $R^{40}$ are H.

Another embodiment of the present invention are compounds according to formula (I) as described herein, wherein $R^{38}$ is H or alkyl, and $R^{39}$ and $R^{40}$ are H.

Also an embodiment of the present invention are compounds according to formula (I) as described herein, wherein $R^{41}$ is selected from the group consisting of H, halogen, alkyl and haloalkyl, and $R^{42}$ and $R^{43}$ are H.

Also an embodiment of the present invention are compounds according to formula (I) as described herein, wherein $R^{41}$ is alkyl, and $R^{42}$ and $R^{43}$ are H.

Also an embodiment of the present invention are compounds according to formula (I) as described herein, wherein $R^{50}$, $R^{51}$ and $R^{52}$ are each independently selected from the group consisting of H, halogen, hydroxy and alkyl, $R^{51}$ is H or halogen, and $R^{52}$ is H.

A particular embodiment of the present invention are compounds according to formula (I) as described herein, wherein $R^{35}$, $R^{36}$, $R^{37}$, $R^{38}$, $R^{39}$, $R^{40}$, $R^{41}$, $R^{42}$ and $R^{43}$ are each independently selected from H and alkyl.

A further particular embodiment of the present invention are compounds according to formula (I) as described herein, wherein p is zero.

A more particular embodiment of the present invention are compounds according to formula (I) as described herein, wherein q is zero.

Another embodiment of the present invention are compounds according to formula (I) as described herein, wherein r is zero or 1.

Another particular embodiment of the present invention are compounds according to formula (I) as described herein, wherein m is zero.

A particular embodiment of the present invention are compounds according to formula (I) as described herein, wherein n is zero.

Another embodiment of the present invention are compounds according to formula (I) as described herein, wherein n is 1.

A particular embodiment of the present invention are compounds according to formula (I) as described herein, wherein $R^2$ and $R^4$ together form a double bond, $R^5$ is H, n is 1 and of formula (Ia).

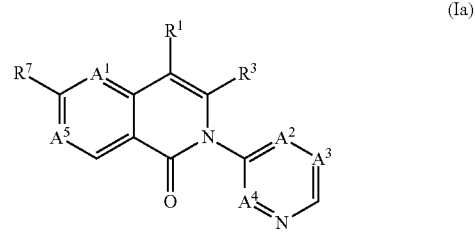

(Ia)

Particular examples of compounds of formula (I) as described herein are selected from the group consisting of
6-Chloro-2-pyridin-3-yl-3,4-dihydro-2H-isoquinolin-1-one;
5-(6-Chloro-1-oxo-3,4-dihydro-1H-isoquinolin-2-yl)-nicotinonitrile;
6-Chloro-2-(5-hydroxymethyl-pyridin-3-yl)-3,4-dihydro-2H-isoquinolin-1-one;
6-Chloro-2-(5-chloro-pyridin-3-yl)-3,4-dihydro-2H-isoquinolin-1-one;
6-Chloro-2-(5-fluoro-pyridin-3-yl)-3,4-dihydro-2H-isoquinolin-1-one;
6-Chloro-2-(4-chloro-pyridin-3-yl)-3,4-dihydro-2H-isoquinolin-1-one;
2-(5-Bromo-pyridin-3-yl)-6-chloro-3,4-dihydro-2H-isoquinolin-1-one;

6-Chloro-2-(5-methyl-pyridin-3-yl)-3,4-dihydro-2H-isoquinolin-1-one;
5-(6-Chloro-1-oxo-3,4-dihydro-1H-isoquinolin-2-yl)-pyridine-3-carbaldehyde;
6-Chloro-2-(5-methoxy-pyridin-3-yl)-3,4-dihydro-2H-isoquinolin-1-one;
6-Chloro-2-(5-isopropoxy-pyridin-3-yl)-3,4-dihydro-2H-isoquinolin-1-one;
6-Chloro-2-[5-(1-hydroxy-1-methyl-ethyl)-pyridin-3-yl]-3,4-dihydro-2H-isoquinolin-1-one;
6-Chloro-2-[5-(1-hydroxy-ethyl)-pyridin-3-yl]-3,4-dihydro-2H-isoquinolin-1-one;
6-Chloro-2-[5-((R)-1-hydroxy-ethyl)-pyridin-3-yl]-3,4-dihydro-2H-isoquinolin-1-one;
6-Chloro-2-[5-((S)-1-hydroxy-ethyl)-pyridin-3-yl]-3,4-dihydro-2H-isoquinolin-1-one;
6-Chloro-2-[5-(1-methoxy-ethyl)-pyridin-3-yl]-3,4-dihydro-2H-isoquinolin-1-one;
2-(5-Amino-pyridin-3-yl)-6-chloro-3,4-dihydro-2H-isoquinolin-1-one;
6-Chloro-2-[5-(2,2,2-trifluoro-1-hydroxy-ethyl)-pyridin-3-yl]-3,4-dihydro-2H-isoquinolin-1-one;
6-Chloro-2-[5-(2,2,2-trifluoro-1-methoxy-ethyl)-pyridin-3-yl]-3,4-dihydro-2H-isoquinolin-1-one
6-Chloro-2-[5-(cyclopropyl-hydroxy-methyl)-pyridin-3-yl]-3,4-dihydro-2H-isoquinolin-1-one;
6-Chloro-2-[5-(cyclopropyl-methoxy-methyl)-pyridin-3-yl]-3,4-dihydro-2H-isoquinolin-1-one;
6-Chloro-2-(4-trifluoromethyl-pyridin-3-yl)-3,4-dihydro-2H-isoquinolin-1-one;
6-Chloro-2-[5-(2-hydroxy-ethyl)-pyridin-3-yl]-3,4-dihydro-2H-isoquinolin-1-one;
6-Chloro-2-[5-(1-methoxy-1-methyl-ethyl)-pyridin-3-yl]-3,4-dihydro-2H-isoquinolin-1-one;
Ethanesulfonic acid [5-(6-chloro-1-oxo-3,4-dihydro-1H-isoquinolin-2-yl)-pyridin-3-ylmethyl]-amide;
6-Chloro-2-[5-(2-oxo-pyrrolidin-1-yl)-pyridin-3-yl]-3,4-dihydro-2H-isoquinolin-1-one;
6-Chloro-2-(1-methyl-1H-pyrazolo[3,4-c]pyridin-4-yl)-3,4-dihydro-2H-isoquinolin-1-one;
6-Chloro-8'-hydroxy-3,4,5',6',7',8'-hexahydro-[2,4']biisoquinolinyl-1-one;
N-(6-Chloro-1-oxo-3,4,5',6',7',8'-hexahydro-1H-[2,4']biisoquinolinyl-8'-yl)-propionamide;
6-Chloro-2-{5-[hydroxy-(1-methyl-1H-imidazol-2-yl)-methyl]-pyridin-3-yl}-3,4-dihydro-2H-isoquinolin-1-one;
6-Chloro-2-{5-[(3,4-difluoro-phenyl)-hydroxy-methyl]-pyridin-3-yl}-3,4-dihydro-2H-isoquinolin-1-one;
6-Chloro-2-{5-[(3,5-difluoro-phenyl)-hydroxy-methyl]-pyridin-3-yl}-3,4-dihydro-2H-isoquinolin-1-one;
6-Chloro-2-{5-[(4-ethyl-phenyl)-hydroxy-methyl]-pyridin-3-yl}-3,4-dihydro-2H-isoquinolin-1-one;
6-Chloro-2-[5-(hydroxy-phenyl-methyl)-pyridin-3-yl]-3,4-dihydro-2H-isoquinolin-1-one;
6-Chloro-2-[5-(1-hydroxy-1-phenyl-ethyl)-pyridin-3-yl]-3,4-dihydro-2H-isoquinolin-1-one;
6-Chloro-2-{5-[1-(3,4-difluoro-phenyl)-1-hydroxy-ethyl]-pyridin-3-yl}-3,4-dihydro-2H-isoquinolin-1-one;
6-Chloro-2-{5-[1-(3,5-difluoro-phenyl)-1-hydroxy-ethyl]-pyridin-3-yl}-3,4-dihydro-2H-isoquinolin-1-one;
6-Chloro-2-(6-methyl-pyrazin-2-yl)-3,4-dihydro-2H-isoquinolin-1-one;
6-Chloro-2-[5-(morpholine-4-carbonyl)-pyridin-3-yl]-3,4-dihydro-2H-isoquinolin-1-one;
6-Chloro-2-[5-(3-hydroxy-pyrrolidine-1-carbonyl)-pyridin-3-yl]-3,4-dihydro-2H-isoquinolin-1-one;
5-(6-Chloro-1-oxo-3,4-dihydro-1H-isoquinolin-2-yl)-N,N-dimethyl-nicotinamide;
6-Chloro-2-[5-(pyrrolidine-1-carbonyl)-pyridin-3-yl]-3,4-dihydro-2H-isoquinolin-1-one;
5-(6-Chloro-1-oxo-3,4-dihydro-1H-isoquinolin-2-yl)-N-methyl-nicotinamide;
5-(6-Chloro-1-oxo-3,4-dihydro-1H-isoquinolin-2-yl)-N-cyclopropyl-nicotinamide;
5-(6-Chloro-1-oxo-3,4-dihydro-1H-isoquinolin-2-yl)-N-(4-fluoro-phenyl)-nicotinamide;
5-(6-Chloro-1-oxo-3,4-dihydro-1H-isoquinolin-2-yl)-N-phenyl-nicotinamide;
6-Chloro-2-[5-(4,4-difluoro-piperidine-1-carbonyl)-pyridin-3-yl]-3,4-dihydro-2H-isoquinolin-1-one;
6-Chloro-2-[5-((S)-2-methoxymethyl-pyrrolidin-1-ylmethyl)-pyridin-3-yl]-3,4-dihydro-2H-isoquinolin-1-one;
6-Chloro-2-[5-((S)-2-methoxymethyl-pyrrolidin-1-yl)-pyridin-3-yl]-3,4-dihydro-2H-isoquinolin-1-one;
6-Chloro-2-[5-((S)-2-hydroxymethyl-5-oxo-pyrrolidin-1-yl)-pyridin-3-yl]-3,4-dihydro-2H-isoquinolin-1-one;
6-Chloro-2-pyrimidin-5-yl-3,4-dihydro-2H-isoquinolin-1-one;
6-Chloro-2-pyridazin-3-yl-3,4-dihydro-2H-isoquinolin-1-one;
6-Chloro-2-pyridin-3-yl-2H-isoquinolin-1-one;
6-Chloro-2-(5-fluoro-pyridin-3-yl)-2H-isoquinolin-1-one;
6-Chloro-2-[4-(1-hydroxy-ethyl)-pyridin-3-yl]-3,4-dihydro-2H-isoquinolin-1-one;
6-Chloro-2-(4-hydroxymethyl-pyridin-3-yl)-3,4-dihydro-2H-isoquinolin-1-one;
2-[5-(1-Amino-cyclopropyl)-pyridin-3-yl]-6-chloro-3,4-dihydro-2H-isoquinolin-1-one;
6-Chloro-2-[5-(4-methyl-4H-[1,2,4]triazol-3-yl)-pyridin-3-yl]-3,4-dihydro-2H-isoquinolin-1-one;
6-Chloro-2-(5-methylsulfanyl-pyridin-3-yl)-3,4-dihydro-2H-isoquinolin-1-one;
6-Chloro-2-(5-difluoromethoxy-pyridin-3-yl)-3,4-dihydro-2H-isoquinolin-1-one;
6-Chloro-2-(4-dimethoxymethyl-pyridin-3-yl)-3,4-dihydro-2H-isoquinolin-1-one;
6-Chloro-2-[5-fluoro-4-(1-hydroxy-ethyl)-pyridin-3-yl]-3,4-dihydro-2H-isoquinolin-1-one;
6-Chloro-2-{4-[(4-fluoro-phenyl)-hydroxy-methyl]-pyridin-3-yl}-3,4-dihydro-2H-isoquinolin-1-one;
6-Chloro-2-[4-(1-methoxy-ethyl)-pyridin-3-yl]-3,4-dihydro-2H-isoquinolin-1-one;
6-Chloro-2-(1-methyl-1H-pyrrolo[3,2-c]pyridin-7-yl)-3,4-dihydro-2H-isoquinolin-1-one;
6-Chloro-2-(5-cyclopropyl-pyridin-3-yl)-3,4-dihydro-2H-isoquinolin-1-one;
6-Chloro-2-[5-(2-methyl-2H-[1,2,4]triazol-3-yl)-pyridin-3-yl]-3,4-dihydro-2H-isoquinolin-1-one;
6-Chloro-2-(5-cyclopropoxy-pyridin-3-yl)-3,4-dihydro-2H-isoquinolin-1-one;
6-Chloro-2-(4-methoxymethyl-pyridin-3-yl)-3,4-dihydro-2H-isoquinolin-1-one;
6-Chloro-2-[5-fluoro-4-(1-hydroxy-1-methyl-ethyl)-pyridin-3-yl]-3,4-dihydro-2H-isoquinolin-1-one;
6-Chloro-2-[5-(5-methyl-pyrazol-1-ylmethyl)-pyridin-3-yl]-3,4-dihydro-2H-isoquinolin-1-one;
6-Chloro-2-(1H-pyrrolo[3,2-c]pyridin-7-yl)-3,4-dihydro-2H-isoquinolin-1-one;
6-Chloro-3,4-dihydro-[2,4']biisoquinolinyl-1-one;
3-(6-Chloro-1-oxo-3,4-dihydro-1H-isoquinolin-2-yl)-isonicotinonitrile;
6-Chloro-2-(5-fluoro-4-methoxymethyl-pyridin-3-yl)-3,4-dihydro-2H-isoquinolin-1-one;

6-Chloro-2-[5-fluoro-4-(1-methoxy-ethyl)-pyridin-3-yl]-3,4-dihydro-2H-isoquinolin-1-one;
6-Chloro-2-(4-isopropoxymethyl-pyridin-3-yl)-3,4-dihydro-2H-isoquinolin-1-one;
6-Chloro-2-[4-(cyclopropyl-methoxy-methyl)-pyridin-3-yl]-3,4-dihydro-2H-isoquinolin-1-one;
6-Chloro-2-[5-(3,5-dimethyl-1H-pyrazol-4-yl)-pyridin-3-yl]-3,4-dihydro-2H-isoquinolin-1-one;
6-Chloro-2-[5-(3,5-dimethyl-3H-imidazol-4-yl)-pyridin-3-yl]-3,4-dihydro-2H-isoquinolin-1-one;
6-Chloro-2-[5-(1,1-dioxo-1λ6-[1,2]thiazinan-2-ylmethyl)-pyridin-3-yl]-3,4-dihydro-2H-isoquinolin-1-one;
6-Chloro-2-[5-(1,1-dioxo-1λ6-isothiazolidin-2-ylmethyl)-pyridin-3-yl]-3,4-dihydro-2H-isoquinolin-1-one;
6-Chloro-2-[5-((S)-2-hydroxymethyl-5-oxo-pyrrolidin-1-ylmethyl)-pyridin-3-yl]-3,4-dihydro-2H-isoquinolin-1-one;
(S)-1-[5-(6-Chloro-1-oxo-3,4-dihydro-1H-isoquinolin-2-yl)-pyridin-3-ylmethyl]-pyrrolidine-2-carboxylic acid methyl ester;
6-Chloro-2-(5-methoxy-pyridin-3-yl)-3-methyl-3,4-dihydro-2H-isoquinolin-1-one;
6-Chloro-2-(5-hydroxymethyl-pyridin-3-yl)-3-methyl-3,4-dihydro-2H-isoquinolin-1-one;
6-Chloro-2-[5-(2-isopropyl-imidazol-1-ylmethyl)-pyridin-3-yl]-3-methyl-3,4-dihydro-2H-isoquinolin-1-one;
6-Chloro-3-methyl-2-pyridin-3-yl-3,4-dihydro-2H-isoquinolin-1-one;
6-Chloro-2-(5-fluoro-pyridin-3-yl)-3-methyl-3,4-dihydro-2H-isoquinolin-1-one;
6-Chloro-3-methyl-2-pyrimidin-5-yl-3,4-dihydro-2H-isoquinolin-1-one;
(R)-6-Chloro-3-methyl-2-pyridin-3-yl-3,4-dihydro-2H-isoquinolin-1-one;
(S)-6-Chloro-3-methyl-2-pyridin-3-yl-3,4-dihydro-2H-isoquinolin-1-one;
8-Chloro-3-methyl-2-pyridin-3-yl-3,4-dihydro-2H-isoquinolin-1-one;
6-Methoxy-2-pyridin-3-yl-3,4-dihydro-2H-isoquinolin-1-one;
5,6-Dichloro-2-pyridin-3-yl-3,4-dihydro-2H-isoquinolin-1-one;
2-Chloro-6-(5-methoxy-pyridin-3-yl)-7,8-dihydro-6H-[1,6]naphthyridin-5-one;
2-Methoxy-6-(5-methoxy-pyridin-3-yl)-7,8-dihydro-6H-[1,6]naphthyridin-5-one;
2-Methoxy-6-pyridin-3-yl-7,8-dihydro-6H-[1,6]naphthyridin-5-one;
6-Chloro-5-fluoro-2-(5-methoxy-pyridin-3-yl)-3,4-dihydro-2H-isoquinolin-1-one;
6-Chloro-7-fluoro-2-(5-methoxy-pyridin-3-yl)-3,4-dihydro-2H-isoquinolin-1-one;
6-Chloro-7-fluoro-2-pyridin-3-yl-3,4-dihydro-2H-isoquinolin-1-one;
6-Chloro-4,4-dimethyl-2-pyridin-3-yl-3,4-dihydro-2H-isoquinolin-1-one;
6-Chloro-2-(5-methoxy-pyridin-3-yl)-4,4-dimethyl-3,4-dihydro-2H-isoquinolin-1-one;
6-Chloro-2-(5-fluoro-pyridin-3-yl)-4,4-dimethyl-3,4-dihydro-2H-isoquinolin-1-one;
6-Chloro-4-methyl-2-pyridin-3-yl-3,4-dihydro-2H-isoquinolin-1-one;
6-Chloro-2-(5-fluoro-pyridin-3-yl)-4-methyl-3,4-dihydro-2H-isoquinolin-1-one;
6-Chloro-2-(5-methoxy-pyridin-3-yl)-4-methyl-3,4-dihydro-2H-isoquinolin-1-one;
5-Chloro-2-pyridin-3-yl-2,3-dihydro-isoindol-1-one;
5-Chloro-2-[5-(2-isopropyl-imidazol-1-ylmethyl)-pyridin-3-yl]-2,3-dihydro-isoindol-1-one;
5-Chloro-2-(5-[1,2,4]triazol-1-ylmethyl-pyridin-3-yl)-2,3-dihydro-isoindol-1-one;
5-Chloro-2-[5-(2-methyl-imidazol-1-ylmethyl)-pyridin-3-yl]-2,3-dihydro-isoindol-1-one;
5-Chloro-2-[5-(2-oxo-pyrrolidin-1-ylmethyl)-pyridin-3-yl]-2,3-dihydro-isoindol-1-one;
5-Chloro-2-[5-((S)-2-methoxymethyl-pyrrolidin-1-ylmethyl)-pyridin-3-yl]-2,3-dihydro-isoindol-1-one;
5-Chloro-2-[5-(2-oxo-piperidin-1-ylmethyl)-pyridin-3-yl]-2,3-dihydro-isoindol-1-one; Ethanesulfonic acid [5-(5-chloro-1-oxo-1,3-dihydro-isoindol-2-yl)-pyridin-3-ylmethyl]-amide;
5-Chloro-2-(1-methyl-1H-pyrazolo[3,4-c]pyridin-4-yl)-2,3-dihydro-isoindol-1-one;
5-Chloro-2-(8-hydroxy-5,6,7,8-tetrahydro-isoquinolin-4-yl)-2,3-dihydro-isoindol-1-one;
5-Chloro-3-methyl-2-pyridin-3-yl-2,3-dihydro-isoindol-1-one;
6-Chloro-3-methyl-2-pyridin-3-yl-2,3-dihydro-isoindol-1-one;
5-Chloro-2-(5-methoxy-pyridin-3-yl)-3-methyl-2,3-dihydro-isoindol-1-one;
5-Chloro-3-methyl-2-(4-methyl-pyridin-3-yl)-2,3-dihydro-isoindol-1-one;
5-Chloro-2-[5-(1-hydroxy-ethyl)-pyridin-3-yl]-3-methyl-2,3-dihydro-isoindol-1-one;
5-Chloro-2-(5-fluoro-pyridin-3-yl)-3-methyl-2,3-dihydro-isoindol-1-one;
3-Benzyl-5-chloro-2-pyridin-3-yl-2,3-dihydro-isoindol-1-one;
5-Chloro-3-ethyl-2-pyridin-3-yl-2,3-dihydro-isoindol-1-one;
5-Chloro-3-ethyl-2-(5-fluoro-pyridin-3-yl)-2,3-dihydro-isoindol-1-one;
5-Chloro-3-ethyl-2-(5-methoxy-pyridin-3-yl)-2,3-dihydro-isoindol-1-one;
5-Chloro-3,3-dimethyl-2-pyridin-3-yl-2,3-dihydro-isoindol-1-one;
5-Chloro-2-(5-fluoro-pyridin-3-yl)-3,3-dimethyl-2,3-dihydro-isoindol-1-one;
5-Chloro-2-(5-methoxy-pyridin-3-yl)-3,3-dimethyl-2,3-dihydro-isoindol-1-one;
5-Chloro-2-(5-difluoromethoxy-pyridin-3-yl)-3,3-dimethyl-2,3-dihydro-isoindol-1-one;
5-Chloro-2-[5-(1-hydroxy-ethyl)-pyridin-3-yl]-3,3-dimethyl-2,3-dihydro-isoindol-1-one;
5-Chloro-2-(5-hydroxymethyl-pyridin-3-yl)-3,3-dimethyl-2,3-dihydro-isoindol-1-one;
5-Chloro-3,3-dimethyl-2-[5-(2-methyl-imidazol-1-ylmethyl)-pyridin-3-yl]-2,3-dihydro-isoindol-1-one;
6-Chloro-2-[5-((S)-2-hydroxymethyl-pyrrolidin-1-yl)-pyridin-3-yl]-3,4-dihydro-2H-isoquinolin-1-one;
5-Chloro-2-[5-((S)-2-hydroxymethyl-pyrrolidin-1-yl)-pyridin-3-yl]-2,3-dihydro-isoindol-1-one;
6-Chloro-2-[5-((R)-3-hydroxy-pyrrolidin-1-yl)-pyridin-3-yl]-3,4-dihydro-2H-isoquinolin-1-one;
5-Chloro-2-[5-((R)-3-hydroxy-pyrrolidin-1-yl)-pyridin-3-yl]-2,3-dihydro-isoindol-1-one;
2-Hydroxy-6-(5-methoxy-pyridin-3-yl)-7,8-dihydro-6H-[1,6]naphthyridin-5-one;
6-Chloro-2-(5-imidazol-1-ylmethyl-pyridin-3-yl)-3,4-dihydro-2H-isoquinolin-1-one;
6-Chloro-2-[5-(2-isopropyl-imidazol-1-ylmethyl)-pyridin-3-yl]-3,4-dihydro-2H-isoquinolin-1-one;

6-Chloro-2-[5-(2-methyl-imidazol-1-ylmethyl)-pyridin-3-yl]-3,4-dihydro-2H-isoquinolin-1-one;
6-Chloro-2-[5-(2-ethyl-4-methyl-imidazol-1-ylmethyl)-pyridin-3-yl]-3,4-dihydro-2H-isoquinolin-1-one;
6-Chloro-2-[5-(3-hydroxy-piperidin-1-ylmethyl)-pyridin-3-yl]-3,4-dihydro-2H-isoquinolin-1-one;
Propane-2-sulfonic acid [5-(6-chloro-1-oxo-3,4-dihydro-1H-isoquinolin-2-yl)-pyridin-3-ylmethyl]-amide
6-Chloro-2-[5-(3-hydroxy-pyrrolidin-1-ylmethyl)-pyridin-3-yl]-3,4-dihydro-2H-isoquinolin-1-one;
6-Chloro-2-[5-((R)-3-hydroxy-pyrrolidin-1-ylmethyl)-pyridin-3-yl]-3,4-dihydro-2H-isoquinolin-1-one;
6-Chloro-2-[5-((S)-3-hydroxy-pyrrolidin-1-ylmethyl)-pyridin-3-yl]-3,4-dihydro-2H-isoquinolin-1-one;
6-Chloro-2-[5-((S)-2-hydroxymethyl-pyrrolidin-1-ylmethyl)-pyridin-3-yl]-3,4-dihydro-2H-isoquinolin-1-one;
6-Chloro-2-[5-((R)-2-hydroxymethyl-pyrrolidin-1-ylmethyl)-pyridin-3-yl]-3,4-dihydro-2H-isoquinolin-1-one;
6-Chloro-2-[5-(3,5-dimethyl-pyrazol-1-ylmethyl)-pyridin-3-yl]-3,4-dihydro-2H-isoquinolin-1-one;
N-[5-(6-Chloro-1-oxo-3,4-dihydro-1H-isoquinolin-2-yl)-pyridin-3-ylmethyl]-methanesulfonamide
N-[5-(6-Chloro-1-oxo-3,4-dihydro-1H-isoquinolin-2-yl)-pyridin-3-ylmethyl]-acetamide
6-Chloro-2-(5-morpholin-4-ylmethyl-pyridin-3-yl)-3,4-dihydro-2H-isoquinolin-1-one;
6-Chloro-2-[5-(2-oxo-pyrrolidin-1-ylmethyl)-pyridin-3-yl]-3,4-dihydro-2H-isoquinolin-1-one;
6-Chloro-2-[5-(1,1-dioxo-1λ6-thiomorpholin-4-ylmethyl)-pyridin-3-yl]-3,4-dihydro-2H-isoquinolin-1-one;
6-Chloro-2-[5-(2-oxo-oxazolidin-3-ylmethyl)-pyridin-3-yl]-3,4-dihydro-2H-isoquinolin-1-one;
6-Chloro-2-[5-(2-oxo-imidazolidin-1-ylmethyl)-pyridin-3-yl]-3,4-dihydro-2H-isoquinolin-1-one;
6-Chloro-2-[5-(3-methyl-2-oxo-imidazolidin-1-ylmethyl)-pyridin-3-yl]-3,4-dihydro-2H-isoquinolin-1-one;
6-Chloro-2-(5-pyrazol-1-ylmethyl-pyridin-3-yl)-3,4-dihydro-2H-isoquinolin-1-one;
6-Chloro-2-[5-(2-propyl-imidazol-1-ylmethyl)-pyridin-3-yl]-3,4-dihydro-2H-isoquinolin-1-one;
1-[5-(6-Chloro-1-oxo-3,4-dihydro-1H-isoquinolin-2-yl)-pyridin-3-ylmethyl]-1H-imidazole-2-carboxylic acid ethyl ester;
6-Chloro-2-[5-(2-hydroxymethyl-imidazol-1-ylmethyl)-pyridin-3-yl]-3,4-dihydro-2H-isoquinolin-1-one;
6-Chloro-2-[5-(oxetan-3-ylaminomethyl)-pyridin-3-yl]-3,4-dihydro-2H-isoquinolin-1-one;
6-Chloro-2-{5-[4-(2-hydroxy-ethyl)-piperazin-1-ylmethyl]-pyridin-3-yl}-3,4-dihydro-2H-isoquinolin-1-one;
6-Chloro-2-[5-(4-isopropyl-piperazin-1-ylmethyl)-pyridin-3-yl]-3,4-dihydro-2H-isoquinolin-1-one;
6-Chloro-2-[5-(4-methyl-piperazin-1-ylmethyl)-pyridin-3-yl]-3,4-dihydro-2H-isoquinolin-1-one;
6-Chloro-2-[5-(4,4-difluoro-piperidin-1-ylmethyl)-pyridin-3-yl]-3,4-dihydro-2H-isoquinolin-1-one;
6-Chloro-2-[5-(3,3-difluoro-pyrrolidin-1-ylmethyl)-pyridin-3-yl]-3,4-dihydro-2H-isoquinolin-1-one;
6-Chloro-2-[5-(2-oxa-6-aza-spiro[3.4]oct-6-ylmethyl)-pyridin-3-yl]-3,4-dihydro-2H-isoquinolin-1-one;
6-Chloro-2-[5-(2-oxa-6-aza-spiro[3.3]hept-6-ylmethyl)-pyridin-3-yl]-3,4-dihydro-2H-isoquinolin-1-one;
6-Chloro-2-[5-(3,3-difluoro-piperidin-1-ylmethyl)-pyridin-3-yl]-3,4-dihydro-2H-isoquinolin-1-one;
6-Chloro-2-[5-(2-oxo-piperidin-1-ylmethyl)-pyridin-3-yl]-3,4-dihydro-2H-isoquinolin-1-one;
6-Chloro-2-(5-[1,2,3]triazol-2-ylmethyl-pyridin-3-yl)-3,4-dihydro-2H-isoquinolin-1-one;
6-Chloro-2-(5-[1,2,3]triazol-1-ylmethyl-pyridin-3-yl)-3,4-dihydro-2H-isoquinolin-1-one;
6-Chloro-2-[5-(2-chloro-imidazol-1-ylmethyl)-pyridin-3-yl]-3,4-dihydro-2H-isoquinolin-1-one;
6-Chloro-2-[5-(3-methyl-[1,2,4]triazol-4-ylmethyl)-pyridin-3-yl]-3,4-dihydro-2H-isoquinolin-1-one;
6-Chloro-2-[5-(5-methyl-[1,2,4]triazol-1-ylmethyl)-pyridin-3-yl]-3,4-dihydro-2H-isoquinolin-1-one;
6-chloro-2-[5-(3-methyl-[1,2,4]triazol-1-ylmethyl)-pyridin-3-yl]-3,4-dihydro-2H-isoquinolin-1-one;
6-Chloro-2-(5-[1,2,4]triazol-4-ylmethyl-pyridin-3-yl)-3,4-dihydro-2H-isoquinolin-1-one;
6-Chloro-2-(5-[1,2,4]triazol-1-ylmethyl-pyridin-3-yl)-3,4-dihydro-2H-isoquinolin-1-one;
6-Chloro-2-[5-(2-methyl-benzoimidazol-1-ylmethyl)-pyridin-3-yl]-3,4-dihydro-2H-isoquinolin-1-one;
6-Chloro-2-(5-indazol-1-ylmethyl-pyridin-3-yl)-3,4-dihydro-2H-isoquinolin-1-one;
6-Chloro-2-(5-indazol-2-ylmethyl-pyridin-3-yl)-3,4-dihydro-2H-isoquinolin-1-one;
6-Chloro-2-[5-(6-fluoro-indol-1-ylmethyl)-pyridin-3-yl]-3,4-dihydro-2H-isoquinolin-1-one;
6-Chloro-2-[5-(7-fluoro-indol-1-ylmethyl)-pyridin-3-yl]-3,4-dihydro-2H-isoquinolin-1-one;
6-Chloro-2-[5-(4-fluoro-indol-1-ylmethyl)-pyridin-3-yl]-3,4-dihydro-2H-isoquinolin-1-one;
6-Chloro-2-[5-(4-methyl-pyrazol-1-ylmethyl)-pyridin-3-yl]-3,4-dihydro-2H-isoquinolin-1-one;
6-Chloro-2-[5-(2-cyclopropyl-imidazol-1-ylmethyl)-pyridin-3-yl]-3,4-dihydro-2H-isoquinolin-1-one;
6-Chloro-2-[5-(2-trifluoromethyl-imidazol-1-ylmethyl)-pyridin-3-yl]-3,4-dihydro-2H-isoquinolin-1-one;
6-Chloro-2-[5-(3-methyl-pyrazol-1-ylmethyl)-pyridin-3-yl]-3,4-dihydro-2H-isoquinolin-1-one;
6-Chloro-2-[5-(2-ethyl-imidazol-1-ylmethyl)-pyridin-3-yl]-3,4-dihydro-2H-isoquinolin-1-one;
2-(5-Aminomethyl-pyridin-3-yl)-6-chloro-3,4-dihydro-2H-isoquinolin-1-one;
6-Chloro-2-(5-methoxymethyl-pyridin-3-yl)-3,4-dihydro-2H-isoquinolin-1-one;
6-Chloro-2-(5-isopropoxymethyl-pyridin-3-yl)-3,4-dihydro-2H-isoquinolin-1-one;
6-Chloro-2-[5-(2,2,2-trifluoro-1-methyl-ethoxymethyl)-pyridin-3-yl]-3,4-dihydro-2H-isoquinolin-1-one;
6-Chloro-2-{5-[2-(1-methyl-pyrrolidin-2-yl)-ethoxymethyl]-pyridin-3-yl}-3,4-dihydro-2H-isoquinolin-1-one;
6-Chloro-2-(5-cyclopentyloxymethyl-pyridin-3-yl)-3,4-dihydro-2H-isoquinolin-1-one;
6-Chloro-2-(5-cyclopropylmethoxymethyl-pyridin-3-yl)-3,4-dihydro-2H-isoquinolin-1-one;
6-Chloro-2-[5-(2-fluoro-phenoxymethyl)-pyridin-3-yl]-3,4-dihydro-2H-isoquinolin-1-one;
6-Chloro-2-[5-(1-methyl-cyclopropylmethoxymethyl)-pyridin-3-yl]-3,4-dihydro-2H-isoquinolin-1-one;
6-Chloro-2-[5-(tetrahydro-furan-2-ylmethoxymethyl)-pyridin-3-yl]-3,4-dihydro-2H-isoquinolin-1-one;
6-Chloro-2-[5-(2,2,2-trifluoro-ethoxymethyl)-pyridin-3-yl]-3,4-dihydro-2H-isoquinolin-1-one;
6-Chloro-2-(5-cyclobutoxymethyl-pyridin-3-yl)-3,4-dihydro-2H-isoquinolin-1-one;
6-Chloro-2-[5-(3,5-dimethyl-isoxazol-4-ylmethyl)-pyridin-3-yl]-3,4-dihydro-2H-isoquinolin-1-one;
6-Chloro-2-[5-(4-methanesulfonyl-benzyl)-pyridin-3-yl]-3,4-dihydro-2H-isoquinolin-1-one;
6-Chloro-2-[5-(6-methyl-pyridin-3-ylmethyl)-pyridin-3-yl]-3,4-dihydro-2H-isoquinolin-1-one;

6-Chloro-2-[5-(6-morpholin-4-yl-pyridin-3-ylmethyl)-pyridin-3-yl]-3,4-dihydro-2H-isoquinolin-1-one;
6-Chloro-2-[5-(2-methyl-2H-pyrazol-3-ylmethyl)-pyridin-3-yl]-3,4-dihydro-2H-isoquinolin-1-one;
6-Chloro-2-[5-(1-methyl-1H-pyrazol-4-ylmethyl)-pyridin-3-yl]-3,4-dihydro-2H-isoquinolin-1-one;
6-Chloro-2-[5-(2,3-difluoro-benzyl)-pyridin-3-yl]-3,4-dihydro-2H-isoquinolin-1-one;
6-Chloro-2-[5-(3,5-difluoro-benzyl)-pyridin-3-yl]-3,4-dihydro-2H-isoquinolin-1-one;
6-Chloro-2-[5-(2,5-difluoro-benzyl)-pyridin-3-yl]-3,4-dihydro-2H-isoquinolin-1-one;
6-Chloro-2-[5-(2-trifluoromethyl-benzyl)-pyridin-3-yl]-3,4-dihydro-2H-isoquinolin-1-one;
6-Chloro-2-[5-(2,6-dichloro-benzyl)-pyridin-3-yl]-3,4-dihydro-2H-isoquinolin-1-one;
6-Chloro-2-[5-(2-chloro-6-fluoro-benzyl)-pyridin-3-yl]-3,4-dihydro-2H-isoquinolin-1-one;
6-Chloro-2-[5-(3,4-dichloro-benzyl)-pyridin-3-yl]-3,4-dihydro-2H-isoquinolin-1-one;
6-Chloro-2-[5-(2,5-dichloro-benzyl)-pyridin-3-yl]-3,4-dihydro-2H-isoquinolin-1-one; Ethanesulfonic acid [5-(6-chloro-1-oxo-3,4-dihydro-1H-isoquinolin-2-yl)-pyridin-3-yl]-amide;
N-[5-(6-Chloro-1-oxo-3,4-dihydro-1H-isoquinolin-2-yl)-pyridin-3-yl]-benzenesulfonamide;
N-[5-(6-Chloro-1-oxo-3,4-dihydro-1H-isoquinolin-2-yl)-pyridin-3-yl]-methanesulfonamide;
Cyclopropanesulfonic acid [5-(6-chloro-1-oxo-3,4-dihydro-1H-isoquinolin-2-yl)-pyridin-3-yl]-amide;
6-Chloro-2-[5-(4-fluoro-benzylamino)-pyridin-3-yl]-3,4-dihydro-2H-isoquinolin-1-one;
6-Chloro-2-[5-(2,2,2-trifluoro-ethylamino)-pyridin-3-yl]-3,4-dihydro-2H-isoquinolin-1-one;
6-Chloro-2-(5-morpholin-4-yl-pyridin-3-yl)-3,4-dihydro-2H-isoquinolin-1-one;
N-[5-(6-Chloro-1-oxo-3,4-dihydro-1H-isoquinolin-2-yl)-pyridin-3-yl]-propionamide;
6-Chloro-2-{5-[(2-methyl-2H-pyrazol-3-ylmethyl)-amino]-pyridin-3-yl}-3,4-dihydro-2H-isoquinolin-1-one;
2-[5-(6-Chloro-1-oxo-3,4-dihydro-1H-isoquinolin-2-yl)-pyridin-3-ylamino]-2-methyl-propionic acid;
6-Chloro-2-{5-[(1-methyl-1H-imidazol-4-ylmethyl)-amino]-pyridin-3-yl}-3,4-dihydro-2H-isoquinolin-1-one;
6-Chloro-2-[5-(1H-pyrazol-4-yl)-pyridin-3-yl]-3,4-dihydro-2H-isoquinolin-1-one;
6-Chloro-2-[5-(3,5-dimethyl-isoxazol-4-yl)-pyridin-3-yl]-3,4-dihydro-2H-isoquinolin-1-one;
6-Chloro-2-[5-(3-fluoro-phenyl)-pyridin-3-yl]-3,4-dihydro-2H-isoquinolin-1-one;
6-Chloro-2-[5-(3,4-difluoro-phenyl)-pyridin-3-yl]-3,4-dihydro-2H-isoquinolin-1-one;
6-Chloro-2-[5-(3,5-difluoro-phenyl)-pyridin-3-yl]-3,4-dihydro-2H-isoquinolin-1-one;
6-Chloro-2-[5-(3-chloro-phenyl)-pyridin-3-yl]-3,4-dihydro-2H-isoquinolin-1-one;
6-Chloro-2-[5-(2,5-difluoro-phenyl)-pyridin-3-yl]-3,4-dihydro-2H-isoquinolin-1-one;
6-Chloro-2-[5-(3-trifluoromethyl-phenyl)-pyridin-3-yl]-3,4-dihydro-2H-isoquinolin-1-one;
6-Chloro-2-[5-(3-trifluoromethoxy-phenyl)-pyridin-3-yl]-3,4-dihydro-2H-isoquinolin-1-one;
6-Chloro-2-[5-(2-methyl-2H-pyrazol-3-yl)-pyridin-3-yl]-3,4-dihydro-2H-isoquinolin-1-one;
6-Chloro-2-[5-(1-methyl-1H-pyrazol-4-yl)-pyridin-3-yl]-3,4-dihydro-2H-isoquinolin-1-one;
6-Chloro-2-[5-(4-chloro-3-fluoro-phenyl)-pyridin-3-yl]-3,4-dihydro-2H-isoquinolin-1-one;
6-Chloro-2-[5-(3,4-dichloro-phenyl)-pyridin-3-yl]-3,4-dihydro-2H-isoquinolin-1-one;
6-Chloro-2-[5-(2-trifluoromethyl-phenyl)-pyridin-3-yl]-3,4-dihydro-2H-isoquinolin-1-one;
6-Chloro-2-(5-isoxazol-4-yl-pyridin-3-yl)-3,4-dihydro-2H-isoquinolin-1-one;
6-Chloro-2-[5-(1-methyl-1H-imidazol-2-yl)-pyridin-3-yl]-3,4-dihydro-2H-isoquinolin-1-one;
6-Chloro-2-[5-(2,4-dimethyl-2H-pyrazol-3-yl)-pyridin-3-yl]-3,4-dihydro-2H-isoquinolin-1-one;
5-[5-(6-Chloro-1-oxo-3,4-dihydro-1H-isoquinolin-2-yl)-pyridin-3-yl]-1-methyl-1H-pyrazole-4-carbonitrile
N-[5-(6-Chloro-1-oxo-3,4-dihydro-1H-isoquinolin-2-yl)-pyridin-3-yl]-isobutyramide
Cyclopropanecarboxylic acid [5-(6-chloro-1-oxo-3,4-dihydro-1H-isoquinolin-2-yl)-pyridin-3-yl]-amide
N-[5-(6-Chloro-1-oxo-3,4-dihydro-1H-isoquinolin-2-yl)-pyridin-3-yl]-4-fluoro-benzamide
1-[5-(6-Chloro-1-oxo-3,4-dihydro-1H-isoquinolin-2-yl)-pyridin-3-yl]-3-cyclohexyl-urea
1-[5-(6-Chloro-1-oxo-3,4-dihydro-1H-isoquinolin-2-yl)-pyridin-3-yl]-3-(3-trifluoromethyl-phenyl)-urea
6-Chloro-2-(5-hydroxy-pyridin-3-yl)-3,4-dihydro-2H-isoquinolin-1-one;
2-[5-(6-Chloro-1-oxo-3,4-dihydro-1H-isoquinolin-2-yl)-pyridin-3-yloxy]-acetamide;
2-[5-(6-Chloro-1-oxo-3,4-dihydro-1H-isoquinolin-2-yl)-pyridin-3-yloxy]-N-methyl-acetamide;
[5-(6-Chloro-1-oxo-3,4-dihydro-1H-isoquinolin-2-yl)-pyridin-3-yloxy]-acetic acid methyl ester;
2-[5-(6-Chloro-1-oxo-3,4-dihydro-1H-isoquinolin-2-yl)-pyridin-3-yloxy]-N,N-dimethyl-acetamide;
6-Chloro-2-(5-phenylaminomethyl-pyridin-3-yl)-3,4-dihydro-2H-isoquinolin-1-one;
6-Chloro-2-{5-[(4-fluoro-phenylamino)-methyl]-pyridin-3-yl}-3,4-dihydro-2H-isoquinolin-1-one;
6-Chloro-2-{5-[(3-fluoro-phenylamino)-methyl]-pyridin-3-yl}-3,4-dihydro-2H-isoquinolin-1-one;
6-Chloro-2-{5-[(4-chloro-phenylamino)-methyl]-pyridin-3-yl}-3,4-dihydro-2H-isoquinolin-1-one;
6-Chloro-2-{5-[(3-chloro-phenylamino)-methyl]-pyridin-3-yl}-3,4-dihydro-2H-isoquinolin-1-one;
6-Chloro-2-{5-[(1H-pyrazol-3-ylamino)-methyl]-pyridin-3-yl}-3,4-dihydro-2H-isoquinolin-1-one;
6-Chloro-2-[5-(2-morpholin-4-yl-2-oxo-ethyl)-pyridin-3-yl]-3,4-dihydro-2H-isoquinolin-1-one;
2-[5-(6-Chloro-1-oxo-3,4-dihydro-1H-isoquinolin-2-yl)-pyridin-3-yl]-N-(2-hydroxy-ethyl)-acetamide;
6-Chloro-2-[5-(1-methylamino-ethyl)-pyridin-3-yl]-3,4-dihydro-2H-isoquinolin-1-one;
6-Chloro-2-[5-(1-dimethylamino-ethyl)-pyridin-3-yl]-3,4-dihydro-2H-isoquinolin-1-one;
6-Chloro-2-[5-(1-methyl-1H-imidazole-2-carbonyl)-pyridin-3-yl]-3,4-dihydro-2H-isoquinolin-1-one;
6-Chloro-2-[5-(4-methyl-4H-[1,2,4]triazol-3-ylmethyl)-pyridin-3-yl]-3,4-dihydro-2H-isoquinolin-1-one;
6-Chloro-2-[5-(1-[1,2,3]triazol-2-yl-ethyl)-pyridin-3-yl]-3,4-dihydro-2H-isoquinolin-1-one;
6-Chloro-2-[5-(1-imidazol-1-yl-ethyl)-pyridin-3-yl]-3,4-dihydro-2H-isoquinolin-1-one;
6-Chloro-2-[5-(1-pyrazol-1-yl-ethyl)-pyridin-3-yl]-3,4-dihydro-2H-isoquinolin-1-one;
6-Chloro-2-{5-[1-(oxazol-2-ylamino)-ethyl]-pyridin-3-yl}-3,4-dihydro-2H-isoquinolin-1-one;

6-Chloro-2-[5-(1-[1,2,4]triazol-1-yl-ethyl)-pyridin-3-yl]-3,4-dihydro-2H-isoquinolin-1-one;
6-Chloro-2-{5-[1-(2-oxo-pyrrolidin-1-yl)-ethyl]-pyridin-3-yl}-3,4-dihydro-2H-isoquinolin-1-one;
6-Chloro-2-{5-[1-(2-oxo-oxazolidin-3-yl)-ethyl]-pyridin-3-yl}-3,4-dihydro-2H-isoquinolin-1-one;
N-{1-[5-(6-Chloro-1-oxo-3,4-dihydro-1H-isoquinolin-2-yl)-pyridin-3-yl]-ethyl}-methanesulfonamide;
6-Chloro-2-{5-[1-(3-fluoro-phenylamino)-ethyl]-pyridin-3-yl}-3,4-dihydro-2H-isoquinolin-1-one;
6-Chloro-2-[5-(1-phenylamino-ethyl)-pyridin-3-yl]-3,4-dihydro-2H-isoquinolin-1-one;
6-Chloro-2-(5-methanesulfinyl-pyridin-3-yl)-3,4-dihydro-2H-isoquinolin-1-one;
6-Chloro-2-[4-(4-methyl-piperazin-1-ylmethyl)-pyridin-3-yl]-3,4-dihydro-2H-isoquinolin-1-one;
and pharmaceutically acceptable salts thereof.

Also particular examples of compounds of formula (I) as described herein are selected from the group consisting of
5-Chloro-3,3-dimethyl-2-[5-(1-methyl-1H-pyrazol-4-ylmethyl)-pyridin-3-yl]-2,3-dihydro-isoindol-1-one;
5-Chloro-2-(5-difluoromethoxy-pyridin-3-yl)-3-ethyl-2,3-dihydro-isoindol-1-one;
5-Chloro-3-ethyl-2-[5-(1-hydroxy-ethyl)-pyridin-3-yl]-2,3-dihydro-isoindol-1-one;
5-Chloro-2-(4-chloro-pyridin-3-yl)-3-ethyl-2,3-dihydro-isoindol-1-one;
5-Chloro-2-(4-chloro-pyridin-3-yl)-3,3-dimethyl-2,3-dihydro-isoindol-1-one;
6-Chloro-5'-nitro-3,4-dihydro-[2,4']biisoquinolinyl-1-one;
6-Chloro-8'-nitro-3,4-dihydro-[2,4']biisoquinolinyl-1-one;
8'-Amino-6-chloro-3,4-dihydro-[2,4']biisoquinolinyl-1-one;
Ethanesulfonic acid (6-chloro-1-oxo-3,4-dihydro-1H-[2,4']biisoquinolinyl-8'-yl)-amide;
6'-Chloro-2'-(5-fluoropyridin-3-yl)spiro[cyclopropane-1,1'-isoindol]-3'(2'H)-one;
6'-Chloro-2'-[5-(difluoromethoxy)pyridin-3-yl]spiro[cyclopropane-1,1'-isoindol]-3'(2'H)-one;
2-Chloro-6-(5-fluoro-pyridin-3-yl)-7,7-dimethyl-6,7-dihydro-pyrrolo[3,4-b]pyridin-5-one;
2-Chloro-6-(5-difluoromethoxy-pyridin-3-yl)-7,7-dimethyl-6,7-dihydro-pyrrolo[3,4-b]pyridin-5-one;
6-(5-Fluoro-pyridin-3-yl)-2-methoxy-7,7-dimethyl-6,7-dihydro-pyrrolo[3,4-b]pyridin-5-one;
6-(5-Difluoromethoxy-pyridin-3-yl)-2-methoxy-7,7-dimethyl-6,7-dihydro-pyrrolo[3,4-b]pyridin-5-one;
6'-Chloro-2'-(pyridin-3-yl)spiro[cyclopropane-1,1'-isoindol]-3'(2'H)-one;
5-Chloro-3-cyclopropyl-2-(5-fluoro-pyridin-3-yl)-2,3-dihydro-isoindol-1-one;
2-Chloro-7,7-dimethyl-6-pyridin-3-yl-6,7-dihydro-pyrrolo[3,4-b]pyridin-5-one;
2-Ethoxy-6-(5-fluoro-pyridin-3-yl)-7,7-dimethyl-6,7-dihydro-pyrrolo[3,4-b]pyridin-5-one;
2-Methoxy-7,7-dimethyl-6-pyridin-3-yl-6,7-dihydro-pyrrolo[3,4-b]pyridin-5-one;
5-Chloro-3-cyclopropyl-2-pyridin-3-yl-2,3-dihydro-isoindol-1-one;
5-Chloro-3-cyclopropyl-2-(5-difluoromethoxy-pyridin-3-yl)-2,3-dihydro-isoindol-1-one;
6-(5-Difluoromethoxy-pyridin-3-yl)-2-ethoxy-7,7-dimethyl-6,7-dihydro-pyrrolo[3,4-b]pyridin-5-one;
5-Chloro-2-(5-isopropoxy-pyridin-3-yl)-3,3-dimethyl-2,3-dihydro-isoindol-1-one;
6'-Chloro-2'-(4-chloropyridin-3-yl)spiro[cyclopropane-1,1'-isoindol]-3'(2'H)-one;
5-Chloro-2-(5-cyclopropoxy-pyridin-3-yl)-3,3-dimethyl-2,3-dihydro-isoindol-1-one;
(S or R)-6-Chloro-3-ethyl-2-(5-fluoro-pyridin-3-yl)-2,3-dihydro-isoindol-1-one;
(R or S)-6-Chloro-3-ethyl-2-(5-fluoro-pyridin-3-yl)-2,3-dihydro-isoindol-1-one;
(R or S)-5-Chloro-3-ethyl-2-(5-fluoro-pyridin-3-yl)-2,3-dihydro-isoindol-1-one;
(S or R)-5-Chloro-3-ethyl-2-(5-fluoro-pyridin-3-yl)-2,3-dihydro-isoindol-1-one;
2-(8-Amino-5,6,7,8-tetrahydro-isoquinolin-4-yl)-5-chloro-2,3-dihydro-isoindol-1-one;
N—[(R or S)-4-((R or S)-5-Chloro-1-ethyl-3-oxo-1,3-dihydro-isoindol-2-yl)-5,6,7,8-tetrahydro-isoquinolin-8-yl]-propionamide;
N—[(R or S)-4-((S or R)-5-Chloro-1-ethyl-3-oxo-1,3-dihydro-isoindol-2-yl)-5,6,7,8-tetrahydro-isoquinolin-8-yl]-propionamide;
N—[(R or S)-4-(5-Chloro-1-oxo-1,3-dihydro-isoindol-2-yl)-5,6,7,8-tetrahydro-isoquinolin-8-yl]-propionamide;
Ethanesulfonic acid [4-(5-chloro-1-oxo-1,3-dihydro-isoindol-2-yl)-5,6,7,8-tetrahydro-isoquinolin-8-yl]-amide;
Ethanesulfonic acid [(R or S)-4-(5-chloro-1-oxo-1,3-dihydro-isoindol-2-yl)-5,6,7,8-tetrahydro-isoquinolin-8-yl]-amide;
Ethanesulfonic acid [(S or R)-4-(5-chloro-1-oxo-1,3-dihydro-isoindol-2-yl)-5,6,7,8-tetrahydro-isoquinolin-8-yl]-amide;
N—[(S or R)-4-(5-Chloro-1-oxo-1,3-dihydro-isoindol-2-yl)-6,7-dihydro-5H-[2]pyrindin-7-yl]-acetamide;
N—[(R or S)-4-(5-Chloro-1-oxo-1,3-dihydro-isoindol-2-yl)-6,7-dihydro-5H-[2]pyrindin-7-yl]-acetamide;
N—((R or S)-6-Chloro-1-oxo-3,4,5',6',7',8'-hexahydro-1H-[2,4']biisoquinolinyl-8'-yl)-acetamide;
N—((S or R)-6-Chloro-1-oxo-3,4,5',6',7',8'-hexahydro-1H-[2,4']biisoquinolinyl-8'-yl)-acetamide;
N—[(S or R)-4-(5-Chloro-1-oxo-1,3-dihydro-isoindol-2-yl)-5,6,7,8-tetrahydro-isoquinolin-8-yl]-acetamide;
N—[(R or S)-4-(5-Chloro-1-oxo-1,3-dihydro-isoindol-2-yl)-5,6,7,8-tetrahydro-isoquinolin-8-yl]-acetamide;
N—((S or R)-6-Chloro-1-oxo-3,4,5',6',7',8'-hexahydro-1H-[2,4']biisoquinolinyl-8'-yl)-methanesulfonamide;
N—((R or S)-6-Chloro-1-oxo-3,4,5',6',7',8'-hexahydro-1H-[2,4']biisoquinolinyl-8'-yl)-methanesulfonamide;
N—[(S or R)-4-(5-Chloro-1-oxo-1,3-dihydro-isoindol-2-yl)-5,6,7,8-tetrahydro-isoquinolin-8-yl]-methanesulfonamide;
N—[(R or S)-4-(5-Chloro-1-oxo-1,3-dihydro-isoindol-2-yl)-5,6,7,8-tetrahydro-isoquinolin-8-yl]-methanesulfonamide;
N—((R or S)-6-Chloro-1-oxo-3,4,5',6',7',8'-hexahydro-1H-[2,4']biisoquinolinyl-8'-yl)-propionamide;
N—((S or R)-6-Chloro-1-oxo-3,4,5',6',7',8'-hexahydro-1H-[2,4']biisoquinolinyl-8'-yl)-propionamide;
N—[(S or R)-4-(6-Chloro-1-oxo-3,4-dihydro-1H-isoquinolin-2-yl)-6,7-dihydro-5H-[2]pyrindin-7-yl]-methanesulfonamide;
N—[(R or S)-4-(6-Chloro-1-oxo-3,4-dihydro-1H-isoquinolin-2-yl)-6,7-dihydro-5H-[2]pyrindin-7-yl]-methanesulfonamide;
N—[(R or S)-4-(6-Chloro-1-oxo-3,4-dihydro-1H-isoquinolin-2-yl)-6,7-dihydro-5H-[2]pyrindin-7-yl]-acetamide;
N—[(S or R)-4-(6-Chloro-1-oxo-3,4-dihydro-1H-isoquinolin-2-yl)-6,7-dihydro-5H-[2]pyrindin-7-yl]-acetamide;
N—[(R or S)-4-(5-Chloro-1-oxo-1,3-dihydro-isoindol-2-yl)-6,7-dihydro-5H-[2]pyrindin-7-yl]-methanesulfonamide;

N—[(S or R)-4-(5-Chloro-1-oxo-1,3-dihydro-isoindol-2-yl)-6,7-dihydro-5H-[2]pyrindin-7-yl]-methanesulfonamide;
Ethanesulfonic acid [(R or S)-4-(5-chloro-1-oxo-1,3-dihydro-isoindol-2-yl)-6,7-dihydro-5H-[2]pyrindin-7-yl]-amide;
Ethanesulfonic acid [(S or R)-4-(5-chloro-1-oxo-1,3-dihydro-isoindol-2-yl)-6,7-dihydro-5H-[2]pyrindin-7-yl]-amide;
N—[(S or R)-4-(5-Chloro-1-oxo-1,3-dihydro-isoindol-2-yl)-6,7-dihydro-5H-[2]pyrindin-7-yl]-propionamide;
N—[(R or S)-4-(5-Chloro-1-oxo-1,3-dihydro-isoindol-2-yl)-6,7-dihydro-5H-[2]pyrindin-7-yl]-propionamide;
5-Chloro-2-((S or R)-8-hydroxy-5,6,7,8-tetrahydro-isoquinolin-4-yl)-2,3-dihydro-isoindol-1-one;
5-Chloro-2-((R or S)-8-hydroxy-5,6,7,8-tetrahydro-isoquinolin-4-yl)-2,3-dihydro-isoindol-1-one;
N—[(S or R)-4-((R or S)-5-Chloro-3-ethyl-1-oxo-1,3-dihydro-isoindol-2-yl)-6,7-dihydro-5H-[2]pyrindin-7-yl]-acetamide;
N—[(R or S)-4-((S or R)-5-Chloro-3-ethyl-1-oxo-1,3-dihydro-isoindol-2-yl)-6,7-dihydro-5H-[2]pyrindin-7-yl]-acetamide;
N—[(R or S)-4-((R or S)-5-Chloro-3-ethyl-1-oxo-1,3-dihydro-isoindol-2-yl)-6,7-dihydro-5H-[2]pyrindin-7-yl]-acetamide;
N—[(S or R)-4-((S or R)-5-Chloro-3-ethyl-1-oxo-1,3-dihydro-isoindol-2-yl)-6,7-dihydro-5H-[2]pyrindin-7-yl]-acetamide;
N-[4-(5-Chloro-3-ethyl-1-oxo-1,3-dihydro-isoindol-2-yl)-5,6,7,8-tetrahydro-isoquinolin-8-yl]-methanesulfonamide;
N—[(R or S)-4-((R or S)-5-Chloro-3-ethyl-1-oxo-1,3-dihydro-isoindol-2-yl)-5,6,7,8-tetrahydro-isoquinolin-8-yl]-methanesulfonamide;
N—[(S or R)-4-((S or R)-5-Chloro-3-ethyl-1-oxo-1,3-dihydro-isoindol-2-yl)-5,6,7,8-tetrahydro-isoquinolin-8-yl]-methanesulfonamide;
N—[(S or R)-4-((R or S)-5-Chloro-3-ethyl-1-oxo-1,3-dihydro-isoindol-2-yl)-5,6,7,8-tetrahydro-isoquinolin-8-yl]-methanesulfonamide;
N—[(R or S)-4-((S or R)-5-Chloro-3-ethyl-1-oxo-1,3-dihydro-isoindol-2-yl)-5,6,7,8-tetrahydro-isoquinolin-8-yl]-methanesulfonamide;
N—[(S or R)-4-((S or R)-5-Chloro-3-ethyl-1-oxo-1,3-dihydro-isoindol-2-yl)-5,6,7,8-tetrahydro-isoquinolin-8-yl]-propionamide;
N—[(S or R)-4-((R or S)-5-Chloro-3-ethyl-1-oxo-1,3-dihydro-isoindol-2-yl)-5,6,7,8-tetrahydro-isoquinolin-8-yl]-propionamide;
N—[(R or S)-4-((S or R)-5-Chloro-3-ethyl-1-oxo-1,3-dihydro-isoindol-2-yl)-5,6,7,8-tetrahydro-isoquinolin-8-yl]-propionamide;
N—[(R or S)-4-((R or S)-5-Chloro-3-ethyl-1-oxo-1,3-dihydro-isoindol-2-yl)-5,6,7,8-tetrahydro-isoquinolin-8-yl]-propionamide;
N—[(S or R)-4-((R or S)-5-Chloro-3-ethyl-1-oxo-1,3-dihydro-isoindol-2-yl)-5,6,7,8-tetrahydro-isoquinolin-8-yl]-acetamide;
N—[(S or R)-4-((S or R)-5-Chloro-3-ethyl-1-oxo-1,3-dihydro-isoindol-2-yl)-5,6,7,8-tetrahydro-isoquinolin-8-yl]-acetamide;
N—[(R or S)-4-((S or R)-5-Chloro-3-ethyl-1-oxo-1,3-dihydro-isoindol-2-yl)-5,6,7,8-tetrahydro-isoquinolin-8-yl]-acetamide;
N—[(R or S)-4-((R or S)-5-Chloro-3-ethyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-5,6,7,8-tetrahydro-isoquinolin-8-yl]-propionamide;
N—[(S or R)-4-((R or S)-5-Chloro-3-methyl-1-oxo-1,3-dihydro-isoindol-2-yl)-5,6,7,8-tetrahydro-isoquinolin-8-yl]-propionamide;
N—[(R or S)-4-((R or S)-5-Chloro-3-methyl-1-oxo-1,3-dihydro-isoindol-2-yl)-5,6,7,8-tetrahydro-isoquinolin-8-yl]-propionamide;
N—[(S or R)-4-((S or R)-5-Chloro-3-methyl-1-oxo-1,3-dihydro-isoindol-2-yl)-5,6,7,8-tetrahydro-isoquinolin-8-yl]-propionamide;
N—[(S or R)-4-((R or S)-5-Chloro-3-methyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-5,6,7,8-tetrahydro-isoquinolin-8-yl]-acetamide;
N—[(S or R)-4-((S or R)-5-Chloro-3-methyl-1-oxo-1,3-dihydro-isoindol-2-yl)-5,6,7,8-tetrahydro-isoquinolin-8-yl]-acetamide;
N—[(R or S)-4-((R or S)-5-Chloro-3-methyl-1-oxo-1,3-dihydro-isoindol-2-yl)-5,6,7,8-tetrahydro-isoquinolin-8-yl]-acetamide;
N—[(S or R)-4-((R or S)-5-Chloro-3-ethyl-1-oxo-1,3-dihydro-isoindol-2-yl)-6,7-dihydro-5H-[2]pyrindin-7-yl]-methanesulfonamide;
N—[(R or S)-4-((S or R)-5-Chloro-3-ethyl-1-oxo-1,3-dihydro-isoindol-2-yl)-6,7-dihydro-5H-[2]pyrindin-7-yl]-methanesulfonamide;
N—[(R or S)-4-((R or S)-5-Chloro-3-ethyl-1-oxo-1,3-dihydro-isoindol-2-yl)-6,7-dihydro-5H-[2]pyrindin-7-yl]-methanesulfonamide;
N—[(S or R)-4-((S or R)-5-Chloro-3-ethyl-1-oxo-1,3-dihydro-isoindol-2-yl)-6,7-dihydro-5H-[2]pyrindin-7-yl]-methanesulfonamide;
N—[(S or R)-4-((S or R)-5-Chloro-3-cyclopropyl-1-oxo-1,3-dihydro-isoindol-2-yl)-5,6,7,8-tetrahydro-isoquinolin-8-yl]-acetamide;
N—[(R or S)-4-((R or S)-5-Chloro-3-cyclopropyl-1-oxo-1,3-dihydro-isoindol-2-yl)-5,6,7,8-tetrahydro-isoquinolin-8-yl]-acetamide;
N—[(S or R)-4-((R or S)-5-Chloro-3-cyclopropyl-1-oxo-1,3-dihydro-isoindol-2-yl)-5,6,7,8-tetrahydro-isoquinolin-8-yl]-acetamide;
N—[(R or S)-4-((S or R)-5-Chloro-3-cyclopropyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-6,7-dihydro-5H-[2]pyrindin-7-yl]-propionamide;
N—[(R or S)-4-((R or S)-5-Chloro-3-methyl-1-oxo-1,3-dihydro-isoindol-2-yl)-6,7-dihydro-5H-[2]pyrindin-7-yl]-propionamide;
N—[(S or R)-4-((R or S)-5-Chloro-3-methyl-1-oxo-1,3-dihydro-isoindol-2-yl)-6,7-dihydro-5H-[2]pyrindin-7-yl]-propionamide;
N—[(S or R)-4-((S or R)-5-Chloro-3-methyl-1-oxo-1,3-dihydro-isoindol-2-yl)-6,7-dihydro-5H-[2]pyrindin-7-yl]-propionamide;
5-Chloro-3,3-dimethyl-2-(5-pyrazol-1-ylmethyl-pyridin-3-yl)-2,3-dihydro-isoindol-1-one;
2-[5-(3-Amino-pyrazol-1-ylmethyl)-pyridin-3-yl]-5-chloro-3,3-dimethyl-2,3-dihydro-isoindol-1-one;
5-Chloro-3,3-dimethyl-2-{5-[(1H-pyrazol-3-ylamino)-methyl]-pyridin-3-yl}-2,3-dihydro-isoindol-1-one;

2-[5-(3-Amino-pyrazol-1-ylmethyl)-pyridin-3-yl]-6-chloro-3,4-dihydro-2H-isoquinolin-1-one;
2-Chloro-7,7-dimethyl-6-{5-[(1H-pyrazol-3-ylamino)-methyl]-pyridin-3-yl}-6,7-dihydro-pyrrolo[3,4-b]pyridin-5-one;
2-Methoxy-7,7-dimethyl-6-{5-[(1H-pyrazol-3-ylamino)-methyl]-pyridin-3-yl}-6,7-dihydro-pyrrolo[3,4-b]pyridin-5-one;
2-Ethoxy-7,7-dimethyl-6-{5-[(1H-pyrazol-3-ylamino)-methyl]-pyridin-3-yl}-6,7-dihydro-pyrrolo[3,4-b]pyridin-5-one;
6'-Chloro-2'-{5-[(1H-pyrazol-3-ylamino)methyl]pyridin-3-yl}Spiro[cyclopropane-1,1'-isoindol]-3'(2'H)-one;
Ethanesulfonic acid [5-(6-chloro-1,1-dimethyl-3-oxo-1,3-dihydro-isoindol-2-yl)-pyridin-3-ylmethyl]-amide;
Ethanesulfonic acid [5-(6-fluoro-1,1-dimethyl-3-oxo-1,3-dihydro-isoindol-2-yl)-pyridin-3-ylmethyl]-amide;
Ethanesulfonic acid [5-(6-cyano-1,1-dimethyl-3-oxo-1,3-dihydro-isoindol-2-yl)-pyridin-3-ylmethyl]-amide;
Ethanesulfonic acid [5-((S or R)-5-chloro-3-ethyl-1-oxo-1,3-dihydro-isoindol-2-yl)-pyridin-3-ylmethyl]-amide;
N-[5-(6-Chloro-1,1-dimethyl-3-oxo-1,3-dihydro-isoindol-2-yl)-pyridin-3-ylmethyl]-methanesulfonamide;
N-[5-(6-Chloro-1,1-dimethyl-3-oxo-1,3-dihydro-isoindol-2-yl)-pyridin-3-ylmethyl]-N-methyl-methanesulfonamide;
N-{[5-(6'-Fluoro-3'-oxospiro[cyclopropane-1,1'-isoindol]-2'(3'H)-yl)pyridin-3-yl]methyl}ethanesulfonamide;
N-{[5-(6'-Fluoro-3'-oxospiro[cyclopropane-1,1'-isoindol]-2'(3'H)-yl)pyridin-3-yl]methyl}-N-methylethanesulfonamide;
Ethanesulfonic acid [5-(6-chloro-1,1-dimethyl-3-oxo-1,3-dihydro-isoindol-2-yl)-pyridin-3-ylmethyl]-methyl-amide;
N-{[5-(6'-Chloro-3'-oxospiro[cyclopropane-1,1'-isoindol]-2'(3'H)-yl)pyridin-3-yl]methyl}propanamide;
N-[5-(6-Chloro-1,1-dimethyl-3-oxo-1,3-dihydro-isoindol-2-yl)-pyridin-3-ylmethyl]-propionamide;
N-[5-(6-Fluoro-1,1-dimethyl-3-oxo-1,3-dihydro-isoindol-2-yl)-pyridin-3-ylmethyl]-propionamide;
N-[5-((S or R)-5-Chloro-3-ethyl-1-oxo-1,3-dihydro-isoindol-2-yl)-pyridin-3-ylmethyl]-propionamide;
N-[5-(6-Chloro-1,1-dimethyl-3-oxo-1,3-dihydro-isoindol-2-yl)-pyridin-3-ylmethyl]-acetamide;
N-{[5-(5'-Fluoro-3'-oxospiro[cyclopropane-1,1'-isoindol]-2'(3'H)-yl)pyridin-3-yl]methyl}methanesulfonamide;
N-[5-(6-Cyano-1,1-dimethyl-3-oxo-1,3-dihydro-isoindol-2-yl)-pyridin-3-ylmethyl]-methanesulfonamide;
N-[5-(6-Fluoro-1,1-dimethyl-3-oxo-1,3-dihydro-isoindol-2-yl)-pyridin-3-ylmethyl]-methanesulfonamide;
N-{[5-(6'-Fluoro-3'-oxospiro[cyclopropane-1,1'-isoindol]-2'(3'H)-yl)pyridin-3-yl]methyl}methanesulfonamide;
N-[5-((S or R)-5-Chloro-1-ethyl-3-oxo-1,3-dihydro-isoindol-2-yl)-pyridin-3-ylmethyl]-methanesulfonamide;
N-[5-(5-Fluoro-1,1-dimethyl-3-oxo-1,3-dihydro-isoindol-2-yl)-pyridin-3-ylmethyl]-methanesulfonamide;
N-[5-((R or S)-5-Chloro-1-ethyl-3-oxo-1,3-dihydro-isoindol-2-yl)-pyridin-3-ylmethyl]-methanesulfonamide;
N-[5-(5-Chloro-1,1-dimethyl-3-oxo-1,3-dihydro-isoindol-2-yl)-pyridin-3-ylmethyl]-methanesulfonamide;
5-Chloro-2-[5-(1,1-dioxo-1λ6-isothiazolidin-2-ylmethyl)-pyridin-3-yl]-3,3-dimethyl-2,3-dihydro-isoindol-1-one;
5-Chloro-3,3-dimethyl-2-[5-(2-oxo-piperidin-1-ylmethyl)-pyridin-3-yl]-2,3-dihydro-isoindol-1-one;
5-Chloro-3,3-dimethyl-2-[5-(2-oxo-imidazolidin-1-ylmethyl)-pyridin-3-yl]-2,3-dihydro-isoindol-1-one;
5-Chloro-3,3-dimethyl-2-[5-(2-oxo-oxazolidin-3-ylmethyl)-pyridin-3-yl]-2,3-dihydro-isoindol-1-one;
5-Chloro-3,3-dimethyl-2-[5-(2-oxo-pyrrolidin-1-ylmethyl)-pyridin-3-yl]-2,3-dihydro-isoindol-1-one;
5-Chloro-3,3-dimethyl-2-[5-(3-methyl-2-oxo-imidazolidin-1-ylmethyl)-pyridin-3-yl]-2,3-dihydro-isoindol-1-one;
5-Chloro-2-[5-(1,1-dioxo-1λ6-[1,2]thiazinan-2-ylmethyl)-pyridin-3-yl]-3,3-dimethyl-2,3-dihydro-isoindol-1-one;
5-Chloro-2-[5-(3-isopropyl-2-oxo-imidazolidin-1-ylmethyl)-pyridin-3-yl]-3,3-dimethyl-2,3-dihydro-isoindol-1-one;
6-Chloro-2-[5-(1,5-dimethyl-1H-imidazol-4-yl)-pyridin-3-yl]-3,4-dihydro-2H-isoquinolin-1-one;
5-Chloro-3,3-dimethyl-2-[5-(2-methyl-2H-pyrazol-3-yl)-pyridin-3-yl]-2,3-dihydro-isoindol-1-one;
6-Chloro-2-[5-(3-methyl-1H-pyrazol-4-yl)-pyridin-3-yl]-3,4-dihydro-2H-isoquinolin-1-one;
6-Chloro-2-[5-(4-methyl-2H-pyrazol-3-yl)-pyridin-3-yl]-3,4-dihydro-2H-isoquinolin-1-one;
6-Chloro-2-[5-(4-chloro-2-methyl-2H-pyrazol-3-yl)-pyridin-3-yl]-3,4-dihydro-2H-isoquinolin-1-one;
6-Chloro-2-[5-(2,5-dimethyl-2H-pyrazol-3-yl)-pyridin-3-yl]-3,4-dihydro-2H-isoquinolin-1-one;
6-Chloro-2-[5-(1,5-dimethyl-1H-pyrazol-4-yl)-pyridin-3-yl]-3,4-dihydro-2H-isoquinolin-1-one;
6-Chloro-2-[4-chloro-5-(2-methyl-2H-pyrazol-3-yl)-pyridin-3-yl]-3,4-dihydro-2H-isoquinolin-1-one;
2-Chloro-7,7-dimethyl-6-[5-(2-methyl-2H-pyrazol-3-yl)-pyridin-3-yl]-6,7-dihydro-pyrrolo[3,4-b]pyridin-5-one;
2-Methoxy-7,7-dimethyl-6-[5-(2-methyl-2H-pyrazol-3-yl)-pyridin-3-yl]-6,7-dihydro-pyrrolo[3,4-b]pyridin-5-one;
5-Chloro-2-[5-(4-chloro-2-methyl-2H-pyrazol-3-yl)-pyridin-3-yl]-3,3-dimethyl-2,3-dihydro-isoindol-1-one;
(R or S)-5-Chloro-3-ethyl-2-[5-(2-methyl-2H-pyrazol-3-yl)-pyridin-3-yl]-2,3-dihydro-isoindol-1-one;
(S or R)-5-Chloro-3-ethyl-2-[5-(2-methyl-2H-pyrazol-3-yl)-pyridin-3-yl]-2,3-dihydro-isoindol-1-one;
3-Methyl-pyridine-2-carboxylic acid [5-(6-chloro-1,1-dimethyl-3-oxo-1,3-dihydro-isoindol-2-yl)-pyridin-3-ylmethyl]-amide;
3-Chloro-pyridine-2-carboxylic acid [5-(6-chloro-1,1-dimethyl-3-oxo-1,3-dihydro-isoindol-2-yl)-pyridin-3-ylmethyl]-amide;
1-Methyl-1H-imidazole-2-carboxylic acid [5-(6-chloro-1,1-dimethyl-3-oxo-1,3-dihydro-isoindol-2-yl)-pyridin-3-ylmethyl]-amide;
2-Chloro-N-[5-(6-chloro-1,1-dimethyl-3-oxo-1,3-dihydro-isoindol-2-yl)-pyridin-3-ylmethyl]-nicotinamide;
Pyridine-2-carboxylic acid [5-(6-chloro-1,1-dimethyl-3-oxo-1,3-dihydro-isoindol-2-yl)-pyridin-3-ylmethyl]-amide;
3-Methyl-3H-imidazole-4-carboxylic acid [5-(6-chloro-1,1-dimethyl-3-oxo-1,3-dihydro-isoindol-2-yl)-pyridin-3-ylmethyl]-amide;
N-[5-(6-Chloro-1,1-dimethyl-3-oxo-1,3-dihydro-isoindol-2-yl)-pyridin-3-ylmethyl]-6-methyl-nicotinamide;
3-Chloro-N-[5-(6-chloro-1,1-dimethyl-3-oxo-1,3-dihydro-isoindol-2-yl)-pyridin-3-ylmethyl]-isonicotinamide;
N-[5-(6-Chloro-1,1-dimethyl-3-oxo-1,3-dihydro-isoindol-2-yl)-pyridin-3-ylmethyl]-nicotinamide;
N-[5-(6-Chloro-1,1-dimethyl-3-oxo-1,3-dihydro-isoindol-2-yl)-pyridin-3-ylmethyl]-2-methyl-nicotinamide;
N-[5-(6-Chloro-1,1-dimethyl-3-oxo-1,3-dihydro-isoindol-2-yl)-pyridin-3-ylmethyl]-4-methyl-nicotinamide;
2-[5-(1-Acetyl-pyrrolidin-3-yloxy)-pyridin-3-yl]-5-chloro-3,3-dimethyl-2,3-dihydro-isoindol-1-one;

2-[5-((R)-1-Acetyl-pyrrolidin-3-yloxy)-pyridin-3-yl]-5-chloro-3,3-dimethyl-2,3-dihydro-isoindol-1-one;
2-[5-((S)-1-Acetyl-pyrrolidin-3-yloxy)-pyridin-3-yl]-5-chloro-3,3-dimethyl-2,3-dihydro-isoindol-1-one;
5-Chloro-3,3-dimethyl-2-[5-(1-propionyl-pyrrolidin-3-yloxy)-pyridin-3-yl]-2,3-dihydro-isoindol-1-one;
5-Chloro-2-[5-(1-methanesulfonyl-pyrrolidin-3-yloxy)-pyridin-3-yl]-3,3-dimethyl-2,3-dihydro-isoindol-1-one;
5-Chloro-2-[5-(1-ethanesulfonyl-pyrrolidin-3-yloxy)-pyridin-3-yl]-3,3-dimethyl-2,3-dihydro-isoindol-1-one;
5-Chloro-2-[5-((R)-1-ethanesulfonyl-pyrrolidin-3-yloxy)-pyridin-3-yl]-3,3-dimethyl-2,3-dihydro-isoindol-1-one;
5-Chloro-2-[5-((S)-1-ethanesulfonyl-pyrrolidin-3-yloxy)-pyridin-3-yl]-3,3-dimethyl-2,3-dihydro-isoindol-1-one;
2-[5-(1-Acetyl-piperidin-4-yloxy)-pyridin-3-yl]-5-chloro-3,3-dimethyl-2,3-dihydro-isoindol-1-one;
2-[5-(1-Acetyl-azetidin-3-yloxy)-pyridin-3-yl]-5-chloro-3,3-dimethyl-2,3-dihydro-isoindol-1-one;
5-Chloro-3,3-dimethyl-2-[5-(1-propionyl-azetidin-3-yloxy)-pyridin-3-yl]-2,3-dihydro-isoindol-1-one;
5-Chloro-2-[5-(1-methanesulfonyl-azetidin-3-yloxy)-pyridin-3-yl]-3,3-dimethyl-2,3-dihydro-isoindol-1-one;
5-Chloro-2-[5-(1-ethanesulfonyl-azetidin-3-yloxy)-pyridin-3-yl]-3,3-dimethyl-2,3-dihydro-isoindol-1-one;
5-Chloro-2-[5-((S)-3-hydroxy-pyrrolidin-1-yl)-pyridin-3-yl]-3,3-dimethyl-2,3-dihydro-isoindol-1-one;
2-[5-(4-Acetyl-piperazin-1-yl)-pyridin-3-yl]-5-chloro-3,3-dimethyl-2,3-dihydro-isoindol-1-one;
5-Chloro-3,3-dimethyl-2-[5-(4-propionyl-piperazin-1-yl)-pyridin-3-yl]-2,3-dihydro-isoindol-1-one;
5-Chloro-2-[5-(4-methanesulfonyl-piperazin-1-yl)-pyridin-3-yl]-3,3-dimethyl-2,3-dihydro-isoindol-1-one;
5-Chloro-2-[5-(4-ethanesulfonyl-piperazin-1-yl)-pyridin-3-yl]-3,3-dimethyl-2,3-dihydro-isoindol-1-one;
5-Chloro-2-{5-[4-(3-chloro-pyridine-2-carbonyl)-piperazin-1-yl]-pyridin-3-yl}-3,3-dimethyl-2,3-dihydro-isoindol-1-one;
2-[5-(1-Acetyl-pyrrolidin-3-yl)-pyridin-3-yl]-5-chloro-3,3-dimethyl-2,3-dihydro-isoindol-1-one;
2-(1'-Acetyl-1',2',3',4',5',6'-hexahydro-[3,4']bipyridinyl-5-yl)-5-chloro-3,3-dimethyl-2,3-dihydro-isoindol-1-one;
2-[6-(1-Acetyl-piperidin-3-yl)-pyrazin-2-yl]-5-chloro-3,3-dimethyl-2,3-dihydro-isoindol-1-one;
5-Chloro-3,3-dimethyl-2-[6-(1-propionyl-piperidin-3-yl)-pyrazin-2-yl]-2,3-dihydro-isoindol-1-one;
5-Chloro-2-[6-(1-ethanesulfonyl-piperidin-3-yl)-pyrazin-2-yl]-3,3-dimethyl-2,3-dihydro-isoindol-1-one;
5-Chloro-2-[6-(1-methanesulfonyl-piperidin-3-yl)-pyrazin-2-yl]-3,3-dimethyl-2,3-dihydro-isoindol-1-one;
N—[(S or R)-4-(6-Chloro-1,1-dimethyl-3-oxo-1,3-dihydro-isoindol-2-yl)-5,6,7,8-tetrahydro-isoquinolin-8-yl]-acetamide;
N—[(R or S)-4-(6-Chloro-1,1-dimethyl-3-oxo-1,3-dihydro-isoindol-2-yl)-5,6,7,8-tetrahydro-isoquinolin-8-yl]-acetamide;
N-[4-(6-Chloro-1,1-dimethyl-3-oxo-1,3-dihydro-isoindol-2-yl)-5,6,7,8-tetrahydro-isoquinolin-8-yl]-propionamide;
and pharmaceutically acceptable salts thereof.

Further particular examples of compounds of formula (I) as described herein are selected from the group consisting of
6-Chloro-2-pyridin-3-yl-3,4-dihydro-2H-isoquinolin-1-one;
6-Chloro-2-(4-chloro-pyridin-3-yl)-3,4-dihydro-2H-isoquinolin-1-one;
6-Chloro-2-(5-isopropoxy-pyridin-3-yl)-3,4-dihydro-2H-isoquinolin-1-one;
6-Chloro-2-[5-((R)-1-hydroxy-ethyl)-pyridin-3-yl]-3,4-dihydro-2H-isoquinolin-1-one;
6-Chloro-2-(5-cyclopropoxy-pyridin-3-yl)-3,4-dihydro-2H-isoquinolin-1-one;
2-Methoxy-6-(5-methoxy-pyridin-3-yl)-7,8-dihydro-6H-[1,6]naphthyridin-5-one;
5-Chloro-3-ethyl-2-(5-fluoro-pyridin-3-yl)-2,3-dihydro-isoindol-1-one;
5-Chloro-2-(5-fluoro-pyridin-3-yl)-3,3-dimethyl-2,3-dihydro-isoindol-1-one;
5-Chloro-2-(5-difluoromethoxy-pyridin-3-yl)-3,3-dimethyl-2,3-dihydro-isoindol-1-one;
6-Chloro-2-[5-(2-oxa-6-aza-spiro[3.4]oct-6-ylmethyl)-pyridin-3-yl]-3,4-dihydro-2H-isoquinolin-1-one;
6-Chloro-2-(5-methoxymethyl-pyridin-3-yl)-3,4-dihydro-2H-isoquinolin-1-one;
6-Chloro-2-[5-(1-methyl-1H-pyrazol-4-ylmethyl)-pyridin-3-yl]-3,4-dihydro-2H-isoquinolin-1-one;
6-Chloro-2-{5-[(2-methyl-2H-pyrazol-3-ylmethyl)-amino]-pyridin-3-yl}-3,4-dihydro-2H-isoquinolin-1-one;
6-Chloro-2-[5-(2-methyl-2H-pyrazol-3-yl)-pyridin-3-yl]-3,4-dihydro-2H-isoquinolin-1-one;
6-Chloro-2-{5-[(1H-pyrazol-3-ylamino)-methyl]-pyridin-3-yl}-3,4-dihydro-2H-isoquinolin-1-one;
and pharmaceutically acceptable salts thereof.

Also further particular examples of compounds of formula (I) as described herein are selected from the group consisting of
(R or S)-5-Chloro-3-ethyl-2-(5-fluoro-pyridin-3-yl)-2,3-dihydro-isoindol-1-one;
(S or R)-5-Chloro-3-ethyl-2-(5-fluoro-pyridin-3-yl)-2,3-dihydro-isoindol-1-one;
N—[(R or S)-4-((R or S)-5-Chloro-3-ethyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-5,6,7,8-tetrahydro-isoquinolin-8-yl]-propionamide;
N—[(R or S)-4-((S or R)-5-Chloro-3-methyl-1-oxo-1,3-dihydro-isoindol-2-yl)-5,6,7,8-tetrahydro-isoquinolin-8-yl]-acetamide;
N—[(R or S)-4-((S or R)-5-Chloro-3-ethyl-1-oxo-1,3-dihydro-isoindol-2-yl)-6,7-dihydro-5H-[2]pyrindin-7-yl]-methanesulfonamide;
N—[(R or S)-4-((R or S)-5-Chloro-3-methyl-1-oxo-1,3-dihydro-isoindol-2-yl)-6,7-dihydro-5H-[2]pyrindin-7-yl]-propionamide;
N—[(S or R)-4-((R or S)-5-Chloro-3-methyl-1-oxo-1,3-dihydro-isoindol-2-yl)-6,7-dihydro-5H-[2]pyrindin-7-yl]-propionamide;
5-Chloro-3,3-dimethyl-2-{5-[(1H-pyrazol-3-ylamino)-methyl]-pyridin-3-yl}-2,3-dihydro-isoindol-1-one;
6'-Chloro-2'-{5-[(1H-pyrazol-3-ylamino)methyl]pyridin-3-yl}spiro[cyclopropane-1,1'-isoindol]-3'(2'H)-one;
N-[5-(6-Chloro-1,1-dimethyl-3-oxo-1,3-dihydro-isoindol-2-yl)-pyridin-3-ylmethyl]-methanesulfonamide;
3-Methyl-pyridine-2-carboxylic acid [5-(6-chloro-1,1-dimethyl-3-oxo-1,3-dihydro-isoindol-2-yl)-pyridin-3-ylmethyl]-amide;
2-[5-((R)-1-Acetyl-pyrrolidin-3-yloxy)-pyridin-3-yl]-5-chloro-3,3-dimethyl-2,3-dihydro-isoindol-1-one;
2-[5-((S)-1-Acetyl-pyrrolidin-3-yloxy)-pyridin-3-yl]-5-chloro-3,3-dimethyl-2,3-dihydro-isoindol-1-one;
5-Chloro-2-[5-(1-methanesulfonyl-pyrrolidin-3-yloxy)-pyridin-3-yl]-3,3-dimethyl-2,3-dihydro-isoindol-1-one;
5-Chloro-2-[5-((R)-1-ethanesulfonyl-pyrrolidin-3-yloxy)-pyridin-3-yl]-3,3-dimethyl-2,3-dihydro-isoindol-1-one;
5-Chloro-2-[5-((S)-1-ethanesulfonyl-pyrrolidin-3-yloxy)-pyridin-3-yl]-3,3-dimethyl-2,3-dihydro-isoindol-1-one;

2-[5-(1-Acetyl-piperidin-4-yloxy)-pyridin-3-yl]-5-chloro-3, 3-dimethyl-2,3-dihydro-isoindol-1-one;
5-Chloro-2-[5-(1-ethanesulfonyl-azetidin-3-yloxy)-pyridin-3-yl]-3,3-dimethyl-2,3-dihydro-isoindol-1-one;
2-[5-(4-Acetyl-piperazin-1-yl)-pyridin-3-yl]-5-chloro-3,3-dimethyl-2,3-dihydro-isoindol-1-one;
5-Chloro-2-[5-(4-methanesulfonyl-piperazin-1-yl)-pyridin-3-yl]-3,3-dimethyl-2,3-dihydro-isoindol-1-one;
5-Chloro-2-[5-(4-ethanesulfonyl-piperazin-1-yl)-pyridin-3-yl]-3,3-dimethyl-2,3-dihydro-isoindol-1-one;
2-(1'-Acetyl-1',2',3',4',5',6'-hexahydro-[3,4']bipyridinyl-5-yl)-5-chloro-3,3-dimethyl-2,3-dihydro-isoindol-1-one;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDT=1,1-carbonyldiimidazole, DCM=dichloromethane, DBU=2,3,4,6,7,8,9,10-octahydropyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, Et$_2$O=diethylether, Et$_3$N=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, IPC=in process control, LAH=lithium aluminium hydride, LDA=lithium diisopropylamide, LiBH$_4$=lithium borohydride, MeOH=methanol, NaBH$_3$CN, sodium cyanoborohydride, NaBH$_4$=sodium borohydride, NaI=sodium iodide, Red-Al=sodium bis(2-methoxyethoxy) aluminium hydride, RT=room temperature, TBDMSCl=t-butyldimethylsilyl chloride, TFA=trifluoroacetic acid, THF=tetrahydrofuran, quant=quantitative.

Halogen or triflate substituted heterocyclic compounds 2 react with aryl lactams 1 in solvents like 1,4-dioxane, in the presence of copper (I) iodide, potassium or cesium carbonate, a chelating 1,2-diamino compound like N,N'-dimethylethylenediamine or trans-1,2-diamino-hexane, at elevated temperatures, preferable with the aid of microwave heating to form lactam substituted heterocyclic compounds 3 (step a) as described in Scheme 1.

Scheme 1

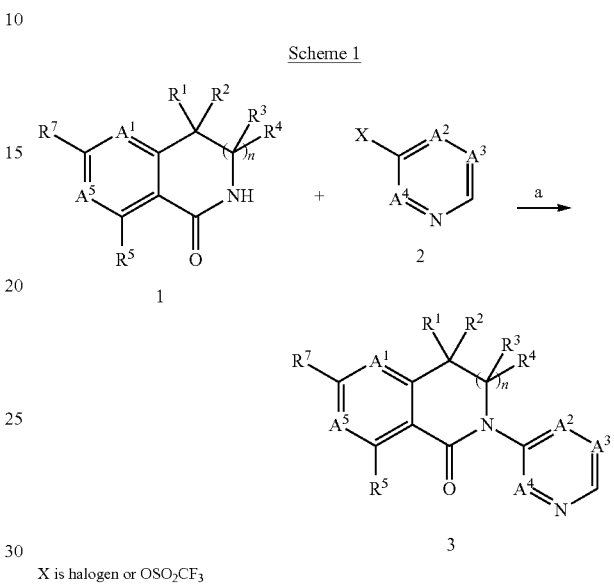

X is halogen or OSO$_2$CF$_3$

Treatment of heteroaryl linked alcohol compounds 51 (Scheme 2b) with a base like sodium hydride in a solvent like THF or DMF and subsequently with a suitable alkylating agent such as a halide, mesylate or tosylate preferably between RT and the reflux temperature of the solvent gives compounds 52 (step a). Alternatively (Scheme 2a), heteroaryl linked alcohol compounds 51 can e.g. be converted into the corresponding chlorides by treatment with thionyl chloride in a solvent like dichloromethane preferably between 0° C. and room temperature (step b). Said heteroaryl linked chlorides, compounds 53, react with nucleophilic amino-moieties 54a or aryl, heteroaryl or heterocycloalkyl compounds 54b per se or after anion formation e.g. with sodium hydride in solvents like N,N'-dimethylformamide in a temperature range between 0° C. and about 100° C. to form adducts 55a or 55b (step c).

Scheme 2a

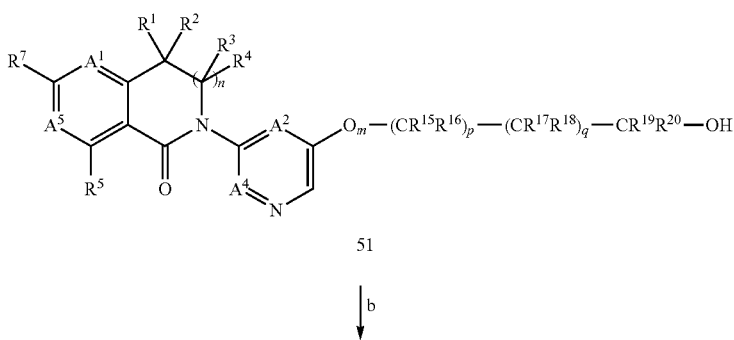

-continued
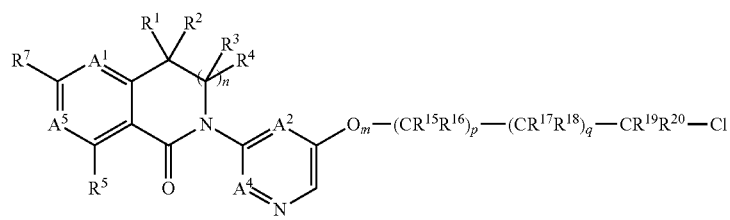
53
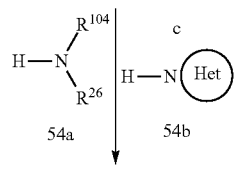
54a  54b
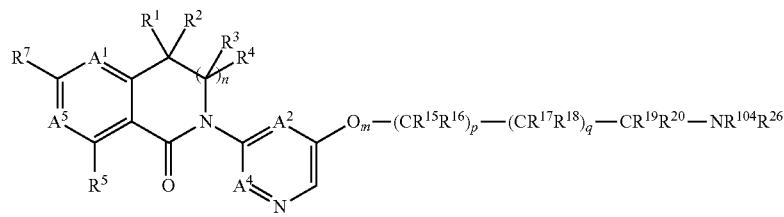
55a
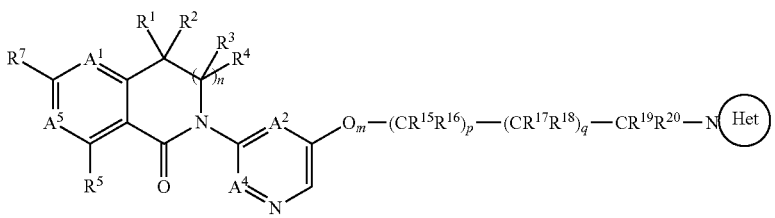
55b
$R^{104}$ is $R^{25}$, —$S(O)_2R^{25}$, —$C(O)R^{25}$, or —$C(O)NR^{25}R^{27}$
H—N(Het) is heteroaryl or heterocyclyl substituted by $R^{38}$, $R^{39}$, $R^{40}$.
Scheme 2b
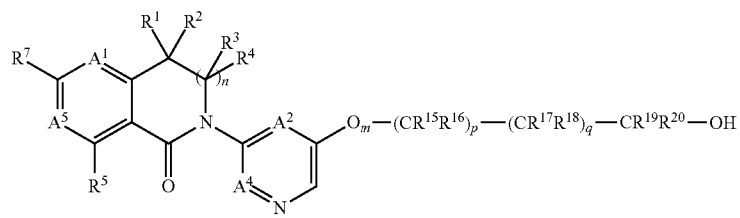
51
↓ a

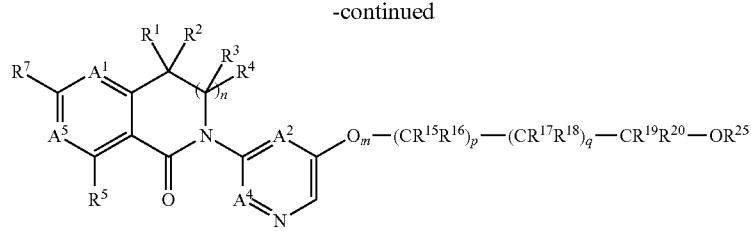

52

Alternatively (Scheme 2c), heteroaryl linked chloride compounds 53 react with boronic acids or esters 56 i) by using Suzuki conditions, e.g. in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non-aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130° C. or ii) by using a nickel (0) catalyst, e.g. bis(1,5-cyclooctadiene)nickel (0) in the presence potassium phosphate, bis(1-methyl-1H-imidazol-2-yl)methane in N,N-dimethyl acetamide at temperatures around 100° C. giving adducts 57 (steps d).

Scheme 2c

53 $\xrightarrow{d}$ 

56

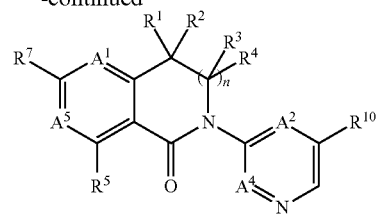

57

$R^{101}$ and $R^{102}$ are H or alkyl, or $R^{101}$ and $R^{102}$ together with the boron atom to which they are attached form $R^{21}$ is substituted aryl or substituted heteroaryl Aldehydes or ketones 58 (Scheme 2d) can be treated with suitable amino-moieties 59 the presence of $NaBH(OAc)_3$ in a one-step procedure in a solvent like methanol preferably around room temperature or in a two-step procedure by first treatment with titanium (IV) isopropoxide in solvents like methanol or toluene preferably at temperatures between room temperature and the reflux temperature of the solvents followed by reaction with $NaBH_4$ preferably between 0° C. and room temperature which converts aldehydes or ketones 58 into amino compounds 60; alternatively imines obtained after treatment with titanium (IV) isopropoxide can be evaporated, then be re-dissolved in a solvent like THF and being treated with a Grignard reagent $R^{20}MgX$, preferably between −40° C. and 0° C. leading to amino compounds 60 carrying the specific $R^{20}$ substituent (step e).

Scheme 2d

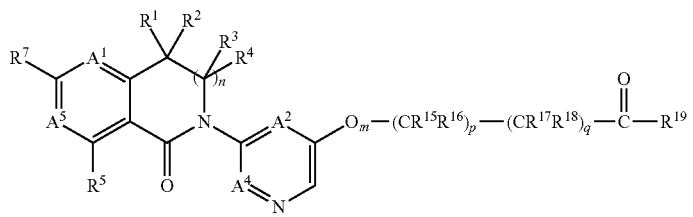

58

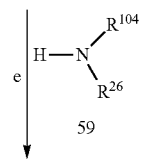

59

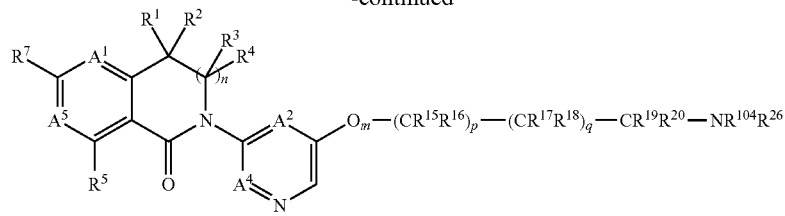

60

$R^{104}$ is $R^{25}$, —S(O)$_2$R$^{25}$, —C(O)R$^{25}$, or —C(O)NR$^{25}$R$^{27}$

Heteroaryl halides 101 (Scheme 2e) react with boronic acids or esters 102 using Suzuki conditions as described above to give adducts 103 (step a). Phenols 104 react with alcohols 105 under Mitsunobu conditions e.g. with triphenylphosphine and di-tert-butyl-, diisopropyl-, diethyl-azodicarboxylate or di-(4-chlorobenzyl)azodicarboxylate as reagents in solvents like toluene, dichloromethane or tetrahydrofuran preferably at ambient temperature to give adducts 106 (step b). Compounds 106 can be transformed by additional standard modifications into synthons 107 (step c).

Scheme 2e

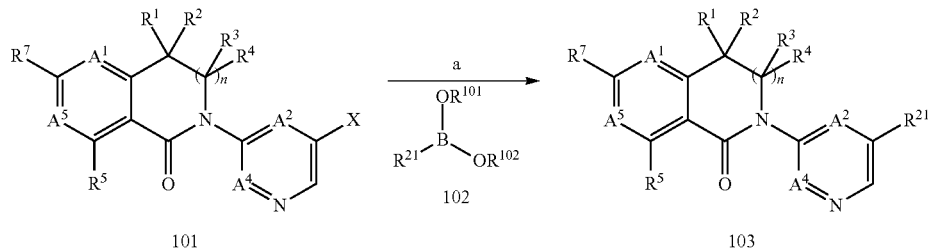

$R^{101}$ and $R^{102}$ are H or alkyl, or $R^{101}$ and $R^{102}$ together with the boron atom to which they are attached form 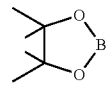

$R^{21}$ is substituted aryl or substituted heteroaryl

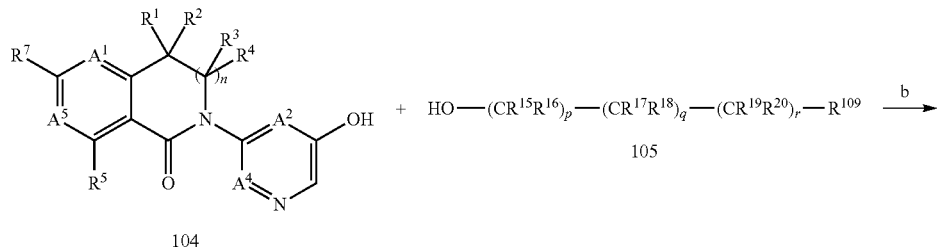

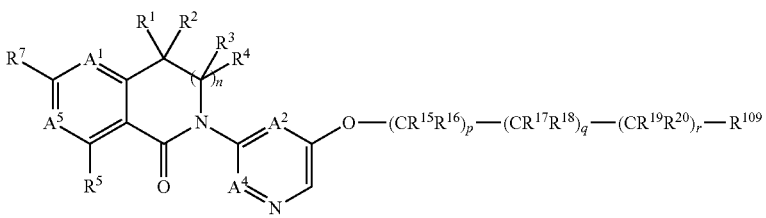

106

106 →c 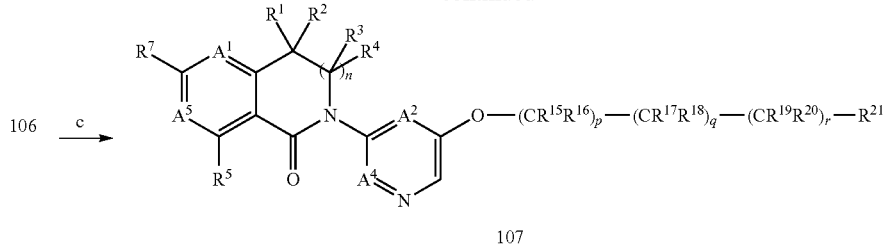 107

X is halogen or $OSO_2CF_3$ $R^{109}$ represents substituents as defined in $R^{21}$ or substituents which can easily be transformed into $R^{21}$ (step c).

Carbamates 201 (Scheme 3) react with polyphosphoric acid at elevated temperature (e.g. 100-180° C.) to form 3,4-dihydro-2H-isoquinolin-1-one derivatives 202 (step a). Trifluoroacetamides 203 can be cyclized to 1-(3,4-dihydro-1H-isoquinolin-2-yl)-2,2,2-trifluoro-ethanone compounds 204 by treatment with paraformaldehyde in a mixture of concentrated sulfuric acid and acetic acid preferably around room temperature (step b). Removal of the trifluoroacetyl group by treatment with e.g. potassium hydroxide in a solvent like ethanol at temperatures around room temperature gives tetrahydro-isoquinoline compounds 205 (step c). Oxidation of tetrahydro-isoquinoline compounds 205 e.g. with iodoso benzene and potassium bromide preferably in water gives 3,4-dihydro-2H-isoquinolin-1-one compounds 202 (step d). Reaction of isoindole-1,3-dione compounds 206 with a Grignard reagent $R^1MgX$ in a solvent like THF preferably around 0° C. gives adducts 207 (step e). Subsequent treatment with triethylsilane and trifluoroboron etherate in a solvent like dichloromethane and in a temperature range preferably between −25° C. and RT gives isoindolone compounds 208 (step f). Introduction a methoxybenzyl protecting group into isoindolone compounds 209 (e.g. by treatment with sodium bis(trimethylsilyl) amide and 1-bromomethyl-4-methoxybenzene in THF between 0° C. and RT) gives protected compounds 210 (step g); similarly, a methoxybenzyl protecting group can be introducted into compounds 208. Treatment of compounds 208 carrying an additional methoxybenzyl protecting group or compounds 210 with a base like sodium hydride in a solvent like THF and then with an alkyl halide, mesylate or tosylate preferably between RT and the reflux temperature of the solvent gives compounds 211 with structurally different or structurally identical $R^1$ and $R^2$ groups (step h). Alternatively, treatment of compounds 208 carrying an additional methoxybenzyl protecting group or compounds 210 with a base like NaH, LDA or LiHMDS in solvents like DMF, tetrahydrofuran or 1,2-dimethoxyethane and then with one or sequentially with two different alkyl halides, mesylates or tosylates preferably between −78° C. and the reflux temperature of the solvent gives compounds 211 with structurally different or structurally identical $R^1$ and $R^2$ groups (step h). Removal of the protecting group, e.g. by treatment with trifluoroacetic acid at elevated temperature gives isoindolone compounds 212 (step i). Treatment of compounds 210 with a base like sodium hydride in a solvent like THF and then with an alpha, omega di-haloalkane or di-haloheteroalkane like e.g. 1,2-dibromoethane, preferably between RT and the reflux temperature of the solvent gives spiro compounds 213 (step k) and after subsequent removal of the protecting group, spiro compounds 214 (step l).

Scheme 3

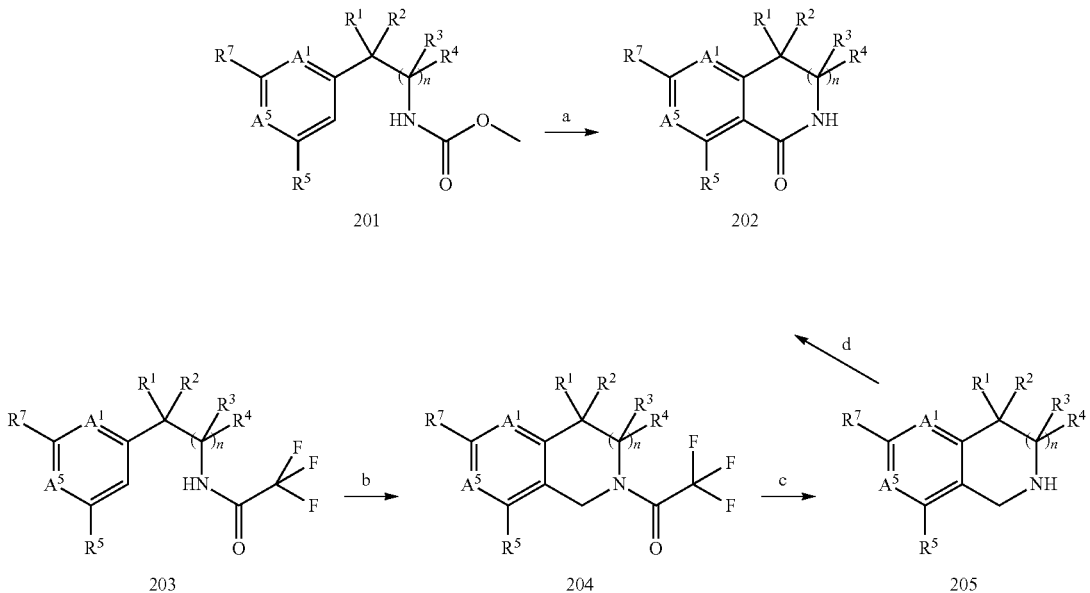

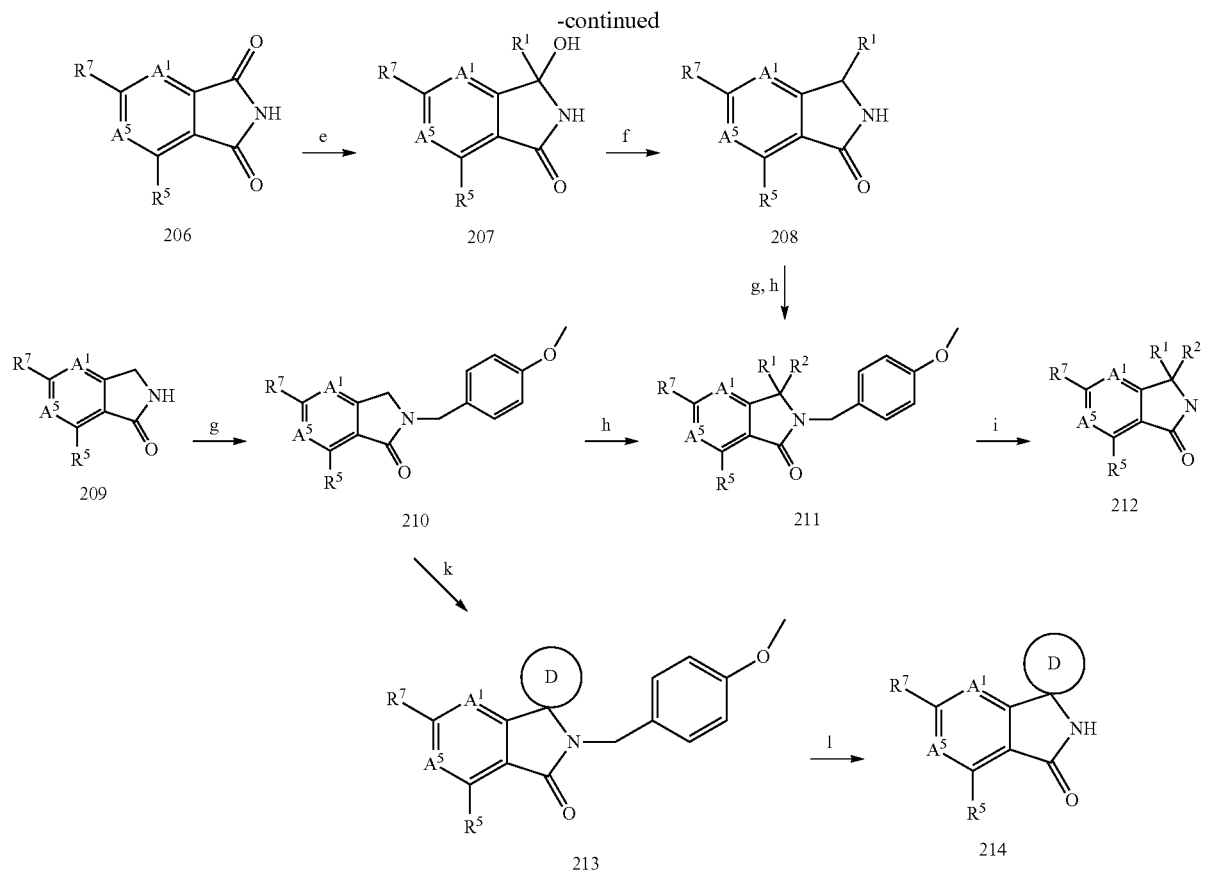

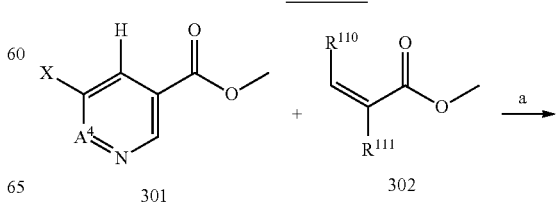

5-Halo-nicotinic acid or pyridazine carboxylic acid compounds 301 or 305 (Scheme 4a) react with acrylic acid ester compounds 302 after deprotonation with base like LDA or LiHMDS in solvents like THF preferably around −78° C. giving cyclic beta keto ester compounds 303 and 306 (step a). Ester compounds 303 or 306 with $R^{111}$=H can be treated with a base like NaH, LDA or LiHMDS in solvents like DMF, tetrahydrofuran or 1,2-dimethoxyethane, followed by addition of an alkyl or cycloalkyl halide, mesylate or tosylate, or e.g. a N-halobenzensulfonamide, a reaction preferably performed between −78° C. and room temperature, to give ester compounds 303 or 306 carrying a substituent $R^{111}$ different from H. Treatment of beta keto-ester compounds 303 or 306 with aqueous acid preferably at reflux induces ester hydrolysis and subsequent decarboxylation providing ketones 304 and 307 (step b). Ketones 304 and 307 with $R^{111}$=H and $R^{113}$=H can be treated with a base like NaH, LDA or LiHMDS in solvents like DMF, tetrahydrofuran or 1,2-dimethoxyethane, followed by addition of one or subsequently two different alkyl or cycloalkyl halides, mesylates or tosylates, or e.g. N-halobenzensulfonamides, a reaction preferably performed between −78° C. and room temperature, to give ketones 304 and 307 carrying at least one of the substituents $R^{111}$ or $R^{113}$ different from H. Optionally, ketones 304 and 307 can be converted into the corresponding imines (e.g. with N-butylamine by using a catalyst like toluene sulfonic acid or pyridinum p-toluenesulfonate in a solvent like ethanol preferably at reflux); such imines with $R^{111}$=H can be reacted with e.g. N-fluorobenzenesulfonimide using $K_2CO_3$ or triethyamine as base in solvents like DMF or acetonitrile or mixtures thereof, in the presence of molecular sieves preferably at room temperature to give imines carrying fluoro substituents and after imine hydrolysis (e.g. with hydrochloric acid in acetonitrile) ketones 304 and 307 with $R^{111}$=F. Ketones 304 and 307, can function as compounds 2 (scheme 1) or can be converted into different compounds 2 (Scheme 1) by further structural modification using methods well known in the art as e.g. reduction of the keto function to a secondary hydroxy group with a reagent like sodium borohydride in methanol or reduction of the keto group to a primary or secondary amino function by reductive amination e.g. by reacting with an amine and $NaBH(OAc)_3$ in methanol.

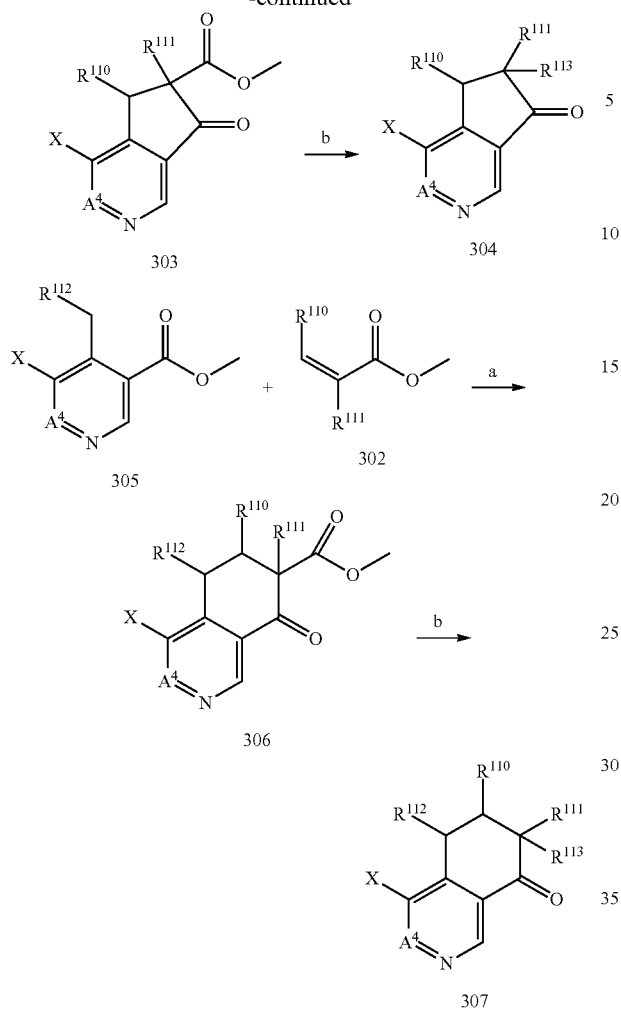

X is halogen or OSO$_2$CF$_3$
Three of R$^{110}$, R$^{111}$, R$^{112}$, and R$^{113}$ are R$^{35}$ or R$^{36}$ or R$^{37}$ and the other one is H.

Dihalopyridine or pyridazine compounds 351 (Scheme 4b) react with bromo-tetramethyl-azadisilolidine reagents 352 after deprotonation with lithium diisopropyl amide in solvents like tetrahydrofuran between −78° C. and 0° C. to give aminoalkyl substituted pyridines or pyridazine 353 (step a). After attachment of a protecting group onto compounds 353 (e.g. by introducing a BOC- or a SES-protecting group by reaction with BOC$_2$O or 2-trimethylsilanyl-ethanesulfonyl chloride, triethylamine, DMF around 0° C.), treatment of amino protected pyridine or pyridazine compounds 354 with a base like potassium carbonate, in a solvent like toluene, and in the presence of a catalyst like tetrakis-(triphenylphosphine)-palladium at temperatures around 100° C. gives bicyclic compounds 355, still carrying a protecting group (step b, c). Standard BOC removal or use of tetrabutylammonium fluoride hydrate, acetonitrile preferably between room temperature and the reflux temperature of acetonitrile then gives bicyclic compounds 356 (step d). Amino compounds 356 can function as compounds 2 (Scheme 1) either as such or after further structural modification by methods well known in the art.

Scheme 4b

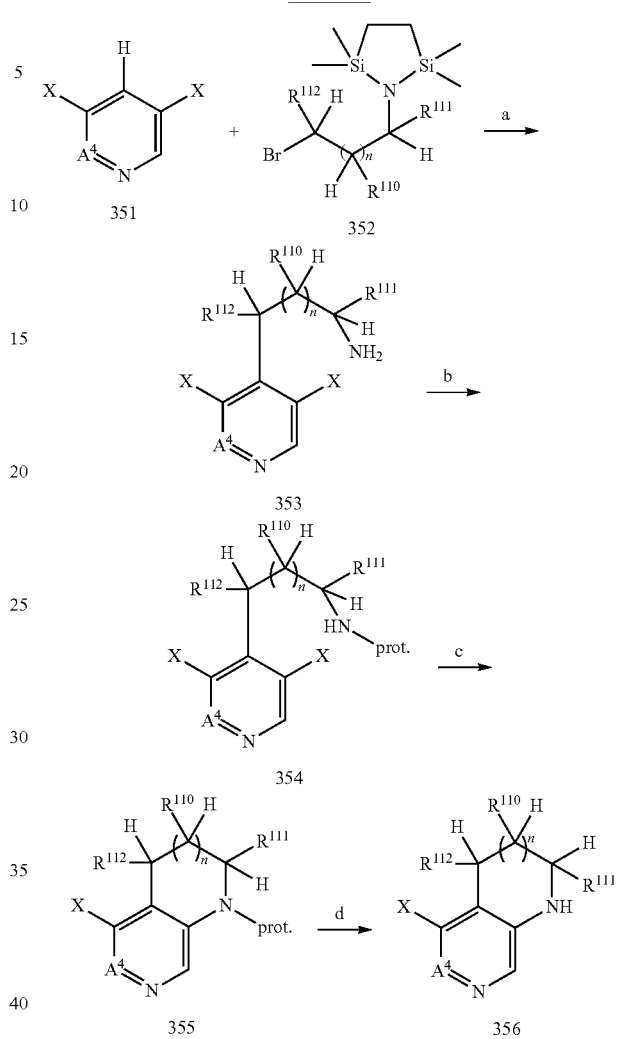

prot. = protecting group
X is halogen or OSO$_2$CF$_3$
R$^{110}$ is R$^{35}$, R$^{36}$ or R$^{37}$.
R$^{111}$ is R$^{35}$, R$^{36}$ or R$^{37}$.
R$^{112}$ is R$^{35}$, R$^{36}$ or R$^{37}$.

5-Halo-nicotinic acid compounds 305 (Scheme 4c) react with alkene compounds 400 after deprotonation with a base like LDA or LiHMDS in solvents like THF preferably around −78° C. giving alkenes 401 (step a). Diester compounds 402 can be synthesized by methods known to persons skilled in the art such as e.g. by ozonolysis of alkenes 401 in the presence of methanolic NaOH to give compounds 402 which can be cyclized using Dieckmann condensation conditions to give beta keto-ester compounds 403 (step b, c). Treatment of beta keto-ester compounds 403 with aqueous acid preferably at reflux temperature induces ester hydrolysis and subsequent decarboxylation providing ketones 404 (step e). Ester compounds 403 (R$^{111}$ is H) can be treated with a base like NaH, LDA or LiHMDS in solvents like DMF, tetrahydrofuran or 1,2-dimethoxyethane, followed by addition of an alkyl or cycloalkyl halide, mesylate or tosylate, or e.g. a N-halobenzensulfonamide, a reaction preferably performed between −78° C. and room temperature, to give ester compounds 403 carrying a substituent R$^{111}$ different from H (step d).

Hydrolyses and decarboxylation as described above gives ketones 404 (step e). Ketone compounds 404 can function as compounds 2 (Scheme 1) either as such or after further structural modification by methods described herein or by methods well known in the art.

Scheme 4c

X is halogen or $OSO_2CF_3$
$X^1$ is Halogen, Mesylate or Tosylate
$R^{110}$ is H, $R^{35}$, $R^{36}$ or $R^{37}$.
$R^{111}$ is H, $R^{35}$, $R^{36}$ or $R^{37}$.
$R^{112}$ is H, $R^{35}$, $R^{36}$ or $R^{37}$.
$R^{113}$ is H, $R^{35}$, $R^{36}$ or $R^{37}$.

Also an embodiment of the present invention is a process to prepare a compound of formula (I) as defined above comprising the reaction of a compound of formula (II) in the presence of a compound of formula (III);

wherein $R^1$, $R^2$, $R^3$, $R^4$, $R^5$, $R^6$, $A^1$, $A^2$, $A^3$, $A^4$, $A^5$ and n are as defined above and wherein, X is halogen or triflate.

In particular, in the presence of copper (I) iodide, potassium or cesium carbonate, a chelating 1,2-diamino compound like N,N'-dimethylethylenediamine or trans-1,2-diaminohexane, at elevated temperatures, preferable with the aid of microwave heating and in solvents like 1,4-dioxane.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of diabetic nephropathy.

The present invention also relates to the use of a compound according to formula (I) as described herein for the treatment or prophylaxis of kidney or heart fibrosis.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of diabetic nephropathy.

Another particular embodiment of the present invention is a compound according to formula (I) as described herein for the treatment or prophylaxis of kidney or heart fibrosis.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

The present invention also relates to the use of a compound according to formula (I) as described herein for the preparation of a medicament for the treatment or prophylaxis of diabetic nephropathy.

The present invention also relates to the use of a compound according to formula (I) as described herein for the preparation of a medicament for the treatment or prophylaxis of kidney or heart fibrosis.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an object of the invention is a method for the treatment or prophylaxis of diabetic nephropathy, which method comprises administering an effective amount of a compound according to formula (I) as described herein.

Also an object of the invention is a method for the treatment or prophylaxis of kidney or heart fibrosis, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Also an embodiment of the present invention is a compound of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC(CRL-1440) and were originally derived from a renal leiomyoblastoma.

The expression plasmids contain the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air.

Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 μM Deoxycorticosterone and variable amounts of inhibitors; Cyp11B1 enzyme activity was tested in presence of 1 μM Deoxycortisol and variable amounts of inhibitors.

| Example | EC50 human CYP11B2 μM | EC50 human CYP11B1 μM |
|---|---|---|
| 1 | 0.0860 | 4.6072 |
| 2 | 0.4421 | 7.3919 |
| 3 | 0.0965 | 3.7211 |
| 4 | 0.0671 | 1.2377 |
| 5 | 0.0925 | 4.2705 |
| 6 | 0.0300 | 1.2079 |
| 7 | 0.0779 | 0.7042 |
| 8 | 0.0449 | 0.8072 |
| 9 | 0.1170 | 4.7416 |
| 10 | 0.0260 | 0.8220 |
| 11 | 0.0127 | 0.2566 |
| 12 | 0.0357 | 0.1177 |
| 13 | 0.0543 | 0.8652 |
| 14 | 0.0550 | 1.0961 |
| 15 | 0.0682 | 0.9130 |
| 16 | 0.0193 | 0.1262 |
| 17 | 0.5967 | 14.0208 |
| 18 | 0.0586 | 0.5071 |
| 19 | 0.0603 | 0.1984 |
| 20 | 0.0859 | 1.0495 |
| 21 | 0.0415 | 0.2632 |
| 22 | 0.0557 | 0.5168 |
| 23 | 0.0640 | 0.5714 |
| 24 | 0.0056 | 0.0214 |
| 25 | 0.4010 | |
| 26 | 0.3214 | 8.1518 |
| 27 | 0.0753 | 0.7309 |
| 28 | 0.1035 | 0.7566 |
| 29 | 0.3184 | 12.9186 |
| 30 | 0.7512 | 2.0686 |
| 31 | 0.0502 | 0.3283 |
| 32 | 0.0468 | 0.5139 |
| 33 | 0.2100 | 0.4847 |
| 34 | 0.0316 | 0.2873 |
| 35 | 0.0188 | 0.1462 |
| 36 | 0.0140 | 0.1881 |
| 37 | 0.0092 | 0.1494 |
| 38 | 1.0661 | 8.3906 |
| 39 | 1.0940 | 10.0398 |
| 40 | 1.6796 | 10.4624 |
| 41 | 3.7521 | 6.0795 |
| 42 | 0.3269 | 7.8639 |
| 43 | 0.3724 | |
| 44 | 5.9322 | 16.9135 |
| 45 | 0.2953 | |
| 46 | 0.6978 | 13.8752 |
| 47 | 1.0252 | 23.2395 |
| 48 | 0.1413 | 1.1052 |
| 49 | 0.0496 | 0.1880 |
| 50 | 1.5035 | |
| 51 | 2.6789 | |
| 52 | 0.3822 | 2.4620 |
| 53 | 0.1204 | 10.7585 |
| 54 | 0.2121 | |
| 55 | 0.3429 | 9.8504 |
| 56 | 0.2968 | 13.7841 |
| 57 | 1.2847 | 7.9991 |
| 58 | 2.0592 | |
| 59 | 0.0081 | 0.1354 |
| 60 | 0.0707 | 0.7938 |
| 61 | 2.8309 | |
| 62 | 0.9355 | |
| 63 | 0.4479 | 4.4257 |
| 64 | 0.1268 | 6.3126 |
| 65 | 0.0973 | 2.3468 |
| 66 | 0.0069 | 0.0697 |
| 67 | 0.1021 | 1.2006 |
| 68 | 0.0067 | 0.1566 |
| 69 | 0.1537 | 7.5432 |
| 70 | 0.4595 | 0.3919 |
| 71 | 0.0902 | 1.5795 |
| 72 | 0.5883 | 16.4938 |
| 73 | 0.0135 | 0.2514 |
| 74 | 0.4490 | |
| 75 | 0.1657 | 2.7583 |
| 76 | 0.4921 | 13.8461 |
| 77 | 0.6653 | 12.7918 |
| 78 | 0.7612 | 1.4503 |
| 79 | 0.0051 | 0.0340 |
| 80 | 0.0047 | 0.0581 |
| 81 | 0.1781 | 2.3633 |
| 82 | 0.0789 | 0.5968 |
| 83 | 0.5896 | 15.7133 |
| 84 | 0.2251 | 4.8264 |
| 85 | 0.0596 | 2.8554 |
| 86 | 0.3767 | 7.7744 |
| 87 | 0.2507 | 9.3698 |
| 88 | 0.7614 | |
| 89 | 0.2715 | 16.8487 |
| 90 | 1.2312 | |
| 91 | 0.3949 | |
| 92 | 0.2682 | 11.3701 |
| 93 | 0.7752 | 14.0060 |
| 94 | 2.0631 | |
| 95 | 0.3272 | 10.2668 |
| 96 | 0.0458 | 0.5326 |
| 97 | 0.0169 | 0.2202 |
| 98 | 0.2274 | 6.8266 |
| 99 | 0.9008 | 7.2722 |
| 100 | 0.0172 | 0.4853 |
| 101 | 0.1042 | 3.5415 |
| 102 | 1.5376 | |
| 103 | 0.5639 | 10.9865 |
| 104 | 2.3394 | 59.7842 |
| 105 | 0.3817 | 4.4881 |

| Example | EC50 human CYP11B2 μM | EC50 human CYP11B1 μM |
|---|---|---|
| 106 | 0.5158 | 8.5638 |
| 107 | 0.0635 | 0.7696 |
| 108 | 0.1626 | 9.7819 |
| 109 | 0.2288 | 1.3489 |
| 110 | 0.1845 | 1.2775 |
| 111 | 0.0642 | 0.9228 |
| 112 | 0.6742 | 11.9975 |
| 113 | 0.3419 | 1.3593 |
| 114 | 0.4240 | 12.7810 |
| 115 | 0.6825 | 13.5418 |
| 116 | 0.1322 | 5.1321 |
| 117 | 0.1267 | 0.8941 |
| 118 | 0.1229 | 1.2484 |
| 119 | 0.7219 | |
| 120 | 0.0247 | 0.2073 |
| 121 | 0.0071 | 0.0390 |
| 122 | 0.0423 | 0.1802 |
| 123 | 0.1220 | 7.7317 |
| 124 | 1.0695 | 0.2249 |
| 125 | 0.1213 | 3.3410 |
| 126 | 0.0379 | 3.5625 |
| 127 | 0.0545 | 0.2657 |
| 128 | 0.1077 | 4.2761 |
| 129 | 0.0636 | 3.1638 |
| 130 | 0.0155 | 0.2398 |
| 131 | 0.0119 | 0.2635 |
| 132 | 0.0378 | 0.5266 |
| 133 | 0.0986 | 1.3716 |
| 134 | 0.0186 | 0.4243 |
| 135 | 0.0931 | 0.5232 |
| 136 | 0.1022 | 2.6575 |
| 137 | 0.0101 | 0.1082 |
| 138 | 0.0162 | 0.1928 |
| 139 | 0.9532 | 11.1720 |
| 140 | 0.0118 | 0.0704 |
| 141 | 0.0405 | 1.3088 |
| 142 | 0.0802 | 0.9809 |
| 143 | 0.2579 | 4.4495 |
| 144 | 0.0237 | 0.1400 |
| 145 | 1.4972 | 1.8956 |
| 146 | 0.0398 | 0.1142 |
| 147 | 0.0367 | 0.2470 |
| 148 | 0.0451 | 0.1391 |
| 149 | 0.1262 | 1.9169 |
| 150 | 0.2266 | 5.3241 |
| 151 | 0.1005 | 3.9244 |
| 152 | 0.2946 | 11.5673 |
| 153 | 0.3021 | 14.9952 |
| 154 | 0.0747 | 0.1929 |
| 155 | 0.1315 | 4.0942 |
| 156 | 0.0439 | 0.3369 |
| 157 | 0.3520 | 11.1514 |
| 158 | 0.1823 | 6.0298 |
| 159 | 0.2090 | 4.4617 |
| 160 | 0.0361 | 0.4182 |
| 161 | 0.1014 | 0.3410 |
| 162 | 0.1866 | 2.0029 |
| 163 | 0.2155 | 3.3596 |
| 164 | 0.1409 | 0.8618 |
| 165 | 0.0035 | 0.0604 |
| 166 | 0.0141 | 0.0963 |
| 167 | 0.0479 | 0.1681 |
| 168 | 0.0034 | 0.0475 |
| 169 | 0.0052 | 0.0381 |
| 170 | 0.0035 | 0.0146 |
| 171 | 0.0172 | 0.0889 |
| 172 | 0.0223 | 0.1441 |
| 173 | 0.3340 | 12.2938 |
| 174 | 0.0258 | 0.2112 |
| 175 | 0.1051 | 0.6564 |
| 176 | 0.0098 | 0.0578 |
| 177 | 0.4116 | 6.3108 |
| 178 | 0.0542 | 0.4797 |
| 179 | 0.6196 | 7.7205 |
| 180 | 0.1233 | 0.8017 |
| 181 | 0.2168 | 1.9663 |
| 182 | 0.0275 | 0.3060 |
| 183 | 0.0299 | 0.3853 |
| 184 | 0.0177 | 0.2712 |
| 185 | 0.0660 | 0.6732 |
| 186 | 0.0232 | 0.2107 |
| 187 | 0.1368 | 2.2324 |
| 188 | 0.2275 | 4.1486 |
| 189 | 0.0553 | 0.7099 |
| 190 | 0.3279 | 7.3219 |
| 191 | 0.3944 | 8.5507 |
| 192 | 2.2023 | 10.3297 |
| 193 | 0.0201 | 0.2168 |
| 194 | 0.0203 | 0.2243 |
| 195 | 0.0373 | 0.4865 |
| 196 | 0.1775 | 1.0297 |
| 197 | 0.0468 | 0.5554 |
| 198 | 2.4539 | 0.9902 |
| 199 | 0.1037 | 0.2818 |
| 200 | 0.0325 | 0.3146 |
| 201 | 0.0304 | 0.2932 |
| 202 | 0.0653 | 0.4734 |
| 203 | 0.0224 | 0.2123 |
| 204 | 0.0408 | 0.9002 |
| 205 | 0.0005 | 0.0006 |
| 206 | 0.0017 | 0.0068 |
| 207 | 0.0028 | 0.0182 |
| 208 | 0.0021 | 0.0189 |
| 209 | 0.0009 | 0.0147 |
| 210 | 0.0186 | 0.1298 |
| 211 | 0.0044 | 0.0532 |
| 212 | 0.0084 | 0.0816 |
| 213 | 0.0391 | 0.2781 |
| 214 | 0.0636 | 0.3003 |
| 215 | 0.0296 | 0.1368 |
| 216 | 0.0381 | 0.3639 |
| 217 | 0.0920 | 0.8026 |
| 218 | 1.5500 | 14.2551 |
| 219 | 2.2159 | 17.5743 |
| 220 | 1.0754 | |
| 221 | 2.1615 | 10.1235 |
| 222 | 0.0803 | 0.3426 |
| 223 | 0.1155 | 1.4171 |
| 224 | 0.0372 | 0.2932 |
| 225 | 2.5506 | |
| 226 | 0.0534 | 3.4026 |
| 227 | 4.2089 | |
| 228 | 0.2634 | 12.3727 |
| 229 | 0.2038 | 0.7447 |
| 230 | 0.0070 | 0.1495 |
| 231 | 0.0233 | 0.4686 |
| 232 | 0.0266 | 1.3509 |
| 233 | 0.2705 | 21.5699 |
| 234 | 0.0445 | 1.5779 |
| 235 | 0.0227 | 0.2211 |
| 236 | 0.1334 | 4.3865 |
| 237 | 0.2044 | 3.6068 |
| 238 | 0.1044 | 5.9872 |
| 239 | 0.0105 | 0.0900 |
| 240 | 0.1148 | 3.2729 |
| 241 | 0.5820 | |
| 242 | 0.0256 | 0.2062 |
| 243 | 0.2678 | 3.3424 |
| 244 | 1.8627 | 4.6905 |
| 245 | 0.0011 | 0.0257 |
| 246 | 0.1023 | 0.5463 |
| 247 | 4.5758 | 7.4708 |
| 248 | | 2.6663 |
| 249 | 3.2181 | 7.6048 |
| 250 | 4.4379 | 12.3402 |
| 251 | 5.8839 | 15.8337 |
| 252 | 0.2721 | 9.7643 |
| 253 | 0.5808 | 10.0383 |

61 -continued

| Example | EC50 human CYP11B2 µM | EC50 human CYP11B1 µM |
| --- | --- | --- |
| 254 | 2.1317 | 32.5224 |
| 255 | 2.8003 | 7.6090 |
| 256 | 0.7744 | |
| 257 | 0.0113 | 0.0954 |
| 258 | 0.0037 | 0.0418 |
| 259 | 0.0122 | 0.0738 |
| 260 | 0.4711 | 0.3450 |
| 261 | 0.0267 | 0.1052 |
| 262 | 0.0141 | 0.3002 |
| 263 | 0.4910 | 4.9268 |
| 264 | 0.8428 | 4.1868 |
| 265 | 0.4373 | 5.0201 |
| 266 | 0.0444 | 0.2756 |
| 267 | 1.6052 | 11.2653 |
| 268 | 1.6485 | 14.1758 |
| 269 | 0.0462 | 0.4253 |
| 270 | 0.0063 | 0.0279 |
| 271 | 0.0248 | 0.2512 |
| 272 | 0.0604 | 0.2099 |
| 273 | 0.0640 | 0.4487 |
| 274 | 0.1275 | 1.0511 |
| 275 | 0.7311 | 7.8164 |
| 276 | 0.2837 | 2.0297 |
| 277 | 0.0641 | 0.1634 |
| 278 | 0.0061 | 0.0344 |
| 279 | 0.6004 | 11.1051 |
| 280 | 1.7985 | |
| 281 | 0.0004 | 0.003 |
| 282 | 0.0429 | 0.4748 |
| 283 | 0.0667 | 0.6328 |
| 284 | 0.0205 | 0.2494 |
| 285 | 0.0076 | 0.3556 |
| 286 | 0.2655 | 3.0382 |
| 287 | 0.5546 | 6.4082 |
| 288 | 0.539 | 8.8668 |
| 289 | 0.0706 | 0.1856 |
| 290 | 0.1012 | 3.91 |
| 291 | 0.0032 | 0.1218 |
| 292 | 0.5152 | 36.2254 |
| 293 | 0.0164 | 0.2848 |
| 294 | 0.2042 | 9.8508 |
| 295 | 0.0488 | 0.8488 |
| 296 | 0.1316 | 4.4957 |
| 297 | 0.2072 | 12.784 |
| 298 | 0.1747 | 13.7042 |
| 299 | 0.7869 | 48.5358 |
| 300 | 0.2161 | 14.2793 |
| 301 | 0.1606 | 32.5099 |
| 302 | 0.0932 | 5.1857 |
| 303 | 0.0936 | 12.5809 |
| 304 | 0.0024 | 0.0781 |
| 305 | 0.0054 | 0.8598 |
| 306 | 0.0058 | 0.1138 |
| 307 | 0.3892 | 15.4452 |
| 308 | 0.3805 | 26.3474 |
| 309 | 0.016 | 2.4468 |
| 310 | 0.0165 | 3.9684 |
| 311 | 0.8134 | 6.4778 |
| 312 | 0.0482 | 4.008 |
| 313 | 0.1184 | 3.5436 |
| 314 | 0.0282 | 5.2254 |
| 315 | 1.0508 | 31.0217 |
| 316 | 0.0402 | 1.831 |
| 317 | 0.1088 | 2.6377 |
| 318 | >30 | |
| 319 | 0.1089 | 5.1301 |
| 320 | 8.0313 | |
| 321 | 0.0556 | 3.995 |
| 322 | 5.1407 | 39.6231 |
| 323 | 0.0442 | 2.3486 |
| 324 | 2.8107 | |
| 325 | 0.0592 | 4.4874 |
| 326 | 1.8693 | 6.6127 |
| 327 | 1.3648 | 10.6987 |

62 -continued

| Example | EC50 human CYP11B2 µM | EC50 human CYP11B1 µM |
| --- | --- | --- |
| 328 | 0.1731 | 18.44 |
| 329 | 6.0154 | 11.9661 |
| 330 | >30 | |
| 331 | 4.3466 | 35.0631 |
| 332 | 14.7777 | |
| 333 | 0.0958 | 5.2386 |
| 334 | 0.3831 | 34.5562 |
| 335 | 13.8179 | |
| 336 | 0.9489 | 29.9696 |
| 337 | 24.2997 | |
| 338 | >30 | |
| 339 | 0.0545 | 7.9851 |
| 340 | 0.0883 | 14.1639 |
| 341 | 0.0321 | 1.6765 |
| 342 | 0.0151 | 0.0947 |
| 343 | 0.1338 | 4.688 |
| 344 | 0.0312 | 1.5032 |
| 345 | 0.0494 | 2.003 |
| 346 | 0.0263 | 2.571 |
| 347 | 0.162 | 22.9422 |
| 348 | 2.8265 | 36.9471 |
| 349 | 0.9822 | 15.1179 |
| 350 | 0.0594 | 3.6822 |
| 351 | 3.6617 | |
| 352 | 0.0965 | 39.4185 |
| 353 | 0.3963 | 16.1819 |
| 354 | 0.0122 | 0.3454 |
| 355 | 0.0153 | 8.1702 |
| 356 | 2.0005 | 0.7368 |
| 357 | 0.0982 | 3.224 |
| 358 | 0.005 | 0.4326 |
| 359 | 0.006 | 0.4113 |
| 360 | 0.8527 | 16.1218 |
| 361 | 0.0656 | 9.4139 |
| 362 | 0.0532 | 6.0869 |
| 363 | 0.1707 | 2.3291 |
| 364 | 0.1303 | 5.5675 |
| 365 | 0.3368 | 15.9004 |
| 366 | 0.0044 | 0.082 |
| 367 | 0.0621 | 5.2403 |
| 368 | 0.0121 | 0.7227 |
| 369 | 0.0403 | 12.4126 |
| 370 | 0.1955 | |
| 371 | 4.2585 | |
| 372 | 0.1 | 22.847 |
| 373 | >30 | |
| 374 | 0.3541 | |
| 375 | 5.6207 | |
| 376 | 0.026 | 7.9592 |
| 377 | 0.0034 | 0.4478 |
| 378 | 0.2125 | 14.6493 |
| 379 | 0.0258 | 0.3698 |
| 380 | 0.0366 | 2.4244 |
| 381 | 0.0034 | 0.1379 |
| 382 | 0.0339 | 1.5202 |
| 383 | 0.021 | 0.7714 |
| 384 | 0.024 | 3.1595 |
| 385 | 0.8927 | |
| 386 | 0.006 | 0.4181 |
| 387 | 0.0922 | 2.8398 |
| 388 | 0.2717 | 3.9689 |
| 389 | 0.1154 | 2.9541 |
| 390 | 0.3159 | 5.4731 |
| 391 | 0.0297 | 1.452 |
| 392 | 0.0092 | 0.3266 |
| 393 | 0.2654 | 8.4296 |
| 394 | 0.0456 | 2.924 |
| 395 | 0.008 | 0.679 |
| 396 | 0.2065 | 5.251 |
| 397 | 0.2819 | 7.9485 |
| 398 | 0.2809 | 2.3021 |
| 399 | 0.3133 | 11.2522 |
| 400 | 0.0589 | 2.7442 |
| 401 | 0.3602 | 9.105 |

-continued

| Example | EC50 human CYP11B2 μM | EC50 human CYP11B1 μM |
|---|---|---|
| 402 | 0.0342 | 2.2146 |
| 403 | 0.0317 | 1.9302 |
| 404 | 0.2977 | 5.4805 |
| 405 | 0.5464 | 35.1743 |
| 406 | 0.1651 | 3.1455 |
| 407 | 0.9865 | 20.6904 |
| 408 | 0.9228 | 14.2627 |
| 409 | 0.0069 | 0.4291 |
| 410 | 0.0165 | 1.7304 |
| 411 | 0.0196 | 0.772 |
| 412 | 0.0466 | 1.6678 |
| 413 | 0.0207 | 0.8128 |
| 414 | 0.0302 | 2.0382 |
| 415 | 0.0055 | 0.4838 |
| 416 | 0.006 | 0.7234 |
| 417 | 0.2243 | 9.0943 |
| 418 | 0.004 | 0.062 |
| 419 | 0.0091 | 0.122 |
| 420 | 0.0274 | 0.281 |
| 421 | 0.0007 | 0.0324 |
| 422 | 0.1544 | 11.0996 |
| 423 | 0.0637 | 1.0188 |
| 424 | 0.0062 | 0.1405 |
| 425 | 0.0562 | 1.2703 |
| 426 | 0.0121 | 0.5715 |
| 427 | 0.0024 | 0.0472 |
| 428 | 0.02 | 0.1054 |
| 429 | 0.0043 | 0.0577 |
| 430 | 0.0069 | 0.7375 |
| 431 | 0.0444 | 0.9117 |
| 432 | 0.0222 | 1.4548 |
| 433 | 0.0143 | 1.313 |
| 434 | 0.0066 | 0.2277 |
| 435 | 0.0088 | 0.256 |
| 436 | 0.0058 | 0.1582 |
| 437 | 0.0776 | 1.6426 |
| 438 | 0.0038 | 0.202 |
| 439 | 0.1189 | 6.9015 |
| 440 | 0.0176 | 1.2703 |
| 441 | 0.0166 | 0.9878 |
| 442 | 0.0056 | 0.4274 |
| 443 | 0.009 | 1.175 |
| 444 | 0.0084 | 0.5143 |
| 445 | 0.0074 | 0.9144 |
| 446 | 0.1852 | 0.2628 |
| 447 | 0.0019 | 0.2332 |
| 448 | 0.0212 | 1.9778 |
| 449 | 0.0028 | 0.2347 |
| 450 | 0.1219 | 20.1047 |
| 451 | 0.0389 | 5.3319 |
| 452 | 0.0268 | 1.7391 |
| 453 | 0.0051 | 0.8761 |
| 454 | 0.0066 | 0.062 |
| 455 | 0.0086 | 0.7169 |
| 456 | 0.0012 | 0.1056 |
| 457 | 0.0018 | 0.2975 |
| 458 | 0.0017 | 0.3511 |
| 459 | 0.0056 | 0.5941 |
| 460 | 0.0123 | 0.5161 |
| 461 | 0.004 | 0.3608 |
| 462 | 0.0326 | 0.7196 |
| 463 | 0.0471 | 0.9322 |
| 464 | 0.0028 | 1.6504 |
| 465 | 0.0669 | 2.2689 |
| 466 | 0.4666 | 21.2595 |
| 467 | 0.0288 | 2.1821 |
| 468 | 0.0528 | 2.6647 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein are inhibitors of CYP11B2. The compounds of formula (I) or their pharmaceutically acceptable salts and esters herein display also variable inhibition of CYP11B1. These compounds may be used for the inhibition of CYP11B2 in combination with variable inhibition of CYP11B1. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), vascular conditions, endothelial dysfunction, baroreceptor dysfunction, renal conditions, liver conditions, fibrotic diseases, inflammatory conditions, retinopathy, neuropathy (such as peripheral neuropathy), pain, insulinopathy, edema, edematous conditions, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, cardiac fibrosis, hypertrophic cardiomyopathy, impaired arterial compliance, impaired diastolic filling, ischemia, left ventricular hypertrophy, myocardial and vascular fibrosis, myocardial infarction, myocardial necrotic lesions, cardiac arrhythmias, prevention of sudden cardiac death, restenosis, stroke, vascular damage.

Renal conditions include acute and chronic renal failure, nephropathy, end-stage renal disease, diabetic nephropathy, decreased creatinine clearance, decreased glomerular filtration rate, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, proteinuria, reduced renal blood flow, renal arteriopathy, swelling and proliferation of intracapillary (endothelial and mesangial) and/or extracapillary cells (crescents).

Renal conditions also include glomerulonephritis (such as diffuse proliferative, focal proliferative, mesangial proliferative, membranoproliferative, minimal change membranous glomerulonephritis), lupus nephritis, non-immune basement membrane abnormalities (such as Alport syndrome), renal fibrosis and glomerulosclerosis (such as nodular or global and focal segmental glomerulosclerosis).

Liver conditions include, but are not limited to, liver steatosis, nonalcoholic steatohepatitis, liver cirrhosis, liver ascites, hepatic congestion and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, liver ascites, splenic congestion, respiratory or lung congestion, and the like.

Insulinopathies include, but are not limited to, insulin resistance, Type I diabetes mellitus, Type II diabetes mellitus, glucose sensitivity, pre-diabetic state, pre-diabetes, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In particular embodiment, the cardiovascular condition is treatment-resistant hypertension.

In another embodiment, the cardiovascular condition is heart failure.

In another embodiment, the cardiovascular condition is left ventricular hypertrophy.

In another embodiment, the cardiovascular condition is congestive heart failure, more particularly in patients with preserved left ventricular ejection fraction.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the renal condition is auto-immune glomerulonephritis.

In another embodiment, the chronic kidney disease is diabetic nephropathy.

In another embodiment, the fibrotic disease is kidney or heart fibrosis.

In another embodiment, the compounds of formula (I) or their pharmaceutically acceptable salts and esters can be used for the treatment or prophylaxis Type II diabetes mellitus.

In another embodiment, the compounds of formula (I) or their pharmaceutically acceptable salts and esters can be used for the treatment or prophylaxis Type I diabetes mellitus.

In another embodiment, the compounds of formula (I) or their pharmaceutically acceptable salts and esters can be used for the treatment or prophylaxis of diabetic retinopathy.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate A-1

6-Chloro-5-fluoro-3,4-dihydro-2H-isoquinolin-1-one

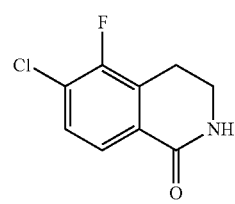 [SMILES: O=C1NCCc2c1ccc(Cl)c2F]

[A] (3-Chloro-2-fluoro-phenyl)-methanol

To a solution of 2-fluoro-3-chloro-benzaldehyde (4.74 g, 30 mmol) in THF (20 mL) was added NaBH₄ (1.48 g, 40 mmol). The resulting mixture was stirred at room temperature for 30 min before diluting with DCM. The organic layer was washed with water and brine. The combined organic layers were dried over anhy. Na₂SO₄, filtered and concentrated in vacuo to give desired product without further purification (4.8 g, 100%). MS: 161.0 (M+H)⁺.

[B] 1-Bromomethyl-3-chloro-2-fluoro-benzene

To a solution of (3-chloro-2-fluoro-phenyl)-methanol (3.2 g, 20 mmol) in DCM (20 mL) was added dropwise PBr₃ (1 mL) at 0° C. The reaction mixture was stirred at room temperature for another 1 hour before quenching with satd. aq. NaHCO₃ solution. The organic layer was washed with brine, dried over anhy. Na₂SO₄, filtered and concentrated in vacuo to give the desired product without further purification (4.1 g, 92%). MS: 223.2 (M+H)⁺.

[C] (3-Chloro-2-fluoro-phenyl)-acetonitrile

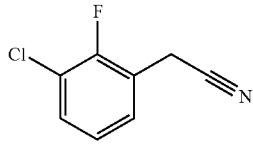 [SMILES: N#CCc1cccc(Cl)c1F]

To a solution of 1-chloro-3-bromomethyl-2-fluoro-benzene (2.22 g, 10 mmol) in CH₃CN (30 mL) was added trimethylsilyl cyanide (1.5 mL) and TBAF (1M in THF, 12 mmol, 12 mL). The resulting reaction mixture was heated at reflux temperature for 30 min. After cooling to room temperature, the volatiles were evaporated under reduced pressure. The residue was partitioned between EtOAc and water. The organic layer was then washed with brine, dried over anhy. Na₂SO₄, filtered and concentrated in vacuo. The crude product was purified by flash column chromatography to give the title compound (1.48 g, 88%). MS: 170.1 (M+H)⁺.

[D] 2-(3-Chloro-2-fluoro-phenyl)-ethylamine

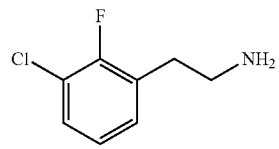 [SMILES: NCCc1cccc(Cl)c1F]

To a solution of (3-chloro-2-fluoro-phenyl)-acetonitrile (1.48 g, 8.8 mmol) in anhydrous THF (20 mL) was added a solution of borane (20 mL, 1M in THF) dropwise. The resulting reaction mixture was heated at reflux temperature for 2 hours. After cooling to room temperature, MeOH was added and the mixture was stirred at room temperature for additional 30 min. After removal of volatiles under reduced pressure, desired title product (1.30 g, 90%) was obtained as oil. MS: 174.0 (M+H)⁺.

[E] [2-(3-Chloro-2-fluoro-phenyl)-ethylamine]-carbamic methyl ester

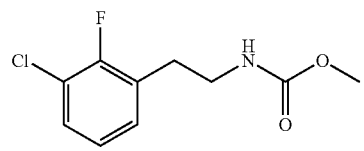

To a solution of 2-(3-chloro-2-fluoro-phenyl)-ethylamine (1.30 g, 7.9 mmol) in CH₂Cl₂ (25 mL) was added dropwise methyl chloroformate (1.04 g, 11 mmol) and Et₃N at 5° C. with vigorous stirring. The solution was then stirred at room temperature for 1 h. The reaction was poured into ice-water (50 mL) and extracted with CH₂Cl₂ (2×25 mL). The organic phase was washed with H₂O (2×25 mL), dried over Na₂SO₄, filtered and evaporated to afford the final product without purification (1.78 g, 98%). MS: 232.1 (M+H)⁺.

[F] 6-Chloro-5-fluoro-3,4-dihydro-2H-isoquinoline-1-one

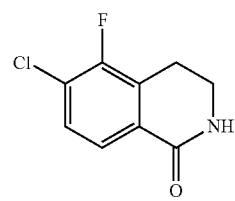 [SMILES: O=C1NCCc2c1ccc(Cl)c2F]

[2-(3-Chloro-2-fluoro-phenyl)-ethylamine]-carbamic methyl ester (890 mg, 3.85 mmol) and polyphosphoric acid (15 mL) were added to a 1-L, round bottom flask equipped with a magnetic stirring bar and reflux condenser. The reaction mixture was heated in an oil bath at 140-160° C. for 2 hours while keeping vigorous stirring. The reaction mixture was then allowed to cool to room temperature and poured into H₂O (100 mL). After extraction with EtOAc, the organic layer was washed with brine, dried over anhy. MgSO₄, filtered and concentrated to give a yellowish oil which was crystallized from Et₂O to give title compound as a white solid (30 mg, 4%). MS: 200.1 (M+H)⁺.

Intermediate A-2

6-Chloro-3,4-dihydro-2H-isoquinolin-1-one

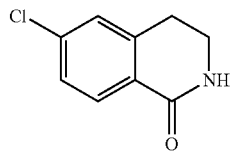 [SMILES: O=C1NCCc2cc(Cl)ccc21]

[A] [2-(3-Chloro-phenyl)-ethyl]-carbamic acid methyl ester

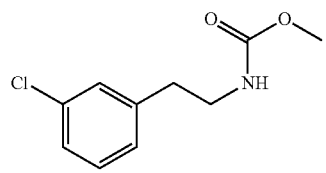

At 0, methyl chloroformate (4.6 g, 48 mmol) was added dropwise to a solution of 2-(3-chloro-phenyl)-ethylamine (5.0 g, 32 mmol) and Et₃N (6.4 g, 64 mmol) in DCM (100 mL). After the addition, the mixture was stirred at room temperature for 0.5 hour. The organic layer was washed with water (3×30 mL), 1N HCl (20 mL) and brine (30 mL), dried over anhy. Na₂SO₄, filtered and concentrated in vacuo. After vacuum drying, the title compound was obtained (6.49 g, 95%) as a white solid. MS: 214.1 (M+H⁺).

[B] 6-Chloro-3,4-dihydro-2H-isoquinolin-1-one

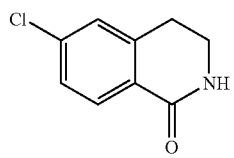 [SMILES: O=C1NCCc2cc(Cl)ccc21]

Under N₂ protection, a mixture of [2-(3-chloro-phenyl)-ethyl]-carbamic acid methyl ester (5.0 g, 23.4 mmol) and PPA (polyphosphoric acid) (20 g) in a 250 mL round-bottom flask was vigorously stirred at 120° C. for 2 hours. After cooling to room temperature, the reaction mixture was treated with ice-water and aqueous ammonia solution to adjust the pH to 8. Then, the mixture was then extracted with EtOAc, and the organic layer was washed with brine, dried over anhy. Na₂SO₄ and filtered. After removal of solvent under reduced pressure, the crude product obtained was further washed with ethyl ether to give title compound (1.66 g, 39%) as a white solid. MS: 182.0 (M+H⁺).

Intermediate A-3-1

6-Chloro-3-methyl-3,4-dihydro-2H-isoquinolin-1-one

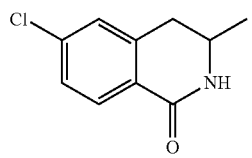

Intermediate A-3-2

8-Chloro-3-methyl-3,4-dihydro-2H-isoquinolin-1-one

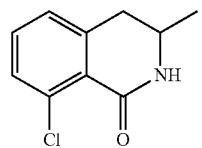

[A] 2-(3-Chloro-phenyl)-1-methyl-ethylamine

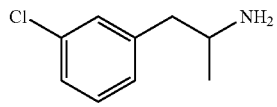

To a solution of 3-chlorobenzylmagnesium chloride (0.1 mol) in anhydrous ether (100 mL) (prepared from 3-chlorobenzyl chloride (16.1 g, 0.1 mol) and magnesium turnings (2.4 g, 0.1 mol) in anhydrous ether (100 mL)) was added anhydrous acetonitrile (4.1 g, 0.1 mol) dropwise at room temperature. When the reaction mixture was stirred at 60° C. for 3 hours, it was cooled to 0° C. followed by addition of THF (50 mL). Lithium aluminum hydride (4.2 g, 0.1 mol) was then added cautiously into the above reaction mixture and it was heated to reflux temperature for 3 hours. Ice-water was added to quench the reaction. After partitioning between ether and H₂O, the separated organic layer was washed with brine, dried over anhy. Na₂SO₄, filtered and concentrated in vacuo.

Flash column chromatography separation (silica gel, 180 g, 5% methanol in DCM) then yielded the title compound as yellowish oil (1.9 g, 11%). MS: 170.1 (M+H⁺).

[B] [2-(3-Chloro-phenyl)-1-methyl-ethyl]-carbamic acid methyl ester

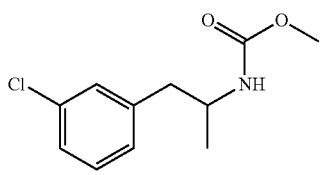

At 0° C., methyl chloroformate (0.67 g, 7.1 mmol) was added dropwise to a mixture of 2-(3-chloro-phenyl)-1-methyl-ethylamine (1.0 g, 5.9 mmol) and potassium carbonate (1.63 g, 11.8 mmol) in THF (20 mL). After the addition, the mixture was stirred at room temperature overnight. After filtration and evaporation of the volatiles, the crude product was purified by flash column chromatography (silica gel, 12 g, 50% hexane in dichloromethane) to give the title compound as a white solid (1.2 g, 90%). MS: 228.1 (M+H⁺).

[C] 6-Chloro-3-methyl-3,4-dihydro-2H-isoquinolin-1-one and 8-chloro-3-methyl-3,4-dihydro-2H-isoquinolin-1-one

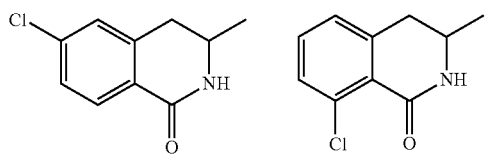

Under N₂ protection, a mixture of [2-(3-chloro-phenyl)-1-methyl-ethyl]-carbamic acid methyl ester (1.2 g, 5.3 mmol) and PPA (polyphosphoric acid) (10 g) in a 100 mL round bottom flask was stirred at 120° C. for 2 hours. After cooling to room temperature, the reaction mixture was treated with ice-water and aqueous ammonia solution to adjust the pH to 8. The mixture was then extracted with ethyl acetate and the organic layer was washed with brine, dried over anhy. Na₂SO₄, filtered and concentrated in vacuo. The crude product obtained was further washed with ether to give 6-chloro-3-methyl-3,4-dihydro-2H-isoquinolin-1-one (0.27 g, 26%) (intermediate A-3-1) as a white solid. MS: 196.1 (M+H⁺). The ether filtrate was concentrated under reduced pressure and purified by flash chromatography to afford 8-chloro-3-methyl-3,4-dihydro-2H-isoquinolin-1-one (intermediate A-3-2) (54 mg, 5.2%) as a white solid. MS: 196.1 (M+H⁺).

Intermediate A-3-1a (R)-6-Chloro-3-methyl-3,4-dihydro-2H-isoquinolin-1-one

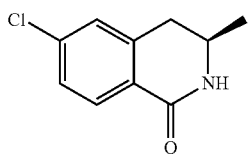

Intermediate A-3-1b (S)-6-Chloro-3-methyl-3,4-dihydro-2H-isoquinolin-1-one

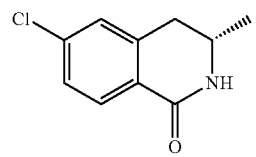

Chiral HPLC separation of 6-chloro-3-methyl-3,4-dihydro-2H-isoquinolin-1-one (0.4 g, 2.05 mmol, intermediate A-3-1) afforded both (R)-6-chloro-3-methyl-3,4-dihydro-2H-isoquinolin-1-one (0.15 g, 37.5%) and (S)-6-chloro-3-methyl-3,4-dihydro-2H-isoquinolin-1-one (0.12 g, 30%) as white solids. MS: 196.1 (M+H⁺).

Intermediate A-4

6-Chloro-4-methyl-3,4-dihydro-2H-isoquinolin-1-one

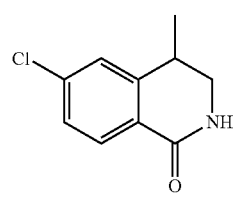

[A] 2-(3-Chloro-phenyl)-propionitrile

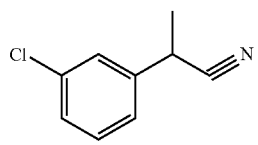

To a solution of 3-chlorobenzylnitrile (15.2 g, 0.1 mol) in THF (300 mL) was added dropwise lithium bis(trimethylsilyl)amide (100 mL, 1M in THF, 0.1 mol) at −78° C. After stirring at −78° C. for 1 hour, iodomethane (14.2 g, 0.1 mol) was added dropwise. After additional stirring at −78° C. for 1 hour and subsequent warming up to room temperature for 2 hours, the reaction was quenched with water and extracted with ether. The organic layer was dried over anhy. Na₂SO₄, filtered and concentrated in vacuo. Flash column chromatography separation (silica gel, 180 g, 1% to 4% ether in hexane) then gave the title compound as an oil (7.3 g, 44%).

[B] 2-(3-Chloro-phenyl)-propylamine hydrochloride

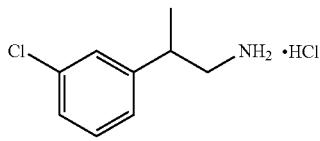

To a solution of 2-(3-chloro-phenyl)-propionitrile (5.0 g, 30.2 mmol) in THF (80 mL) was added borane-tetrahydrofuran complex solution (45 mL, 45.3 mmol). The reaction mixture was stirred at room temperature overnight. Ethanol (10 mL) was then added to the reaction mixture; after stirring at room temperature for 20 min, a solution of HCl in ether (2 M, 12.5 mL) was added. After stirring for another 1 hour, water was added to induce the precipitation of the product. The white solid was collected by filtration and dried in vacuo to give the title compound (3.6 g, 70%). MS (for free amine): 170.1 (M+H$^+$).

[C] [2-(3-Chloro-phenyl)-propyl]-carbamic acid methyl ester

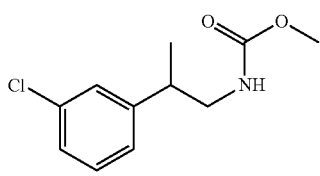

To a solution of 2-(3-chloro-phenyl)-ethylamine hydrochloride (6.22 g, 30.2 mmol) and Et$_3$N (6.1 g, 60.4 mmol) in DCM (20 mL) was added methyl chloroformate (4.28 g, 45 mmol) dropwise at 0° C., and the resulting mixture was stirred at room temperature for 0.5 hour. The reaction mixture was then washed with water (3×10 mL), 1N HCl (10 mL) and brine (10 mL). The organic layer was dried over anhy. Na$_2$SO$_4$, filtered and concentrated in vacuo. The residue formed was dried in vacuo to give the title compound (5.5 g, 80%) as yellow oil. MS: 228.1 (M+H$^+$).

[D] [6-Chloro-4-methyl-3,4-dihydro-2H-isoquinolin-1-one

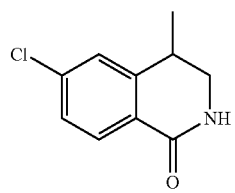

Under N$_2$ protection, a mixture of [2-(3-chloro-phenyl)-propyl]-carbamic acid methyl ester (3.0 g, 13.2 mmol) and PPA (polyphosphoric acid) (10 g) in a 100 mL flask was stirred at 120° C. for 2 hours. After cooling to room temperature, the reaction mixture was treated with ice-water and aqueous ammonia solution to adjust the pH to 8. The mixture was extracted with EtOAc, and the organic layer was washed with brine, dried over anhy. Na$_2$SO$_4$, filtered and concentrated in vacuo. The crude product formed was further washed with ether to give the title compound (0.52 g, 20%) as a white solid. MS: 196.1 (M+H$^+$).

Intermediate A-5

6-Chloro-4,4-dimethyl-3,4-dihydro-2H-isoquinolin-1-one

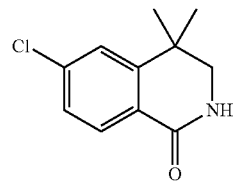

[A] 2-(3-Chloro-phenyl)-2-methyl-propionitrile

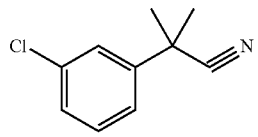

To a solution of 3-chlorobenzylnitrile (15.2 g, 0.1 mol) in DMF (100 mL) at 0° C. was added sodium hydride (6.0 g, 0.15 mol) portionwise. After stirring at 0° C. for 0.5 hours, iodomethane (14.2 g, 0.1 mol) was added dropwise. The reaction mixture was warmed up to room temperature and stirred for additional 2 hours before quenching with water. The mixture was extracted ether and H$_2$O, the organic layer was dried over anhy. Na$_2$SO$_4$, filtered and concentrated in vacuo. The crude product was purified by flash column chromatography (silica gel, 180 g, 1% to 4% ether in hexane) to yield the title compound as oil (6.4 g, 36%).

[B] 2-(3-Chloro-phenyl)-2-methyl-propylamine

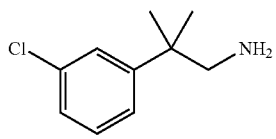

To a solution of 2-(3-chloro-phenyl)-2-methyl-propionitrile (6.4 g, 35.7 mmol) in THF (80 mL) was added borane-tetrahydrofuran complex solution (71.3 mL, 71.3 mmol), and the resulting mixture was heated to reflux for 5 hours. After cooling to 0° C., aq. HCl (2 M, 10 mL) was added dropwise to quench the reaction. The mixture was then concentrated in vacuo to afford a solid residue, which was treated with aq. ammonia solution (6M in H$_2$O). After extraction with ethyl acetate, the organic layer was dried over anhy. Na$_2$SO$_4$, filtered and concentrated in vacuo. The crude product was purified by flash column chromatography (silica gel, 180 g, 5% methanol in dichloromethane) to yield the title compound as oil (2.8 g, 43%). MS: 184.1 (M+H+).

[C] [2-(3-Chloro-phenyl)-2-methyl-propyl]-carbamic acid methyl ester

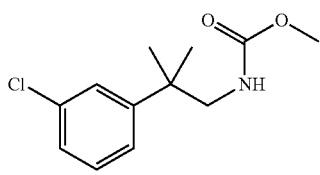 [SMILES: COC(=O)NCC(C)(C)c1cccc(Cl)c1]

To a solution of 2-(3-chloro-phenyl)-2-methyl-propylamine (1.4 g, 7.63 mmol) and Et₃N (1.54 g, 15.26 mmol) in DCM (20 mL) was added dropwise methyl chloroformate (1.08 g, 11.4 mmol) at 0° C. After the addition, the mixture was stirred at room temperature for 0.5 hour. The reaction mixture was then washed with water (3×10 mL), 1N HCl (10 mL) and brine (10 mL). The organic layer was dried over anhy. Na₂SO₄, filtered and concentrated in vacuo. The residue formed was dried in vacuo give the title compound (1.84 g, 100%) as yellow oil. MS: 242.1 (M+H+).

[D] 6-Chloro-4,4-dimethyl-3,4-dihydro-2H-isoquinolin-1-one

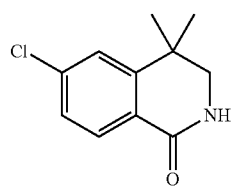

Under N₂ protection, a mixture of [2-(3-chloro-phenyl)-2-methyl-propyl]-carbamic acid methyl ester (1.84 g, 7.63 mmol) and PPA (polyphosphoric acid) (8 g) in a 100 mL round bottom flask was stirred at 120° C. for 2 hours. After cooling to room temperature, the mixture was treated with ice-water and aq. ammonia solution to adjust the pH to 8. After extraction with ethyl acetate, the organic layer was washed with brine, dried over anhy. Na₂SO₄, filtered and concentrated in vacuo. The crude product formed was further washed with ether to give the title compound (0.32 g, 20%) as a white solid. MS: 210.1 (M+H+).

Intermediate A-6

6-Chloro-2H-isoquinolin-1-one

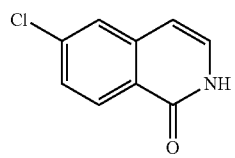 [SMILES: O=c1[nH]ccc2cc(Cl)ccc12]

A mixture of 6-chloro-3,4-dihydro-2H-isoquinolin-1-one (181.5 mg, 1 mmol, intermediate A-2) and DDQ (227 mg, 1 mmol) in dioxane (3 mL) was refluxed overnight. After cooling to room temperature, the reaction mixture was treated with satd. aq. NaHCO₃ solution, and then extracted with ethyl acetate (2×10 mL). The organic layers were dried over anhy. Na₂SO₄, filtered, and concentrated in vacuo to afford a crude product which was then purified by silica gel flash chromatography to give title compound (108 mg, 60%) as a white solid. MS: 180.0 (M+H+).

Intermediate A-7

6-Chloro-7-fluoro-3,4-dihydro-2H-isoquinolin-1-one

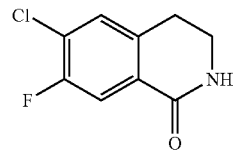

[A] 4-Bromomethyl-2-chloro-1-fluoro-benzene

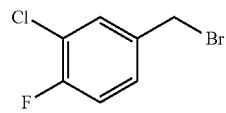

To a solution of (3-chloro-4-fluoro-phenyl)-methanol (4.3 g, 26.8 mmol) in DCM (20 mL) was added PBr₃ (1 mL) at 0° C. The resulting mixture was stirred at room temperature for 1 hour before it was quenched with satd. aq. NaHCO₃ solution. The organic solution was washed with water, brine, dried over anhy. Na₂SO₄ and concentrated in vacuo to give the desired product (3.7 g, 61.9%). It was used directly in the next step, without further purification.

[B] (3-Chloro-4-fluoro-phenyl)-acetonitrile

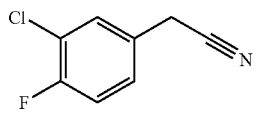 [SMILES: N#CCc1ccc(F)c(Cl)c1]

To a solution of 4-bromomethyl-2-chloro-1-fluoro-benzene (3.7 g, 16.5 mmol) in CH₃CN (30 mL) was added trimethylsilyl cyanide (2.1 mL) and TBAF (4.8 g, 18.4 mmol). The resulting mixture was heated at reflux for 30 min. After cooling of the mixture to room temperature, it was extracted with EtOAc. The organic layer was washed with brine, dried over anhy. Na₂SO₄, filtered and concentrated in vacuo to give a crude product which was then purified by silica gel flash column chromatography to give the title compound (1.7 g, 60.7%) as an oil.

[C] 2-(3-Chloro-4-fluoro-phenyl)-ethylamine

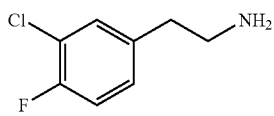 [SMILES: NCCc1ccc(F)c(Cl)c1]

To a solution of (3-chloro-4-fluoro-phenyl)-acetonitrile (1 g, 5.9 mmol) in THF (30 mL) was slowly added $BH_3$-THF (8.26 ml). After the addition, the reaction mixture was heated to reflux for 3 hours. MeOH was added to quench the reaction and volatiles were removed under reduced pressure. The crude product was first dissolved in aq. HCl solution (30 mL) and impurities were removed by exaction with EtOAc (2×30 mL). The pH of the aqueous solution was adjusted to 8 using $K_2CO_3$ and the mixture was then extracted with DCM (3×30 mL). The combined organic layers were then washed with brine, dried with anhy. $Na_2SO_4$, filtered and concentrated in vacuo to give the title compound (570 mg, 55.8%) as an oil.

[D] N-[2-(3-Chloro-4-fluoro-phenyl)-ethyl]-2,2,2-trifluoro-acetamide

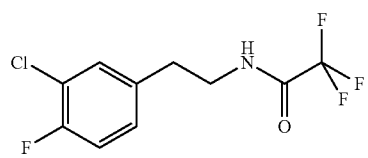 [SMILES: O=C(NCCc1ccc(F)c(Cl)c1)C(F)(F)F]

To a solution of 2-(3-chloro-4-fluoro-phenyl)-ethylamine (570 mg, 3.3 mmol) and $Et_3N$ (1 mL) in $CH_2Cl_2$ (25 mL) was added trifluoroacetic anhydride (761 mg, 3.6 mmol) at 5° C. dropwise and with vigorous stirring. Then, the solution was allowed to stir at room temperature for 3 hours before it was poured into ice-water (50 mL) and extracted with DCM (2×25 mL). The organic layer was washed with $H_2O$ (2×25 mL), dried over anhy. $Na_2SO_4$, filtered and concentrated in vacuo to give the title compound (700 mg, 78.6%) as a white solid. It was used directly in the next step without further purification.

[E] 1-(6-Chloro-7-fluoro-3,4-dihydro-1H-isoquinolin-2-yl)-2,2,2-trifluoro-ethanone

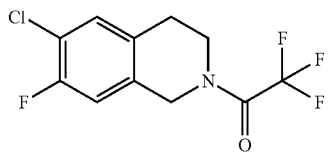 [SMILES: O=C(N1CCc2cc(Cl)c(F)cc2C1)C(F)(F)F]

N-[2-(3-Chloro-4-fluoro-phenyl)-ethyl]-2,2,2-trifluoro-acetamide (400 mg, 1.48 mmol) and paraformaldehyde (89 mg, 2.96 mmol) were added sequentially at 0° C. to a solution of acetic acid (3 mL) in sulfuric acid (2 mL). After stirring of the reaction mixture at room temperature for 16 hours, the clear colorless solution was poured into ice-water (20 mL). The mixture was extracted with EtOAc (2×30 mL) and the organic layer was washed with satd. aq. $NaHCO_3$ (20 mL), $H_2O$ (2×25 mL), dried over anhy. $Na_2SO_4$, filtered and concentrated in vacuo to give the crude title product together with a regioisomer (400 mg) as white solid.

[F] 6-Chloro-7-fluoro-1,2,3,4-tetrahydro-isoquinoline

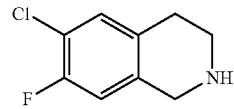

To a solution of 1-(6-chloro-7-fluoro-3,4-dihydro-1H-isoquinolin-2-yl)-2,2,2-trifluoroethanone (400 mg) in MeOH (15 mL) was added $K_2CO_3$ (572 mg, 4 mmol) in $H_2O$ (10 mL). The resulting reaction mixture was stirred at room temperature for 2 hours before it was acidified with HCl (1N) to pH 8. It was then extracted with EtOAc and the organic layer was washed with $H_2O$ (2×25 mL), dried over anhy. $Na_2SO_4$, filtered and concentrated in vacuo to tive the crude title product together with a regioisomer (170 mg). Prep-TLC separation (30% EtOAc in petroleum ether) then gave the desired title compound (130 mg) as a white solid.

[G] 6-Chloro-7-fluoro-3,4-dihydro-2H-isoquinoline-1-one

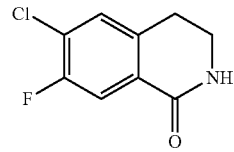 [SMILES: O=C1NCCc2cc(Cl)c(F)cc21]

A mixture of 6-chloro-7-fluoro-1,2,3,4-tetrahydro-isoquinoline (130 mg, 0.7 mmol), potassium bromide (83.5 mg, 0.7 mmol) and iodoso benzene (0.46 g, 2.1 mmol) in water (4 mL) was stirred at room temperature overnight. The mixture was then extracted with EtOAc and the organic layer was dried over anhy. $Na_2SO_4$, filtered and concentrated in vacuo to give a crude product. Flash column chromatography separation (silica gel, 12 g, 30% EtOAc in hexane) then afforded the tile compound (58 mg, 41%) as a white solid.

Intermediate A-8

2-Chloro-7,8-dihydro-6H-[1,6]naphthyridin-5-one

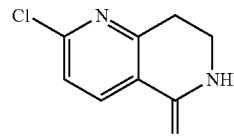

[A] 2-Chloro-7,8-dihydro-5H-[1,6]naphthyridine-6-carboxylic acid methyl ester

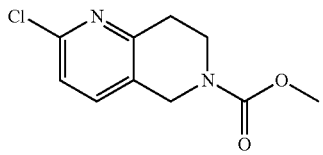

To a solution of 2-chloro-5,6,7,8-tetrahydro-[1,6]naphthyridine hydrochloride (1.54 g, 7.5 mmol) in DCM (25 mL) was added Et₃N (3.1 mL, 22 mmol). After the addition and stirring at room temperature for 5 min, the solution was cooled to 0° C., followed by the addition of methylchloroformate (0.85 mL, 11 mmol). The resulting reaction mixture was then allowed to stir at room temperature for 2 hours. It was then washed with satd. aq. NaHCO₃ solution and brine. The organic layer was dried over anhy. Na₂SO₄, filtered and concentrated in vacuo to give a crude product. Flash column chromatography separation (silica gel, 40 g, 30% EtOAc in hexane) then afforded the tile compound (1.53 g, 90%) as a white solid. MS: 227.3 (M+H⁺).

[B] 2-Chloro-5-oxo-7,8-dihydro-5H-[1,6]naphthyridine-6-carboxylic acid methyl ester

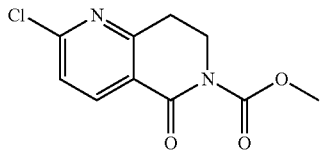 [SMILES: COC(=O)N1CCc2nc(Cl)ccc2C1=O]

2-Chloro-7,8-dihydro-5H-[1,6]naphthyridine-6-carboxylic acid methyl ester (226.7 mg, 1 mmol) was dissolved in CCl₄ (3.57 mL) and MeCN (0.357 mL) at room temperature before adding NaIO₄ (0.643 g) in 1 mL of H₂O, followed by RuCl₃·hydrate (62.2 mg). The reaction mixture was stirred vigorously at room temperature for 2 hours. After dilution with DCM, it was filtered through Celite and the filter cake was washed three times with DCM. The combined organic solution was concentrated in vacuo to give a crude product. Flash column chromatography separation (silica gel, 12 g, 20% EtOAc in hexane) then afforded the tile compound (143 mg, 60%) as a white solid. MS: 241.1 (M+H⁺).

[C] 2-Chloro-7,8-dihydro-6H-[1,6]naphthyridin-5-one

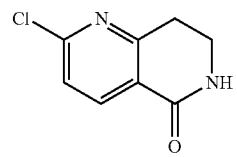 [SMILES: O=C1NCCc2nc(Cl)ccc21]

A mixture of 2-chloro-5-oxo-7,8-dihydro-5H-[1,6]naphthyridine-6-carboxylic acid methyl ester (60 mg, 0.25 mmol) and sodium methoxide (40 mg, 0.75 mmol) in 2 mL of 1,4-dioxane was subject to microwave reaction at 110° C. for 30 min. After removal of 1,4-dioxane, the residue was dissolved in DCM and the DCM solution was washed with water and brine. The organic layer was then dried over anhy. Na₂SO₄, filtered and concentrated in vacuo to give a crude product. Prep-TLC separation (30% EtOAc in hexane) then afforded the tile compound (28 mg, 63%) as a white solid. MS: 183.1 (M+H⁺).

Intermediate A-9

2-Methoxy-7,8-dihydro-6H-[1,6]naphthyridin-5-one

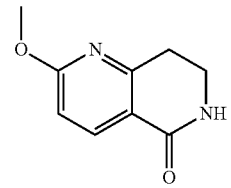

[A] 2-Chloro-7,8-dihydro-5H-[1,6]naphthyridine-6-carboxylic acid tert-butyl ester To a solution of 2-chloro-5,6,7,8-tetrahydro-[1,6]naphthyridine hydrochloride (1.54 g, 7.5 mmol) in DCM (25 mL) was added Et₃N (2 mL, 15 mmol). After the addition and stirring at room temperature for 5 min, the solution was cooled to 0° C., followed by the addition of (Boc)₂O (1.88 g, 8.63 mmol). The resulting reaction mixture was then allowed to stir at room temperature for 2 hours. It was then washed with H₂O and brine. The organic layer was dried over anhy. Na₂SO₄, filtered and concentrated in vacuo to give the title compound (1.87 g, 93%) as a white solid. MS: 269.1 (M+H⁺). It was used directly in the next step without further purification.

[B] 2-Chloro-5-oxo-7,8-dihydro-5H-[1,6]naphthyridine-6-carboxylic acid tert-butyl ester

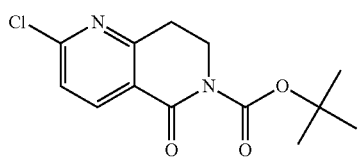 [SMILES: CC(C)(C)OC(=O)N1CCc2nc(Cl)ccc2C1=O]

In analogy to the procedure described for the preparation of intermediates A-8 [B], 2-chloro-7,8-dihydro-5H-[1,6]naphthyridine-6-carboxylic acid tert-butyl ester was used to yield the title compound as a white solid. MS: 283.1 (M+H⁺).

[C]
2-Methoxy-7,8-dihydro-6H-[1,6]naphthyridin-5-one

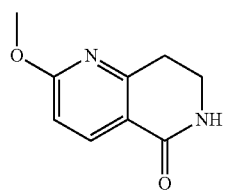

In analogy to the procedure described for the preparation of intermediates A-8 [C], 2-chloro-5-oxo-7,8-dihydro-5H-[1,6]naphthyridine-6-carboxylic acid tert-butyl ester was used to yield the title compound as a white solid. MS: 179.2 (M+H⁺).

Intermediate A-10

5-Chloro-3-methyl-2,3-dihydro-isoindol-1-one

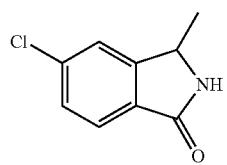

Intermediate A-11

6-Chloro-3-methyl-2,3-dihydro-isoindol-1-one

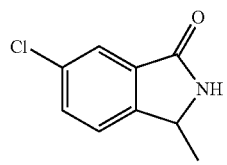

[A] 5-Chloro-3-hydroxy-3-methyl-2,3-dihydro-isoindol-1-one and 6-chloro-3-hydroxy-3-methyl-2,3-dihydro-isoindol-1-one

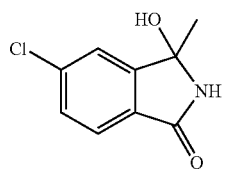 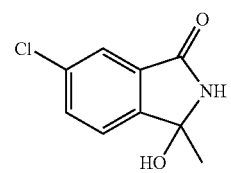

To a solution of 5-chloro-isoindole-1,3-dione (3.63 g, 20 mmol) in DCM (150 mL) was added methylmagnesium chloride (3 M in THF, 20 mL) dropwise at 0° C. After the addition, the mixture was stirred at 0° C. for 3 hours before it was quenched with satd. aq. NH₄Cl solution. After extraction with DCM, the organic layer was washed with brine, dried over anhy. Na₂SO₄, filtered and concentrated in vacuo to give a crude product containing a mixture of two regioisomers (3.95 g, 100%). MS: 198.1 (M+H⁺).

[B] 5-Chloro-3-methyl-2,3-dihydro-isoindol-1-one and 6-chloro-3-methyl-2,3-dihydro-isoindol-1-one

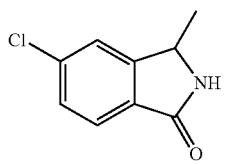 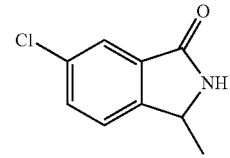

Under N₂ protection, triethylsilane (23 g, 200 mmol) and trifluoroboron etherate (8.51 g, 60 mmol) were added successively at −15° C. to a mixture of 5-chloro-3-hydroxy-3-methyl-2,3-dihydro-isoindol-1-one and 6-chloro-3-hydroxy-3-methyl-2,3-dihydro-isoindol-1-one (3.95 g, 20 mmol) in dry DCM (100 mL). Afterwards, the reaction mixture was stirred at room temperature for 2 hours and a saturated aqueous solution of NaHCO₃ (30 mL) was added. The mixture was then extracted with DCM and the organic layer was washed with brine, dried over anhy. Na₂SO₄, filtered and concentrated in vacuo to give a crude mixture of products. The two regioisomers were separated by prep-HPLC to give the title compounds, 5-chloro-3-methyl-2,3-dihydro-isoindol-1-one (0.4 g, 11%) and 6-chloro-3-methyl-2,3-dihydro-isoindol-1-one (0.35 g, 9.6%) as white solids. MS: 182.0 (M+H⁺).

Intermediate A-12

5-Chloro-3,3-dimethyl-2,3-dihydro-isoindol-1-one

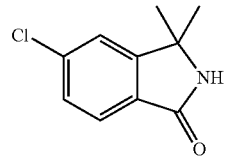

[A] 5-Chloro-2-(4-methoxy-benzyl)-2,3-dihydro-isoindol-1-one

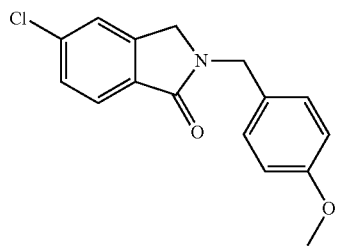 [SMILES: COc1ccc(CN2Cc3cc(Cl)ccc3C2=O)cc1]

Sodium bis(trimethylsilyl) amide (2 mL, 2 M in THF, 2 mmol) was added dropwise at 0° C. to a solution of 5-chloro-2,3-dihydro-isoindol-1-one (0.34 g, 2 mmol) in THF (10 mL). After stirring for 10 min, 1-bromomethyl-4-methoxy-benzene (0.52 g, 2.6 mmol) was added dropwise. The resulting reaction mixture was allowed to stir at room temperature for 48 hours before quenching with saturated aqueous ammonium chloride solution. After extraction with EtOAc, the organic layer was washed with brine, dried over anhy. $Na_2SO_4$, filtered and concentrated in vacuo to give the crude product (0.6 g, 100%) as a yellow oil. MS: 288.0 (M+H$^+$). It was used directly in the next step, without further purification.

[B] 5-Chloro-2-(4-methoxy-benzyl)-3,3-dimethyl-2,3-dihydro-isoindol-1-one

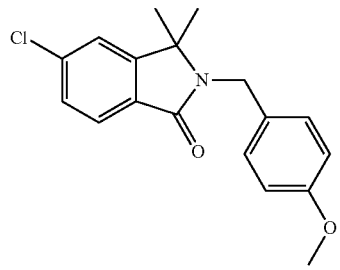 [SMILES: COc1ccc(CN2C(=O)c3ccc(Cl)cc3C2(C)C)cc1]

To a solution of 5-chloro-2-(4-methoxy-benzyl)-2,3-dihydro-isoindol-1-one (0.6 g, 2.0 mmol) in THF (10 mL) was added sodium hydride (60% in mineral oil, 0.17 g, 4.2 mmol) at room temperature. The resulting reaction mixture was stirred for 30 min before iodomethane (0.60 g, 4.2 mmol) was added. After stirring at room temperature overnight, the mixture was quenched with brine and extracted with EtOAc. The organic layer was then washed with brine, dried over anhy. $Na_2SO_4$, filtered and concentrated in vacuo to give the crude product which was then purified by flash column chromatography (silica gel 14 g, 5% to 20% ethyl acetate in DCM). The title compound was obtained (0.38 g, 57%) as a white solid. MS: 316.2 (M+H$^+$).

[C]
5-Chloro-3,3-dimethyl-2,3-dihydro-isoindol-1-one

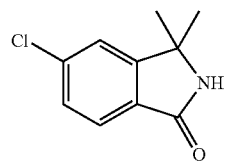

A solution of 5-chloro-2-(4-methoxy-benzyl)-3,3-dimethyl-2,3-dihydro-isoindol-1-one (0.38 g, 1.2 mmol) in trifluoro acetic acid (5 mL) was heated to reflux for 20 hours. After removal of trifluoro acetic acid under reduced pressure, the crude product was purified by flash column chromatography (silica gel 14 g, 5% to 50% ethyl acetate in DCM) to give the title compound (0.20 g, 85%) as a white solid. MS: 196.1 (M+H$^+$).

Intermediate A-12-1

5-Chloro-2-(5-chloromethyl-pyridin-3-yl)-3,3-dimethyl-2,3-dihydro-isoindol-1-one

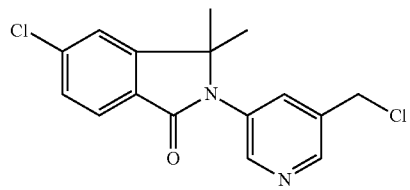 [SMILES: CC1(C)c2cc(Cl)ccc2C(=O)N1c1cncc(CCl)c1]

[A] (5-Bromo-pyridin-3-yl)-methanol

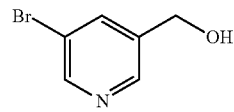

Sodium borohydride (2.2 g, 59.1 mmol) was added to a suspension of 5-bromo-pyridine-3-carbaldehyde (10.0 g, 53.7 mmol) in MeOH (100 mL) at 0° C. The mixture was stirred at 0° C. for 1 hour before it was quenched by the addition of water (5.0 mL). Evaporation of solvents afforded a light yellowish oil which was re-dissolved in EtOAc and washed with water. The organic layer was dried over anhy. $Na_2SO_4$, filtered and concentrated in vacuo to give the title compound (9.6 g, 95%) as colorless oil. MS: 188.0 & 190.0 (M+H$^+$).

[B] 5-Chloro-2-(5-hydroxymethyl-pyridin-3-yl)-3,3-dimethyl-2,3-dihydro-isoindol-1-one

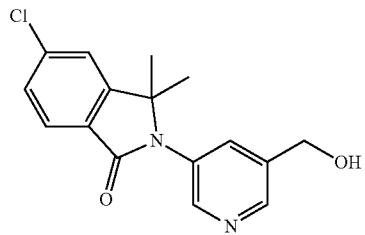 [SMILES: CC1(C)c2cc(Cl)ccc2C(=O)N1c1cncc(CO)c1]

In a 25-mL sealed tube, (5-bromo-pyridin-3-yl)-methanol (900 mg, 4.8 mmol), 5-chloro-3,3-dimethyl-2,3-dihydro-isoindol-1-one (intermediate A-12 [C], 858 mg, 4.4 mmol), CuI (200 mg, 1.1 mmol), $Cs_2CO_3$ (3.0 g, 9.2 mmol) and (+)-(S,S)-1,2-diaminocyclohexane (0.4 mL, 3.2 mmol) were dissolved in dioxane (8.0 mL). The resulting reaction mixture was heated at 150° C. for 3 hours before it was poured into $H_2O$ (50 mL) and extracted with EtOAc (2×125 mL). The organic layer was washed with brine, dried over anhy. $Na_2SO_4$, filtered and concentrated in vacuo to give a crude product which was purified by silica gel flash chromatography (30-100% EtOAc-hexane gradient) to yield the title compound (1.2 g, 90%) as a light yellow solid. MS: 303.2 (M+H⁺).

[C] 5-Chloro-2-(5-chloromethyl-pyridin-3-yl)-3,3-dimethyl-2,3-dihydro-isoindol-1-one

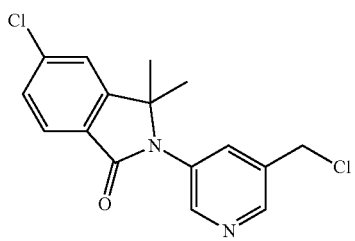 [SMILES: CC1(C)c2cc(Cl)ccc2C(=O)N1c1cncc(CCl)c1]

Thionyl chloride (1.4 mL, 19.0 mmol) was added slowly at 0° C. to a solution of 5-chloro-2-(5-hydroxymethyl-pyridin-3-yl)-3,3-dimethyl-2,3-dihydro-isoindol-1-one (1.14 g, 3.8 mmol) in DCM (50 mL). After the addition, the reaction mixture was stirred at 2-5° C. for 2 hours before it was poured into satd. aq. NaHCO₃ solution (50 mL) and extracted with EtOAc (2×150 mL). The organic layer was washed with brine, dried over anhy. Na₂SO₄, filtered and concentrated in vacuo to give a crude product (1.42 g, 92%) as a light yellowish solid. MS: 322.1 (M+H⁺).

Intermediate A-13

5-Chloro-3-ethyl-2,3-dihydro-isoindol-1-one

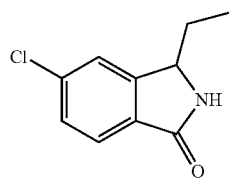

[A] 5-Chloro-3-ethyl-3-hydroxy-2,3-dihydro-isoindol-1-one and 6-chloro-3-ethyl-3-hydroxy-2,3-dihydro-isoindol-1-one

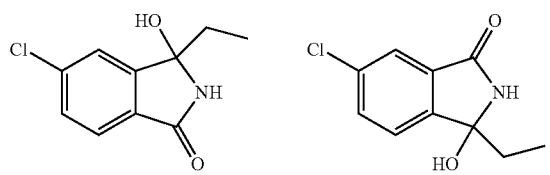

To a solution of 5-chloro-isoindole-1,3-dione (5.0 g, 27.5 mmol) in DCM (200 mL) was added ethylmagnesium chloride (2 M in THF, 41.3 mL) dropwise at 0° C. After the addition, the mixture was allowed to stir at 0° C. for 3 hours before it was quenched with satd. aq. NH₄Cl solution. After extraction with DCM, the organic layer was washed with brine, dried over anhy. Na₂SO₄, filtered and concentrated in vacuo to give a crude product containing a mixture of two regioisomers (5.82 g, 100%). MS: 212.0 (M+H⁺).

[B] 5-Chloro-3-ethyl-2,3-dihydro-isoindol-1-one

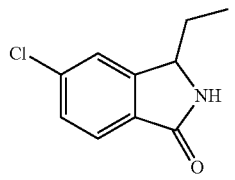

Under N₂ protection, triethylsilane (19.3 g, 166 mmol) and TFA (20 mL) were added successively to a mixture of 5-chloro-3-ethyl-3-hydroxy-2,3-dihydro-isoindol-1-one and 6-chloro-3-ethyl-3-hydroxy-2,3-dihydro-isoindol-1-one (3.52 g, 16.6 mmol). After stirring at room temperature for 2 hours, the reaction mixture was concentrated under reduced pressure. The residue was treated with a satd. aq. solution of NaHCO₃ (30 mL) and extracted with DCM (2×30 mL). The combined organic layers were washed with brine, dried over anhy. Na₂SO₄, filtered and concentrated in vacuo to give a crude mixture of products. The desired regioisomer, 5-chloro-3-ethyl-2,3-dihydro-isoindol-1-one was obtained by prep-HPLC separation as a white solid (0.65 g, 20%). MS: 196.1 (M+H⁺).

Intermediate A-13-1

5-Chloro-3-ethyl-2,3-dihydro-isoindol-1-one

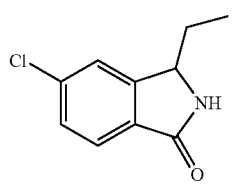

Intermediate A-13-2

6-Chloro-3-ethyl-2,3-dihydro-isoindol-1-one

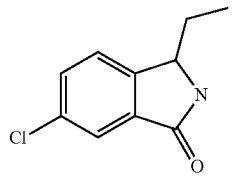

[A] 5-Chloro-3-ethyl-3-hydroxy-2,3-dihydro-isoindol-1-one and 6-chloro-3-ethyl-3-hydroxy-2,3-dihydro-isoindol-1-one

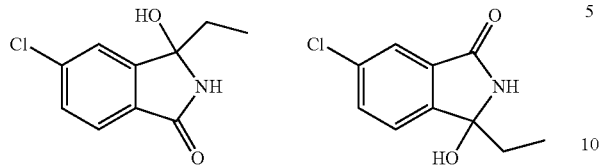

To a solution of 5-chloro-isoindole-1,3-dione (5.0 g, 27.5 mmol) in DCM (200 mL) was added ethylmagnesium chloride (2 M in THF, 41.3 mL) dropwise at 0° C. After the addition, the mixture was allowed to stir at 0° C. for 3 hours before it was quenched with satd. aq. NH$_4$Cl solution. After extraction with DCM, the organic layer was washed with brine, dried over anhy. Na$_2$SO$_4$, filtered and concentrated in vacuo to give a crude product containing a mixture of two regioisomers (5.82 g, 100%). MS: 212.0 (M+H$^+$).

[B] 5-Chloro-3-ethyl-2,3-dihydro-isoindol-1-one and 6-Chloro-3-ethyl-2,3-dihydro-isoindol-1-one

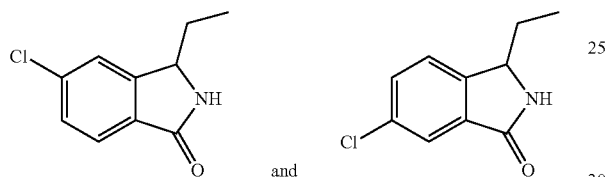

Under N$_2$ protection, triethylsilane (19.3 g, 166 mmol) and TFA (20 mL) were added successively to a mixture of 5-chloro-3-ethyl-3-hydroxy-2,3-dihydro-isoindol-1-one and 6-chloro-3-ethyl-3-hydroxy-2,3-dihydro-isoindol-1-one (3.52 g, 16.6 mmol). After stirring at room temperature for 2 hours, the reaction mixture was concentrated under reduced pressure. The residue was treated with a satd. aq. solution of NaHCO$_3$ (30 mL) and extracted with DCM (2×30 mL). The combined organic layers were washed with brine, dried over anhy. Na$_2$SO$_4$, filtered and concentrated in vacuo to give a crude mixture of products. Both 5-chloro-3-ethyl-2,3-dihydro-isoindol-1-one (0.65 g, 20%) MS: 196.1 (M+H$^+$) and 6-chloro-3-ethyl-2,3-dihydro-isoindol-1-one (0.62 g, 19%) MS: 196.1 (M+H$^+$) were obtained by prep-HPLC separation as white solids.

Intermediate A-13-1a (R or S)-5-Chloro-3-ethyl-2,3-dihydro-isoindol-1-one

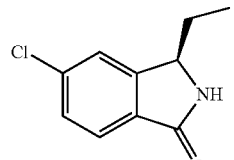

Intermediate A-13-1b (S or R)-5-Chloro-3-ethyl-2,3-dihydro-isoindol-1-one

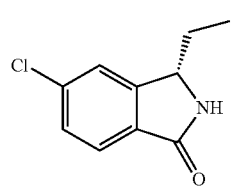

Intermediate A-13-2a (R or S)-6-Chloro-3-ethyl-2,3-dihydro-isoindol-1-one

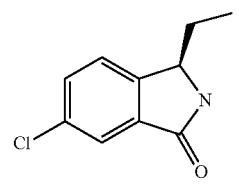

Intermediate A-13-2b (S or R)-6-Chloro-3-ethyl-2,3-dihydro-isoindol-1-one

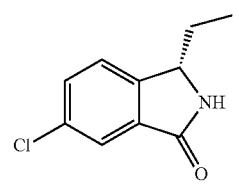

The mixture of 5-chloro-3-ethyl-2,3-dihydro-isoindol-1-one and 6-chloro-3-ethyl-2,3-dihydro-isoindol-1-one was subject to SFC separation (IC 250 mm×50 mm, 5 um, mobile phase A: supercritical CO2, B: IPA (0.05% NH3H2O), A:B=60:40 at 140 mL/min) to give (R or S)-5-chloro-3-ethyl-2,3-dihydro-isoindol-1-one (intermediate A-13-1a) and (S or R)-5-chloro-3-ethyl-2,3-dihydro-isoindol-1-one as one pair of enantiomers and (R or S)-6-chloro-3-ethyl-2,3-dihydro-isoindol-1-one and (S or R)-6-chloro-3-ethyl-2,3-dihydro-isoindol-1-one as another pair of enantiomers.

Intermediate A-13-3

(S or R)-5-Chloro-2-(5-chloromethyl-pyridin-3-yl)-3-ethyl-2,3-dihydro-isoindol-1-one

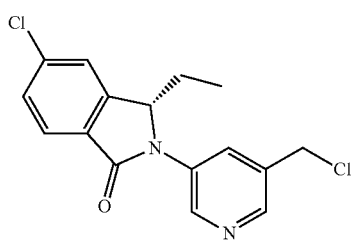 [SMILES: CC[C@H]1c2cc(Cl)ccc2C(=O)N1c1cncc(CCl)c1]

In analogy to the procedure described for the preparation of intermediate A-12-1, (S or R)-5-chloro-3-ethyl-2,3-dihydro-isoindol-1-one was used to afford the title compound as yellowish oil. MS: 322.1 (M+H⁺).

Intermediate A-13-4

(R or S)-5-Chloro-2-(5-chloromethyl-pyridin-3-yl)-3-ethyl-2,3-dihydro-isoindol-1-one

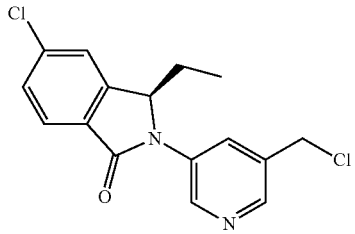 [SMILES: CC[C@@H]1c2cc(Cl)ccc2C(=O)N1c1cncc(CCl)c1]

In analogy to the procedure described for the preparation of intermediate A-12-1, (R or S)-5-chloro-3-ethyl-2,3-dihydro-isoindol-1-one was used to afford the title compound as yellowish oil. MS: 322.1 (M+H⁺).

Intermediate A-14

3-Benzyl-5-chloro-2,3-dihydro-isoindol-1-one

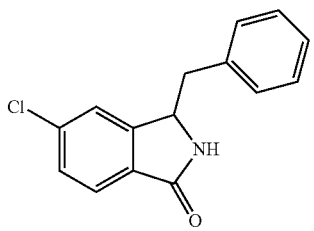 [SMILES: O=C1NC(Cc2ccccc2)c2cc(Cl)ccc21]

[A] 3-Benzyl-5-chloro-3-hydroxy-2,3-dihydro-isoindol-1-one and 3-benzyl-6-chloro-3-hydroxy-2,3-dihydro-isoindol-1-one

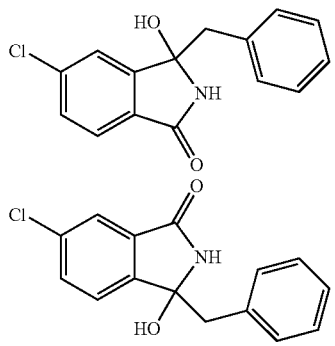

To a solution of 5-chloro-isoindole-1,3-dione (3.63 g, 20 mmol) in DCM (150 mL) was added benzylmagnesium chloride (2 M in THF, 30 mL) dropwise at 0° C. After the addition, the reaction mixture was allowed to stir at 0° C. for 3 hours before it was quenched with satd. aq. NH₄Cl solution. After extraction with DCM, the organic layer was washed with brine, dried over anhy. Na₂SO₄, filtered and concentrated in vacuo to give a crude product containing a mixture of two regioisomers (5.47 g, 100%). MS: 274.1 (M+H⁺).

[B] 3-Benzyl-5-chloro-2,3-dihydro-isoindol-1-one

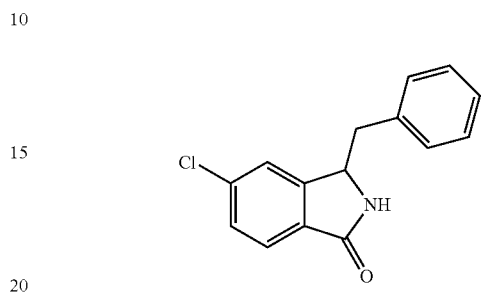

Under N₂ protection, triethylsilane (23 g, 200 mmol) and TFA (10 mL) were added successively to a mixture of 3-benzyl-5-chloro-3-hydroxy-2,3-dihydro-isoindol-1-one and 3-benzyl-6-chloro-3-hydroxy-2,3-dihydro-isoindol-1-one (5.47 g, 20 mmol). After stirring at room temperature for 2 hours, the reaction mixture was concentrated under reduced pressure. The residue was treated with a satd. aq. NaHCO₃ solution (30 mL) and extracted with DCM (2×30 mL). The combined organic layers were washed with brine, dried over anhy. Na₂SO₄, filtered and concentrated in vacuo to give a crude mixture of products. The desired regioisomer, 3-benzyl-5-chloro-2,3-dihydro-isoindol-1-one was obtained by prep-HPLC separation as a white solid (1.03 g, 20%). MS: 258.1 (M+H⁺).

Intermediate A-15

5-Chloro-3-cyclopropyl-2,3-dihydro-isoindol-1-one

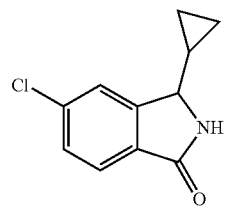 [SMILES: O=C1NC(C2CC2)c2cc(Cl)ccc21]

[A] (2-bromo-5-chlorophenyl)(cyclopropyl)methanamine

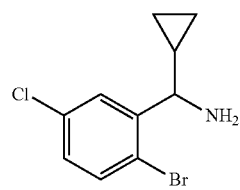 [SMILES: NC(c1cc(Cl)ccc1Br)C1CC1]

To a solution of 2-bromo-5-chlorobenzonitrile (20 g, 93 mmol) in THF (200 mL) was added cyclopropylmagnesiumbromide (558 mL, 279 mmol) at 0° C. The resulting reaction mixture was stirred at 0-5° C. for 5 hours before MeOH (100 mL) was added and stirring continued at room temperature for 15 min. NaBH₄ (7.1 g, 186 mmol) was added subsequently and the reaction mixture was stirred at room temperature overnight. Water was added and reaction mixture was exacted with AcOEt (300 mL×3). The combined organic layers were concentrated in vacuo to give a crude product which was then purified by chromatography to give (2-bromo-5-chlorophenyl)(cyclopropyl)methanamine (8.2 g, yield 34%).

[B]
5-Chloro-3-cyclopropyl-2,3-dihydro-isoindol-1-one

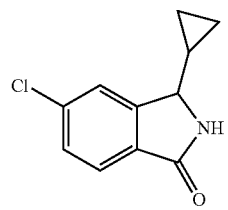

A mixture of (2-bromo-5-chlorophenyl)(cyclopropyl) methanamine (2 g, 7.7 mmol), Pd(dppf)Cl₂ (0.2 g), DIPEA (3 g, 23.1 mmol) in 20 mL of DMF was heated in an autoclave at 130° C. under 2 MPa of CO (g) for 16 hours. After the reaction, the mixture was diluted with AcOEt (150 mL) and washed with brine (30 mL×3). The organic layer was dried over anhy. Na₂SO₄, filtered, and concentrated in vacuo to give a crude product which was purified by chromatography to give title compound (1.1 g, yield 68.7%) as a yellow solid. MS: 207.9 (M+H⁺, 1Cl).

Intermediate A-16

2-Chloro-7,7-dimethyl-6,7-dihydro-pyrrolo[3,4-b]pyridin-5-one

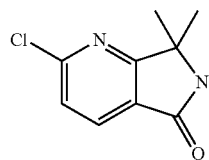

[A] 3-(Methoxycarbonyl)-2-methylpyridine 1-oxide

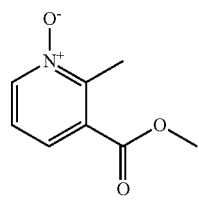

To a stirred solution of methyl-2-methylnicotinate (95 g, 629 mmol) in DCM (1.5 L) was added m-CPBA (119 g, 692 mmol) at 0° C. After the reaction mixture was stirred at room temperature for 16 hours, it was washed with a mixture of satd. aq. Na₂SO₃ and NaHCO₃ solution. The organic layer was then dried over anhy. Na₂SO₄, filtered, and concentrated in vacuo to give a crude product (60 g, yield 57%), which was used in the next step reaction without further purification.

[B] Methyl 2-(chloromethyl)nicotinate

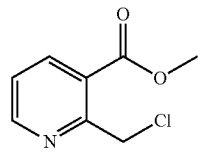

The crude 3-(methoxycarbonyl)-2-methylpyridine-1-oxide (35 g, 210 mmol) was added in small portion to POCl₃ (300 g) at room temperature. After the addition, the reaction mixture was refluxed for 3 hours before it was concentrated in vacuo. The residue was poured into ice-water, neutralized with aq. NaHCO₃ solution and extracted with AcOEt (125 mL×3). The combined organic layers were washed with brine, dried over anhy. Na₂SO₄, filtered, and concentrated in vacuo to afford a crude product which was then purified by column chromatography to give title compound (12 g, yield 30%).

[C] 2-(Chloromethyl)-3-(methoxycarbonyl)pyridine 1-oxide

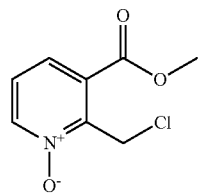

To a stirred solution of methyl-2-(chloromethyl)nicotinate (20 g, 108 mmol) in DCM (300 mL) was added m-CPBA (20.5 g, 119 mmol) at 0° C. After it was stirred at room temperature for 16 hours, the reaction mixture was washed with a mixture of satd. aq. Na₂SO₃ and NaHCO₃ solution. The organic layer was dried over anhy. Na₂SO₄, filtered, and concentrated in vacuo to give the crude title product (20 g, yield 92%), which was used in the next step reaction without further purification.

[D] Methyl 6-chloro-2-(chloromethyl)nicotinate

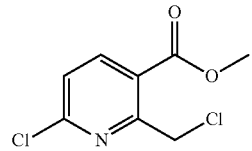

The crude of 2-(chloromethyl)-3-(methoxycarbonyl)pyridine-1-oxide (20 g, 99.5 mmol) was added in small portion to POCl₃ (200 g) at room temperature. The mixture was refluxed for 3 hours before it was concentrated in vacuo. The residue was poured into ice-water, neutralized with NaHCO$_3$ solution, and extracted with AcOEt (125 mL×3). The combined organic layers were concentrated to give the crude title product (17 g, yield 78%), which was used in the next step reaction without further purification.

[E] 2-Chloro-6-(4-methoxybenzyl)-6,7-dihydro-5H-pyrrolo[3,4-b]pyridin-5-one

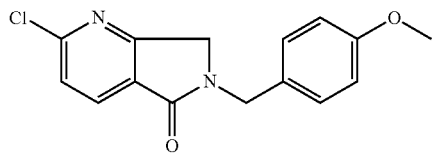 [SMILES: COc1ccc(CN2Cc3nc(Cl)ccc3C2=O)cc1]

To a stirred solution of crude methyl 6-chloro-2-(chloromethyl)nicotinate (10 g, 45.4 mmol) in THF (150 mL) was added PMBNH$_2$ (15.5 g, 113.5 mmol) at 0° C. The resulting reaction mixture was stirred at room temperature for 16 hours before it was concentrated under reduced pressure to give a crude product. After washing with MTBE (100 mL×3), the title compound was obtained (8.8 g, yield 67%) as a white solid. MS: 288.8 (M+H$^+$, 10).

[F] 2-Chloro-6-(4-methoxy-benzyl)-7,7-dimethyl-6,7-dihydro-pyrrolo[3,4-b]pyridin-5-one

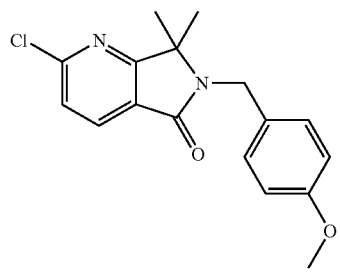 [SMILES: COc1ccc(CN2C(=O)c3ccc(Cl)nc3C2(C)C)cc1]

To a solution of 2-chloro-6-(4-methoxy-benzyl)-6,7-dihydro-pyrrolo[3,4-b]pyridin-5-one (5.8 g, 20.0 mmol) in THF (50 mL) was added sodium hydride (60% in mineral oil, 1.7 g, 42.0 mmol) at room temperature. The resulting reaction mixture was stirred for 30 min before iodomethane (6.0 g, 42.0 mmol) was added. After stirring at room temperature overnight, the mixture was quenched with water and extracted with EtOAc. The organic layer was then washed with brine, dried over anhy. Na$_2$SO$_4$, filtered and concentrated in vacuo to give the crude product which was then purified by flash column chromatography (silica gel 20 g, 5% to 20% ethyl acetate in DCM). The title compound was obtained (3.8 g, 57%) as a white solid. MS: 316.2 (M+H$^+$).

[G] 2-Chloro-7,7-dimethyl-6,7-dihydro-pyrrolo[3,4-b]pyridin-5-one

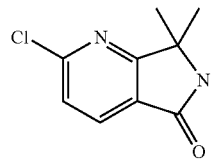

To solution of 2-chloro-6-(4-methoxy-benzyl)-7,7-dimethyl-6,7-dihydro-pyrrolo[3,4-b]pyridin-5-one (1.58 g, 5.0 mmol) in CH$_3$CN (20 mL) was added ceric ammonium nitrate (8.2 g, 15.0 mmol) at room temperature. The reaction mixture was stirred at room temperature for 3 hours before water and EtOAc was added into the mixture. The organic layer was separated, dried over anhy. Na$_2$SO$_4$, filtered and concentrated in vacuo to give a crude product which was then purified by silica gel column chromatography to give title compound (617 mg, 63%) as a solid. MS: 197.2 (M+H$^+$).

Intermediate A-16-1

2-Chloro-6-(5-chloromethyl-pyridin-3-yl)-7,7-dimethyl-6,7-dihydro-pyrrolo[3,4-b]pyridin-5-one

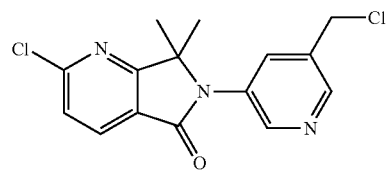 [SMILES: CC1(C)c2nc(Cl)ccc2C(=O)N1c1cncc(CCl)c1]

[A] 2-Chloro-6-(5-hydroxymethyl-pyridin-3-yl)-7,7-dimethyl-6,7-dihydro-pyrrolo[3,4-b]pyridin-5-one

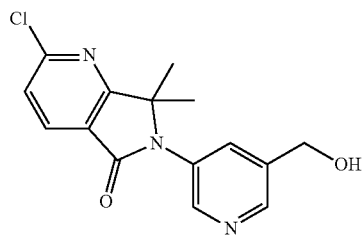 [SMILES: CC1(C)c2nc(Cl)ccc2C(=O)N1c1cncc(CO)c1]

2-Chloro-7,7-dimethyl-6,7-dihydro-pyrrolo[3,4-b]pyridin-5-one (intermediate A-16 [G], 39.2 mg, 0.2 mmol), (5-bromo-pyridin-3-yl)-methanol (example 3 [A], 74.8 mg, 0.4 mmol), CuI (3.8 mg, 0.02 mmol), (1S,2S)-cyclohexane-1,2-diamine (4.5 mg, 0.04 mmol) and Cs$_2$CO$_3$ (130 mg, 0.4 mmol) were dissolved in dioxane (5 mL). The reaction mixture was subjected to microwave reaction at 140° C. for 1 hours before it was poured into H$_2$O (50 mL) and extracted with EtOAc (2×25 mL). The organic layer was washed with brine, dried over anhy. Na₂SO₄, filtered and concentrated in vacuo to give a crude product (55.7 mg, 92%) as solid. MS: 304.1 (M+H⁺).

[B] 2-Chloro-6-(5-chloro-methyl-pyridin-3-yl)-7,7-dimethyl-6,7-dihydro-pyrrolo[3,4-b]pyridin-5-one

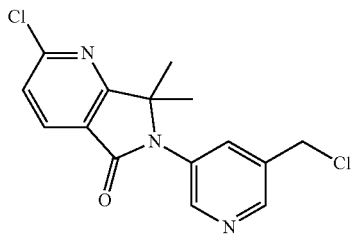 [SMILES: CC1(C)c2nc(Cl)ccc2C(=O)N1c1cncc(CCl)c1]

Thionyl chloride (0.14 mL, 1.9 mmol) was added slowly at 0° C. to a solution of 2-chloro-6-(5-hydroxymethyl-pyridin-3-yl)-7,7-dimethyl-6,7-dihydro-pyrrolo[3,4-b]pyridin-5-one (55.7 mg, 0.18 mmol) in DCM (10 mL). After the addition, the reaction mixture was stirred at 2-5° C. for 0.5 hours before it was poured into satd. aq. NaHCO₃ solution (10 mL) and extracted with DCM (2×15 mL). The organic layer was washed with brine, dried over anhy. Na₂SO₄, filtered and concentrated in vacuo to give a crude product (58 mg 100%) as light yellowish solid. MS: 322.1 (M+H⁺).

Intermediate A-17

2-Methoxy-7,7-dimethyl-6,7-dihydro-pyrrolo[3,4-b]pyridin-5-one

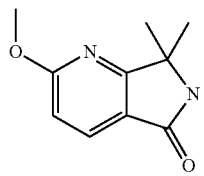

[A] 2-Methoxy-6-(4-methoxy-benzyl)-7,7-dimethyl-6,7-dihydro-pyrrolo[3,4-b]pyridin-5-one

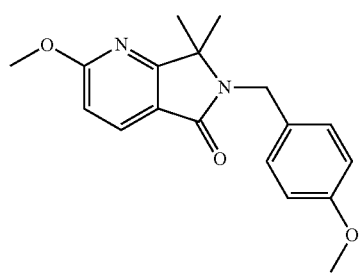 [SMILES: COc1ccc(CN2C(=O)c3ccc(OC)nc3C2(C)C)cc1]

To solution of 2-chloro-6-(4-methoxy-benzyl)-7,7-dimethyl-6,7-dihydro-pyrrolo[3,4-b]pyridin-5-one (intermediate A-16 [F], 3.15 g, 10 mmol) in DMF (30 mL) was added sodium methanolate (0.813 g, 15 mmol) at room temperature. The reaction mixture was stirred at room temperature for 4 hours before it was quenched with water and extracted with EtOAc. The organic layer was washed with brine, dried over anhy. Na₂SO₄, filtered and concentrated in vacuo to give title compound (2.8 g, 90%) as a solid. MS: 313.1 (M+H⁺).

[B] 2-Methoxy-7,7-dimethyl-6,7-dihydro-pyrrolo[3,4-b]pyridin-5-one

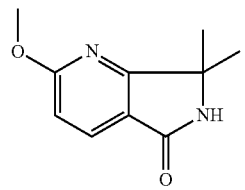

To solution of 2-methoxy-6-(4-methoxy-benzyl)-7,7-dimethyl-6,7-dihydro-pyrrolo[3,4-b]pyridin-5-one (0.31 g, 1.0 mmol) in CH₃CN (5 mL) was added ceric ammonium nitrate (1.64 g, 3.0 mmol) at room temperature. The reaction mixture was stirred at room temperature for 3 hours before water and EtOAc were added into the mixture. The organic layer was separated, dried over anhy. Na₂SO₄, filtered and concentrated in vacuo to give a crude product which was then purified by silica gel column chromatography to give the title compound (0.12 g, 63%) as a solid. MS: 193.1 (M+H⁺).

Intermediate A-17-1

6-(5-Chloromethyl-pyridin-3-yl)-2-methoxy-7,7-dimethyl-6,7-dihydro-pyrrolo[3,4-b]pyridin-5-one

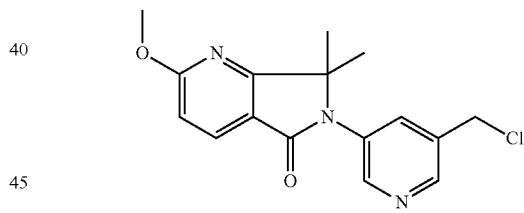

In analogy to the procedure described for the preparation of intermediate A-12-1, the title compound was obtained as yellowish oil. MS: 318.3 (M+H⁺).

Intermediate A-18

2-Ethoxy-7,7-dimethyl-6,7-dihydro-pyrrolo[3,4-b]pyridin-5-one

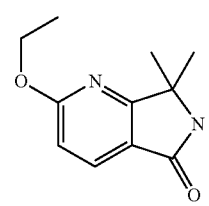

[A] 2-Ethoxy-6-(4-methoxy-benzyl)-7,7-dimethyl-6,7-dihydro-pyrrolo[3,4-b]pyridin-5-one

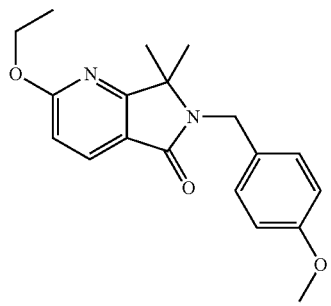

To solution of 2-chloro-6-(4-methoxy-benzyl)-7,7-dimethyl-6,7-dihydro-pyrrolo[3,4-b]pyridin-5-one (intermediate A-16 [F], 3.15 g, 10 mmol) in DMF (30 mL) was added sodium ethoxide (1.02 g, 15 mmol) at room temperature. The reaction mixture was stirred at room temperature for 4 hours before it was quenched by water and extracted with EtOAc. The organic layer was washed with brine, dried over anhy. $Na_2SO_4$, filtered and concentrated in vacuo to give title product (2.9 g, 89%) as a solid. MS: 327.2 (M+H$^+$).

[B] 2-Ethoxy-7,7-dimethyl-6,7-dihydro-pyrrolo[3,4-b]pyridin-5-one

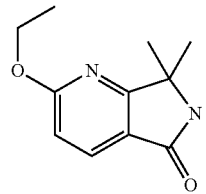

To solution of 2-methoxy-6-(4-methoxy-benzyl)-7,7-dimethyl-6,7-dihydro-pyrrolo[3,4-b]pyridin-5-one (0.33 g, 1.0 mmol) in CH$_3$CN (5 mL) was added eerie ammonium nitrate (1.64 g, 3.0 mmol) at room temperature. The reaction mixture was stirred at room temperature for 3 hours before water and EtOAc were added into the mixture. The organic layer was separated, dried over anhy. Na$_2$SO$_4$, filtered and concentrated in vacuo to give a crude product which was then purified by silica gel column chromatography to give the title compound (0.15 g, 72%) as a solid. MS: 207.1 (M+H$^+$).

Intermediate A-18-1

6-(5-Chloromethyl-pyridin-3-yl)-2-ethoxy-7,7-dimethyl-6,7-dihydro-pyrrolo[3,4-b]pyridin-5-one

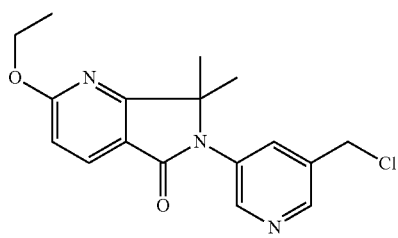 [SMILES: CCOc1ccc2c(n1)C(C)(C)N(c1cncc(CCl)c1)C2=O]

In analogy to the procedure described for the preparation of intermediate A-12-1, the title compound was obtained as yellowish oil. MS: 332.1 (M+H$^+$).

Intermediate A-19

5-Fluoro-3,3-dimethyl-2,3-dihydro-isoindol-1-one

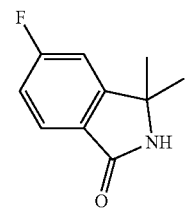

[A] 4-Fluoro-2-methyl-benzoic acid methyl ester

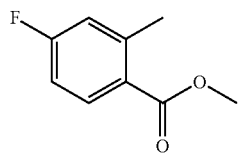

To a stirred solution of 4-fluoro-2-methyl-benzoic acid (13 g, 84 mmol) in MeOH (500 mL) was added SOCl$_2$ (20 g, 168 mmol) dropwise at 0° C. After the addition, the reaction mixture was stirred at room temperature for 16 hours. When TLC indicated that no starting material was left, the mixture was concentrated under reduced pressure to give a crude product (12.7 g, yield 90.7%), which was used in the next step reaction without further purification.

[B] 2-Bromomethyl-4-fluoro-benzoic acid methyl ester

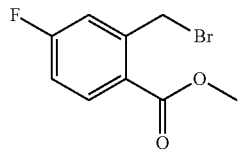

A mixture of 4-fluoro-2-methyl-benzoic acid methyl ester (12.7 g, 75.5 mmol), NBS (13.4 g, 75.5 mmol), and di-benzoyl peroxide (BPO) (0.85 g, 3.5 mmol) in CCl$_4$ (200 mL) was heated to reflux for 3 hours until all starting material was consumed. After vacuum filtration, the filtrate concentrated in vacuo to give a crude product (17 g, yield 91%), which was used in the next step reaction without further purification.

[C] 5-Fluoro-2-(4-methoxy-benzyl)-2,3-dihydro-isoindol-1-one

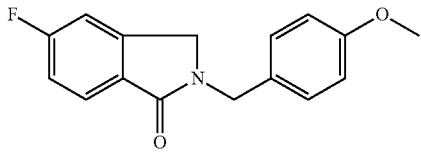 [SMILES: COc1ccc(CN2Cc3cc(F)ccc3C2=O)cc1]

To a stirred solution of 2-bromomethyl-4-fluoro-benzoic acid methyl ester (17 g, 68.8 mmol) in THF (200 mL) was added PMBNH$_2$ (23.6 g, 172 mmol) at 0° C. After stirring at room temperature for 16 hours, the reaction mixture was concentrated in vacuo to give a crude product which was then purified by column chromatography to give the title compound (13 g, yield 69%) as a solid.

[D] 5-Fluoro-2-(4-methoxy-benzyl)-3,3-dimethyl-2,3-dihydro-isoindol-1-one

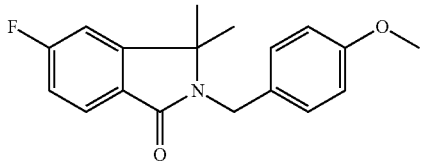 [SMILES: COc1ccc(CN2C(=O)c3ccc(F)cc3C2(C)C)cc1]

To a solution of 5-fluoro-2-(4-methoxy-benzyl)-2,3-dihydro-isoindol-1-one (6 g, 22 mmol) in THF (30 mL) was added NaH (4.42 g, 110 mmol) slowly at 0° C. After stirred at 0° C. for 30 min, MeI (18.8 g, 132 mmol) was added dropwise and the resulting reaction mixture was heated to 70° C. for 5 hours. After cooling to room temperature, the reaction mixture was poured into aq. NH$_4$Cl solution and exacted with EtOAc. The organic layer was dried over anhy. Na$_2$SO$_4$, filtered, and then concentrated to give a crude product which was then purified by column chromatography to give tile product (4.8 g, yield 72.5%) as a solid.

[E] 5-Fluoro-3,3-dimethyl-2,3-dihydro-isoindol-1-one

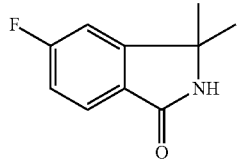

To a stirred solution of 5-fluoro-2-(4-methoxy-benzyl)-3,3-dimethyl-2,3-dihydro-isoindol-1-one (3.8 g, 12.7 mmol) in MeCN (80 ml) and H$_2$O (40 mL) was added CAN (20.9 g, 38.1 mmol) at 0° C. After stirring for 2 hours at 0° C., the reaction mixture was diluted with EtOAc and washed with brine. The organic layers were dried over anhy. Na$_2$SO$_4$, filtered and concentrated in vacuo to provide a crude product, which was purified by column chromatography to give tile product (1.03 g, yield 45%) as a solid.

Intermediate A-19-1

2-(5-Chloromethyl-pyridin-3-yl)-5-fluoro-3,3-dimethyl-2,3-dihydro-isoindol-1-one

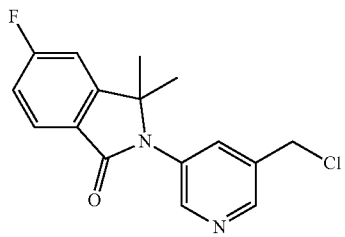 [SMILES: CC1(C)c2cc(F)ccc2C(=O)N1c1cncc(CCl)c1]

In analogy to the procedure described for the preparation of intermediate A-12-1, the title compound was obtained as yellowish oil. MS: 305.1 (M+H$^+$).

Intermediate A-20

6-Fluoro-3,3-dimethyl-2,3-dihydro-isoindol-1-one

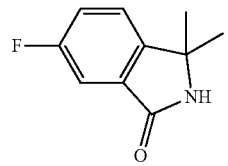

[A] 1-(2-Bromo-4-fluoro-phenyl)-1-methyl-ethylamine

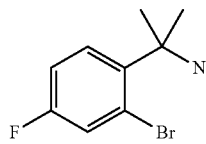

To a stirred solution of 2-bromo-4-fluorobenzonitrile (5 g, 25 mmol) in ether (100 mL) was added MeMgBr (25 mL, 75 mmol) at room temperature. The solution was stirred at room temperature for 0.5 hour before Ti(Oi-Pr)$_4$ (41 mL, 25 mmol) was added and the resulting mixture was heated to reflux for 6 hours. Aqueous NaOH (10%, 200 mL) solution was then slowly added to the reaction mixture at 0° C. and the reaction mixture was stirred at room temperature for additional 30 minutes. After dilution with aq. Na$_2$CO$_3$ (5%, 400 mL) solution, it was extracted with t-BuOMe (100 mL×3). The combined organic layers were concentrated under reduced pressure. The residue obtained was diluted with aq. HCl solution (5%) and the aqueous layer was washed with t-BuOMe (50 mL×2) and basified with 20% aq. NaOH to pH~10. The resulting aqueous layer was further extracted with t-BuOMe (100 mL×3). The combined organic layers were then dried over anhy. Na$_2$SO$_4$, filtered, and concentrated in vacuo to give a crude product, which was purified by column chromatography to give the title product (3.0 g, yield 51.7%) as yellowish oil. MS: 231.7 (M+H⁺, 1Br)

[B]
6-Fluoro-3,3-dimethyl-2,3-dihydro-isoindol-1-one

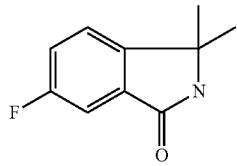

A mixture of 1-(2-bromo-4-fluoro-phenyl)-1-methylethylamine (1.5 g, 6.52 mmol), Pd(dppf)Cl₂ (0.15 g), DIPEA (2.52 g, 19.6 mmol) in DMF (20 mL) was stirred in an autoclave under 2 MPa of CO (g) at 130° C. for 16 hours. After it was cooled to room temperature, the reaction mixture was diluted with EtOAc (300 mL). The organic layer was washed with brine, filtered, and concentrated under reduced pressure to give a crude product which was purified by chromatography to give the title compound (100 mg, yield 8.6%) as a brown solid.

Intermediate A-20-1

2-(5-Chloromethyl-pyridin-3-yl)-6-fluoro-3,3-dimethyl-2,3-dihydro-isoindol-1-one

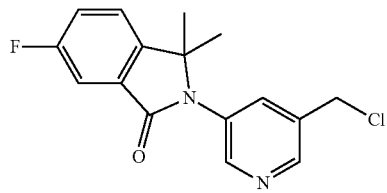 [SMILES: CC1(C)c2ccc(F)cc2C(=O)N1c1cncc(CCl)c1]

[A] 6-Fluoro-2-(5-hyroxymethyl-pyridin-3-yl)-3,3-dimethyl-2,3-dihydro-isoindol-1-one

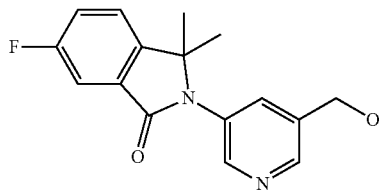 [SMILES: CC1(C)c2ccc(F)cc2C(=O)N1c1cncc(CO)c1]

A mixture of 6-fluoro-3,3-dimethyl-2,3-dihydro-isoindol-1-one (intermediate A-20 [B], 35.8 mg, 0.2 mmol), (5-bromo-pyridin-3-yl)-methanol (74.8 mg, 0.4 mmol), CuI (3.8 mg, 0.02 mmol), (1S,2S)-cyclohexane-1,2-diamine (4.5 mg, 0.04 mmol) and Cs₂CO₃ (130 mg, 0.4 mmol) were dissolved in dioxane (5 mL). The reaction mixture was subjected to microwave reaction at 140° C. for 1 hour before it was poured into H₂O (50 mL) and extracted with EtOAc (2×25 mL). The organic layer was washed with brine, dried over anhy. Na₂SO₄, filtered and concentrated in vacuo to give a crude product (52 mg, 92%) as a solid. MS: 287.1 (M+H⁺).

[B] 2-(5-Chloromethyl-pyridin-3-yl)-6-fluoro-3,3-dimethyl-2,3-dihydro-isoindol-1-one

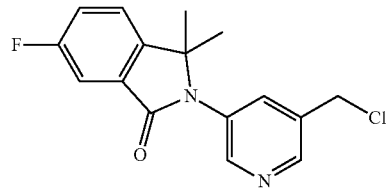 [SMILES: CC1(C)c2ccc(F)cc2C(=O)N1c1cncc(CCl)c1]

To a solution of 6-fluoro-2-(5-hyroxymethyl-pyridin-3-yl)-3,3-dimethyl-2,3-dihydro-isoindol-1-one (52 mg) in DCM (10 mL) was added thionyl chloride (0.14 mL, 1.9 mmol) slowly at 0° C. After the addition, the reaction mixture was stirred at 2-5° C. for 0.5 hour before it was poured into satd. aq. NaHCO₃ solution (10 mL) and extracted with DCM (2×15 mL). The combined organic layers were washed with brine, dried over anhy. Na₂SO₄, filtered and concentrated in vacuo to give a crude product (58 mg 100%) as light yellowish solid. MS: 322.1 (M+H⁺).

Intermediate A-21

3,3-Dimethyl-1-oxo-2,3-dihydro-1H-isoindole-5-carbonitrile

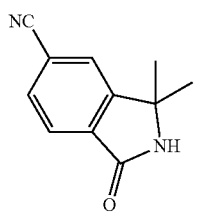

[A]-4-Bromo-2-methyl-benzoic acid methyl ester

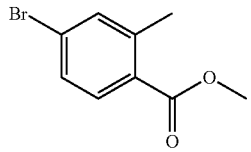

To a solution of 4-bromo-2-methyl-benzoic acid (30.0 g, 0.14 mol) in 115 mL of methanol was added thionyl chloride (20.25 mL, 0.28 mol) slowly and the reaction mixture was stirred at 70° C. for 2 hours before it was concentrated to afford a crude product which was then purified by column chromatography to give the title compound (30.03 g, 93.6%) as a solid.

[B] 4-Cyano-2-methyl-benzoic acid methyl ester

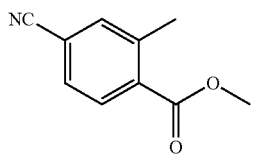

A mixture of 4-bromo-2-methyl-benzoic acid methyl ester (26.0 g, 113.5 mmol) and CuCN (12.48 g, 140.7 mmol) was heated at 180° C. for 5 hours before it was poured into ice-water. The solid precipitate was collected by vacuum filtration to give a crude product which was then purified by column chromatography to afford the title compound (12.53 g, 63%) as a solid.

[C] 2-Bromomethyl-4-cyano-benzoic acid methyl ester

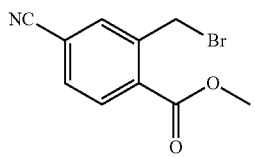

A mixture of 4-cyano-2-methyl-benzoic acid methyl ester (12.5 g, 71.35 mmol), NBS (12.7 g, 71.35 mmol) and dibenzoyl peroxide (BPO) (0.8 g, 3.28 mmol) in $CCl_4$ (200 mL) was heated to reflux temperature for 3 hours. After it was cooled to room temperature, the reaction mixture was filtered. The filtrate was concentrated in vacuo to give a crude product (18.2 g) which was used in the next step reaction without further purification.

[D] 2-(4-Methoxy-benzyl)-1-oxo-2,3-dihydro-1H-isoindole-5-carbonitrile

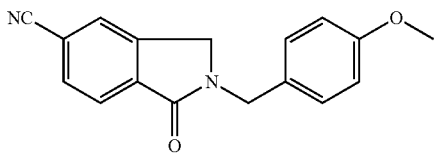 [SMILES: COc1ccc(CN2Cc3cc(C#N)ccc3C2=O)cc1]

To a solution of 2-bromomethyl-4-cyano-benzoic acid methyl ester (18.1 g, 71.24 mmol) in THF (300 mL) was added $PMBNH_2$ (23.4 g, 178.1 mmol) at 0° C. and the reaction mixture was stirred at room temperature for 16 hours. After vacuum filtration, the filtrate was concentrated in vacuo. The residue obtained was re-dissolved in EtOAc and washed with water and brine. The organic layer was dried over anhy. $Na_2SO_4$, filtered, and concentrated in vacuo to give a crude product which was purified by column chromatography (11.69 g, 56.0%) as a solid.

[E] 2-(4-Methoxy-benzyl)-3,3-dimethyl-1-oxo-2,3-dihydro-1H-isoindole-5-carbonitrile

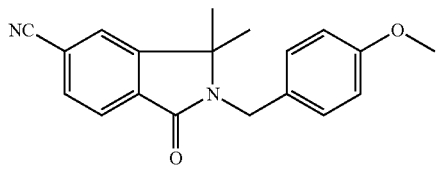 [SMILES: COc1ccc(CN2C(=O)c3ccc(C#N)cc3C2(C)C)cc1]

To a solution of 2-(4-methoxy-benzyl)-1-oxo-2,3-dihydro-1H-isoindole-5-carbonitrile (11.6 g, 41.7 mmol) in THF (300 mL) was added NaH (8.34 g, 208.4 mmol, 60% in mineral oil) and the reaction mixture was stirred at room temperature for 1 hour before iodomethane (35.5 g, 250.1 mmol) was added. After the addition, the reaction mixture was stirred at 70° C. for 2 hours until all the starting material was consumed. After it was cooled to room temperature, satd. aq. $NH_4Cl$ solution was added and the mixture was extracted with EtOAc (200 mL×3). The combined organic layers were dried over anhy. $MgSO_4$, filtered, and concentrated under reduced pressure to give a crude product which was purified by column chromatography to afford the title compound (7.22 g, 56.5%) as a solid.

[F] 3,3-Dimethyl-1-oxo-2,3-dihydro-1H-isoindole-5-carbonitrile

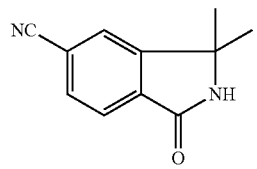

To a solution of 2-(4-methoxy-benzyl)-3,3-dimethyl-1-oxo-2,3-dihydro-1H-isoindole-5-carbonitrile (3.5 g, 11.42 mmol) in MeCN (70 mL) was added CAN (18.79 g, 34.27 mmol) in 30 mL of water at 0° C. The resulting reaction mixture was stirred at 0° C. for 1 hour until all the starting material was consumed. The reaction mixture was extracted between water and EtOAc and the combined organic layers were dried over anhy. $MgSO_4$, filtered, and concentrated under reduced pressure to give a crude product which was purified by column chromatography to afford the title compound (1.06 g, 49.8%) as a solid.

Intermediate A-21-1

2-(5-Chloromethyl-pyridin-3-yl)-3,3-dimethyl-1-oxo-2,3-dihydro-1H-isoindole-5-carbonitrile

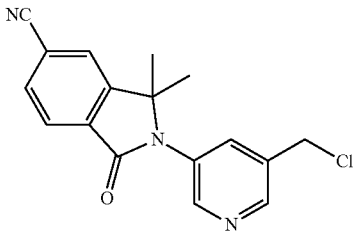 [SMILES: CC1(C)c2cc(C#N)ccc2C(=O)N1c1cncc(CCl)c1]

In analogy to the procedure described for the preparation of intermediate A-12-1, the title compound was obtained as yellowish oil. MS: 312.1 (M+H⁺).

Intermediate A-22

6'-Chlorospiro[cyclopropane-1,1'-isoindolin]-3'-one

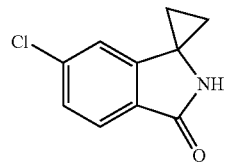 [SMILES: O=C1NC2(CC2)c2cc(Cl)ccc21]

[A] 1-(2-Bromo-5-chlorophenyl)cyclopropanamine

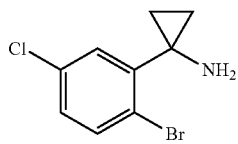 [SMILES: NC1(c2cc(Cl)ccc2Br)CC1]

To a stirred solution of 2-bromo-5-chlorobenzonitrile (10 g, 46 mmol) and Ti(Oi-Pr)₄ (16.64 mL, 55 mmol) in THF (200 mL) at −78° C. was added EtMgBr (138 mL, 138 mmol) dropwise. The reaction mixture was allowed to warm up to room temperature and stirred for 2 hours. BF₃-Et₂O (17.2 mL) was added, and the solution was stirred for another 16 hours before it was quenched with aq. HCl solution and washed with EtOAc. The aqueous phase was adjusted to pH~10 with aq. NaOH solution, and exacted with EtOAc (3×). The combined organic layers were concentrated to give a crude product which was purified by chromatography to afford title compound (2 g, yield 17.6%). MS: 246.7 (M+H⁺, 1Cl) as oil.

[B] 6'-Chlorospiro[cyclopropane-1,1'-isoindolin]-3'-one

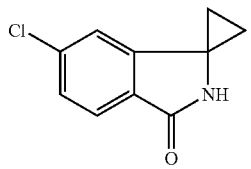

A mixture of 1-(2-bromo-5-chlorophenyl)cyclopropanamine (2 g, 8.1 mmol), Pd(dppf)Cl₂ (0.2 g), DIPEA (3.1 g, 24.3 mmol) in DMF (20 mL) was stirred in an autoclave under 2 MPa of CO (g) at 130° C. for 16 hours. The reaction mixture was diluted with EtOAc (300 mL), and washed with brine. The organic layer was dried over anhy. Na₂SO₄, filtered, and concentrated under reduced pressure to give a crude product which was purified by chromatography to afford title compound (700 mg, yield 44.6%) as a yellow solid. MS: 193.8 (M+H⁺, 1Cl).

Intermediate A-22-1

6'-Chloro-2'-(5-(chloromethyl)pyridin-3-yl)spiro[cyclopropane-1,1'-isoindolin]-3'-one

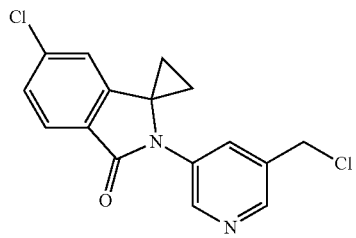 [SMILES: O=C1c2ccc(Cl)cc2C2(CC2)N1c1cncc(CCl)c1]

In analogy to the procedure described for the preparation of intermediate A-12-1, title compound was obtained as yellowish oil. MS: 320.1 (M+H⁺).

Intermediate A-23

6'-Fluorospiro[cyclopropane-1,1'-isoindolin]-3'-one

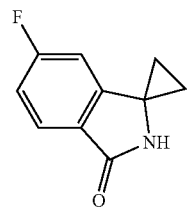 [SMILES: O=C1NC2(CC2)c2cc(F)ccc21]

[A] 1-(2-Bromo-5-fluoro-phenyl)-cyclopropylamine

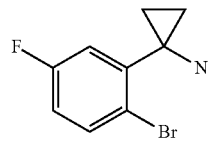 [SMILES: NC1(c2cc(F)ccc2Br)CC1]

To a stirred solution of 2-bromo-5-fluoro-benzonitrile (1 g, 5 mmol) and Ti(Oi-Pr)₄ (1.81 mL, 5.5 mmol) in ether (20 mL) was added EtMgBr (3.67 mL, 11 mmol) at −78° C. After stirring at −78° C. for 10 min, the solution was warmed up to room temperature and stirred for 1 hour. BF₃-Et₂O (1.25 mL) was added before it was stirred for another 1 hour. After addition of 1 N aq. HCl (15 mL) and ether (30 mL), aq. NaOH (10%, 45 mL) solution was added to give two clear phases. The mixture was exacted with EtOAc (30 mL×5). The combined organic layers were dried over anhy. Na₂SO₄, filtered, and concentrated in vacuo to give a crude product, which was

[B] 6'-Fluorospiro[cyclopropane-1,1'-isoindolin]-3'-one

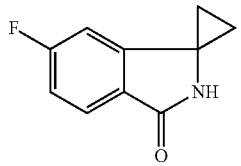 [SMILES: O=C1NC2(CC2)c2cc(F)ccc21]

A solution of 1-(2-bromo-5-fluoro-phenyl)-cyclopropylamine (4.2 g, 18.3 mmol), Pd(dppf)Cl$_2$ (0.42 g), DIPEA (7 g, 54.8 mmol) in 40 mL of DMF was heated at 130° C. under 2 MPa of CO for 12 hours. After it was cooled to room temperature, EtOAc was added it was washed with brine. The organic layer was dried over anhy. Na$_2$SO$_4$, filtered, and concentrated in vacuo. The crude product was purified by column chromatography to give title compound (0.3 g, yield 65.2%) as a solid; meanwhile, 3.3 g of starting material was recovered.

Intermediate A-23-1

2'-(5-(Chloromethyl)pyridin-3-yl)-6'-fluorospiro[cyclopropane-1,1'-isoindolin]-3'-one

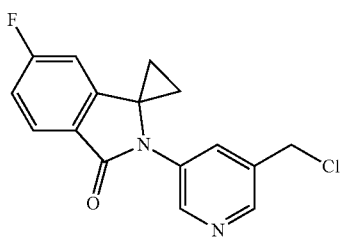 [SMILES: O=C1c2ccc(F)cc2C2(CC2)N1c1cncc(CCl)c1]

In analogy to the procedure described for the preparation of intermediate A-12-1, the title compound was obtained as yellowish oil. MS: 303.1 (M+H$^+$).

Intermediate A-24

5'-Fluorospiro[cyclopropane-1,1'-isoindolin]-3'-one

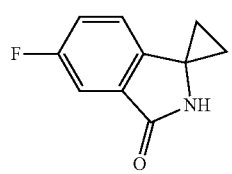 [SMILES: O=C1NC2(CC2)c2ccc(F)cc21]

[A] 1-(2-Bromo-4-fluorophenyl)cyclopropanamine

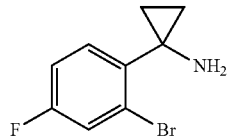 [SMILES: NC1(c2ccc(F)cc2Br)CC1]

To a stirred solution of 2-bromo-4-fluorobenzonitrile (5 g, 25 mmol) and Ti(Oi-Pr)$_4$ (9.05 mL, 27.5 mmol) in ether (100 mL) at −78° C. was added EtMgBr (18.3 mL, 55 mmol) dropwise. The solution was allowed to warm to room temperature and stirred for 1 hour before BF$_3$-Et$_2$O (6.25 mL) was added and stirring continued at room temperature for another 1 hour. The reaction solution was quenched with 1 N HCl solution, and washed with EtOAc. The aqueous layer was adjusted to pH∼10 with aq. NaOH (2 N) solution and then exacted with EtOAc (3×). The combined organic layers were dried over anhy. Na$_2$SO$_4$, filtered, and concentrated in vacuo. The residue was then purified by column chromatography to give title compound (3.0 g, yield 52.2%) as yellowish oil.

[B] 5'-Fluorospiro[cyclopropane-1,1'-isoindolin]-3'-one

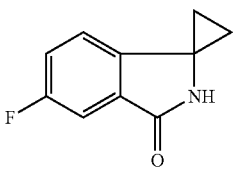

A mixture of 1-(2-bromo-4-fluorophenyl)cyclopropanamine (3.0 g, 17.4 mmol), Pd(dppf)Cl$_2$ (0.4 g), DIPEA (5.05 g, 39.1 mmol) in DMF (40 mL) was stirred in an autoclave under 2 MPa of CO (g) at 130° C. for 16 hours. After it was cooled down to room temperature, the reaction mixture was diluted with EtOAt (300 mL) and washed with brine. The organic layer was dried over anhy. Na$_2$SO$_4$, filtered, and concentrated under reduced pressure to give a crude product which was purified by chromatography to afford title compound (600 mg, yield 26%) as a brown solid.

Intermediate A-24-1

2'-(5-(Chloromethyl)pyridin-3-yl)-6'-fluorospiro[cyclopropane-1,1'-isoindolin]-3'-one

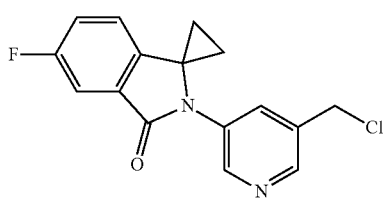 [SMILES: O=C1c2cc(F)ccc2C2(CC2)N1c1cncc(CCl)c1]

In analogy to the procedure described for the preparation of intermediate A-12-1, the title compound was obtained as yellowish oil. MS: 303.1 (M+H⁺).

Intermediate A-25

6-Chloro-3,3-dimethyl-2,3-dihydro-isoindol-1-one

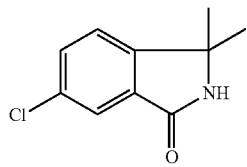

In analogy to the procedure described for the preparation of intermediate A-20, 2-bromo-4-chloro-benzonitrile (step A) and 1-(2-bromo-4-chloro-phenyl)-1-methyl-ethylamine (step B) were used to yield the title compound as a solid (yield 40%). MS: 196.1 (M+H⁺).

Intermediate A-25-1

6-Chloro-2-(5-chloromethyl-pyridin-3-yl)-3,3-dimethyl-2,3-dihydro-isoindol-1-one

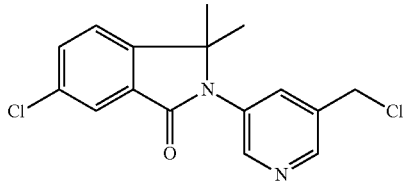 [SMILES: CC1(C)c2ccc(Cl)cc2C(=O)N1c1cncc(CCl)c1]

In analogy to the procedure described for the preparation of intermediate A-12-1, the title compound was obtained as yellowish oil. MS: 322.1 (M+H⁺).

Intermediate B-1

3-Bromo-5-(2-isopropyl-imidazol-1-ylmethyl)-pyridine

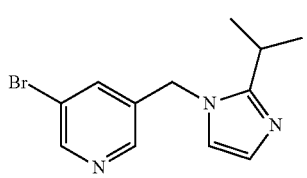 [SMILES: CC(C)c1nccn1Cc1cncc(Br)c1]

[A] 3-Bromo-5-chloromethyl-pyridine

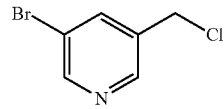

To a solution of (5-bromopyridin-3-yl)methanol (3 g, 16.0 mmol) in DCM (15 mL) cooled to 0° C. was added thionylchloride (7.59 g, 63.8 mmol) dropwise and the reaction mixture was stirred at room temperature overnight. The mixture was poured onto ice/water (20 mL), basified with NaOH conc. (8 mL) and extracted with EtOAc (2×50 mL). Combined organics were dried over $Na_2SO_4$, filtered and evaporated to dryness. The residue was purified by silica gel flash chromatography eluting with a 0 to 40% EtOAc-heptane gradient to give the title compound (3.08 g, 93%) as a white solid. MS: 206.0, 207.9 (M+H⁺).

[B] 3-Bromo-5-(2-isopropyl-imidazol-1-ylmethyl)-pyridine

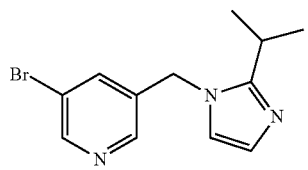

To a suspension of sodium hydride (60% in mineral oil, 0.073 g, 1.82 mmol) in DMF (3 mL) was added 2-isopropyl-1H-imidazole (0.173 g, 1.57 mmol) and the reaction mixture was stirred at room temperature for 20 min. Then, 3-bromo-5-chloromethyl-pyridine (0.25 g, 1.21 mmol) was added and the resulting suspension was heated at 60° C. overnight. The mixture was quenched with water (2 mL) and extracted with EtOAc (2×10 mL). Combined organics were dried over $Na_2SO_4$, filtered and concentrated in vacuo. The residue was purified by silica gel flash chromatography eluting with a 0 to 5% MeOH-DCM gradient to give the title compound (0.275 g, 81%) as a light yellow oil. MS: 280.0, 282.0 (M+H⁺).

Intermediate B-2

3-Bromo-5-(2-methyl-imidazol-1-ylmethyl)-pyridine

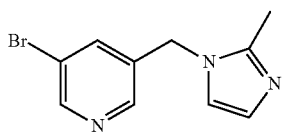

In analogy to the procedure described for the preparation of intermediates B-1 [B], 2-methyl-imidazol has been coupled to 3-bromo-5-chloromethyl-pyridine (intermediate B-1 [A]) to yield the title compound as a light brown solid. MS: 251.9, 254.0 (M+H+).

Intermediate B-3

3-Bromo-5-[1,2,4]triazol-1-ylmethyl-pyridine

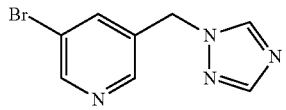 [SMILES: Brc1cncc(Cn2cncn2)c1]

In analogy to the procedure described for the preparation of intermediates B-1 [B], 1H-1,2,4-triazole has been coupled to 3-bromo-5-chloromethyl-pyridine (intermediate B-1 [A]) to yield the title compound as a white solid. MS: 238.9, 241.3 (M+H+).

Intermediate B-4

1-(5-Bromo-pyridin-3-ylmethyl)-pyrrolidin-2-one

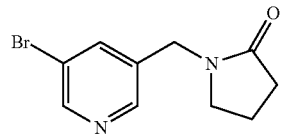 [SMILES: O=C1CCCN1Cc1cncc(Br)c1]

In analogy to the procedure described for the preparation of intermediates B-1 [B], pyrrolidin-2-one has been coupled to 3-bromo-5-chloromethyl-pyridine (intermediate B-1 [A]) to yield the title compound as a white solid. MS: 251.1, 257.1 (M+H+).

Intermediate B-5

1-(5-Bromo-pyridin-3-ylmethyl)-piperidin-2-one

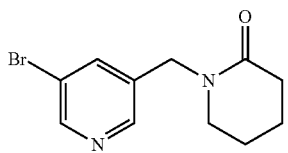 [SMILES: O=C1CCCCN1Cc1cncc(Br)c1]

In analogy to the procedure described for the preparation of intermediates B-1 [B], piperidin-2-one has been coupled to 3-bromo-5-chloromethyl-pyridine (intermediate B-1 [A]) to yield the title compound as a colorless oil. MS: 269.2, 271.2 (M+H+).

Intermediate B-6

3-Bromo-5-((S)-2-methoxymethyl-pyrrolidin-1-ylmethyl)-pyridine

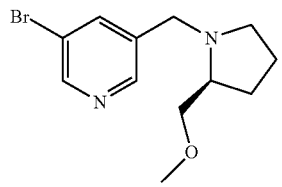 [SMILES: COC[C@@H]1CCCN1Cc1cncc(Br)c1]

In analogy to the procedure described for the preparation of intermediates B-1 [B], (S)-2-(methoxymethyl)pyrrolidine has been coupled to 3-bromo-5-chloromethyl-pyridine (intermediate B-1 [A]) to yield the title compound as a yellow oil. MS: 285.0, 286.9 (M+H+).

Intermediate B-7

Ethanesulfonic acid (5-bromo-pyridin-3-ylmethyl)-amide

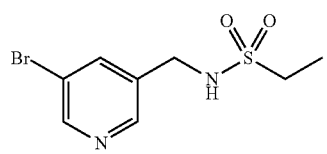

A flask was charged with 5-bromonicotinaldehyde (2.55 g, 13.7 mmol), ethanesulfonamide (2.99 g, 27.4 mmol) and toluene (250 mL), then titanium isopropoxide (5.84 g, 20.6 mmol) was added dropwise. The reaction mixture was stirred at 115° C. overnight and then concentrated in vacuo. The residue was taken up in DCM (200 mL) and MeOH (200 mL) and NaBH$_4$ (1.04 g, 27.4 mmol) was added portionwise at 0° C. The reaction mixture was stirred at 0° C. for 30 min and then poured into water (100 mL) and the resulting suspension was filtered through a pad of dicalite. The dicalite layer was washed with DCM (3×100 mL). The resulting aqueous layer was separated and extracted with DCM (500 mL). Combined organics were dried over Na$_2$SO$_4$, filtered and preadsorbed on silica gel. The residue was purified by silica gel flash chromatography eluting with a 0 to 5% MeOH-DCM gradient to give the title compound (3.01 g, 79%) as an orange solid. MS: 279.0, 281.0 (M+H+).

Intermediate B-8

(S)-1-(5-Bromo-pyridin-3-yl)-5-hydroxymethyl-pyrrolidin-2-one

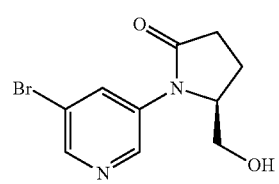 [SMILES: O=C1CC[C@@H](CO)N1c1cncc(Br)c1]

In a sealed tube, 3,5-dibromopyridine (0.5 g, 2.11 mmol) was combined with (S)-5-(hydroxymethyl)pyrrolidin-2-one (0.243 g, 2.11 mmol), copper (I) iodide (0.040 g, 0.021 mmol), potassium carbonate (0.583 g, 4.22 mmol) and N,N'-dimethylethylenediamine (0.037 g, 0.042 mmol) in 1,4-dioxane (20 mL). The reaction mixture was heated at 110° C. overnight. The mixture was cooled to room temperature, filtered through dicalite and washed with DCM. The residue was purified by silica gel flash chromatography eluting with a 0 to 10% MeOH-DCM gradient to give the title compound (0.140 g, 25%) as a light yellow oil. MS: 271.1, 273.1 (M+H$^+$).

Intermediate B-9

1-(5-Bromo-pyridin-3-yl)-pyrrolidin-2-one

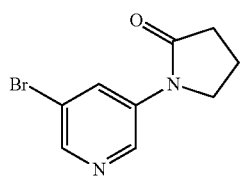

In analogy to the procedure described for the preparation of intermediate B-8, pyrrolidin-2-one has been coupled to 3,5-dibromopyridine to yield the title compound as a light yellow solid. MS: 241.0, 243.0 (M+H$^+$).

Intermediate B-10

3-Bromo-5-((S)-2-methoxymethyl-pyrrolidin-1-yl)-pyridine

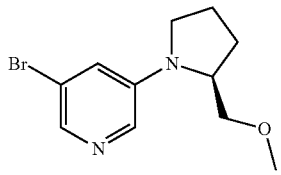

In analogy to the procedure described for the preparation of example 135 [B], (S)-2-methoxymethyl-pyrrolidine was reacted with 3,5-dibromopyridine in the presence of Pd$_2$(dba)$_3$, rac-BINAP and sodium tert-butoxide to give the title compound as a yellow oil. MS: 271.1, 273.1 (M+H$^+$).

Intermediate B-11

4-Bromo-5,6,7,8-tetrahydroisoquinolin-8-ol

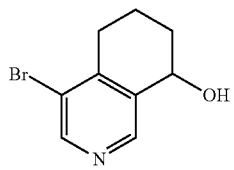

[A] Ethyl 5-bromo-4-methylnicotinate

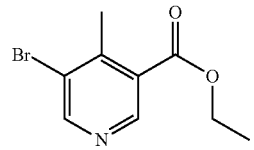

To a stirred light brown suspension of 5-bromo-4-methylnicotinic acid (10.00 g, 46.3 mmol) and ethanol (2.97 mL) in DCM (231 mL) at 0° C. under argon was added EDCI (10.9 g, 55.5 mmol) and DMAP (566 mg, 4.63 mmol); stirring was continued overnight and the reaction mixture was allowed to warm up to room temperature. The reaction mixture was then poured on aq. 10% KH$_2$PO$_4$ solution followed by extraction with AcOEt (3×). The organic phases were washed once with aq. 10% KH$_2$PO$_4$, with sat. NaHCO$_3$ and with aq. sat. NaCl solution. The combined organic phases were dried (Na$_2$SO$_4$), filtered and evaporated to afford the title compound (9.49 g, 84%) as brown solid. MS: 244.0 (M+H$^+$, 1Br).

[B] Methyl 4-bromo-8-oxo-5,6,7,8-tetrahydroisoquinoline-7-carboxylate

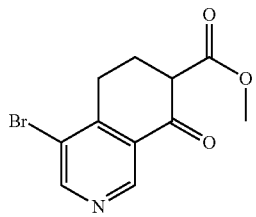 [SMILES: COC(=O)C1CCc2c(Br)cncc2C1=O]

Ethyl 5-bromo-4-methylnicotinate (7.04 g, 28.8 mmol) in THF (28.8 mL) was added over a period of 20 min to a solution of LDA (31.7 mmol) [generated from N,N-diisopropylamine (4.52 ml, 31.7 mmol) and n-butyllithium (19.8 mL, 31.7 mmol, 1.6M in hexane) in 144 mL THF] at −78° C. The resulting dark red solution was stirred for 20 min, then methyl acrylate (6.21 g, 72.1 mmol) in THF (28.8 mL) was added over 15 min. The reaction was stirred an additional 1.5 h, then aq. 10% AcOH was added (resulting pH=4-5) and the reaction was allowed to warm to room temperature. After evaporation, the residue was poured on aq. sat. NaHCO$_3$ and extracted with EtOAc (3×). The combined organic layers were dried (Na$_2$SO$_4$) and concentrated to afford the title compound (7.80 g, 95% in 70% purity with 30% starting material) as brown solid. MS: 284.0 (M+H$^+$, 1Br).

[C] 4-Bromo-6,7-dihydroisoquinolin-8(5H)-one

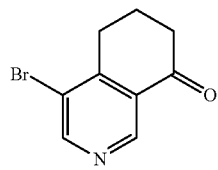 [SMILES: O=C1CCCc2c(Br)cncc21]

The crude methyl 4-bromo-8-oxo-5,6,7,8-tetrahydroisoquinoline-7-carboxylate (7.79 g, 27.4 mmol) was dissolved (small amount of not dissolved material) in aq. 6M HCl (84.1 ml, 505 mmol) and heated at reflux for 2.5 h. The acidic solution was concentrated in vacuo, suspended in water (ca. 25 mL), cooled in ice and basified with 6.0 M KOH. The aqueous solution was extracted with ether (2×) and CH$_2$Cl$_2$ (3×), the combined organic layers were dried over Na$_2$SO$_4$, filtered and concentrated to afford the title compound (4.30 g, 69%) as a brown solid. MS: 226.0 (M+H$^+$, 1Br).

[D] 4-Bromo-5,6,7,8-tetrahydroisoquinolin-8-ol

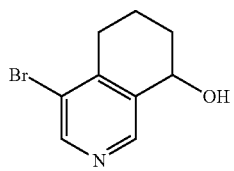 [SMILES: OC1CCCc2c(Br)cncc21]

4-Bromo-6,7-dihydroisoquinolin-8(5H)-one (2.135 g, 9.44 mmol) was suspended in MeOH (18.9 mL), cooled to 0° C. and treated with NaBH$_4$ (357 mg, 9.44 mmol) in 5 portions over 30 min; then, the reaction was stirred for ¾ h at 0° C. (TLC after 30 min showed no more starting material). AcOH was then added dropwise until pH~5-6 and the reaction mixture was evaporated. The residue was diluted with water and poured on aq. sat. NaHCO$_3$-sol. followed by extraction with EtOAc (3×). The organic layers were washed once with aq. sat. NaHCO$_3$-sol. and aq. 10% NaCl-sol., dried over Na$_2$SO$_4$ and concentrated in vacuo. The residue was re-dissolved in CH$_2$Cl$_2$, evaporated with n-pentane (3×) to around 20 ml each time, while the product precipitates; then, the solvent was decanted and the residue washed with n-pentane and dried in high vacuum to afford the title compound (1.98 g, 92%) as dark brown viscous oil. MS: 227 (M$^+$, 1Br).

Intermediate B-12

N-(4-Bromo-5,6,7,8-tetrahydroisoquinolin-8-yl)propionamide

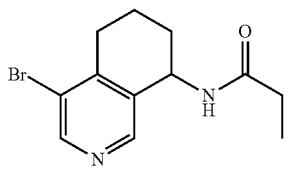 [SMILES: CCC(=O)NC1CCCc2c(Br)cncc21]

[A] 4-Bromo-5,6,7,8-tetrahydroisoquinolin-8-amine

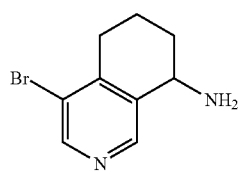 [SMILES: NC1CCCc2c(Br)cncc21]

4-Bromo-6,7-dihydroisoquinolin-8(5H)-one (intermediate B-11 [C]) (4.81 g, 21.3 mmol), titanium (IV) isopropoxide (12.1 g, 42.6 mmol) and ammonia, 2.0 M solution in MeOH (53.2 mL, 106 mmol) were stirred at room temperature for 5 h. The reaction was cooled to 0° C. and NaBH$_4$ (1.21 g, 31.9 mmol) was added portionwise over 10 min; the resulting mixture was stirred at room temperature for an additional 2 h. The reaction was quenched by pouring it into aq ammonium hydroxide 25%, the precipitate was filtered and washed with EtOAc (3×, each time suspended in AcOEt and stirred for 5 min). The organic layer was separated and the remaining aqueous layer was extracted with EtOAc. The combined organic extracts were extracted with 1 M HCl. The acidic aqueous extracts were washed with ethyl acetate (1×), then treated with aqueous sodium hydroxide (2 M) to give pH 10-12 and extracted with EtOAc (3×). The combined organic extracts were washed with brine, dried (Na$_2$SO$_4$), and concentrated in vacuo to afford the title compound (4.11 g, 85%) as brown solid. MS: 225 (M$^+$, 1Br).

[B] N-(4-Bromo-5,6,7,8-tetrahydroisoquinolin-8-yl)propionamide

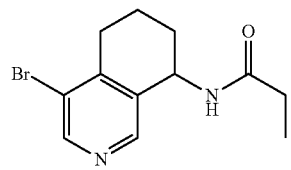

To a stirred brown solution of 4-bromo-5,6,7,8-tetrahydroisoquinolin-8-amine (318 mg, 1.4 mmol) and propionic acid (114 mg, 1.54 mmol) in CH$_2$Cl$_2$ (7.0 mL) at 0° C. under argon was added EDCI (63.3 mg, 0.330 mmol). Stirring was continued overnight and the reaction mixture was allowed to warm up to room temperature. The reaction mixture was poured onto aq. 10% KH$_2$PO$_4$ solution followed by extraction with AcOEt (3×). The organic phases were washed once with aq. 10% KH$_2$PO$_4$, aq. sat. NaHCO$_3$ and with aq. sat. NaCl solution; the combined organic phases were dried over Na$_2$SO$_4$, filtered and evaporated. The residue was dissolved in CH$_2$Cl$_2$, evaporated with n-pentane (3×) to ca. 10 ml each time, while the product precipitated; then, the solvent was decanted and the residue washed twice with n-pentane to afford the title compound (0.365 g, 92%) as light brown solid. MS: 283.0 (M+H$^+$, 1Br).

Intermediate B-13

2-(5-Bromo-pyridin-3-ylmethyl)-[1,2]thiazinane 1,1-dioxide

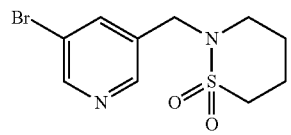 [SMILES: O=S1(=O)CCCCN1Cc1cncc(Br)c1]

In analogy to the procedure described for the preparation of intermediates B-1 [B], [1,2]thiazinane 1,1-dioxide has been coupled to 3-bromo-5-chloromethyl-pyridine (intermediate B-1 [A]) to yield the title compound as off-white solid. MS: 305.1, 307.1 (M+H⁺).

Intermediate B-14

3-Bromo-5-(1,1-dioxo-1⁶-isothiazolidin-2-ylmethyl)-pyridine

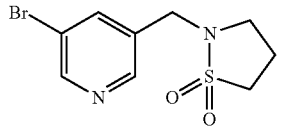 [SMILES: O=S1(=O)CCCN1Cc1cncc(Br)c1]

In analogy to the procedure described for the preparation of intermediates B-1 [B], isothiazolidine 1,1-dioxide has been coupled to 3-bromo-5-chloromethyl-pyridine (intermediate B-1 [A]) to yield the title compound as a light yellow oil. MS: 290.9, 292.8 (M+H⁺).

Intermediate B-15

(S)-1-(5-Bromo-pyridin-3-ylmethyl)-5-(tert-butyl-dimethyl-silanyloxymethyl)-pyrrolidin-2-one

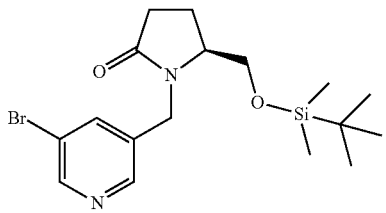 [SMILES: CC(C)(C)[Si](C)(C)OC[C@@H]1CCC(=O)N1Cc1cncc(Br)c1]

In analogy to the procedure described for the preparation of intermediates B-1 [B], (S)-5-(tert-butyl-dimethyl-silanyloxymethyl)-pyrrolidin-2-one has been coupled to 3-bromo-5-chloromethyl-pyridine (intermediate B-1 [A]) to yield the title compound as colorless oil. MS: 399.2, 401.2 (M+H⁺).

Intermediate B-16

(S)-1-(5-Bromo-pyridin-3-ylmethyl)-pyrrolidine-2-carboxylic acid methyl ester

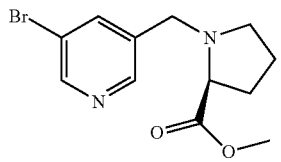 [SMILES: COC(=O)[C@@H]1CCCN1Cc1cncc(Br)c1]

In analogy to the procedure described for the preparation of intermediates B-1 [B], (S)-pyrrolidine-2-carboxylic acid methyl ester has been coupled to 3-bromo-5-chloromethyl-pyridine (intermediate B-1 [A]) to yield the title compound as light yellow oil. MS: 299.2, 301.1 (M+H⁺).

Intermediate B-17

N-(4-Bromo-5,6,7,8-tetrahydro-isoquinolin-8-yl)-acetamide

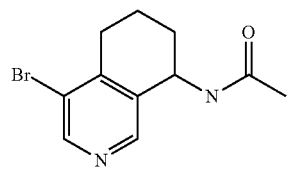

To a stirred solution of 4-bromo-5,6,7,8-tetrahydroisoquinolin-8-amine (intermediate B-12 [A], 318 mg, 1.4 mmol) and Et₃N (3.0 mL) in DCM (10 mL) was added acetyl chloride (0.106 mL, 1.4 mmol) at 0° C. and stirring was continued at 0° C. for 1 hour. The resulting mixture was extracted with EtOAc (2×100 mL). The combined organics were washed with brine, dried over anhy. Na₂SO₄, filtered and concentrated in vacuo to afford a crude product which was purified by silica gel flash chromatography eluting with a 0 to 50% EtOAc-heptane gradient to give the title compound (346 mg, 92%) as light yellow solid. MS: 269.1 & 271.1 (M+H⁺).

Intermediate B-18

N-(4-Bromo-6,7-dihydro-5H-[2]pyrindin-7-yl)-propionamide

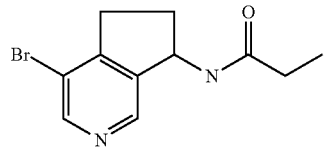

[A] Ethyl 3-(3,5-dibromopyridin-4-yl)propanoate

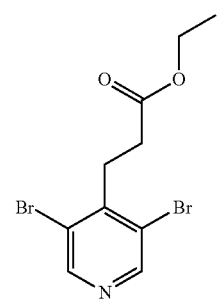

A solution of 3,5-dibromo-4-methylpyridine (20 g, 0.08 mol) in THF (50 mL) was added over a period of 1 hour to a solution of LDA (0.088 mol) [generated from N,N-diisopropylamine (8.9 g, 0.088 mol) and n-butyllithium (35 mL, 0.088 mol, 2.5 M in hexane) in 400 mL THF] at −78° C. The resulting dark red solution was stirred at −78° C. for 30 min before ethylbromoacetate (33.4 g, 0.2 mol) in THF (50 mL) was added over a period of 30 min. The reaction mixture was stirred for an additional 2.5 hour at −78° C. before 10% AcOH was added (resulting in a pH=4-5). The reaction mixture was then allowed to warm up to room temperature. After evaporation of the solvents, the residue was poured into satd. aq. NaHCO$_3$ solution and extracted with EtOAc (100 mL×3). The combined organic layers were dried over anhy. Na$_2$SO$_4$, filtered, and concentrated in vacuo. The residue was purified by column chromatography to afford the title compound (9 g, 33.5%) as a yellow solid. MS: 337.7 (M+H$^+$, 2Br).

[B] 4-Bromo-5H-cyclopenta[c]pyridin-7(6H)-one

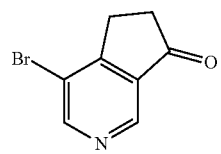

To a solution of ethyl 3-(3,5-dibromopyridin-4-yl)propanoate (4 g, 11.9 mmol) in THF (60 mL) was slowly added n-BuLi (9.52 mL, 23.8 mmol, 2.5 M in hexane) while keeping the inner temperature below −70° C. After the addition, the reaction mixture was stirred below −65° C. for additional 2 hours. The reaction was quenched with water and then extracted with EtOAc (100 mL×3). The combined organic layers were dried over anhy. Na$_2$SO$_4$, filtered, and concentrated in vacuo. The residue was then purified by column chromatography to afford the title compound (1.2 g, 47.6%) as a solid. MS: MS: 213.7 (M+H$^+$, 1Br).

[C] 4-Bromo-6,7-dihydro-5H-[2]pyrindin-7-ylamine

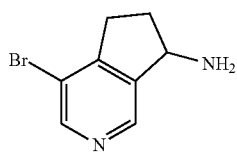 [SMILES: NC1CCc2c(Br)cncc21]

CH$_3$COONH$_4$ (4.8 g, 62 mmol), NaCNBH$_3$ (315 mg, 5 mmol) and 4-bromo-5H-cyclopenta[c]pyridin-7(6H)-one (1.0 g, 4.15 mmol) in EtOH (10 mL) was added to a sealed microwave vial. The mixture was subject to microwave radiation at 130° C. for 4 min. After the majority of EtOH was evaporated under reduced pressure, it was treated with aq. 2 N NaOH until pH>10 and extracted with EtOAc (50 mL x2). The combined organic layers were dried over anhy. Na$_2$SO$_4$, filtered, and concentrated under reduced pressure to give a crude title product (800 mg) which was used in the next step reaction without further purification. MS: 212.9 (M+H$^+$, 1Br).

[D] N-(4-Bromo-6,7-dihydro-5H-cyclopenta[c]pyridin-7-yl)propionamide

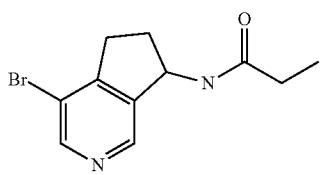

To a solution of 4-bromo-6,7-dihydro-5H-cyclopenta[c]pyridin-7-amine (650 mg, 3.05 mmol, 65% purity) and Et$_3$N (400 mg, 3.97 mmol) in THF (20 mL) was added propionyl chloride (219 mg, 2.38 mmol) at 0° C. and stirring continued for 2 hours. Water (10 mL) and EtOAc (10 mL) were added and the aqueous layer was extracted with EtOAc (10 mL×3). The combined organic layers were dried over anhy. Na$_2$SO$_4$, filtered and concentrated in vacuo to give a crude product which was purified by column chromatography to afford the title compound (200 mg, 37.6%) as a white solid. MS: 270.9 (M+H$^+$, 1Br).

Intermediate B-19

N-(4-Bromo-6,7-dihydro-5H-[2]pyrindin-7-yl)-acetamide

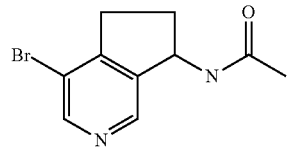

In analogy to the procedure describe for the preparation of intermediate B-18 (step D), the title compound was obtained as a white solid using acetyl chloride as starting material. MS: 256.9 (M+H$^+$, 1Br).

Example 1

6-Chloro-2-pyridin-3-yl-3,4-dihydro-2H-isoquinolin-1-one

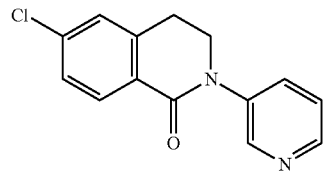 [SMILES: O=C1c2ccc(Cl)cc2CCN1c1cccnc1]

In a sealed tube, 3-bromopyridine (0.1 g, 0.633 mmol) was combined with 6-chloro-3,4-dihydroisoquinolin-1(2H)-one (intermediate A-2) (0.115 g, 633 mmol), copper (I) iodide (0.012 g, 0.063 mmol), potassium carbonate (0.175 g, 1.27 mmol) and N,N'-dimethylethylenediamine (0.013 g, 0.127 mmol) in 1,4-dioxane (2 mL). The reaction mixture was heated at 110° C. overnight. The mixture was cooled to room temperature, filtered through dicalite and washed with DCM. The residue was purified by silica gel flash chromatography eluting with a 5 to 100% EtOAc-heptane gradient to give the title compound (0.107 g, 65%) as a white solid. MS: 259.1 (M+H$^+$).

Example 2

5-(6-Chloro-1-oxo-3,4-dihydro-1H-isoquinolin-2-yl)-nicotinonitrile

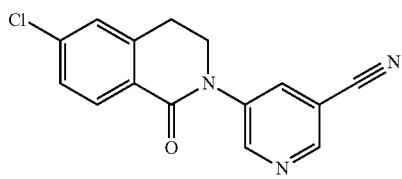 [SMILES: N#Cc1cncc(N2CCc3cc(Cl)ccc3C2=O)c1]

6-Chloro-3,4-dihydro-2H-isoquinolin-1-one (intermediate A-2) (36 mg, 0.2 mmol), 5-bromo-nicotinonitrile (73 mg, 0.4 mmol), CuI (3.8 mg, 0.02 mmol), (1S,2S)-cyclohexane-1,2-diamine (4.5 mg, 0.04 mmol) and $Cs_2CO_3$ (130 mg, 0.4 mmol) were dissolved in dioxane (5 mL). The reaction mixture was subjected to microwave reaction at 150° C. for 2.5 hours before it was poured into $H_2O$ (50 mL) and extracted with EtOAc (2×25 mL). The organic layer was washed with brine, dried over anhy. $Na_2SO_4$, filtered and concentrated in vacuo to give a crude product which was purified by prep-HPLC to yield the title compound (15 mg, 26%) as a white solid. MS: 284.1 (M+H$^+$).

Example 3

6-Chloro-2-(5-hydroxymethyl-pyridin-3-yl)-3,4-dihydro-2H-isoquinolin-1-one

[A] (5-Bromo-pyridin-3-yl)-methanol

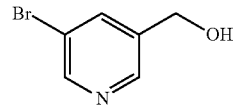

Sodium borohydride (2.2 g, 59.1 mmol) was added at 0° C. to a suspension of 5-bromo-pyridine-3-carbaldehyde (10.0 g, 53.7 mmol) in MeOH (100 mL). The mixture was stirred at 0° C. for 1 hour before it was quenched by addition of water (5.0 mL). Evaporation of solvents afforded a light yellowish oil which was re-dissolved in EtOAc and washed with water. The organic layer was dried over $Na_2SO_4$, filtered and concentrated in vacuo to give the title compound (9.6 g, 95%) as colorless oil. MS: 188.0 & 190.0 (M+H$^+$).

[B] 6-Chloro-2-(5-hydroxymethyl-pyridin-3-yl)-3,4-dihydro-2H-isoquinolin-1-one

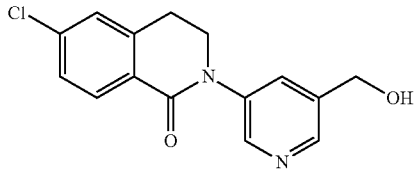 [SMILES: O=C1c2ccc(Cl)cc2CCN1c1cncc(CO)c1]

In a 25 mL sealed tube, (5-bromo-pyridin-3-yl)-methanol (900 mg, 4.8 mmol), 6-chloro-3,4-dihydro-2H-isoquinolin-1-one (intermediate A-2) (800 mg, 4.4 mmol), CuI (200 mg, 1.1 mmol), $Cs_2CO_3$ (3.0 g, 9.2 mmol) and (+)-(S,S)-1,2-diaminocyclohexane (0.4 mL, 3.2 mmol) were dissolved in dioxane (8.0 mL). The resulting reaction mixture was heated at 150° C. for 3 hours before it was poured into $H_2O$ (50 mL) and extracted with EtOAc (2×125 mL). The organic layer was washed with brine, dried over anhy. $Na_2SO_4$, filtered and concentrated in vacuo to give a crude product which was purified by silica gel flash chromatography (30-100% EtOAc-hexane gradient) to yield the title compound (1.1 g, 90%) as a light yellow solid. MS: 289.2 (M+H$^+$).

The following compounds listed in Table 1 were prepared in analogy to the procedures described for the preparation of examples 1, 2 or 3 [B] using appropriate starting materials.

TABLE 1

| Ex | Compound Name | Compound Structure | Starting Materials | Prepared by analogy to example | MS (M + H)$^+$ |
|---|---|---|---|---|---|
| 4 | 6-Chloro-2-(5-chloro-pyridin-3-yl)-3,4-dihydro-2H-isoquinolin-1-one | 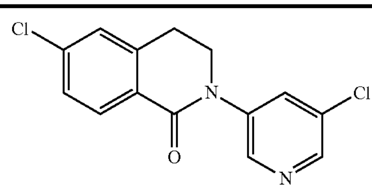 | 6-Chloro-3,4-dihydro-2H-isoquinolin-1-one (intermediate A-2) and 1-bromo-3-chloro-benzene | 2 | 293.1 |
| 5 | 6-Chloro-2-(5-fluoro-pyridin-3-yl)-3,4-dihydro-2H-isoquinolin-1-one | 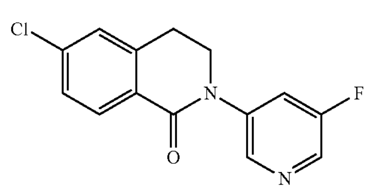 [SMILES: O=C1c2ccc(Cl)cc2CCN1c1cncc(F)c1] | 6-Chloro-3,4-dihydro-2H-isoquinolin-1-one (intermediate A-2) and 3-bromo-5-fluoro-pyridine | 3[B] | 277.1 |

TABLE 1-continued

| Ex | Compound Name | Compound Structure | Starting Materials | Prepared by analogy to example | MS (M + H)+ |
|---|---|---|---|---|---|
| 6 | 6-Chloro-2-(4-chloro-pyridin-3-yl)-3,4-dihydro-2H-isoquinolin-1-one | 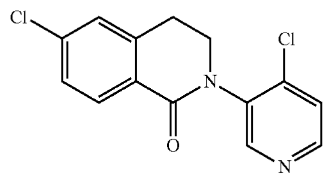 [SMILES: O=C1c2ccc(Cl)cc2CCN1c1cnccc1Cl] | 6-Chloro-3,4-dihydro-2H-isoquinolin-1-one (intermediate A-2) and 3-bromo-4-chloro-pyridine | 2 | 293.1 |
| 7 | 2-(5-Bromo-pyridin-3-yl)-6-chloro-3,4-dihydro-2H-isoquinolin-1-one | 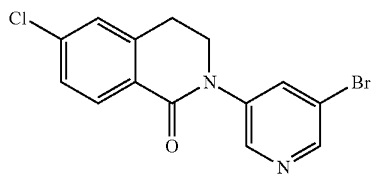 [SMILES: O=C1c2ccc(Cl)cc2CCN1c1cncc(Br)c1] | 6-Chloro-3,4-dihydro-2H-isoquinolin-1-one (intermediate A-2) and 3-bromo-5-iodo-pyridine | 2 | 337.1 |
| 8 | 6-Chloro-2-(5-methyl-pyridin-3-yl)-3,4-dihydro-2H-isoquinolin-1-one | 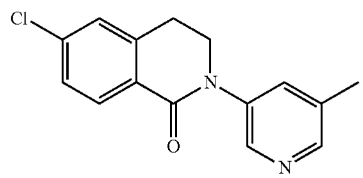 [SMILES: Cc1cncc(N2CCc3cc(Cl)ccc3C2=O)c1] | 6-Chloro-3,4-dihydro-2H-isoquinolin-1-one (intermediate A-2) and 3-bromo-5-methyl-pyridine | 3[B] | 273.1 |
| 9 | 5-(6-Chloro-1-oxo-3,4-dihydro-1H-isoquinolin-2-yl)-pyridine-3-carbaldehyde | 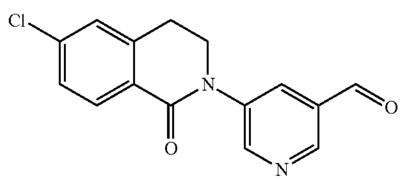 [SMILES: O=Cc1cncc(N2CCc3cc(Cl)ccc3C2=O)c1] | 6-Chloro-3,4-dihydro-2H-isoquinolin-1-one (intermediate A-2) and 5-bromo-pyridine-3-carbaldehyde | 2 | 287.1 |
| 10 | 6-Chloro-2-(5-methoxy-pyridin-3-yl)-3,4-dihydro-2H-isoquinolin-1-one | 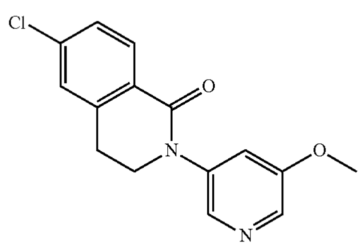 [SMILES: COc1cncc(N2CCc3cc(Cl)ccc3C2=O)c1] | 6-Chloro-3,4-dihydro-2H-isoquinolin-1-one (intermediate A-2) and 3-bromo-5-methoxy-pyridine | 1 | |
| 11 | 6-Chloro-2-(5-isopropoxy-pyridin-3-yl)-3,4-dihydro-2H-isoquinolin-1-one | 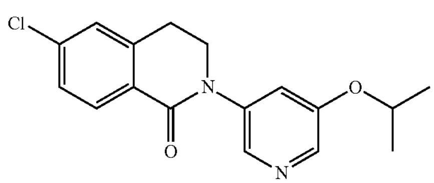 [SMILES: CC(C)Oc1cncc(N2CCc3cc(Cl)ccc3C2=O)c1] | 6-Chloro-3,4-dihydro-2H-isoquinolin-1-one (intermediate A-2) and 3-bromo-5-isopropoxy-pyridine | 2 | 317.2 |
| 12 | 6-Chloro-2-[5-(1-hydroxy-1-methyl-ethyl)-pyridin-3-yl]-3,4-dihydro-2H-isoquinolin-1-one | 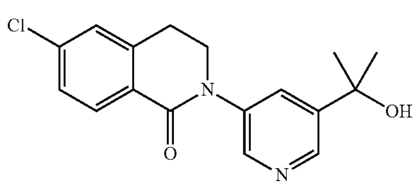 [SMILES: CC(C)(O)c1cncc(N2CCc3cc(Cl)ccc3C2=O)c1] | 6-Chloro-3,4-dihydro-2H-isoquinolin-1-one (intermediate A-2) and 2-(5-bromo-pyridin-3-yl)-propan-2-ol | 2 | 317.2 |
| 13 | 6-Chloro-2-[5-(1-hydroxy-ethyl)-pyridin-3-yl]-3,4-dihydro-2H-isoquinolin-1-one | 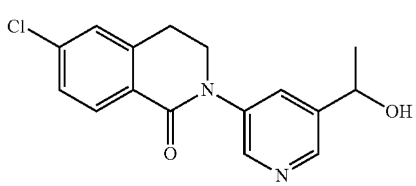 [SMILES: CC(O)c1cncc(N2CCc3cc(Cl)ccc3C2=O)c1] | 6-Chloro-3,4-dihydro-2H-isoquinolin-1-one (intermediate A-2) and 1-(5-bromo-pyridin-3-yl)-ethanol | 2 | 303.1 |

TABLE 1-continued

| Ex | Compound Name | Compound Structure | Starting Materials | Prepared by analogy to example | MS (M + H)+ |
|---|---|---|---|---|---|
| 14 | 6-Chloro-2-[5-((R)-1-hydroxy-ethyl)-pyridin-3-yl]-3,4-dihydro-2H-isoquinolin-1-one | 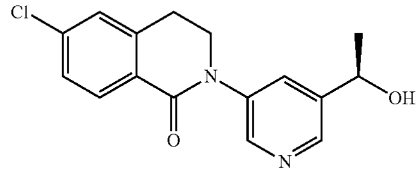 [SMILES: C[C@@H](O)c1cncc(N2CCc3cc(Cl)ccc3C2=O)c1] | 6-Chloro-3,4-dihydro-2H-isoquinolin-1-one (intermediate A-2) and (R)-1-1-(5-bromo-pyridin-3-yl)-ethanol | 2 | 303.1 |
| 15 | 6-Chloro-2-[5-((S)-1-hydroxy-ethyl)-pyridin-3-yl]-3,4-dihydro-2H-isoquinolin-1-one | 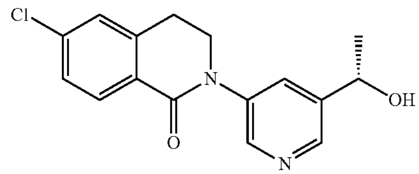 [SMILES: C[C@H](O)c1cncc(N2CCc3cc(Cl)ccc3C2=O)c1] | 6-Chloro-3,4-dihydro-2H-isoquinolin-1-one (intermediate A-2) and (S)-1-1-(5-bromo-pyridin-3-yl)-ethanol | 2 | 303.1 |
| 16 | 6-Chloro-2-[5-(1-methoxy-ethyl)-pyridin-3-yl]-3,4-dihydro-2H-isoquinolin-1-one | 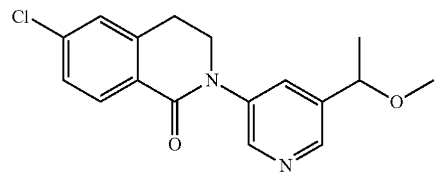 [SMILES: COC(C)c1cncc(N2CCc3cc(Cl)ccc3C2=O)c1] | 6-Chloro-3,4-dihydro-2H-isoquinolin-1-one (intermediate A-2) and 3-bromo-5-(1-methoxy-ethyl)-pyridine | 2 | 317.2 |
| 17 | 2-(5-Aminopyridin-3-yl)-6-chloro-3,4-dihydro-2H-isoquinolin-1-one | 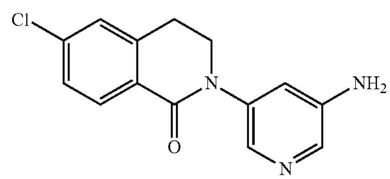 [SMILES: Nc1cncc(N2CCc3cc(Cl)ccc3C2=O)c1] | 6-Chloro-3,4-dihydro-2H-isoquinolin-1-one (intermediate A-2) and 5-bromo-pyridin-3-ylamine | 2 | 274.1 |
| 18 | 6-Chloro-2-[5-(2,2,2-trifluoro-1-hydroxy-ethyl)-pyridin-3-yl]-3,4-dihydro-2H-isoquinolin-1-one | 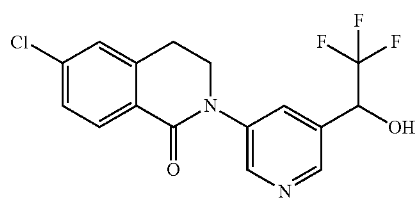 [SMILES: O=C1c2ccc(Cl)cc2CCN1c1cncc(C(O)C(F)(F)F)c1] | 6-Chloro-3,4-dihydro-2H-isoquinolin-1-one (intermediate A-2) and 1-(5-bromo-pyridin-3-yl)-2,2,2-trifluoro-ethanol | 2 | 357.2 |
| 19 | 6-Chloro-2-[5-(2,2,2-trifluoro-1-methoxy-ethyl)-pyridin-3-yl]-3,4-dihydro-2H-isoquinolin-1-one | 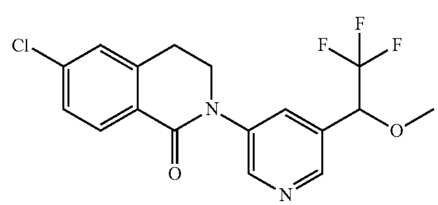 [SMILES: COC(c1cncc(N2CCc3cc(Cl)ccc3C2=O)c1)C(F)(F)F] | 6-Chloro-3,4-dihydro-2H-isoquinolin-1-one (intermediate A-2) and 3-bromo-5-(2,2,2-trifluoro-1-methoxy-ethyl)-pyridine | 2 | 371.2 |
| 20 | 6-Chloro-2-[5-(cyclopropyl-hydroxy-methyl)-pyridin-3-yl]-3,4-dihydro-2H-isoquinolin-1-one | 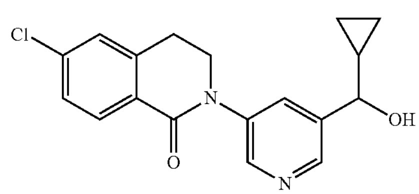 [SMILES: O=C1c2ccc(Cl)cc2CCN1c1cncc(C(O)C2CC2)c1] | 6-Chloro-3,4-dihydro-2H-isoquinolin-1-one (intermediate A-2) and (5-bromo-pyridin-3-yl)-cyclopropyl-methanol | 2 | 329.2 |
| 21 | 6-Chloro-2-[5-(cyclopropyl-methoxy-methyl)-pyridin-3-yl]-3,4-dihydro-2H-isoquinolin-1-one | 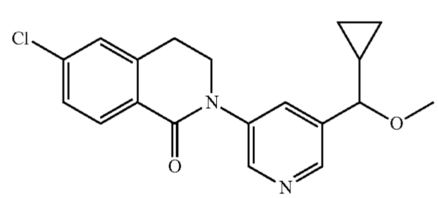 [SMILES: COC(c1cncc(N2CCc3cc(Cl)ccc3C2=O)c1)C1CC1] | 6-Chloro-3,4-dihydro-2H-isoquinolin-1-one (intermediate A-2) and 3-bromo-5-(cyclopropyl-methoxy-methyl)-pyridine | 2 | 343.2 |

TABLE 1-continued

| Ex | Compound Name | Compound Structure | Starting Materials | Prepared by analogy to example | MS (M + H)+ |
|---|---|---|---|---|---|
| 22 | 6-Chloro-2-(4-trifluoromethyl-pyridin-3-yl)-3,4-dihydro-2H-isoquinolin-1-one | 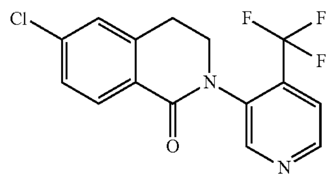 [SMILES: O=C1c2ccc(Cl)cc2CCN1c1cnccc1C(F)(F)F] | 6-Chloro-3,4-dihydro-2H-isoquinolin-1-one (intermediate A-2) and 3-bromo-4-trifluoromethyl-pyridine | 3[B] | 327.1 |
| 23 | 6-Chloro-2-[5-(2-hydroxy-ethyl)-pyridin-3-yl]-3,4-dihydro-2H-isoquinolin-1-one | 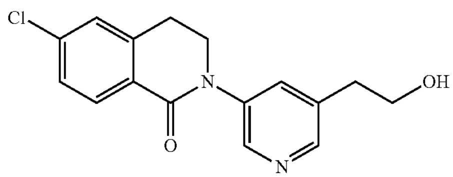 [SMILES: O=C1c2ccc(Cl)cc2CCN1c1cncc(CCO)c1] | 6-Chloro-3,4-dihydro-2H-isoquinolin-1-one (intermediate A-2) and 2-(5-bromo-pyridin-3-yl)-ethanol | 2 | 303.1 |
| 24 | 6-Chloro-2-[5-(1-methoxy-1-methyl-ethyl)-pyridin-3-yl]-3,4-dihydro-2H-isoquinolin-1-one | 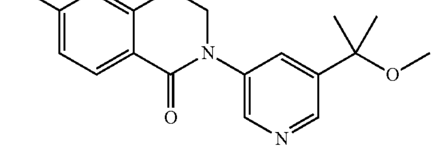 | 6-Chloro-3,4-dihydro-2H-isoquinolin-1-one (intermediate A-2) and 3-bromo-5-(1-methoxy-1-methyl-ethyl)-pyridine | 2 | 331.2 |
| 25 | Ethanesulfonic acid [5-(6-chloro-1-oxo-3,4-dihydro-1H-isoquinolin-2-yl)-pyridin-3-ylmethyl]-amide | 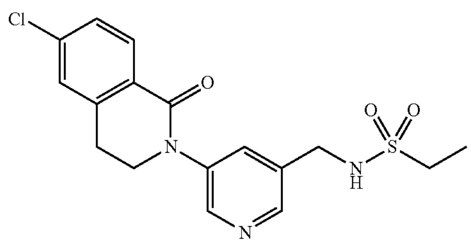 [SMILES: CCS(=O)(=O)NCc1cncc(N2CCc3cc(Cl)ccc3C2=O)c1] | 6-Chloro-3,4-dihydroisoquinolin-1(2H)-one (intermediate A-2) and ethanesulfonic acid (5-bromo-pyridin-3-ylmethyl)-amide (intermediate B-7) | 1 | 380.1 |
| 26 | 6-Chloro-2-[5-(2-oxo-pyrrolidin-1-yl)-pyridin-3-yl]-3,4-dihydro-2H-isoquinolin-1-one | 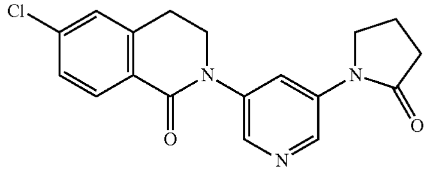 [SMILES: O=C1CCCN1c1cncc(N2CCc3cc(Cl)ccc3C2=O)c1] | 6-Chloro-3,4-dihydroisoquinolin-1(2H)-one (intermediate A-2) and 1-(5-bromo-pyridin-3-yl)-pyrrolidin-2-one (intermediate B-9) | 1 | 342.0 |
| 27 | 6-Chloro-2-(1-methyl-1H-pyrazolo[3,4-c]pyridin-4-yl)-3,4-dihydro-2H-isoquinolin-1-one | 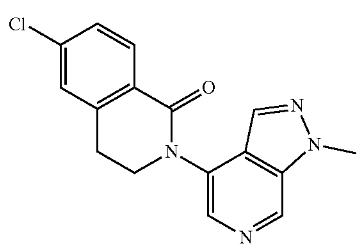 [SMILES: Cn1ncc2c(N3CCc4cc(Cl)ccc4C3=O)cncc21] | 6-Chloro-3,4-dihydroisoquinolin-1(2H)-one (intermediate A-2) and 4-bromo-1-methyl-1H-pyrazolo[3,4-c]pyridine | 1 | 313.2 |
| 28 | 6-Chloro-8'-hydroxy-3,4,5',6',7',8'-hexahydro-[2,4']biisoquinolinyl-1-one | 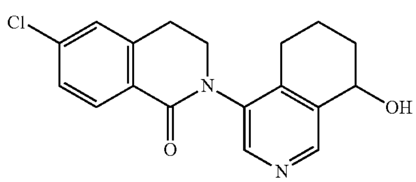 [SMILES: O=C1c2ccc(Cl)cc2CCN1c1cncc2c1CCCC2O] | 6-Chloro-3,4-dihydroisoquinolin-1(2H)-one (intermediate A-2) and 4-bromo-5,6,7,8-tetrahydro-isoquinolin-8-ol (intermediate B-11) | 1 | 329.1 |

TABLE 1-continued

| Ex | Compound Name | Compound Structure | Starting Materials | Prepared by analogy to example | MS (M + H)+ |
|---|---|---|---|---|---|
| 29 | N-(6-Chloro-1-oxo-3,4,5',6',7',8'-hexahydro-1H-[2,4']biisoquinolinyl-8'-yl)-propionamide | 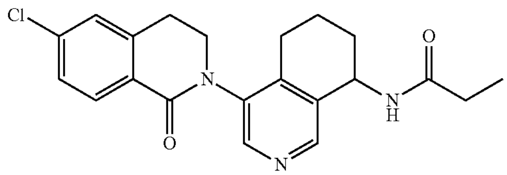 [SMILES: CCC(=O)NC1CCCc2c1cncc2N1CCc2cc(Cl)ccc2C1=O] | 6-Chloro-3,4-dihydroisoquinolin-1(2H)-one (intermediate A-2) and N-(4-bromo-5,6,7,8-tetrahydroisoquinolin-8-yl)propionamide (intermediate B-12) | 1 | 384.1 |
| 30 | 6-Chloro-2-{5-[hydroxy-(1-methyl-1H-imidazol-2-yl)-methyl]-pyridin-3-yl}-3,4-dihydro-2H-isoquinolin-1-one | 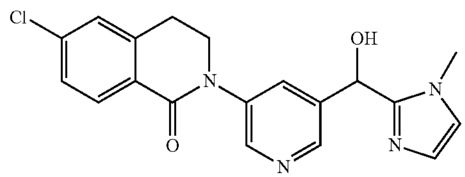 [SMILES: Cn1ccnc1C(O)c1cncc(N2CCc3cc(Cl)ccc3C2=O)c1] | 6-Chloro-3,4-dihydro-2H-isoquinolin-1-one (intermediate A-2) and (5-bromo-pyridin-3-yl)-(1-methyl-1H-imidazol-2-yl)-methanol | 3[B] | 369.1 |
| 31 | 6-Chloro-2-{5-[(3,4-difluoro-phenyl)-hydroxy-methyl]-pyridin-3-yl}-3,4-dihydro-2H-isoquinolin-1-one | 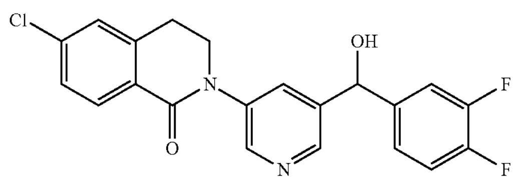 [SMILES: O=C1c2ccc(Cl)cc2CCN1c1cncc(C(O)c2ccc(F)c(F)c2)c1] | 6-Chloro-3,4-dihydro-2H-isoquinolin-1-one (intermediate A-2) and (5-bromo-pyridin-3-yl)-(3,4-difluoro-phenyl)-methanol | 3[B] | 401.1 |
| 32 | 6-Chloro-2-{5-[(3,5-difluoro-phenyl)-hydroxy-methyl]-pyridin-3-yl}-3,4-dihydro-2H-isoquinolin-1-one | 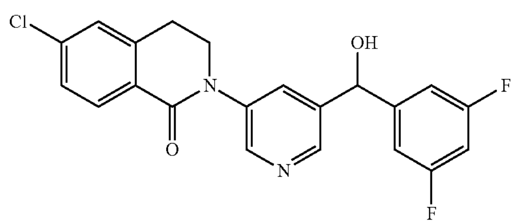 [SMILES: O=C1c2ccc(Cl)cc2CCN1c1cncc(C(O)c2cc(F)cc(F)c2)c1] | 6-Chloro-3,4-dihydro-2H-isoquinolin-1-one (intermediate A-2) and (5-bromo-pyridin-3-yl)-(3,5-difluoro-phenyl)-methanol | 3[B] | 401.1 |
| 33 | 6-Chloro-2-{5-[(4-ethyl-phenyl)-hydroxy-methyl]-pyridin-3-yl}-3,4-dihydro-2H-isoquinolin-1-one | 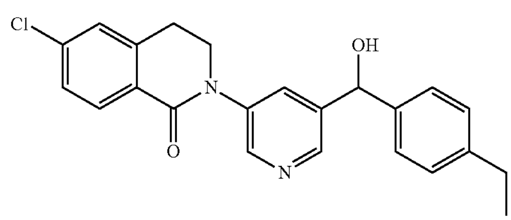 [SMILES: CCc1ccc(C(O)c2cncc(N3CCc4cc(Cl)ccc4C3=O)c2)cc1] | 6-Chloro-3,4-dihydro-2H-isoquinolin-1-one (intermediate A-2) and (5-bromo-pyridin-3-yl)-(4-ethyl-phenyl)-methanol | 3[B] | 393.2 |
| 34 | 6-Chloro-2-[5-(hydroxy-phenyl-methyl)-pyridin-3-yl]-3,4-dihydro-2H-isoquinolin-1-one | 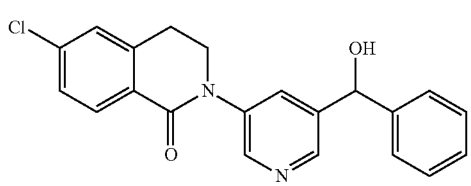 [SMILES: O=C1c2ccc(Cl)cc2CCN1c1cncc(C(O)c2ccccc2)c1] | 6-Chloro-3,4-dihydro-2H-isoquinolin-1-one (intermediate A-2) and (5-bromo-pyridin-3-yl)-phenyl-methanol | 3[B] | 365.1 |
| 35 | 6-Chloro-2-[5-(1-hydroxy-1-phenyl-ethyl)-pyridin-3-yl]-3,4-dihydro-2H-isoquinolin-1-one | 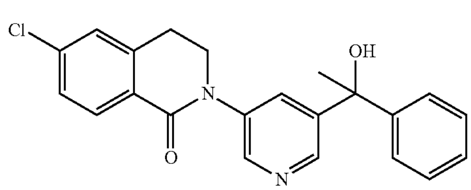 [SMILES: CC(O)(c1ccccc1)c1cncc(N2CCc3cc(Cl)ccc3C2=O)c1] | 6-Chloro-3,4-dihydro-2H-isoquinolin-1-one (intermediate A-2) and 1-(5-bromo-pyridin-3-yl)-1-phenyl-ethanol | 3[B] | 379.2 |

TABLE 1-continued

| Ex | Compound Name | Compound Structure | Starting Materials | Prepared by analogy to example | MS (M + H)+ |
|---|---|---|---|---|---|
| 36 | 6-Chloro-2-{5-[1-(3,4-difluoro-phenyl)-1-hydroxy-ethyl]-pyridin-3-yl}-3,4-dihydro-2H-isoquinolin-1-one | 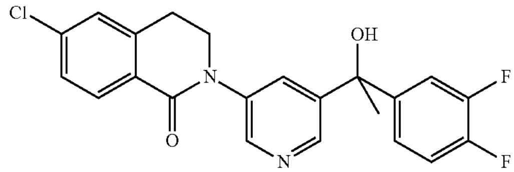 [SMILES: CC(O)(c1cncc(N2CCc3cc(Cl)ccc3C2=O)c1)c1ccc(F)c(F)c1] | 6-Chloro-3,4-dihydro-2H-isoquinolin-1-one (intermediate A-2) and 1-(5-bromo-pyridin-3-yl)-1-(3,4-difluoro-phenyl)-ethanol | 3[B] | 415.1 |
| 37 | 6-Chloro-2-{5-[1-(3,5-difluoro-phenyl)-1-hydroxy-ethyl]-pyridin-3-yl}-3,4-dihydro-2H-isoquinolin-1-one | 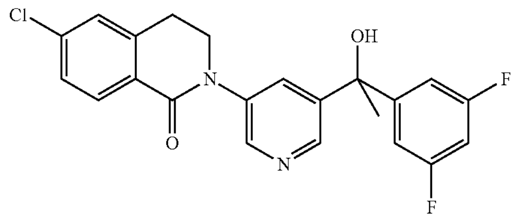 [SMILES: CC(O)(c1cc(F)cc(F)c1)c1cncc(N2CCc3cc(Cl)ccc3C2=O)c1] | 6-Chloro-3,4-dihydro-2H-isoquinolin-1-one (intermediate A-2) and 1-(5-bromo-pyridin-3-yl)-1-(3,5-difluoro-phenyl)-ethanol | 3[B] | 415.1 |
| 38 | 6-Chloro-2-(6-methyl-pyrazin-2-yl)-3,4-dihydro-2H-isoquinolin-1-one | 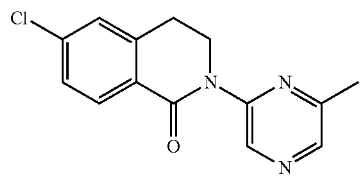 [SMILES: Cc1cncc(N2CCc3cc(Cl)ccc3C2=O)n1] | 6-Chloro-3,4-dihydro-2H-isoquinolin-1-one (intermediate A-2) and 2-bromo-6-methyl-pyrazine | 3[B] | 274.1 |
| 39 | 6-Chloro-2-[5-(morpholine-4-carbonyl)-pyridin-3-yl]-3,4-dihydro-2H-isoquinolin-1-one | 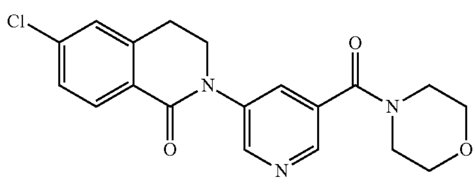 [SMILES: O=C(c1cncc(N2CCc3cc(Cl)ccc3C2=O)c1)N1CCOCC1] | 6-Chloro-3,4-dihydro-2H-isoquinolin-1-one (intermediate A-2) and (5-bromo-pyridin-3-yl)-morpholin-4-yl-methanone | 2 | 372.1 |
| 40 | 6-Chloro-2-[5-(3-hydroxy-pyrrolidine-1-carbonyl)-pyridin-3-yl]-3,4-dihydro-2H-isoquinolin-1-one | 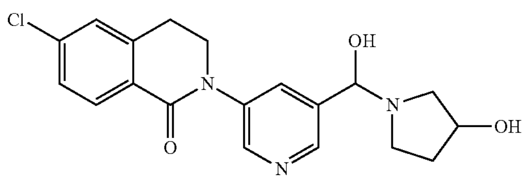 [SMILES: O=C1c2ccc(Cl)cc2CCN1c1cncc(C(O)N2CCC(O)C2)c1] | 6-Chloro-3,4-dihydro-2H-isoquinolin-1-one (intermediate A-2) and (5-bromo-pyridin-3-yl)-(3-hydroxy-pyrrolidin-1-yl)-methanone | 2 | 372.1 |
| 41 | 5-(6-Chloro-1-oxo-3,4-dihydro-1H-isoquinolin-2-yl)-N,N-dimethyl-nicotinamide | 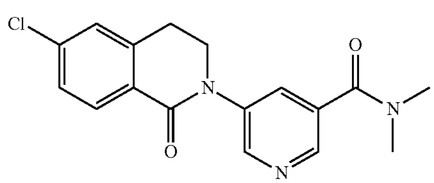 [SMILES: CN(C)C(=O)c1cncc(N2CCc3cc(Cl)ccc3C2=O)c1] | 6-Chloro-3,4-dihydro-2H-isoquinolin-1-one (intermediate A-2) and 5-bromo-N,N-dimethyl-nicotinamide | 2 | 330.1 |
| 42 | 6-Chloro-2-[5-(pyrrolidine-1-carbonyl)-pyridin-3-yl]-3,4-dihydro-2H-isoquinolin-1-one | 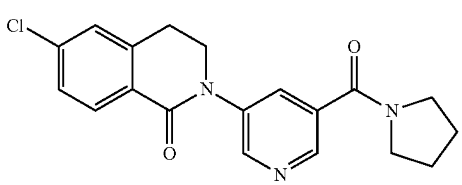 [SMILES: O=C(c1cncc(N2CCc3cc(Cl)ccc3C2=O)c1)N1CCCC1] | 6-Chloro-3,4-dihydro-2H-isoquinolin-1-one (intermediate A-2) and (5-bromo-pyridin-3-yl)-pyrrolidin-1-yl-methanone | 2 | 356.2 |
| 43 | 5-(6-Chloro-1-oxo-3,4-dihydro-1H-isoquinolin-2-yl)-N-methyl-nicotinamide | 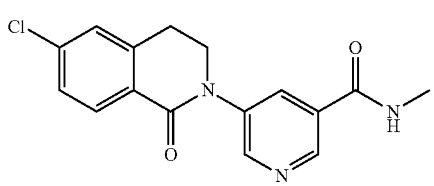 [SMILES: CNC(=O)c1cncc(N2CCc3cc(Cl)ccc3C2=O)c1] | 6-Chloro-3,4-dihydro-2H-isoquinolin-1-one (intermediate A-2) and 5-bromo-N-methyl-nicotinamide | 2 | 316.1 |

TABLE 1-continued

| Ex | Compound Name | Compound Structure | Starting Materials | Prepared by analogy to example | MS (M + H)+ |
|---|---|---|---|---|---|
| 44 | 5-(6-Chloro-1-oxo-3,4-dihydro-1H-isoquinolin-2-yl)-N-cyclopropyl-nicotinamide | 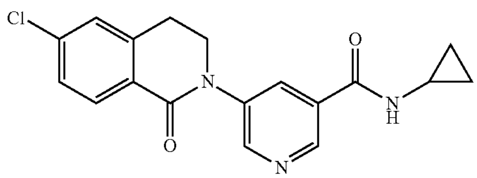 [SMILES: O=C(NC1CC1)c1cncc(N2CCc3cc(Cl)ccc3C2=O)c1] | 6-Chloro-3,4-dihydro-2H-isoquinolin-1-one (intermediate A-2) and 5-bromo-N-cyclopropyl-nicotinamide | 2 | 342.2 |
| 45 | 5-(6-Chloro-1-oxo-3,4-dihydro-1H-isoquinolin-2-yl)-N-(4-fluoro-phenyl)-nicotinamide | 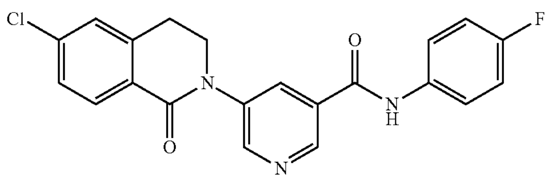 [SMILES: O=C(Nc1ccc(F)cc1)c1cncc(N2CCc3cc(Cl)ccc3C2=O)c1] | 6-Chloro-3,4-dihydro-2H-isoquinolin-1-one (intermediate A-2) and 5-bromo-N-(4-fluoro-phenyl)-nicotinamide | 2 | 396.0 |
| 46 | 5-(6-Chloro-1-oxo-3,4-dihydro-1H-isoquinolin-2-yl)-N-phenyl-nicotinamide | 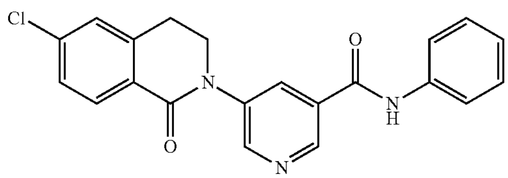 [SMILES: O=C(Nc1ccccc1)c1cncc(N2CCc3cc(Cl)ccc3C2=O)c1] | 6-Chloro-3,4-dihydro-2H-isoquinolin-1-one (intermediate A-2) and 5-bromo-N-phenyl-nicotinamide | 2 | 378.2 |
| 47 | 6-Chloro-2-[5-(4,4-difluoro-piperidine-1-carbonyl)-pyridin-3-yl]-3,4-dihydro-2H-isoquinolin-1-one | 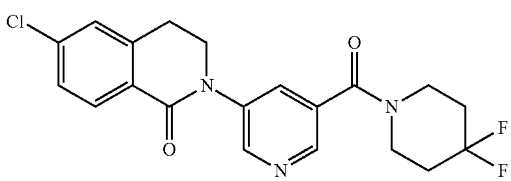 [SMILES: O=C(c1cncc(N2CCc3cc(Cl)ccc3C2=O)c1)N1CCC(F)(F)CC1] | 6-Chloro-3,4-dihydro-2H-isoquinolin-1-one (intermediate A-2) and (3-bromo-phenyl)-(4,4-difluoro-piperidin-1-yl)-methanone | 2 | 406.2 |
| 48 | 6-Chloro-2-[5-((S)-2-methoxymethyl-pyrrolidin-1-ylmethyl)-pyridin-3-yl]-3,4-dihydro-2H-isoquinolin-1-one | 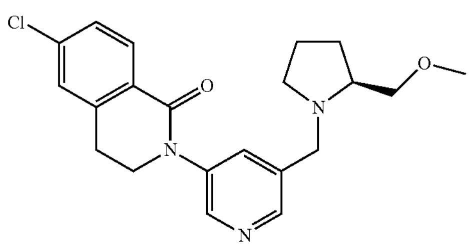 [SMILES: COC[C@@H]1CCCN1Cc1cncc(N2CCc3cc(Cl)ccc3C2=O)c1] | 6-Chloro-3,4-dihydro-2H-isoquinolin-1-one (intermediate A-2) and 3-bromo-5-((S)-2-methoxymethyl-pyrrolidin-1-ylmethyl)-pyridine (intermediate B-6) | 1 | 386.3 |
| 49 | 6-Chloro-2-[5-((S)-2-methoxymethyl-pyrrolidin-1-yl)-pyridin-3-yl]-3,4-dihydro-2H-isoquinolin-1-one | 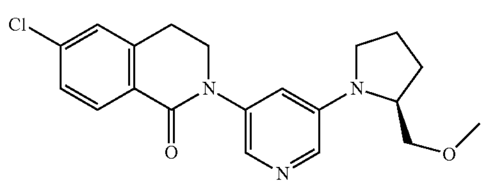 [SMILES: COC[C@@H]1CCCN1c1cncc(N2CCc3cc(Cl)ccc3C2=O)c1] | 6-Chloro-3,4-dihydro-2H-isoquinolin-1-one (intermediate A-2) and 3-bromo-5-((S)-2-methoxymethyl-pyrrolidin-1-yl)-pyridine (intermediate B-10) | 1 | 372.0 |
| 50 | 6-Chloro-2-[5-((S)-2-hydroxymethyl-5-oxo-pyrrolidin-1-yl)-pyridin-3-yl]-3,4-dihydro-2H-isoquinolin-1-one | 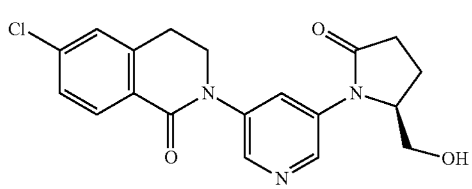 [SMILES: O=C1c2ccc(Cl)cc2CCN1c1cncc(N2C(=O)CC[C@H]2CO)c1] | 6-Chloro-3,4-dihydro-2H-isoquinolin-1-one (intermediate A-2) and (S)-1-(5-bromo-pyridin-3-yl)-5-hydroxymethyl-pyrrolidin-2-one (intermediate B-8) | 1 | 372.0 |

TABLE 1-continued

| Ex | Compound Name | Compound Structure | Starting Materials | Prepared by analogy to example | MS (M + H)+ |
|---|---|---|---|---|---|
| 51 | 6-Chloro-2-pyrimidin-5-yl-3,4-dihydro-2H-isoquinolin-1-one | 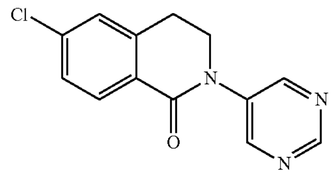 [SMILES: O=C1c2ccc(Cl)cc2CCN1c1cncnc1] | 6-Chloro-3,4-dihydro-2H-isoquinolin-1-one (intermediate A-2) and 5-bromo-pyrimidine | 3[B] | 260.1 |
| 52 | 6-Chloro-2-pyridazin-3-yl-3,4-dihydro-2H-isoquinolin-1-one | 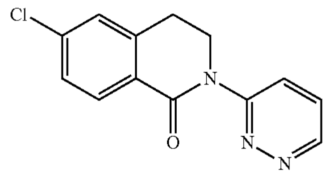 [SMILES: O=C1c2ccc(Cl)cc2CCN1c1cccnn1] | 6-Chloro-3,4-dihydro-2H-isoquinolin-1-one (intermediate A-2) and 3-bromo-pyridazine | 2 | 260.1 |
| 53 | 6-Chloro-2-pyridin-3-yl-2H-isoquinolin-1-one | 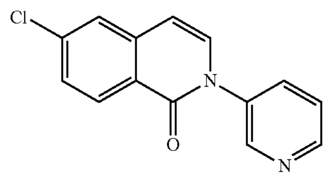 [SMILES: O=c1c2ccc(Cl)cc2ccn1-c1cccnc1] | 6-Chloro-2H-isoquinolin-1-one (intermediate A-6) and 3-bromo-pyridine | 3[B] | 257.1 |
| 54 | 6-Chloro-2-(5-fluoro-pyridin-3-yl)-2H-isoquinolin-1-one | 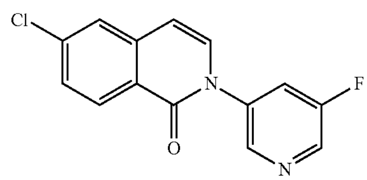 [SMILES: O=c1c2ccc(Cl)cc2ccn1-c1cncc(F)c1] | 6-Chloro-2H-isoquinolin-1-one (intermediate A-6) and 3-bromo-5-fluoro-pyridine | 3[B] | 275.1 |
| 55 | 6-Chloro-2-[4-(1-hydroxy-ethyl)-pyridin-3-yl]-3,4-dihydro-2H-isoquinolin-1-one | 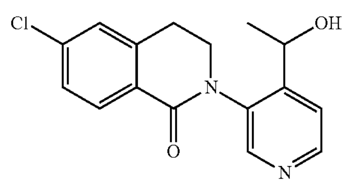 [SMILES: CC(O)c1ccncc1N1CCc2cc(Cl)ccc2C1=O] | 6-Chloro-3,4-dihydro-2H-isoquinolin-1-one (intermediate A-2) and 1-(3-bromo-pyridin-4-yl)-ethanol | 2 | 303.1 |
| 56 | 6-Chloro-2-(4-hydroxymethyl-pyridin-3-yl)-3,4-dihydro-2H-isoquinolin-1-one; compound with trifluoro-acetic acid | 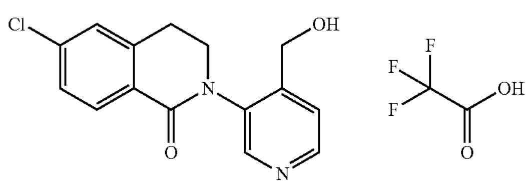 [SMILES: O=C1c2ccc(Cl)cc2CCN1c1cnccc1CO ; O=C(O)C(F)(F)F] | 6-Chloro-3,4-dihydro-2H-isoquinolin-1-one (intermediate A-2) and (3-bromo-4-pyridin-4-yl)-methanol | 2 | 289.1 |
| 57 | 2-[5-(1-Amino-cyclopropyl)-pyridin-3-yl]-6-chloro-3,4-dihydro-2H-isoquinolin-1-one | 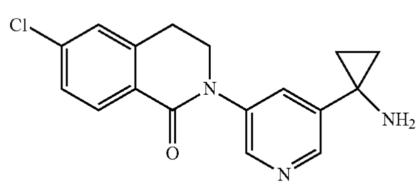 [SMILES: NC1(c2cncc(N3CCc4cc(Cl)ccc4C3=O)c2)CC1] | 6-Chloro-3,4-dihydro-2H-isoquinolin-1-one (intermediate A-2) and 1-(5-bromo-pyridin-3-yl)-cyclopropylamine | 2 | 314.1 |
| 58 | 6-Chloro-2-[5-(4-methyl-4H-[1,2,4]triazol-3-yl)-pyridin-3-yl]-3,4-dihydro-2H-isoquinolin-1-one | 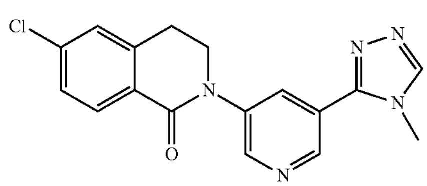 [SMILES: Cn1cnnc1-c1cncc(N2CCc3cc(Cl)ccc3C2=O)c1] | 6-Chloro-3,4-dihydro-2H-isoquinolin-1-one (intermediate A-2) and 3-bromo-5-(4-methyl-4H-[1,2,4]triazol-3-yl)-pyridine | 2 | 339.2 |

TABLE 1-continued

| Ex | Compound Name | Compound Structure | Starting Materials | Prepared by analogy to example | MS (M + H)+ |
|---|---|---|---|---|---|
| 59 | 6-Chloro-2-(5-methylsulfanyl-pyridin-3-yl)-3,4-dihydro-2H-isoquinolin-1-one | 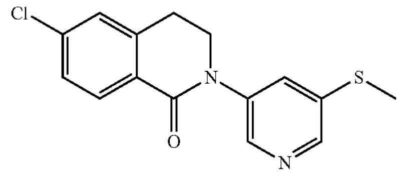 [SMILES: CSc1cncc(N2CCc3cc(Cl)ccc3C2=O)c1] | 6-Chloro-3,4-dihydro-2H-isoquinolin-1-one (intermediate A-2) and 3-bromo-5-methylsulfanyl-pyridine | 2 | 305.1 |
| 60 | 6-Chloro-2-(5-difluoromethoxy-pyridin-3-yl)-3,4-dihydro-2H-isoquinolin-1-one | 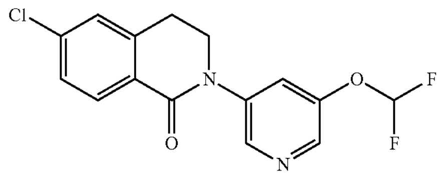 [SMILES: O=C1c2ccc(Cl)cc2CCN1c1cncc(OC(F)F)c1] | 6-Chloro-3,4-dihydro-2H-isoquinolin-1-one (intermediate A-2) and 3-bromo-5-difluoromethoxy-pyridine | 2 | 325.1 |
| 61 | 6-Chloro-2-(4-dimethoxymethyl-pyridin-3-yl)-3,4-dihydro-2H-isoquinolin-1-one | 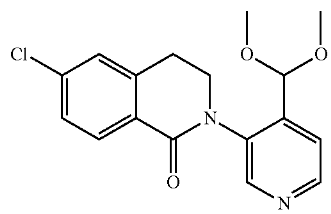 [SMILES: COC(OC)c1ccncc1N1CCc2cc(Cl)ccc2C1=O] | 6-Chloro-3,4-dihydro-2H-isoquinolin-1-one (intermediate A-2) and 3-bromo-4-dimethoxymethyl-pyridine | 2 | 333.1 |
| 62 | 6-Chloro-2-[5-fluoro-4-(1-hydroxy-ethyl)-pyridin-3-yl]-3,4-dihydro-2H-isoquinolin-1-one | 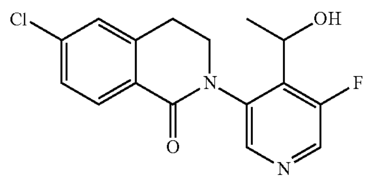 [SMILES: CC(O)c1c(F)cncc1N1CCc2cc(Cl)ccc2C1=O] | 6-Chloro-3,4-dihydro-2H-isoquinolin-1-one (intermediate A-2) and 1-(3-bromo-5-fluoro-pyridin-4-yl)-ethanol | 2 | 321.1 |
| 63 | 6-Chloro-2-{4-[(4-fluoro-phenyl)-hydroxy-methyl]-pyridin-3-yl}-3,4-dihydro-2H-isoquinolin-1-one | 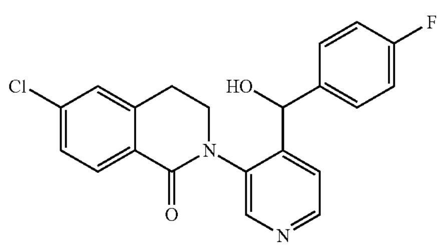 [SMILES: O=C1c2ccc(Cl)cc2CCN1c1cnccc1C(O)c1ccc(F)cc1] | 6-Chloro-3,4-dihydro-2H-isoquinolin-1-one (intermediate A-2) and (3-bromo-pyridin-4-yl)-(4-fluoro-phenyl)-methanol | 2 | 383.1 |
| 64 | 6-Chloro-2-[4-(1-methoxy-ethyl)-pyridin-3-yl]-3,4-dihydro-2H-isoquinolin-1-one | 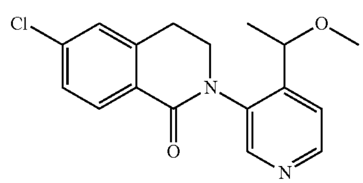 [SMILES: COC(C)c1ccncc1N1CCc2cc(Cl)ccc2C1=O] | 6-Chloro-3,4-dihydro-2H-isoquinolin-1-one (intermediate A-2) and 3-bromo-4-(1-methoxy-ethyl)-pyridine | 2 | 317.1 |
| 65 | 6-Chloro-2-(1-methyl-1H-pyrrolo[3,2-c]pyridin-7-yl)-3,4-dihydro-2H-isoquinolin-1-one | 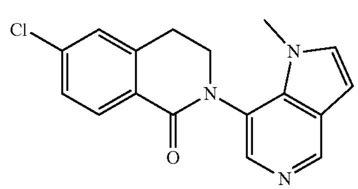 [SMILES: Cn1ccc2cncc(N3CCc4cc(Cl)ccc4C3=O)c21] | 6-Chloro-3,4-dihydro-2H-isoquinolin-1-one (intermediate A-2) and 7-bromo-1-methyl-1H-pyrrolo[3,2-c]-pyridine | 2 | 312.1 |
| 66 | 6-Chloro-2-(5-cyclopropyl-pyridin-3-yl)-3,4-dihydro-2H-isoquinolin-1-one | 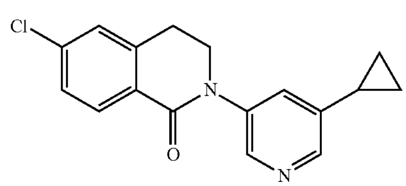 [SMILES: O=C1c2ccc(Cl)cc2CCN1c1cncc(C2CC2)c1] | 6-Chloro-3,4-dihydro-2H-isoquinolin-1-one (intermediate A-2) and 3-bromo-5-cyclopropyl-pyridine | 2 | 299.1 |

TABLE 1-continued

| Ex | Compound Name | Compound Structure | Starting Materials | Prepared by analogy to example | MS (M + H)+ |
|---|---|---|---|---|---|
| 67 | 6-Chloro-2-[5-(2-methyl-2H-[1,2,4]triazol-3-yl)-pyridin-3-yl]-3,4-dihydro-2H-isoquinolin-1-one | 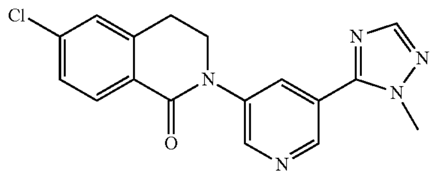 [SMILES: Cn1ncnc1-c1cncc(N2CCc3cc(Cl)ccc3C2=O)c1] | 6-Chloro-3,4-dihydro-2H-isoquinolin-1-one (intermediate A-2) and 3-bromo-5-(2-methyl-2H-[1,2,4]triazol-3-yl)-pyridine | 3[B] | 340.1 |
| 68 | 6-Chloro-2-(5-cyclopropoxy-pyridin-3-yl)-3,4-dihydro-2H-isoquinolin-1-one | 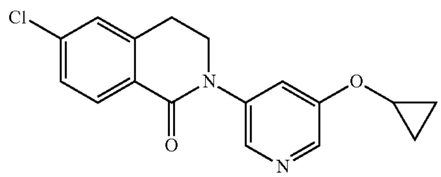 [SMILES: O=C1c2ccc(Cl)cc2CCN1c1cncc(OC2CC2)c1] | 6-Chloro-3,4-dihydro-2H-isoquinolin-1-one (intermediate A-2) and 3-bromo-5-cyclopropoxy-pyridine | 2 | 315.1 |
| 69 | 6-Chloro-2-(4-methoxymethyl-pyridin-3-yl)-3,4-dihydro-2H-isoquinolin-1-one | 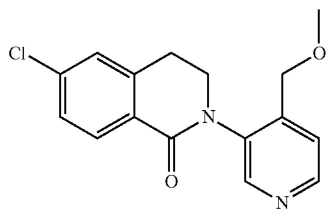 [SMILES: COCc1ccncc1N1CCc2cc(Cl)ccc2C1=O] | 6-Chloro-3,4-dihydro-2H-isoquinolin-1-one (intermediate A-2) and 3-bromo-4-methoxymethyl-pyridine | 2 | 303.1 |
| 70 | 6-Chloro-2-[5-fluoro-4-(1-hydroxy-1-methyl-ethyl)-pyridin-3-yl]-3,4-dihydro-2H-isoquinolin-1-one | 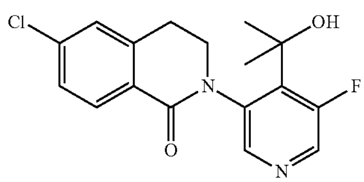 [SMILES: CC(C)(O)c1c(F)cncc1N1CCc2cc(Cl)ccc2C1=O] | 6-Chloro-3,4-dihydro-2H-isoquinolin-1-one (intermediate A-2) and 2-(3-bromo-5-fluoro-pyridin-4-yl)-propan-2-ol | 2 | 335.1 |
| 71 | 6-Chloro-2-[5-(5-methyl-pyrazol-1-ylmethyl)-pyridin-3-yl]-3,4-dihydro-2H-isoquinolin-1-one | 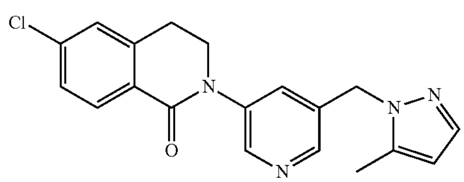 [SMILES: Cc1ccnn1Cc1cncc(N2CCc3cc(Cl)ccc3C2=O)c1] | 6-Chloro-3,4-dihydro-2H-isoquinolin-1-one (intermediate A-2) and 3-bromo-5-(5-methyl-pyrazol-1-ylmethyl)-pyridine | 3[B] | 353.1 |
| 72 | 6-Chloro-2-(1H-pyrrolo[3,2-c]pyridin-7-yl)-3,4-dihydro-2H-isoquinolin-1-one | 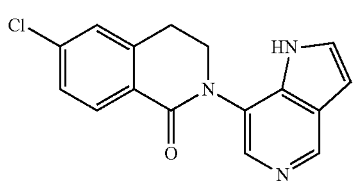 [SMILES: O=C1c2ccc(Cl)cc2CCN1c1cncc2cc[nH]c12] | 6-Chloro-3,4-dihydro-2H-isoquinolin-1-one (intermediate A-2) and 7-bromo-1H-pyrrolo[3,2-c]pyridine | 2 | 298.1 |
| 73 | 6-Chloro-3,4-dihydro-[2,4']biisoquinolinyl-1-one | 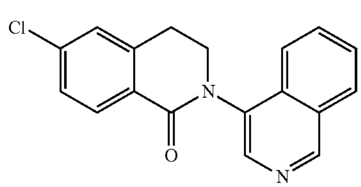 [SMILES: O=C1c2ccc(Cl)cc2CCN1c1cncc2ccccc12] | 6-Chloro-3,4-dihydro-2H-isoquinolin-1-one (intermediate A-2) and 4-bromo-isoquinoline | 3[B] | 309.1 |
| 74 | 3-(6-Chloro-1-oxo-3,4-dihydro-1H-isoquinolin-2-yl)-isonicotinonitrile | 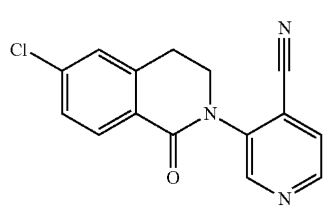 [SMILES: N#Cc1ccncc1N1CCc2cc(Cl)ccc2C1=O] | 6-Chloro-3,4-dihydro-2H-isoquinolin-1-one (intermediate A-2) and 3-bromo-isonicotinonitrile | 2 | 284.1 |

TABLE 1-continued

| Ex | Compound Name | Compound Structure | Starting Materials | Prepared by analogy to example | MS (M + H)+ |
|---|---|---|---|---|---|
| 75 | 6-Chloro-2-(5-fluoro-4-methoxymethyl-pyridin-3-yl)-3,4-dihydro-2H-isoquinolin-1-one | 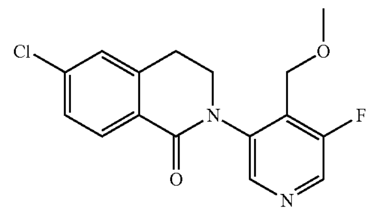 [SMILES: COCc1c(F)cncc1N1CCc2cc(Cl)ccc2C1=O] | 6-Chloro-3,4-dihydro-2H-isoquinolin-1-one (intermediate A-2) and 3-bromo-5-fluoro-4-methoxymethyl-pyridine | 2 | 321.1 |
| 76 | 6-Chloro-2-[5-fluoro-4-(1-methoxy-ethyl)-pyridin-3-yl]-3,4-dihydro-2H-isoquinolin-1-one | 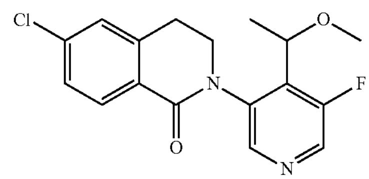 [SMILES: COC(C)c1c(F)cncc1N1CCc2cc(Cl)ccc2C1=O] | 6-Chloro-3,4-dihydro-2H-isoquinolin-1-one (intermediate A-2) and 3-bromo-5-fluoro-4-(1-methoxy-ethyl)-pyridine | 2 | 335.1 |
| 77 | 6-Chloro-2-(4-isopropoxy-methyl-pyridin-3-yl)-3,4-dihydro-2H-isoquinolin-1-one | 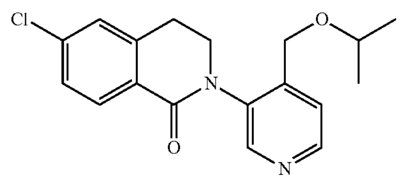 [SMILES: CC(C)OCc1ccncc1N1CCc2cc(Cl)ccc2C1=O] | 6-Chloro-3,4-dihydro-2H-isoquinolin-1-one (intermediate A-2) and 3-bromo-4-isopropoxymethyl-pyridine | 2 | 333.1 |
| 78 | 6-Chloro-2-[4-(cyclopropyl-methoxy-methyl)-pyridin-3-yl]-3,4-dihydro-2H-isoquinolin-1-one | 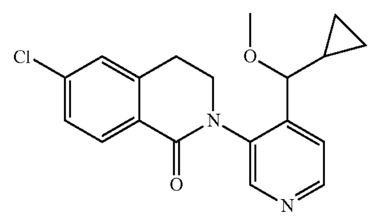 [SMILES: COC(c1ccncc1N1CCc2cc(Cl)ccc2C1=O)C1CC1] | 6-Chloro-3,4-dihydro-2H-isoquinolin-1-one (intermediate A-2) and 3-bromo-4-(cyclopropyl-methoxy-methyl)-pyridine | 2 | 343.1 |
| 79 | 6-Chloro-2-[5-(3,5-dimethyl-1H-pyrazol-4-yl)-pyridin-3-yl]-3,4-dihydro-2H-isoquinolin-1-one | 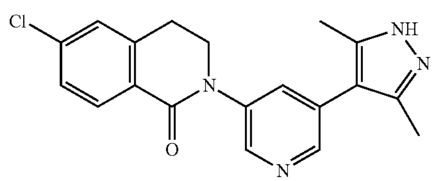 [SMILES: Cc1n[nH]c(C)c1-c1cncc(N2CCc3cc(Cl)ccc3C2=O)c1] | 6-Chloro-3,4-dihydro-2H-isoquinolin-1-one (intermediate A-2) and 3-bromo-5-(3,5-dimethyl-1H-pyrazol-4-yl)-pyridine | 3[B] | 353.1 |
| 80 | 6-Chloro-2-[5-(3,5-dimethyl-3H-imidazol-4-yl)-pyridin-3-yl]-3,4-dihydro-2H-isoquinolin-1-one | 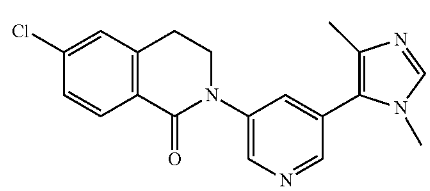 [SMILES: Cc1ncn(C)c1-c1cncc(N2CCc3cc(Cl)ccc3C2=O)c1] | 6-Chloro-3,4-dihydro-2H-isoquinolin-1-one (intermediate A-2) and 3-bromo-5-(3,5-dimethyl-3H-imidazol-4-yl)-pyridine | 3[B] | 353.1 |
| 81 | 6-Chloro-2-[5-(1,1-dioxo-1$\lambda^6$-[1,2]thiazinan-2-ylmethyl)-pyridin-3-yl]-3,4-dihydro-2H-isoquinolin-1-one | 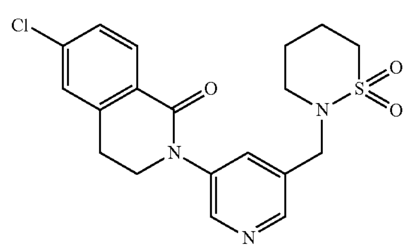 [SMILES: O=C1c2ccc(Cl)cc2CCN1c1cncc(CN2CCCCS2(=O)=O)c1] | 6-Chloro-3,4-dihydro-2H-isoquinolin-1-one (intermediate A-2) and 2-(5-bromo-pyridin-3-ylmethyl)-[1,2]thiazinane 1,1-dioxide (intermediate B-13) | 1 | 406.3 |

TABLE 1-continued

| Ex | Compound Name | Compound Structure | Starting Materials | Prepared by analogy to example | MS (M + H)+ |
|---|---|---|---|---|---|
| 82 | 6-Chloro-2-[5-(1,1-dioxo-1$\lambda$6-isothiazolidin-2-ylmethyl)-pyridin-3-yl]-3,4-dihydro-2H-isoquinolin-1-one | 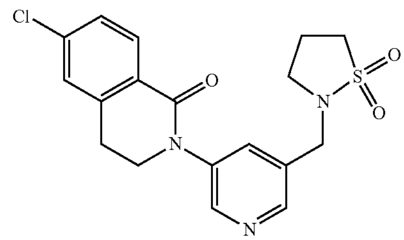 [SMILES: O=C1c2ccc(Cl)cc2CCN1c1cncc(CN2CCCS2(=O)=O)c1] | 6-Chloro-3,4-dihydro-2H-isoquinolin-1-one (intermediate A-2) and 3-bromo-5-(1,1-dioxo-1$\lambda$6-isothiazolidin-2-ylmethyl)-pyridine (intermediate B-14) | 1 | 392.1 |
| 83 | 6-Chloro-2-[5-((S)-2-hydroxymethyl-5-oxo-pyrrolidin-1-ylmethyl)-pyridin-3-yl]-3,4-dihydro-2H-isoquinolin-1-one | 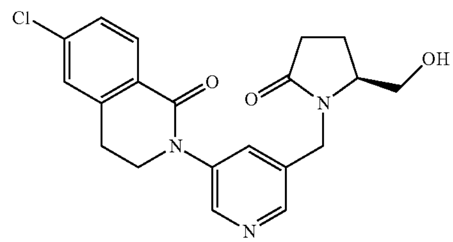 [SMILES: O=C1c2ccc(Cl)cc2CCN1c1cncc(CN2C(=O)CC[C@H]2CO)c1] | 6-Chloro-3,4-dihydro-2H-isoquinolin-1-one (intermediate A-2) and (S)-1-(5-bromo-pyridin-3-ylmethyl)-5-(tert-butyl-dimethyl-silanyloxymethyl)-pyrrolidin-2-one (intermediate B-15) to 2-{5-[(S)-2-(tert-butyl-dimethyl-silanyloxymethyl)-5-oxo-pyrrolidin-1-ylmethyl]-pyridin-3-yl}-6-chloro-3,4-dihydro-2H-isoquinolin-1-one (light brown amorphous solid, MS: 500.3, 502.3 (M + H+)) and subsequent removal of the protecting group (4M HCl in dioxane, MeOH 2h, RT). | 1 | 386.0 |
| 84 | (S)-1-[5-(6-Chloro-1-oxo-3,4-dihydro-1H-isoquinolin-2-yl)-pyridin-3-ylmethyl]-pyrrolidine-2-carboxylic acid methyl ester | 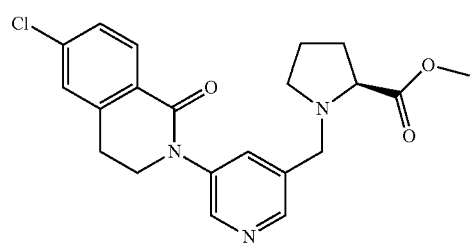 [SMILES: COC(=O)[C@@H]1CCCN1Cc1cncc(N2CCc3cc(Cl)ccc3C2=O)c1] | 6-Chloro-3,4-dihydro-2H-isoquinolin-1-one (intermediate A-2) and (S)-1-(5-bromo-pyridin-3-ylmethyl)-pyrrolidine-2-carboxylic acid methyl ester (intermediate B-16) | 1 | 400.0 |
| 85 | 6-Chloro-2-(5-methoxy-pyridin-3-yl)-3-methyl-3,4-dihydro-2H-isoquinolin-1-one | 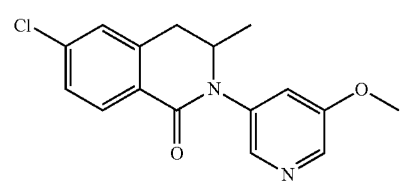 [SMILES: COc1cncc(N2C(=O)c3ccc(Cl)cc3CC2C)c1] | 6-Chloro-3-methyl-3,4-dihydro-2H-isoquinolin-1-one (intermediate A-3-1) and 3-bromo-5-methoxy-pyridine | 3[B] | 303.1 |
| 86 | 6-Chloro-2-(5-hydroxymethyl-pyridin-3-yl)-3-methyl-3,4-dihydro-2H-isoquinolin-1-one | 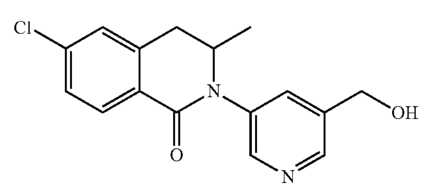 [SMILES: CC1Cc2cc(Cl)ccc2C(=O)N1c1cncc(CO)c1] | 6-Chloro-3-methyl-3,4-dihydro-2H-isoquinolin-1-one (intermediate A-3-1) and (5-bromo-pyridin-3-yl)-methanol | 3[B] | 303.1 |

TABLE 1-continued

| Ex | Compound Name | Compound Structure | Starting Materials | Prepared by analogy to example | MS (M + H)+ |
|---|---|---|---|---|---|
| 87 | 6-Chloro-2-[5-(2-isopropyl-imidazol-1-ylmethyl)-pyridin-3-yl]-3-methyl-3,4-dihydro-2H-isoquinolin-1-one | 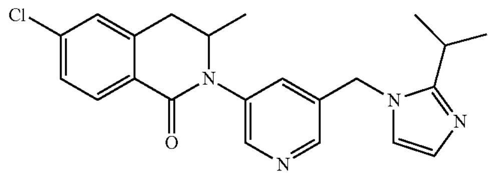 [SMILES: CC(C)c1nccn1Cc1cncc(N2C(=O)c3ccc(Cl)cc3CC2C)c1] | 6-Chloro-3-methyl-3,4-dihydro-2H-isoquinolin-1-one (intermediate A-3-1) and 3-bromo-5-(2-isopropyl-imidazol-1-ylmethyl)-pyridine (intermediate B-1) | 3[B] | 395.3 |
| 88 | 6-Chloro-3-methyl-2-pyridin-3-yl-3,4-dihydro-2H-isoquinolin-1-one | 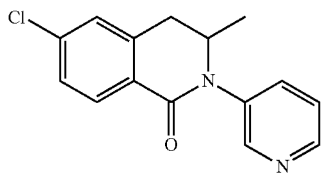 [SMILES: CC1Cc2cc(Cl)ccc2C(=O)N1c1cccnc1] | 6-Chloro-3-methyl-3,4-dihydro-2H-isoquinolin-1-one (intermediate A-3-1) and 3-bromo-pyridine | 3[B] | 273.1 |
| 89 | 6-Chloro-2-(5-fluoro-pyridin-3-yl)-3-methyl-3,4-dihydro-2H-isoquinolin-1-one | 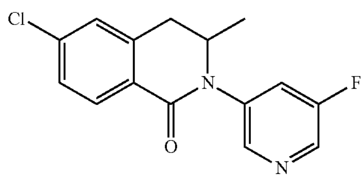 [SMILES: CC1Cc2cc(Cl)ccc2C(=O)N1c1cncc(F)c1] | 6-Chloro-3-methyl-3,4-dihydro-2H-isoquinolin-1-one (intermediate A-3-1) and 3-bromo-5-fluoro-pyridine | 3[B] | 291.1 |
| 90 | 6-Chloro-3-methyl-2-pyrimidin-5-yl-3,4-dihydro-2H-isoquinolin-1-one | 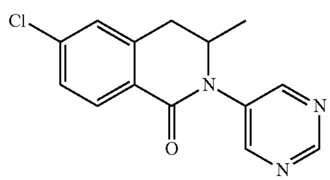 [SMILES: CC1Cc2cc(Cl)ccc2C(=O)N1c1cncnc1] | 6-Chloro-3-methyl-3,4-dihydro-2H-isoquinolin-1-one (intermediate A-3-1) and 5-bromo-pyrimidine | 3[B] | 274.1 |
| 91 | (R)-6-Chloro-3-methyl-2-pyridin-3-yl-3,4-dihydro-2H-isoquinolin-1-one | 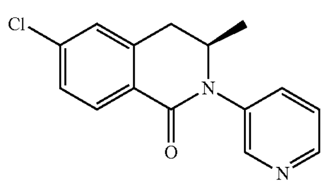 [SMILES: C[C@@H]1Cc2cc(Cl)ccc2C(=O)N1c1cccnc1] | (R)-6-Chloro-3-methyl-3,4-dihydro-2H-isoquinolin-1-one (intermediate A-3-1a) and 3-bromo-pyridine | 3[B] | 273.1 |
| 92 | (S)-6-Chloro-3-methyl-2-pyridin-3-yl-3,4-dihydro-2H-isoquinolin-1-one | 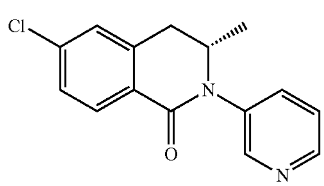 [SMILES: C[C@H]1Cc2cc(Cl)ccc2C(=O)N1c1cccnc1] | (S)-6-Chloro-3-methyl-3,4-dihydro-2H-isoquinolin-1-one (intermediate A-3-1b) and 3-bromo-pyridine | 3[B] | 273.1 |
| 93 | 8-Chloro-3-methyl-2-pyridin-3-yl-3,4-dihydro-2H-isoquinolin-1-one | 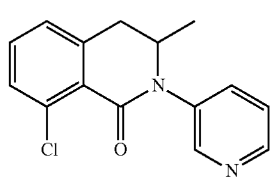 [SMILES: CC1Cc2cccc(Cl)c2C(=O)N1c1cccnc1] | 8-Chloro-3-methyl-3,4-dihydro-2H-isoquinolin-1-one (intermediate A-3-2) and 3-bromo-pyridine | 3[B] | 273.1 |

TABLE 1-continued

| Ex | Compound Name | Compound Structure | Starting Materials | Prepared by analogy to example | MS (M + H)+ |
|---|---|---|---|---|---|
| 94 | 6-Methoxy-2-pyridin-3-yl-3,4-dihydro-2H-isoquinolin-1-one | 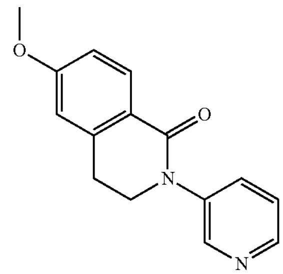 [SMILES: COc1ccc2c(c1)CCN(c1cccnc1)C2=O] | 6-Methoxy-3,4-dihydroisoquinolin-1(2H)-one and 3-bromopyridine | 1 | 255.2 |
| 95 | 5,6-Dichloro-2-pyridin-3-yl-3,4-dihydro-2H-isoquinolin-1-one | 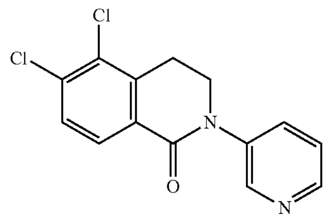 [SMILES: O=C1c2ccc(Cl)c(Cl)c2CCN1c1cccnc1] | 5,6-Dichloro-3,4-dihydroisoquinolin-1(2H)-one and 3-iodopyridine | 1 | 293.0 |
| 96 | 2-Chloro-6-(5-methoxy-pyridin-3-yl)-7,8-dihydro-6H-[1,6]naphthyridin-5-one | 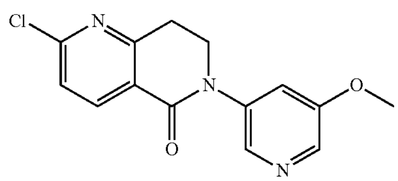 [SMILES: COc1cncc(N2CCc3nc(Cl)ccc3C2=O)c1] | 2-Chloro-7,8-dihydro-6H-[1,6]naphthyridin-5-one (intermediate A-8) and 3-bromo-5-methoxy-pyridine | 2 | 290.2 |
| 97 | 2-Methoxy-6-(5-methoxy-pyridin-3-yl)-7,8-dihydro-6H-[1,6]naphthyridin-5-one | 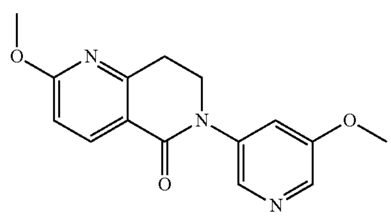 [SMILES: COc1cncc(N2CCc3nc(OC)ccc3C2=O)c1] | 2-Methoxy-7,8-dihydro-6H-[1,6]naphthyridin-5-one (intermediate A-9) and 3-bromo-5-methoxy-pyridine | 2 | 286.2 |
| 98 | 2-Methoxy-6-pyridin-3-yl-7,8-dihydro-6H-[1,6]naphthyridin-5-one | 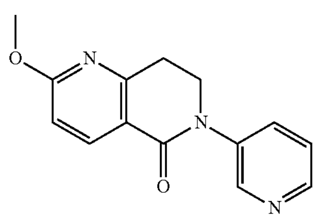 [SMILES: COc1ccc2c(n1)CCN(c1cccnc1)C2=O] | 2-Methoxy-7,8-dihydro-6H-[1,6]naphthyridin-5-one (intermediate A-9) and 3-bromo-pyridine | 3[B] | 256.1 |
| 99 | 6-Chloro-5-fluoro-2-(5-methoxy-pyridin-3-yl)-3,4-dihydro-2H-isoquinolin-1-one | 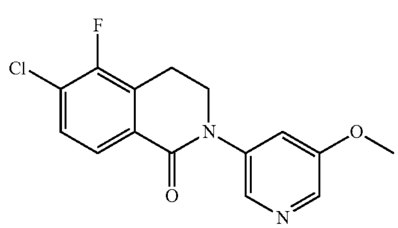 [SMILES: COc1cncc(N2CCc3c(ccc(Cl)c3F)C2=O)c1] | 6-Chloro-5-fluoro-3,4-dihydro-2H-isoquinolin-1-one (intermediate A-1) and 3-bromo-5-methoxy-pyridine | 2 | 307.1 |
| 100 | 6-Chloro-7-fluoro-2-(5-methoxy-pyridin-3-yl)-3,4-dihydro-2H-isoquinolin-1-one | 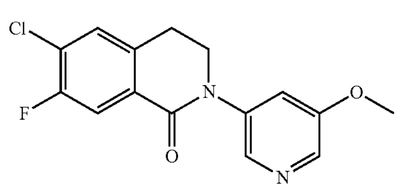 [SMILES: COc1cncc(N2CCc3cc(Cl)c(F)cc3C2=O)c1] | 6-Chloro-7-fluoro-3,4-dihydro-2H-isoquinolin-1-one (intermediate A-7) and 3-bromo-5-methoxy-pyridine | 2 | 307.1 |

TABLE 1-continued

| Ex | Compound Name | Compound Structure | Starting Materials | Prepared by analogy to example | MS (M + H)+ |
|---|---|---|---|---|---|
| 101 | 6-Chloro-7-fluoro-2-pyridin-3-yl-3,4-dihydro-2H-isoquinolin-1-one | 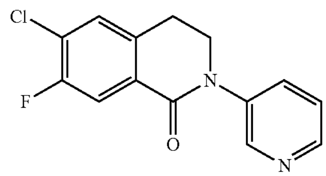 [SMILES: O=C1c2cc(F)c(Cl)cc2CCN1c1cccnc1] | 6-Chloro-7-fluoro-3,4-dihydro-2H-isoquinolin-1-one (intermediate A-7) and 3-bromo-pyridine | 2 | 277.1 |
| 102 | 6-Chloro-4,4-dimethyl-2-pyridin-3-yl-3,4-dihydro-2H-isoquinolin-1-one | 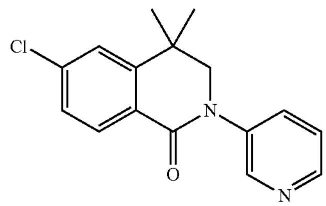 [SMILES: CC1(C)CN(c2cccnc2)C(=O)c2ccc(Cl)cc21] | 6-Chloro-4,4-dimethyl-3,4-dihydro-2H-isoquinolin-1-one (intermediate A-5) and 3-bromo-pyridine | 3[B] | 287.2 |
| 103 | 6-Chloro-2-(5-methoxy-pyridin-3-yl)-4,4-dimethyl-3,4-dihydro-2H-isoquinolin-1-one | 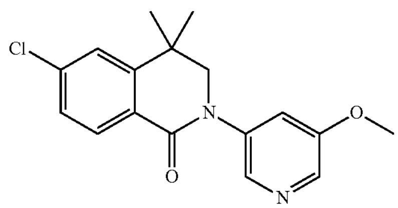 [SMILES: COc1cncc(N2CC(C)(C)c3cc(Cl)ccc3C2=O)c1] | 6-Chloro-4,4-dimethyl-3,4-dihydro-2H-isoquinolin-1-one (intermediate A-5) and 3-bromo-5-methoxy-pyridine | 3[B] | 317.2 |
| 104 | 6-Chloro-2-(5-fluoro-pyridin-3-yl)-4,4-dimethyl-3,4-dihydro-2H-isoquinolin-1-one | 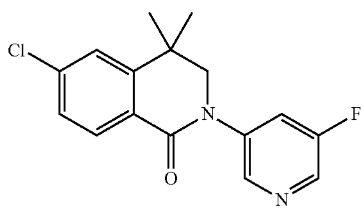 [SMILES: CC1(C)CN(c2cncc(F)c2)C(=O)c2ccc(Cl)cc21] | 6-Chloro-4,4-dimethyl-3,4-dihydro-2H-isoquinolin-1-one (intermediate A-5) and 3-bromo-5-fluoro-pyridine | 3[B] | 305.2 |
| 105 | 6-Chloro-4-methyl-2-pyridin-3-yl-3,4-dihydro-2H-isoquinolin-1-one | 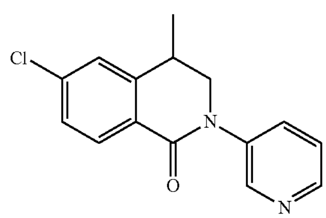 [SMILES: CC1CN(c2cccnc2)C(=O)c2ccc(Cl)cc21] | 6-Chloro-4-methyl-3,4-dihydro-2H-isoquinolin-1-one (intermediate A-4) and 3-bromopyridine | 3[B] | 273.1 |
| 106 | 6-Chloro-2-(5-fluoro-pyridin-3-yl)-4-methyl-3,4-dihydro-2H-isoquinolin-1-one | 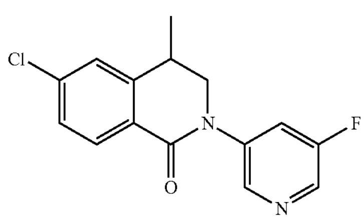 [SMILES: CC1CN(c2cncc(F)c2)C(=O)c2ccc(Cl)cc21] | 6-Chloro-4-methyl-3,4-dihydro-2H-isoquinolin-1-one (intermediate A-4) and 3-bromo-5-fluoro-pyridine | 3[B] | 291.1 |
| 107 | 6-Chloro-2-(5-methoxy-pyridin-3-yl)-4-methyl-3,4-dihydro-2H-isoquinolin-1-one | 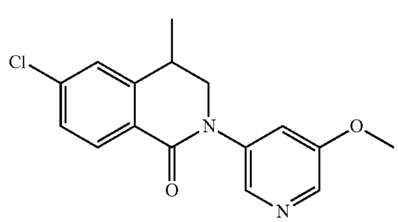 [SMILES: COc1cncc(N2CC(C)c3cc(Cl)ccc3C2=O)c1] | 6-Chloro-4-methyl-3,4-dihydro-2H-isoquinolin-1-one (intermediate A-4) and 3-bromo-5-methoxy-pyridine | 3[B] | 303.2 |

TABLE 1-continued

| Ex | Compound Name | Compound Structure | Starting Materials | Prepared by analogy to example | MS (M + H)+ |
|---|---|---|---|---|---|
| 108 | 5-Chloro-2-pyridin-3-yl-2,3-dihydro-isoindol-1-one | 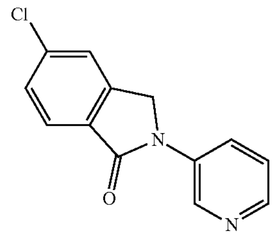 [SMILES: O=C1c2ccc(Cl)cc2CN1c1cccnc1] | 5-Chloro-2,3-dihydro-isoindol-1-one and 3-iodopyridine | 1 | 245.1 |
| 109 | 5-Chloro-2-[5-(2-isopropyl-imidazol-1-ylmethyl)-pyridin-3-yl]-2,3-dihydro-isoindol-1-one | 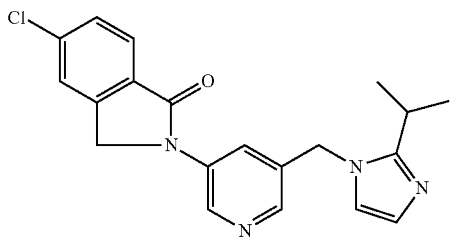 [SMILES: CC(C)c1nccn1Cc1cncc(N2Cc3cc(Cl)ccc3C2=O)c1] | 5-Chloro-2,3-dihydro-isoindol-1-one and 3-bromo-5-(2-isopropyl-imidazol-1-ylmethyl)-pyridine (intermediate B-1) | 1 | 367.0 |
| 110 | 5-Chloro-2-(5-[1,2,4]triazol-1-ylmethyl-pyridin-3-yl)-2,3-dihydro-isoindol-1-one | 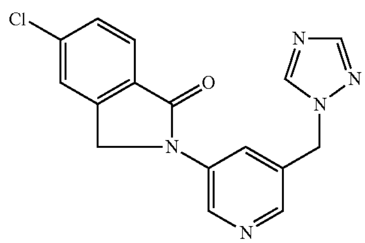 [SMILES: O=C1c2ccc(Cl)cc2CN1c1cncc(Cn2cncn2)c1] | 5-Chloro-2,3-dihydro-isoindol-1-one and 3-bromo-5-[1,2,4]triazol-1-ylmethyl-pyridine (intermediate B-3) | 1 | 326.2 |
| 111 | 5-Chloro-2-[5-(2-methyl-imidazol-1-ylmethyl)-pyridin-3-yl]-2,3-dihydro-isoindol-1-one | 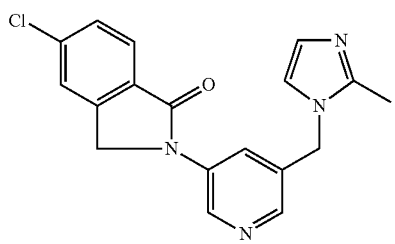 [SMILES: Cc1nccn1Cc1cncc(N2Cc3cc(Cl)ccc3C2=O)c1] | 5-Chloro-2,3-dihydro-isoindol-1-one and 3-bromo-5-(2-methyl-imidazol-1-ylmethyl)-pyridine (intermediate B-2) | 1 | 339.1 |
| 112 | 5-Chloro-2-[5-(2-oxo-pyrrolidin-1-ylmethyl)-pyridin-3-yl]-2,3-dihydro-isoindol-1-one | 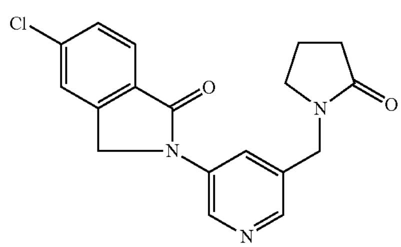 [SMILES: O=C1CCCN1Cc1cncc(N2Cc3cc(Cl)ccc3C2=O)c1] | 5-Chloro-2,3-dihydro-isoindol-1-one and 1-(5-bromo-pyridin-3-ylmethyl)-pyrrolidin-2-one (intermediate B-4) | 1 | 342.1 |
| 113 | 5-Chloro-2-[5-((S)-2-methoxymethyl-pyrrolidin-1-ylmethyl)-pyridin-3-yl]-2,3-dihydro-isoindol-1-one | 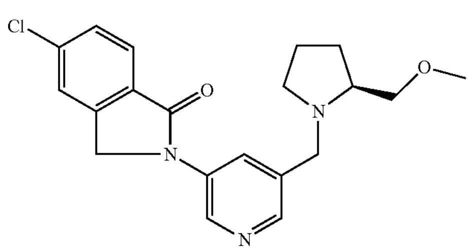 [SMILES: COC[C@@H]1CCCN1Cc1cncc(N2Cc3cc(Cl)ccc3C2=O)c1] | 5-Chloro-2,3-dihydro-isoindol-1-one and 3-bromo-5-((S)-2-methoxymethyl-pyrrolidin-1-ylmethyl)-pyridine (intermediate B-6) | 1 | 372.2 |

TABLE 1-continued

| Ex | Compound Name | Compound Structure | Starting Materials | Prepared by analogy to example | MS (M + H)+ |
|---|---|---|---|---|---|
| 114 | 5-Chloro-2-[5-(2-oxo-piperidin-1-ylmethyl)-pyridin-3-yl]-2,3-dihydro-isoindol-1-one | 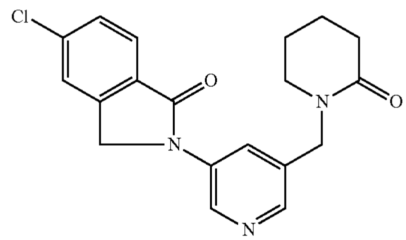 [SMILES: O=C1CCCCN1Cc1cncc(N2Cc3cc(Cl)ccc3C2=O)c1] | 5-Chloro-2,3-dihydro-isoindol-1-one and 1-(5-bromo-pyridin-3-ylmethyl)-piperidin-2-one (intermediate B-5) | 1 | 356.3 |
| 115 | Ethanesulfonic acid [5-(5-chloro-1-oxo-1,3-dihydro-isoindol-2-yl)-pyridin-3-ylmethyl]-amide | 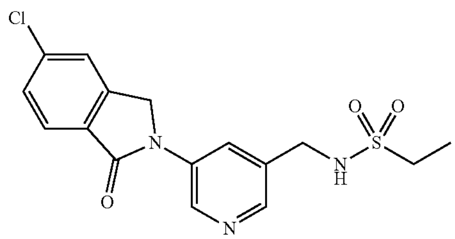 [SMILES: CCS(=O)(=O)NCc1cncc(N2Cc3cc(Cl)ccc3C2=O)c1] | 5-Chloro-2,3-dihydro-isoindol-1-one and ethanesulfonic acid (5-bromo-pyridin-3-ylmethyl)-amide (intermediate B-7) | 1 | 366.0 |
| 116 | 5-Chloro-2-(1-methyl-1H-pyrazolo[3,4-c]pyridin-4-yl)-2,3-dihydro-isoindol-1-one | 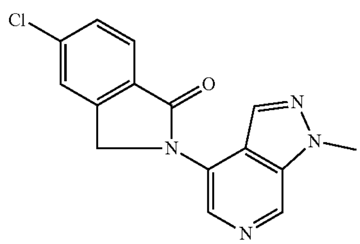 [SMILES: Cn1ncc2c(N3Cc4cc(Cl)ccc4C3=O)cncc21] | 5-Chloro-2,3-dihydro-isoindol-1-one and 4-bromo-1-methyl-1H-pyrazolo[3,4-c]pyridine | 1 | 299.2 |
| 117 | 5-Chloro-2-(8-hydroxy-5,6,7,8-tetrahydro-isoquinolin-4-yl)-2,3-dihydro-isoindol-1-one | 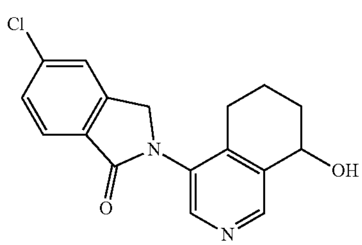 [SMILES: O=C1c2ccc(Cl)cc2CN1c1cncc2c1CCCC2O] | 5-Chloro-2,3-dihydro-isoindol-1-one and 4-bromo-5,6,7,8-tetrahydroisoquinolin-8-ol (intermediate B-11) | 1 | 315.0 |
| 118 | 5-Chloro-3-methyl-2-pyridin-3-yl-2,3-dihydro-isoindol-1-one | 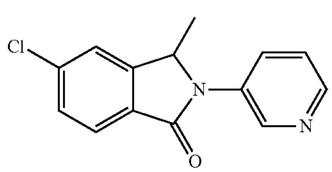 [SMILES: CC1c2cc(Cl)ccc2C(=O)N1c1cccnc1] | 5-Chloro-3-methyl-2,3-dihydro-isoindol-1-one (intermediate A-10) and 3-bromopyridine | 3[B] | 259.1 |
| 119 | 6-Chloro-3-methyl-2-pyridin-3-yl-2,3-dihydro-isoindol-1-one | 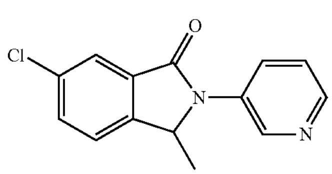 [SMILES: CC1c2ccc(Cl)cc2C(=O)N1c1cccnc1] | 6-Chloro-3-methyl-2,3-dihydro-isoindol-1-one (intermediate A-11) and 3-bromopyridine | 3[B] | 259.1 |
| 120 | 5-Chloro-2-(5-methoxy-pyridin-3-yl)-3-methyl-2,3-dihydro-isoindol-1-one | 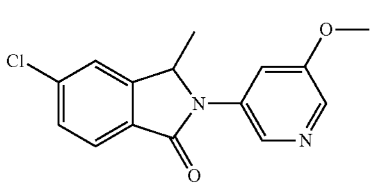 [SMILES: COc1cncc(N2C(=O)c3ccc(Cl)cc3C2C)c1] | 5-Chloro-3-methyl-2,3-dihydro-isoindol-1-one (intermediate A-10) and 3-bromo-5-methoxy-pyridine | 2 | 289.1 |

TABLE 1-continued

| Ex | Compound Name | Compound Structure | Starting Materials | Prepared by analogy to example | MS (M + H)+ |
|---|---|---|---|---|---|
| 121 | 5-Chloro-3-methyl-2-(4-methyl-pyridin-3-yl)-2,3-dihydro-isoindol-1-one | 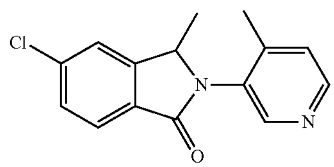 [SMILES: Cc1ccncc1N1C(=O)c2ccc(Cl)cc2C1C] | 5-Chloro-3-methyl-2,3-dihydro-isoindol-1-one (intermediate A-10) and 3-bromo-5-methyl-pyridine | 2 | 273.1 |
| 122 | 5-Chloro-2-[5-(1-hydroxy-ethyl)-pyridin-3-yl]-3-methyl-2,3-dihydro-isoindol-1-one | 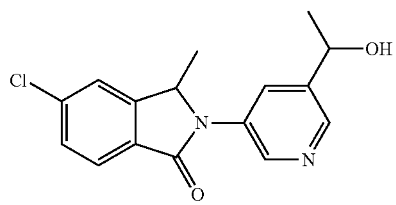 [SMILES: CC(O)c1cncc(N2C(=O)c3ccc(Cl)cc3C2C)c1] | 5-Chloro-3-methyl-2,3-dihydro-isoindol-1-one (intermediate A-10) and 1-(5-bromo-pyridin-3-yl)-ethanol | 2 | 303.1 |
| 123 | 5-Chloro-2-(5-fluoro-pyridin-3-yl)-3-methyl-2,3-dihydro-isoindol-1-one | 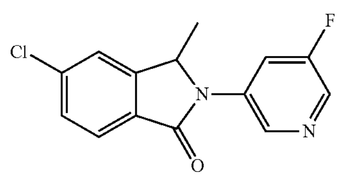 [SMILES: CC1c2cc(Cl)ccc2C(=O)N1c1cncc(F)c1] | 5-Chloro-3-methyl-2,3-dihydro-isoindol-1-one (intermediate A-10) and 3-bromo-5-fluoro-pyridine | 2 | 277.1 |
| 124 | 3-Benzyl-5-chloro-2-pyridin-3-yl-2,3-dihydro-isoindol-1-one | 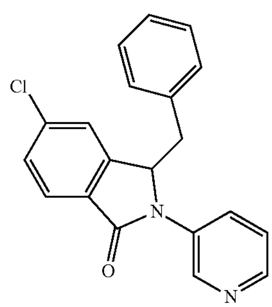 [SMILES: O=C1c2ccc(Cl)cc2C(Cc2ccccc2)N1c1cccnc1] | 3-Benzyl-5-chloro-2,3-dihydro-isoindol-1-one (intermediate A-14) and 3-bromo-pyridine | 2 | 335.1 |
| 125 | 5-Chloro-3-ethyl-2-pyridin-3-yl-2,3-dihydro-isoindol-1-one | 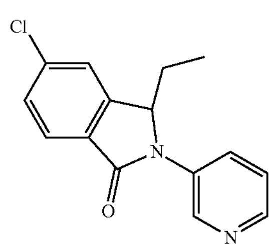 [SMILES: CCC1c2cc(Cl)ccc2C(=O)N1c1cccnc1] | 5-Chloro-3-ethyl-2,3-dihydro-isoindol-1-one (intermediate A-13) and 3-bromo-pyridine | 2 | 273.2 |
| 126 | 5-Chloro-3-ethyl-2-(5-fluoro-pyridin-3-yl)-2,3-dihydro-isoindol-1-one | 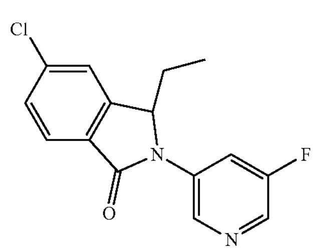 [SMILES: CCC1c2cc(Cl)ccc2C(=O)N1c1cncc(F)c1] | 5-Chloro-3-ethyl-2,3-dihydro-isoindol-1-one (intermediate A-13) and 3-bromo-5-fluoro-pyridine | 2 | 291.2 |

TABLE 1-continued

| Ex | Compound Name | Compound Structure | Starting Materials | Prepared by analogy to example | MS (M + H)+ |
|---|---|---|---|---|---|
| 127 | 5-Chloro-3-ethyl-2-(5-methoxy-pyridin-3-yl)-2,3-dihydro-isoindol-1-one | 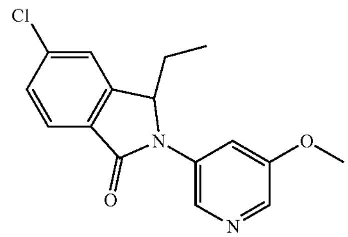 [SMILES: CCC1c2cc(Cl)ccc2C(=O)N1c1cncc(OC)c1] | 5-Chloro-3-ethyl-2,3-dihydro-isoindol-1-one (intermediate A-13) and 3-bromo-5-methoxy-pyridine | 2 | 303.2 |
| 128 | 5-Chloro-3,3-dimethyl-2-pyridin-3-yl-2,3-dihydro-isoindol-1-one | 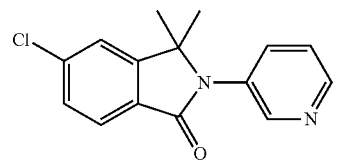 [SMILES: CC1(C)c2cc(Cl)ccc2C(=O)N1c1cccnc1] | 5-Chloro-3,3-dimethyl-2,3-dihydro-isoindol-1-one (intermediate A-12) and 3-bromopyridine | 3[B] | 273.1 |
| 129 | 5-Chloro-2-(5-fluoro-pyridin-3-yl)-3,3-dimethyl-2,3-dihydro-isoindol-1-one | 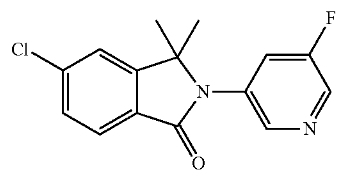 [SMILES: CC1(C)c2cc(Cl)ccc2C(=O)N1c1cncc(F)c1] | 5-Chloro-3,3-dimethyl-2,3-dihydro-isoindol-1-one (intermediate A-12) and 3-bromo-5-fluoro-pyridine | 3[B] | 291.1 |
| 130 | 5-Chloro-2-(5-methoxy-pyridin-3-yl)-3,3-dimethyl-2,3-dihydro-isoindol-1-one | 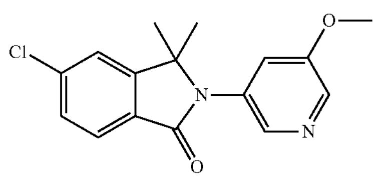 [SMILES: COc1cncc(N2C(=O)c3ccc(Cl)cc3C2(C)C)c1] | 5-Chloro-3,3-dimethyl-2,3-dihydro-isoindol-1-one (intermediate A-12) and 3-bromo-5-methoxy-pyridine | 3[B] | 303.1 |
| 131 | 5-Chloro-2-(5-difluoromethoxy-pyridin-3-yl)-3,3-dimethyl-2,3-dihydro-isoindol-1-one | 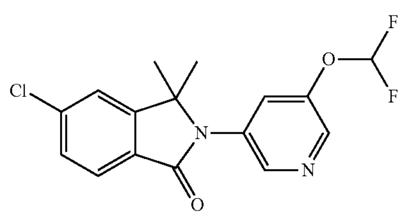 [SMILES: CC1(C)c2cc(Cl)ccc2C(=O)N1c1cncc(OC(F)F)c1] | 5-Chloro-3,3-dimethyl-2,3-dihydro-isoindol-1-one (intermediate A-12) and 3-bromo-5-difluoromethoxy-pyridine | 2 | 339.2 |
| 132 | 5-Chloro-2-[5-(1-hydroxy-ethyl)-pyridin-3-yl]-3,3-dimethyl-2,3-dihydro-isoindol-1-one | 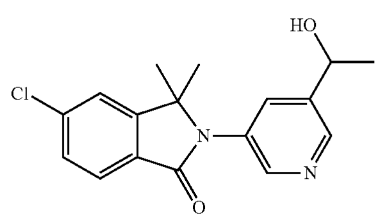 [SMILES: CC(O)c1cncc(N2C(=O)c3ccc(Cl)cc3C2(C)C)c1] | 5-Chloro-3,3-dimethyl-2,3-dihydro-isoindol-1-one (intermediate A-12) and 1-(5-bromo-pyridin-3-yl)-ethanol | 2 | 317.2 |
| 133 | 5-Chloro-2-(5-hydroxymethyl-pyridin-3-yl)-3,3-dimethyl-2,3-dihydro-isoindol-1-one | 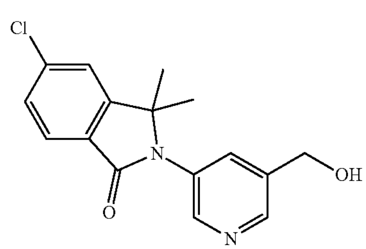 [SMILES: CC1(C)c2cc(Cl)ccc2C(=O)N1c1cncc(CO)c1] | 5-Chloro-3,3-dimethyl-2,3-dihydro-isoindol-1-one (intermediate A-12) and (5-bromo-pyridin-3-yl)-methanol | 2 | 303.2 |

TABLE 1-continued

| Ex | Compound Name | Compound Structure | Starting Materials | Prepared by analogy to example | MS (M + H)+ |
|---|---|---|---|---|---|
| 134 | 5-Chloro-3,3-dimethyl-2-[5-(2-methyl-imidazol-1-ylmethyl)-pyridin-3-yl]-2,3-dihydro-isoindol-1-one | 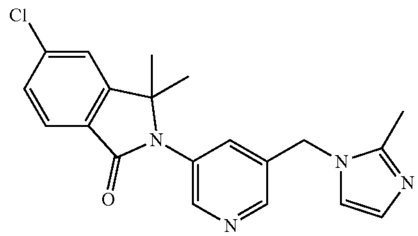 [SMILES: Cc1nccn1Cc1cncc(N2C(=O)c3ccc(Cl)cc3C2(C)C)c1] | 5-Chloro-3,3-dimethyl-2,3-dihydro-isoindol-1-one (intermediate A-12) and 3-bromo-5-(2-methyl-imidazol-1-ylmethyl)-pyridine (intermediate B-2) | 3[B] | 367.1 |

Example 135

6-Chloro-2-[5-((S)-2-hydroxymethyl-pyrrolidin-1-yl)-pyridin-3-yl]-3,4-dihydro-2H-isoquinolin-1-one

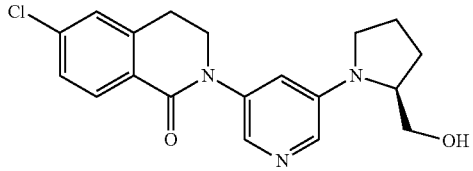 [SMILES: O=C1c2ccc(Cl)cc2CCN1c1cncc(N2CCC[C@H]2CO)c1]

[A] (S)-2-(tert-Butyl-dimethyl-silanyloxymethyl)-pyrrolidine

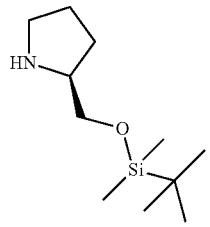

To a solution of (S)-pyrrolidin-2-ylmethanol (0.69 g, 6.82 mmol) in DCM (3 mL) cooled to 0° C. was added TEA (1.38 g, 13.6 mmol) followed by TBDMS-Cl (1.03 g, 6.82 mmol) in DCM (3 mL). The reaction mixture was then stirred at room temperature overnight and poured into NH$_4$Cl (20 mL). The aqueous layer was extracted with DCM (2×50 mL). Combined organics were washed with brine, dried over Na$_2$SO$_4$, filtered and evaporated to dryness to give the title compound (1.11 g, 76%) as a yellow oil. MS: 216.2 (M+H$^+$).

[B] 3-Bromo-5-[(S)-2-(tert-butyl-dimethyl-silanyloxymethyl)-pyrrolidin-1-yl]-pyridine

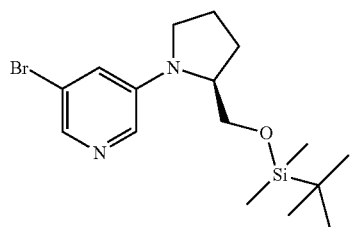 [SMILES: CC(C)(C)[Si](C)(C)OC[C@@H]1CCCN1c1cncc(Br)c1]

To a solution of crude (S)-2-((tert-butyldimethylsilyloxy)methyl)pyrrolidine (0.455 g, 2.11 mmol) in toluene (20 mL) were added Pd$_2$(dba)$_3$ (0.039 g, 0.042 mmol) and rac-BINAP (0.066 g, 0.106 mmol). The solution was purged with argon and heated to 85° C. for 10 min. After cooling to room temperature, sodium tert-butoxide (0.406 g, 4.22 mmol) and 3,5-dibromopyridine (0.5 g, 2.11 mmol) were added and the reaction mixture was then heated at 85° C. overnight. The mixture was poured into sat NH$_4$Cl (20 mL) and the aqueous layer was extracted with DCM (2×25 mL). Combined organics were washed with brine, dried over Na$_2$SO$_4$, filtered and evaporated to dryness. The residue was purified by silica gel flash chromatography eluting with a 0 to 5% MeOH-DCM gradient to give the title compound (0.412 g, 53%) as a yellow oil. MS: 371.0, 372.9 (M+H$^+$).

[C] 2-{5-[(S)-2-(tert-Butyl-dimethyl-silanyloxymethyl)-pyrrolidin-1-yl]-pyridin-3-yl}-6-chloro-3,4-dihydro-2H-isoquinolin-1-one

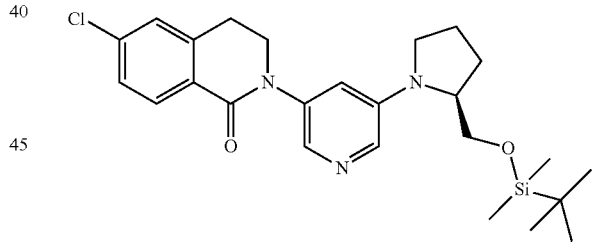

In analogy to the procedure described for the preparation of intermediate B-8,6-chloro-3,4-dihydroisoquinolin-1(2H)-one (intermediate A-2) has been coupled to 3-bromo-5-[(S)-2-(tert-butyl-dimethyl-silanyloxymethyl)-pyrrolidin-1-yl]-pyridine to yield the title compound as a yellow oil. MS: 472.2 (M+H$^+$).

[D] 6-Chloro-2-[5-((S)-2-hydroxymethyl-pyrrolidin-1-yl)-pyridin-3-yl]-3,4-dihydro-2H-isoquinolin-1-one

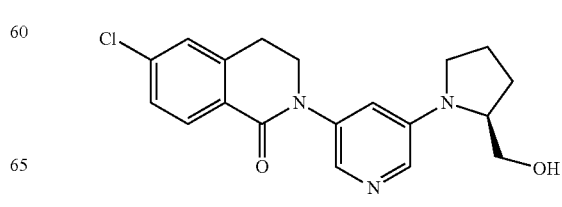

To a solution of 2-{5-[(S)-2-(tert-butyl-dimethyl-silanyloxymethyl)-pyrrolidin-1-yl]-pyridin-3-yl}-6-chloro-3,4-dihydro-2H-isoquinolin-1-one (0.110 g, 0.233 mmol) in MeOH (2 mL) was added 4M HCl in dioxane (0.233 ml, 0.932 mmol) and the reaction mixture was stirred at room temperature for 2 h. The mixture was evaporated to dryness, the residue was diluted with DCM (20 mL) and washed with NaHCO₃ (10 mL). The organic layer was dried over Na₂SO₄, filtered and evaporated to dryness. The residue was purified by silica gel flash chromatography eluting with a 0 to 5% MeOH (1% NH₄OH)-DCM gradient to give the title compound (0.06 g, 72%) as a light yellow solid. MS: 358.0 (M+H⁺).

Example 136

5-Chloro-2-[5-((S)-2-hydroxymethyl-pyrrolidin-1-yl)-pyridin-3-yl]-2,3-dihydro-isoindol-1-one

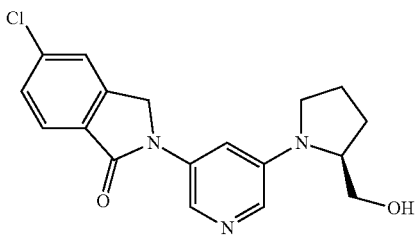 [SMILES: O=C1c2ccc(Cl)cc2CN1c1cncc(N2CCC[C@H]2CO)c1]

In analogy to the procedures described for the preparation of example 135, 3-bromo-5-[(S)-2-(tert-butyl-dimethyl-silanyloxymethyl)-pyrrolidin-1-yl]-pyridine (example 135[B]) has been reacted with 5-chloro-2,3-dihydro-isoindol-1-one to give 2-{5-[(S)-2-(tert-butyl-dimethyl-silanyloxymethyl)-pyrrolidin-1-yl]-pyridin-3-yl}-5-chloro-2,3-dihydro-isoindol-1-one, which was then deprotected with 4M HCl in dioxane to give the title compound as white solid. MS: 344.0 (M+H⁺).

Example 137

6-Chloro-2-[5-((R)-3-hydroxy-pyrrolidin-1-yl)-pyridin-3-yl]-3,4-dihydro-2H-isoquinolin-1-one

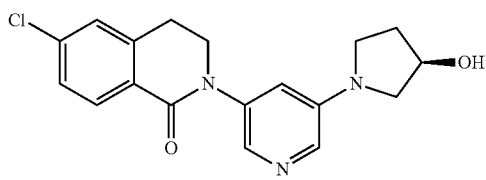 [SMILES: O=C1c2ccc(Cl)cc2CCN1c1cncc(N2CC[C@@H](O)C2)c1]

[A] (R)-3-bromo-5-(3-(tert-butyldimethylsilyloxy)pyrrolidin-1-yl)pyridine

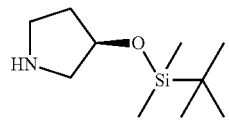

In analogy to the procedure described for the preparation of example 135 [A], (R)-pyrrolidin-3-ol was reacted with TBDMS-Cl in the presence of TEA to give the title compound as a yellow oil. MS: 202.2 (M+H⁺).

[B] 3-Bromo-5-[(R)-3-(tert-butyl-dimethyl-silanyloxy)-pyrrolidin-1-yl]-pyridine

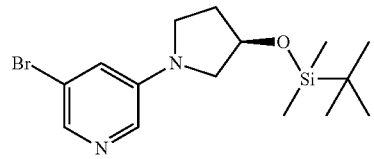 [SMILES: CC(C)(C)[Si](C)(C)O[C@@H]1CCN(c2cncc(Br)c2)C1]

In analogy to the procedure described for the preparation of 135 [B], (R)-3-bromo-5-(3-(tert-butyldimethylsilyloxy)pyrrolidin-1-yl)pyridine was reacted with 3,5-dibromopyridine in the presence of Pd₂(dba)₃, rac-BINAP and sodium tert-butoxide to give the title compound as a yellow oil. MS: 357.1, 359.0 (M+H⁺).

[C] 2-{5-[(R)-3-(tert-Butyl-dimethyl-silanyloxy)-pyrrolidin-1-yl]-pyridin-3-yl}-6-chloro-3,4-dihydro-2H-isoquinolin-1-one

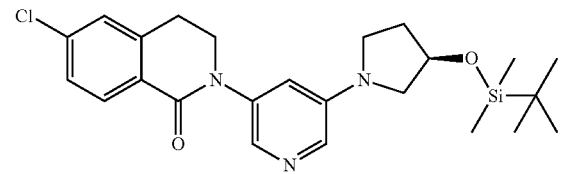 [SMILES: CC(C)(C)[Si](C)(C)O[C@@H]1CCN(c2cncc(N3CCc4cc(Cl)ccc4C3=O)c2)C1]

In analogy to the procedure described for the preparation of intermediate B-8,6-chloro-3,4-dihydroisoquinolin-1(2H)-one (intermediate A-2) has been coupled to 3-bromo-5-[(R)-3-(tert-butyl-dimethyl-silanyloxy)-pyrrolidin-1-yl]-pyridine to give the title compound as a yellow oil. MS: 458.2 (M+H⁺).

[D] 6-Chloro-2-[5-((R)-3-hydroxy-pyrrolidin-1-yl)-pyridin-3-yl]-3,4-dihydro-2H-isoquinolin-1-one

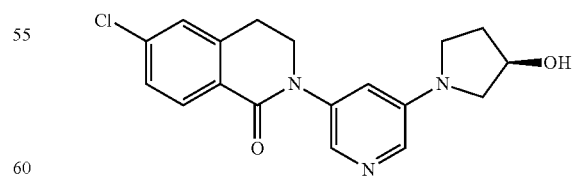

In analogy to the procedure described in example 135 [D], 2-{5-[(R)-3-(tert-butyl-dimethyl-silanyloxy)-pyrrolidin-1-yl]-pyridin-3-yl}-6-chloro-3,4-dihydro-2H-isoquinolin-1-one was deprotected with 4M HCl in dioxane to give the title compound as a white foam. MS: 344.0 (M+H⁺).

Example 138

5-Chloro-2-[5-((R)-3-hydroxy-pyrrolidin-1-yl)-pyridin-3-yl]-2,3-dihydro-isoindol-1-one

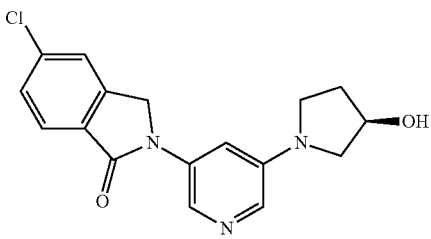 [SMILES: O=C1c2ccc(Cl)cc2CN1c1cncc(N2CC[C@@H](O)C2)c1]

In analogy to the procedures described for the preparation of example 137, 3-bromo-5-[(R)-3-(tert-butyl-dimethyl-silanyloxy)-pyrrolidin-1-yl]-pyridine (example 137 [B]) has been reacted with 5-chloro-2,3-dihydro-isoindol-1-one to give 2-{5-[(R)-3-(tert-butyl-dimethyl-silanyloxy)-pyrrolidin-1-yl]-pyridin-3-yl}-5-chloro-2,3-dihydro-isoindol-1-one, which was then deprotected with 4M HCl in dioxane to give the title compound as light yellow solid. MS: 330.1 (M+H+).

Example 139

2-Hydroxy-6-(5-methoxy-pyridin-3-yl)-7,8-dihydro-6H-[1,6]naphthyridin-5-one

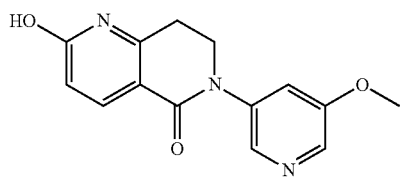 [SMILES: COc1cncc(N2CCc3nc(O)ccc3C2=O)c1]

2-Methoxy-6-(5-methoxy-pyridin-3-yl)-7,8-dihydro-6H-[1,6]naphthyridin-5one (445 mg, 1.56 mmol) (example 97) was suspended in 2 mL of aq. conc. HCl in 1,4-dioxane (2:1) and heated at 80° C. for 3 hours before the solvent was removed in vacuo. After extraction between EtOAc and H₂O, the organic layer was washed with aq. satd. NaHCO₃ solution, brine, dried over anhy. Na₂SO₄, filtered and concentrated in vacuo to give a crude product which was purified by prep-HPLC to yield the title compound (4.9 mg) as a white solid. MS: 270.2 (M+H+).

Example 140

6-Chloro-2-(5-imidazol-1-ylmethyl-pyridin-3-yl)-3,4-dihydro-2H-isoquinolin-1-one

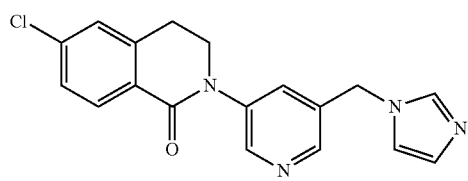

[A] 6-Chloro-2-(5-chloromethyl-pyridin-3-yl)-3,4-dihydro-2H-isoquinolin-1-one

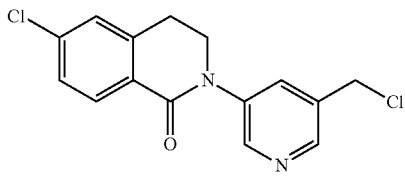 [SMILES: O=C1c2ccc(Cl)cc2CCN1c1cncc(CCl)c1]

Thionyl chloride (1.4 mL, 19.0 mmol) was added slowly at 0° C. to a solution of 6-chloro-2-(5-hydroxymethyl-pyridin-3-yl)-3,4-dihydro-2H-isoquinolin-1-one (example 3 [B]) (1.1 g, 3.8 mmol) in DCM (50 mL). After the addition, the reaction mixture was stirred at 2-5° C. for 2 hours before it was poured into satd. aq. NaHCO₃ solution (50 mL) and extracted with EtOAc (2×150 mL). The organic layer was washed with brine, dried over anhy. Na₂SO₄, filtered and concentrated in vacuo to give a crude product (1.42 g, 92%) as light yellowish solid. MS: 307.0 & 309.0 (M+H+).

[B] 6-Chloro-2-(5-imidazol-1-ylmethyl-pyridin-3-yl)-3,4-dihydro-2H-isoquinolin-1 one

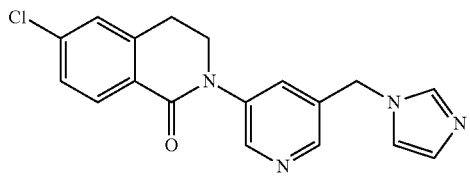 [SMILES: O=C1c2ccc(Cl)cc2CCN1c1cncc(Cn2ccnc2)c1]

To a solution of 1H-imidazole (50 mg, 0.73 mmol) dissolved in DMF (5.0 mL) was added NaH (60% dispersion in mineral oil, 25 mg, 0.63 mmol) at 0° C. The reaction mixture was stirred at 2-5° C. for 0.5 h before 6-chloro-2-(5-chloromethyl-pyridin-3-yl)-3,4-dihydro-2H-isoquinolin-1-one (example 140 [A]) (85 mg, 0.28 mmol) was added. The mixture was then stirred at 2-5° C. for additional 2 hours before it was warmed up to room temperature and poured into water (5.0 mL). After extraction with EtOAc (2×50 mL), the organic layer was washed with brine, dried over anhy. Na₂SO₄, filtered and concentrated in vacuo to give a crude product which was purified by prep-HPLC to give the title compound (30 mg, 31%) as a white foam. MS: 339.2 (M+H+).

The following compounds listed in Table 2 were prepared in analogy to the procedure described for the preparation of example 140 using appropriate starting materials.

TABLE 2

| Ex | Compound Name | Starting Materials | MS (M + H)+ |
|---|---|---|---|
| 141 | 6-Chloro-2-[5-(2-isopropyl-imidazol-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and 2-isopropyl-1H-imidazole | 381.1 |
| 142 | 6-Chloro-2-[5-(2-methyl-imidazol-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and 2-methyl-1H-imidazole | 353.1 |
| 143 | 6-Chloro-2-[5-(2-ethyl-4-methyl-imidazol-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and 2-ethyl-4-methyl-1H-imidazole | 381.2 |
| 144 | 6-Chloro-2-[5-(3-hydroxy-piperidin-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and piperidin-3-ol | 372.2 |
| 145 | Propane-2-sulfonic acid [5-(6-chloro-1-oxo-3,4-dihydro-1H-isoquinolin-2-yl)-pyridin-3-ylmethyl]-amide | 6-Chloro-2-(5-chloromethyl-pyridin-3-yl)-3,4-dihydro-2H-isoquinolin-1-one (example 140[A]) and propane-2-sulfonic acid amide | 394.2 |
| 146 | 6-Chloro-2-[5-(3-hydroxy-pyrrolidin-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and pyrrolidin-3-ol | 358.2 |
| 147 | 6-Chloro-2-[5-((R)-3-hydroxy-pyrrolidin-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and (R)-pyrrolidin-3-ol | 358.2 |
| 148 | 6-Chloro-2-[5-((S)-3-hydroxy-pyrrolidin-1-ylmethyl)-pyridin-3-yl]-3,4-dihydro-2H-isoquinolin-1-one | 6-Chloro-2-(5-chloromethyl-pyridin-3-yl)-3,4-dihydro-2H-isoquinolin-1-one (example 140[A]) and (S)-pyrrolidin-3-ol | 358.2 |

TABLE 2-continued

| Ex | Compound Name | Compound Structure | Starting Materials | MS (M + H)+ |
|---|---|---|---|---|
| 149 | 6-Chloro-2-[5-((S)-2-hydroxymethyl-pyrrolidin-1-ylmethyl)-pyridin-3-yl]-3,4-dihydro-2H-isuquinolin-1-one | 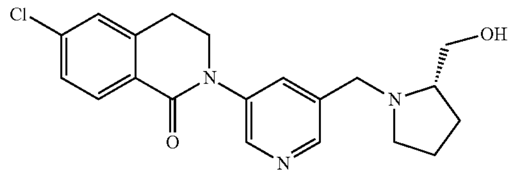 [SMILES: O=C1c2ccc(Cl)cc2CCN1c1cncc(CN2CCC[C@H]2CO)c1] | 6-Chloro-2-(5-chloromethyl-pyridin-3-yl)-3,4-dihydro-2H-isoquinolin-1-one (example 140[A]) and (S)-1-pyrrolidin-2-yl-methanol | 372.2 |
| 150 | 6-Chloro-2-[5-((R)-2-hydroxymethyl-pyrrolidin-1-ylmethyl)-pyridin-3-yl]-3,4-dihydro-2H-isoquinolin-1-one | 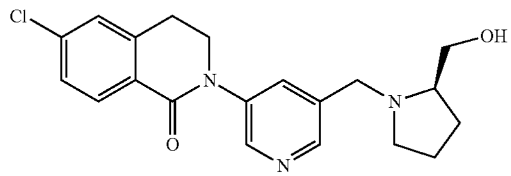 [SMILES: O=C1c2ccc(Cl)cc2CCN1c1cncc(CN2CCC[C@@H]2CO)c1] | 6-Chloro-2-(5-chloromethyl-pyridin-3-yl)-3,4-dihydro-2H-isoquinolin-1-one (example 140[A]) and (R)-1-pyrrolidin-2-yl-methanol | 372.2 |
| 151 | 6-Chloro-2-[5-(3,5-dimethyl-pyrazol-1-ylmethyl)-pyridin-3-yl]-3,4-dihydro-2H-isoquinolin-1-one | 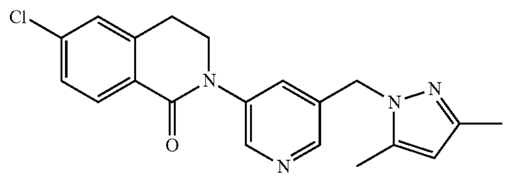 [SMILES: Cc1cc(C)n(Cc2cncc(N3CCc4cc(Cl)ccc4C3=O)c2)n1] | 6-Chloro-2-(5-chloromethyl-pyridin-3-yl)-3,4-dihydro-2H-isoquinolin-1-one (example 140[A]) and 3,5-dimethyl-1H-pyrazole | 367.1 |
| 152 | N-[5-(6-Chloro-1-oxo-3,4-dihydro-1H-isoquinolin-2-yl)-pyridin-3-ylmethyl]-methanesulfonamide | 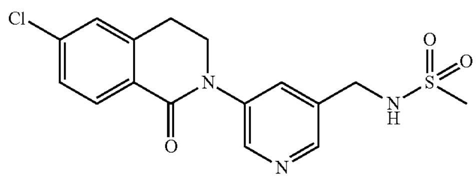 [SMILES: CS(=O)(=O)NCc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and methanesulfonamide | 366.1 |
| 153 | N-[5-(6-Chloro-1-oxo-3,4-dihydro-1H-isoquinolin-2-yl)-pyridin-3-ylmethyl]-acetamide | 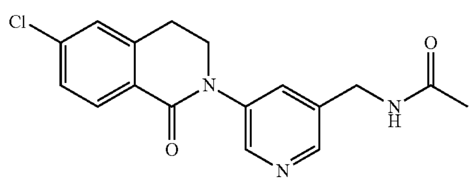 [SMILES: CC(=O)NCc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and acetamide | 330.2 |
| 154 | 6-Chloro-2-(5-morpholin-4-ylmethyl-pyridin-3-yl)-3,4-dihydro-2H-isoquinolin-1-one | 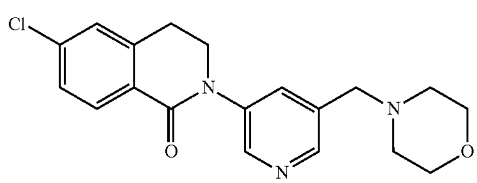 [SMILES: O=C1c2ccc(Cl)cc2CCN1c1cncc(CN2CCOCC2)c1] | 6-Chloro-2-(5-chloromethyl-pyridin-3-yl)-3,4-dihydro-2H-isoquinolin-1-one (example 140[A]) and morpholine | 358.3 |
| 155 | 6-Chloro-2-[5-(2-oxo-pyrrolidin-1-ylmethyl)-pyridin-3-yl]-3,4-dihydro-2H-isoquinolin-1-one | 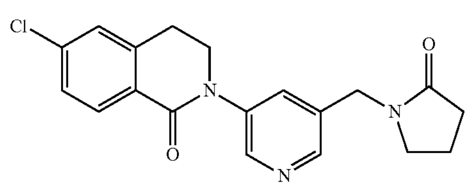 [SMILES: O=C1CCCN1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and pyrrolidin-2-one | 356.2 |
| 156 | 6-Chloro-2-[5-(1,1-dioxo-1λ$^6$-thiomorpholin-4-ylmethyl)-pyridin-3-yl]-3,4-dihydro-2H-isoquinolin-1-one | 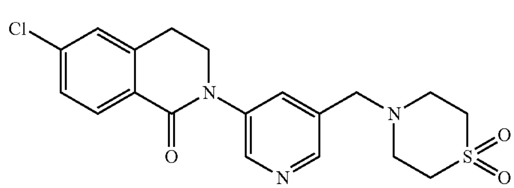 [SMILES: O=C1c2ccc(Cl)cc2CCN1c1cncc(CN2CCS(=O)(=O)CC2)c1] | 6-Chloro-2-(5-chloromethyl-pyridin-3-yl)-3,4-dihydro-2H-isoquinolin-1-one (example 140[A]) and thiomorpholine 1,1-dioxide | 406.1 |

TABLE 2-continued

| Ex | Compound Name | Compound Structure | Starting Materials | MS (M + H)+ |
|---|---|---|---|---|
| 157 | 6-Chloro-2-[5-(2-oxo-oxazolidin-3-ylmethyl)-pyridin-3-yl]-3,4-dihydro-2H-isoquinolin-1-one | 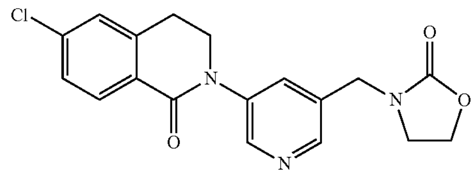 [SMILES: O=C1OCCN1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and oxazolidin-2-one | 358.1 |
| 158 | 6-Chloro-2-[5-(2-oxo-imidazolidin-1-ylmethyl)-pyridin-3-yl]-3,4-dihydro-2H-isoquinolin-1-one | 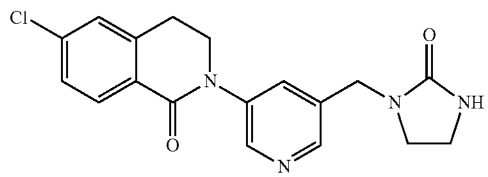 [SMILES: O=C1NCCN1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and imidazolidin-2-one | 357.1 |
| 159 | 6-Chloro-2-[5-(3-methyl-2-oxo-imidazolidin-1-ylmethyl)-pyridin-3-yl]-3,4-dihydro-2H-isoquinolin-1-one | 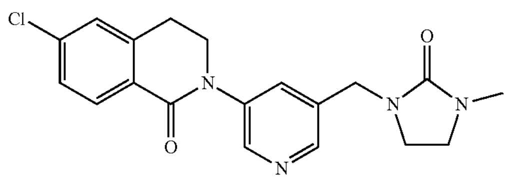 [SMILES: CN1CCN(Cc2cncc(N3CCc4cc(Cl)ccc4C3=O)c2)C1=O] | 6-Chloro-2-(5-chloromethyl-pyridin-3-yl)-3,4-dihydro-2H-isoquinolin-1-one (example 140[A]) and 1-methyl-imidazolidin-2-one | 371.2 |
| 160 | 6-Chloro-2-(5-pyrazol-1-ylmethyl-pyridin-3-yl)-3,4-dihydro-2H-isoquinolin-1-one | 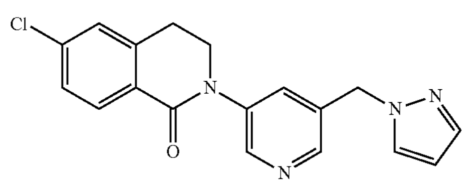 | 6-Chloro-2-(5-chloromethyl-pyridin-3-yl)-3,4-dihydro-2H-isoquinolin-1-one (example 140[A]) and 1H-pyrazole | 339.1 |
| 161 | 6-Chloro-2-[5-(2-propyl-imidazol-1-ylmethyl)-pyridin-3-yl]-3,4-dihydro-2H-isoquinolin-1-one | 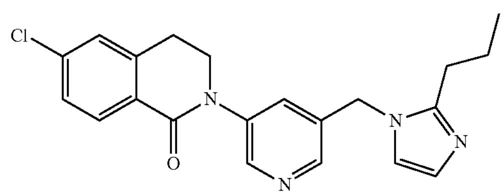 [SMILES: CCCc1nccn1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 2-propyl-1H-imidazole | 381.2 |
| 162 | 1-[5-(6-Chloro-1-oxo-3,4-dihydro-1H-isoquinolin-2-yl)-pyridin-3-ylmethyl]-1H-imidazole-2-carboxylic acid ethyl ester | 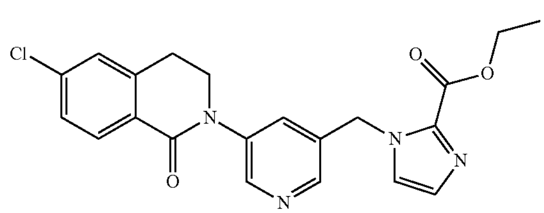 [SMILES: CCOC(=O)c1nccn1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 1H-imidazole-2-carboxylic acid ethyl ester | 411.2 |
| 163 | 6-Chloro-2-[5-(2-hydroxymethyl-imidazol-1-ylmethyl)-pyridin-3-yl]-3,4-dihydro-2H-isoquinolin-1-one | 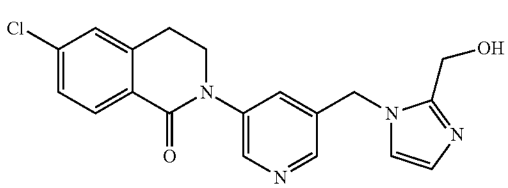 [SMILES: O=C1c2ccc(Cl)cc2CCN1c1cncc(Cn2ccnc2CO)c1] | 6-Chloro-2-(5-chloromethyl-pyridin-3-yl)-3,4-dihydro-2H-isoquinolin-1-one (example 140[A]) and (1H-imidazol-2-yl)-methanol | 369.1 |
| 164 | 6-Chloro-2-[5-(oxetan-3-ylaminomethyl)-pyridin-3-yl]-3,4-dihydro-2H-isoquinolin-1-one | 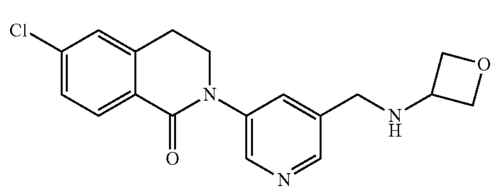 [SMILES: O=C1c2ccc(Cl)cc2CCN1c1cncc(CNC2COC2)c1] | 6-Chloro-2-(5-chloromethyl-pyridin-3-yl)-3,4-dihydro-2H-isoquinolin-1-one (example 140[A]) and oxetan-3-ylamine | 344.1 |

TABLE 2-continued

| Ex | Compound Name | Compound Structure | Starting Materials | MS (M + H)+ |
|---|---|---|---|---|
| 165 | 6-Chloro-2-{5-[4-(2-hydroxy-ethyl)-piperazin-1-ylmethyl]-pyridin-3-yl}-3,4-dihydro-2H-isoquinolin-1-one | 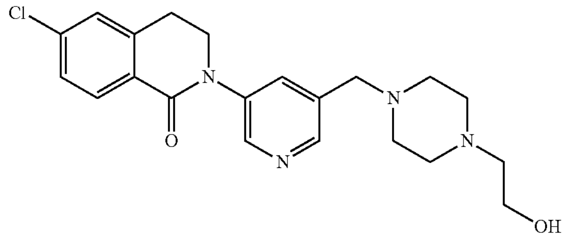 [SMILES: O=C1c2ccc(Cl)cc2CCN1c1cncc(CN2CCN(CCO)CC2)c1] | 6-Chloro-2-(5-chloromethyl-pyridin-3-yl)-3,4-dihydro-2H-isoquinolin-1-one (example 140[A]) and 2-piperazin-1-yl-ethanol | 401.2 |
| 166 | 6-Chloro-2-[5-(4-isopropyl-piperazin-1-ylmethyl)-pyridin-3-yl]-3,4-dihydro-2H-isoquinolin-1-one | 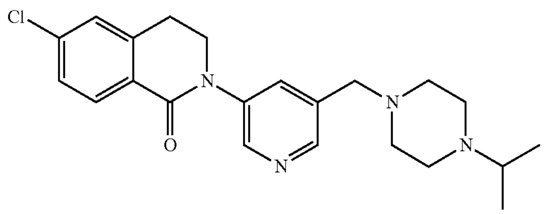 [SMILES: CC(C)N1CCN(Cc2cncc(N3CCc4cc(Cl)ccc4C3=O)c2)CC1] | 6-Chloro-2-(5-chloromethyl-pyridin-3-yl)-3,4-dihydro-2H-isoquinolin-1-one (example 140[A]) and 1-isopropyl-piperazine | 399.2 |
| 167 | 6-Chloro-2-[5-(4-methyl-piperazin-1-ylmethyl)-pyridin-3-yl]-3,4-dihydro-2H-isuquinolin-1-one | 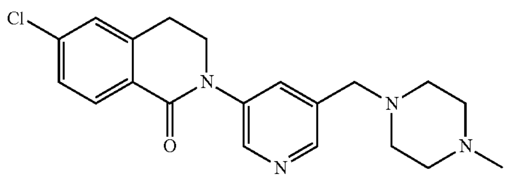 [SMILES: CN1CCN(Cc2cncc(N3CCc4cc(Cl)ccc4C3=O)c2)CC1] | 6-Chloro-2-(5-chloromethyl-pyridin-3-yl)-3,4-dihydro-2H-isoquinolin-1-one (example 140[A]) and 1-methyl-piperazine | 371.2 |
| 168 | 6-Chloro-2-[5-(4,4-difluoro-piperidin-1-ylmethyl)-pyridin-3-yl]-3,4-dihydro-2H-isoquinolin-1-one | 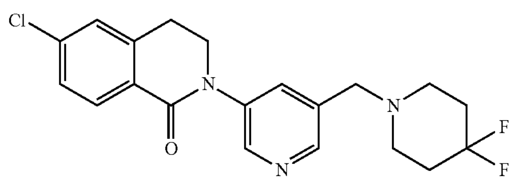 [SMILES: O=C1c2ccc(Cl)cc2CCN1c1cncc(CN2CCC(F)(F)CC2)c1] | 6-Chloro-2-(5-chloromethyl-pyridin-3-yl)-3,4-dihydro-2H-isoquinolin-1-one (example 140[A]) and 4,4-difluoro-piperidine | 392.1 |
| 169 | 6-Chloro-2-[5-(3,3-difluoro-pyrrolidin-1-ylmethyl)-pyridin-3-yl]-3,4-dihydro-2H-isoquinolin-1-one | 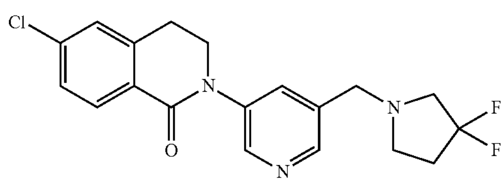 [SMILES: O=C1c2ccc(Cl)cc2CCN1c1cncc(CN2CCC(F)(F)C2)c1] | 6-Chloro-2-(5-chloromethyl-pyridin-3-yl)-3,4-dihydro-2H-isoquinolin-1-one (example 140[A]) and 3,3-difluoro-pyrrolidine | 378.2 |
| 170 | 6-Chloro-2-[5-(2-oxa-6-aza-spiro[3.4]oct-6-ylmethyl)-pyridin-3-yl]-3,4-dihydro-2H-isoquinolin-1-one | 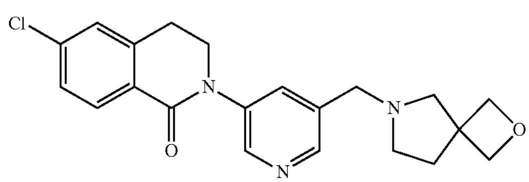 [SMILES: O=C1c2ccc(Cl)cc2CCN1c1cncc(CN2CCC3(COC3)C2)c1] | 6-Chloro-2-(5-chloromethyl-pyridin-3-yl)-3,4-dihydro-2H-isoquinolin-1-one (example 140[A]) and 2-oxa-6-aza-spiro[3.4]octane | 384.2 |
| 171 | 6-Chloro-2-[5-(2-oxa-6-aza-spiro[3.3]hept-6-ylmethyl)-pyridin-3-yl]-3,4-dihydro-2H-isoquinolin-1-one | 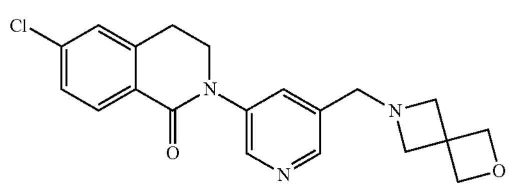 [SMILES: O=C1c2ccc(Cl)cc2CCN1c1cncc(CN2CC3(COC3)C2)c1] | 6-Chloro-2-(5-chloromethyl-pyridin-3-yl)-3,4-dihydro-2H-isoquinolin-1-one (example 140[A]) and 2-oxa-6-aza-spiro[3.3]heptane | 370.2 |
| 172 | 6-Chloro-2-[5-(3,3-difluoro-piperidin-1-ylmethyl)-pyridin-3-yl]-3,4-dihydro-2H-isoquinolin-1-one | 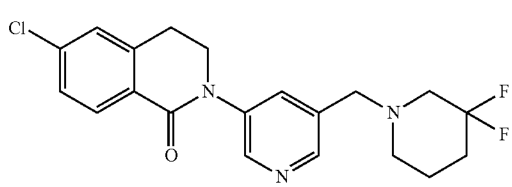 [SMILES: O=C1c2ccc(Cl)cc2CCN1c1cncc(CN2CCCC(F)(F)C2)c1] | 6-Chloro-2-(5-chloromethyl-pyridin-3-yl)-3,4-dihydro-2H-isoquinolin-1-one (example 140[A]) and 3,3-difluoro-piperidine | 392.2 |

TABLE 2-continued

| Ex | Compound Name | Compound Structure | Starting Materials | MS (M + H)+ |
|---|---|---|---|---|
| 173 | 6-Chloro-2-[5-(2-oxo-piperidin-1-ylmethyl)-pyridin-3-yl]-3,4-dihydro-2H-isoquinolin-1-one | 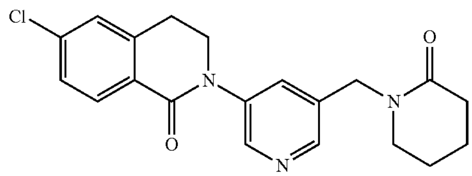 [SMILES: O=C1CCCCN1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and piperidin-2-one | 370.2 |
| 174 | 6-Chloro-2-(5-[1,2,3]triazol-2-ylmethyl-pyridin-3-yl)-3,4-dihydro-2H-isoquinolin-1-one | 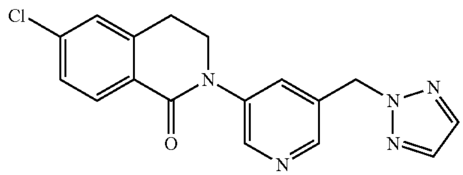 [SMILES: O=C1c2ccc(Cl)cc2CCN1c1cncc(Cn2nccn2)c1] | 6-Chloro-2-(5-chloromethyl-pyridin-3-yl)-3,4-dihydro-2H-isoquinolin-1-one (example 140[A]) and 2H-[1,2,3]triazole | 340.2 |
| 175 | 6-Chloro-2-(5-[1,2,3]triazol-1-ylmethyl-pyridin-3-yl)-3,4-dihydro-2H-isoquinolin-1-one | 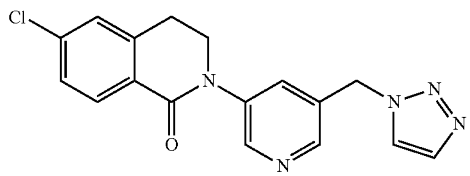 [SMILES: O=C1c2ccc(Cl)cc2CCN1c1cncc(Cn2ccnn2)c1] | 6-Chloro-2-(5-chloromethyl-pyridin-3-yl)-3,4-dihydro-2H-isoquinolin-1-one (example 140[A]) and 1H-[1,2,3]triazole | 340.2 |
| 176 | 6-Chloro-2-[5-(2-chloro-imidazol-1-ylmethyl)-pyridin-3-yl]-3,4-dihydro-2H-isoquinolin-1-one | 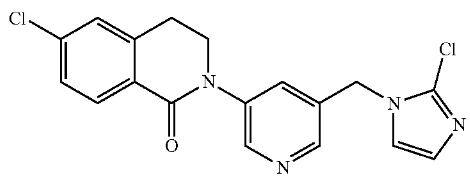 [SMILES: O=C1c2ccc(Cl)cc2CCN1c1cncc(Cn2ccnc2Cl)c1] | 6-Chloro-2-(5-chloromethyl-pyridin-3-yl)-3,4-dihydro-2H-isoquinolin-1-one (example 140[A]) and 2-chloro-1H-imidazole | 373.1 |
| 177 | 6-Chloro-2-[5-(3-methyl-[1,2,4]triazol-4-ylmethyl)-pyridin-3-yl]-3,4-dihydro-2H-isoquinolin-1-one | 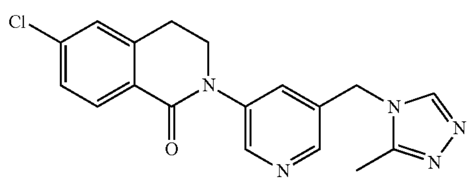 [SMILES: Cc1nncn1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 3-methyl-4H-[1,2,4]triazole | 354.1 |
| 178 | 6-Chloro-2-[5-(5-methyl-[1,2,4]triazol-1-ylmethyl)-pyridin-3-yl]-3,4-dihydro-2H-isoquinolin-1-one; compound with 6-chloro-2-[5-(3-methyl-[1,2,4]triazol-1-ylmethyl)-pyridin-3-yl]-3,4-dihydro-2H-isoquinolin-1-one | 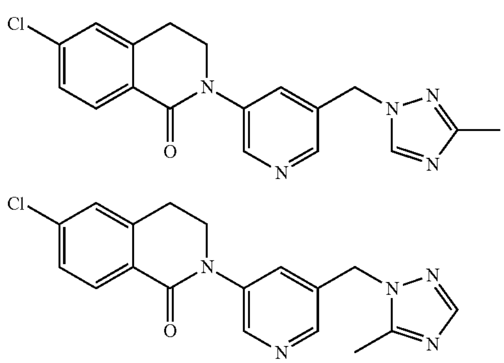 | 6-Chloro-2-(5-chloromethyl-pyridin-3-yl)-3,4-dihydro-2H-isoquinolin-1-one (example 140[A]) and 5-methyl-1H-[1,2,4]triazole | 354.1 |
| 179 | 6-Chloro-2-(5-[1,2,4]triazol-4-ylmethyl-pyridin-3-yl)-3,4-dihydro-2H-isoquinolin-1-one | 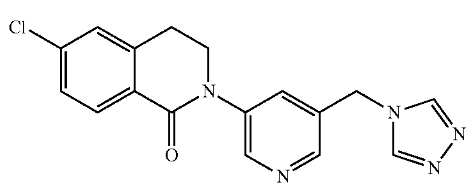 [SMILES: O=C1c2ccc(Cl)cc2CCN1c1cncc(Cn2cnnc2)c1] | 6-Chloro-2-(5-chloromethyl-pyridin-3-yl)-3,4-dihydro-2H-isoquinolin-1-one (example 140[A]) and 4H-[1,2,4]triazole | 340.1 |

TABLE 2-continued

| Ex | Compound Name | Compound Structure | Starting Materials | MS (M + H)+ |
|---|---|---|---|---|
| 180 | 6-Chloro-2-(5-[1,2,4]triazol-1-ylmethyl-pyridin-3-yl)-3,4-dihydro-2H-isoquinolin-1-one | 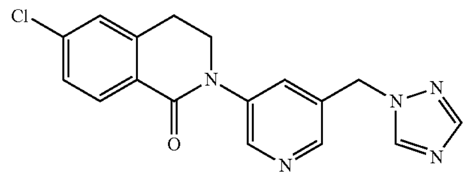 [SMILES: O=C1c2ccc(Cl)cc2CCN1c1cncc(Cn2cncn2)c1] | 6-Chloro-2-(5-chloromethyl-pyridin-3-yl)-3,4-dihydro-2H-isoquinolin-1-one (example 140[A]) and 1H-[1,2,4]triazole | 340.1 |
| 181 | 6-Chloro-2-[5-(2-methyl-benzoimidazol-1-ylmethyl)-pyridin-3-yl]-3,4-dihydro-2H-isoquinolin-1-one | 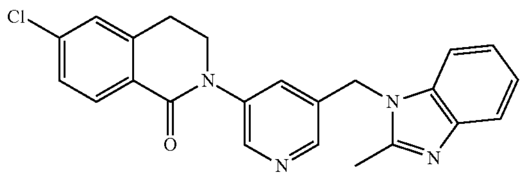 [SMILES: Cc1nc2ccccc2n1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 2-methyl-1H-benzoimidazole | 403.1 |
| 182 | 6-Chloro-2-(5-indazol-1-ylmethyl-pyridin-3-yl)-3,4-dihydro-2H-isoquinolin-1-one | 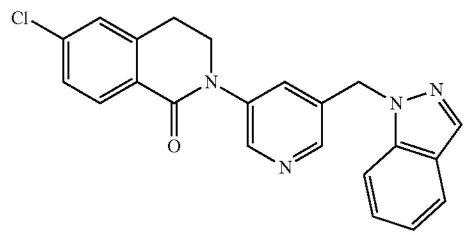 [SMILES: O=C1c2ccc(Cl)cc2CCN1c1cncc(Cn2ncc3ccccc32)c1] | 6-Chloro-2-(5-chloromethyl-pyridin-3-yl)-3,4-dihydro-2H-isoquinolin-1-one (example 140[A]) and 1H-indazole | 389.2 |
| 183 | 6-Chloro-2-(5-indazol-2-ylmethyl-pyridin-3-yl)-3,4-dihydro-2H-isoquinolin-1-one | 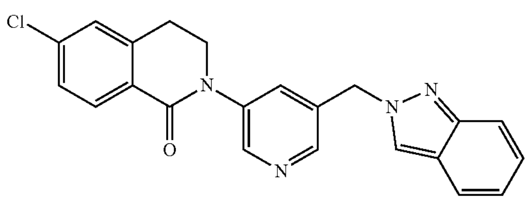 [SMILES: O=C1c2ccc(Cl)cc2CCN1c1cncc(Cn2cc3ccccc3n2)c1] | 6-Chloro-2-(5-chloromethyl-pyridin-3-yl)-3,4-dihydro-2H-isoquinolin-1-one (example 140[A]) and 2H-indazole | 389.1 |
| 184 | 6-Chloro-2-[5-(6-fluoro-indol-1-ylmethyl)-pyridin-3-yl]-3,4-dihydro-2H-isoquinolin-1-one | 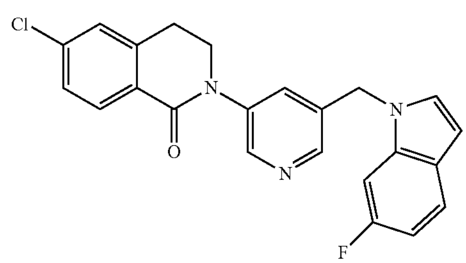 [SMILES: O=C1c2ccc(Cl)cc2CCN1c1cncc(Cn2ccc3ccc(F)cc32)c1] | 6-Chloro-2-(5-chloromethyl-pyridin-3-yl)-3,4-dihydro-2H-isoquinolin-1-one (example 140[A]) and 6-fluoro-1H-indole | 406.2 |
| 185 | 6-Chloro-2-[5-(7-fluoro-indol-1-ylmethyl)-pyridin-3-yl]-3,4-dihydro-2H-isoquinolin-1-one | 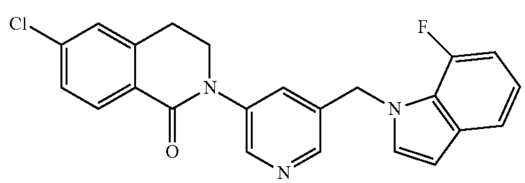 [SMILES: O=C1c2ccc(Cl)cc2CCN1c1cncc(Cn2ccc3cccc(F)c32)c1] | 6-Chloro-2-(5-chloromethyl-pyridin-3-yl)-3,4-dihydro-2H-isoquinolin-1-one (example 140[A]) and 7-fluoro-1H-indole | 406.1 |
| 186 | 6-Chloro-2-[5-(4-fluoro-indol-1-ylmethyl)-pyridin-3-yl]-3,4-dihydro-2H-isoquinolin-1-one | 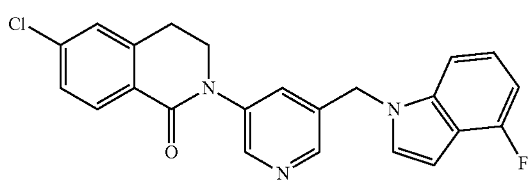 [SMILES: O=C1c2ccc(Cl)cc2CCN1c1cncc(Cn2ccc3c(F)cccc32)c1] | 6-Chloro-2-(5-chloromethyl-pyridin-3-yl)-3,4-dihydro-2H-isoquinolin-1-one (example 140[A]) and 4-fluoro-1H-indole | 406.2 |

TABLE 2-continued

| Ex | Compound Name | Compound Structure | Starting Materials | MS (M + H)+ |
|---|---|---|---|---|
| 187 | 6-Chloro-2-[5-(4-methyl-pyrazol-1-ylmethyl)-pyridin-3-yl]-3,4-dihydro-2H-isoquinolin-1-one | 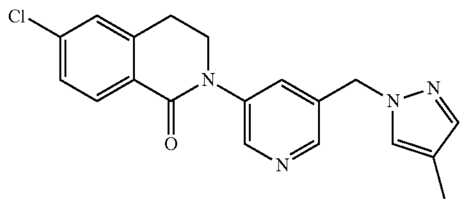 [SMILES: Cc1cnn(Cc2cncc(N3CCc4cc(Cl)ccc4C3=O)c2)c1] | 6-Chloro-2-(5-chloromethyl-pyridin-3-yl)-3,4-dihydro-2H-isoquinolin-1-one (example 140[A]) and 4-methyl-1H-pyrazole | 353.1 |
| 188 | 6-Chloro-2-[5-(2-cyclopropyl-imidazol-1-ylmethyl)-pyridin-3-yl]-3,4-dihydro-2H-isoquinolin-1-one | 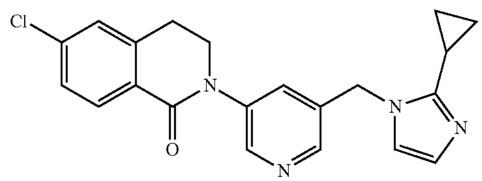 [SMILES: O=C1c2ccc(Cl)cc2CCN1c1cncc(Cn2ccnc2C2CC2)c1] | 6-Chloro-2-(5-chloromethyl-pyridin-3-yl)-3,4-dihydro-2H-isoquinolin-1-one (example 140[A]) and 2-cyclopropyl-1H-imidazole | 379.3 |
| 189 | 6-Chloro-2-[5-(2-trifluoromethyl-imidazol-1-ylmethyl)-pyridin-3-yl]-3,4-dihydro-2H-isoquinolin-1-one | 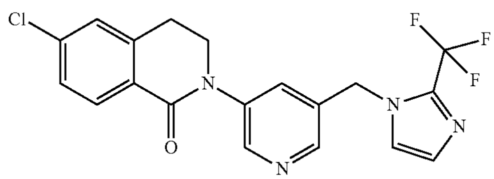 [SMILES: O=C1c2ccc(Cl)cc2CCN1c1cncc(Cn2ccnc2C(F)(F)F)c1] | 6-Chloro-2-(5-chloromethyl-pyridin-3-yl)-3,4-dihydro-2H-isoquinolin-1-one (example 140[A]) and 2-trifluoromethyl-1H-imidazole | 407.2 |
| 190 | 6-Chloro-2-[5-(3-methyl-pyrazol-1-ylmethyl)-pyridin-3-yl]-3,4-dihydro-2H-isoquinolin-1-one | 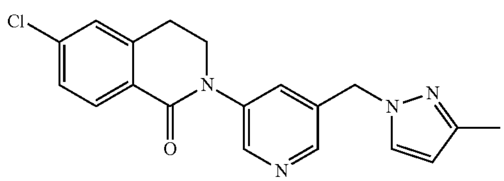 | 6-Chloro-2-(5-chloromethyl-pyridin-3-yl)-3,4-dihydro-2H-isoquinolin-1-one (example 140[A]) and 3-methyl-1H-pyrazole | 353.2 |
| 191 | 6-Chloro-2-[5-(2-ethyl-imidazol-1-ylmethyl)-pyridin-3-yl]-3,4-dihydro-2H-isoquinolin-1-one | 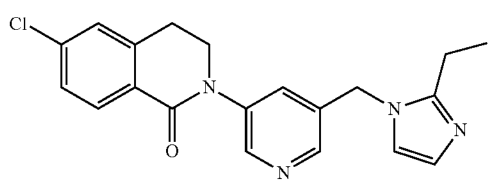 | 6-Chloro-2-(5-chloromethyl-pyridin-3-yl)-3,4-dihydro-2H-isoquinolin-1-one (example 140[A]) and 2-ethyl-1H-imidazole | 367.1 |
| 192 | 2-(5-Aminomethyl-pyridin-3-yl)-6-chloro-3,4-dihydro-2H-isoquinolin-1-one | 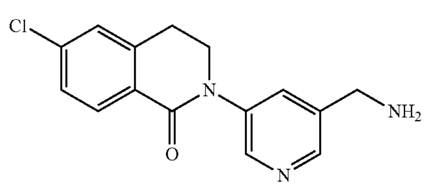 [SMILES: NCc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 1.6M ammonia in dioxane | 288.2 |

Example 193

6-Chloro-2-(5-methoxymethyl-pyridin-3-yl)-3,4-dihydro-2H-isoquinolin-1-one

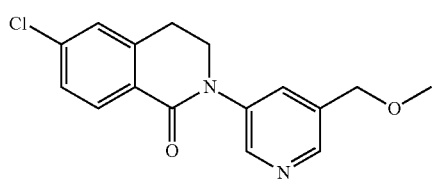

To a solution of 6-chloro-2-(5-hydroxymethyl-pyridin-3-yl)-3,4-dihydro-2H-isoquinolin-1-one (example 3) (28.8 mg, 0.1 mmol) in THF (5 mL) was added NaH (8 mg, 0.2 mmol, 60% dispersion in mineral oil) at room temperature. After hydrogen evolution ceased, a solution of methyliodide (0.2 mmol) in THF (5 mL) was added dropwise, and the resulting mixture was stirred at room temperature for 1 hour. The mixture was then treated with satd. aqueous NH₄Cl solution and extracted three times with EtOAc. The combined organic layer was washed with water and brine, dried over anhy. Na₂SO₄ and concentrated in vacuo. The crude product was purified by prep-HPLC to give the title compound (4.5 mg, 14.8%) as a white solid. MS: (M+H)⁺ 303.1

Example 194

6-Chloro-2-(5-isopropoxymethyl-pyridin-3-yl)-3,4-dihydro-2H-isoquinolin-1-one

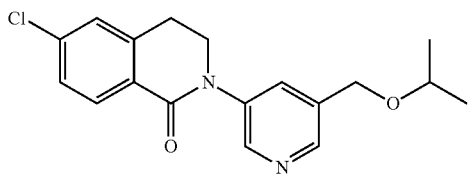 [SMILES: CC(C)OCc1cncc(N2CCc3cc(Cl)ccc3C2=O)c1]

To solution of propan-2-ol (3.6 mg, 0.06 mmol) in dry DMF (1 mL) was added NaH (1.5 mg, 0.06 mmol) at 0° C. The reaction mixture was stirred at room temperature for 5 min before 6-chloro-2-(5-chloromethyl-pyridin-3-yl)-3,4-dihydro-2H-isoquinolin-1-one (15 mg, 0.05 mmol, example 140 [A]) was added. The resulting reaction mixture was then stirred at room temperature for 1 hour before it was poured into ice-water and extracted with EtOAc (2×5 mL). The organic layer was dried over anhy. Na₂SO₄, filtered and concentrated in vacuo to give a crude product which was then purified by prep-HPLC to give title compound (8 mg, 48%) as a white solid. MS: 331.1 (M+H⁺).

The following compounds listed in Table 3 were prepared in analogy to the procedure described for the preparation of example 194 using appropriate starting materials.

TABLE 3

| Ex | Compound Name | Compound Structure | Starting Materials | MS (M + H)⁺ |
|---|---|---|---|---|
| 195 | 6-Chloro-2-[5-(2,2,2-trifluoro-1-methyl-ethoxymethyl)-pyridin-3-yl]-3,4-dihydro-2H-isoquinolin-1-one | 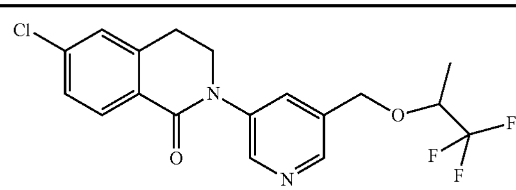 | 6-Chloro-2-(5-chloromethyl-pyridin-3-yl)-3,4-dihydro-2H-isoquinolin-1-one (example 140[A]) and 1,1,1-trifluoro-propan-2-ol | 385.1 |
| 196 | 6-Chloro-2-{5-[2-(1-methyl-pyrrolidin-2-yl)-ethoxymethyl]-pyridin-3-yl}-3,4-dihydro-2H-isoquinolin-1-one | 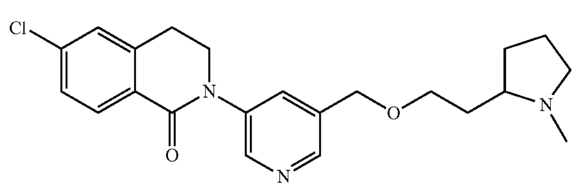 [SMILES: CN1CCCC1CCOCc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 2-(1-methyl-pyrrolidin-2-yl)-ethanol | 400.2 |
| 197 | 6-Chloro-2-(5-cyclopentyloxymethyl-pyridin-3-yl)-3,4-dihydro-2H-isoquinolin-1-one | 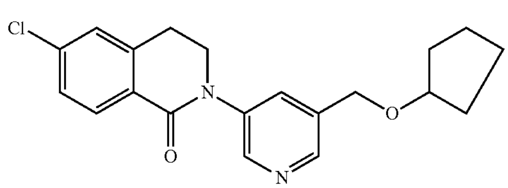 [SMILES: O=C1c2ccc(Cl)cc2CCN1c1cncc(COC2CCCC2)c1] | 6-Chloro-2-(5-chloromethyl-pyridin-3-yl)-3,4-dihydro-2H-isoquinolin-1-one (example 140[A]) and cyclopentanol | 357.2 |
| 198 | 6-Chloro-2-(5-cyclopropylmethoxymethyl-pyridin-3-yl)-3,4-dihydro-2H-isoquinolin-1-one | 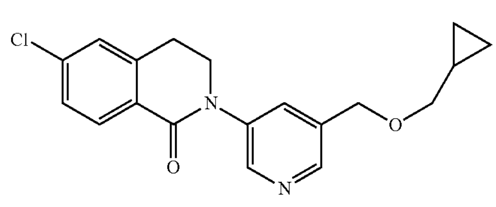 [SMILES: O=C1c2ccc(Cl)cc2CCN1c1cncc(COCC2CC2)c1] | 6-Chloro-2-(5-chloromethyl-pyridin-3-yl)-3,4-dihydro-2H-isoquinolin-1-one (example 140[A]) and cyclopropyl-methanol | 343.2 |

TABLE 3-continued

| Ex | Compound Name | Compound Structure | Starting Materials | MS (M + H)+ |
|---|---|---|---|---|
| 199 | 6-Chloro-2-[5-(2-fluoro-phenoxymethyl)-pyridin-3-yl]-3,4-dihydro-2H-isoquinolin-1-one | 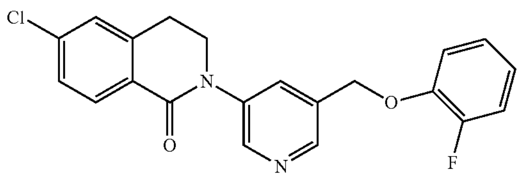 [SMILES: O=C1c2ccc(Cl)cc2CCN1c1cncc(COc2ccccc2F)c1] | 6-Chloro-2-(5-chloromethyl-pyridin-3-yl)-3,4-dihydro-2H-isoquinolin-1-one (example 140[A]) and 2-fluoro-phenol | 383.1 |
| 200 | 6-Chloro-2-[5-(1-methyl-cyclopropylmethoxymethyl)-pyridin-3-yl]-3,4-dihydro-2H-isoquinolin-1-one | 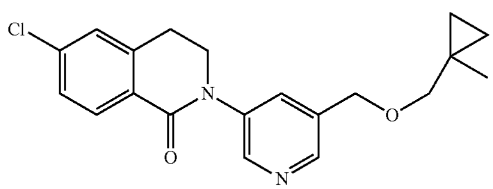 [SMILES: CC1(COCc2cncc(N3CCc4cc(Cl)ccc4C3=O)c2)CC1] | 6-Chloro-2-(5-chloromethyl-pyridin-3-yl)-3,4-dihydro-2H-isoquinolin-1-one (example 140[A]) and (1-methyl-cyclopropyl)-methanol | 357.2 |
| 201 | 6-Chloro-2-[5-(tetrahydro-furan-2-ylmethoxymethyl)-pyridin-3-yl]-3,4-dihydro-2H-isoquinolin-1-one | 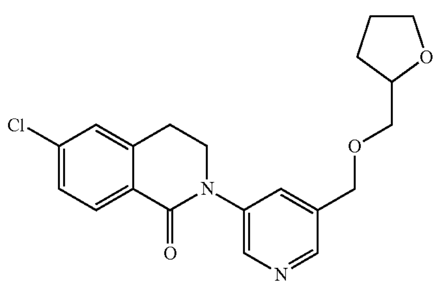 [SMILES: O=C1c2ccc(Cl)cc2CCN1c1cncc(COCC2CCCO2)c1] | 6-Chloro-2-(5-chloromethyl-pyridin-3-yl)-3,4-dihydro-2H-isoquinolin-1-one (example 140[A]) and (tetrahydro-furan-2-yl)-methanol | 373.1 |
| 202 | 6-Chloro-2-[5-(2,2,2-trifluoro-ethoxymethyl)-pyridin-3-yl]-3,4-dihydro-2H-isoquinolin-1-one | 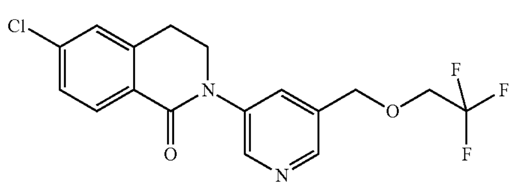 [SMILES: O=C1c2ccc(Cl)cc2CCN1c1cncc(COCC(F)(F)F)c1] | 6-Chloro-2-(5-chloromethyl-pyridin-3-yl)-3,4-dihydro-2H-isoquinolin-1-one (example 140[A]) and 2,2,2-trifluoro-ethanol | 371.1 |
| 203 | 6-Chloro-2-(5-cyclobutoxymethyl-pyridin-3-yl)-3,4-dihydro-2H-isoquinolin-1-one | 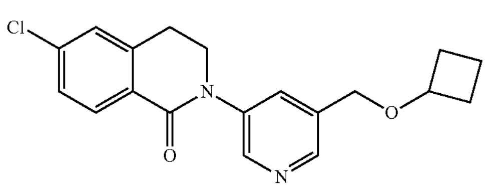 [SMILES: O=C1c2ccc(Cl)cc2CCN1c1cncc(COC2CCC2)c1] | 6-Chloro-2-(5-chloromethyl-pyridin-3-yl)-3,4-dihydro-2H-isoquinolin-1-one (example 140[A]) and cyclobutanol | 343.2 |

Example 204

6-Chloro-2-[5-(3,5-dimethyl-isoxazol-4-ylmethyl)-pyridin-3-yl]-3,4-dihydro-2H-isoquinolin-1-one

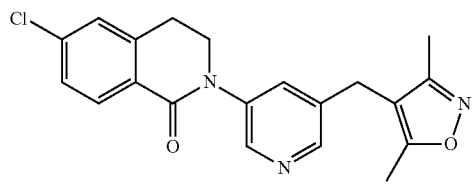 [SMILES: Cc1noc(C)c1Cc1cncc(N2CCc3cc(Cl)ccc3C2=O)c1]

6-Chloro-2-(5-chloromethyl-pyridin-3-yl)-3,4-dihydro-2H-isoquinolin-1-one (example 140 [A]) (75 mg, 0.25 mmol), Pd(PPh$_3$)$_2$Cl$_2$ (18 mg, 0.025 mmol), Na$_2$CO$_3$ (80 mg, 0.75 mmol) and 3,5-dimethylisoxazole-4-boronic acid (45 mg, 0.32 mmol) were dissolved in dioxane (4.0 mL). The resulting reaction mixture was heated at 120° C. for 3 hours before it was poured into H$_2$O (50 mL) and extracted with EtOAc (2×125 mL). The combined organic layers were washed with brine, dried over anhy. Na$_2$SO$_4$, filtered and concentrated in vacuo to give a crude product which was then purified by prep-HPLC to give title compound (10 mg, 10.9%) as a light yellowish solid. MS: 368.2 (M+H$^+$).

The following compounds listed in Table 4 were prepared in analogy to the procedure described for the preparation of example 204 using appropriate starting materials.

TABLE 4

| Ex | Compound Name | Compound Structure | Starting Materials | MS (M + H)$^+$ |
|---|---|---|---|---|
| 205 | 6-Chloro-2-[5-(4-methanesulfonyl-benzyl)-pyridin-3-yl]-3,4-dihydro-2H-isoquinolin-1-one | 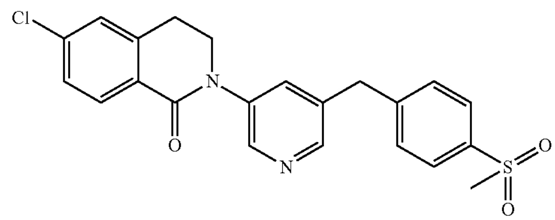 [SMILES: CS(=O)(=O)c1ccc(Cc2cncc(N3CCc4cc(Cl)ccc4C3=O)c2)cc1] | 6-Chloro-2-(5-chloromethyl-pyridin-3-yl)-3,4-dihydro-2H-isoquinolin-1-one (example 140[A]) and 4-(methylsulfonyl)phenyl-boronic acid | 427.2 |
| 206 | 6-Chloro-2-[5-(6-methyl-pyridin-3-ylmethyl)-pyridin-3-yl]-3,4-dihydro-2H-isoquinolin-1-one | 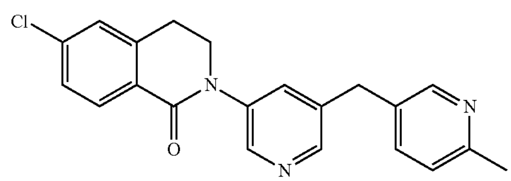 [SMILES: Cc1ccc(Cc2cncc(N3CCc4cc(Cl)ccc4C3=O)c2)cn1] | 6-Chloro-2-(5-chloromethyl-pyridin-3-yl)-3,4-dihydro-2H-isoquinolin-1-one (example 140[A]) and 2-methyl-5-pyridinylboronic acid | 364.1 |
| 207 | 6-Chloro-2-[5-(6-morpholin-4-yl-pyridin-3-ylmethyl)-pyridin-3-yl]-3,4-dihydro-2H-isoquinolin-1-one | 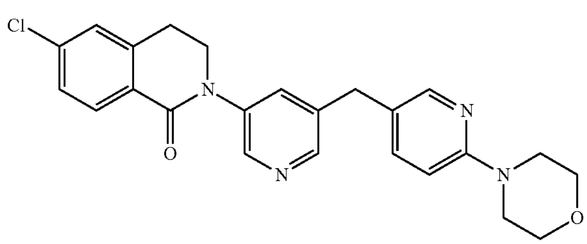 [SMILES: O=C1c2ccc(Cl)cc2CCN1c1cncc(Cc2ccc(N3CCOCC3)nc2)c1] | 6-Chloro-2-(5-chloromethyl-pyridin-3-yl)-3,4-dihydro-2H-isoquinolin-1-one (example 140[A]) and 2-(morpholin-4-yl)pyridine-5-boronic acid pinacol ester | 435.1 |
| 208 | 6-Chloro-2-[5-(2-methyl-2H-pyrazol-3-ylmethyl)-pyridin-3-yl]-3,4-dihydro-2H-isoquinolin-1-one | 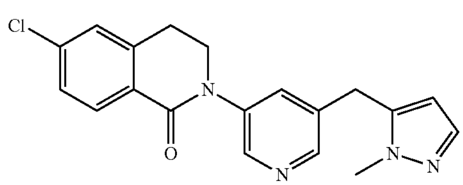 [SMILES: Cn1nccc1Cc1cncc(N2CCc3cc(Cl)ccc3C2=O)c1] | 6-Chloro-2-(5-chloromethyl-pyridin-3-yl)-3,4-dihydro-2H-isoquinolin-1-one (example 140[A]) and 1-methyl-1H-pyrazole-5-boronic acid pinacol ester | 353.1 |
| 209 | 6-Chloro-2-[5-(1-methyl-1H-pyrazol-4-ylmethyl)-pyridin-3-yl]-3,4-dihydro-2H-isoquinolin-1-one | 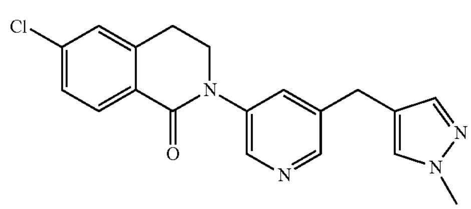 [SMILES: Cn1cc(Cc2cncc(N3CCc4cc(Cl)ccc4C3=O)c2)cn1] | 6-Chloro-2-(5-chloromethyl-pyridin-3-yl)-3,4-dihydro-2H-isoquinolin-1-one (example 140[A]) and 1-methylpyrazole-4-boronic acid pinacol ester | 353.1 |

TABLE 4-continued

| Ex | Compound Name | Compound Structure | Starting Materials | MS (M + H)+ |
|---|---|---|---|---|
| 210 | 6-Chloro-2-[5-(2,3-difluoro-benzyl)-pyridin-3-yl]-2H-isoquinolin-1-one | 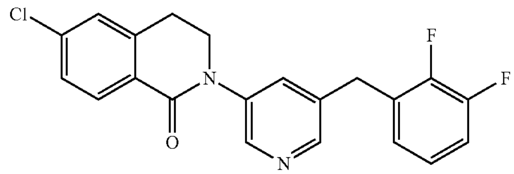 [SMILES: O=C1c2ccc(Cl)cc2CCN1c1cncc(Cc2cccc(F)c2F)c1] | 6-Chloro-2-(5-chloromethyl-pyridin-3-yl)-3,4-dihydro-2H-isoquinolin-1-one (example 140[A]) and 2,3-difluorophenylboronic acid | 385.1 |
| 211 | 6-Chloro-2-[5-(3,5-difluoro-benzyl)-pyridin-3-yl]-3,4-dihydro-2H-isoquinolin-1-one | 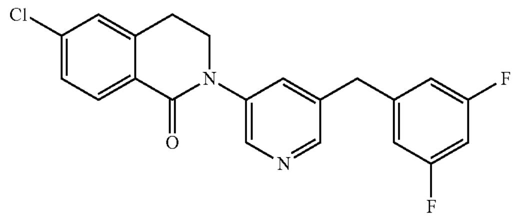 [SMILES: O=C1c2ccc(Cl)cc2CCN1c1cncc(Cc2cc(F)cc(F)c2)c1] | 6-Chloro-2-(5-chloromethyl-pyridin-3-yl)-3,4-dihydro-2H-isoquinolin-1-one (example 140[A]) and 3,5-difluorophenylboronic acid | 385.1 |
| 212 | 6-Chloro-2-[5-(2,5-difluoro-benzyl)-pyridin-3-yl]-3,4-dihydro-2H-isoquinolin-1-one | 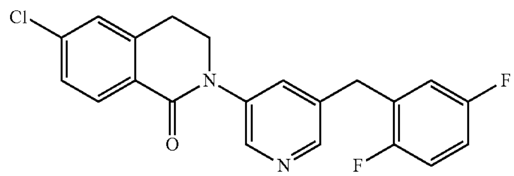 [SMILES: O=C1c2ccc(Cl)cc2CCN1c1cncc(Cc2cc(F)ccc2F)c1] | 6-Chloro-2-(5-chloromethyl-pyridin-3-yl)-3,4-dihydro-2H-isoquinolin-1-one (example 140[A]) and 2,5-difluorophenylboronic acid | 385.1 |
| 213 | 6-Chloro-2-[5-(2-trifluoromethyl-benzyl)-pyridin-3-yl]-3,4-dihydro-2H-isoquinolin-1-one | 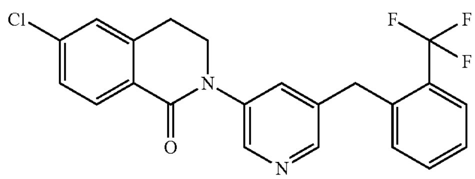 [SMILES: O=C1c2ccc(Cl)cc2CCN1c1cncc(Cc2ccccc2C(F)(F)F)c1] | 6-Chloro-2-(5-chloromethyl-pyridin-3-yl)-3,4-dihydro-2H-isoquinolin-1-one (example 140[A]) and 2-trifluoromethylphenylboronic acid | 417.1 |
| 214 | 6-Chloro-2-[5-(2,6-dichloro-benzyl)-pyridin-3-yl]-3,4-dihydro-2H-isoquinolin-1-one | 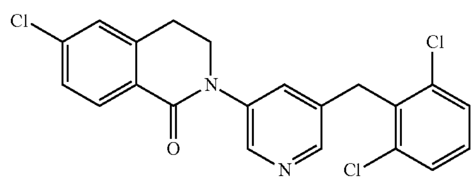 [SMILES: O=C1c2ccc(Cl)cc2CCN1c1cncc(Cc2c(Cl)cccc2Cl)c1] | 6-Chloro-2-(5-chloromethyl-pyridin-3-yl)-3,4-dihydro-2H-isoquinolin-1-one (example 140[A]) and 2,6-dichlorophenylboronic acid | 417.1 |
| 215 | 6-Chloro-2-[5-(2-chloro-6-fluoro-benzyl)-pyridin-3-yl]-3,4-dihydro-2H-isoquinolin-1-one | 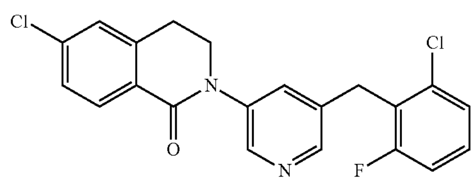 [SMILES: O=C1c2ccc(Cl)cc2CCN1c1cncc(Cc2c(F)cccc2Cl)c1] | 6-Chloro-2-(5-chloromethyl-pyridin-3-yl)-3,4-dihydro-2H-isoquinolin-1-one (example 140[A]) and 2,6-dichlorophenylboronic acid | 401.1 |
| 216 | 6-Chloro-2-[5-(3,4-dichloro-benzyl)-pyridin-3-yl]-3,4-dihydro-2H-isoquinolin-1-one | 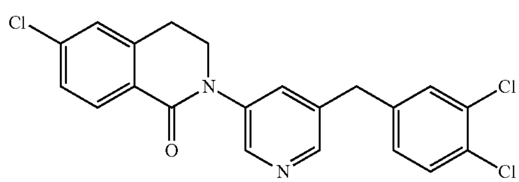 [SMILES: O=C1c2ccc(Cl)cc2CCN1c1cncc(Cc2ccc(Cl)c(Cl)c2)c1] | 6-Chloro-2-(5-chloromethyl-pyridin-3-yl)-3,4-dihydro-2H-isoquinolin-1-one (example 140[A]) and 3,4-dichlorophenylboronic acid | 417.1 |
| 217 | 6-Chloro-2-[5-(2,5-dichloro-benzyl)-pyridin-3-yl]-3,4-dihydro-2H-isoquinolin-1-one | 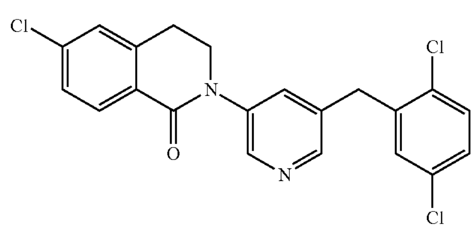 [SMILES: O=C1c2ccc(Cl)cc2CCN1c1cncc(Cc2cc(Cl)ccc2Cl)c1] | 6-Chloro-2-(5-chloromethyl-pyridin-3-yl)-3,4-dihydro-2H-isoquinolin-1-one (example 140[A]) and 2,5-dichlorophenylboronic acid | 417.1 |

Example 218

Ethanesulfonic acid [5-(6-chloro-1-oxo-3,4-dihydro-1H-isoquinolin-2-yl)-pyridin-3-yl]-amide

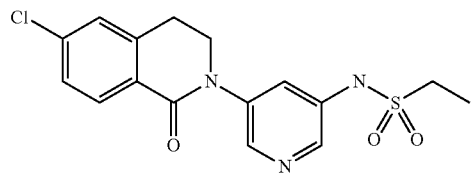 [SMILES: CCS(=O)(=O)Nc1cncc(N2CCc3cc(Cl)ccc3C2=O)c1]

CuI (1.9 mg, 0.01 mmol), L-proline (2.3 mg, 0.02 mmol) and Cs$_2$CO$_3$ (65 mg, 0.2 mmol) were added to a dioxane (3 mL) solution of 2-(5-bromo-pyridin-3-yl)-6-chloro-3,4-dihydro-2H-isoquinolin-1-one (example 7) (33.7 mg, 0.1 mmol) and ethanesulfonic acid amide (10.9 mg, 0.1 mmol). The resulting reaction mixture was subject to microwave reaction at 150° C. for 2.5 hours. The reaction mixture was filtered and concentrated in vacuo to give a crude product which was then purified by prep-HPLC to give title compound (7.3 mg, 20%) as a white solid. MS: 366.1 (M+H$^+$).

The following compounds listed in Table 5 were prepared in analogy to the procedure described for the preparation of example 218 using appropriate starting materials.

TABLE 5

| Ex | Compound Name | Compound Structure | Starting Materials | MS (M + H)$^+$ |
|---|---|---|---|---|
| 219 | N-[5-(6-Chloro-1-oxo-3,4-dihydro-1H-isoquinolin-2-yl)-pyridin-3-yl]-benzenesulfonamide | 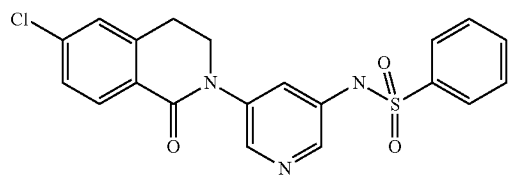 [SMILES: O=C1c2ccc(Cl)cc2CCN1c1cncc(NS(=O)(=O)c2ccccc2)c1] | 2-(5-Bromo-pyridin-3-yl)-6-chloro-3,4-dihydro-2H-isoquinolin-1-one (example 7) and benzenesulfonamide | 414.1 |
| 220 | N-[5-(6-Chloro-1-oxo-3,4-dihydro-1H-isoquinolin-2-yl)-pyridin-3-yl]-methanesulfonamide | 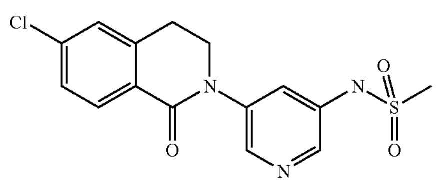 [SMILES: CS(=O)(=O)Nc1cncc(N2CCc3cc(Cl)ccc3C2=O)c1] | 2-(5-Bromo-pyridin-3-yl)-6-chloro-3,4-dihydro-2H-isoquinolin-1-one (example 7) and methanesulfonamide | 352.1 |
| 221 | Cyclopropanesulfonic acid [5-(6-chloro-1-oxo-3,4-dihydro-1H-isoquinolin-2-yl)-pyridin-3-yl]-amide | 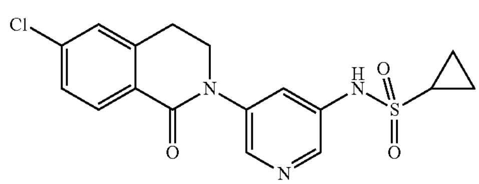 [SMILES: O=C1c2ccc(Cl)cc2CCN1c1cncc(NS(=O)(=O)C2CC2)c1] | 2-(5-Bromo-pyridin-3-yl)-6-chloro-3,4-dihydro-2H-isoquinolin-1-one (example 7) and cyclopropanesulfonic acid amide | 378.1 |
| 222 | 6-Chloro-2-[5-(4-fluoro-benzylamino)-pyridin-3-yl]-3,4-dihydro-2H-isoquinolin-1-one | 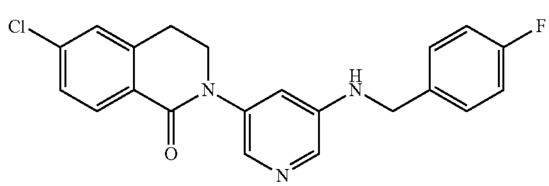 [SMILES: O=C1c2ccc(Cl)cc2CCN1c1cncc(NCc2ccc(F)cc2)c1] | 2-(5-Bromo-pyridin-3-yl)-6-chloro-3,4-dihydro-2H-isoquinolin-1-one (example 7) and 4-fluoro-benzylamine | 382.1 |
| 223 | 6-Chloro-2-[5-(2,2,2-trifluoro-ethylamino)-pyridin-3-yl]-3,4-dihydro-2H-isoquinolin-1-one | 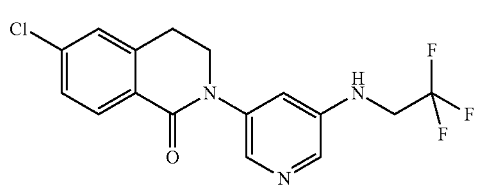 [SMILES: O=C1c2ccc(Cl)cc2CCN1c1cncc(NCC(F)(F)F)c1] | 2-(5-Bromo-pyridin-3-yl)-6-chloro-3,4-dihydro-2H-isoquinolin-1-one (example 7) and 2,2,2-trifluoro-ethylamine | 356.1 |
| 224 | 6-Chloro-2-(5-morpholin-4-yl-pyridin-3-yl)-3,4-dihydro-2H-isoquinolin-1-one | 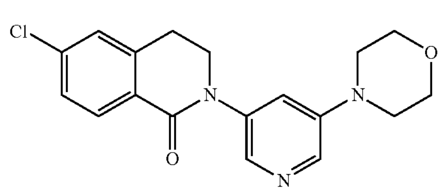 [SMILES: O=C1c2ccc(Cl)cc2CCN1c1cncc(N2CCOCC2)c1] | 2-(5-Bromo-pyridin-3-yl)-6-chloro-3,4-dihydro-2H-isoquinolin-1-one (example 7) and morpholine | 344.2 |

TABLE 5-continued

| Ex | Compound Name | Compound Structure | Starting Materials | MS (M + H)+ |
|---|---|---|---|---|
| 225 | N-[5-(6-Chloro-1-oxo-3,4-dihydro-1H-isoquinolin-2-yl)-pyridin-3-yl]-propionamide | 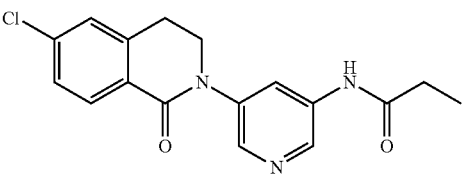 [SMILES: CCC(=O)Nc1cncc(N2CCc3cc(Cl)ccc3C2=O)c1] | 2-(5-Bromo-pyridin-3-yl)-6-chloro-3,4-dihydro-2H-isoquinolin-1-one (example 7) and propionamide | 330.1 |
| 226 | 6-Chloro-2-{5-[(2-methyl-2H-pyrazol-3-ylmethyl)-amino]-pyridin-3-yl}-3,4-dihydro-2H-isoquinolin-1-one | 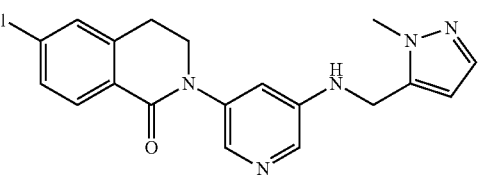 | 2-(5-Bromo-pyridin-3-yl)-6-chloro-3,4-dihydro-2H-isoquinolin-1-one (example 7) and 1-(1-methyl-1H-pyrazol-5-yl)methanamine | 368.1 |
| 227 | 2-[5-(6-Chloro-1-oxo-3,4-dihydro-1H-isoquinolin-2-yl)-pyridin-3-ylamino]-2-methyl-propionic acid | 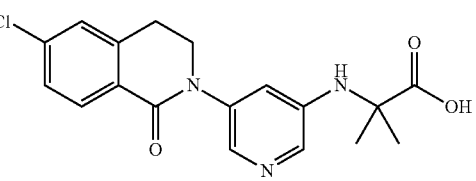 | 2-(5-Bromo-pyridin-3-yl)-6-chloro-3,4-dihydro-2H-isoquinolin-1-one (example 7) and 2-amino-2-methyl-propionic acid | 360.1 |
| 228 | 6-Chloro-2-{5-[(1-methyl-1H-imidazol-4-ylmethyl)-amino]-pyridin-3-yl}-3,4-dihydro-2H-isoquinolin-1-one | 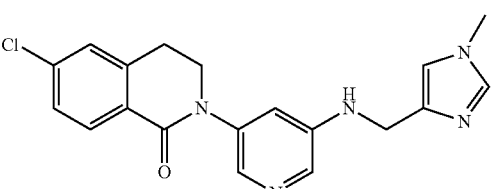 | 2-(5-Bromo-pyridin-3-yl)-6-chloro-3,4-dihydro-2H-isoquinolin-1-one (example 7) and 4-(aminomethyl)-1-methyl-1H-imidazole | 368.1 |

Example 229

6-Chloro-2-[5-(1H-pyrazol-4-yl)-pyridin-3-yl]-3,4-dihydro-2H-isoquinolin-1-one

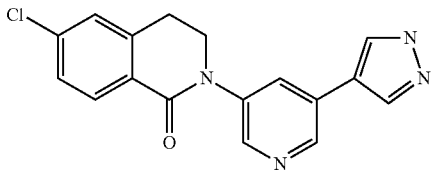 [SMILES: O=C1c2ccc(Cl)cc2CCN1c1cncc(-c2cn[nH]c2)c1]

2-(5-Bromo-pyridin-3-yl)-6-chloro-3,4-dihydro-2H-isoquinolin-1-one (example 7) (34 mg, 0.1 mmol), Pd(PPh₃)₄ (5.8 mg, 0.005 mmol), K₂CO₃ (27.6 mg, 0.2 mmol) and 1H-pyrazole-4-boronic acid pinacol ester (29.1 mg, 0.15 mmol) were dissolved in dioxane (1 mL). The resulting reaction mixture was subject to microwave reaction at 150° C. for 45 min before it was poured into H₂O (25 mL) and extracted with EtOAc (2×25 mL). The combined organic layers were washed with brine, dried over anhy. Na₂SO₄, filtered and concentrated in vacuo to give a crude product which was then purified by prep-HPLC to give title compound (9 mg, 28%) as a white solid. MS: 325.1 (M+H⁺).

The following compounds listed in Table 6 were prepared in analogy to the procedure described for the preparation of example 229 using appropriate starting materials.

TABLE 6

| Ex | Compound Name | Compound Structure | Starting Materials | MS (M + H)+ |
|---|---|---|---|---|
| 230 | 6-Chloro-2-[5-(3,5-dimethyl-isoxazol-4-yl)-pyridin-3-yl]-3,4-dihydro-2H-isoquinolin-1-one | 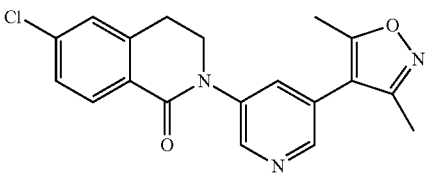 [SMILES: Cc1noc(C)c1-c1cncc(N2CCc3cc(Cl)ccc3C2=O)c1] | 2-(5-Bromo-pyridin-3-yl)-6-chloro-3,4-dihydro-2H-isoquinolin-1-one (example 7) and 3,5-dimethylisoxazole-4-boronic acid | 354.1 |

TABLE 6-continued

| Ex | Compound Name | Compound Structure | Starting Materials | MS (M + H)+ |
|---|---|---|---|---|
| 231 | 6-Chloro-2-[5-(3-fluoro-phenyl)-pyridin-3-yl]-3,4-dihydro-2H-isoquinolin-1-one | 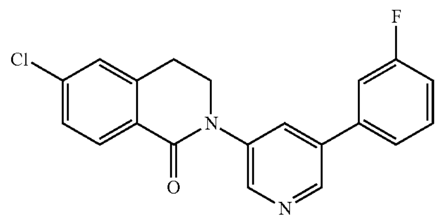 [SMILES: O=C1c2ccc(Cl)cc2CCN1c1cncc(-c2cccc(F)c2)c1] | 2-(5-Bromo-pyridin-3-yl)-6-chloro-3,4-dihydro-2H-isoquinolin-1-one (example 7) and 3-fluorophenylboronic acid | 353.1 |
| 232 | 6-Chloro-2-[5-(3,4-difluoro-phenyl)-pyridin-3-yl]-3,4-dihydro-2H-isoquinolin-1-one | 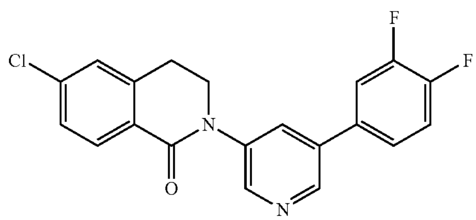 [SMILES: O=C1c2ccc(Cl)cc2CCN1c1cncc(-c2ccc(F)c(F)c2)c1] | 2-(5-Bromo-pyridin-3-yl)-6-chloro-3,4-dihydro-2H-isoquinolin-1-one (example 7) and 3,4-difluorophenylboronic acid | 371.1 |
| 233 | 6-Chloro-2-[5-(3,5-difluoro-phenyl)-pyridin-3-yl]-3,4-dihydro-2H-isoquinolin-1-one | 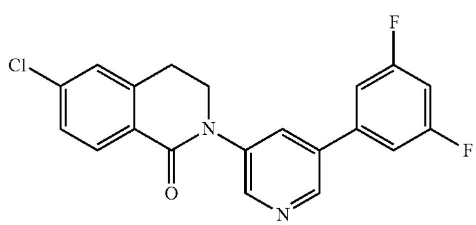 [SMILES: O=C1c2ccc(Cl)cc2CCN1c1cncc(-c2cc(F)cc(F)c2)c1] | 2-(5-Bromo-pyridin-3-yl)-6-chloro-3,4-dihydro-2H-isoquinolin-1-one (example 7) and 3,5-difluorophenylboronic acid | 371.1 |
| 234 | 6-Chloro-2-[5-(3-chloro-phenyl)-pyridin-3-yl]-3,4-dihydro-2H-isoquinolin-1-one | 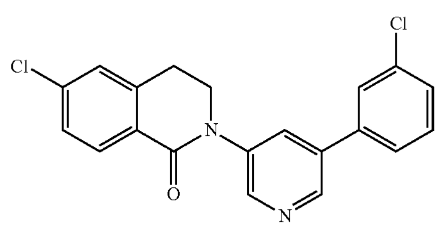 [SMILES: O=C1c2ccc(Cl)cc2CCN1c1cncc(-c2cccc(Cl)c2)c1] | 2-(5-Bromo-pyridin-3-yl)-6-chloro-3,4-dihydro-2H-isoquinolin-1-one (example 7) and 3-chlorophenylboronic acid | 369.1 |
| 235 | 6-Chloro-2-[5-(2,5-difluoro-phenyl)-pyridin-3-yl]-3,4-dihydro-2H-isoquinolin-1-one | 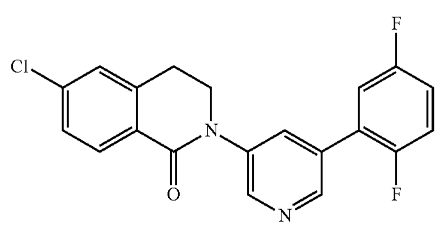 [SMILES: O=C1c2ccc(Cl)cc2CCN1c1cncc(-c2cc(F)ccc2F)c1] | 2-(5-Bromo-pyridin-3-yl)-6-chloro-3,4-dihydro-2H-isoquinolin-1-one (example 7) and 2,5-difluorophenylboronic acid | 371.1 |
| 236 | 6-Chloro-2-[5-(3-trifluoromethyl-phenyl)-pyridin-3-yl]-3,4-dihydro-2H-isoquinolin-1-one | 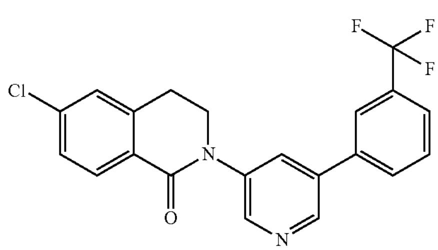 [SMILES: O=C1c2ccc(Cl)cc2CCN1c1cncc(-c2cccc(C(F)(F)F)c2)c1] | 2-(5-Bromo-pyridin-3-yl)-6-chloro-3,4-dihydro-2H-isoquinolin-1-one (example 7) and 3-trifluoromethylphenylboronic acid | 403.2 |

TABLE 6-continued

| Ex | Compound Name | Compound Structure | Starting Materials | MS (M + H)+ |
|---|---|---|---|---|
| 237 | 6-Chloro-2-[5-(3-trifluoromethoxy-phenyl)-pyridin-3-yl]-3,4-dihydro-2H-isoquinolin-1-one | 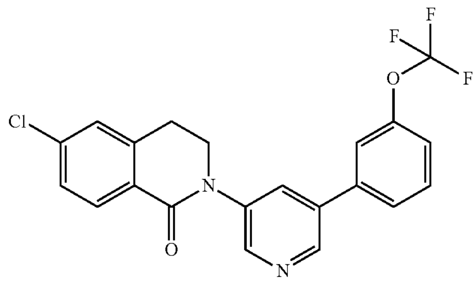 [SMILES: O=C1c2ccc(Cl)cc2CCN1c1cncc(-c2cccc(OC(F)(F)F)c2)c1] | 2-(5-Bromo-pyridin-3-yl)-6-chloro-3,4-dihydro-2H-isoquinolin-1-one (example 7) and 3-trifluoromethoxyphenylboronic acid | 419.2 |
| 238 | 6-Chloro-2-[5-(2-methyl-2H-pyrazol-3-yl)-pyridin-3-yl]-3,4-dihydro-2H-isoquinolin-1-one | 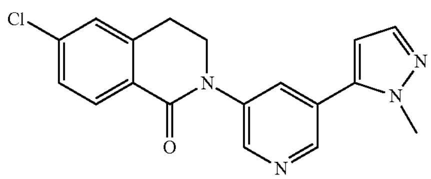 | 2-(5-Bromo-pyridin-3-yl)-6-chloro-3,4-dihydro-2H-isoquinolin-1-one (example 7) and 1-methyl-1H-pyrazole-5-boronic acid pinacol ester | 339.2 |
| 239 | 6-Chloro-2-[5-(1-methyl-1H-pyrazol-4-yl)-pyridin-3-yl]-3,4-dihydro-2H-isoquinolin-1-one | 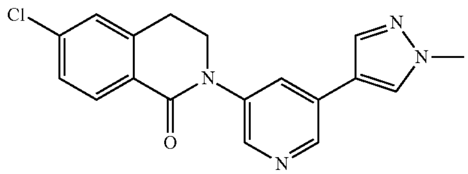 | 2-(5-Bromo-pyridin-3-yl)-6-chloro-3,4-dihydro-2H-isoquinolin-1-one (example 7) and (1-methyl-1H-pyrazol-4-yl)boronic acid | 339.1 |
| 240 | 6-Chloro-2-[5-(4-chloro-3-fluoro-phenyl)-pyridin-3-yl]-3,4-dihydro-2H-isoquinolin-1-one | 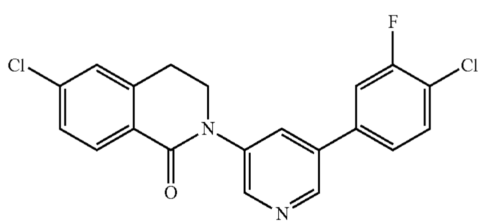 [SMILES: O=C1c2ccc(Cl)cc2CCN1c1cncc(-c2ccc(Cl)c(F)c2)c1] | 2-(5-Bromo-pyridin-3-yl)-6-chloro-3,4-dihydro-2H-isoquinolin-1-one (example 7) and 4-chloro-3-fluorophenylboronic acid | 387.1 |
| 241 | 6-Chloro-2-[5-(3,4-dichloro-phenyl)-pyridin-3-yl]-3,4-dihydro-2H-isoquinolin-1-one | 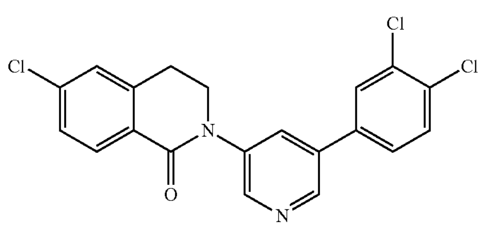 [SMILES: O=C1c2ccc(Cl)cc2CCN1c1cncc(-c2ccc(Cl)c(Cl)c2)c1] | 2-(5-Bromo-pyridin-3-yl)-6-chloro-3,4-dihydro-2H-isoquinolin-1-one (example 7) and 3,4-dichlorophenylboronic acid | 403.1 |
| 242 | 6-Chloro-2-[5-(2-trifluoromethyl-phenyl)-pyridin-3-yl]-3,4-dihydro-2H-isoquinolin-1-one | 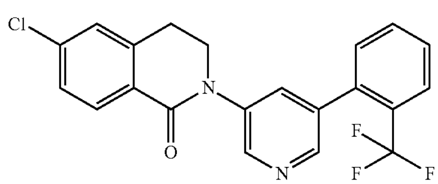 [SMILES: O=C1c2ccc(Cl)cc2CCN1c1cncc(-c2ccccc2C(F)(F)F)c1] | 2-(5-Bromo-pyridin-3-yl)-6-chloro-3,4-dihydro-2H-isoquinolin-1-one (example 7) and 2-trifluoromethylphenylboronic acid | 403.1 |
| 243 | 6-Chloro-2-(5-isoxazol-4-yl-pyridin-3-yl)-3,4-dihydro-2H-isoquinolin-1-one | 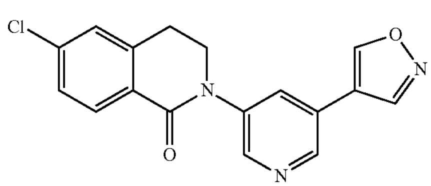 [SMILES: O=C1c2ccc(Cl)cc2CCN1c1cncc(-c2cnoc2)c1] | 2-(5-Bromo-pyridin-3-yl)-6-chloro-3,4-dihydro-2H-isoquinolin-1-one (example 7) and 4-isoxazoleboronic acid pinacol ester | 326.1 |

Example 244

6-Chloro-2-[5-(1-methyl-1H-imidazol-2-yl)-pyridin-3-yl]-3,4-dihydro-2H-isoquinolin-1-one

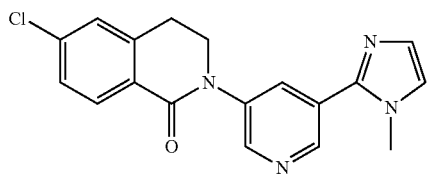 [SMILES: Cn1ccnc1-c1cncc(N2CCc3cc(Cl)ccc3C2=O)c1]

To a stirred suspension of zinc dust (130 mg, 1.98 mmol) in THF (2.0 mL) was added 1,2-dibromoethane (0.02 mL). The mixture was heated with a hair dryer until the evolution of ethylene gas was complete. TMS-Cl (0.02 mL) and 2-bromo-1-methyl-1H-imidazole (0.07 mL, 0.66 mmol) were then added to the above suspension and it was allowed to stir at RT for 30 minutes before the addition of 2-(5-bromo-pyridin-3-yl)-6-chloro-3,4-dihydro-2H-isoquinolin-1-one (74 mg, 0.22 mmol, example 7) and Pd(PPh$_3$)$_4$ (14 mg, 0.011 mmol). The resulting reaction mixture was then heated to 90° C. for 6 hours before it was poured into H$_2$O (50 mL) and extracted with EtOAc (2×80 mL). The combined organic layers were washed with brine, dried over anhy. Na$_2$SO$_4$, filtered and concentrated in vacuo to give a crude product which was then purified by prep-HPLC to give title compound (12.0 mg, 16.2%) as a white foam. MS: 339.1 (M+H$^+$).

Example 245

6-Chloro-2-[5-(2,4-dimethyl-2H-pyrazol-3-yl)-pyridin-3-yl]-3,4-dihydro-2H-isoquinolin 1-one

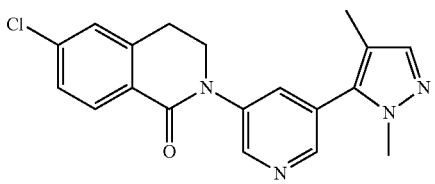 [SMILES: Cc1cnn(C)c1-c1cncc(N2CCc3cc(Cl)ccc3C2=O)c1]

To a stirred solution of 2-(5-bromo-pyridin-3-yl)-6-chloro-3,4-dihydro-2H-isoquinolin-1-one (example 7) (80 mg, 0.25 mmol) and 1,4-dimethyl-1H-pyrazole (23 mg, 0.25 mmol) in NMP (2.0 mL) were added Pd(OAc)$_2$ (2.0 mg, 0.008 mmol), 2-dicyclohexylphosphino-2'-(N,N-dimethylamino)biphenyl (DavePhos) (6.3 mg, 0.016 mmol), Bu$_4$NOAc (153 mg, 0.5 mmol) and isobutyric acid (0.085 mL, 0.08 mmol). The resulting reaction mixture was heated to 100° C. for 6 hours before it was poured into H$_2$O (25 mL) and extracted with EtOAc (2×90 mL). The combined organic layers were washed with brine, dried over anhy. Na$_2$SO$_4$, filtered and concentrated in vacuo to give a crude product which was then purified by prep-HPLC to give title compound (8.7 mg, 9.9%) as a yellow solid. MS: 353.1 (M+H$^+$).

Example 246

5-[5-(6-Chloro-1-oxo-3,4-dihydro-1H-isoquinolin-2-yl)-pyridin-3-yl]-1-methyl-1H-pyrazole-4-carbonitrile

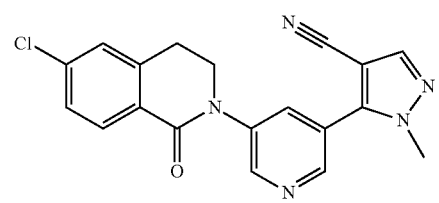 [SMILES: Cn1ncc(C#N)c1-c1cncc(N2CCc3cc(Cl)ccc3C2=O)c1]

The title compound was prepared in analogy to the procedure described for the preparation of example 245 using 1-methyl-1H-pyrazole-4-carbonitrile as starting material.

Example 247

N-[5-(6-Chloro-1-oxo-3,4-dihydro-1H-isoquinolin-2-yl)-pyridin-3-yl]-isobutyramide

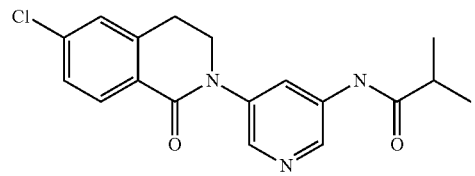 [SMILES: CC(C)C(=O)Nc1cncc(N2CCc3cc(Cl)ccc3C2=O)c1]

To a solution of 2-(5-amino-pyridin-3-yl)-6-chloro-3,4-dihydro-2H-isoquinolin-1-one (27.3 mg, 0.1 mmol, example 15) in dry DMF (2 mL) was added at 0° C. NaH (3.0 mg, 0.12 mmol). The reaction mixture was allowed to stir at room temperature for 5 min before isobutyryl chloride (12.7 mg, 0.12 mmol) was added into the reaction mixture. The reaction mixture was stirred for additional 1 hour and then poured into ice-water and extracted with EtOAc (2×5 mL). The organic layer was dried over anhy. Na$_2$SO$_4$, filtered and concentrated in vacuo to give a crude product which was then purified by prep-HPLC to give title compound (8.1 mg, 24%) as a white solid. MS: 344.1 (M+H$^+$).

Example 248

Cyclopropanecarboxylic acid [5-(6-chloro-1-oxo-3,4-dihydro-1H-isoquinolin-2-yl)-pyridin-3-yl]-amide

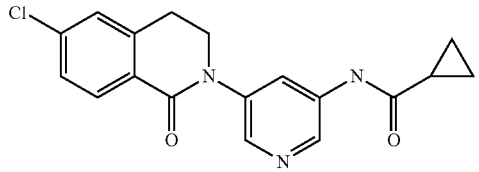 [SMILES: O=C(Nc1cncc(N2CCc3cc(Cl)ccc3C2=O)c1)C1CC1]

In analogy to the procedure described for the preparation of example 247, the title compound was synthesized using cyclopropanecarboxylic acid chloride as corresponding starting material. MS: 342.1 (M+H$^+$).

Example 249

N-[5-(6-Chloro-1-oxo-3,4-dihydro-1H-isoquinolin-2-yl)-pyridin-3-yl]-4-fluoro-benzamide

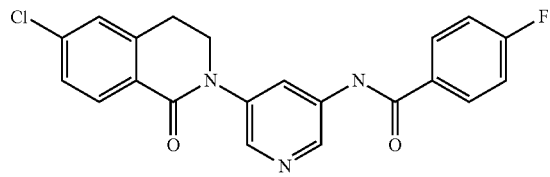 [SMILES: O=C(Nc1cncc(N2CCc3cc(Cl)ccc3C2=O)c1)c1ccc(F)cc1]

In analogy to the procedure described for the preparation of example 247, the title compound was synthesized using 4-fluoro-benzoyl chloride as corresponding starting material. MS: 396.1 (M+H$^+$).

Example 250

1-[5-(6-Chloro-1-oxo-3,4-dihydro-1H-isoquinolin-2-yl)-pyridin-3-yl]-3-cyclohexyl-urea

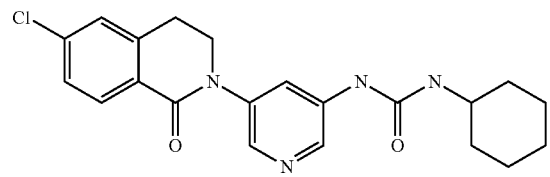 [SMILES: O=C(Nc1cncc(N2CCc3cc(Cl)ccc3C2=O)c1)NC1CCCCC1]

2-(5-Amino-pyridin-3-yl)-6-chloro-3,4-dihydro-2H-isoquinolin-1-one (27.3 mg, 0.1 mmol, example 17) was added to a solution of isocyanato-cyclohexane (12.5 mg, 0.1 mmol) in DCM (2 mL). The reaction mixture was stirred at RT for 2 hours. After evaporation of solvent under reduced pressure, a crude product was obtained which was purified by prep-HPLC to give title compound as a white solid (8.0 mg, 20%). MS: 399.2 (M+H$^+$).

Example 251

1-[5-(6-Chloro-1-oxo-3,4-dihydro-1H-isoquinolin-2-yl)-pyridin-3-yl]-3-(3-trifluoromethyl-phenyl)-urea

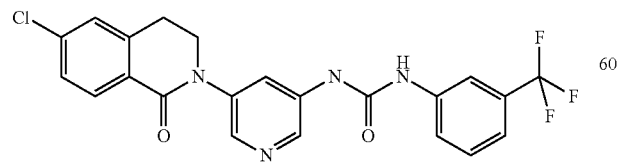

In analogy to the procedure described for the preparation of example 250, the title compound was synthesized using 1-isocyanato-3-trifluoromethyl-benzene as corresponding starting material. MS: 461.3 (M+H$^+$).

Example 252

6-Chloro-2-(5-hydroxy-pyridin-3-yl)-3,4-dihydro-2H-isoquinolin-1-one

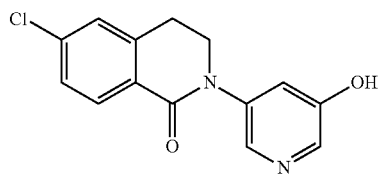 [SMILES: O=C1c2ccc(Cl)cc2CCN1c1cncc(O)c1]

6-Chloro-2-(5-methoxy-pyridin-3-yl)-3,4-dihydro-2H-isoquinolin-1-one (1.44 g, 5 mmol, example 10) was dissolved in aq. HBr (48%, 20 mL). The reaction mixture was heated to reflux temperature and stirred overnight. After cooling to room temperature, it was carefully neutralized with satd. aq. NaHCO$_3$ solution and extracted with EtOAc (2×25 mL). The organic layer was dried over anhy. Na$_2$SO$_4$, filtered and concentrated in vacuo to give a crude product (1.02 g, 74%) as brown oil. MS: 275.1 (M+H$^+$).

Example 253

2-[5-(6-Chloro-1-oxo-3,4-dihydro-1H-isoquinolin-2-yl)-pyridin-3-yloxy]-acetamide

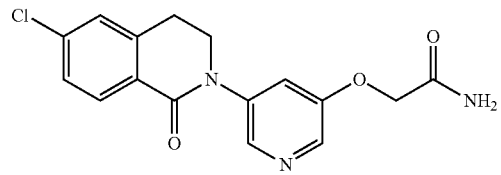 [SMILES: NC(=O)COc1cncc(N2CCc3cc(Cl)ccc3C2=O)c1]

[A] [5-(6-Chloro-1-oxo-3,4-dihydro-1H-isoquinolin-2-yl)-pyridin-3-yloxy]-acetic acid tert-butyl ester

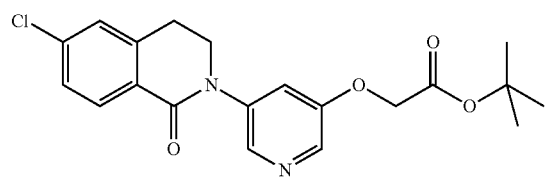 [SMILES: CC(C)(C)OC(=O)COc1cncc(N2CCc3cc(Cl)ccc3C2=O)c1]

NaH (38 mg, 1.5 mmol) was added to a solution of 6-chloro-2-(5-hydroxy-pyridin-3-yl)-3,4-dihydro-2H-isoquinolin-1-one (288 mg, 1.0 mmol, example 252) in dry DMF (5 mL) at 0° C. After stirred at RT for 10 minutes, bromoacetic acid tert-butyl ester (234 mg, 1.2 mmol) was added and the reaction mixture was stirred at RT for 1 hour before it was poured into ice-water and extracted with EtOAc (2×10 mL).

The combined organic layers were dried over anhy. Na$_2$SO$_4$, filtered and concentrated in vacuo to give a crude product (320 mg, 82%) as a solid MS: 389.8 (M+H$^+$).

[B] [5-(6-Chloro-1-oxo-3,4-dihydro-1H-isoquinolin-2-yl)-pyridin-3-yloxy]-acetic acid

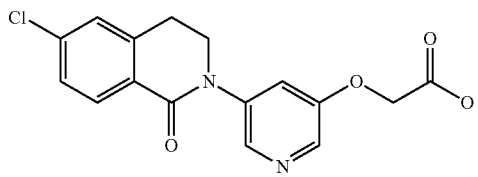 [SMILES: O=C(O)COc1cncc(N2CCc3cc(Cl)ccc3C2=O)c1]

Trifluoroacetic acid (3 mL) was added to a solution of 5-(6-chloro-1-oxo-3,4-dihydro-1H-isoquinolin-2-yl)-pyridin-3-yloxy]-acetic acid tert-butyl ester (388 mg, 1 mmol) in DCM (5 mL) and the reaction mixture was stirred at RT for 2 hours before it was poured into water and extracted with EtOAc (2×10 mL). The organic layers were dried over anhy. Na$_2$SO$_4$, filtered and concentrated in vacuo to give a crude product (320 mg, 96%) as a solid MS: 333.1 (M+H$^+$).

[C] 2-[5-(6-Chloro-1-oxo-3,4-dihydro-1H-isoquinolin-2-yl)-pyridin-3-yloxy]-acetamide

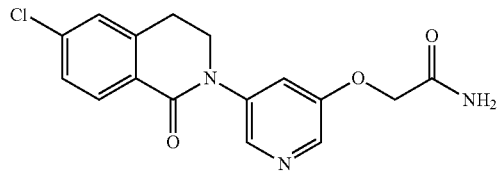 [SMILES: NC(=O)COc1cncc(N2CCc3cc(Cl)ccc3C2=O)c1]

HATU (38 mg, 0.1 mmol), Et$_3$N (10.1 mg, 0.1 mmol) and ammonia (1.6 M in 1,4-dioxane, 125 µL, 0.2 mmol) were added to a solution of [5-(6-chloro-1-oxo-3,4-dihydro-1H-isoquinolin-2-yl)-pyridin-3-yloxy]-acetic acid (33.2 mg, 0.1 mmol) in DMF (2 mL). The reaction mixture was stirred at RT overnight before it was poured into water and extracted with EtOAc (2×5 mL). The organic layers were dried over anhy. Na$_2$SO$_4$, filtered and concentrated in vacuo to give a crude product which was purified by prep-HPLC to give title compound (5.4 mg, 16%) as a white solid. MS: 332.1 (M+H$^+$).

Example 254

2-[5-(6-Chloro-1-oxo-3,4-dihydro-1H-isoquinolin-2-yl)-pyridin-3-yloxy]-N-methyl-acetamide

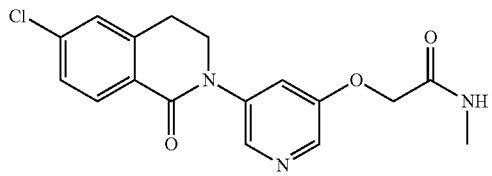 [SMILES: CNC(=O)COc1cncc(N2CCc3cc(Cl)ccc3C2=O)c1]

In analogy to the procedure described for the preparation of example 253 [C], the title compound was synthesized using methylamine as corresponding starting material. MS: 346.2 (M+H$^+$).

Example 255

[5-(6-Chloro-1-oxo-3,4-dihydro-1H-isoquinolin-2-yl)-pyridin-3-yloxy]-acetic acid methyl ester

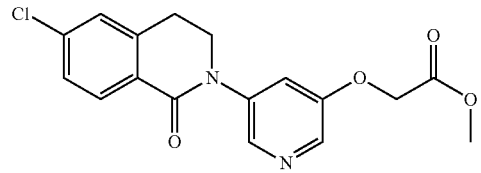 [SMILES: COC(=O)COc1cncc(N2CCc3cc(Cl)ccc3C2=O)c1]

In analogy to the procedure described for the preparation of example 253 [A], the title compound was synthesized using bromo-acetic acid methyl ester as corresponding starting material. MS: 347.1 (M+H$^+$).

Example 256

2-[5-(6-Chloro-1-oxo-3,4-dihydro-1H-isoquinolin-2-yl)-pyridin-3-yloxy]-N,N-dimethyl-acetamide

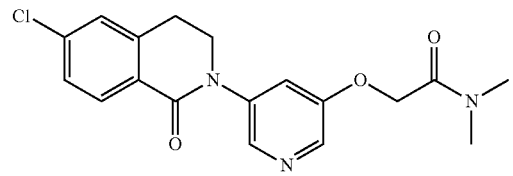 [SMILES: CN(C)C(=O)COc1cncc(N2CCc3cc(Cl)ccc3C2=O)c1]

In analogy to the procedure described for the preparation of example 253 [C], the title compound was synthesized using dimethylamine as corresponding starting material. MS: 360.1 (M+H$^+$).

Example 257

6-Chloro-2-(5-phenylaminomethyl-pyridin-3-yl)-3,4-dihydro-2H-isoquinolin-1-one

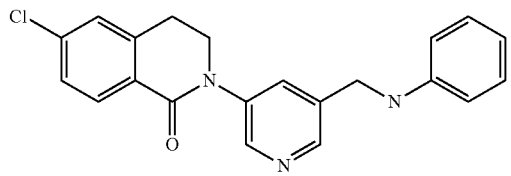 [SMILES: O=C1c2ccc(Cl)cc2CCN1c1cncc(CNc2ccccc2)c1]

NaBH(OAc)$_3$ (84 mg, 0.4 mmol) was added to a solution of 5-(6-chloro-1-oxo-3,4-dihydro-1H-isoquinolin-2-yl)-pyridine-3-carbaldehyde (28.6 mg, 0.1 mmol, example 9) and aniline (9.3 mg 0.1 mmol) in MeOH (3 mL) and the resulting reaction mixture was stirred at RT overnight before it was poured into ice-water and extracted with EtOAc (2×10 mL).

The organic layers were dried over anhy. Na$_2$SO$_4$, filtered and concentrated in vacuo to give a crude product which was purified by prep-HPLC to give title compound (7.2 mg, 20%) as a white solid. MS: 364.2 (M+H$^+$).

The following compounds listed in Table 7 were prepared in analogy to the procedure described for the preparation of example 257 using appropriate starting materials.

TABLE 7

| Ex | Compound Name | Compound Structure | Starting Materials | MS (M + H)$^+$ |
|---|---|---|---|---|
| 258 | 6-Chloro-2-{5-[(4-fluoro-phenylamino)-methyl]-pyridin-3-yl}-3,4-dihydro-2H-isoquinolin-1-one | 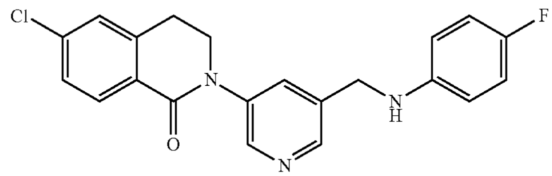 [SMILES: O=C1c2ccc(Cl)cc2CCN1c1cncc(CNc2ccc(F)cc2)c1] | 5-(6-Chloro-1-oxo-3,4-dihydro-1H-isoquinolin-2-yl)-pyridine-3-carbaldehyde (example 9) and 4-fluoro-phenylamine | 382.2 |
| 259 | 6-Chloro-2-{5-[(3-fluoro-phenylamino)-methyl]-pyridin-3-yl}-3,4-dihydro-2H-isoquinolin-1-one | 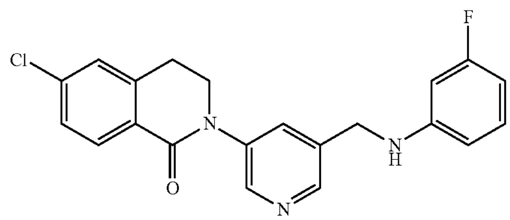 [SMILES: O=C1c2ccc(Cl)cc2CCN1c1cncc(CNc2cccc(F)c2)c1] | 5-(6-Chloro-1-oxo-3,4-dihydro-1H-isoquinolin-2-yl)-pyridine-3-carbaldehyde (example 9) and 3-fluoro-phenylamine | 382.2 |
| 260 | 6-Chloro-2-{5-[(4-chloro-phenylamino)-methyl]-pyridin-3-yl}-3,4-dihydro-2H-isoquinolin-1-one | 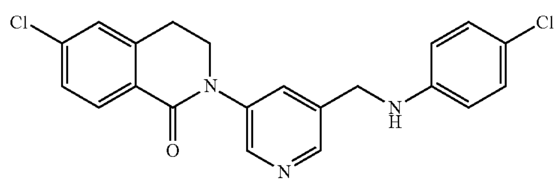 [SMILES: O=C1c2ccc(Cl)cc2CCN1c1cncc(CNc2ccc(Cl)cc2)c1] | 5-(6-Chloro-1-oxo-3,4-dihydro-1H-isoquinolin-2-yl)-pyridine-3-carbaldehyde (example 9) and 4-chloro-phenylamine | 398.2 |
| 261 | 6-Chloro-2-{5-[(3-chloro-phenylamino)-methyl]-pyridin-3-yl}-3,4-dihydro-2H-isoquinolin-1-one | 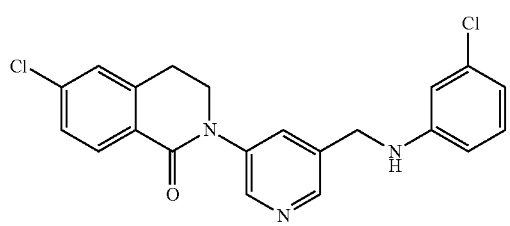 [SMILES: O=C1c2ccc(Cl)cc2CCN1c1cncc(CNc2cccc(Cl)c2)c1] | 5-(6-Chloro-1-oxo-3,4-dihydro-1H-isoquinolin-2-yl)-pyridine-3-carbaldehyde (example 9) and 3-chloro-phenylamine | 398.2 |
| 262 | 6-Chloro-2-{5-[(1H-pyrazol-3-ylamino)-methyl]-pyridin-3-yl}-3,4-dihydro-2H-isoquinolin-1-one | 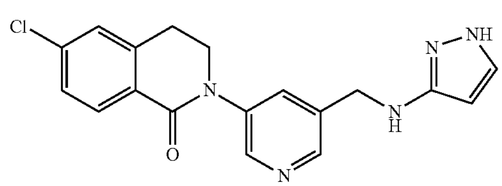 [SMILES: O=C1c2ccc(Cl)cc2CCN1c1cncc(CNc2cc[nH]n2)c1] | 5-(6-Chloro-1-oxo-3,4-dihydro-1H-isoquinolin-2-yl)-pyridine-3-carbaldehyde (example 9) and 1H-pyrazol-3-ylamine | 354.2 |

Example 263

6-Chloro-2-[5-(2-morpholin-4-yl-2-oxo-ethyl)-pyridin-3-yl]-3,4-dihydro-2H-isoquinolin-1-one

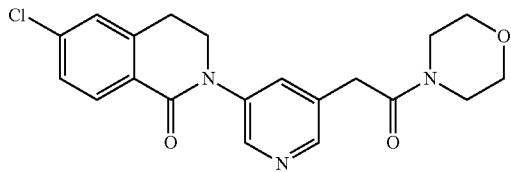 [SMILES: O=C(Cc1cncc(N2CCc3cc(Cl)ccc3C2=O)c1)N1CCOCC1]

[A] (5-Bromo-pyridin-3-yl)-acetic acid methyl ester

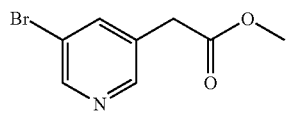

To a solution of (5-bromo-pyridin-3-yl)-acetic acid (4.2 g, 20 mmol) in methanol (50 mL) was added thionyl chloride (4.4 mL, 60 mmol) slowly at 0° C. After the addition, the reaction mixture was warmed up and heated to reflux temperature for 2 hours. After cooling back to room temperature, the reaction mixture was concentrated in vacuo and the residue was re-dissolved in EtOAc (250 mL) and washed with aq. NaHCO$_3$ solution and brine. The organic layer was dried over Na$_2$SO$_4$, filtered and concentrated in vacuo to give a crude product (4.6 g, quant.) as light yellow solid. MS: 230.1 & 232.0 (M+H$^+$).

[B] [5-(6-Chloro-1-oxo-3,4-dihydro-1H-isoquinolin-2-yl)-pyridin-3-yl]-acetic acid

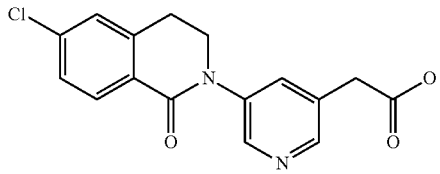 [SMILES: O=C(O)Cc1cncc(N2CCc3cc(Cl)ccc3C2=O)c1]

(5-Bromo-pyridin-3-yl)-acetic acid methyl ester (230 mg, 1.0 mmol), 6-chloro-3,4-dihydro-2H-isoquinolin-1-one (intermediate A-2) (182 mg, 1.0 mmol), CuI (40 mg, 0.21 mmol), Cs$_2$CO$_3$ (650 mg, 2.0 mmol) and (+)-(1S,1S)-1,2-diaminocyclohexane (0.1 mL, 0.8 mmol) were dissolved in dioxane (4.0 ml) and the resulting reaction mixture was heated at 150° C. for 2 hours before it was poured into H$_2$O (20 mL) and extracted with EtOAc (2×100 mL). The combined organic layer was washed with brine, dried over anhy. Na$_2$SO$_4$, filtered and concentrated in vacuo to give a crude product (230 mg, 72.5%) as light brown oil. MS: 317.1 (M+H$^+$).

[C] 6-Chloro-2-[5-(2-morpholin-4-yl-2-oxo-ethyl)-pyridin-3-yl]-3,4-dihydro-2H-isoquinolin-1-one

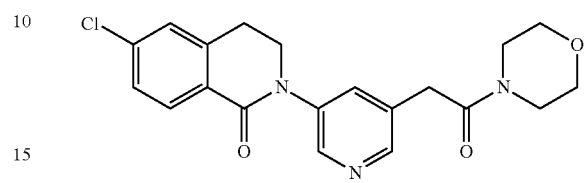

[5-(6-Chloro-1-oxo-3,4-dihydro-1H-isoquinolin-2-yl)-pyridin-3-yl]-acetic acid (50 mg, 0.16 mmol), HATU (122 mg, 0.32 mmol), Et$_3$N (64 mg, 0.64 mmol) and morpholine (56 mg, 0.64 mmol) were dissolved in DCM (4.0 mL) and the resulting reaction mixture was stirred at room temperature overnight. After evaporating off the DCM, the residue was re-dissolved in EtOAc and was washed with brine. The organic layer was dried over anhy. Na$_2$SO$_4$, filtered and concentrated in vacuo to give a crude product which was then purified by prep-HPLC to give the title compound (8.5 mg, 13.9%) as light yellow oil. MS: 386.1 (M+H$^+$).

Example 264

2-[5-(6-Chloro-1-oxo-3,4-dihydro-4H-isoquinolin-2-yl)-pyridin-3-yl]-N-(2-hydroxy-ethyl)-acetamide

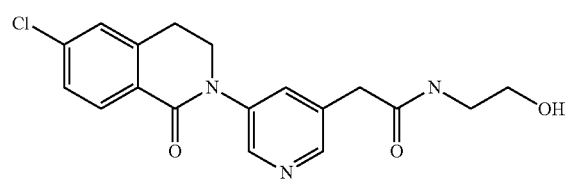 [SMILES: O=C(Cc1cncc(N2CCc3cc(Cl)ccc3C2=O)c1)NCCO]

The title compound was synthesized in analogy to the procedure described for the preparation of example 263 [C] using [5-(6-chloro-1-oxo-3,4-dihydro-1H-isoquinolin-2-yl)-pyridin-3-yl]-acetic acid and 2-amino-ethanol as starting material. MS: 360.1 (M+H$^+$).

Example 265

6-Chloro-2-[5-(1-methylamino-ethyl)-pyridin-3-yl]-3,4-dihydro-2H-isoquinolin-1-one

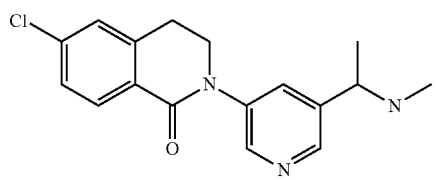 [SMILES: CNC(C)c1cncc(N2CCc3cc(Cl)ccc3C2=O)c1]

[A] 1-(5-Bromo-pyridin-3-yl)-ethanol

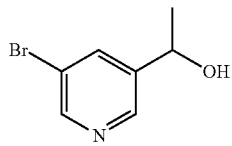

Methylmagnesium bromide (1M in THF, 12 mL, 12 mmol) was added dropwise to a solution of 5-bromo-pyridine-3-carbaldehyde (1.85, 10 mmol) in dry THF (20 mL) at −78° C. The resulting mixture was slowly warmed up to 0° C. during a 2 hour period and then quenched by aq. satd. NH$_4$Cl solution. After extraction with DCM, the organic layer was washed with brine, dried over anhy. Na$_2$SO4, filtered and concentrated in vacuo to give title compound as a crude product (1.9 g, 98%).

[B] 3-Bromo-5-(1-chloro-ethyl)-pyridine

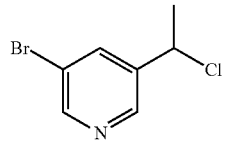

To a solution of 1-(5-bromo-pyridine-3-yl)-ethanol (201 mg, 1 mmol) in DCM (10 mL) was added dropwise thionyl chloride (200 uL). The resulting reaction mixture was heated to reflux for 3 hours before the solvent was removed in vacuo to give a crude product as a white solid. It was used directly in the next step without further purification.

[C] [1-(5-Bromo-pyridin-3-yl)-ethyl]-methyl-amine

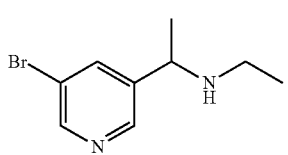

To a solution of 3-bromo-5-(1-chloro-ethyl)-pyridine (221 mg, 1 mmol) in DMF (10 mL) was added methylamine hydrochloride (134 mg, 2 mmol) and K$_2$CO$_3$ (572 mg, 4 mmol). The resulting reaction mixture was heated to reflux for 3 hours before it was quenched by H$_2$O. After extraction with DCM, the organic layer was dried over anhy. Na$_2$SO$_4$, filtered and concentrated to give title compound as a crude product which was used directly in the next step without further purification.

[D] 6-Chloro-2-[5-(1-methylamino-ethyl)-pyridin-3-yl]-3,4-dihydro-2H-isoquinolin-1-one

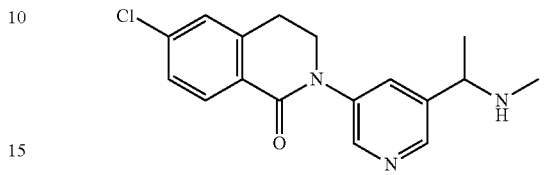

6-Chloro-3,4-dihydro-2H-isoquinolin-1-one (intermediate A-2) (36 mg, 0.2 mmol), [1-(5-bromo-pyridin-3-yl)-ethyl]-methyl-amine (85.6 mg, 0.4 mmol), CuI (3.8 mg, 0.02 mmol), (1S,2S)-cyclohexane-1,2-diamine (4.5 mg, 0.04 mmol) and Cs$_2$CO$_3$ (130 mg, 0.4 mmol) were dissolved in 1,4-dioxane (5 mL). The reaction mixture was subject to microwave reaction at 150° C. for 2.5 hours before it was poured into H$_2$O (15 mL) and extracted with EtOAc (2×10 mL). The organic layer was washed with brine, dried over anhy. Na$_2$SO$_4$, filtered and concentrated in vacuo to give a crude product which was purified by prep-HPLC to yield the title compound (15 mg, 26%) as a white solid. MS: 316.2 (M+H$^+$).

Example 266

6-Chloro-2-[5-(1-dimethylamino-ethyl)-pyridin-3-yl]-3,4-dihydro-2H-isoquinolin-1-one

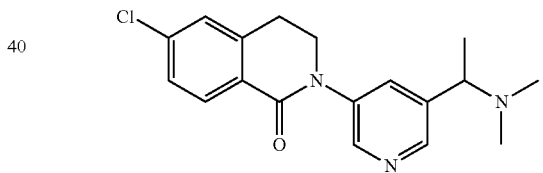

In analogy to the procedures described for the preparation of example 265, the title compound was synthesized using dimethylamine (step C) and [1-(5-bromo-pyridin-3-yl)-ethyl]-dimethyl-amine (step D) as corresponding starting materials. MS: 330.2 (M+H$^+$).

Example 267

6-Chloro-2-[5-(1-methyl-4H-imidazole-2-carbonyl)-pyridin-3-yl]-3,4-dihydro-2H-isoquinolin-1-one

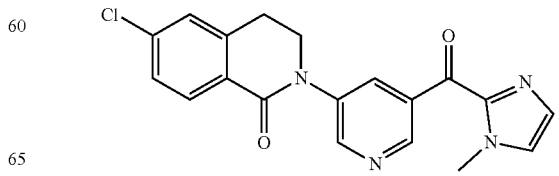

207

[A] (5-Bromo-pyridin-3-yl)-(1-methyl-1H-imidazol-2-yl)-methanol

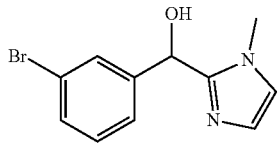

At −78° C., under $N_2$ protection, n-BuLi (0.16 mL, 1.6 M, 1.0 mmol) was added to a solution of 1-methyl-1H-imidazole (82 mg, 1.0 mmol) in THF (10 mL) and the reaction mixture was stirred at −78° C. for 0.5 hour; then, 5-bromo-pyridine-3-carbaldehyde (186 mg, 1.0 mmol) was added to the above solution and stirring continued at −78° C. for additional 2 hours. The reaction mixture was poured into water (5.0 mL) and extracted with EtOAc (2×50 mL). The organic layer was dried over anhy. $Na_2SO_4$, filtered and concentrated in vacuo to give a crude product (210 mg, 78.4%) as white solid. MS: 268.1 & 270.1 (M+H$^+$).

[B] 6-Chloro-2-[5-(1-methyl-1H-imidazole-2-carbonyl)-pyridin-3-yl]-3,4-dihydro-2H-isoquinolin-1-one

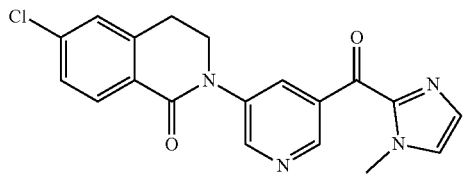 [SMILES: Cn1ccnc1C(=O)c1cncc(N2CCc3cc(Cl)ccc3C2=O)c1]

(5-Bromo-pyridin-3-yl)-(1-methyl-1H-imidazol-2-yl)-methanol (150 mg, 0.56 mmol), 6-chloro-3,4-dihydro-2H-isoquinolin-1-one (90 mg, 0.49 mmol) (intermediate A-2), CuI (30 mg, 0.16 mmol), $Cs_2CO_3$ (330 mg, 1.0 mmol) and (+)-(1S,1S)-1,2-diaminocyclohexane (0.08 mL, 0.64 mmol) were dissolved in dioxane (4.0 mL). The resulting mixture was heated at 150° C. for 2 hours before it was poured into $H_2O$ (50 mL) and extracted with EtOAc (2×75 mL). The organic layer was washed with brine, dried over anhy. $Na_2SO_4$, filtered and concentrated in vacuo to give a crude product which was then purified by prep-HPLC to give the title compound (4.5 mg, 2.5%) as light yellow oil. MS: 367.1 (M+H$^+$).

Example 268

6-Chloro-2-[5-(4-methyl-4H-[1,2,4]-triazol-3-ylmethyl)-pyridin-3-yl]-3,4-dihydro-2H-isoquinolin-1-one

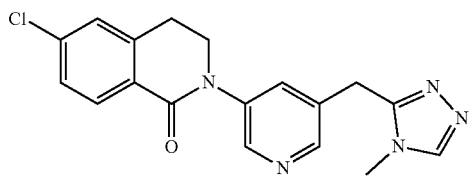 [SMILES: Cn1cnnc1Cc1cncc(N2CCc3cc(Cl)ccc3C2=O)c1]

208

[A] [5-(6-Chloro-1-oxo-3,4-dihydro-1H-isoquinolin-2-yl)-pyridin-3-yl]-acetic acid methyl ester

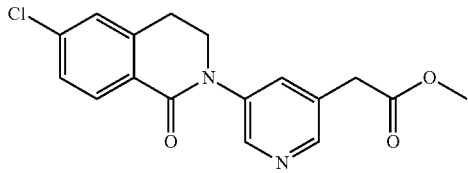 [SMILES: COC(=O)Cc1cncc(N2CCc3cc(Cl)ccc3C2=O)c1]

To a solution of [5-(6-chloro-1-oxo-3,4-dihydro-1H-isoquinolin-2-yl)-pyridin-3-yl]-acetic acid (example 263 [B]) (217 mg, 0.68 mmol) in methanol (25 mL) was added thionyl chloride (0.44 mL, 6.0 mmol) slowly at 0° C. After the addition, the reaction mixture was warmed up and heated at 80° C. for 2 hours. After cooling back to room temperature, it was concentrated in vacuo and the residue was dissolved in EtOAc (150 mL) and washed with satd. aq. $NaHCO_3$ solution and then brine. The organic layer was dried over anhy. $Na_2SO_4$, filtered and concentrated in vacuo to give a crude product (224 mg, quant.) as light brown oil. MS: 331.1 (M+H$^+$).

[B] [5-(6-Chloro-1-oxo-3,4-dihydro-1H-isoquinolin-2-yl)-pyridin-3-yl]-acetic acid hydrazide

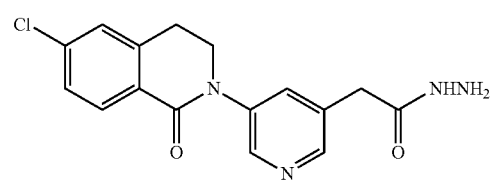 [SMILES: NNC(=O)Cc1cncc(N2CCc3cc(Cl)ccc3C2=O)c1]

[5-(6-Chloro-1-oxo-3,4-dihydro-1H-isoquinolin-2-yl)-pyridin-3-yl]-acetic acid methyl ester (100 mg, 0.30 mmol) and hydrazine monohydrate (0.75 mL) were dissolved in ethanol (8.0 mL) and the reaction mixture was heated at 90° C. for 3 h before it was cooled and concentrated in vacuo to give a crude product (100 mg, quant.) as light yellow oil. MS: 331.1 (M+H$^+$).

[C] 6-Chloro-2-[5-(4-methyl-4H-[1,2,4]triazol-3-ylmethyl)-pyridin-3-yl]-3,4-dihydro-2H-isoquinolin-1-one

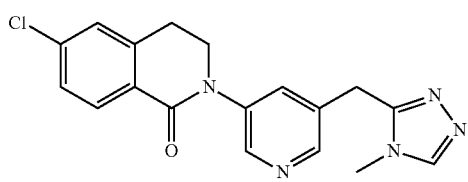 [SMILES: Cn1cnnc1Cc1cncc(N2CCc3cc(Cl)ccc3C2=O)c1]

In a 5 mL sealed tube, [5-(6-chloro-1-oxo-3,4-dihydro-1H-isoquinolin-2-yl)-pyridin-3-yl]-acetic acid hydrazide (100 mg, 0.30 mmol) and trimethyl orthoformate (0.07 mL) were dissolved in dioxane (0.8 mL) and heated at 100° C. for 2 hours. After cooling to room temperature, methylamine (1.0 mL, 2.0 M in THF), acetic acid (0.03 mL) and dioxane (2.0 mL) were added. The vial was re-sealed and heated to 130° C.

for 2 hours. The reaction mixture was concentrated in vacuo to give a crude product which was then purified by prep-HPLC to give title compound (8.3 mg, 7.8%) as light yellowish oil. MS: 354.1 (M+H⁺).

Example 269

6-Chloro-2-[5-(1-[1,2,3]triazol-2-yl-ethyl)-pyridin-3-yl]-3,4-dihydro-2H-isoquinolin-1-one

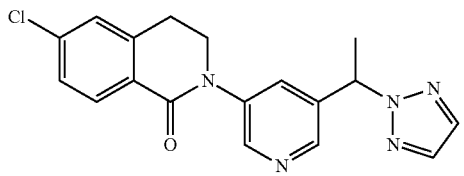

[A] 2-[5-(1-Bromo-ethyl)-pyridin-3-yl]-6-chloro-3,4-dihydro-2H-isoquinolin-1-one

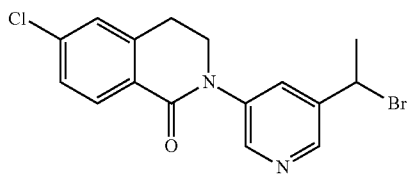 [SMILES: CC(Br)c1cncc(N2CCc3cc(Cl)ccc3C2=O)c1]

PBr₃ (541 mg, 2 mmol) was added dropwise into a solution of 6-chloro-2-[5-(1-hydroxy-ethyl)-pyridin-3-yl]-3,4-dihydro-2H-isoquinolin-1-one (example 13) (302 mg, 1 mmol) in 5 mL DCM at 0° C. The reaction was stirred at RT for 2 hours before it was neutralized with satd. aq. NaHCO₃ solution and extracted with DCM (10 mL, 2×). The organic layers were washed with brine, dried over anhy. Na₂SO₄, filtered and concentrated in vacuo to afford a crude product as an oil which was used in the next step without further purification (380 mg, 100%). MS: 365.2 (M+H)⁺.

[B] 6-Chloro-2-[5-(1-[1,2,3]triazol-2-yl-ethyl)-pyridin-3-yl]-3,4-dihydro-2H-isoquinolin-1-one

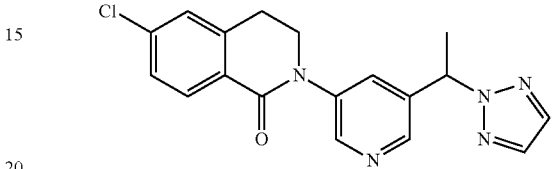

NaH (30 mg, 0.12 mmol) was added to a solution of 2H-[1,2,3]triazole (8.3 mg, 0.12 mmol) in DMF (5 mL) at 0° C. and the resulting reaction mixture was stirred for 10 min before 2-[5-(1-bromo-ethyl)-pyridin-3-yl]-6-chloro-3,4-dihydro-2H-isoquinolin-1-one (36.5 mg, 0.1 mmol) was added. After additional stirring at RT for 1 hour, it was poured into ice-water (5 mL) and extracted with EtOAc (2×10 mL). The organic layers were washed with brine, dried over anhy. Na₂SO₄, filtered and concentrated in vacuo to give a crude product which was then purified by prep-HPLC to give title compound (7.5 mg, 21%) as a white solid. MS: 354.2 (M+H⁺).

The following compounds listed in Table 8 were prepared in analogy to the procedure described for the preparation of example 269 using appropriate starting materials.

TABLE 8

| Ex | Compound Name | Compound Structure | Starting Materials | MS (M + H)⁺ |
|---|---|---|---|---|
| 270 | 6-Chloro-2-[5-(1-imidazol-1-yl-ethyl)-pyridin-3-yl]-3,4-dihydro-2H-isoquinolin-1-one | 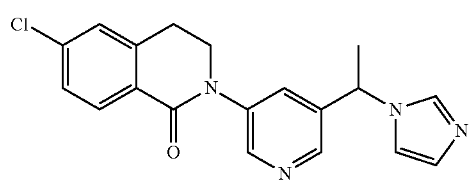 [SMILES: CC(c1cncc(N2CCc3cc(Cl)ccc3C2=O)c1)n1ccnc1] | 2-[5-(1-Bromo-ethyl)-pyridin-3-yl]-6-chloro-3,4-dihydro-2H-isoquinolin-1-one (example 269[A]) and 1H-Imidazole | 353.1 |
| 271 | 6-Chloro-2-[5-(1-pyrazol-1-yl-ethyl)-pyridin-3-yl]-3,4-dihydro-2H-isoquinolin-1-one | 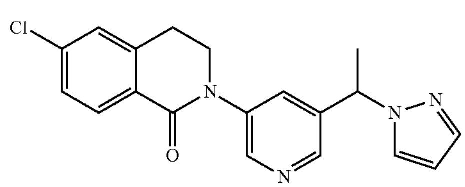 [SMILES: CC(c1cncc(N2CCc3cc(Cl)ccc3C2=O)c1)n1cccn1] | 2-[5-(1-Bromo-ethyl)-pyridin-3-yl]-6-chloro-3,4-dihydro-2H-isoquinolin-1-one (example 269[A]) and 1H-pyrazole | 353.1 |
| 272 | 6-Chloro-2-{5-[1-(oxazol-2-ylamino)-ethyl]-pyridin-3-yl}-3,4-dihydro-2H-isoquinolin-1-one | 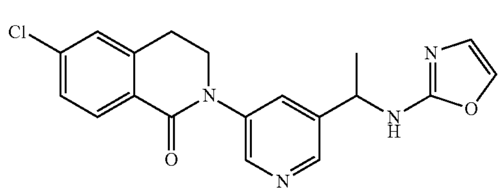 [SMILES: CC(Nc1ncco1)c1cncc(N2CCc3cc(Cl)ccc3C2=O)c1] | 2-[5-(1-Bromo-ethyl)-pyridin-3-yl]-6-chloro-3,4-dihydro-2H-isoquinolin-1-one (example 269[A]) and oxazol-2-ylamine | 369.1 |

TABLE 8-continued

| Ex | Compound Name | Compound Structure | Starting Materials | MS (M + H)+ |
|---|---|---|---|---|
| 273 | 6-Chloro-2-[5-(1-[1,2,4]triazol-1-yl-ethyl)-pyridin-3-yl]-3,4-dihydro-2H-isoquinolin-1-one | 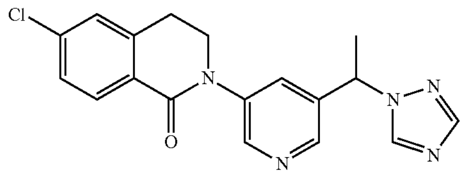 [SMILES: CC(c1cncc(N2CCc3cc(Cl)ccc3C2=O)c1)n1cncn1] | 2-[5-(1-Bromo-ethyl)-pyridin-3-yl]-6-chloro-3,4-dihydro-2H-isoquinolin-1-one (example 269[A]) and 1H-[1,2,4]triazole | 354.2 |
| 274 | 6-Chloro-2-{5-[1-(2-oxo-pyrrolidin-1-yl)-ethyl]-pyridin-3-yl}-3,4-dihydro-2H-isoquinolin-1-one | 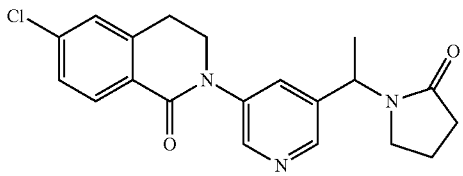 [SMILES: CC(c1cncc(N2CCc3cc(Cl)ccc3C2=O)c1)N1CCCC1=O] | 2-[5-(1-Bromo-ethyl)-pyridin-3-yl]-6-chloro-3,4-dihydro-2H-isoquinolin-1-one (example 269[A]) and pyrrolidin-2-one | 370.2 |
| 275 | 6-Chloro-2-{5-[1-(2-oxo-oxazolidin-3-yl)-ethyl]-pyridin-3-yl}-3,4-dihydro-2H-isoquinolin-1-one | 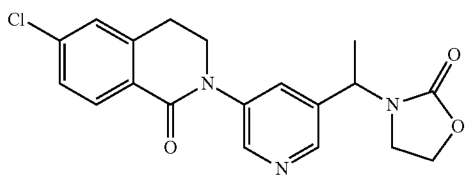 [SMILES: CC(c1cncc(N2CCc3cc(Cl)ccc3C2=O)c1)N1CCOC1=O] | 2-[5-(1-Bromo-ethyl)-pyridin-3-yl]-6-chloro-3,4-dihydro-2H-isoquinolin-1-one (example 269[A]) and oxazolidin-2-one | 372.1 |
| 276 | N-{1-[5-(6-Chloro-1-oxo-3,4-dihydro-1H-isoquinolin-2-yl)-pyridin-3-yl]-ethyl}-methanesulfonamide | 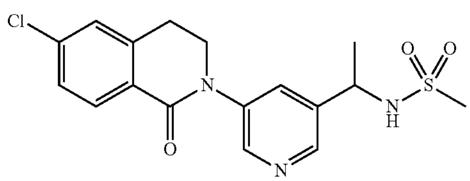 [SMILES: CC(NS(C)(=O)=O)c1cncc(N2CCc3cc(Cl)ccc3C2=O)c1] | 2-[5-(1-Bromo-ethyl)-pyridin-3-yl]-6-chloro-3,4-dihydro-2H-isoquinolin-1-one (example 269[A]) and methanesulfonamide | 380.2 |
| 277 | 6-Chloro-2-{5-[1-(3-fluoro-phenylamino)-ethyl]-pyridin-3-yl}-3,4-dihydro-2H-isoquinolin-1-one | 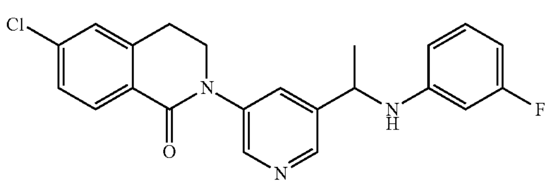 [SMILES: CC(Nc1cccc(F)c1)c1cncc(N2CCc3cc(Cl)ccc3C2=O)c1] | 2-[5-(1-Bromo-ethyl)-pyridin-3-yl]-6-chloro-3,4-dihydro-2H-isoquinolin-1-one (example 269[A]) and 3-fluoro-phenylamine | 396.2 |
| 278 | 6-Chloro-2-[5-(1-phenylamino-ethyl)-pyridin-3-yl]-3,4-dihydro-2H-isoquinolin-1-one | 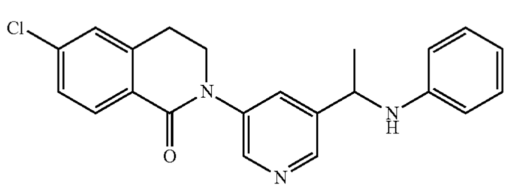 [SMILES: CC(Nc1ccccc1)c1cncc(N2CCc3cc(Cl)ccc3C2=O)c1] | 2-[5-(1-Bromo-ethyl)-pyridin-3-yl]-6-chloro-3,4-dihydro-2H-isoquinolin-1-one (example 269[A]) and phenylamine | 378.2 |

Example 279

6-Chloro-2-(5-methanesulfinyl-pyridin-3-yl)-3,4-dihydro-2H-isoquinolin-1-one

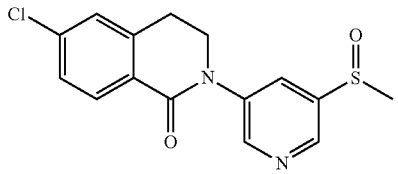 [SMILES: CS(=O)c1cncc(N2CCc3cc(Cl)ccc3C2=O)c1]

MCPBA (17.3 mg, 0.1 mmol) was added into a solution of 6-chloro-2-(5-methylsulfanyl-pyridin-3-yl)-3,4-dihydro-2H-isoquinolin-1-one (example 59) (30.5 mg, 0.1 mmol) in DCM (2 mL). The reaction mixture was stirred at RT for 2 hours before it was neutralized with 5% aq. NaOH and extracted with DCM (5 mL, 2×). The organic layers were washed with brine, dried over anhy. Na$_2$SO$_4$, filtered and concentrated in vacuo to give a crude product which was then purified by prep-HPLC to give title compound (6 mg, 19%) as a white solid. MS: 321.1 (M+H$^+$).

Example 280

6-Chloro-2-[4-(4-methyl-piperazin-1-ylmethyl)-pyridin-3-yl]-3,4-dihydro-2H-isoquinolin-1-one

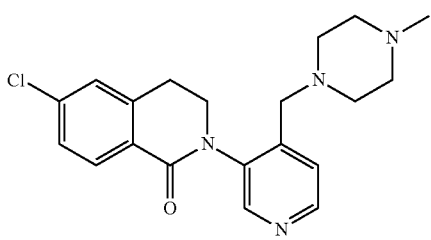 [SMILES: CN1CCN(Cc2ccncc2N2CCc3cc(Cl)ccc3C2=O)CC1]

[A] 5-(6-Chloro-1-oxo-3,4-dihydro-1H-isoquinolin-2-yl)-pyridine-3-carbaldehyde

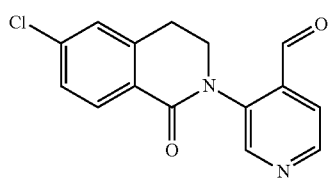 [SMILES: O=Cc1ccncc1N1CCc2cc(Cl)ccc2C1=O]

CuI (190 mg, 1 mmol), (1S,2S)-cyclohexane-1,2-diamine (228 mg, 2 mmol) and Cs$_2$CO$_3$ (6.5 g, 20 mmol) were added to a solution of 6-chloro-3,4-dihydro-2H-isoquinolin-1-one (1.82 g, 10 mmol, intermediate A-2) and 5-bromo-pyridine-4-carbaldehyde (3.72 g, 20 mmol) in dioxane (15 mL). The reaction mixture was heated to 150° C. using microwave for 2.5 hours before it was poured into H$_2$O (50 mL) and extracted with EtOAc (2×20 mL). The organic layers were washed with brine, dried over anhy. Na$_2$SO$_4$, filtered and concentrated in vacuo to give a crude product (2.0 g, 70%) as brown oil. MS: 287.0 (M+H$^+$).

[B] 6-Chloro-2-[4-(4-methyl-piperazin-1-ylmethyl)-pyridin-3-yl]-3,4-dihydro-2H-isoquinolin-1-one

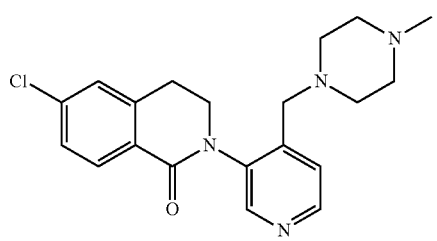 [SMILES: CN1CCN(Cc2ccncc2N2CCc3cc(Cl)ccc3C2=O)CC1]

NaBH(OAc)$_3$ (84 mg, 0.4 mmol) was added into a solution of 5-(6-chloro-1-oxo-3,4-dihydro-1H-isoquinolin-2-yl)-pyridine-4-carbaldehyde (28.6 mg, 0.1 mmol) and 1-methyl-piperazine (10 mg 0.1 mmol) in DCM and MeOH (10 mL, 1:1). The reaction mixture was stirred at RT overnight before it was poured into ice-water (10 mL) and extracted with EtOAc (2×10 mL). The organic layers were washed with brine, dried over anhy. MgSO$_4$, filtered and concentrated in vacuo to give a crude product which was then purified by prep-HPLC to give title compound (7.2 mg, 16%) as a white solid. MS: 371.1 (M+H$^+$).

Example 281

5-Chloro-3,3-dimethyl-2-[5-(1-methyl-1H-pyrazol-4-ylmethyl)-pyridin-3-yl]-2,3-dihydro-isoindol-1-one

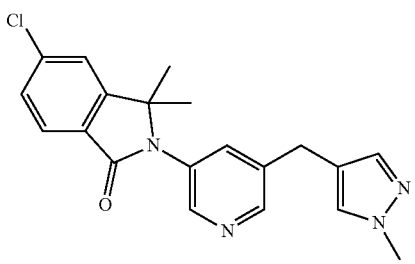 [SMILES: Cn1cc(Cc2cncc(N3C(=O)c4ccc(Cl)cc4C3(C)C)c2)cn1]

In analogy to the procedure described for the preparation of example 204, 5-chloro-2-(5-chloromethyl-pyridin-3-yl)-3,3-dimethyl-2,3-dihydro-isoindol-1-one (intermediate A-12-1) and 1-methylpyrazole-4-boronic acid pinacol ester were used to yield the title compound as a light yellowish solid (yield 15%). MS: 367.2 (M+H$^+$).

The following compounds listed in Table 9 were prepared in analogy to the procedures described for the preparation of examples 1, 2 or 3 [B] using appropriate starting materials, followed by separation by prep. chiral HPLC when appropriate.

TABLE 9

| Ex | Compound Name | Compound Structure | Starting Materials | Prepared by analogy to example | MS (M + H)+ |
|---|---|---|---|---|---|
| 282 | 5-Chloro-2-(5-difluoromethoxy-pyridin-3-yl)-3-ethyl-2,3-dihydro-isoindol-1-one | 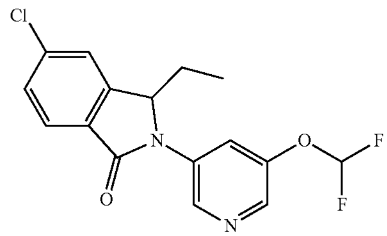 [SMILES: CCC1c2cc(Cl)ccc2C(=O)N1c1cncc(OC(F)F)c1] | 5-Chloro-3-ethyl-2,3-dihydro-isoindol-1-one (intermediate A-13-1) and 3-bromo-5-difluoromethoxy-pyridine | 2 | 339.2 |
| 283 | 5-Chloro-3-ethyl-2-[5-(1-hydroxy-ethyl)-pyridin-3-yl]-2,3-dihydro-isoindol-1-one | 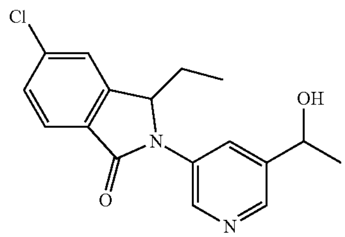 [SMILES: CCC1c2cc(Cl)ccc2C(=O)N1c1cncc(C(C)O)c1] | 5-Chloro-3-ethyl-2,3-dihydro-isoindol-1-one (intermediate A-13-1) and 1-(5-bromo-pyridin-3-yl)-ethanol | 2 | 317.3 |
| 284 | 5-Chloro-2-(4-chloro-pyridin-3-yl)-3-ethyl-2,3-dihydro-isoindol-1-one | 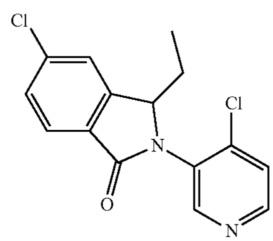 [SMILES: CCC1c2cc(Cl)ccc2C(=O)N1c1cnccc1Cl] | 5-Chloro-3-ethyl-2,3-dihydro-isoindol-1-one (intermediate A-13-1) and 3-bromo-4-chloro-pyridine | 2 | 307.2 |
| 285 | 5-Chloro-2-(4-chloro-pyridin-3-yl)-3,3-dimethyl-2,3-dihydro-isoindol-1-one | 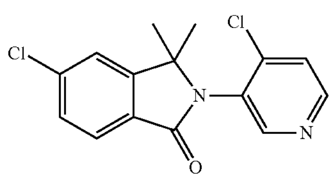 [SMILES: CC1(C)c2cc(Cl)ccc2C(=O)N1c1cnccc1Cl] | 5-Chloro-3,3-dimethyl-2,3-dihydro-isoindol-1-one (intermediate A-12) and 3-bromo-4-chloro-pyridine | 2 | 307.2 |
| 286 | 6-Chloro-5'-nitro-3,4-dihydro-[2,4']biisoquinolinyl-1-one | 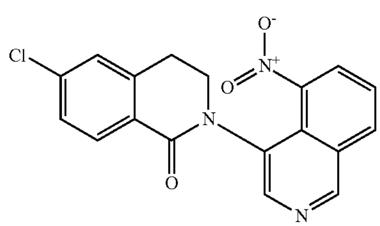 [SMILES: O=C1c2ccc(Cl)cc2CCN1c1cncc2cccc([N+](=O)[O-])c12] | 6-Chloro-3,4-dihydro-2H-isoquinolin-1-one (intermediate A-2) and 4-bromo-5-nitro-isoquinoline | 2 | 354.1 |
| 287 | 6-Chloro-8'-nitro-3,4-dihydro-[2,4']biisoquinolinyl-1-one | 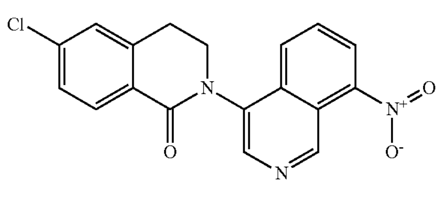 [SMILES: O=C1c2ccc(Cl)cc2CCN1c1cncc2c([N+](=O)[O-])cccc12] | 6-Chloro-3,4-dihydro-2H-isoquinolin-1-one (intermediate A-2) and 4-bromo-8-nitro-isoquinoline | 2 | 354.2 |
| 288 | 8'-Amino-6-chloro-3,4-dihydro-[2,4']biisoquinolinyl-1-one | 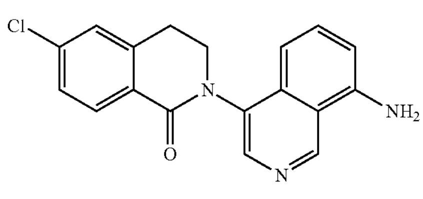 [SMILES: Nc1cccc2c(N3CCc4cc(Cl)ccc4C3=O)cncc12] | 6-Chloro-3,4-dihydro-2H-isoquinolin-1-one (intermediate A-2) and 4-bromo-isoquinolin-8-ylamine | 2 | 324.1 |

TABLE 9-continued

| Ex | Compound Name | Compound Structure | Starting Materials | Prepared by analogy to example | MS (M + H)+ |
|---|---|---|---|---|---|
| 289 | Ethanesulfonic acid (6-chloro-1-oxo-3,4-dihydro-1H-[2,4']biisoquinolinyl-8'-yl)-amide | 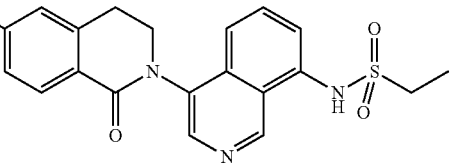 | 6-Chloro-3,4-dihydro-2H-isoquinolin-1-one (intermediate A-2) and ethanesulfonic acid (4-bromo-isoquinolin-8-yl)-amide | 2 | 416.0 |
| 290 | 6'-Chloro-2'-(5-fluoropyridin-3-yl)spiro[cyclopropane-1,1'-isoindol]-3'(2'H)-one | 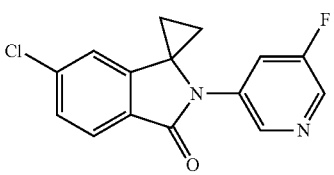 [SMILES: O=C1c2ccc(Cl)cc2C2(CC2)N1c1cncc(F)c1] | 6'-Chlorospirocyclopropane-1,1'-isoindolin]-3'-one (intermediate A-22) and 3-bromo-5-fluoro-pyridine | 2 | 289.1 |
| 291 | 6'-Chloro-2'-[5-(difluoromethoxy)pyridin-3-yl]spiro[cyclopropane-1,1'-isoindol]-3'(2'H)-one | 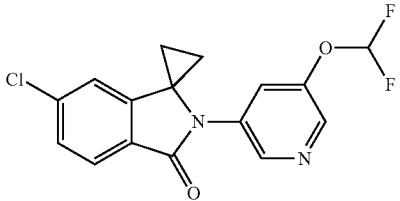 [SMILES: O=C1c2ccc(Cl)cc2C2(CC2)N1c1cncc(OC(F)F)c1] | 6'-Chlorospiro[cyclopropane-1,1'-isoindolin]-3'-one (intermediate A-22) and 3-bromo-5-difluoromethoxy-pyridine | 3[B] | 337.2 |
| 292 | 2-Chloro-6-(5-fluoro-pyridin-3-yl)-7,7-dimethyl-6,7-dihydro-pyrrolo[3,4-b]pyridin-5-one | 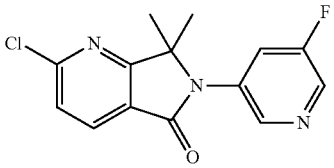 [SMILES: CC1(C)c2nc(Cl)ccc2C(=O)N1c1cncc(F)c1] | 2-Chloro-7,7-dimethyl-6,7-dihydro-pyrrolo[3,4-b]pyridin-5-one (intermediate A-16) and 3-bromo-5-fluoro-pyridine | 2 | 292.1 |
| 293 | 2-Chloro-6-(5-difluoromethoxy-pyridin-3-yl)-7,7-dimethyl-6,7-dihydro-pyrrolo[3,4-b]pyridin-5-one | 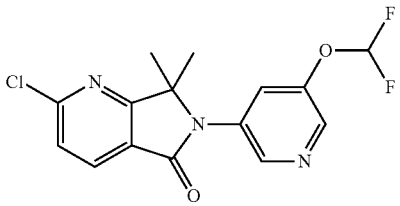 [SMILES: CC1(C)c2nc(Cl)ccc2C(=O)N1c1cncc(OC(F)F)c1] | 2-Chloro-7,7-dimethyl-6,7-dihydro-pyrrolo[3,4-b]pyridin-5-one (intermediate A-16) and 3-bromo-5-difluoromethoxy-pyridine | 2 | 340.1 |
| 294 | 6-(5-Fluoro-pyridin-3-yl)-2-methoxy-7,7-dimethyl-6,7-dihydro-pyrrolo[3,4-b]pyridin-5-one | 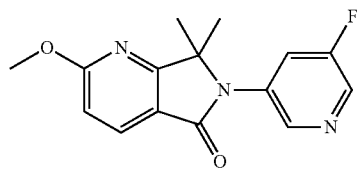 [SMILES: COc1ccc2c(n1)C(C)(C)N(c1cncc(F)c1)C2=O] | 2-Methoxy-7,7-dimethyl-6,7-dihydro-pyrrolo[3,4-b]pyridin-5-one (intermediate A-17) and 3-bromo-5-fluoro-pyridine | 2 | 288.2 |

TABLE 9-continued

| Ex | Compound Name | Compound Structure | Starting Materials | Prepared by analogy to example | MS (M + H)+ |
|---|---|---|---|---|---|
| 295 | 6-(5-Difluoromethoxy-pyridin-3-yl)-2-methoxy-7,7-dimethyl-6,7-dihydro-pyrrolo[3,4-b]pyridin-5-one | 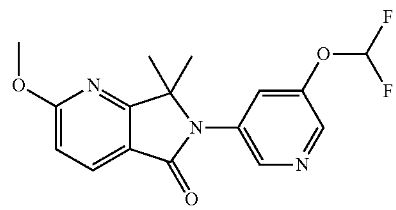 [SMILES: COc1ccc2c(n1)C(C)(C)N(c1cncc(OC(F)F)c1)C2=O] | 2-Methoxy-7,7-dimethyl-6,7-dihydro-pyrrolo[3,4-b]pyridin-5-one (intermediate A-17) and 3-bromo-5-difluoromethoxy-pyridine | 2 | 336.2 |
| 296 | 6'-Chloro-2'-(pyridin-3-yl)spiro[cyclopropane-1,1'-isoindol]-3'(2'H)-one | 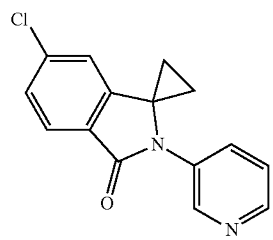 [SMILES: O=C1c2ccc(Cl)cc2C2(CC2)N1c1cccnc1] | 6'-Chlorospiro cyclopropane-1,1'-isoindolin]-3'-one (intermediate A-22) and 3-bromo-pyridine | 2 | 271.1 |
| 297 | 5-Chloro-3-cyclopropyl-2-(5-fluoro-pyridin-3-yl)-2,3-dihydro-isoindol-1-one | 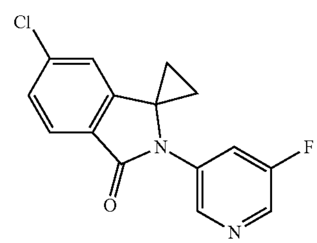 [SMILES: O=C1c2ccc(Cl)cc2C2(CC2)N1c1cncc(F)c1] | 5-Chloro-3-cyclopropyl-2,3-dihydro-isoindol-1-one (intermediate A-15) and 3-bromo-pyridine | 2 | 303.2 |
| 298 | 2-Chloro-7,7-dimethyl-6-pyridin-3-yl-6,7-dihydro-pyrrolo[3,4-b]pyridin-5-one | 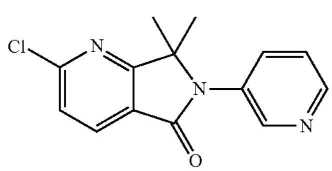 [SMILES: CC1(C)c2nc(Cl)ccc2C(=O)N1c1cccnc1] | 2-Chloro-7,7-dimethyl-6,7-dihydro-pyrrolo[3,4-b]pyridin-5-one (intermediate A-16) and 3-bromo-pyridine | 2 | 274.1 |
| 299 | 2-Ethoxy-6-(5-fluoro-pyridin-3-yl)-7,7-dimethyl-6,7-dihydro-pyrrolo[3,4-b]pyridin-5-one | 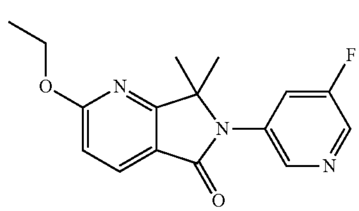 [SMILES: CCOc1ccc2c(n1)C(C)(C)N(c1cncc(F)c1)C2=O] | 2-Ethoxy-7,7-dimethyl-6,7-dihydro-pyrrolo[3,4-b]pyridin-5-one (intermediate A-18) and 3-bromo-5-fluoro-pyridine | 2 | 302.2 |
| 300 | 2-Methoxy-7,7-dimethyl-6-pyridin-3-yl-6,7-dihydro-pyrrolo[3,4-b]pyridin-5-one | 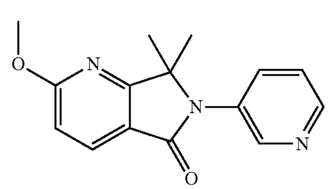 [SMILES: COc1ccc2c(n1)C(C)(C)N(c1cccnc1)C2=O] | 2-Methoxy-7,7-dimethyl-6,7-dihydro-pyrrolo[3,4-b]pyridin-5-one (intermediate A-17) and 3-bromo-pyridine | 2 | N.D. |

TABLE 9-continued

| Ex | Compound Name | Compound Structure | Starting Materials | Prepared by analogy to example | MS (M + H)+ |
|---|---|---|---|---|---|
| 301 | 5-Chloro-3-cyclopropyl-2-pyridin-3-yl-2,3-dihydro-isoindol-1-one | 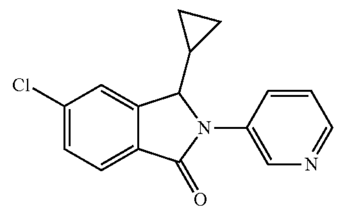 [SMILES: O=C1c2ccc(Cl)cc2C(C2CC2)N1c1cccnc1] | 5-Chloro-3-cyclopropyl-2,3-dihydro-isoindol-1-one (intermediate A-15) and 3-bromo-pyridine | 2 | 285.1 |
| 302 | 5-Chloro-3-cyclopropyl-2-(5-difluoromethoxy-pyridin-3-yl)-2,3-dihydro-isoindol-1-one | 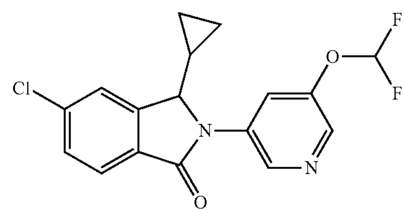 [SMILES: O=C1c2ccc(Cl)cc2C(C2CC2)N1c1cncc(OC(F)F)c1] | 5-Chloro-3-cyclopropyl-2,3-dihydro-isoindol-1-one (intermediate A-15) and 3-bromo-5-difluoromethoxy-pyridine | 2 | 351.1 |
| 303 | 6-(5-Difluoromethoxy-pyridin-3-yl)-2-ethoxy-7,7-dimethyl-6,7-dihydro-pyrrolo[3,4-b]pyridin-5-one | 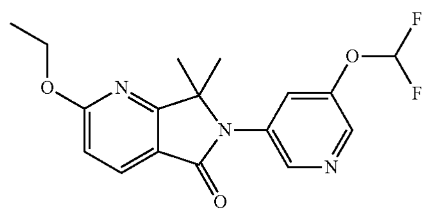 [SMILES: CCOc1ccc2c(n1)C(C)(C)N(c1cncc(OC(F)F)c1)C2=O] | 2-Ethoxy-7,7-dimethyl-6,7-dihydro-pyrrolo[3,4-b]pyridin-5-one (intermediate A-18) and 3-bromo-5-difluoromethoxy-pyridine | 2 | 350.1 |
| 304 | 5-Chloro-2-(5-isopropoxy-pyridin-3-yl)-3,3-dimethyl-2,3-dihydro-isoindol-1-one | 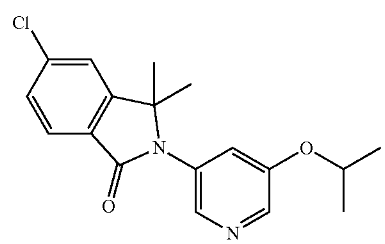 [SMILES: CC(C)Oc1cncc(N2C(=O)c3ccc(Cl)cc3C2(C)C)c1] | 5-Chloro-3,3-dimethyl-2,3-dihydro-isoindol-1-one (intermediate A-12) and 3-bromo-5-isopropoxy-pyridine | 3[B] | 331.1 |
| 305 | 6'-Chloro-2'-(4-chloropyridin-3-yl)spiro[cyclopropane-1,1'-isoindol]-3'(2'H)-one | 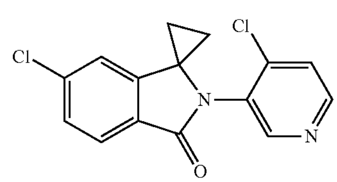 [SMILES: O=C1c2ccc(Cl)cc2C2(CC2)N1c1cnccc1Cl] | 6'-Chlorospiro[cyclopropane-1,1'-isoindolin]-3'-one (intermediate A-22) and 3-bromo-4-chloro-pyridine | 2 | 305.0 |
| 306 | 5-Chloro-2-(5-cyclopropoxy-pyridin-3-yl)-3,3-dimethyl-2,3-dihydro-isoindol-1-one | 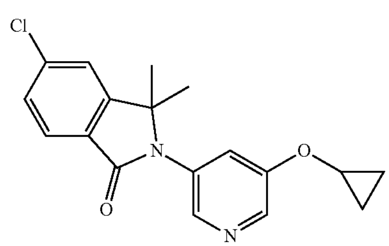 [SMILES: CC1(C)c2cc(Cl)ccc2C(=O)N1c1cncc(OC2CC2)c1] | 5-Chloro-3,3-dimethyl-2,3-dihydro-isoindol-1-one (intermediate A-12) and 3-bromo-5-cyclopropoxy-pyridine | 3[B] | 329.1 |

TABLE 9-continued

| Ex | Compound Name | Compound Structure | Starting Materials | Prepared by analogy to example | MS (M + H)+ |
|---|---|---|---|---|---|
| 307 | (S or R)-6-Chloro-3-ethyl-2-(5-fluoro-pyridin-3-yl)-2,3-dihydro-isoindol-1-one | 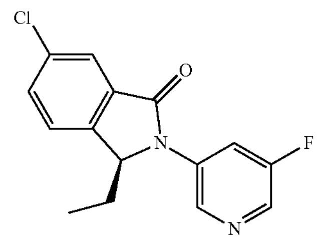 [SMILES: CC[C@H]1c2ccc(Cl)cc2C(=O)N1c1cncc(F)c1] | (S or R)-6-Chloro-3-ethyl-2,3-dihydro-isoindol-1-one (intermediate A-13-2b) and 3-bromo-pyridine | 2 | 291.2 |
| 308 | (R or S)-6-Chloro-3-ethyl-2-(5-fluoro-pyridin-3-yl)-2,3-dihydro-isoindol-1-one | 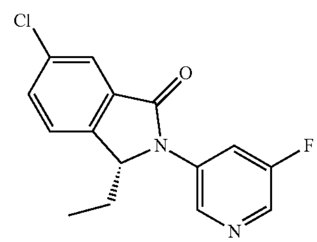 [SMILES: CC[C@@H]1c2ccc(Cl)cc2C(=O)N1c1cncc(F)c1] | (R or S)-6-Chloro-3-ethyl-2,3-dihydro-isoindol-1-one (intermediate A-13-2a) and 3-bromo-pyridine | 2 | 291.2 |
| 309 | (R or S)-5-Chloro-3-ethyl-2-(5-fluoro-pyridin-3-yl)-2,3-dihydro-isoindol-1-one | 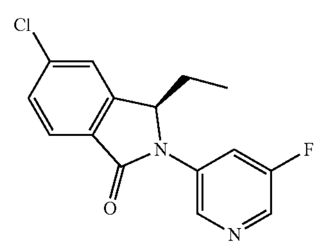 [SMILES: CC[C@@H]1c2cc(Cl)ccc2C(=O)N1c1cncc(F)c1] | (R or S)-5-Chloro-3-ethyl-2,3-dihydro-isoindol-1-one (intermediate A-13-1a) and 3-bromo-pyridine | 2 | 291.2 |
| 310 | (S or R)-5-Chloro-3-ethyl-2-(5-fluoro-pyridin-3-yl)-2,3-dihydro-isoindol-1-one | 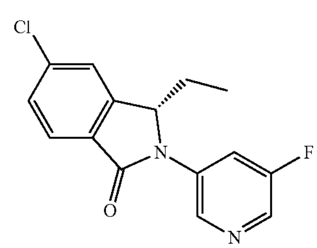 [SMILES: CC[C@H]1c2cc(Cl)ccc2C(=O)N1c1cncc(F)c1] | (S or R)-5-Chloro-3-ethyl-2,3-dihydro-isoindol-1-one (intermediate A-13-1b) and 3-bromo-pyridine | 2 | 291.2 |
| 311 | 2-(8-Amino-5,6,7,8-tetrahydro-isoquinolin-4-yl)-5-chloro-2,3-dihydro-isoindol-1-one | 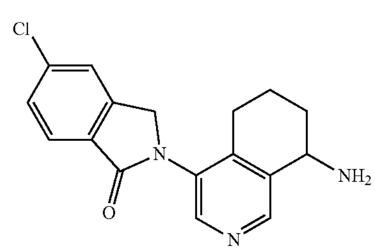 [SMILES: NC1CCCc2c1cncc2N1Cc2cc(Cl)ccc2C1=O] | 5-Chloro-2,3-dihydro-isoindol-1-one and 4-bromo-5,6,7,8-tetrahydro-isoquinolin-8-ylamine (intermediate B-12[A]) | 3[B] | 314.2 |

TABLE 9-continued

| Ex | Compound Name | Compound Structure | Starting Materials | Prepared by analogy to example | MS (M + H)+ |
|---|---|---|---|---|---|
| 312 | N-[(R or S)-4-((R or S)-5-Chloro-1-ethyl-3-oxo-1,3-dihydro-isoindol-2-yl)-5,6,7,8-tetrahydro-isoquinolin-8-yl]-propionamide | 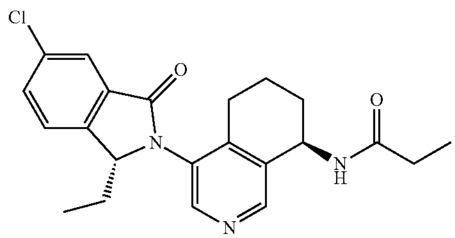 [SMILES: CCC(=O)N[C@@H]1CCCc2c1cncc2N1C(=O)c2cc(Cl)ccc2[C@H]1CC] | (R or S)-5-Chloro-3-ethyl-2,3-dihydro-isoindol-1-one (intermediate A-13-2a) and (+)-(R)-N-(4-bromo-5,6,7,8-tetrahydro-isoquinolin-8-yl)-propionamide (prep. by separation of intermediate B-12 with prep. chiral HPLC) | 3[B] | 398.1 |
| 313 | N-[(R or S)-4-((S or R)-5-Chloro-1-ethyl-3-oxo-1,3-dihydro-isoindol-2-yl)-5,6,7,8-tetrahydro-isoquinolin-8-yl]-propionamide | 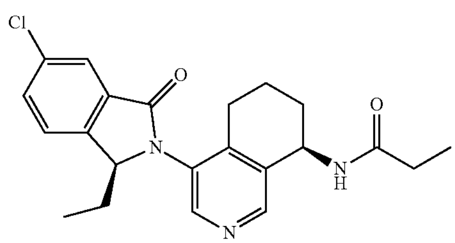 [SMILES: CCC(=O)N[C@@H]1CCCc2c1cncc2N1C(=O)c2cc(Cl)ccc2[C@@H]1CC] | (S or R)-5-Chloro-3-ethyl-2,3-dihydro-isoindol-1-one (intermediate A-13-2b) and (+)-(R)-N-(4-bromo-5,6,7,8-tetrahydro-isoquinolin-8-yl)-propionamide (prep. by separation of intermediate B-12 with prep. chiral HPLC) | 3[B] | 398.1 |
| 314 | N-[(R or S)-4-(5-Chloro-1-oxo-1,3-dihydro-isoindol-2-yl)-5,6,7,8-tetrahydro-isoquinolin-8-yl]-propionamide | 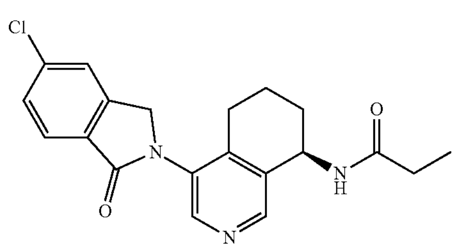 [SMILES: CCC(=O)N[C@@H]1CCCc2c1cncc2N1Cc2cc(Cl)ccc2C1=O] | 5-Chloro-2,3-dihydro-isoindol-1-one and N-(4-bromo-5,6,7,8-tetrahydro-isoquinolin-8-yl)-propionamide (intermediate B-12) | 3[B] | 370.1 |

Example 315

Ethanesulfonic acid [4-(5-chloro-1-oxo-1,3-dihydro-isoindol-2-yl)-5,6,7,8-tetrahydro-isoquinolin-8-yl]-amide

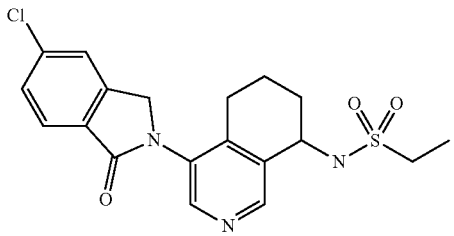 [SMILES: CCS(=O)(=O)NC1CCCc2c1cncc2N1Cc2cc(Cl)ccc2C1=O]

[A] 2-(8-Amino-5,6,7,8-tetrahydro-isoquinolin-4-yl)-5-chloro-2,3-dihydro-isoindol-1-one

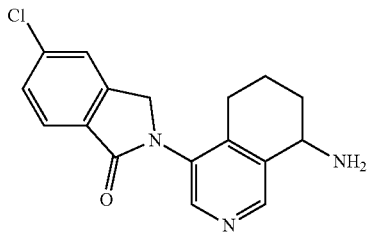 [SMILES: NC1CCCc2c1cncc2N1Cc2cc(Cl)ccc2C1=O]

In a 25 mL sealed tube, 5-chloro-2,3-dihydro-isoindol-1-one (801 mg, 4.8 mmol), 4-bromo-5,6,7,8-tetrahydroisoquinolin-8-ylamine (intermediate B-12 [A], 999 mg, 4.4 mmol), CuI (200 mg, 1.1 mmol), Cs$_2$CO$_3$ (3.0 g, 9.2 mmol) and (+)-(S,S)-1,2-diaminocyclohexane (0.4 mL, 3.2 mmol) were dissolved in dioxane (16 mL). The resulting reaction mixture was heated at 150° C. for 3 hours before it was poured into H$_2$O (50 mL) and extracted with EtOAc (2×125 mL). The organic layer was washed with brine, dried over anhydrous Na$_2$SO$_4$, filtered and concentrated in vacuo to give a crude product which was purified by silica gel flash chromatography (30-100% EtOAc-hexane gradient) to yield the title compound (1.2 g, 80%) as a light yellow solid. MS: 314.2 (M+H$^+$).

[B] Ethanesulfonic acid [4-(5-chloro-1-oxo-1,3-dihydro-isoindol-2-yl)-5,6,7,8-tetrahydro-isoquinolin-8-yl]-amide

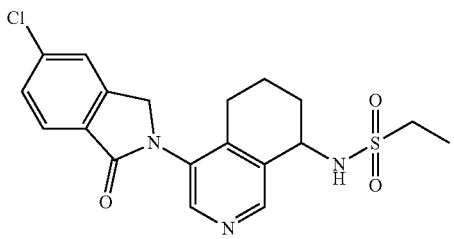 [SMILES: CCS(=O)(=O)NC1CCCc2c1cncc2N1Cc2cc(Cl)ccc2C1=O]

To a stirred solution of 2-(8-amino-5,6,7,8-tetrahydro-isoquinolin-4-yl)-5-chloro-2,3-dihydro-isoindol-1-one (156 mg, 0.5 mmol) and Et$_3$N (210 uL) in DCM (10 mL) was added ethanesulfonyl chloride (48 uL mg, 0.5 mmol) at 0° C. and stirring continued at 0° C. for 1 h. The resulting mixture was extracted with EtOAc (2×50 mL). Combined organics were washed with brine, dried over Na$_2$SO$_4$, filtered and concentrated to afford the title compound. The residue was separated by prep-HPLC to give a racemic mixture of title compound (170 mg, 84%) as a light yellow solid. MS: 406.1 (M+H$^+$).

Example 316

(+)-Ethanesulfonic acid [(R or S)-4-(5-chloro-1-oxo-1,3-dihydro-isoindol-2-yl)-5,6,7,8-tetrahydro-isoquinolin-8-yl]-amide

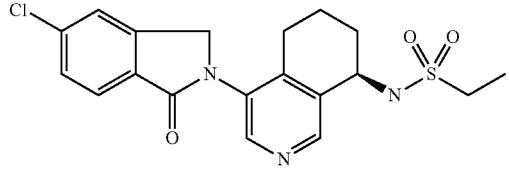 [SMILES: CCS(=O)(=O)N[C@@H]1CCCc2c1cncc2N1Cc2cc(Cl)ccc2C1=O]

Example 317

(−)-Ethanesulfonic acid [(S or R)-4-(5-chloro-1-oxo-1,3-dihydro-isoindol-2-yl)-5,6,7,8-tetrahydro-isoquinolin-8-yl]-amide

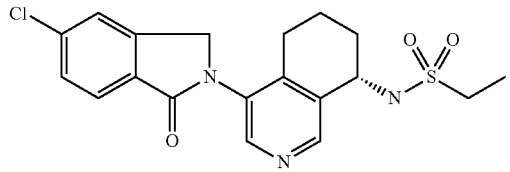 [SMILES: CCS(=O)(=O)N[C@H]1CCCc2c1cncc2N1Cc2cc(Cl)ccc2C1=O]

The racemic mixture of ethanesulfonic acid [4-(5-chloro-1-oxo-1,3-dihydro-isoindol-2-yl)-5,6,7,8-tetrahydro-isoquinolin-8-yl]-amide (170 mg, example 315) was subject to chiral HPLC separation to afford (+)-ethanesulfonic acid [(R or S)-4-(5-chloro-1-oxo-1,3-dihydro-isoindol-2-yl)-5,6,7,8-tetrahydro-isoquinolin-8-yl]-amide (47 mg, example 316), MS: 406.2 (M+H$^+$) and (−)-ethanesulfonic acid [(S or R)-4-(5-chloro-1-oxo-1,3-dihydro-isoindol-2-yl)-5,6,7,8-tetrahydro-isoquinolin-8-yl]-amide (39 mg, example 317). MS: 406.2 (M+H)$^+$.

Example 318

(−)-N—[(S or R)-4-(5-Chloro-1-oxo-1,3-dihydro-isoindol-2-yl)-6,7-dihydro-5H-[2]pyrindin-7-yl]-acetamide

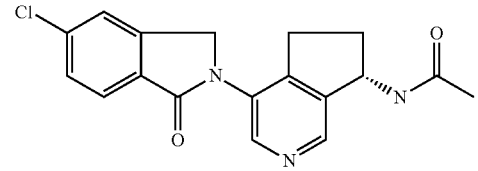 [SMILES: CC(=O)N[C@H]1CCc2c1cncc2N1Cc2cc(Cl)ccc2C1=O]

Example 319

(+)-N—[(R or S)-4-(5-Chloro-1-oxo-1,3-dihydro-isoindol-2-yl)-6,7-dihydro-5H-[2]pyrindin-7-yl]-acetamide

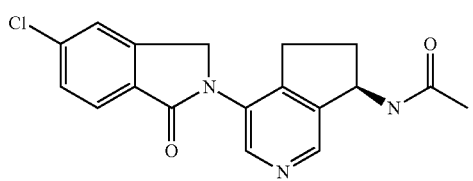 [SMILES: CC(=O)N[C@@H]1CCc2c1cncc2N1Cc2cc(Cl)ccc2C1=O]

[A] 2-(7-Amino-6,7-dihydro-5H-[2]pyrindin-4-yl)-5-chloro-2,3-dihydro-isoindol-1-one

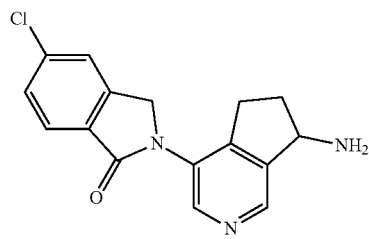 [SMILES: NC1CCc2c1cncc2N1Cc2cc(Cl)ccc2C1=O]

In a 25 mL sealed tube, 5-chloro-2,3-dihydro-isoindol-1-one (801 mg, 4.8 mmol), 4-bromo-6,7-dihydro-5H-[2]pyrindin-7-ylamine (intermediate B-18 [C], 937 mg, 4.4 mmol), CuI (200 mg, 1.1 mmol), $Cs_2CO_3$ (3.0 g, 9.2 mmol) and (+)-(S,S)-1,2-diaminocyclohexane (0.4 mL, 3.2 mmol) were dissolved in dioxane (16 mL). The resulting reaction mixture was heated at 150° C. for 3 hours before it was poured into $H_2O$ (50 mL) and extracted with EtOAc (2×125 mL). The organic layer was washed with brine, dried over anhydrous $Na_2SO_4$, filtered and concentrated in vacuo to give a crude product which was purified by silica gel flash chromatography (30-100% EtOAc-hexane gradient) to yield the title compound (1.02 g, 80%) as a light yellow solid. MS: 300.2 $(M+H^+)$.

[B] N-[4-(5-Chloro-1-oxo-1,3-dihydro-isoindol-2-yl)-6,7-dihydro-5H-[2]pyrindin-7-yl]-acetamide

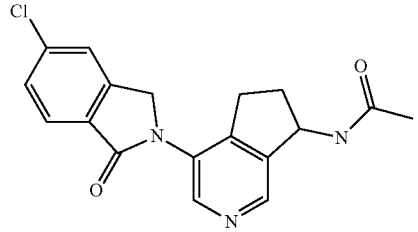 [SMILES: CC(=O)NC1CCc2c1cncc2N1Cc2cc(Cl)ccc2C1=O]

To a stirred solution of 2-(7-amino-6,7-dihydro-5H-[2]pyrindin-4-yl)-5-chloro-2,3-dihydro-isoindol-1-one (126 mg, 0.42 mmol) and $Et_3N$ (1.0 mL) in DCM (10 mL) was added acetyl chloride (0.032 mL, 0.44 mmol) at 0° C. and stirred at 0° C. for 1 hour. The resulting mixture was extracted with EtOAc (2×100 mL) and the combined organic layers were washed with brine, dried over anhy. $Na_2SO_4$, filtered and concentrated in vacuo. The residue was purified by silica gel flash chromatography eluting with a 0 to 50% EtOAc-heptane gradient to give a racemic mixture of title compound (121 mg, 85%) as light yellow solid. MS: 342.1 $(M+H^+)$. This racemic mixture was then separated by chiral HPLC to afford (−)-N-[(S or R)-4-(5-chloro-1-oxo-1,3-dihydro-isoindol-2-yl)-6,7-dihydro-5H-[2]pyrindin-7-yl]-acetamide (33 mg, example 318), MS: 342.1 $(M+H^+)$ and (+)-N—[(R or S)-4-(5-chloro-1-oxo-1,3-dihydro-isoindol-2-yl)-6,7-dihydro-5H-[2]pyrindin-7-yl]-acetamide (27 mg, example 319). MS: 342.1 $(M+H)^+$.

The following compounds listed in Table 10 were prepared in analogy to the procedures described for the preparation of examples 316 and 317 or 318 and 319 using appropriate starting materials.

TABLE 10

| Ex | Compound Name | Compound Structure | Starting Materials | Sign of Optical Rotation | MS $(M + S)^+$ |
|---|---|---|---|---|---|
| 320 | N-((R or S)-6-Chloro-1-oxo-3,4,5',6',7',8'-hexahydro-1H-[2,4']biisoquinolinyl-8'-yl)-acetamide | 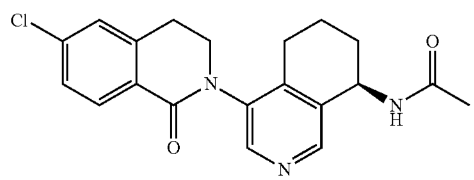 [SMILES: CC(=O)N[C@@H]1CCCc2c1cncc2N1CCc2cc(Cl)ccc2C1=O] | 6-Chloro-3,4-dihydro-2H-isoquinolin-1-one (intermediate A-2) and 4-bromo-5,6,7,8-tetrahydro-isoquinolin-8-ylamine (intermediate B-12[A]) | (+) | 370.0 |
| 321 | N-((S or R)-6-Chloro-1-oxo-3,4,5',6',7',8'-hexahydro-1H-[2,4']biisoquinolinyl-8'-yl)-acetamide | 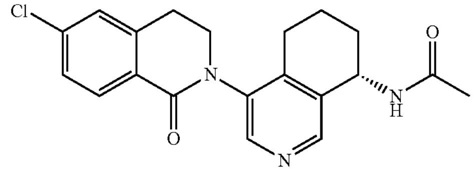 [SMILES: CC(=O)N[C@H]1CCCc2c1cncc2N1CCc2cc(Cl)ccc2C1=O] | Same as Example 320 | (−) | 370.0 |

TABLE 10-continued

| Ex | Compound Name | Compound Structure | Starting Materials | Sign of Optical Rotation | MS (M + S)+ |
|---|---|---|---|---|---|
| 322 | N-[(S or R)-4-(5-Chloro-1-oxo-1,3-dihydro-isoindol-2-yl)-5,6,7,8-tetrahydro-isoquinolin-8-yl]-acetamide | 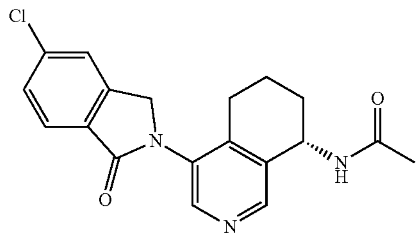 | 5-Chloro-2,3-dihydro-isoindol-1-one and 4-bromo-5,6,7,8-tetrahydro-isoquinolin-8-ylamine (intermediate B-12[A]) | (−) | 356.1 |
| 323 | N-[(R or S)-4-(5-Chloro-1-oxo-1,3-dihydro-isoindol-2-yl)-5,6,7,8-tetrahydro-isoquinolin-8-yl]-acetamide | 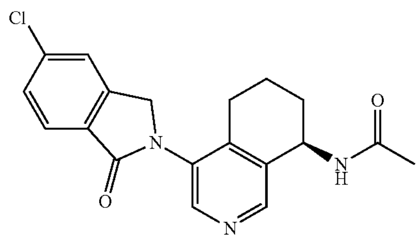 [SMILES: CC(=O)N[C@@H]1CCCc2c1cncc2N1Cc2cc(Cl)ccc2C1=O] | Same as Example 322 | (+) | 356.1 |
| 324 | N-((S or R)-6-Chloro-1-oxo-3,4,5',6',7',8'-hexahydro-1H-[2,4']biisoquinolinyl-8'-yl)-methanesulfonamide | 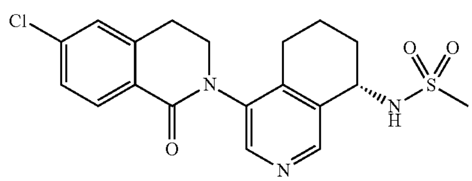 [SMILES: CS(=O)(=O)N[C@H]1CCCc2c1cncc2N1CCc2cc(Cl)ccc2C1=O] | 6-Chloro-3,4-dihydro-2H-isoquinolin-1-one (intermediate A-2) and 4-bromo-5,6,7,8-tetrahydro-isoquinolin-8-ylamine (intermediate B-12[A]) | (−) | 406.0 |
| 325 | N-((R or S)-6-Chloro-1-oxo-3,4,5',6',7',8'-hexahydro-1H-[2,4']biisoquinolinyl-8'-yl)-methanesulfonamide | 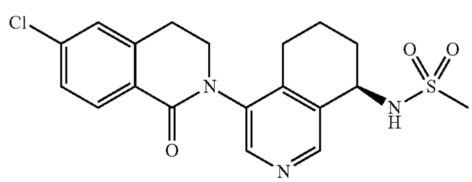 [SMILES: CS(=O)(=O)N[C@@H]1CCCc2c1cncc2N1CCc2cc(Cl)ccc2C1=O] | Same as Example 324 | (+) | 406.0 |
| 326 | N-[(S or R)-4-(5-Chloro-1-oxo-1,3-dihydro-isoindol-2-yl)-5,6,7,8-tetrahydro-isoquinolin-8-yl]-methanesulfonamide | 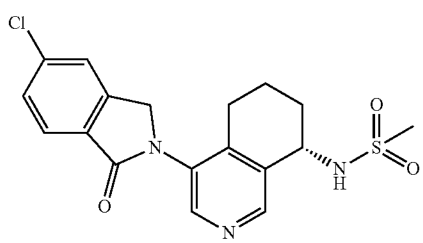 [SMILES: CS(=O)(=O)N[C@H]1CCCc2c1cncc2N1Cc2cc(Cl)ccc2C1=O] | 5-Chloro-2,3-dihydro-isoindol-1-one and 4-bromo-5,6,7,8-tetrahydro-isoquinolin-8-ylamine (intermediate B-12[A]) | (−) | 392.1 |
| 327 | N-[(R or S)-4-(5-Chloro-1-oxo-1,3-dihydro-isoindol-2-yl)-5,6,7,8-tetrahydro-isoquinolin-8-yl]-methanesulfonamide | 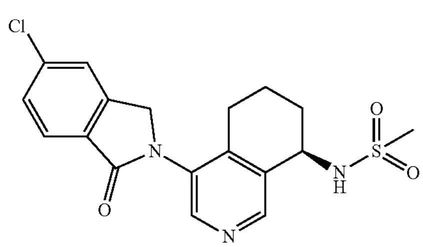 [SMILES: CS(=O)(=O)N[C@@H]1CCCc2c1cncc2N1Cc2cc(Cl)ccc2C1=O] | Same as Example 326 | (+) | 392.1 |

TABLE 10-continued

| Ex | Compound Name | Compound Structure | Starting Materials | Sign of Optical Rotation | MS (M + S)+ |
|---|---|---|---|---|---|
| 328 | N-((R or S)-6-Chloro-1-oxo-3,4,5',6',7',8'-hexahydro-1H-[2,4']biisoquinolinyl-8'-yl)-propionamide | 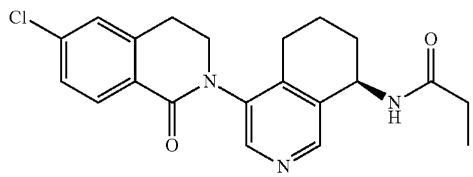 [SMILES: CCC(=O)N[C@@H]1CCCc2c1cncc2N1CCc2cc(Cl)ccc2C1=O] | 6-Chloro-3,4-dihydro-2H-isoquinolin-1-one (intermediate A-2) and 4-bromo-5,6,7,8-tetrahydro-isoquinolin-8-ylamine (intermediate B-12[A]) | (+) | 384.1 |
| 329 | N-((S or R)-6-Chloro-1-oxo-3,4,5',6',7',8'-hexahydro-1H-[2,4']biisoquinolinyl-8'-yl)-propionamide | 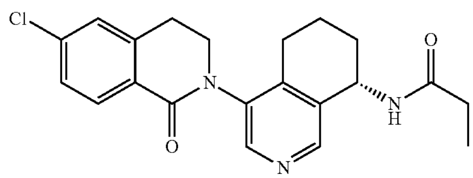 [SMILES: CCC(=O)N[C@H]1CCCc2c1cncc2N1CCc2cc(Cl)ccc2C1=O] | Same as Example 328 | (−) | 384.1 |
| 330 | N-[(S or R)-4-(6-Chloro-1-oxo-3,4-dihydro-1H-isoquinolin-2-yl)-6,7-dihydro-5H-[2]pyrindin-7-yl]-methanesulfonamide | 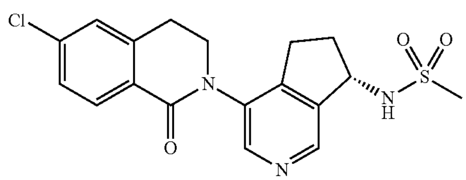 [SMILES: CS(=O)(=O)N[C@H]1CCc2c1cncc2N1CCc2cc(Cl)ccc2C1=O] | 6-Chloro-3,4-dihydro-2H-isoquinolin-1-one (intermediate A-2) and 4-bromo-6,7-dihydro-5H-[2]pyrindin-7-ylamine (intermediate B-18[C]) | (−) | 392.1 |
| 331 | N-[(R or S)-4-(6-Chloro-1-oxo-3,4-dihydro-1H-isoquinolin-2-yl)-6,7-dihydro-5H-[2]pyrindin-7-yl]-methanesulfonamide | 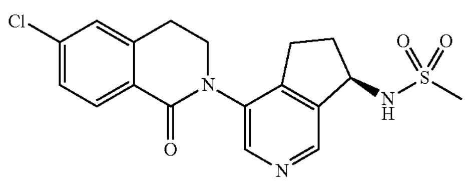 [SMILES: CS(=O)(=O)N[C@@H]1CCc2c1cncc2N1CCc2cc(Cl)ccc2C1=O] | Same as Example 330 | (+) | 392.1 |
| 332 | N-[(R or S)-4-(6-Chloro-1-oxo-3,4-dihydro-1H-isoquinolin-2-yl)-6,7-dihydro-5H-[2]pyrindin-7-yl]-acetamide | 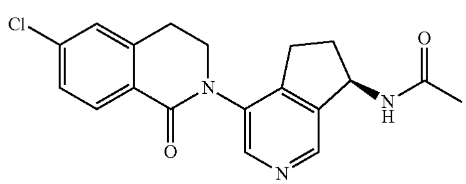 [SMILES: CC(=O)N[C@@H]1CCc2c1cncc2N1CCc2cc(Cl)ccc2C1=O] | 6-Chloro-3,4-dihydro-2H-isoquinolin-1-one (intermediate A-2) and 4-bromo-6,7-dihydro-5H-[2]pyrindin-7-ylamine (intermediate B-18[C]) | (+) | 356.1 |
| 333 | N-[(S or R)-4-(6-Chloro-1-oxo-3,4-dihydro-1H-isoquinolin-2-yl)-6,7-dihydro-5H-[2]pyrindin-7-yl]-acetamide | 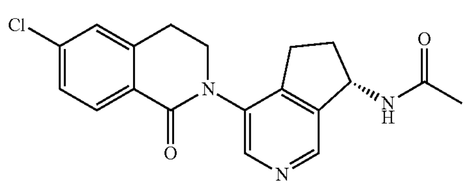 [SMILES: CC(=O)N[C@H]1CCc2c1cncc2N1CCc2cc(Cl)ccc2C1=O] | Same as Example 332 | (−) | 356.1 |
| 334 | N-[(R or S)-4-(5-Chloro-1-oxo-1,3-dihydro-isoindol-2-yl)-6,7-dihydro-5H-[2]pyrindin-7-yl]-methanesulfonamide | 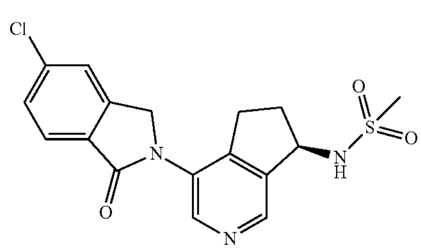 [SMILES: CS(=O)(=O)N[C@@H]1CCc2c1cncc2N1Cc2cc(Cl)ccc2C1=O] | 5-Chloro-2,3-dihydro-isoindol-1-one and 4-bromo-6,7-dihydro-5H-[2]pyrindin-7-ylamine (intermediate B-18[C]) | (+) | 378.1 |

TABLE 10-continued

| Ex | Compound Name | Compound Structure | Starting Materials | Sign of Optical Rotation | MS (M + S)+ |
|---|---|---|---|---|---|
| 335 | N-[(S or R)-4-(5-Chloro-1-oxo-1,3-dihydro-isoindol-2-yl)-6,7-dihydro-5H-[2]pyrindin-7-yl]-methanesulfonamide | 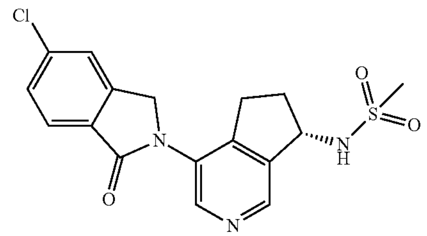 [SMILES: CS(=O)(=O)N[C@H]1CCc2c1cncc2N1Cc2cc(Cl)ccc2C1=O] | Same as Example 334 | (−) | 378.1 |
| 336 | Ethanesulfonic acid [(R or S)-4-(5-chloro-1-oxo-1,3-dihydro-isoindol-2-yl)-6,7-dihydro-5H-[2]pyrindin-7-yl]-amide | 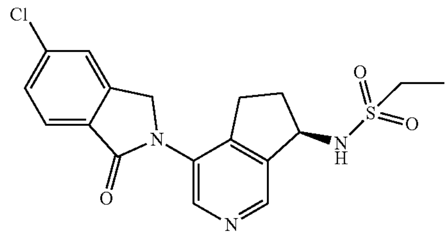 [SMILES: CCS(=O)(=O)N[C@@H]1CCc2c1cncc2N1Cc2cc(Cl)ccc2C1=O] | 5-Chloro-2,3-dihydro-isoindol-1-one and 4-bromo-6,7-dihydro-5H-[2]pyrindin-7-ylamine (intermediate B-18[C]) | (+) | 392.1 |
| 337 | Ethanesulfonic acid [(S or R)-4-(5-chloro-1-oxo-1,3-dihydro-isoindol-2-yl)-6,7-dihydro-5H-[2]pyrindin-7-yl]-amide | 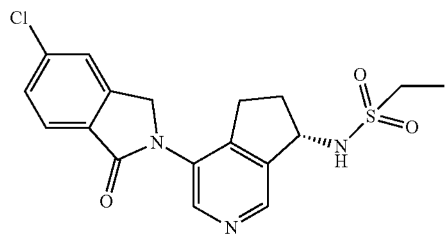 [SMILES: CCS(=O)(=O)N[C@H]1CCc2c1cncc2N1Cc2cc(Cl)ccc2C1=O] | Same as Example 336 | (−) | 392.1 |
| 338 | N-[(S or R)-4-(5-Chloro-1-oxo-1,3-dihydro-isoindol-2-yl)-6,7-dihydro-5H-[2]pyrindin-7-yl]-propionamide | 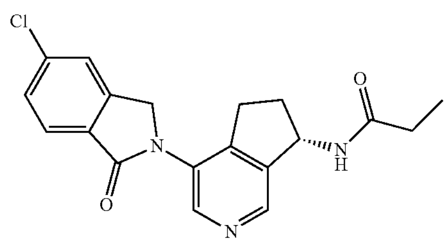 [SMILES: CCC(=O)N[C@H]1CCc2c1cncc2N1Cc2cc(Cl)ccc2C1=O] | 5-Chloro-2,3-dihydro-isoindol-1-one and 4-bromo-6,7-dihydro-5H-[2]pyrindin-7-ylamine (intermediate B-18[C]) | (−) | 356.2 |
| 339 | N-[(R or S)-4-(5-Chloro-1-oxo-1,3-dihydro-isoindol-2-yl)-6,7-dihydro-5H-[2]pyrindin-7-yl]-propionamide | 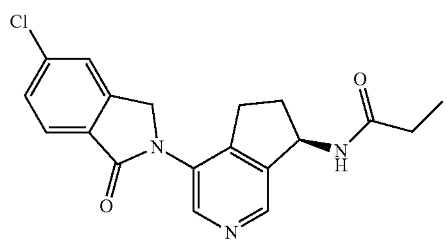 [SMILES: CCC(=O)N[C@@H]1CCc2c1cncc2N1Cc2cc(Cl)ccc2C1=O] | Same as Example 338 | (+) | 356.2 |
| 340 | 5-Chloro-2-((S)-8-hydroxy-5,6,7,8-tetrahydro-isoquinolin-4-yl)-2,3-dihydro-isoindol-1-one | 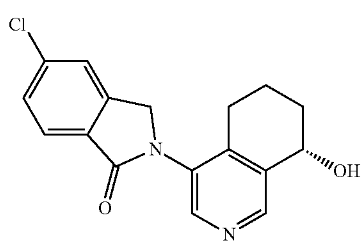 [SMILES: O=C1c2ccc(Cl)cc2CN1c1cncc2c1CCC[C@@H]2O] | 5-Chloro-2,3-dihydro-isoindol-1-one and 4-bromo-5,6,7,8-tetrahydro-isoquinolin-8-ol (intermediate B-11) | (−) | 315.1 |

TABLE 10-continued

| Ex | Compound Name | Compound Structure | Starting Materials | Sign of Optical Rotation | MS (M + S)+ |
|---|---|---|---|---|---|
| 341 | 5-Chloro-2-((R)-8-hydroxy-5,6,7,8-tetrahydro-isoquinolin-4-yl)-2,3-dihydro-isoindol-1-one | 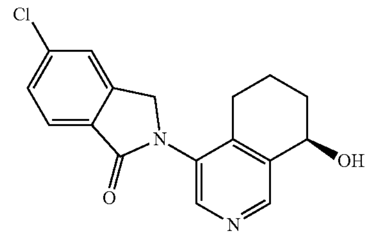 [SMILES: O=C1c2ccc(Cl)cc2CN1c1cncc2c1CCC[C@H]2O] | 5-Chloro-2,3-dihydro-isoindol-1-one and 4-bromo-5,6,7,8-tetrahydro-isoquinolin-8-ol (intermediate B-11) | (+) | 315.1 |

Example 342

(+)-N—[(S or R)-4-((R or S)-5-Chloro-3-ethyl-1-oxo-1,3-dihydro-isoindol-2-yl)-6,7-dihydro-5H-[2]pyrindin-7-yl]-acetamide

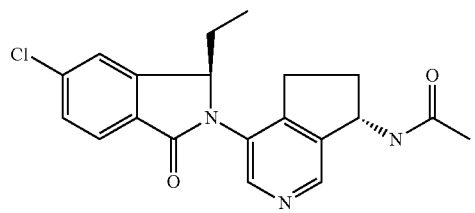 [SMILES: CC[C@@H]1c2cc(Cl)ccc2C(=O)N1c1cncc2c1CC[C@@H]2NC(C)=O]

Example 343

(−)-N—[(R or S)-4-((S or R)-5-Chloro-1-oxo-1,3-dihydro-isoindol-2-yl)-6,7-dihydro-5H-[2]pyrindin-7-yl]-acetamide

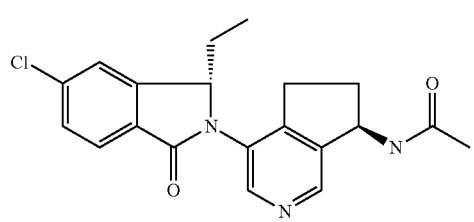 [SMILES: CC[C@H]1c2cc(Cl)ccc2C(=O)N1c1cncc2c1CC[C@H]2NC(C)=O]

Example 344

(+)-N—[(R or S)-4-((R or S)-5-Chloro-3-ethyl-1-oxo-1,3-dihydro-isoindol-2-yl)-6,7-dihydro-5H-[2]pyrindin-7-yl]-acetamide

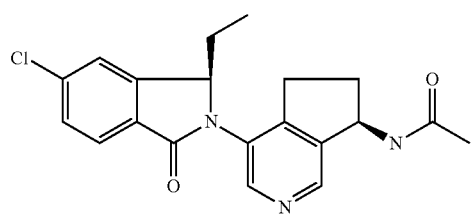 [SMILES: CC[C@@H]1c2cc(Cl)ccc2C(=O)N1c1cncc2c1CC[C@H]2NC(C)=O]

Example 345

(−)-N—[(S or R)-4-((S or R)-5-Chloro-3-ethyl-1-oxo-1,3-dihydro-isoindol-2-yl)-6,7-dihydro-5H-[2]pyrindin-7-yl]-acetamide

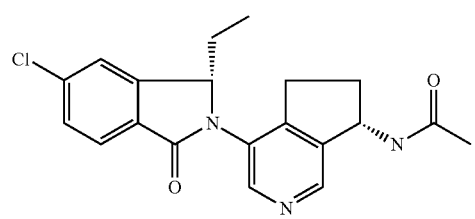 [SMILES: CC[C@H]1c2cc(Cl)ccc2C(=O)N1c1cncc2c1CC[C@@H]2NC(C)=O]

[A] 2-(7-Amino-6,7-dihydro-5H[2]pyrindin-4-yl)-5-chloro-3,3-dimethyl-2,3-dihydro-isoindol-1-one

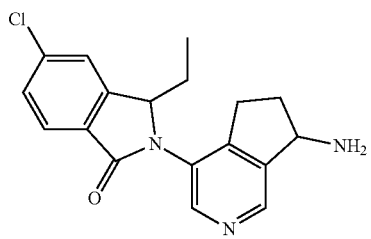 [SMILES: CCC1c2cc(Cl)ccc2C(=O)N1c1cncc2c1CCC2N]

A mixture of 5-chloro-3-ethyl-2,3-dihydro-isoindol-1-one (intermediate A-13-1, 390 mg, 2 mmol), 4-bromo-6,7-dihydro-5H-[2]pyrindin-7-ylamine (intermediate B-18[C], 318 mg, 1.5 mmol), CuI (38 mg, 0.2 mmol), (1S,2S)-cyclohexane-1,2-diamine (45 mg, 0.4 mmol) and CsCO₃ (750 mg, 4 mmol) were dissolved in dioxane (10 mL). The resulting reaction mixture was heated at 140° C. for 12 hours before it was cooled to room temperature and filtered through a pad of silica gel (0.5-1 cm) and washed with diethyl ether. The combined filtrate was concentrated in vacuo to give a crude product which was used in the next step reaction without purification. MS: 328.1 (M+H⁺).

[B] N-[4-(5-Chloro-3-ethyl-1-oxo-1,3-dihydro-isoindol-2-yl)-6,7-dihydro-5H-[2]pyrindin-7-yl]-acetamide

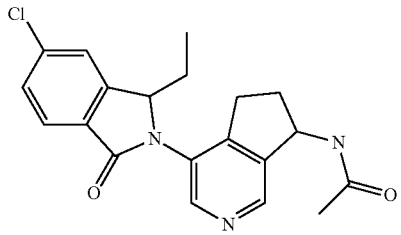 [SMILES: CCC1c2cc(Cl)ccc2C(=O)N1c1cncc2c1CCC2NC(C)=O]

To a solution of 2-(7-amino-6,7-dihydro-5H[2]pyrindin-4-yl)-5-chloro-3,3-dimethyl-2,3-dihydro-isoindol-1-one (490 mg, 1.5 mmol) in DCM (15 mL) was added Et₃N (3 mmol) and acetyl chloride (156 mg, 2 mmol) at 0° C. The resulting reaction mixture was stirred at room temperature for 1 hour before it was poured into 1 N HCl in dioxane (15 mL) and washed with EtOAc (15 mL×2). After the organic layer was decanted, the aqueous layer was adjusted to pH>8 with satd. aq. sodium bicarbonate solution. It was extracted with EtOAc (20 mL×2) and the combined organic layers was washed with brine, dried over anhy. Na₂SO₄, filtered and concentrated in vacuo to give the desired product (228 mg, 62%) as mixture of four diastereomers, which was subject to SFC separation (IC 250 mm×50 mm, 5 um, mobile phase A: supercritical CO₂, B: IPA (0.05% NH₃H₂O), A:B=60:40 at 140 mL/min) to give (+)-N—[(S or R)-4-((R or S)-5-chloro-3-ethyl-1-oxo-1,3-dihydro-isoindol-2-yl)-6,7-dihydro-5H-[2]pyrindin-7-yl]-acetamide (31 mg, example 342), MS: 370.1 (M+H⁺), (−)-N—[(R or S)-4-((S or R)-5-chloro-1-oxo-1,3-dihydro-isoindol-2-yl)-6,7-dihydro-5H-[2]pyrindin-7-yl]-acetamide (35 mg, example 343), MS: 370.1 (M+H⁺), (+)-N—[(R or S)-4-((R or S)-5-chloro-3-ethyl-1-oxo-1,3-dihydro-isoindol-2-yl)-6,7-dihydro-5H-[2]pyrindin-7-yl]-acetamide (39 mg, example 344), MS: 370.1 (M+H⁺), and (−)-N—[(S or R)-4-((S or R)-5-chloro-3-ethyl-1-oxo-1,3-dihydro-isoindol-2-yl)-6,7-dihydro-5H-[2]pyrindin-7-yl]-acetamide (34 mg, example 345), MS: 370.1 (M+H⁺).

Example 346

N-[4-(5-Chloro-3-ethyl-1-oxo-1,3-dihydro-isoindol-2-yl)-5,6,7,8-tetrahydro-isoquinolin-8-yl]-methanesulfonamide

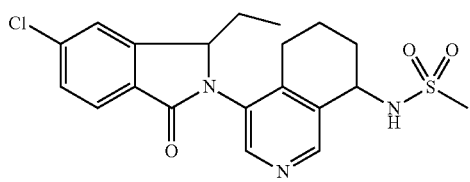 [SMILES: CCC1c2cc(Cl)ccc2C(=O)N1c1cncc2c1CCCC2NS(C)(=O)=O]

[A] 2-(8-Amino-5,6,7,8-tetrahydro-isoquinolin-4-yl)-5-chloro-3-ethyl-2,3-dihydro-isoindol-1-one

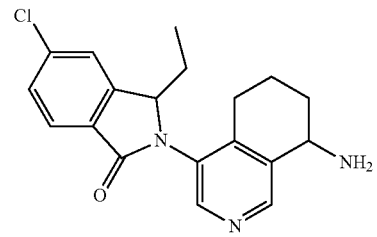 [SMILES: CCC1c2cc(Cl)ccc2C(=O)N1c1cncc2c1CCCC2N]

A mixture of 5-chloro-3-ethyl-2,3-dihydro-isoindol-1-one (intermediate A-13-1, 390 mg, 2 mmol), 4-bromo-5,6,7,8-tetrahydroisoquinoline-8-amine (intermediate B-12[A], 339 mg, 1.5 mmol), CuI (38 mg, 0.2 mmol), (1S,2S)-cyclohexane-1,2-diamine (45 mg, 0.4 mmol) and CsCO₃ (750 mg, 4 mmol) were dissolved in dioxane (10 mL) and heated at 140° C. for 12 hours. After cooling to room temperature, the reaction mixture was filtered through a pad of silica gel (0.5-1 cm) and rinsed with diethyl ether. The combined filtrate was concentrated in vacuo to afford a crude product which was used in the next step reaction without further purification. MS: 342.1 (M+H⁺)

[B] N-[4-(5-Chloro-3-ethyl-1-oxo-1,3-dihydro-isoindol-2-yl)-5,6,7,8-tetrahydro-isoquinolin-8-yl]-methanesulfonamide

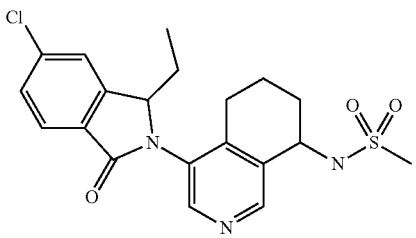 [SMILES: CCC1c2cc(Cl)ccc2C(=O)N1c1cncc2c1CCCC2NS(C)(=O)=O]

To a solution of 2-(8-amino-5,6,7,8-tetrahydro-isoquinolin-4-yl)-5-chloro-3-ethyl-2,3-dihydro-isoindol-1-one (511.5 mg, 1.5 mmol) in DCM (15 mL) was added Et₃N (3 mmol) and methanesulfonyl chloride (228 mg, 2 mmol) at 0° C. The resulting reaction mixture was stirred at room temperature for 1 hour before it was poured into 1 N HCl in dioxane (15 mL) and washed with EtOAc (15 mL×2). After the organic layer was decanted, the aqueous layer was basified to pH>8 with satd. aq. NaHCO₃ solution. After extracted with EtOAc (20 mL×2), the combined organic layers were washed with brine, dried over anhy. Na₂SO₄, filtered and concentrated in vacuo to give the title compound (228 mg, 62%) as a mixture of four diastereomers. MS: 420.1 (M+H⁺).

This mixture of diasteromers were then subject to SFC separation (IC 250 mm×50 mm, 5 um, mobile phase A: supercritical CO₂, B: IPA (0.05% NH₃H₂O), A:B=60:40 at 140 mL/min) to give four individual diasteromers (examples 347, 348, 349 and 350). MS: 420.1 (M+H⁺).

| Ex | Compound Name | Compound Structure | Sign of Optical Rotation | MS (M + S)+ |
|---|---|---|---|---|
| 347 | N-[(R or S)-4-((R or S)-5-Chloro-3-ethyl-1-oxo-1,3-dihydro-isoindol-2-yl)-5,6,7,8-tetrahydro-isoquinolin-8-yl]-methanesulfonamide | 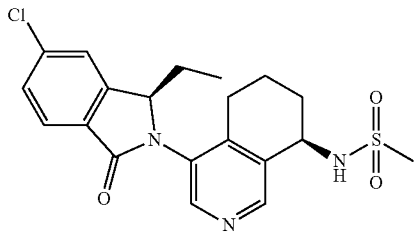 [SMILES: CC[C@@H]1c2cc(Cl)ccc2C(=O)N1c1cncc2c1CCC[C@H]2NS(C)(=O)=O] | (+) | 420.1 |
| 348 | N-[(S or R)-4-((S or R)-5-Chloro-3-ethyl-1-oxo-1,3-dihydro-isoindol-2-yl)-5,6,7,8-tetrahydro-isoquinolin-8-yl]-methanesulfonamide | 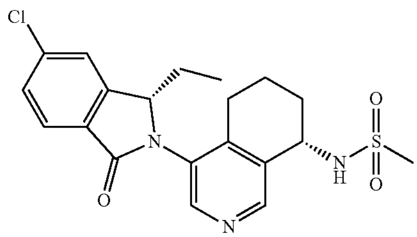 [SMILES: CC[C@H]1c2cc(Cl)ccc2C(=O)N1c1cncc2c1CCC[C@@H]2NS(C)(=O)=O] | (−) | 420.1 |
| 349 | N-[(S or R)-4-((R or S)-5-Chloro-3-ethyl-1-oxo-1,3-dihydro-isoindol-2-yl)-5,6,7,8-tetrahydro-isoquinolin-8-yl]-methanesulfonamide | 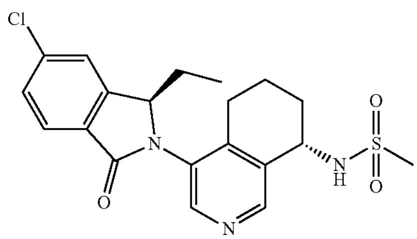 [SMILES: CC[C@@H]1c2cc(Cl)ccc2C(=O)N1c1cncc2c1CCC[C@@H]2NS(C)(=O)=O] | (+) | 420.1 |
| 350 | N-[(R or S)-4-((S or R)-5-Chloro-3-ethyl-1-oxo-1,3-dihydro-isoindol-2-yl)-5,6,7,8-tetrahydro-isoquinolin-8-yl]-methanesulfonamide | 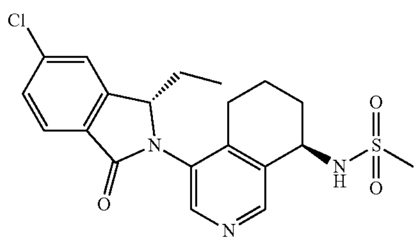 [SMILES: CC[C@H]1c2cc(Cl)ccc2C(=O)N1c1cncc2c1CCC[C@H]2NS(C)(=O)=O] | (−) | 420.1 |

The following compounds listed in Table 11 were prepared in analogy to the procedures described for the preparation of example 342, 343, 344, and 345 or examples 347, 348, 349, and 350 using appropriate starting materials.

TABLE 11

| Ex | Compound Name | Compound Structure | Optical Rotation Sign | MS (M + S)+ |
|---|---|---|---|---|
| 351 | N-[(S or R)-4-((S or R)-5-Chloro-3-ethyl-1-oxo-1,3-dihydro-isoindol-2-yl)-5,6,7,8-tetrahydro-isoquinolin-8-yl]-propionamide | 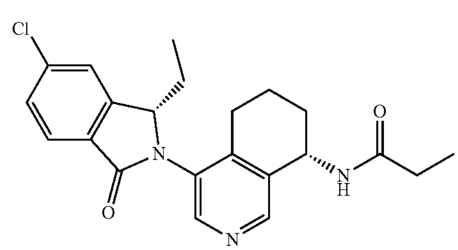 [SMILES: CCC(=O)N[C@H]1CCCc2c1cncc2N1C(=O)c2ccc(Cl)cc2[C@@H]1CC] | ND | 398.1 |

TABLE 11-continued

| Ex | Compound Name | Compound Structure | Optical Rotation Sign | MS (M + S)+ |
|---|---|---|---|---|
| 352 | N-[(S or R)-4-((R or S)-5-Chloro-3-ethyl-1-oxo-1,3-dihydro-isoindol-2-yl)-5,6,7,8-tetrahydro-isoquinolin-8-yl]-propionamide | 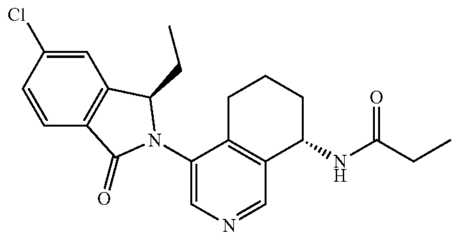 [SMILES: CCC(=O)N[C@H]1CCCc2c1cncc2N1C(=O)c2ccc(Cl)cc2[C@H]1CC] | ND | 398.1 |
| 353 | N-[(R or S)-4-((S or R)-5-Chloro-3-ethyl-1-oxo-1,3-dihydro-isoindol-2-yl)-5,6,7,8-tetrahydro-isoquinolin-8-yl]-propionamide | 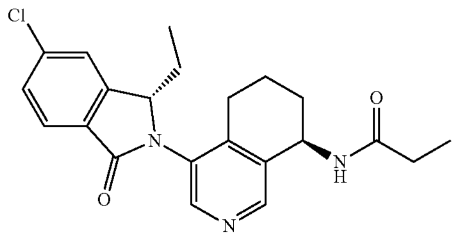 [SMILES: CCC(=O)N[C@@H]1CCCc2c1cncc2N1C(=O)c2ccc(Cl)cc2[C@@H]1CC] | ND | 398.1 |
| 354 | N-[(R or S)-4-((R or S)-5-Chloro-3-ethyl-1-oxo-1,3-dihydro-isoindol-2-yl)-5,6,7,8-tetrahydro-isoquinolin-8-yl]-propionamide | 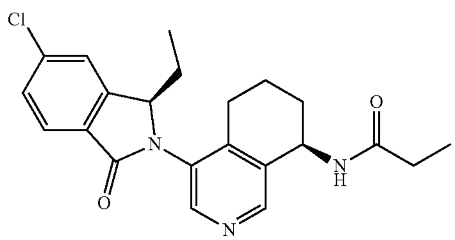 [SMILES: CCC(=O)N[C@@H]1CCCc2c1cncc2N1C(=O)c2ccc(Cl)cc2[C@H]1CC] | ND | 398.1 |
| 355 | N-[(S or R)-4-((R or S)-5-Chloro-3-ethyl-1-oxo-1,3-dihydro-isoindol-2-yl)-5,6,7,8-tetrahydro-isoquinolin-8-yl]-acetamide | 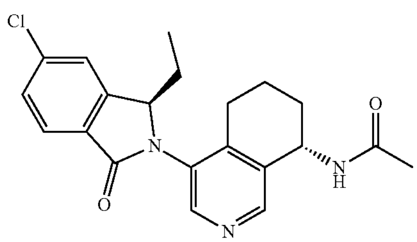 | (−) | 384.1 |
| 356 | N-[(S or R)-4-((S or R)-5-Chloro-3-ethyl-1-oxo-1,3-dihydro-isoindol-2-yl)-5,6,7,8-tetrahydro-isoquinolin-8-yl]-acetamide | 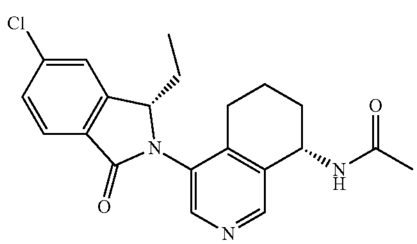 [SMILES: CC[C@H]1c2cc(Cl)ccc2C(=O)N1c1cncc2c1CCC[C@@H]2NC(C)=O] | (−) | 384.1 |
| 357 | N-[(R or S)-4-((S or R)-5-Chloro-3-ethyl-1-oxo-1,3-dihydro-isoindol-2-yl)-5,6,7,8-tetrahydro-isoquinolin-8-yl]-acetamide | 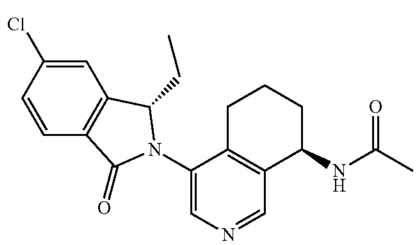 [SMILES: CC[C@H]1c2cc(Cl)ccc2C(=O)N1c1cncc2c1CCC[C@H]2NC(C)=O] | (+) | 384.1 |

TABLE 11-continued

| Ex | Compound Name | Compound Structure | Optical Rotation Sign | MS (M + S)+ |
|---|---|---|---|---|
| 358 | N-[(R or S)-4-((R or S)-5-Chloro-3-ethyl-1-oxo-1,3-dihydro-isoindol-2-yl)-5,6,7,8-tetrahydro-isoquinolin-8-yl]-acetamide | 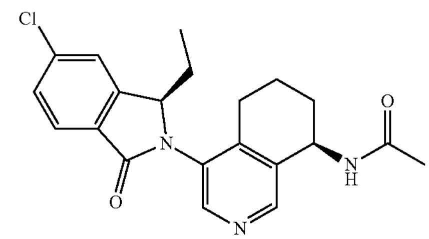 [SMILES: CC[C@@H]1c2cc(Cl)ccc2C(=O)N1c1cncc2c1CCC[C@H]2NC(C)=O] | (+) | 384.1 |
| 359 | N-[(R or S)-4-((S or R)-5-Chloro-3-methyl-1-oxo-1,3-dihydro-isoindol-2-yl)-5,6,7,8-tetrahydro-isoquinolin-8-yl]-propionamide | 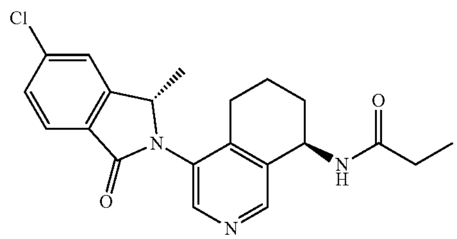 [SMILES: CCC(=O)N[C@@H]1CCCc2c1cncc2N1C(=O)c2ccc(Cl)cc2[C@@H]1C] | (+) | 384.3 |
| 360 | N-[(S or R)-4-((R or S)-5-Chloro-3-methyl-1-oxo-1,3-dihydro-isoindol-2-yl)-5,6,7,8-tetrahydro-isoquinolin-8-yl]-propionamide | 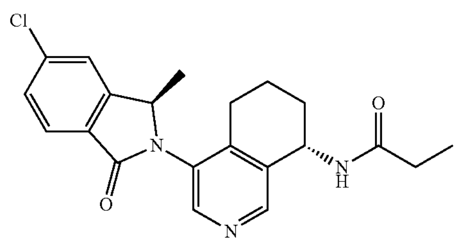 [SMILES: CCC(=O)N[C@H]1CCCc2c1cncc2N1C(=O)c2ccc(Cl)cc2[C@H]1C] | (−) | 384.3 |
| 361 | N-[(R or S)-4-((R or S)-5-Chloro-3-methyl-1-oxo-1,3-dihydro-isoindol-2-yl)-5,6,7,8-tetrahydro-isoquinolin-8-yl]-propionamide | 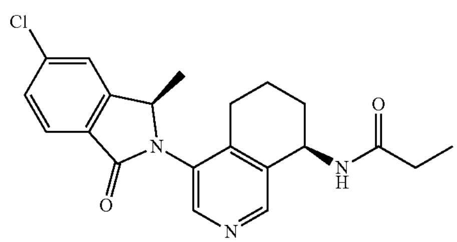 [SMILES: CCC(=O)N[C@@H]1CCCc2c1cncc2N1C(=O)c2ccc(Cl)cc2[C@H]1C] | (+) | 384.3 |
| 362 | N-[(S or R)-4-((S or R)-5-Chloro-3-methyl-1-oxo-1,3-dihydro-isoindol-2-yl)-5,6,7,8-tetrahydro-isoquinolin-8-yl]-propionamide | 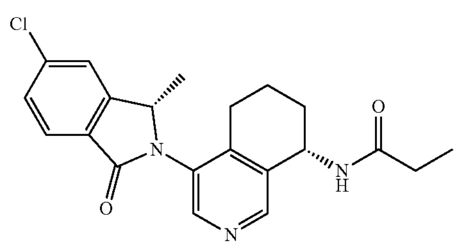 [SMILES: CCC(=O)N[C@H]1CCCc2c1cncc2N1C(=O)c2ccc(Cl)cc2[C@@H]1C] | (−) | 384.3 |
| 363 | N-[(S or R)-4-((R or S)-5-Chloro-3-methyl-1-oxo-1,3-dihydro-isoindol-2-yl)-5,6,7,8-tetrahydro-isoquinolin-8-yl]-acetamide | 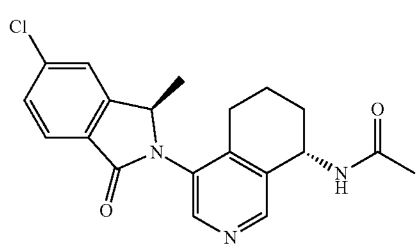 [SMILES: CC(=O)N[C@H]1CCCc2c1cncc2N1C(=O)c2ccc(Cl)cc2[C@H]1C] | (−) | 370.2 |

TABLE 11-continued

| Ex | Compound Name | Compound Structure | Optical Rotation Sign | MS (M + S)+ |
|---|---|---|---|---|
| 364 | N-[(R or S)-4-((R or S)-5-Chloro-3-methyl-1-oxo-1,3-dihydro-isoindol-2-yl)-5,6,7,8-tetrahydro-isoquinolin-8-yl]-acetamide | 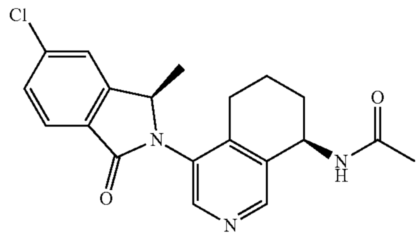 [SMILES: CC(=O)N[C@@H]1CCCc2c1cncc2N1C(=O)c2ccc(Cl)cc2[C@H]1C] | (+) | 370.2 |
| 365 | N-[(S or R)-4-((S or R)-5-Chloro-3-methyl-1-oxo-1,3-dihydro-isoindol-2-yl)-5,6,7,8-tetrahydro-isoquinolin-8-yl]-acetamide | 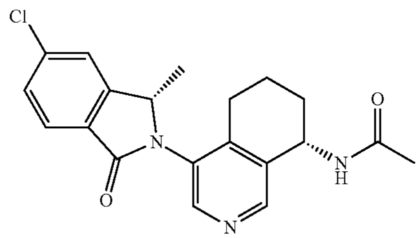 [SMILES: CC(=O)N[C@H]1CCCc2c1cncc2N1C(=O)c2ccc(Cl)cc2[C@@H]1C] | (−) | 370.2 |
| 366 | N-[(R or S)-4-((S or R)-5-Chloro-3-methyl-1-oxo-1,3-dihydro-isoindol-2-yl)-5,6,7,8-tetrahydro-isoquinolin-8-yl]-acetamide | 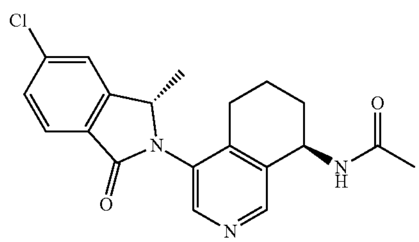 | (+) | 370.2 |
| 367 | N-[(S or R)-4-((R or S)-5-Chloro-3-ethyl-1-oxo-1,3-dihydro-isoindol-2-yl)-6,7-dihydro-5H-[2]pyrindin-7-yl]-methanesulfonamide | 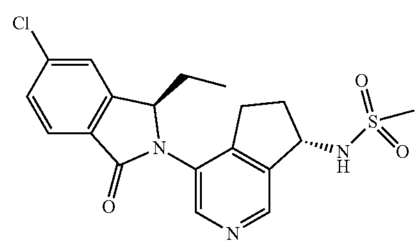 | (+) | 406.1 |
| 368 | N-[(R or S)-4-((S or R)-5-Chloro-3-ethyl-1-oxo-1,3-dihydro-isoindol-2-yl)-6,7-dihydro-5H-[2]pyrindin-7-yl]-methanesulfonamide | 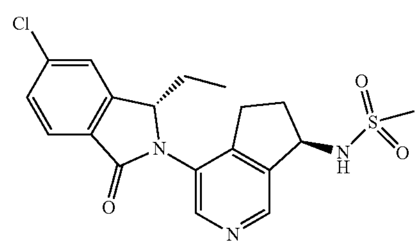 [SMILES: CC[C@H]1c2cc(Cl)ccc2C(=O)N1c1cncc2c1CC[C@H]2NS(C)(=O)=O] | (−) | 406.1 |
| 369 | N-[(R or S)-4-((R or S)-5-Chloro-3-ethyl-1-oxo-1,3-dihydro-isoindol-2-yl)-6,7-dihydro-5H-[2]pyrindin-7-yl]-methanesulfonamide | 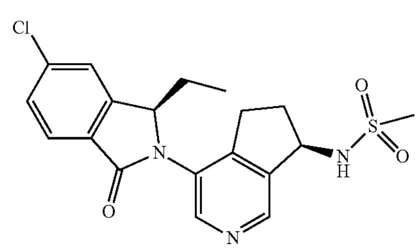 [SMILES: CC[C@@H]1c2cc(Cl)ccc2C(=O)N1c1cncc2c1CC[C@H]2NS(C)(=O)=O] | (+) | 406.1 |

TABLE 11-continued

| Ex | Compound Name | Compound Structure | Optical Rotation Sign | MS (M + S)+ |
|---|---|---|---|---|
| 370 | N-[(S or R)-4-((S or R)-5-Chloro-3-ethyl-1-oxo-1,3-dihydro-isoindol-2-yl)-6,7-dihydro-5H-[2]pyrindin-7-yl]-methanesulfonamide | 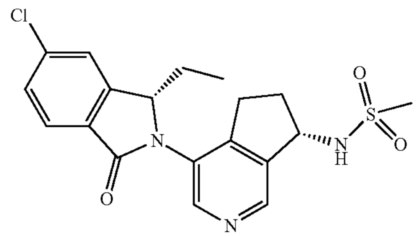 [SMILES: CC[C@H]1c2cc(Cl)ccc2C(=O)N1c1cncc2c1CC[C@@H]2NS(C)(=O)=O] | (−) | 406.1 |
| 371 | N-[(S or R)-4-((S or R)-5-Chloro-3-cyclopropyl-1-oxo-1,3-dihydro-isoindol-2-yl)-5,6,7,8-tetrahydro-isoquinolin-8-yl]-acetamide | 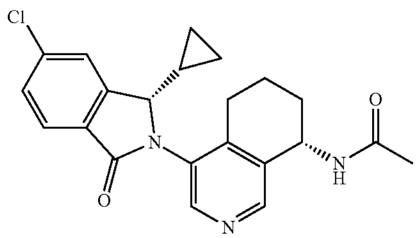 [SMILES: CC(=O)N[C@H]1CCCc2c1cncc2N1C(=O)c2ccc(Cl)cc2[C@@H]1C1CC1] | (−) | 396.1 |
| 372 | N-[(R or S)-4-((R or S)-5-Chloro-3-cyclopropyl-1-oxo-1,3-dihydro-isoindol-2-yl)-5,6,7,8-tetrahydro-isoquinolin-8-yl]-acetamide | 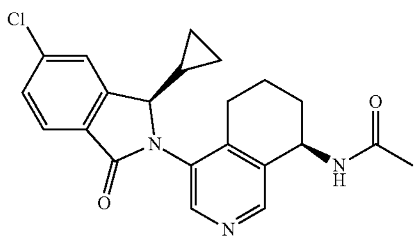 [SMILES: CC(=O)N[C@@H]1CCCc2c1cncc2N1C(=O)c2ccc(Cl)cc2[C@H]1C1CC1] | (+) | 396.1 |
| 373 | N-[(S or R)-4-((R or S)-5-Chloro-3-cyclopropyl-1-oxo-1,3-dihydro-isoindol-2-yl)-5,6,7,8-tetrahydro-isoquinolin-8-yl]-acetamide | 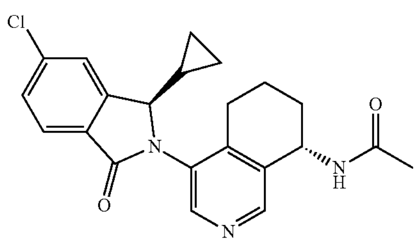 [SMILES: CC(=O)N[C@H]1CCCc2c1cncc2N1C(=O)c2ccc(Cl)cc2[C@H]1C1CC1] | (+) | 396.1 |
| 374 | N-[(R or S)-4-((S or R)-5-Chloro-3-cyclopropyl-1-oxo-1,3-dihydro-isoindol-2-yl)-5,6,7,8-tetrahydro-isoquinolin-8-yl]-acetamide | 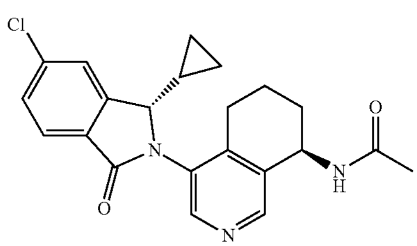 [SMILES: CC(=O)N[C@@H]1CCCc2c1cncc2N1C(=O)c2ccc(Cl)cc2[C@@H]1C1CC1] | (−) | 396.1 |
| 375 | N-[(R or S)-4-((S or R)-5-Chloro-3-methyl-1-oxo-1,3-dihydro-isoindol-2-yl)-6,7-dihydro-5H-[2]pyrindin-7-yl]-propionamide | 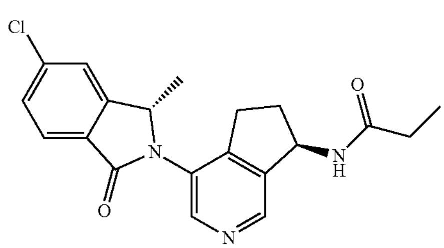 [SMILES: CCC(=O)N[C@@H]1CCc2c1cncc2N1C(=O)c2ccc(Cl)cc2[C@@H]1C] | (−) | 370.1 |

TABLE 11-continued

| Ex | Compound Name | Compound Structure | Optical Rotation Sign | MS (M + S)+ |
|---|---|---|---|---|
| 376 | N-[(R or S)-4-((R or S)-5-Chloro-3-methyl-1-oxo-1,3-dihydro-isoindol-2-yl)-6,7-dihydro-5H-[2]pyrindin-7-yl]-propionamide | 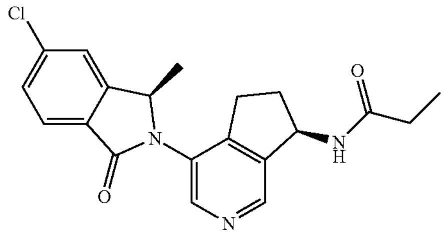 [SMILES: CCC(=O)N[C@@H]1CCc2c1cncc2N1C(=O)c2ccc(Cl)cc2[C@H]1C] | (+) | 370.1 |
| 377 | N-[(S or R)-4-((R or S)-5-Chloro-3-methyl-1-oxo-1,3-dihydro-isoindol-2-yl)-6,7-dihydro-5H-[2]pyrindin-7-yl]-propionamide | 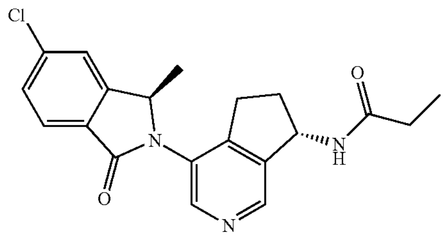 [SMILES: CCC(=O)N[C@H]1CCc2c1cncc2N1C(=O)c2ccc(Cl)cc2[C@H]1C] | (+) | 370.1 |
| 378 | N-[(S or R)-4-((S or R)-5-Chloro-3-methyl-1-oxo-1,3-dihydro-isoindol-2-yl)-6,7-dihydro-5H-[2]pyrindin-7-yl]-propionamide | 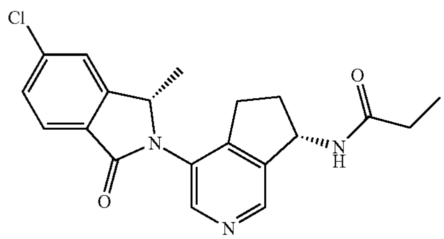 [SMILES: CCC(=O)N[C@H]1CCc2c1cncc2N1C(=O)c2ccc(Cl)cc2[C@@H]1C] | (−) | 370.1 |

The following compounds listed in Table 12 were prepared in analogy to the procedure described for the preparation of example 140 using appropriate starting materials.

TABLE 12

| Ex | Compound Name | Compound Structure | Starting Materials | MS (M + H)+ |
|---|---|---|---|---|
| 379 | 5-Chloro-3,3-dimethyl-2-(5-pyrazol-1-ylmethyl-pyridin-3-yl)-2,3-dihydro-isoindol-1-one | 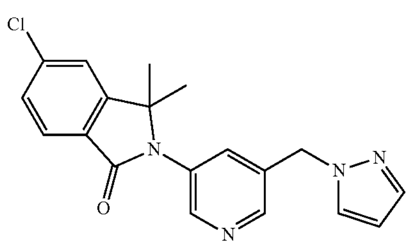 [SMILES: CC1(C)c2cc(Cl)ccc2C(=O)N1c1cncc(Cn2cccn2)c1] | 5-Chloro-2-(5-chloromethyl-pyridin-3-yl)-3,3-dimethyl-2,3-dihydro-isoindol-1-one (intermediate A-12-1) and 1H-pyrazole | 353.1 |
| 380 | 2-[5-(3-Amino-pyrazol-1-ylmethyl)-pyridin-3-yl]-5-chloro-3,3-dimethyl-2,3-dihydro-isoindol-1-one | 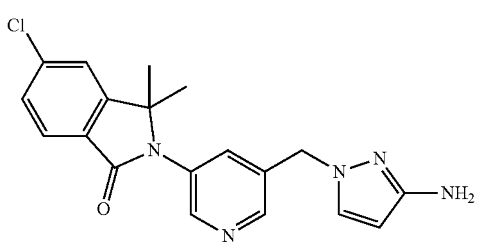 [SMILES: CC1(C)c2cc(Cl)ccc2C(=O)N1c1cncc(Cn2ccc(N)n2)c1] | 5-Chloro-2-(5-chloromethyl-pyridin-3-yl)-3,3-dimethyl-2,3-dihydro-isoindol-1-one (intermediate A-12-1) and 3-aminopyrazole | 368.2 |

TABLE 12-continued

| Ex | Compound Name | Compound Structure | Starting Materials | MS (M + H)+ |
|---|---|---|---|---|
| 381 | 5-Chloro-3,3-dimethyl-2-{5-[(1H-pyrazol-3-ylamino)-methyl]-pyridin-3-yl}-2,3-dihydro-isoindol-1-one | 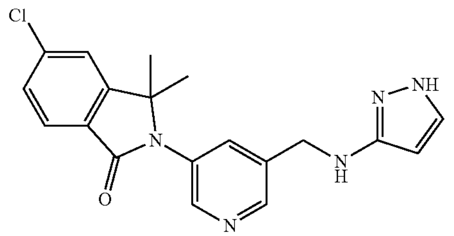 [SMILES: CC1(C)c2cc(Cl)ccc2C(=O)N1c1cncc(CNc2cc[nH]n2)c1] | 5-Chloro-2-(5-chloromethyl-pyridin-3-yl)-3,3-dimethyl-2,3-dihydro-isoindol-1-one (intermediate A-12-1) and 3-aminopyrazole | 368.2 |
| 382 | 2-[5-(3-Amino-pyrazol-1-ylmethyl)-pyridin-3-yl]-6-chloro-3,4-dihydro-2H-isoquinolin-1-one | 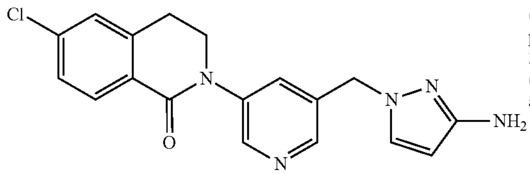 [SMILES: Nc1ccn(Cc2cncc(N3CCc4cc(Cl)ccc4C3=O)c2)n1] | 6-Chloro-2-(5-chloromethyl-pyridin-3-yl)-3,4-dihydro-2H-isoquinolin-1-one (example 140 [A]) and 3-aminopyrazole | 354.0 |
| 383 | 2-Chloro-7,7-dimethyl-6-{5-[(1H-pyrazol-3-ylamino)-methyl]-pyridin-3-yl}-6,7-dihydro-pyrrolo[3,4-b]pyridin-5-one | 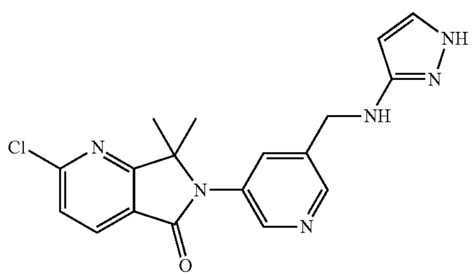 [SMILES: CC1(C)c2nc(Cl)ccc2C(=O)N1c1cncc(CNc2cc[nH]n2)c1] | 2-Chloro-6-(5-chloromethyl-pyridin-3-yl)-7,7-dimethyl-6,7-dihydro-pyrrolo[3,4-b]pyridin-5-one (intermediate A-16-1) and 3-aminopyrazole | 369.1 |
| 384 | 2-Methoxy-7,7-dimethyl-6-{5-[(1H-pyrazol-3-ylamino)-methyl]-pyridin-3-yl}-6,7-dihydro-pyrrolo[3,4-b]pyridin-5-one | 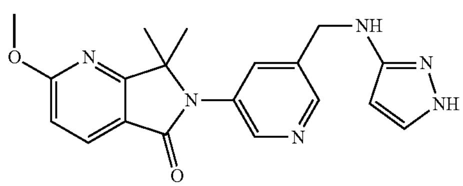 [SMILES: COc1ccc2c(n1)C(C)(C)N(c1cncc(CNc3cc[nH]n3)c1)C2=O] | 6-(5-Chloromethyl-pyridin-3-yl)-2-methoxy-7,7-dimethyl-6,7-dihydro-pyrrolo[3,4-b]pyridin-5-one (intermediate A-17-1) and 3-aminopyrazole | 365.2 |
| 385 | 2-Ethoxy-7,7-dimethyl-6-{5-[(1H-pyrazol-3-ylamino)-methyl]-pyridin-3-yl}-6,7-dihydro-pyrrolo[3,4-b]pyridin-5-one | 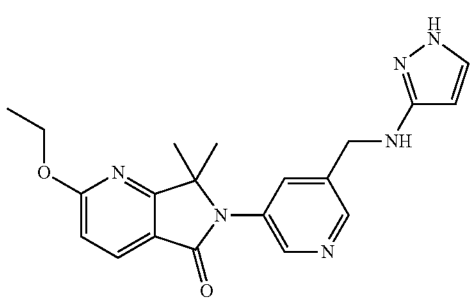 [SMILES: CCOc1ccc2c(n1)C(C)(C)N(c1cncc(CNc3cc[nH]n3)c1)C2=O] | 6-(5-Chloromethyl-pyridin-3-yl)-2-ethoxy-7,7-dimethyl-6,7-dihydro-pyrrolo[3,4-b]pyridin-5-one (intermediate A-18-1) and 3-aminopyrazole | 379.2 |
| 386 | 6'-Chloro-2'-{5-[(1H-pyrazol-3-ylamino)methyl]pyridin-3-yl}spiro[cyclopropane-1,1'-isoindol]-3'(2'H)-one | 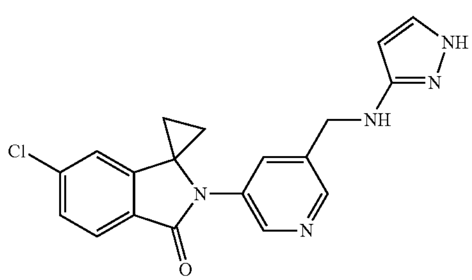 [SMILES: O=C1c2ccc(Cl)cc2C2(CC2)N1c1cncc(CNc2cc[nH]n2)c1] | 6'-Chloro-2'-(5-(chloromethyl)pyridin-3-yl)spiro[cyclopropane-1,1'-isoindolin]-3'-one (intermediate A-22-1) and 3-aminopyrazole | 366.2 |

TABLE 12-continued

| Ex | Compound Name | Compound Structure | Starting Materials | MS (M + H)+ |
|---|---|---|---|---|
| 387 | Ethanesulfonic acid [5-(6-chloro-1,1-dimethyl-3-oxo-1,3-dihydro-isoindol-2-yl)-pyridin-3-ylmethyl]-amide | 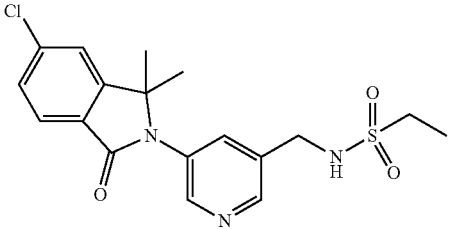 | 5-Chloro-2-(5-chloromethyl-pyridin-3-yl)-3,3-dimethyl-2,3-dihydro-isoindol-1-one (intermediate A-12-1) and ethanesulfonic acid amide | 394.1 |
| 388 | Ethanesulfonic acid [5-(6-fluoro-1,1-dimethyl-3-oxo-1,3-dihydro-isoindol-2-yl)-pyridin-3-ylmethyl]-amide | 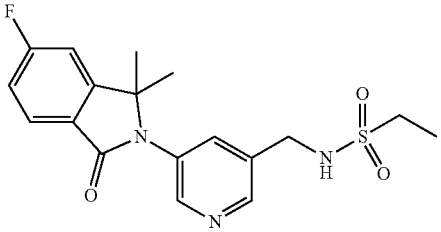 [SMILES: CCS(=O)(=O)NCc1cncc(N2C(=O)c3ccc(F)cc3C2(C)C)c1] | 2-(5-Chloromethyl-pyridin-3-yl)-5-fluoro-3,3-dimethyl-2,3-dihydro-isoindol-1-one (intermediate A-19-1) and ethanesulfonic acid amide | 378.1 |
| 389 | Ethanesulfonic acid [5-(6-cyano-1,1-dimethyl-3-oxo-1,3-dihydro-isoindol-2-yl)-pyridin-3-ylmethyl]-amide | 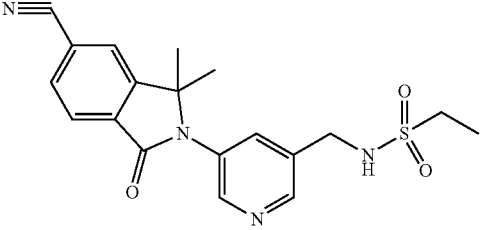 [SMILES: CCS(=O)(=O)NCc1cncc(N2C(=O)c3ccc(C#N)cc3C2(C)C)c1] | 2-(5-Chloromethyl-pyridin-3-yl)-3,3-dimethyl-1-oxo-2,3-dihydro-1H-isoindole-5-carbonitrile (intermediate A-21-1) and ethanesulfonic acid amide | 385.1 |
| 390 | Ethanesulfonic acid [5-((S or R)-5-chloro-3-ethyl-1-oxo-1,3-dihydro-isoindol-2-yl)-pyridin-3-ylmethyl]-amide | 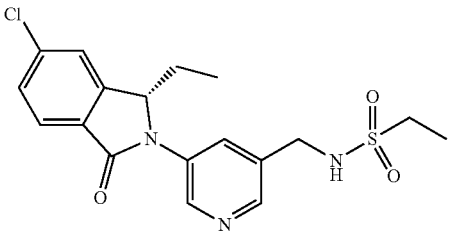 [SMILES: CC[C@H]1c2cc(Cl)ccc2C(=O)N1c1cncc(CNS(=O)(=O)CC)c1] | (S or R)-5-Chloro-2-(5-chloromethyl-pyridin-3-yl)-3-ethyl-2,3dihydro-isoindol-1-one (intermediate A-13-3) and ethanesulfonic acid amide | 394.1 |
| 391 | N-[5-(6-Chloro-1,1-dimethyl-3-oxo-1,3-dihydro-isoindol-2-yl)-pyridin-3-ylmethyl]-methanesulfonamide | 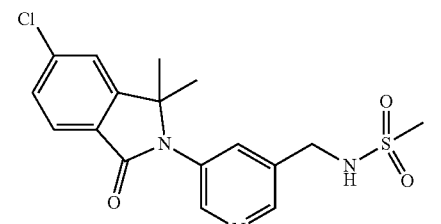 | 5-Chloro-2-(5-chloromethyl-pyridin-3-yl)-3,3-dimethyl-2,3-dihydro-isoindol-1-one (intermediate A-12-1) and methanesulfonamide | 380.1 |
| 392 | N-[5-(6-Chloro-1,1-dimethyl-3-oxo-1,3-dihydro-isoindol-2-yl)-pyridin-3-ylmethyl]-N-methyl-methanesulfonamide | 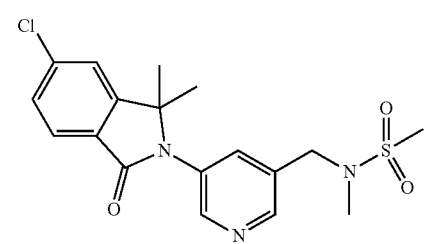 [SMILES: CN(Cc1cncc(N2C(=O)c3ccc(Cl)cc3C2(C)C)c1)S(C)(=O)=O] | 5-Chloro-2-(5-chloromethyl-pyridin-3-yl)-3,3-dimethyl-2,3-dihydro-isoindol-1-one (intermediate A-12-1) and N-methyl-methanesulfonic acid amide | 394.1 |

TABLE 12-continued

| Ex | Compound Name | Compound Structure | Starting Materials | MS (M + H)+ |
|---|---|---|---|---|
| 393 | N-{[5-(6'-Fluoro-3'-oxospiro[cyclopropane-1,1'-isoindol]-2'(3'H)-yl)pyridin-3-yl]methyl}ethanesulfonamide | 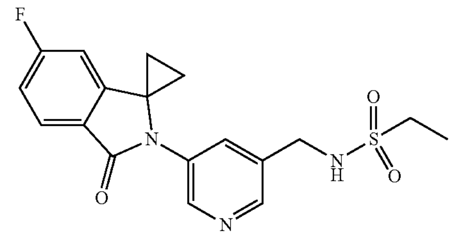 [SMILES: CCS(=O)(=O)NCc1cncc(N2C(=O)c3ccc(F)cc3C23CC3)c1] | 2'-(5-(Chloromethyl)pyridin-3-yl)-6'-fluorospiro[cyclopropane-1,1'-isoindolin]-3'-one (intermediate A-23-1) and ethanesulfonamide | 376.1 |
| 394 | N-{[5-(6'-Fluoro-3'-oxospiro[cyclopropane-1,1'-isoindol]-2'(3'H)-yl)pyridin-3-yl]methyl}-N-methylethanesulfonamide | 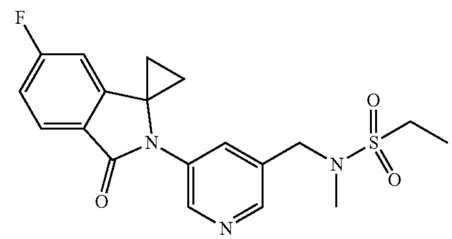 [SMILES: CCS(=O)(=O)N(C)Cc1cncc(N2C(=O)c3ccc(F)cc3C23CC3)c1] | 2'-(5-(Chloromethyl)pyridin-3-yl)-6'-fluorospiro[cyclopropane-1,1'-isoindolin]-3'-one (intermediate A-23-1) and ethanesulfonic acid methylamide | 390.1 |
| 395 | Ethanesulfonic acid [5-(6-chloro-1,1-dimethyl-3-oxo-1,3-dihydro-isoindol-2-yl)-pyridin-3-ylmethyl]-methyl-amide | 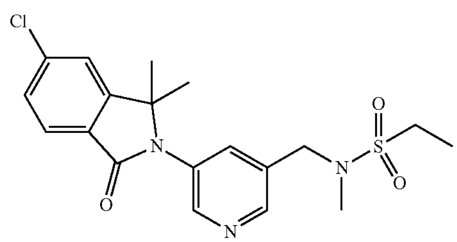 [SMILES: CCS(=O)(=O)N(C)Cc1cncc(N2C(=O)c3ccc(Cl)cc3C2(C)C)c1] | 5-Chloro-2-(5-chloromethyl-pyridin-3-yl)-3,3-dimethyl-2,3-dihydro-isoindol-1-one (intermediate A-12-1) and ethanesulfonic acid methylamide | 408.1 |
| 396 | N-{[5-(6'-Chloro-3'-oxospiro[cyclopropane-1,1'-isoindol]-2'(3'H)-yl)pyridin-3-yl]methyl}propanamide | 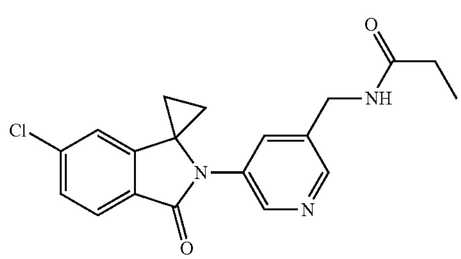 [SMILES: CCC(=O)NCc1cncc(N2C(=O)c3ccc(Cl)cc3C23CC3)c1] | 6'-Chloro-2'-(5-(chloromethyl)pyridin 3 yl)spiro[cyclopropane-1,1'-isoindolin]-3'-one (intermediate A-22-1) and propionamide | 356.1 |
| 397 | N-[5-(6-Chloro-1,1-dimethyl-3-oxo-1,3-dihydro-isoindol-2-yl)-pyridin-3-ylmethyl]-propionamide | 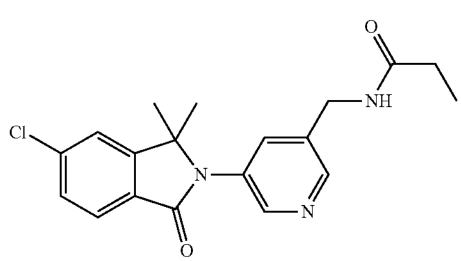 [SMILES: CCC(=O)NCc1cncc(N2C(=O)c3ccc(Cl)cc3C2(C)C)c1] | 5-Chloro-2-(5-chloromethyl-pyridin-3-yl)-3,3-dimethyl-2,3-dihydro-isoindol-1-one (intermediate A-12-1) and propionamide | 358.1 |
| 398 | N-[5-(6-Fluoro-1,1-dimethyl-3-oxo-1,3-dihydro-isoindol-2-yl)-pyridin-3-ylmethyl]-propionamide | 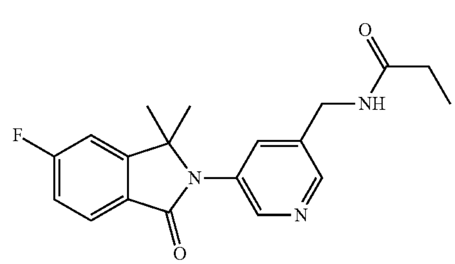 [SMILES: CCC(=O)NCc1cncc(N2C(=O)c3ccc(F)cc3C2(C)C)c1] | 2-(5-Chloromethyl-pyridin-3-yl)-5-fluoro-3,3-dimethyl-2,3-dihydro-isoindol-1-one (intermediate A-19-1) and propionamide | 342.1 |

TABLE 12-continued

| Ex | Compound Name | Compound Structure | Starting Materials | MS (M + H)+ |
|---|---|---|---|---|
| 399 | N-[5-((S or R)-5-Chloro-3-ethyl-1-oxo-1,3-dihydro-isoindol-2-yl)-pyridin-3-ylmethyl]-propionamide | 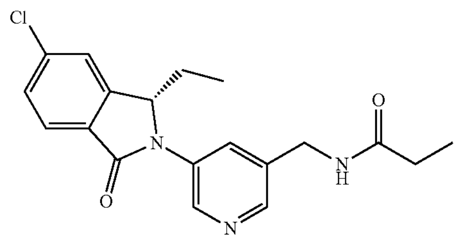 [SMILES: CCC(=O)NCc1cncc(N2C(=O)c3ccc(Cl)cc3[C@@H]2CC)c1] | (S or R)-5-Chloro-2-(5-chloromethyl-pyridin-3-yl)-3-ethyl-2,3-dihydro-isoindol-1-one (intermediate A-13-3) and propionamide | 358.1 |
| 400 | N-[5-(6-Chloro-1,1-dimethyl-3-oxo-1,3-dihydro-isoindol-2-yl)-pyridin-3-ylmethyl]-acetamide | 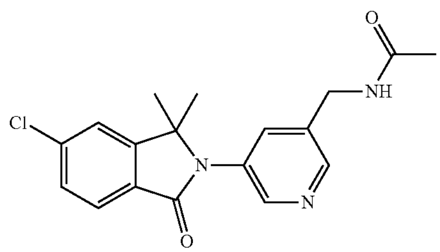 [SMILES: CC(=O)NCc1cncc(N2C(=O)c3ccc(Cl)cc3C2(C)C)c1] | 5-Chloro-2-(5-chloromethyl-pyridin-3-yl)-3,3-dimethyl-2,3-dihydro-isoindol-1-one (intermediate A-12-1) and acetamide | 344.1 |
| 401 | N-{[5-(5'-Fluoro-3'-oxospiro[cyclopropane-1,1'-isoindol]-2'(3'H)-yl)pyridin-3-yl]methyl}methane-sulfonamide | 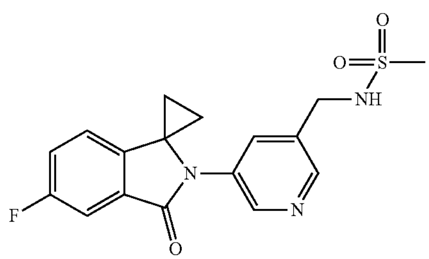 [SMILES: CS(=O)(=O)NCc1cncc(N2C(=O)c3cc(F)ccc3C23CC3)c1] | 2'-(5-(Chloromethyl)pyridin-3-yl)-6'-fluorospiro[cyclopropane-1,1'-isoindolin]-3'-one (intermediate A-24-1) and methanesulfonamide | 362.1 |
| 402 | N-[5-(6-Cyano-1,1-dimethyl-3-oxo-1,3-dihydro-isoindol-2-yl)-pyridin-3-ylmethyl]-methane-sulfonamide | 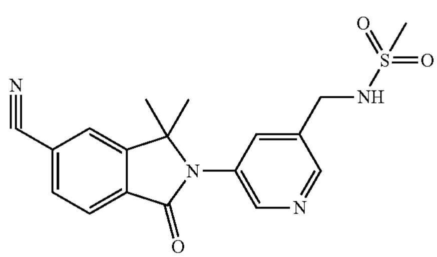 [SMILES: CC1(C)c2cc(C#N)ccc2C(=O)N1c1cncc(CNS(C)(=O)=O)c1] | 2-(5-Chloromethyl-pyridin-3-yl)-3,3-dimethyl-1-oxo-2,3-dihydro-1H-isoindole-5-carbonitrile (intermediate A-21-1) and methanesulfonamide | 371.1 |
| 403 | N-[5-(6-Fluoro-1,1-dimethyl-3-oxo-1,3-dihydro-isoindol-2-yl)-pyridin-3-ylmethyl]-methane-sulfonamide | 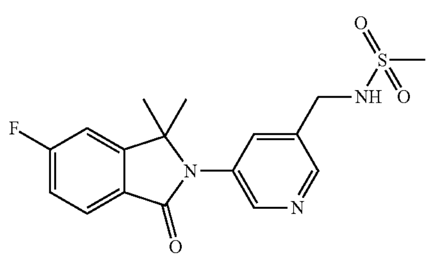 [SMILES: CC1(C)c2cc(F)ccc2C(=O)N1c1cncc(CNS(C)(=O)=O)c1] | 2-(5-Chloromethyl-pyridin-3-yl)-5-fluoro-3,3-dimethyl-2,3-dihydro-isoindol-1-one (intermediate A-19-1) and methanesulfonamide | 364.4 |
| 404 | N-{[5-(6'-Fluoro-3'-oxospiro[cyclopropane-1,1'-isoindol]-2'(3'H)-yl)pyridin-3-yl]methyl}methane-sulfonamide | 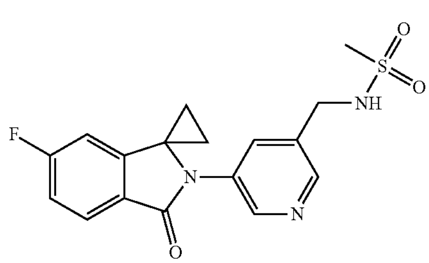 [SMILES: CS(=O)(=O)NCc1cncc(N2C(=O)c3ccc(F)cc3C23CC3)c1] | 2'-(5-(Chloromethyl)pyridin-3-yl)-6'-fluorospiro[cyclopropane-1,1'-isoindolin]-3'-one(intermediate A-23-1) and methanesulfonamide | 362.0 |

TABLE 12-continued

| Ex | Compound Name | Compound Structure | Starting Materials | MS (M + H)+ |
|---|---|---|---|---|
| 405 | N-[5-((S or R)-5-Chloro-1-ethyl-3-oxo-1,3-dihydro-isoindol-2-yl)-pyridin-3-ylmethyl]-methane-sulfonamide | 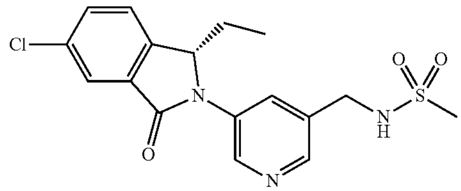 [SMILES: CC[C@H]1c2ccc(Cl)cc2C(=O)N1c1cncc(CNS(C)(=O)=O)c1] | (S or R)-5-Chloro-2-(5-chloromethyl-pyridin-3-yl)-3-ethyl-2,3-dihydro-isoindol-1-one (intermediate A-13-3) and methanesulfonamide | 380.1 |
| 406 | N-[5-(5-Fluoro-1,1-dimethyl-3-oxo-1,3-dihydro-isoindol-2-yl)-pyridin-3-ylmethyl]-methane-sulfonamide | 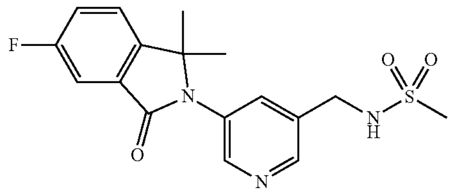 [SMILES: CC1(C)c2ccc(F)cc2C(=O)N1c1cncc(CNS(C)(=O)=O)c1] | 2-(5-Chloromethyl-pyridin-3-yl)-6-fluoro-3,3-dimethyl-2,3-dihydro-isoindol-1-one (intermediate A-20-1) and methanesulfonamide | 364.4 |
| 407 | N-[5-((R or S)-5-Chloro-1-ethyl-3-oxo-1,3-dihydro-isoindol-2-yl)-pyridin-3-ylmethyl]-methane-sulfonamide | 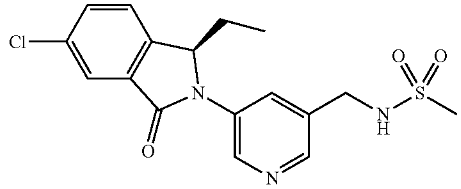 [SMILES: CC[C@@H]1c2ccc(Cl)cc2C(=O)N1c1cncc(CNS(C)(=O)=O)c1] | (R or S)-5-Chloro-2-(5-chloromethyl-pyridin-3-yl)-3-ethyl-2,3-dihydro-isoindol-1-one (intermediate A-13-4) and methanesulfonamide | 380.1 |
| 408 | N-[5-(5-Chloro-1,1-dimethyl-3-oxo-1,3-dihydro-isoindol-2-yl)-pyridin-3-ylmethyl]-methane-sulfonamide | 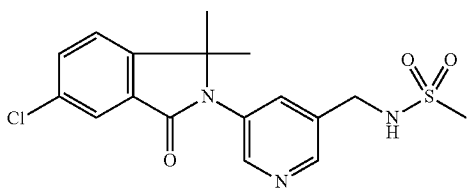 [SMILES: CC1(C)c2ccc(Cl)cc2C(=O)N1c1cncc(CNS(C)(=O)=O)c1] | 6-Chloro-2-(5-chloromethyl-pyridin-3-yl)-3,3-dimethyl-2,3-dihydro-isoindol-1-one (intermediate A-25-1) and methanesulfonamide | 380.1 |
| 409 | 5-Chloro-2-[5-(1,1-dioxo-1λ6-isothiazolidin-2-ylmethyl)-pyridin-3-yl]-3,3-dimethyl-2,3-dihydro-isoindol-1-one | 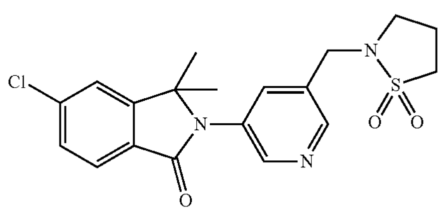 [SMILES: CC1(C)c2cc(Cl)ccc2C(=O)N1c1cncc(CN2CCCS2(=O)=O)c1] | 5-Chloro-2-(5-chloromethyl-pyridin-3-yl)-3,3-dimethyl-2,3-dihydro-isoindol-1-one (intermediate A-12-1) and isothiazolidine 1,1-dioxide | 406.1 |
| 410 | 5-Chloro-3,3-dimethyl-2-[5-(2-oxo-piperidin-1-ylmethyl)-pyridin-3-yl]-2,3-dihydro-isoindol-1-one | 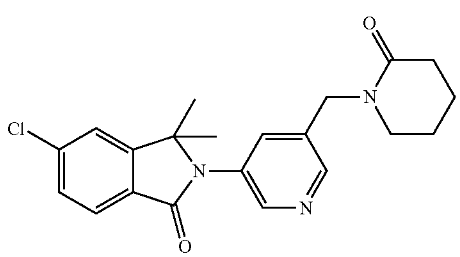 [SMILES: CC1(C)c2cc(Cl)ccc2C(=O)N1c1cncc(CN2CCCCC2=O)c1] | 5-Chloro-2-(5-chloromethyl-pyridin-3-yl)-3,3-dimethyl-2,3-dihydro-isoindol-1-one (intermediate A-12-1) and piperidin-2-one | 384.0 |
| 411 | 5-Chloro-3,3-dimethyl-2-[5-(2-oxo-imidazolidin-1-ylmethyl)-pyridin-3-yl]-2,3-dihydro-isoindol-1-one | 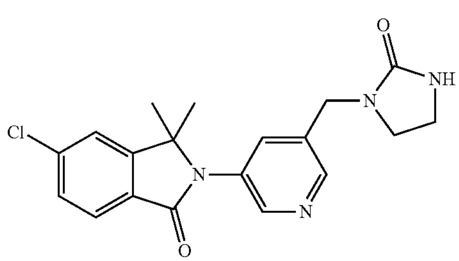 [SMILES: CC1(C)c2cc(Cl)ccc2C(=O)N1c1cncc(CN2CCNC2=O)c1] | 5-Chloro-2-(5-chloromethyl-pyridin-3-yl)-3,3-dimethyl-2,3-dihydro-isoindol-1-one (intermediate A-12-1) and imidazolidin-2-one | 371.2 |

TABLE 12-continued

| Ex | Compound Name | Compound Structure | Starting Materials | MS (M + H)+ |
|---|---|---|---|---|
| 412 | 5-Chloro-3,3-dimethyl-2-[5-(2-oxo-oxazolidin-3-ylmethyl)-pyridin-3-yl]-2,3-dihydro-isoindol-1-one | 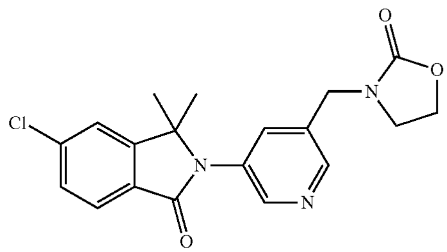 [SMILES: CC1(C)c2cc(Cl)ccc2C(=O)N1c1cncc(CN2CCOC2=O)c1] | 5-Chloro-2-(5-chloromethyl-pyridin-3-yl)-3,3-dimethyl-2,3-dihydro-isoindol-1-one (intermediate A-12-1) and oxazolidin-2-one | 372.2 |
| 413 | 5-Chloro-3,3-dimethyl-2-[5-(2-oxo-pyrrolidin-1-ylmethyl)-pyridin-3-yl]-2,3-dihydro-isoindol-1-one | 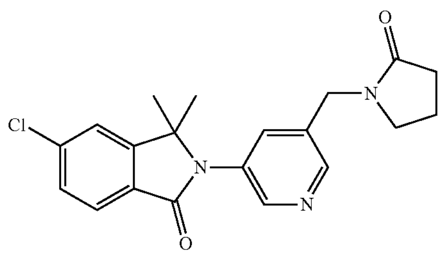 [SMILES: CC1(C)c2cc(Cl)ccc2C(=O)N1c1cncc(CN2CCCC2=O)c1] | 5-Chloro-2-(5-chloromethyl-pyridin-3-yl)-3,3-dimethyl-2,3-dihydro-isoindol-1-one (intermediate A-12-1) and oxazolidin-2-one | 370.1 |
| 414 | 5-Chloro-3,3-dimethyl-2-[5-(3-methyl-2-oxo-imidazolidin-1-ylmethyl)-pyridin-3-yl]-2,3-dihydro-isoindol-1-one | 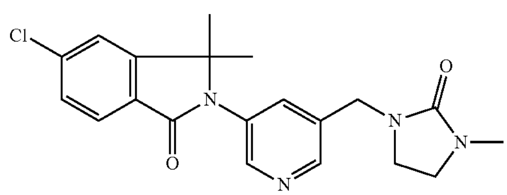 [SMILES: CN1CCN(Cc2cncc(N3C(=O)c4ccc(Cl)cc4C3(C)C)c2)C1=O] | 5-Chloro-3,3-dimethyl-2,3-dihydro-isoindol-1-one (intermediate A-12-1) and 1-methyl-imidazolidin-2-one | 385.1 |
| 415 | 5-Chloro-2-[5-(1,1-dioxo-1λ6-[1,2]thiazinan-2-ylmethyl)-pyridin-3-yl]-3,3-dimethyl-2,3-dihydro-isoindol-1-one | 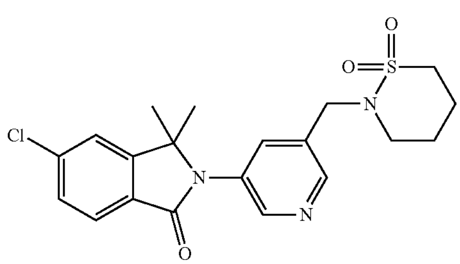 [SMILES: CC1(C)c2cc(Cl)ccc2C(=O)N1c1cncc(CN2CCCCS2(=O)=O)c1] | 5-Chloro-2-(5-chloromethyl-pyridin-3-yl)-3,3-dimethyl-2,3-dihydro-isoindol-1-one (intermediate A-12-1) and [1,2]thiazinane 1,1-dioxide | 420.2 |
| 416 | 5-Chloro-2-[5-(3-isopropyl-2-oxo-imidazolidin-1-ylmethyl)-pyridin-3-yl]-3,3-dimethyl-2,3-dihydro-isoindol-1-one | 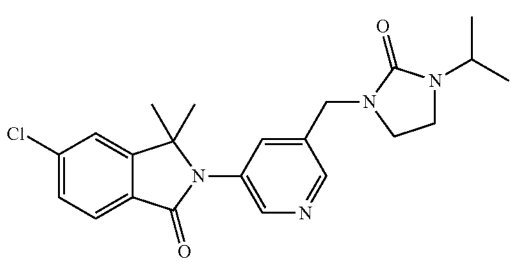 [SMILES: CC(C)N1CCN(Cc2cncc(N3C(=O)c4ccc(Cl)cc4C3(C)C)c2)C1=O] | 5-Chloro-2-(5-chloromethyl-pyridin-3-yl)-3,3-dimethyl-2,3-dihydro-isoindol-1-one (intermediate A-12-1)) and 1-isopropyl-imidazolidin-2-one | 385.1 |

The following compounds listed in Table 13 were prepared in analogy to the procedure described for the preparation of example 229 using appropriate starting materials, which have been prepared as indicated or in close analogy the procedure described for the preparation of example 7.

TABLE 13

| Ex | Compound Name | Compound Structure | Starting Materials | MS (M + H)+ |
|---|---|---|---|---|
| 417 | 6-Chloro-2-[5-(1,5-dimethyl-1H-imidazol-4-yl)-pyridin-3-yl]-3,4-dihydro-2H-isoquinolin-1-one | 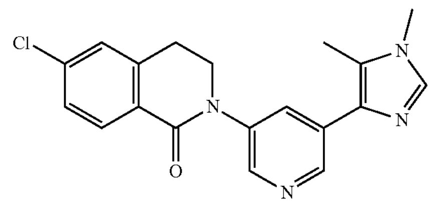 [SMILES: Cc1c(-c2cncc(N3CCc4cc(Cl)ccc4C3=O)c2)ncn1C] | 2-(5-Bromo-pyridin-3-yl)-6-chloro-3,4-dihydro-2H-isoquinolin-1-one (example 7) and 1,5-dimethyl-4-(4,4,5,5-tetramethyl-[1,3,2]dioxaborolan-2-yl)-1H-imidazole | 353.1 |
| 418 | 5-Chloro-3,3-dimethyl-2-[5-(2-methyl-2H-pyrazol-3-yl)-pyridin-3-yl]-2,3-dihydro-isoindol-1-one | 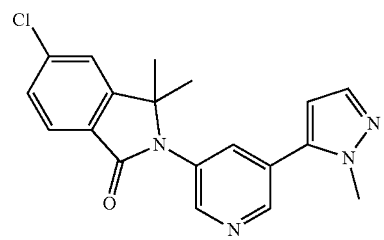 [SMILES: Cn1nccc1-c1cncc(N2C(=O)c3ccc(Cl)cc3C2(C)C)c1] | 2-(5-Bromo-pyridin-3-yl)-5-chloro-3,3-dimethyl-2,3-dihydro-isoindol-1-one and 1-methyl-5-(4,4,5,5-tetramethyl-[1,3,2]dioxaborolan-2-yl)-1H-pyrazole | 353.1 |
| 419 | 6-Chloro-2-[5-(3-methyl-1H-pyrazol-4-yl)-pyridin-3-yl]-3,4-dihydro-2H-isoquinolin-1-one | 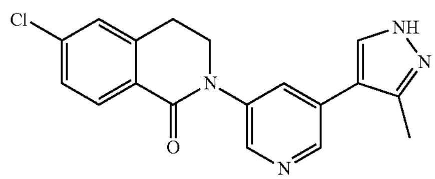 [SMILES: Cc1n[nH]cc1-c1cncc(N2CCc3cc(Cl)ccc3C2=O)c1] | 2-(5-Bromo-pyridin-3-yl)-6-chloro-3,4-dihydro-2H-isoquinolin-1-one (example 7) and 3-methyl-4-(4,4,5,5-tetramethyl-[1,3,2]dioxaborolan-2-yl)-1H-pyrazole | 339.1 |
| 420 | 6-Chloro-2-[5-(4-methyl-2H-pyrazol-3-yl)-pyridin-3-yl]-3,4-dihydro-2H-isoquinolin-1-one | 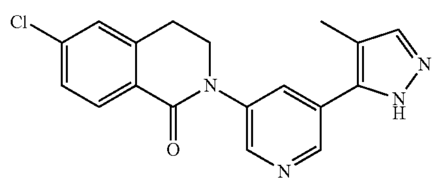 [SMILES: Cc1cn[nH]c1-c1cncc(N2CCc3cc(Cl)ccc3C2=O)c1] | 2-(5-Bromo-pyridin-3-yl)-6-chloro-3,4-dihydro-2H-isoquinolin-1-one (example 7) and 4-methyl-5-(4,4,5,5-tetramethyl-[1,3,2]dioxaborolan-2-yl)-1H-pyrazole | 339.2 |
| 421 | 6-Chloro-2-[5-(4-chloro-2-methyl-2H-pyrazol-3-yl)-pyridin-3-yl]-3,4-dihydro-2H-isoquinolin-1-one | 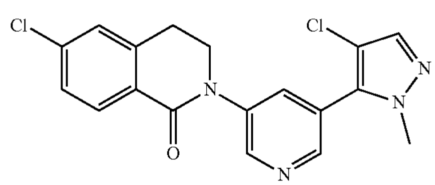 [SMILES: Cn1ncc(Cl)c1-c1cncc(N2CCc3cc(Cl)ccc3C2=O)c1] | 2-(5-Bromo-pyridin-3-yl)-6-chloro-3,4-dihydro-2H-isoquinolin-1-one (example 7) and 4-chloro-1-methyl-5-(4,4,5,5-tetramethyl-[1,3,2]dioxaborolan-2-yl)-1H-pyrazole | 373.1 |
| 422 | 6-Chloro-2-[5-(2,5-dimethyl-2H-pyrazol-3-yl)-pyridin-3-yl]-3,4-dihydro-2H-isoquinolin-1-one | 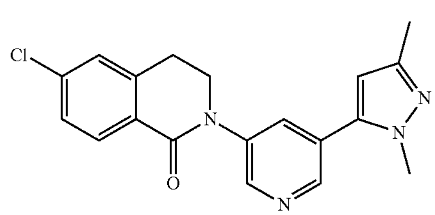 [SMILES: Cc1cc(-c2cncc(N3CCc4cc(Cl)ccc4C3=O)c2)n(C)n1] | 2-(5-Bromo-pyridin-3-yl)-6-chloro-3,4-dihydro-2H-isoquinolin-1-one (example 7) and 1,3-dimethyl-5-(4,4,5,5-tetramethyl-[1,3,2]dioxaborolan-2-yl)-1H-pyrazole | 353.1 |

TABLE 13-continued

| Ex | Compound Name | Compound Structure | Starting Materials | MS (M + H)+ |
|---|---|---|---|---|
| 423 | 6-Chloro-2-[5-(1,5-dimethyl-1H-pyrazol-4-yl)-pyridin-3-yl]-3,4-dihydro-2H-isoquinolin-1-one | 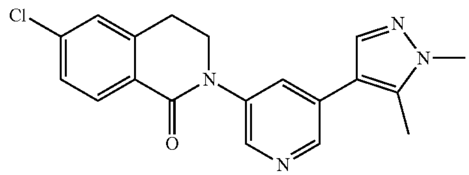 [SMILES: Cc1c(-c2cncc(N3CCc4cc(Cl)ccc4C3=O)c2)cnn1C] | 2-(5-Bromo-pyridin-3-yl)-6-chloro-3,4-dihydro-2H-isoquinolin-1-one (example 7) and 1,5-dimethyl-4-(4,4,5,5-tetramethyl-[1,3,2]dioxaborolan-2-yl)-1H-pyrazole | 353.1 |
| 424 | 6-Chloro-2-[4-chloro-5-(2-methyl-2H-pyrazol-3-yl)-pyridin-3-yl]-3,4-dihydro-2H-isoquinolin-1-one | 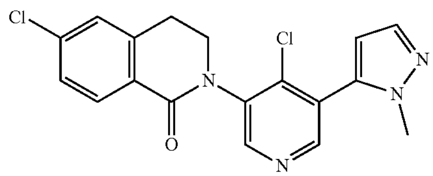 [SMILES: Cn1nccc1-c1cncc(N2CCc3cc(Cl)ccc3C2=O)c1Cl] | 2-(5-Bromo-4-chloro-pyridin-3-yl)-6-chloro-3,4-dihydro-2H-isoquinolin-1-one and 1-methyl-5-(4,4,5,5-tetramethyl-[1,3,2]dioxaborolan-2-yl)-1H-pyrazole | 373.1 |
| 425 | 2-Chloro-7,7-dimethyl-6-[5-(2-methyl-2H-pyrazol-3-yl)-pyridin-3-yl]-6,7-dihydro-pyrrolo[3,4-b]pyridin-5-one | 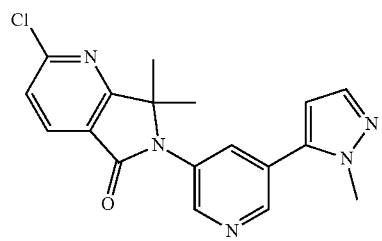 [SMILES: Cn1nccc1-c1cncc(N2C(=O)c3ccc(Cl)nc3C2(C)C)c1] | 6-(5-Bromo-pyridin-3-yl)-2-chloro-7,7-dimethyl-6,7-dihydro-pyrrolo[3,4-b]pyridin-5-one and 1-methyl-5-(4,4,5,5-tetramethyl-[1,3,2]dioxaborolan-2-yl)-1H-pyrazole | 354.1 |
| 426 | 2-Methoxy-7,7-dimethyl-6-[5-(2-methyl-2H-pyrazol-3-yl)-pyridin-3-yl]-6,7-dihydro-pyrrolo[3,4-b]pyridin-5-one | 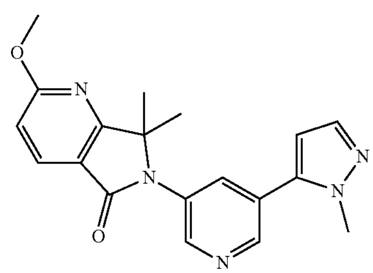 [SMILES: COc1ccc2c(n1)C(C)(C)N(c1cncc(-c3ccnn3C)c1)C2=O] | 6-(5-Bromo-pyridin-3-yl)-2-methoxy-7,7-dimethyl-6,7-dihydro-pyrrolo[3,4-b]pyridin-5-one and 1-methyl-5-(4,4,5,5-tetramethyl-[1,3,2]dioxaborolan-2-yl)-1H-pyrazole | 350.1 |
| 427 | 5-Chloro-2-[5-(4-chloro-2-methyl-2H-pyrazol-3-yl)-pyridin-3-yl]-3,3-dimethyl-2,3-dihydro-isoindol-1-one | 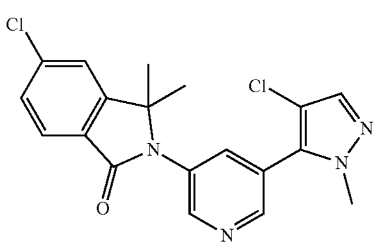 [SMILES: Cn1ncc(Cl)c1-c1cncc(N2C(=O)c3ccc(Cl)cc3C2(C)C)c1] | 2-(5-Bromo-pyridin-3-yl)-5-chloro-3,3-dimethyl-2,3-dihydro-isoindol-1-one and 4-chloro-1-methyl-5-(4,4,5,5-tetramethyl-[1,3,2]dioxaborolan-2-yl)-1H-pyrazole | 387.1 |
| 428 | (R or S)-5-Chloro-3-ethyl-2-[5-(2-methyl-2H-pyrazol-3-yl)-pyridin-3-yl]-2,3-dihydro-isoindol-1-one | 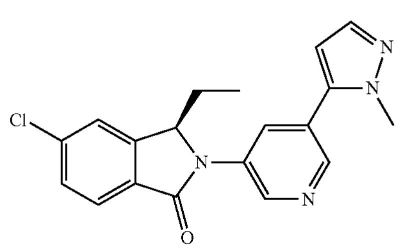 [SMILES: CC[C@@H]1c2cc(Cl)ccc2C(=O)N1c1cncc(-c2ccnn2C)c1] | (R or S)-2-(5-Bromo-pyridin-3-yl)-5-chloro-3-ethyl-2,3-dihydro-isoindol-1-one and 1-methyl-5-(4,4,5,5-tetramethyl-[1,3,2]dioxaborolan-2-yl)-1H-pyrazole | 353.2 |

TABLE 13-continued

| Ex | Compound Name | Compound Structure | Starting Materials | MS (M + H)+ |
|---|---|---|---|---|
| 429 | (S or R)-5-Chloro-3-ethyl-2-[5-(2-methyl-2H-pyrazol-3-yl)-pyridin-3-yl]-2,3-dihydro-isoindol-1-one | 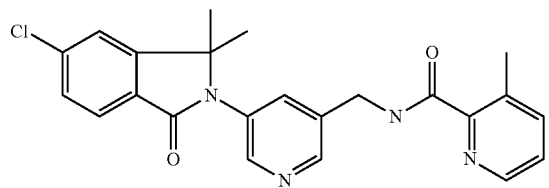 [SMILES: Cc1cccnc1C(=O)NCc1cncc(N2C(=O)c3ccc(Cl)cc3C2(C)C)c1] | (S or R)-2-(5-Bromo-pyridin-3-yl)-5-chloro-3-ethyl-2,3-dihydro-isoindol-1-one and 1-methyl-5-(4,4,5,5-tetramethyl-[1,3,2]dioxaborolan-2-yl)-1H-pyrazole | 353.2 |

Example 430

3-Methyl-pyridine-2-carboxylic acid [5-(6-chloro-1,1-dimethyl-3-oxo-1,3-dihydro-isoindol-2-yl)-pyridin-3-ylmethyl]-amide

[A] (5-Bromo-pyridin-3-yl)-methanol

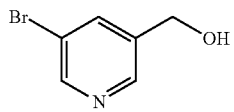

To a suspension of 5-bromo-pyridine-3-carbaldehyde (10.0 g, 53.7 mmol) in MeOH (100 mL) was added sodium borohydride (2.2 g, 59.1 mmol) at 0° C. The reaction mixture was stirred at 0° C. for 1 hour before it was quenched with water (5.0 mL). Evaporation of solvents afforded light yellowish oil which was re-dissolved in EtOAc and washed with brine. The organic layer was dried over anhy. $Na_2SO_4$, filtered and concentrated in vacuo to give the title compound (9.6 g, 95%) as colorless oil. MS: 188.0 & 190.0 (M+H+).

[B] 3-Bromo-5-chloromethyl-pyridine

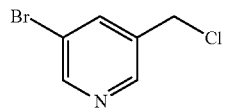

At 0° C., to a solution of (5-bromopyridin-3-yl)methanol (3 g, 16.0 mmol) in DCM (15 mL) was added thionylchloride (7.59 g, 63.8 mmol) dropwise and the reaction mixture was stirred at room temperature overnight. The mixture was poured onto ice/water (20 mL), and basified with conc. NaOH solution (8 mL). The mixture was extracted with EtOAc (2×50 mL) and combined organic layers were dried over anhy. $Na_2SO_4$, filtered and evaporated to dryness. The residue was purified by silica gel flash chromatography eluting with a 0 to 40% EtOAc-heptane gradient to give the title compound (3.08 g, 93%) as a white solid. MS: 206.0, 207.9 (M+H+).

[C] (5-Bromo-pyridin-3-yl)-methylamine

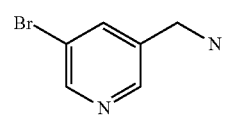

3-Bromo-5-chloromethyl-pyridine (10.3 g, 50 mmol) was dissolved in ammonia methanol solution (7 N, 250 ml) and heated at 60° C. overnight. After aq. NaOH (1N) solution was added to adjust the pH to >12, the mixture was extracted with EtOAc. The organic layer was washed with brine, dried over anhy. $Na_2SO_4$, filtered and concentrated in vacuo. The crude product was purified by recrystallization to give title compound as a solid (2.5 g, 27%). MS: 187.1 (M+H+).

[D] 2-(5-Aminomethyl-pyridin-3-yl)-5-chloro-3,3dimethyl -2,3-dihydro-isoindol-1-one

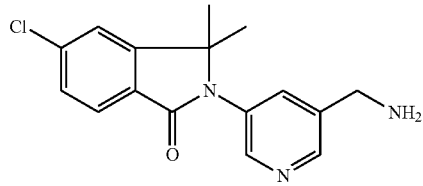 [SMILES: CC1(C)c2cc(Cl)ccc2C(=O)N1c1cncc(CN)c1]

In a 25 mL sealed tube, a mixture of (5-bromo-pyridin-3-yl)-methylamine (281 mg, 1.5 mmol), 5-chloro-3,3-dimethyl-2,3-dihydro-isoindol-1-one (intermediate A-12, 196 mg, 1.0 mmol), CuI (38 mg, 0.2 mmol), $Cs_2CO_3$ (652 mg, 2.0 mmol) and (+)—(S,S)—1,2-diaminocyclohexane (68.4 mL, 0.6 mmol) were dissolved in dioxane (3 mL). The resulting reaction mixture was heated at 150° C. for 7 hours before it was poured into water (10 mL) and extracted with EtOAc (20 mL×2). The combined organic layers were washed with brine, dried over anhy. $Na_2SO_4$, filtered and concentrated in vacuo to give a crude product (320 mg, 100%). Without further purification, it was used directly in the next step. MS: 302.1 (M+H⁺).

[E] 3-Methyl-pyridine-2-carboxylic acid [5-(6-chloro-1,1-dimethyl-3-oxo-1,3-dihydro-isoindol-2-yl)-pyridin-3-ylmethyl]-amide

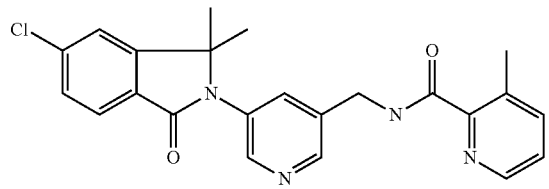 [SMILES: Cc1cccnc1C(=O)NCc1cncc(N2C(=O)c3ccc(Cl)cc3C2(C)C)c1]

To solution of 2-(5-aminomethyl-pyridin-3-yl)-5-chloro-3,3-dimethyl-2,3-dihydro-isoindol-1-one (30 mg, 0.1 mmol), Et₃N (15.3 mg, 0.15 mmol) and 3-methyl-pyridine-2-carboxylic acid (13.7 mg, 0.1 mmol) in DMF (3 mL) was added HATU (57.0 mg, 0.15 mmol) at room temperature. The reaction mixture was stirred at room temperature for 1 hour. Both water and EtOAc were added and the organic layer was dried over anhy. Na₂SO₄, filtered and concentrated in vacuo to give a residue which was then purified by Prep HPLC to give the title compound (10 mg, 24%) as a solid. MS: 421.2 (M+H⁺).

The following compounds listed in Table 14 were prepared in analogy to the procedure described for the preparation of example 430 using appropriate starting materials.

TABLE 14

| Ex | Compound Name | Compound Structure | Starting Materials | MS (M + H)⁺ |
|---|---|---|---|---|
| 431 | 3-Chloro-pyridine-2-carboxylic acid [5-(6-chloro-1,1-dimethyl-3-oxo-1,3-dihydro-isoindol-2-yl)-pyridin-3-ylmethyl]-amide | 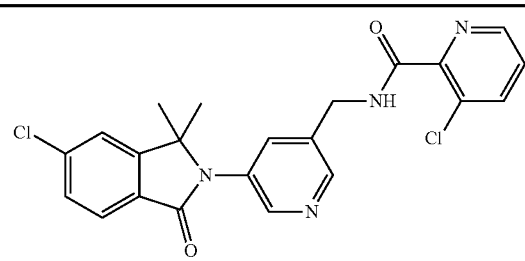 | Example 430 (step D) and 3-chloro-pyridine-2-carboxylic acid | 441.1 |
| 432 | 1-Methyl-1H-imidazole-2-carboxylic acid [5-(6-chloro-1,1-dimethyl-3-oxo-1,3-dihydro-isoindol-2-yl)-pyridin-3-ylmethyl]-amide | 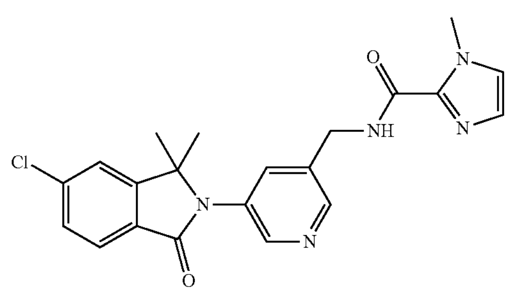 [SMILES: Cn1ccnc1C(=O)NCc1cncc(N2C(=O)c3ccc(Cl)cc3C2(C)C)c1] | Example 430 (step D) and 1-methyl-1H-imidazole-2-carboxylic acid | 410.2 |
| 433 | 2-Chloro-N-[5-(6-chloro-1,1-dimethyl-3-oxo-1,3-dihydro-isoindol-2-yl)-pyridin-3-ylmethyl]-nicotinamide | 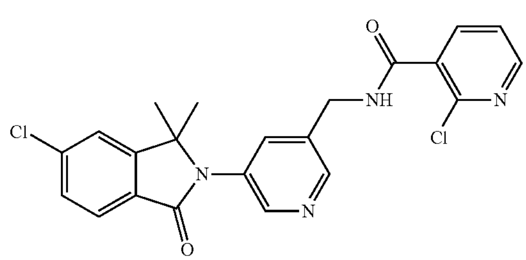 [SMILES: CC1(C)c2cc(Cl)ccc2C(=O)N1c1cncc(CNC(=O)c2cccnc2Cl)c1] | Example 430 (step D) and 2-chloro-nicotinic acid | 441.2 |
| 434 | Pyridine-2-carboxylic acid [5-(6-chloro-1,1-dimethyl-3-oxo-1,3-dihydro-isoindol-2-yl)-pyridin-3-ylmethyl]-amide | 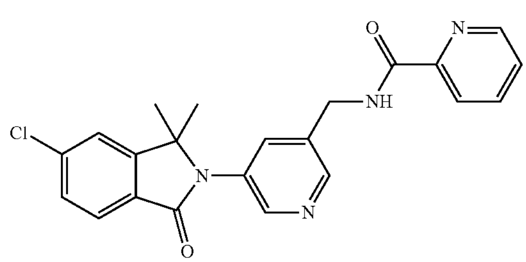 [SMILES: CC1(C)c2cc(Cl)ccc2C(=O)N1c1cncc(CNC(=O)c2ccccn2)c1] | Example 430 (step D) and pyridine-2-carboxylic acid | 407.1 |

TABLE 14-continued

| Ex | Compound Name | Compound Structure | Starting Materials | MS (M + H)+ |
|---|---|---|---|---|
| 435 | 3-Methyl-3H-imidazole-4-carboxylic acid [5-(6-chloro-1,1-dimethyl-3-oxo-1,3-dihydro-isoindol-2-yl)-pyridin-3-ylmethyl]-amide | 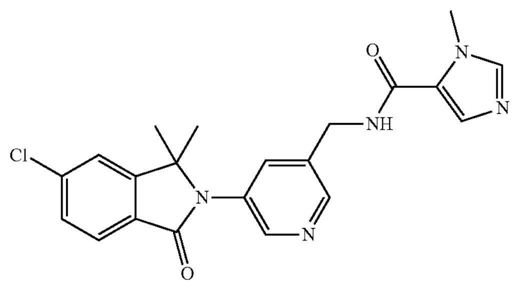 [SMILES: Cn1cncc1C(=O)NCc1cncc(N2C(=O)c3ccc(Cl)cc3C2(C)C)c1] | Example 430 (step D) and 3-methyl-3H-imidazole-4-carboxylic acid | 410.1 |
| 436 | N-[5-(6-Chloro-1,1-dimethyl-3-oxo-1,3-dihydro-isoindol-2-yl)-pyridin-3-ylmethyl]-6-methyl-nicotinamide | 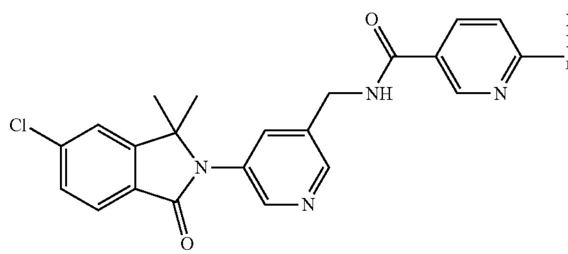 [SMILES: Cc1ccc(C(=O)NCc2cncc(N3C(=O)c4ccc(Cl)cc4C3(C)C)c2)cn1] | Example 430 (step D) and 6-methyl-nicotinic acid | 421.3 |
| 437 | 3-Chloro-N-[5-(6-chloro-1,1-dimethyl-3-oxo-1,3-dihydro-isoindol-2-yl)-pyridin-3-ylmethyl]-isonicotinamide | 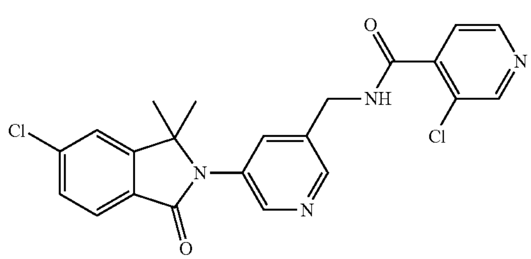 [SMILES: CC1(C)c2cc(Cl)ccc2C(=O)N1c1cncc(CNC(=O)c2ccncc2Cl)c1] | Example 430 (step D) and 3-chloro-isonicotinic acid | 441.2 |
| 438 | N-[5-(6-Chloro-1,1-dimethyl-3-oxo-1,3-dihydro-isoindol-2-yl)-pyridin-3-ylmethyl]-nicotinamide | 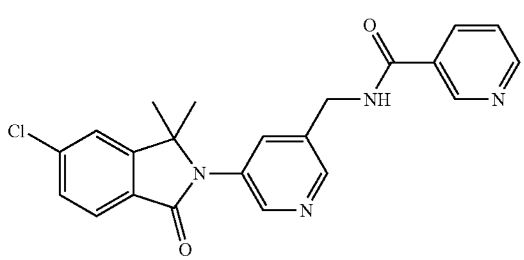 [SMILES: CC1(C)c2cc(Cl)ccc2C(=O)N1c1cncc(CNC(=O)c2cccnc2)c1] | Example 430 (step D) and nicotinic acid | 407.2 |
| 439 | N-[5-(6-Chloro-1,1-dimethyl-3-oxo-1,3-dihydro-isoindol-2-yl)-pyridin-3-ylmethyl]-2-methyl-nicotinamide | 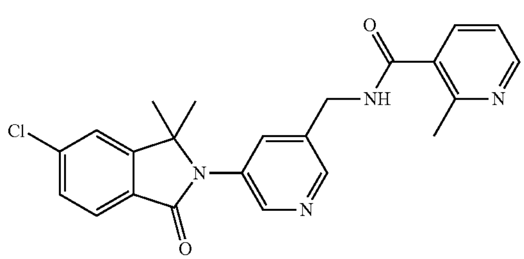 [SMILES: Cc1ncccc1C(=O)NCc1cncc(N2C(=O)c3ccc(Cl)cc3C2(C)C)c1] | Example 430 (step D) and 2-methyl-nicotinic acid | 421.3 |

TABLE 14-continued

| Ex | Compound Name | Compound Structure | Starting Materials | MS (M + H)+ |
|---|---|---|---|---|
| 440 | N-[5-(6-Chloro-1,1-dimethyl-3-oxo-1,3-dihydro-isoindol-2-yl)-pyridin-3-ylmethyl]-4-methyl-nicotinamide | 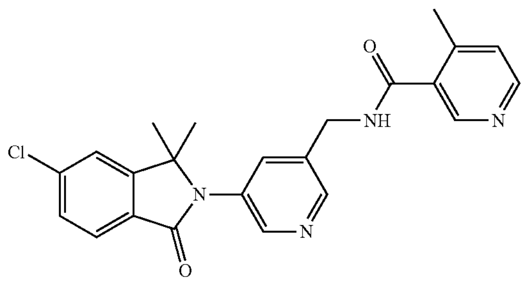 [SMILES: Cc1ccncc1C(=O)NCc1cncc(N2C(=O)c3ccc(Cl)cc3C2(C)C)c1] | Example 430 (step D) and 4-methyl-nicotinic acid | 421.3 |

Example 441

2-[5-(1-Acetyl-pyrrolidin-3-yloxy)-pyridin-3-yl]-5-chloro-3,3-dimethyl-2,3-dihydro-isoindol-1-one

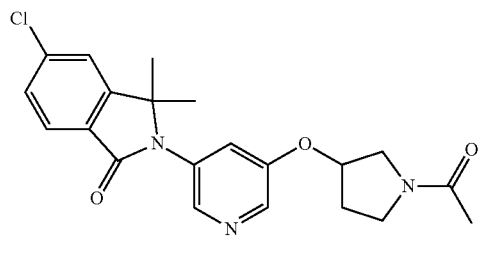

[A] 5-Chloro-2-(5-iodo-pyridin-3-yl)-3,3-dimethyl-2,3-dihydro-isoindol-1-one

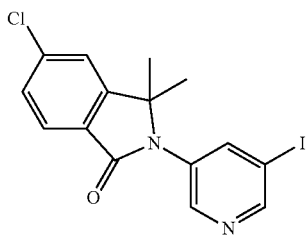 [SMILES: CC1(C)c2cc(Cl)ccc2C(=O)N1c1cncc(I)c1]

A mixture of 5-chloro-3,3-dimethyl-2,3-dihydro-isoindol-1-one (intermediate A-12) (390 mg, 2 mmol), 3,5-diiodo-pyridine (662 mg, 2 mmol), CuI (38 mg, 0.2 mmol), (1S,2S)-cyclohexane-1,2-diamine (45 mg, 0.4 mmol) and $K_3PO_4$ (888 mg, 4 mmol) were dissolved in dioxane (10 mL). The reaction mixture was heated at 110° C. for 3 hours before it was poured into $H_2O$ (50 mL) and extracted with EtOAc (25 mL×2). The combined organic layers were washed with brine, dried over anhy. $Na_2SO_4$, filtered and concentrated in vacuo to give a crude product which was then purified by silica gel flash chromatography (30-100% EtOAc-hexane gradient) to yield the title compound (495 mg, 62%) as a white solid. MS: 399.0 (M+H+).

[B] 3-[5-(6-Chloro-1,1-dimethyl-3-oxo-3-dihydro-isoindol-2yl)-pyridin-3-yloxy]-pyrrolidine-1-carboxylic acid tert-butyl ester

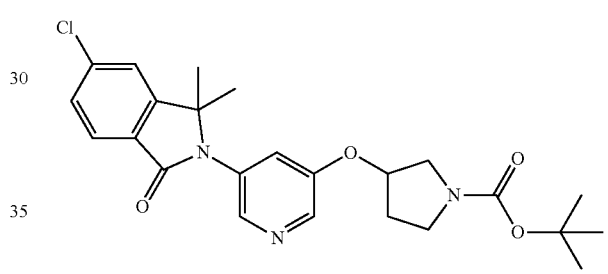

A sealed microwave tube was charged with CuI (19.1 mg, 0.1 mmol), 1,10-phenanthroline (36 mg, 0.2 mmol), $Cs_2CO_3$ (750 mg, 2.0 mmol), 5-chloro-2-(5-iodo-pyridin-3-yl)-3,3-dimethyl-2,3-dihydro-isoindol-1-one (399 mg, 1.0 mmol), 3-hydroxy-pyrrolidine-1-carboxylic acid tert-butyl ester (374 mg, 2 mmol) and toluene (5 mL). The reaction mixture was heated at 110° C. for 24 hours. The resulting suspension was cooled to room temperature and filtered through a pad of silica gel (0.5-1 cm) and rinsed with diethyl ether. The filtrate was concentrated in vacuo and the residue was purified by silica gel flash chromatography to give the title compound (310 mg, 68%). MS: 458 (M+H+).

[C] 5-Chloro-3,3-dimethyl-2-[5-(pyrrolidin-3-yloxy)-pyridin-3-yl]-2,3-dihydro-isoindol-1-one trifluoro acetic acid salt

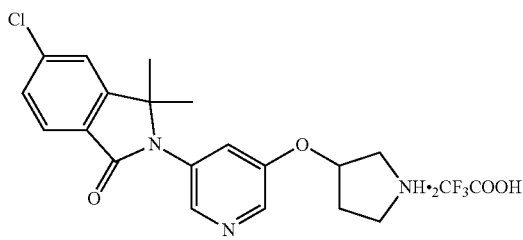

To a solution of 3-[5-(6-chloro-1,1-dimethyl-3-oxo-3-di-hydro-isoindol-2yl)-pyridin-3-yloxy]-pyrrolidine-1-carboxylic acid tert-butyl ester (310 mg, 0.67 mmol) in DCM was added TFA (1 mL) and the resulting mixture was stirred at room temperature for 3 hours. After the solvent was removed in vacuo, the crude product was obtained as yellowish oil and was used in the next step without further purification.

[D] 2-[5-(1-Acetyl-pyrrolidin-3-yloxy)-pyridin-3-yl]-5-chloro-3,3-dimethyl-2,3-dihydro-isoindol-1-one

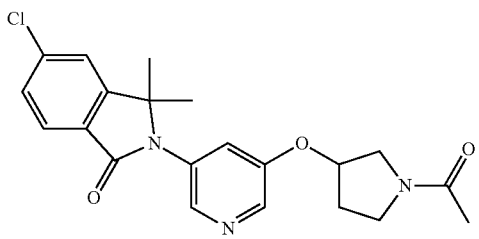 [SMILES: CC(=O)N1CCC(Oc2cncc(N3C(=O)c4ccc(Cl)cc4C3(C)C)c2)C1]

To a solution of 5-chloro-3,3-dimethyl-2-[5-(pyrrolidin-3-yloxy)-pyridin-3-yl]-2,3-dihydro-isoindol-1-one trifluoro acetic acid salt (94.2 mg, 0.2 mmol) was added Et$_3$N (1 mmol) and acetyl chloride (23.4 mg, 0.3 mmol) at 0° C. The resulting reaction mixture was stirred at room temperature for 1 hour before it was poured into H$_2$O (1 mL) and extracted with EtOAc (15 mL×2). The combined organic layers were washed with brine, dried over anhy. Na$_2$SO$_4$, filtered and concentrated in vacuo to give a crude product which was purified by PrepHPLC to give the title compound (25.5 mg, 35%) as a white solid. MS: 400.2 (M+H$^+$).

Example 442

2-[5-((R)-1-Acetyl-pyrrolidin-3-yloxy)-pyridin-3-yl]-5-chloro-3,3-dimethyl-2,3-dihydro-isoindol-1-one

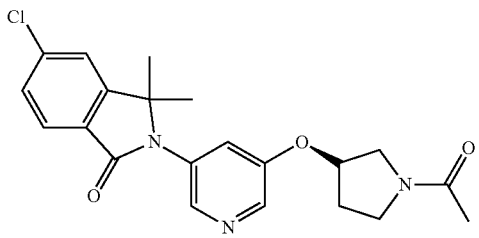

In analogy to the procedure described for the preparation of example 441, (R)-3-hydroxy-pyrrolidine-1-carboxylic acid tert-butyl ester was used (step B) to yield the title compound as a white solid. MS: 400.2 (M+H$^+$).

Example 443

2-[5-((S)-1-Acetyl-pyrrolidin-3-yloxy)-pyridin-3-yl]-5-chloro-3,3-dimethyl-2,3-dihydro-isoindol-1-one

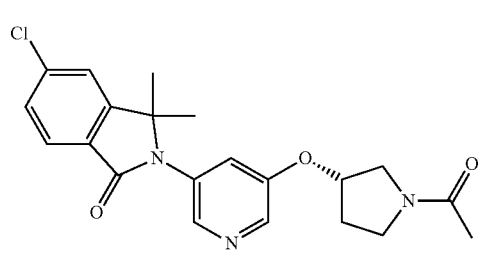

In analogy to the procedure described for the preparation of example 441, (S)-3-hydroxy-pyrrolidine-1-carboxylic acid tert-butyl ester was used (step B) to yield the title compound as a white solid. MS: 400.2 (M+H$^+$).

Example 444

5-Chloro-3,3-dimethyl-2-[5-(1-propionyl-pyrrolidin-3-yloxy)-pyridin-3-yl]-2,3-dihydro-isoindol-1-one

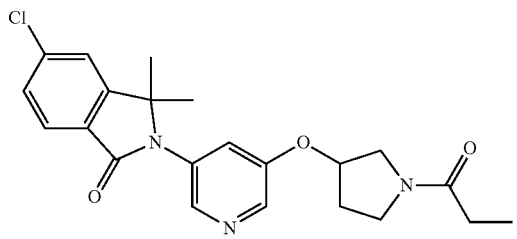 [SMILES: CCC(=O)N1CCC(Oc2cncc(N3C(=O)c4ccc(Cl)cc4C3(C)C)c2)C1]

In analogy to the procedure described for the preparation of example 441, propionyl chloride was used (step D) to yield the title compound as a white solid. MS: 414.2 (M+H$^+$).

Example 445

5-Chloro-2-[5-(1-methanesulfonyl-pyrrolidin-3-yloxy)-pyridin-3-yl]-3,3-dimethyl-2,3-dihydro-isoindol-1-one

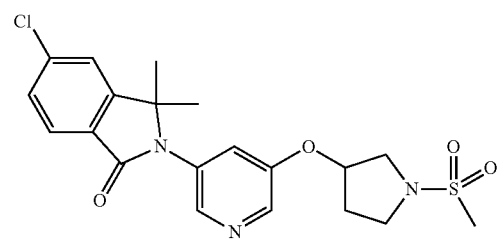 [SMILES: CC1(C)c2cc(Cl)ccc2C(=O)N1c1cncc(OC2CCN(S(C)(=O)=O)C2)c1]

In analogy to the procedure described for the preparation of example 441, methanesulfonyl chloride was used (step D) to yield the title compound as a white solid. MS: 436.2 (M+H⁺).

Example 446

5-Chloro-2-[5-(1-ethanesulfonyl-pyrrolidin-3-yloxy)-pyridin-3-yl]-3,3-dimethyl-2,3-dihydro-isoindol-1-one

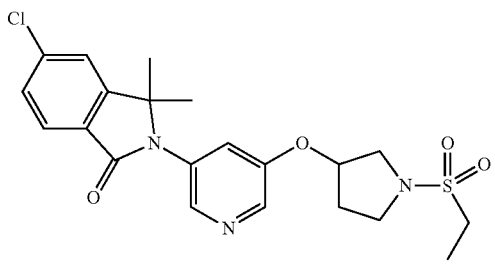 [SMILES: CCS(=O)(=O)N1CCC(Oc2cncc(N3C(=O)c4ccc(Cl)cc4C3(C)C)c2)C1]

In analogy to the procedure described for the preparation of example 441, ethanesulfonyl chloride was used (step D) to yield the title compound as a white solid. MS: 450.2 (M+H⁺).

Example 447

5-Chloro-2-[5-((R)-1-ethanesulfonyl-pyrrolidin-3-yloxy)-pyridin-3-yl]-3,3-dimethyl-2,3-dihydro-isoindol-1-one

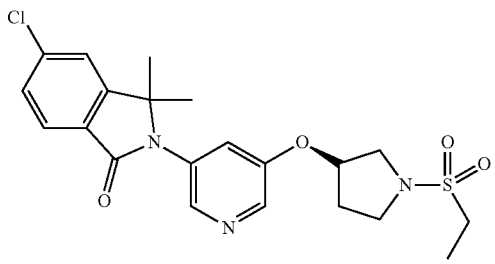

In analogy to the procedure described for the preparation of example 441, (R)-3-hydroxy-pyrrolidine-1-carboxylic acid tert-butyl ester (step B) and ethanesulfonyl chloride (step D) were used to yield the title compound as a white solid. MS: 450.2 (M+H⁺).

Example 448

5-Chloro-2-[5-((S)-1-ethanesulfonyl-pyrrolidin-3-yloxy)-pyridin-3-yl]-3,3-dimethyl-2,3-dihydro-isoindol-1-one

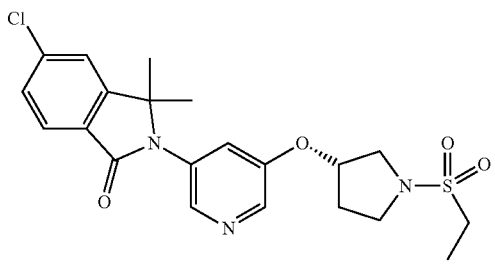

In analogy to the procedure described for the preparation of example 441, (S)-3-hydroxy-pyrrolidine-1-carboxylic acid tert-butyl ester (step B) and ethanesulfonyl chloride (step D) were used to yield the title compound as a white solid. MS: 450.2 (M+H⁺).

Example 449

2-[5-(1-Acetyl-piperidin-4-yloxy)-pyridin-3-yl]-5-chloro-3,3-dimethyl-2,3-dihydro-isoindol-1-one

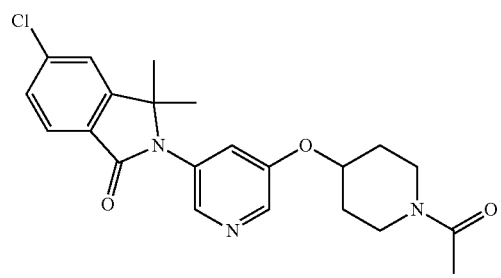 [SMILES: CC(=O)N1CCC(Oc2cncc(N3C(=O)c4ccc(Cl)cc4C3(C)C)c2)CC1]

In analogy to the procedure described for the preparation of example 441, 4-hydroxy-piperidine-1-carboxylic acid tert-butyl ester (step B) was used to yield the title compound as a white solid. MS: 414.3 (M+H⁺)

Example 450

2-[5-(1-Acetyl-azetidin-3-yloxy)-pyridin-3-yl]-5-chloro-3,3-dimethyl-2,3-dihydro-isoindol-1-one

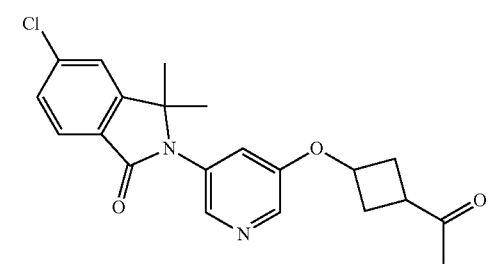 [SMILES: CC(=O)C1CC(Oc2cncc(N3C(=O)c4ccc(Cl)cc4C3(C)C)c2)C1]

In analogy to the procedure described for the preparation of example 441, 3-hydroxy-cyclobutanecarboxylic acid tert-butyl ester (step B) was used to yield the title compound as a white solid. MS: 386.2 (M+H⁺).

Example 451

5-Chloro-3,3-dimethyl-2-[5-(1-propionyl-azetidin-3-yloxy)-pyridin-3-yl]-2,3-dihydro-isoindol-1-one

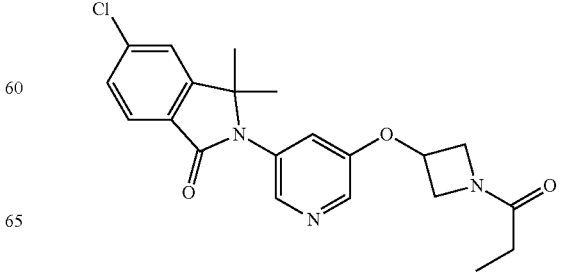

In analogy to the procedure described for the preparation of example 441, 3-hydroxy-cyclobutanecarboxylic acid tert-butyl ester (step B) and propionyl chloride were used (step D) to yield the title compound as a white solid. MS: 400.1 (M+H⁺).

Example 452

5-Chloro-2-[5-(1-methanesulfonyl-azetidin-3-yloxy)-pyridin-3-yl]-3,3-dimethyl-2,3-dihydro-isoindol-1-one

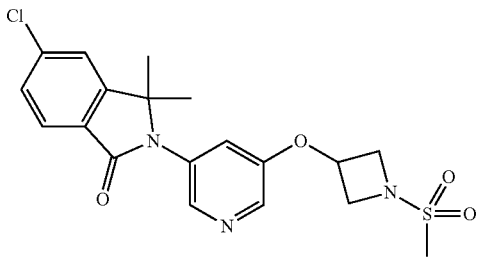 [SMILES: CC1(C)c2cc(Cl)ccc2C(=O)N1c1cncc(OC2CN(S(C)(=O)=O)C2)c1]

In analogy to the procedure described for the preparation of example 441, 3-hydroxy-cyclobutanecarboxylic acid tert-butyl ester (step B) and methanesulfonyl chloride were used (step D) to yield the title compound as a white solid. MS: 422.1 (M+H⁺).

Example 453

5-Chloro-2-[5-(1-ethanesulfonyl-azetidin-3-yloxy)-pyridin-3-yl]-3,3-dimethyl-2,3-dihydro-isoindol-1-one

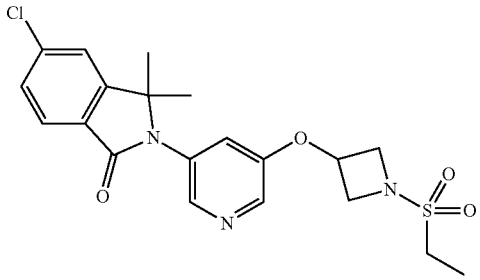 [SMILES: CCS(=O)(=O)N1CC(Oc2cncc(N3C(=O)c4ccc(Cl)cc4C3(C)C)c2)C1]

In analogy to the procedure described for the preparation of example 441, 3-hydroxy-cyclobutanecarboxylic acid tert-butyl ester (step B) and ethanesulfonyl chloride were used (step D) to yield the title compound as a white solid. MS: 436.1 (M+H⁺).

Example 454

5-Chloro-2-[5-((S)-3-hydroxy-pyrrolidin-1-yl)-pyridin-3-yl]-3,3-dimethyl-2,3-dihydro-isoindol-1-one

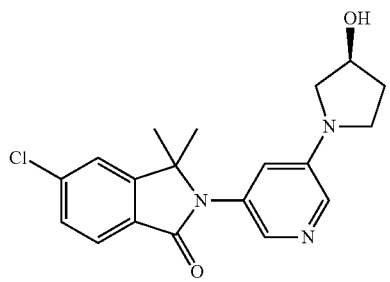 [SMILES: CC1(C)c2cc(Cl)ccc2C(=O)N1c1cncc(N2CC[C@H](O)C2)c1]

In analogy to the procedure described for the preparation of example 137, 5-chloro-3,3-dimethyl-2,3-dihydro-isoindol-1-one (intermediate A-12), 3-bromo-5-[(S)-3-(tert-butyl-dimethyl-silanyloxy)-pyrrolidin-1-yl]-pyridine was used (step C) to yield the title compound as a white solid. MS: 358.1 (M+H⁺).

Example 455

2-[5-(4-Acetyl-piperazin-1-yl)-pyridin-3-yl]-5-chloro-3,3-dimethyl-2,3-dihydro-isoindol-1-one

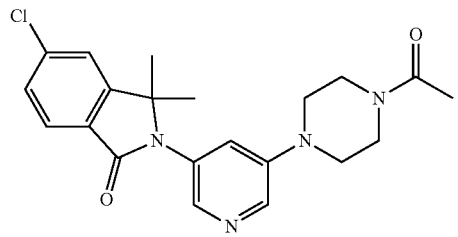

[A] 4-(5-Bromo-pyridin-3-yl)-piperazine-1-carboxylic acid tert-butyl ester

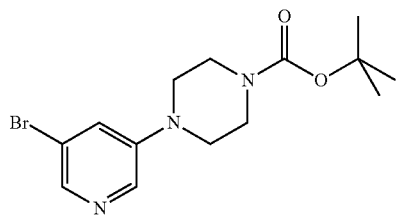 [SMILES: CC(C)(C)OC(=O)N1CCN(c2cncc(Br)c2)CC1]

A mixture of piperazine-1-carboxylic acid tert-butyl ester (1.86 g, 10 mmol), 3,5-dibromopyridine (2.37 g, 10 mmol), palladium(II) acetate (0.11 g, 0.5 mmol), anphos (0.35 g, 0.6 mmol), and sodium tert-butoxide (1.68 g, 15 mmol) in dioxane (10 mL) was heated at 130° C. in a microwave reactor for 2 hours. The mixture was then diluted with water, and extracted with EtOAc. The organic layer was dried over anhy. Na₂SO₄, filtered, and concentrated under reduced pressure. The residue was purified by flash chromatography (eluent with ethyl acetate:hexane=1:5) to afford the title compound as a white solid (1.84 g, 54%). MS: 342.2 (M⁺).

[B] 4-[5-6-Chloro-1,1-dimethyl-3-oxo-1,3-dihydro-isoindol-2-yl)-pyridin-3-yl]-piperazine-1-carboxylic acid tert-butyl ester

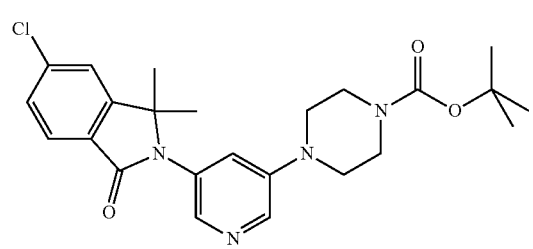 [SMILES: CC(C)(C)OC(=O)N1CCN(c2cncc(N3C(=O)c4ccc(Cl)cc4C3(C)C)c2)CC1]

5-Chloro-3,3-dimethyl-2,3-dihydro-isoindol-1-one (intermediate A-12, 690 mg, 3.51 mmol), 4-(5-bromo-pyridin-3-yl)-piperazine-1-carboxylic acid tert-butyl ester (1.0 g, 2.92 mmol), CuI (166.8 mg, 0.88 mmol), (1S,2S)-cyclohexane-1,2-diamine (120 mg, 1.75 mmol) and $Cs_2CO_3$ (1.90 g, 5.84 mmol) were dissolved in dioxane (10 mL). The reaction mixture was subjected to microwave reaction at 150° C. for 2.5 hours before it was poured into $H_2O$ (50 mL) and extracted with EtOAc (50 mL×2). The combined organic layers were washed with brine, dried over anhy. $Na_2SO_4$, filtered and concentrated in vacuo to give a crude product which was purified by flash chromatography (eluent with ethyl acetate:hexane=1:1) to yield the title compound as yellowish oil (340 mg, 25.6%). MS: 457.3 (M+H$^+$).

[C] 5-Chloro-3,3-dimethyl-2-(5-piperazin-1-yl-pyridin-3-yl)-2,3-dihydro-isoindol-1-one

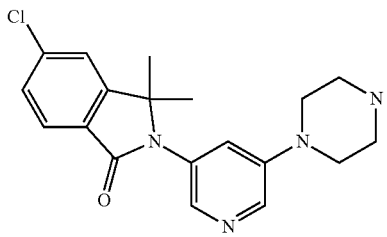 [SMILES: CC1(C)c2cc(Cl)ccc2C(=O)N1c1cncc(N2CCNCC2)c1]

A mixture of 4-[5-(6-chloro-1,1-dimethyl-3-oxo-1,3-dihydro-isoindol-2-yl)-pyridin-3-yl]-piperazine-1-carboxylic acid tert-butyl ester (0.34 g, 0.74 mmol) and trifluoroacetic acid (2 mL) in DCM (5 mL) was stirred for 1 hour at room temperature. After removal of solvent, the residue was treated with aq ammonia to adjust the pH to ~9, and then extracted with DCM. The organic layer was washed with water and dried over anhy. $Na_2SO_4$. After removal of solvent, the crude product was obtained as yellowish oil (266 mg, 100%). MS: 357.2 (M+H$^+$).

[D] 2-[5-(4-Acetyl-piperazin-1-yl)-pyridin-3-yl]-5-chloro-3,3-dimethyl-2,3-dihydro-isoindol-1-one

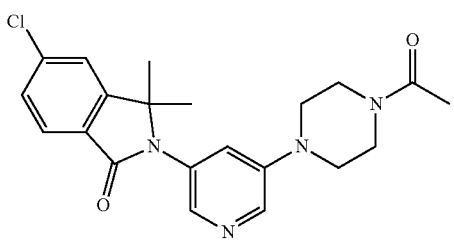 [SMILES: CC(=O)N1CCN(c2cncc(N3C(=O)c4ccc(Cl)cc4C3(C)C)c2)CC1]

To a solution of 5-chloro-3,3-dimethyl-2-(5-piperazin-1-yl-pyridin-3-yl)-2,3-dihydro-isoindol-1-one (52 mg, 0.146 mmol) and TEA (29.5 mg, 0.292 mmol) in DCM (5 mL) was added acetyl chloride (17.2 mg, 0.219 mmol) dropwise at 0° C. After stirring for 1 hour at room temperature, the mixture was treated with water and extracted with DCM. The organic layer was dried over anhy. $Na_2SO_4$. After removal of solvent, the residue was purified by preparative HPLC to afford the title compound as a white solid (23 mg, 40%). MS: 399.2 (M+H$^+$).

Example 456

5-Chloro-3,3-dimethyl-2-[5-(4-propionyl-piperazin-1-yl)-pyridin-3-yl]-2,3-dihydro-isoindol-1-one

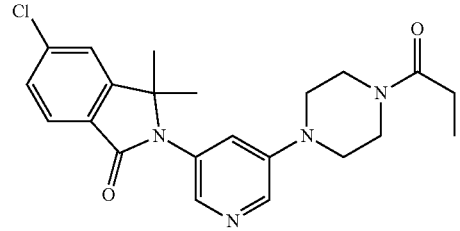 [SMILES: CCC(=O)N1CCN(c2cncc(N3C(=O)c4ccc(Cl)cc4C3(C)C)c2)CC1]

In analogy to the procedure described for the preparation of example 455, propionyl chloride was used (step D) to yield the title compound as a white solid (yield 41%). MS: 413.2 (M+H$^+$).

Example 457

5-Chloro-2-[5-(4-methanesulfonyl-piperazin-1-yl)-pyridin-3-yl]-3,3-dimethyl-2,3-dihydroisoindol-1-one

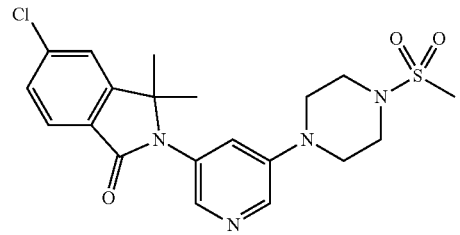 [SMILES: CC1(C)c2cc(Cl)ccc2C(=O)N1c1cncc(N2CCN(S(C)(=O)=O)CC2)c1]

In analogy to the procedure described for the preparation of example 455, methanesulfonyl chloride was used (step D) to yield the title compound as a white solid (yield 35%). MS: 435.2 (M+H$^+$).

Example 458

5-Chloro-2-[5-(4-ethanesulfonyl-piperazin-1-yl)-pyridin-3-yl]-3,3-dimethyl-2,3-dihydroisoindol-1-one

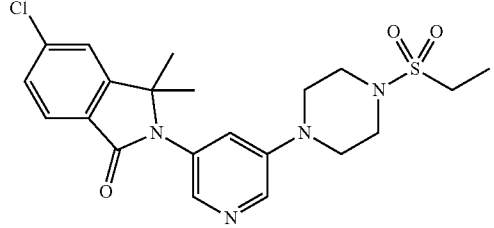 [SMILES: CCS(=O)(=O)N1CCN(c2cncc(N3C(=O)c4ccc(Cl)cc4C3(C)C)c2)CC1]

In analogy to the procedure described for the preparation of example 455, ethanesulfonyl chloride was used (step D) to yield the title compound as a white solid (yield 40%). MS: 449.2 (M+H$^+$).

Example 459

5-Chloro-2-{5-[4-(3-chloro-pyridine-2-carbonyl)-piperazin-1-yl]-pyridin-3-yl}-3,3-dimethyl-2,3-dihydro-isoindol-1-one

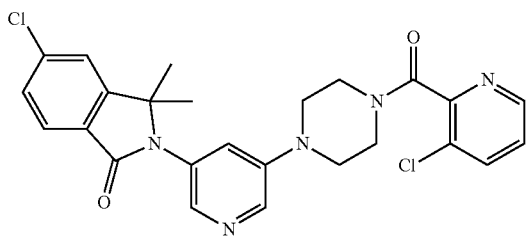 [SMILES: CC1(C)c2cc(Cl)ccc2C(=O)N1c1cncc(N2CCN(C(=O)c3ncccc3Cl)CC2)c1]

A mixture of 5-chloro-3,3-dimethyl-2-(5-piperazin-1-yl-pyridin-3-yl)-2,3-dihydro-isoindol-1-one (example 455 [C]) (52 mg, 0.146 mmol), 3-chloro-pyridine-2-carboxylic acid (25.3 mg, 0.161 mmol), HATU (83.3 mg, 0.219 mmol) and Et$_3$N (29.5 mg, 0.292 mmol) in DCM (5 mL) was stirred for 2 hours at room temperature. The mixture was treated with water, and extracted with DCM. The organic layer was dried over anhy. Na$_2$SO$_4$ and after removal of solvent, the residue was purified by preparative HPLC to afford the title compound (33 mg, 45%) as a white solid. MS: 496.3 (M+H$^+$).

Example 460

2-[5-(1-Acetyl-pyrrolidin-3-yl)-pyridin-3-yl]-5-chloro-3,3-dimethyl-2,3-dihydro-isoindol-1-one

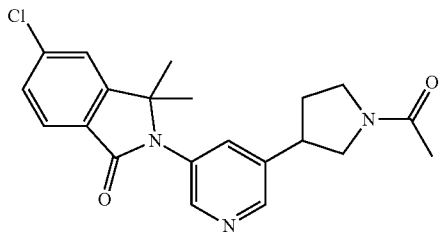 [SMILES: CC(=O)N1CCC(c2cncc(N3C(=O)c4ccc(Cl)cc4C3(C)C)c2)C1]

[A] 1-(2,5-Dihydro-pyrrol-1-yl)-ethanone

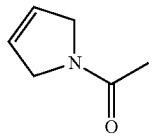

To a solution of 2,5-dihydro-1H-pyrrole (1.0 g, 14.5 mmol) and triethylamine (2.93 g, 29 mmol) in DCM (20 mL) was added acetic anhydride (2.2 g, 21.7 mmol) dropwise. After the addition, the mixture was stirred for 30 minutes at room temperature before water was added. The organic layer was washed with satd. aq. sodium bicarbonate solution and brine in sequence and dried over anhy. Na$_2$SO$_4$. After removal of solvents, the crude product was obtained as a white solid (2.89 g) and was used in the next step without further purification.

MS: 112.2 (M+H$^+$).

[B] 1-[3-(5-Bromo-pyridin-3-yl)-pyrrolidin-1-yl]-ethanone

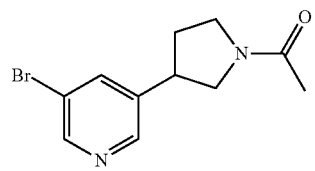

A mixture of 1-(2,5-dihydro-pyrrol-1-yl)-ethanone (70 mg, 0.63 mmol), 3-bromo-5-iodo-pyridine (283 mg, 1 mmol), triethyl amine (130 mg, 1.26 mmol), formic acid (41 mg, 0.88 mmol) and tetrakis(triphenylphosphine)palladium (0) (72.8 mg, 0.063 mmol) in DMF (3 mL) was stirred for 24 hours at 90° C. under nitrogen. After cooling to room temperature, the mixture was treated with water and extracted with ethyl acetate. The organic layer was dried over sodium sulfate. After removal of solvents, the residue was purified by flash chromatography to afford the title compound as yellowish oil (25 mg, 15%). MS: 269.1 (M+H$^+$).

[C] 2-[5-(1-Acetyl-pyrrolidin-3-yl)-pyridin-3-yl]-5-chloro-3,3-dimethyl-2,3-dihydro-isoindol-1-one

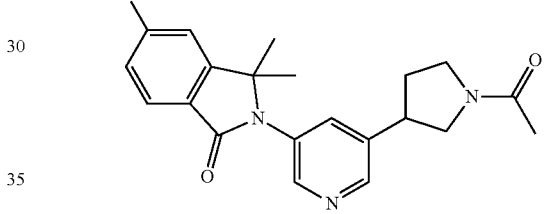

A mixture of 5-chloro-3,3-dimethyl-2,3-dihydro-isoindol-1-one (intermediate A-12, 160 mg, 0.82 mmol), 1-[3-(5-bromo-pyridin-3-yl)-pyrrolidin-1-yl]-ethanone (160 mg, 0.6 mmol), CuI (34 mg, 0.8 mmol), (1S,2S)-cyclohexane-1,2-diamine (41 mg, 0.36 mmol) and Cs$_2$CO$_3$ (390 mg, 1.2 mmol) were dissolved in dioxane (5 mL). The reaction mixture was subjected to microwave reaction at 150° C. for 2.5 hours before it was poured into H$_2$O (50 mL) and extracted with EtOAc (25 mL×2). The combined organic layers were washed with brine, dried over anhy. Na$_2$SO$_4$, filtered and concentrated in vacuo to give a crude product which was then purified by Prep-HPLC to yield the title compound (23 mg, 10%) as a white solid. MS: 384.2 (M+H$^+$).

Example 461

2-(1'-Acetyl-1',2',3',4',5',6'-hexahydro-[3,4']bipyridinyl-5-yl)-5-chloro-3,3-dimethyl-2,3-dihydro-isoindol-1-one

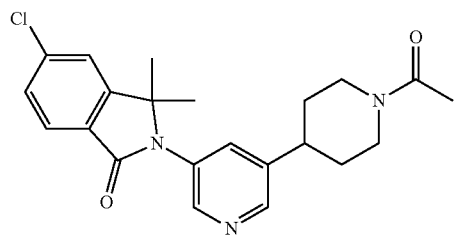

287

[A] 1-(3,6-Dihydro-2H-pyridin-1-yl)-ethanone

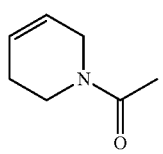

In analogy to the procedure described for the preparation of example 460 [A], 1,2,3,6-tetrahydropyridine was used to yield a crude product as a white solid (yield 90%). MS: 126.0 (M+H$^+$).

[B] 1-(5-Bromo-3',4',5',6'-tetrahydro-2'H-[3,4']bipyridinyl-1'-yl)-ethanone

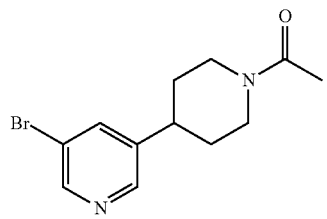 [SMILES: CC(=O)N1CCC(c2cncc(Br)c2)CC1]

In analogy to the procedure described for the preparation of example 460 [B], 1 43, 6-dihydro-2H-pyridin-1-yl)-ethanone was used to yield the tile compound as yellowish oil (yield 15%). MS: 283.2 (M+H$^+$).

[C] 2-(1'-Acetyl-1',2',3',4',5',6'-hexahydro-[3,4']bipyridinyl-5-yl)-5-chloro-3,3-dimethyl-2,3-dihydro-isoindol-1-one

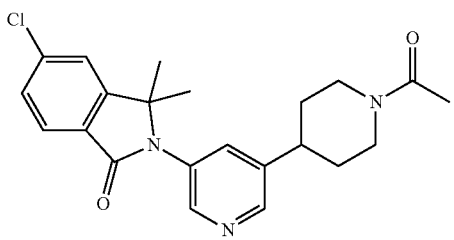 [SMILES: CC(=O)N1CCC(c2cncc(N3C(=O)c4ccc(Cl)cc4C3(C)C)c2)CC1]

In analogy to the procedure described for the preparation of example 460 [C], 1-(5-bromo-3',4',5',6'-tetrahydro-2'H-[3,4']bipyridinyl-F-yl)-ethanone was used to yield the tile compound (28 mg, 10%) as a white solid. MS: 398.2 (M+H$^+$).

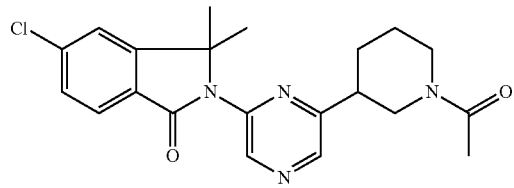 [SMILES: CC(=O)N1CCCC(c2cncc(N3C(=O)c4ccc(Cl)cc4C3(C)C)n2)C1]

288

[A] 3-(6-Chloro-pyrazin-2-yl)-piperidine-1,3-dicarboxylic acid 1-tert-butyl ester 3-ethyl ester

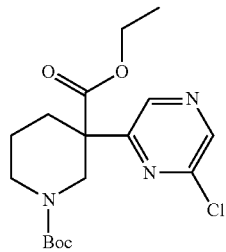 [SMILES: CCOC(=O)C1(c2cncc(Cl)n2)CCCN(C(=O)OC(C)(C)C)C1]

To a solution of piperidine-1,3-dicarboxylic acid 1-tert-butyl ester 3-ethyl ester (90 g, 350.1 mmol) in dry THF (180 mL) at 0° C. was slowly added sodium-bis-(trimethylsilyl)-amide (1 M in THF, 450 mL, 450 mmol). The reaction mixture was stirred at the same temperature for 0.5 hr before it was slowly added to a solution of 2,6-dichloropyrazine (60 g, 401.6 mmol) in dry THF (180 mL) under argon. The resulting reaction mixture was stirred at 0° C. for 1 hr, and then allowed to warm up to room temperature, and quenched by the addition of satd. aq. solution of NH$_4$Cl (360 mL). The organic layer was dried over anhy. Na$_2$SO$_4$, filtered, and concentrated in vacuo to afford a crude title product. It was then used directly in the next step without further purification.

[B] 3-(6-Chloro-pyrazin-2-yl)-piperidine-1,3-dicarboxylic acid 1-tert-butyl ester

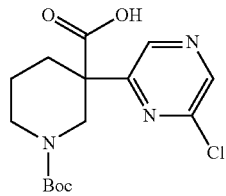 [SMILES: CC(C)(C)OC(=O)N1CCCC(C(=O)O)(c2cncc(Cl)n2)C1]

A solution of 3-(6-chloro-pyrazin-2-yl)-piperidine-1,3-dicarboxylic acid 1-tert-butyl ester 3-ethyl ester (350.1 mmol) in THF (360 mL) and 1.5 N aqueous NaOH (360 mL) was heated at 80° C. for 5 hr. After it was cooled to room temperature, the aqueous layer was separated and then carefully acidified to pH=5 by the addition of 1 N aqueous HCl solution. The resulting mixture was extracted with DCM (300 mL×3) and the combined organic layers were dried over anhy. Na$_2$SO$_4$, filtered and concentrated under reduced pressure to give a crude tile compound (46 g), which was used directly in the next step without further purification.

[C] 3-(6-Chloro-pyrazin-2-yl)-piperidine-1-carboxylic acid tert-butyl ester

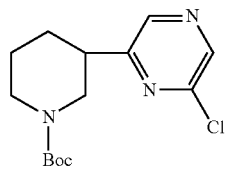 [SMILES: CC(C)(C)OC(=O)N1CCCC(c2cncc(Cl)n2)C1]

A solution of 3-(6-chloro-pyrazin-2-yl)-piperidine-1,3-dicarboxylic acid 1-tert-butyl ester (46 g) in o-xylene (300 mL) and DMA (30 mL) was heated under reflux for 5 hrs. After cooling to room temperature, it was washed with brine (200 mL×2). The organic layer was then dried over anhy. Na$_2$SO$_4$, filtered, and concentrated in vacuo. The residue obtained was then purified on a silica gel column eluting with EA:DCM: Hex=1:1:3 to give the title compound (18 g) as a white solid. MS: 298.7 (M+H$^+$).

[D] 3-[6-(6-Chloro-1,1-dimethyl-3-oxo-1,3-dihydro-isoindol-2-yl)-pyrazin-2-yl]-piperidine-1-carboxylic acid tert-butyl ester

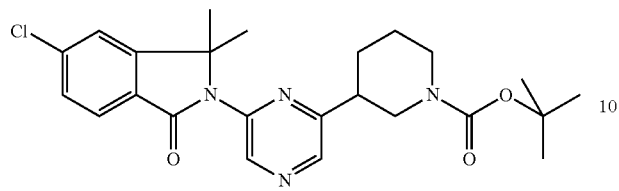

A mixture of 3-(6-chloro-pyrazin-2-yl)-piperidine-1-carboxylic acid tert-butyl ester (892.5 mg, 3.0 mmol), 5-chloro-3,3-dimethyl-2,3-dihydro-isoindol-1-one (intermediate A-12, 586.5 mg, 3.0 mmol), CuI (171.4 mg, 0.9 mmol), (1S,2S)-cyclohexane-1,2-diamine (205.2 mg, 1.8 mmol) and Cs$_2$CO$_3$ (1.956 g, 6.0 mmol) were dissolved in dioxane (15 mL). The reaction mixture was subjected to microwave reaction at 150° C. for 2.5 hours before it was poured into H$_2$O (50 mL) and extracted with EtOAc (50 mL×2). The combined organic layers were washed with brine, dried over anhy. Na$_2$SO$_4$, filtered and concentrated in vacuo to give a crude product which was then purified by flash chromatography to afford the title compound (450 mg, 33%) as a white solid. MS: 457.2 (M+H$^+$).

[E] 5-Chloro-3,3-dimethyl-2-(6-piperidin-3-yl-pyrazin-2-yl)-2,3-dihydro-isoindol-1-one

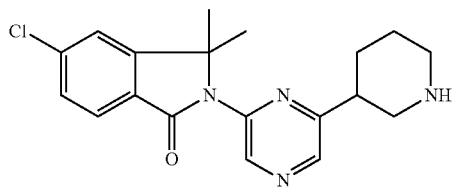 [SMILES: CC1(C)c2cc(Cl)ccc2C(=O)N1c1cncc(C2CCCNC2)n1]

A mixture of 3-[6-(6-chloro-1,1-dimethyl-3-oxo-1,3-dihydro-isoindol-2-yl)-pyrazin-2-yl]-piperidine-1-carboxylic acid tert-butyl ester (0.45 g, 0.99 mmol) and trifluoroacetic acid (2 mL) in DCM (10 mL) was stirred for 1 hour at room temperature. After removal of solvent, the residue was treated with water, and extracted with DCM. The aqueous solution treated with satd. aq. sodium carbonate solution, and extracted with EtOAc. The combined organic layers were dried over anhy. Na$_2$SO$_4$. After removal of solvent, the crude product was obtained as yellowish oil (352.9 mg, 100%). MS: 357.2 (M+H$^+$).

[F] 2-[6-(1-Acetyl-piperidin-3-yl)-pyrazin-2-yl]-5-chloro-3,3-dimethyl-2,3-dihydro-isoindol-1-one

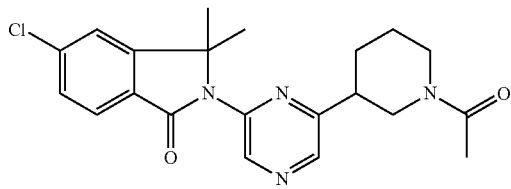 [SMILES: CC(=O)N1CCCC(c2cncc(N3C(=O)c4ccc(Cl)cc4C3(C)C)n2)C1]

To a mixture of 5-chloro-3,3-dimethyl-2-(6-piperidin-3-yl-pyrazin-2-yl)-2,3-dihydro-isoindol-1-one (80 mg, 0.22 mmol) and Et$_3$N (44.4 mg, 0.44 mmol) in DCM (2 mL) was added acetyl chloride (26.4 mg, 0.34 mmol) at 0° C. After removal of solvent, the residue was purified by prep-HPLC to yield the title compound (30.6 mg, 35%) as a white solid. MS: 399.2 (M+H$^+$).

Example 463

5-Chloro-3,3-dimethyl-2-[6-(1-propionyl-piperidin-3-yl)-pyrazin-2-yl]-2,3-dihydro-isoindol-1-one

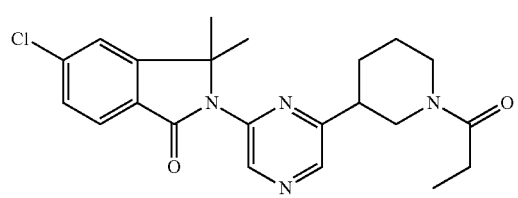 [SMILES: CCC(=O)N1CCCC(c2cncc(N3C(=O)c4ccc(Cl)cc4C3(C)C)n2)C1]

In analogy to the procedure described for the preparation of example 462, propionyl chloride was used (step F) to yield the tile compound (36.3 mg, 40%) as a white solid. MS: 413.2 (M+H$^+$).

Example 464

5-Chloro-2-[6-(1-ethanesulfonyl-piperidin-3-yl)-pyrazin-2-yl]-3,3-dimethyl-2,3-dihydro-isoindol-1-one

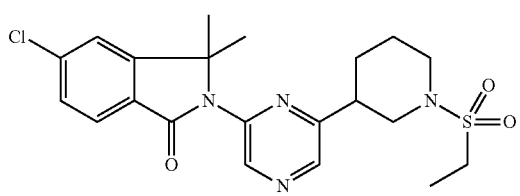 [SMILES: CCS(=O)(=O)N1CCCC(c2cncc(N3C(=O)c4ccc(Cl)cc4C3(C)C)n2)C1]

In analogy to the procedure described for the preparation of example 462, ethanesulfonyl chloride was used (step F) to yield the tile compound (29.6 mg, 30%) as a white solid. MS: 449.2 (M+H$^+$).

Example 465

5-Chloro-2-[6-(1-methanesulfonyl-piperidin-3-yl)-pyrazin-2-yl]-3,3-dimethyl-2,3-dihydro-isoindol-1-one

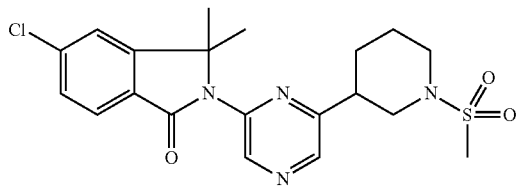 [SMILES: CC1(C)c2cc(Cl)ccc2C(=O)N1c1cncc(C2CCCN(S(C)(=O)=O)C2)n1]

In analogy to the procedure described for the preparation of example 462, methanesulfonyl chloride was used (step F) to yield the tile compound (19.1 mg, 20% yield) as a white solid. MS: 435.0 (M+H⁺).

Example 466

N—[(S or R)-4-(6-Chloro-1,1-dimethyl-3-oxo-1,3-dihydro-isoindol-2-yl)-5,6,7,8-tetrahydro-isoquinolin-8-yl]-acetamide

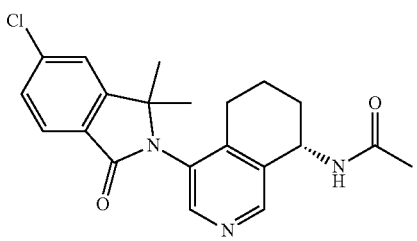 [SMILES: CC(=O)N[C@H]1CCCc2c1cncc2N1C(=O)c2ccc(Cl)cc2C1(C)C]

Example 467

N—[(R or S)-4-(6-Chloro-1,1-dimethyl-3-oxo-1,3-dihydro-isoindol-2-yl)-5,6,7,8-tetrahydro-isoquinolin-8-yl]-acetamide

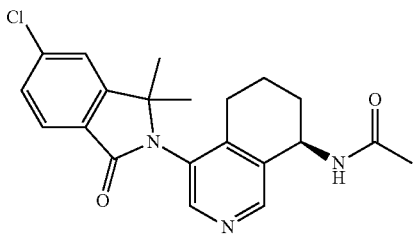 [SMILES: CC(=O)N[C@@H]1CCCc2c1cncc2N1C(=O)c2ccc(Cl)cc2C1(C)C]

[A] 4'-Bromo-5,5-dimethyl-6',7'-dihydro-5'H-spiro[1,3-dioxane-2,8'-isoquinoline]

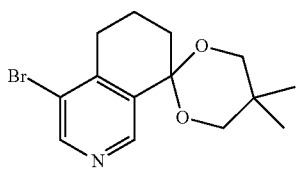 [SMILES: CC1(C)COC2(CCCc3c(Br)cncc32)OC1]

A reaction mixture of 4-bromo-6,7-dihydro-5H-isoquinolin-8-one (intermediate B-11 [C], 5.0 g, 22 mmol), 2,2-dimethyl-propane-1,3-diol (2.8 g, 26.5 mmol) and toluene-4-sulfonic acid (85 mg, 0.44 mmol) in toluene (100 mL) was heated at 135° C. for 12 hours. After cooling to room temperature, it was concentrated under reduced pressure to give a residue which was extracted between EtOAc and water. The organic layer was washed with brine, dried over anhy. Na₂SO₄, filtered, and concentrated in vacuo to give a crude product (6.1 g, 88.9%) as a light yellow solid. MS: 312.2 & 314.2 (M+H⁺).

[B] 5-Chloro-2-(5,5-dimethyl-6',7'-dihydro-5'H-spiro[1,3-dioxane-2,8'-isoquinolin]-4'-yl)-2,3-dihydro-1H-isoindol-1-one

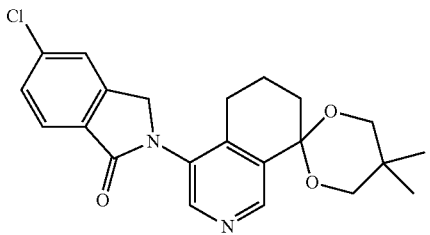 [SMILES: CC1(C)COC2(CCCc3c(N4Cc5cc(Cl)ccc5C4=O)cncc32)OC1]

A mixture of 4'-bromo-5,5-dimethyl-6',7'-dihydro-5'H-spiro[1,3-dioxane-2,8'-isoquinoline](5.0 g, 16 mmol), 5-chloro-2,3-dihydro-isoindol-1-one (2.7 g, 16 mmol), (+)-(1S,1S)-1,2-diaminocyclohexane (0.576 mL, 4.8 mmol), copper (I) iodide (456 mg, 2.4 mmol) and Cs₂CO₃ (10.4 g, 32 mmol) in dioxane (80 mL) was heated at 150° C. for 4 hours. After cooling to room temperature, it was diluted with water (50 mL) and extracted with EtOAc (200 mL×2). The combined organic layers were dried over anhy. Na₂SO₄, filtered and concentrated in vacuo to afford a crude product (5.5 g, 86%) as light yellow solid. MS: 399.1 (M+H⁺).

[C] 5-Chloro-2-(5,5-dimethyl-6',7'-dihydro-5'H-spiro[1,3-dioxane-2,8'-isoquinolin]-4'-yl)-3,3-dimethyl-2,3-dihydro-1H-isoindol-1-one

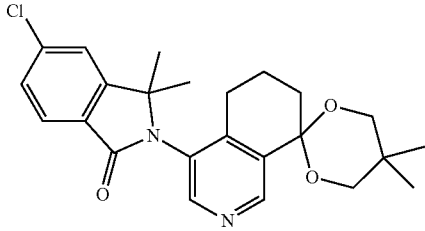 [SMILES: CC1(C)COC2(CCCc3c(N4C(=O)c5ccc(Cl)cc5C4(C)C)cncc32)OC1]

To a stirred solution of 5-chloro-2-(5,5-dimethyl-6',7'-dihydro-5'H-spiro[1,3-dioxane-2,8'-isoquinolin]-4'-yl)-2,3-dihydro-1H-isoindol-1-one (2.38 g, 6 mmol) in THF was added LiHMDS (18 mL 1.0 M in THF, 18 mmol) at 0° C. It was stirred at 0° C. 30 min before CH₃I (1.5 mL, 24 mmol) was added. The resulting mixture was stirred at 0° C. for another 30 min. before it was diluted with water (10 mL) and extracted with EtOAc (2×100 mL). The combined organic layers were dried over anhy.Na₂SO₄, filtered and concentrated in vacuo to afford a crude product which was then purified by silica gel flash chromatography eluting with a 0 to 5% MeOH-DCM gradient to give the title compound (664 mg, 26%) as a yellow foam. MS: 427.1 (M+H⁺).

[D] 4-(6-Chloro-1,1-dimethyl-3-oxo-1,3-dihydro-isoindol-2-yl)-6,7-dihydro-5H-isoquinolin-8-one

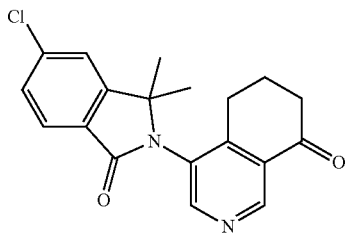 [SMILES: CC1(C)c2cc(Cl)ccc2C(=O)N1c1cncc2c1CCCC2=O]

To a solution of 5-chloro-2-(5,5-dimethyl-6',7'-dihydro-5'H-spiro[1,3-dioxane-2,8'-isoquinolin]-4'-yl)-3,3-dimethyl-2,3-dihydro-1H-isoindol-1-one (0.66 g, 1.55 mmol) in MeOH (2 mL) was added 4 N HCl in dioxane (1.5 mL, 6 mmol) and the reaction mixture was stirred at room temperature for 2 hours. After evaporation of the solvent, the residue was diluted with DCM (20 mL) and washed with satd. aq. NaHCO₃ (10 mL) solution. The organic layer was dried over anhy. Na₂SO₄, filtered and evaporated to dryness. The residue obtained was purified by silica gel flash chromatography eluting with a 0 to 50% hexane-ethyl acetate gradient to give the title compound (421 mg, 80%) as a light yellow solid. MS: 341.1 (M+H⁺).

[E] 2-(8-Amino-5,6,7,8-tetrahydro-isoquinolin-4-yl)-5-chloro-3,3-dimethyl-2,3-dihydro-isoindol-1-one

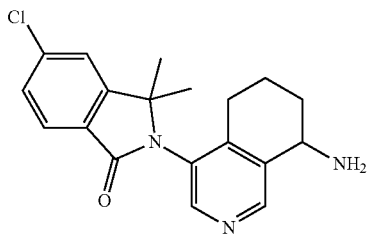 [SMILES: CC1(C)c2cc(Cl)ccc2C(=O)N1c1cncc2c1CCCC2N]

A mixture of 4-(6-chloro-1,1-dimethyl-3-oxo-1,3-dihydro-isoindol-2-yl)-6,7-dihydro-5H-isoquinolin-8-one (408 mg, 1.2 mmol), NaBH₃CN (75 mg, 1.2 mmol) and CH₃COONH₄ (1.0 g, 12 mmol) in isopropanol (10 mL) was heated to reflux for 3 hours. After cooling to room temperature, it was concentrated to afford a yellowish oil which was extracted between water with EtOAc (2×100 mL). The combined organic layers were washed with brine, dried over anhy. Na₂SO₄, filtered and concentrated in vacuo to afford the crude title compound (327 mg, 80%) as a brown solid. MS: 342.1 & 325.1 (M+H⁺).

[F] N-[4-(6-Chloro-1,1-dimethyl-3-oxo-1,3-dihydro-isoindol-2-yl)-5,6,7,8-tetrahydro-isoquinolin-8-yl]-acetamide

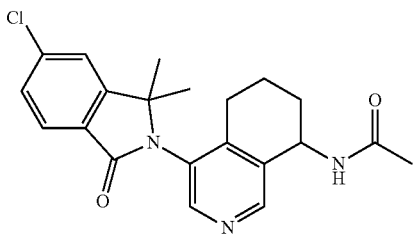 [SMILES: CC(=O)NC1CCCc2c1cncc2N1C(=O)c2ccc(Cl)cc2C1(C)C]

To a stirred solution of 2-(8-amino-5,6,7,8-tetrahydro-isoquinolin-4-yl)-5-chloro-3,3-dimethyl-2,3-dihydro-isoindol-1-one (140 mg, 0.42 mmol) and Et₃N (1.0 mL) in DCM (10 mL) was added acetyl chloride (0.032 mL, 0.44 mmol) at 0° C. and stirring was continued at 0° C. for 1 hour. After evaporation of solvent, the residule was extracted between water with EtOAc (2×100 mL). The combined organic layers were washed with brine, dried over anhy. Na₂SO₄, filtered and concentrated in vacuo to afford a crude product which was then purified by silica gel flash chromatography eluting with a 0 to 50% EtOAc-heptane gradient to give a racemic mixture of the title compound (117 mg, 73%) as light yellow solid. MS: 384.1 (M+H⁺). This racemic mixture was then separated by chiral HPLC to afford N—[(S or R)-4-(6-chloro-1,1-dimethyl-3-oxo-1,3-dihydro-isoindol-2-yl)-5,6,7,8-tetrahydro-isoquinolin-8-yl]-acetamide (35 mg, example 466), MS: 384.1 (M+H⁺) and N—[(R or S)-4-(6-chloro-1,1-dimethyl-3-oxo-1,3-dihydro-isoindol-2-yl)-5,6,7,8-tetrahydro-isoquinolin-8-yl]-acetamide (38 mg, example 467) MS: 384.1 (M+H)⁺.

Example 468

N-[4-(6-Chloro-1,1-dimethyl-3-oxo-1,3-dihydro-isoindol-2-yl)-5,6,7,8-tetrahydro-isoquinolin-8-yl]-propionamide

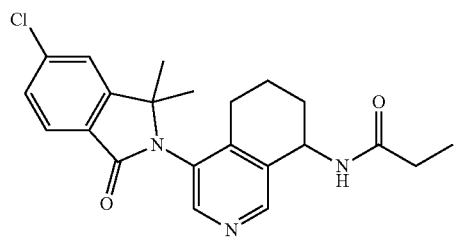 [SMILES: CCC(=O)NC1CCCc2c1cncc2N1C(=O)c2ccc(Cl)cc2C1(C)C]

In analogy to the procedure described for the preparation of Examples 466 and 467, propionyl chloride was used (step E) to afford a racemic mixture of the title compound (19.1 mg, 20%) as a white solid. MS: 398.1 (M+H⁺).

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound according to formula (I),

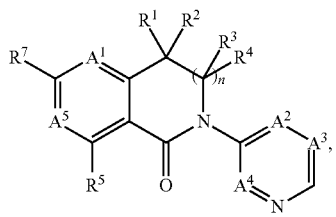

wherein $R^1$, $R^2$, $R^3$ and $R^4$ are independently selected from the group consisting of H, alkyl, cycloalkyl, cycloalkylalkyl, haloalkyl, halocycloalkyl, hydroxyalkyl, alkoxyalkyl, haloalkoxyalkyl, halocycloalkylalkyl, substituted heterocycloalkyl, substituted heterocycloalkylalkyl, substituted arylalkyl and substituted heteroarylalkyl, wherein substituted heterocycloalkyl, substituted heterocycloalkylalkyl, substituted arylalkyl and substituted heteroarylalkyl are substituted with $R^{12}$, $R^{13}$ and $R^{14}$;

or $R^2$ and $R^4$ together form a double bond, wherein in case $R^2$ and $R^4$ together form a double bond, then $R^5$ is H;

or $R^1$ and $R^2$ together with the carbon atom to which they are attached form a substituted cycloalkyl or a substituted heterocycloalkyl, wherein substituted cycloalkyl and substituted heterocycloalkyl are substituted with $R^{22}$, $R^{23}$ and $R^{24}$;

or $R^3$ and $R^4$ together with the carbon atom to which they are attached form a substituted cycloalkyl or a substituted heterocycloalkyl, wherein substituted cycloalkyl and substituted heterocycloalkyl are substituted with $R^{29}$, $R^{30}$ and $R^{31}$;

or $R^1$ and $R^3$ together with the carbon atom to which they are attached form a substituted cycloalkyl or a substituted heterocycloalkyl, wherein substituted cycloalkyl and substituted heterocycloalkyl are substituted with $R^{44}$, $R^{45}$ and $R^{46}$;

$A^1$ is $CR^8$ or N;
$A^2$ is $CR^9$ or N;
$A^3$ is $CR^{10}$ or N;
$A^4$ is $CR^{11}$ or N;
$A^5$ is $CR^6$;
one of $R^5$, $R^6$, $R^7$ and $R^8$ is selected from the group consisting of halogen, cyano, alkoxy, hydroxyalkoxy, haloalkyl, haloalkoxy and hydroxy and the others are each independently selected from the group consisting of H, halogen, cyano, alkoxy, hydroxyalkoxy, haloalkoxy and hydroxy;

$R^9$ is selected from the group consisting of H, halogen, hydroxy, cyano, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, alkoxycycloalkylalkyl, dialkoxyalkyl, haloalkoxy, haloalkoxyalkyl, alkoxyalkoxy, alkoxyalkoxyalkyl, haloalkoxyalkoxy, haloalkoxyalkoxyalkyl, substituted arylalkyl, substituted arylhydroxyalkyl, substituted heterocycloalkylalkyl and substituted heteroarylalkyl, wherein substituted arylalkyl, substituted arylhydroxyalkyl, substituted heterocycloalkylalkyl and substituted heteroarylalkyl are substituted with $R^{32}$, $R^{33}$ and $R^{34}$;

$R^{10}$ is $-O_m-(CR^{15}R^{16})_p-(CR^{17}R^{18})_q-(CR^{19}R^{20})_r-R^{21}$;

or $R^9$ and $R^{10}$ together with the carbon atoms to which they are attached form a substituted cycloalkyl, a substituted heterocycloalkyl, a substituted aryl or a substituted heteroaryl, wherein substituted cycloalkyl, substituted heterocycloalkyl, substituted aryl and substituted heteroaryl are substituted with $R^{35}$, $R^{36}$ and $R^{37}$;

$R^{11}$ is H;

$R^{15}$, $R^{17}$ and $R^{19}$ are each independently selected from the group consisting of H, alkyl, cycloalkyl, haloalkyl and halocycloalkyl;

$R^{16}$, $R^{18}$ and $R^{20}$ are each independently selected from the group consisting of H, hydroxy, halogen and alkyl;

or $R^{15}$ and $R^{16}$ together with the carbon atom to which they are attached form a cycloalkyl;

or $R^{17}$ and $R^{18}$ together with the carbon atom to which they are attached form a cycloalkyl;

or $R^{19}$ and $R^{20}$ together with the carbon atom to which they are attached form a cycloalkyl;

or $R^{15}$ and $R^{17}$ together form $-(CH_2)_v-$;
or $R^{15}$ and $R^{19}$ together form $-(CH_2)_w-$;
or $R^{17}$ and $R^{19}$ together form $-(CH_2)_x-$;

$R^{21}$ is selected from the group consisting of H, halogen, cyano, $-OR^{25}$, $-SR^{25}$, $-S(O)R^{25}$, $-S(O)_2R^{25}$, $-NR^{25}R^{26}$, $-NR^{26}SO_2R^{25}$, $-NR^{26}SO_2NR^{25}R^{27}$, $-NR^{26}C(O)R^{25}$, $-HR^{26}C(O)NR^{25}R^{27}$, $-C(O)R^{28}$, $-C(O)NR^{25}R^{26}$, cycloalkyl, substituted heterocycloalkyl, substituted heteroaryl and substituted aryl, wherein substituted heterocycloalkyl, substituted heteroaryl, substituted heteroarylalkyl and substituted aryl are substituted with $R^{38}$, $R^{39}$ and $R^{40}$;

$R^{25}$ is selected from the group consisting of H, alkyl, hydroxyalkyl, carboxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxyalkyl, cycloalkoxyalkyl, halocycloalkoxyalkyl, alkylcycloalkoxyalkyl, alkoxyalkyl, haloalkoxyalkyl, alkoxyalkoxyalkyl, haloalkoxyalkoxyalkyl, substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{41}$, $R^{42}$ and $R^{43}$;

$R^{26}$ and $R^{27}$ are each independently selected from the group consisting of H, alkyl, cycloalkyl, haloalkyl and halocycloalkyl;

or $R^{15}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

or $R^{17}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and R49;

or $R^{19}$ and $R^{26}$ together with the nitrogen atom and carbon atom to which they are attached form a substituted heterocycloalkyl or a substituted heteroaryl, wherein substituted heterocycloalkyl and substituted heteroaryl are substituted with $R^{47}$, $R^{48}$ and $R^{49}$;

$R^{28}$ is selected from the group consisting of H, hydroxy, alkyl, hydroxyalkyl, haloalkyl, cycloalkyl, cycloalkylalkyl, alkylcycloalkyl, halocycloalkyl, alkylcycloalkylalkyl, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxyalkyl, haloalkoxy, haloalkoxyalkyl, alkoxyalkoxy, alkoxyalkoxyalkyl, haloalkoxyalkoxy, haloalkoxyalkoxyalkyl substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{50}$, $R^{51}$ and $R^{52}$;

$R^{12}$, $R^{13}$, $R^{14}$, $R^{22}$, $R^{23}$, $R^{24}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$ and $R^{52}$ are each independently selected from the group consisting of H, halogen, hydroxy, amino, nitro, cyano, oxo, alkyl, alkylcarbonyl, alkylsulfonyl, hydroxyalkyl, haloalkyl, cycloalkyl, cycloalkylalkyl, alkylcycloalkyl, halocycloalkyl, alkylcycloalkylalkyl, alkylcarbonylamino, alkylsulfonyl, alkylsulfonylamino, alkoxycycloalkylalkyl, halocycloalkylalkyl, cycloalkylalkoxy, cycloalkylalkoxyalkyl, cycloalkoxy, cycloalkoxyalkyl, halocycloalkoxy, halocycloalkoxyalkyl, alkylcycloalkoxy, alkylcycloalkoxyalkyl, alkoxy, alkoxycarbonyl, alkoxyalkyl, haloalkoxy, haloalkoxyalkyl, alkoxyalkoxy, alkoxyalkoxyalkyl, haloalkoxyalkoxy, haloalkoxyalkoxyalkyl, chloropyridinylcarbonyl and heterocycloalkyl;

n is zero or 1;
m is zero or 1;
p, q and r are independently selected from zero and 1;
v and x are independently 1, 2, 3 or 4; and
w is zero, 1, 2 or 3;
with the proviso that no more than one of $A^2$, $A^3$ and $A^4$ is N;

or a pharmaceutically acceptable salt thereof.

2. The compound according to claim 1, wherein $R^1$, $R^2$, $R^3$ and $R^4$ are independently selected from the group consisting of H, alkyl, cycloalkyl, cycloalkylalkyl, haloalkyl, halocycloalkyl, hydroxyalkyl, alkoxyalkyl, haloalkoxyalkyl, halocycloalkylalkyl, substituted heterocycloalkyl, substituted heterocycloalkylalkyl, substituted arylalkyl and substituted heteroarylalkyl, wherein substituted heterocycloalkyl, substituted heterocycloalkylalkyl, substituted arylalkyl and substituted heteroarylalkyl are substituted with $R^{12}R^{13}$ and $R^{14}$.

3. The compound according to claim 1, wherein $R^1$ is selected from the group consisting of H, alkyl and arylalkyl substituted with $R^{12}$, $R^{13}$ and $R^{14}$.

4. The compound according to claim 1, wherein $R^2$ is H or alkyl.

5. The compound according to claim 1, wherein $R^1$ and $R^2$ together with the carbon atom to which they are attached form a substituted cycloalkyl or a substituted heterocycloalkyl, wherein substituted cycloalkyl and substituted heterocycloalkyl are substituted with $R^{22}$, $R^{23}$ and $R^{24}$.

6. The compound according to claim 1, wherein $R^1$ and $R^2$ together with the carbon atom to which they are attached form a cycloalkyl substituted with $R^{22}$, $R^{23}$ and $R^{24}$.

7. The compound according to claim 1, wherein $R^3$ is H or alkyl.

8. The compound according to claim 1, wherein $R^4$ is H.

9. The compound according to claim 1, wherein $A^1$ is $CR^8$.

10. The compound according to claim 1, wherein $A^2$ is $CR^9$.

11. The compound according to claim 1, wherein $A^3$ is $CR^{10}$.

12. The compound according to claim 1, wherein $A^4$ is $CR^{11}$.

13. The compound according to claim 1, wherein one of $R^5$, $R^6$, $R^7$ and $R^8$ is selected from the group consisting of halogen, alkoxy and hydroxy and the others are each independently selected from H and halogen.

14. The compound according to claim 1, wherein $R^9$ is selected from the group consisting of H, halogen, cyano, alkyl, hydroxyalkyl, haloalkyl, alkoxyalkyl, alkoxycycloalkylalkyl, dialkoxyalkyl, substituted arylhydroxyalkyl and substituted heterocycloalkylalkyl, wherein substituted arylhydroxyalkyl and substituted heterocycloalkylalkyl are substituted with $R^{32}$, $R^{33}$ and $R^{34}$.

15. The compound according to claim 1, wherein $R^9$ and $R^{10}$ together with the carbon atoms to which they are attached form a substituted cycloalkyl, a substituted aryl or a substituted heteroaryl, wherein substituted cycloalkyl, substituted aryl and substituted heteroaryl are substituted with $R^{35}$, $R^{36}$ and $R^{37}$.

16. The compound according to claim 1, wherein $R^{15}$, $R^{17}$ and $R^{19}$ are each independently selected from the group consisting of H, alkyl, cycloalkyl, haloalkyl and halocycloalkyl.

17. The compound according to claim 1, wherein $R^{16}$, $R^{18}$ and $R^{20}$ are each independently selected from the group consisting of H, hydroxy, halogen and alkyl.

18. The compound according to claim 1, wherein $R^{21}$ is selected from the group consisting of H, halogen, cyano, —$OR^{25}$, —$SR^{25}$, —$S(O)R^{25}$, —$NR^{25}R^{26}$, —$NR^{26}SO_2R^{25}$, —$NR^{26}C(O)R^{25}$, —$NR^{26}C(O)NR^{25}R^{27}$, —$C(O)R^{28}$, —$C(O)NR^{25}R^{26}$, cycloalkyl, substituted heterocycloalkyl, substituted heteroaryl and substituted aryl, wherein substituted heterocycloalkyl, substituted heteroaryl and substituted aryl are substituted with $R^{38}$, $R^{39}$ and $R^{40}$.

19. The compound according to claim 1, wherein $R^{25}$ is selected from the group consisting of H, alkyl, hydroxyalkyl, carboxyalkyl, haloalkyl, cycloalkyl, cycloalkylalkyl, substituted heterocycloalkyl, substituted heterocycloalkylalkyl, substituted heteroaryl, substituted heteroarylalkyl, substituted aryl and substituted arylalkyl, wherein substituted heterocycloalkyl, substituted heterocycloalkylalkyl, substituted heteroaryl, substituted heteroarylalkyl, substituted aryl and substituted arylalkyl are substituted with $R^{41}$, $R^{42}$ and $R^{43}$.

20. The compound according to claim 1, wherein $R^{26}$ and $R^{27}$ are each independently selected from the group consisting of H, alkyl, cycloalkyl, haloalkyl and halocycloalkyl.

21. The compound according to claim 1, wherein $R^{12}$, $R^{13}$, $R^{14}$, $R^{22}$, $R^{23}$, $R^{24}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$ and $R^{52}$ are each independently selected from the group consisting of H, halogen, hydroxy, amino, nitro, cyano, oxo, alkyl, alkylcarbonyl, alkylsulfonyl, hydroxyalkyl, haloalkyl, cycloalkyl, alkylcarbonylamino, alkoxycarbonyl, alkoxyalkyl, haloalkoxy, chloropyridinylcarbonyl and heterocycloalkyl.

22. The compound according to claim 1, selected from the group consisting of
6-Chloro-2-pyridin-3-yl-3,4-dihydro-2H-isoquinolin-1-one;
5-(6-Chloro-1-oxo-3,4-dihydro-1H-isoquinolin-2-yl)-nicotinonitrile;
6-Chloro-2-(5-hydroxymethyl-pyridin-3-yl)-3,4-dihydro-2H-isoquinolin-1-one;
6-Chloro-2-(5-chloro-pyridin-3-yl)-3,4-dihydro-2H-isoquinolin-1-one;
6-Chloro-2-(5-fluoro-pyridin-3-yl)-3,4-dihydro-2H-isoquinolin-1-one;
6-Chloro-2-(4-chloro-pyridin-3-yl)-3,4-dihydro-2H-isoquinolin-1-one;
2-(5-Bromo-pyridin-3-yl)-6-chloro-3,4-dihydro-2H-isoquinolin-1-one;
6-Chloro-2-(5-methyl-pyridin-3-yl)-3,4-dihydro-2H-isoquinolin-1-one;
5-(6-Chloro-1-oxo-3,4-dihydro-1H-isoquinolin-2-yl)-pyridine-3-carbaldehyde;
6-Chloro-2-(5-methoxy-pyridin-3-yl)-3,4-dihydro-2H-isoquinolin-1-one;
6-Chloro-2-(5-isopropoxy-pyridin-3-yl)-3,4-dihydro-2H-isoquinolin-1-one;
6-Chloro-2-[5-(1-hydroxy-1-methyl-ethyl)-pyridin-3-yl]-3,4-dihydro-2H-isoquinolin-1-one;
6-Chloro-2-[5-(1-hydroxy-ethyl)-pyridin-3-yl]-3,4-dihydro-2H-isoquinolin-1-one;
6-Chloro-2-[5-((R)-1-hydroxy-ethyl)-pyridin-3-yl]-3,4-dihydro-2H-isoquinolin-1-one;
6-Chloro-2-[5-((S)-1-hydroxy-ethyl)-pyridin-3-yl]-3,4-dihydro-2H-isoquinolin-1-one;
and pharmaceutically acceptable salts thereof.

23. The compound according to claim 1, selected from the group consisting of
6-Chloro-2-[5-(1-methoxy-ethyl)-pyridin-3-yl]-3,4-dihydro-2H-isoquinolin-1-one;
2-(5-Amino-pyridin-3-yl)-6-chloro-3,4-dihydro-2H-isoquinolin-1-one;
6-Chloro-2-[5-(2,2,2-trifluoro-1-hydroxy-ethyl)-pyridin-3-yl]-3,4-dihydro-2H-isoquinolin-1-one;
6-Chloro-2-[5-(2,2,2-trifluoro-1-methoxy-ethyl)-pyridin-3-yl]-3,4-dihydro-2H-isoquinolin-1-one
6-Chloro-2-[5-(cyclopropyl-hydroxy-methyl)-pyridin-3-yl]-3,4-dihydro-2H-isoquinolin-1-one;
6-Chloro-2-[5-(cyclopropyl-methoxy-methyl)-pyridin-3-yl]-3,4-dihydro-2H-isoquinolin-1-one;
6-Chloro-2-(4-trifluoromethyl-pyridin-3-yl)-3,4-dihydro-2H-isoquinolin-1-one;
6-Chloro-2-[5-(2-hydroxy-ethyl)-pyridin-3-yl]-3,4-dihydro-2H-isoquinolin-1-one;
6-Chloro-2-[5-(1-methoxy-1-methyl-ethyl)-pyridin-3-yl]-3,4-dihydro-2H-isoquinolin-1-one;
Ethanesulfonic acid [5-(6-chloro-1-oxo-3,4-dihydro-1H-isoquinolin-2-yl)-pyridin-3-ylmethyl]-amide;
6-Chloro-2-[5-(2-oxo-pyrrolidin-1-yl)-pyridin-3-yl]-3,4-dihydro-2H-isoquinolin-1-one;
6-Chloro-2-(1-methyl-1H-pyrazolo[3,4-c]pyridin-4-yl)-3,4-dihydro-2H-isoquinolin-1-one;
6-Chloro-8'-hydroxy-3,4,5',6',7',8'-hexahydro-[2,4']biisoquinolinyl-1-one;
N-(6-Chloro-1-oxo-3,4,5',6',7',8'-hexahydro-1H-[2,4']biisoquinolinyl-8'-yl)-propionamide;
6-Chloro-2-{5-[hydroxy-(1-methyl-1H-imidazol-2-yl)-methyl]-pyridin-3-yl}-3,4-dihydro-2H-isoquinolin-1-one;
and pharmaceutically acceptable salts thereof.

24. The compound according to claim 1, selected from the group consisting of
6-Chloro-2-{5-[(3,4-difluoro-phenyl)-hydroxy-methyl]-pyridin-3-yl}-3,4-dihydro-2H-isoquinolin-1-one;
6-Chloro-2-{5-[(3,5-difluoro-phenyl)-hydroxy-methyl]-pyridin-3-yl}-3,4-dihydro-2H-isoquinolin-1-one;
6-Chloro-2-{5-[(4-ethyl-phenyl)-hydroxy-methyl]-pyridin-3-yl}-3,4-dihydro-2H-isoquinolin-1-one;
6-Chloro-2-[5-(hydroxy-phenyl-methyl)-pyridin-3-yl]-3,4-dihydro-2H-isoquinolin-1-one;
6-Chloro-2-[5-(1-hydroxy-1-phenyl-ethyl)-pyridin-3-yl]-3,4-dihydro-2H-isoquinolin-1-one;
6-Chloro-2-{5-[1-(3,4-difluoro-phenyl)-1-hydroxy-ethyl]-pyridin-3-yl}-3,4-dihydro-2H-isoquinolin-1-one;
6-Chloro-2-{5-[1-(3,5-difluoro-phenyl)-1-hydroxy-ethyl]-pyridin-3-yl}-3,4-dihydro-2H-isoquinolin-1-one;
6-Chloro-2-(6-methyl-pyrazin-2-yl)-3,4-dihydro-2H-isoquinolin-1-one;
6-Chloro-2-[5-(morpholine-4-carbonyl)-pyridin-3-yl]-3,4-dihydro-2H-isoquinolin-1-one;
6-Chloro-2-[5-(3-hydroxy-pyrrolidine-1-carbonyl)-pyridin-3-yl]-3,4-dihydro-2H-isoquinolin-1-one;
5-(6-Chloro-1-oxo-3,4-dihydro-1H-isoquinolin-2-yl)-N,N-dimethyl-nicotinamide;
6-Chloro-2-[5-(pyrrolidine-1-carbonyl)-pyridin-3-yl]-3,4-dihydro-2H-isoquinolin-1-one;
5-(6-Chloro-1-oxo-3,4-dihydro-1H-isoquinolin-2-yl)-N-methyl-nicotinamide;
5-(6-Chloro-1-oxo-3,4-dihydro-1H-isoquinolin-2-yl)-N-cyclopropyl-nicotinamide;
5-(6-Chloro-1-oxo-3,4-dihydro-1H-isoquinolin-2-yl)-N-(4-fluoro-phenyl)-nicotinamide;
and pharmaceutically acceptable salts thereof.

25. The compound according to claim 1, selected from the group consisting of
5-(6-Chloro-1-oxo-3,4-dihydro-1H-isoquinolin-2-yl)-N-phenyl-nicotinamide;
6-Chloro-2-[5-(4,4-difluoro-piperidine-1-carbonyl)-pyridin-3-yl]-3,4-dihydro-2H-isoquinolin-1-one;
6-Chloro-2-[5-((S)-2-methoxymethyl-pyrrolidin-1-ylmethyl)-pyridin-3-yl]-3,4-dihydro-2H-isoquinolin-1-one;
6-Chloro-2-[5-((S)-2-methoxymethyl-pyrrolidin-1-yl)-pyridin-3-yl]-3,4-dihydro-2H-isoquinolin-1-one;
6-Chloro-2-[5-((S)-2-hydroxymethyl-5-oxo-pyrrolidin-1-yl)-pyridin-3-yl]-3,4-dihydro-2H-isoquinolin-1-one;
6-Chloro-2-pyrimidin-5-yl-3,4-dihydro-2H-isoquinolin-1-one;
6-Chloro-2-pyridazin-3-yl-3,4-dihydro-2H-isoquinolin-1-one;
6-Chloro-2-pyridin-3-yl-2H-isoquinolin-1-one;
6-Chloro-2-(5-fluoro-pyridin-3-yl)-2H-isoquinolin-1-one;

6-Chloro-2-[4-(1-hydroxy-ethyl)-pyridin-3-yl]-3,4-dihydro-2H-isoquinolin-1-one;
6-Chloro-2-(4-hydroxymethyl-pyridin-3-yl)-3,4-dihydro-2H-isoquinolin-1-one;
2-[5-(1-Amino-cyclopropyl)-pyridin-3-yl]-6-chloro-3,4-dihydro-2H-isoquinolin-1-one;
6-Chloro-2-[5-(4-methyl-4H-[1,2,4]triazol-3-yl)-pyridin-3-yl]-3,4-dihydro-2H-isoquinolin-1-one;
6-Chloro-2-(5-methylsulfanyl-pyridin-3-yl)-3,4-dihydro-2H-isoquinolin-1-one;
6-Chloro-2-(5-difluoromethoxy-pyridin-3-yl)-3,4-dihydro-2H-isoquinolin-1-one;
and pharmaceutically acceptable salts thereof.

26. The compound according to claim 1, selected from the group consisting of
6-Chloro-2-(4-dimethoxymethyl-pyridin-3-yl)-3,4-dihydro-2H-isoquinolin-1-one;
6-Chloro-2-[5-fluoro-4-(1-hydroxy-ethyl)-pyridin-3-yl]-3,4-dihydro-2H-isoquinolin-1-one;
6-Chloro-2-{4-[(4-fluoro-phenyl)-hydroxy-methyl]-pyridin-3-yl}-3,4-dihydro-2H-isoquinolin-1-one;
6-Chloro-2-[4-(1-methoxy-ethyl)-pyridin-3-yl]-3,4-dihydro-2H-isoquinolin-1-one;
6-Chloro-2-(1-methyl-1H-pyrrolo[3,2-c]pyridin-7-yl)-3,4-dihydro-2H-isoquinolin-1-one;
6-Chloro-2-(5-cyclopropyl-pyridin-3-yl)-3,4-dihydro-2H-isoquinolin-1-one;
6-Chloro-2-[5-(2-methyl-2H-[1,2,4]triazol-3-yl)-pyridin-3-yl]-3,4-dihydro-2H-isoquinolin-1-one;
6-Chloro-2-(5-cyclopropoxy-pyridin-3-yl)-3,4-dihydro-2H-isoquinolin-1-one;
6-Chloro-2-(4-methoxymethyl-pyridin-3-yl)-3,4-dihydro-2H-isoquinolin-1-one;
6-Chloro-2-[5-fluoro-4-(1-hydroxy-1-methyl-ethyl)-pyridin-3-yl]-3,4-dihydro-2H-isoquinolin-1-one;
6-Chloro-2-[5-(5-methyl-pyrazol-1-ylmethyl)-pyridin-3-yl]-3,4-dihydro-2H-isoquinolin-1-one;
6-Chloro-2-(1H-pyrrolo[3,2-c]pyridin-7-yl)-3,4-dihydro-2H-isoquinolin-1-one;
6-Chloro-3,4-dihydro-[2,4']biisoquinolinyl-1-one;
3-(6-Chloro-1-oxo-3,4-dihydro-1H-isoquinolin-2-yl)-isonicotinonitrile;
6-Chloro-2-(5-fluoro-4-methoxymethyl-pyridin-3-yl)-3,4-dihydro-2H-isoquinolin-1-one;
and pharmaceutically acceptable salts thereof.

27. The compound according to claim 1, selected from the group consisting of
6-Chloro-2-[5-fluoro-4-(1-methoxy-ethyl)-pyridin-3-yl]-3,4-dihydro-2H-isoquinolin-1-one;
6-Chloro-2-(4-isopropoxymethyl-pyridin-3-yl)-3,4-dihydro-2H-isoquinolin-1-one;
6-Chloro-2-[4-(cyclopropyl-methoxy-methyl)-pyridin-3-yl]-3,4-dihydro-2H-isoquinolin-1-one;
6-Chloro-2-[5-(3,5-dimethyl-1H-pyrazol-4-yl)-pyridin-3-yl]-3,4-dihydro-2H-isoquinolin-1-one;
6-Chloro-2-[5-(3,5-dimethyl-3H-imidazol-4-yl)-pyridin-3-yl]-3,4-dihydro-2H-isoquinolin-1-one;
6-Chloro-2-[5-(1,1-dioxo-1λ6-[1,2]thiazinan-2-ylmethyl)-pyridin-3-yl]-3,4-dihydro-2H-isoquinolin-1-one;
6-Chloro-2-[5-(1,1-dioxo-1λ6-isothiazolidin-2-ylmethyl)-pyridin-3-yl]-3,4-dihydro-2H-isoquinolin-1-one;
6-Chloro-2-[5-((S)-2-hydroxymethyl-5-oxo-pyrrolidin-1-ylmethyl)-pyridin-3-yl]-3,4-dihydro-2H-isoquinolin-1-one;
(S)-1-[5-(6-Chloro-1-oxo-3,4-dihydro-1H-isoquinolin-2-yl)-pyridin-3-ylmethyl]-pyrrolidine-2-carboxylic acid methyl ester;
6-Chloro-2-(5-methoxy-pyridin-3-yl)-3-methyl-3,4-dihydro-2H-isoquinolin-1-one;
6-Chloro-2-(5-hydroxymethyl-pyridin-3-yl)-3-methyl-3,4-dihydro-2H-isoquinolin-1-one;
6-Chloro-2-[5-(2-isopropyl-imidazol-1-ylmethyl)-pyridin-3-yl]-3-methyl-3,4-dihydro-2H-isoquinolin-1-one;
6-Chloro-3-methyl-2-pyridin-3-yl-3,4-dihydro-2H-isoquinolin-1-one;
6-Chloro-2-(5-fluoro-pyridin-3-yl)-3-methyl-3,4-dihydro-2H-isoquinolin-1-one;
6-Chloro-3-methyl-2-pyrimidin-5-yl-3,4-dihydro-2H-isoquinolin-1-one;
and pharmaceutically acceptable salts thereof.

28. The compound according to claim 1, selected from the group consisting of
(R)-6-Chloro-3-methyl-2-pyridin-3-yl-3,4-dihydro-2H-isoquinolin-1-one;
(S)-6-Chloro-3-methyl-2-pyridin-3-yl-3,4-dihydro-2H-isoquinolin-1-one;
8-Chloro-3-methyl-2-pyridin-3-yl-3,4-dihydro-2H-isoquinolin-1-one;
6-Methoxy-2-pyridin-3-yl-3,4-dihydro-2H-isoquinolin-1-one;
5,6-Dichloro-2-pyridin-3-yl-3,4-dihydro-2H-isoquinolin-1-one;
2-Chloro-6-(5-methoxy-pyridin-3-yl)-7,8-dihydro-6H-[1,6]naphthyridin-5-one;
2-Methoxy-6-(5-methoxy-pyridin-3-yl)-7,8-dihydro-6H-[1,6]naphthyridin-5-one;
2-Methoxy-6-pyridin-3-yl-7,8-dihydro-6H-[1,6]naphthyridin-5-one;
6-Chloro-5-fluoro-2-(5-methoxy-pyridin-3-yl)-3,4-dihydro-2H-isoquinolin-1-one;
6-Chloro-7-fluoro-2-(5-methoxy-pyridin-3-yl)-3,4-dihydro-2H-isoquinolin-1-one;
6-Chloro-7-fluoro-2-pyridin-3-yl-3,4-dihydro-2H-isoquinolin-1-one;
6-Chloro-4,4-dimethyl-2-pyridin-3-yl-3,4-dihydro-2H-isoquinolin-1-one;
6-Chloro-2-(5-methoxy-pyridin-3-yl)-4,4-dimethyl-3,4-dihydro-2H-isoquinolin-1-one;
6-Chloro-2-(5-fluoro-pyridin-3-yl)-4,4-dimethyl-3,4-dihydro-2H-isoquinolin-1-one;
6-Chloro-4-methyl-2-pyridin-3-yl-3,4-dihydro-2H-isoquinolin-1-one;
and pharmaceutically acceptable salts thereof.

29. The compound according to claim 1, selected from the group consisting of
6-Chloro-2-(5-fluoro-pyridin-3-yl)-4-methyl-3,4-dihydro-2H-isoquinolin-1-one;
6-Chloro-2-(5-methoxy-pyridin-3-yl)-4-methyl-3,4-dihydro-2H-isoquinolin-1-one;
5-Chloro-2-pyridin-3-yl-2,3-dihydro-isoindol-1-one;
5-Chloro-2-[5-(2-isopropyl-imidazol-1-ylmethyl)-pyridin-3-yl]-2,3-dihydro-isoindol-1-one;
5-Chloro-2-(5-[1,2,4]triazol-1-ylmethyl-pyridin-3-yl)-2,3-dihydro-isoindol-1-one;
5-Chloro-2-[5-(2-methyl-imidazol-1-ylmethyl)-pyridin-3-yl]-2,3-dihydro-isoindol-1-one;
5-Chloro-2-[5-(2-oxo-pyrrolidin-1-ylmethyl)-pyridin-3-yl]-2,3-dihydro-isoindol-1-one;
5-Chloro-2-[5-((S)-2-methoxymethyl-pyrrolidin-1-ylmethyl)-pyridin-3-yl]-2,3-dihydro-isoindol-1-one;

5-Chloro-2-[5-(2-oxo-piperidin-1-ylmethyl)-pyridin-3-yl]-2,3-dihydro-isoindol-1-one;
Ethanesulfonic acid [5-(5-chloro-1-oxo-1,3-dihydro-isoindol-2-yl)-pyridin-3-ylmethyl]-amide;
5-Chloro-2-(1-methyl-1H-pyrazolo[3,4-c]pyridin-4-yl)-2,3-dihydro-isoindol-1-one;
5-Chloro-2-(8-hydroxy-5,6,7,8-tetrahydro-isoquinolin-4-yl)-2,3-dihydro-isoindol-1-one;
5-Chloro-3-methyl-2-pyridin-3-yl-2,3-dihydro-isoindol-1-one;
6-Chloro-3-methyl-2-pyridin-3-yl-2,3-dihydro-isoindol-1-one;
5-Chloro-2-(5-methoxy-pyridin-3-yl)-3-methyl-2,3-dihydro-isoindol-1-one;
and pharmaceutically acceptable salts thereof.

30. The compound according to claim 1, selected from the group consisting of
5-Chloro-3-methyl-2-(4-methyl-pyridin-3-yl)-2,3-dihydro-isoindol-1-one;
5-Chloro-2-[5-(1-hydroxy-ethyl)-pyridin-3-yl]-3-methyl-2,3-dihydro-isoindol-1-one;
5-Chloro-2-(5-fluoro-pyridin-3-yl)-3-methyl-2,3-dihydro-isoindol-1-one;
3-Benzyl-5-chloro-2-pyridin-3-yl-2,3-dihydro-isoindol-1-one;
5-Chloro-3-ethyl-2-pyridin-3-yl-2,3-dihydro-isoindol-1-one;
5-Chloro-3-ethyl-2-(5-fluoro-pyridin-3-yl)-2,3-dihydro-isoindol-1-one;
5-Chloro-3-ethyl-2-(5-methoxy-pyridin-3-yl)-2,3-dihydro-isoindol-1-one;
5-Chloro-3,3-dimethyl-2-pyridin-3-yl-2,3-dihydro-isoindol-1-one;
5-Chloro-2-(5-fluoro-pyridin-3-yl)-3,3-dimethyl-2,3-dihydro-isoindol-1-one;
5-Chloro-2-(5-methoxy-pyridin-3-yl)-3,3-dimethyl-2,3-dihydro-isoindol-1-one;
5-Chloro-2-(5-difluoromethoxy-pyridin-3-yl)-3,3-dimethyl-2,3-dihydro-isoindol-1-one;
5-Chloro-2-[5-(1-hydroxy-ethyl)-pyridin-3-yl]-3,3-dimethyl-2,3-dihydro-isoindol-1-one;
5-Chloro-2-(5-hydroxymethyl-pyridin-3-yl)-3,3-dimethyl-2,3-dihydro-isoindol-1-one;
5-Chloro-3,3-dimethyl-2-[5-(2-methyl-imidazol-1-ylmethyl)-pyridin-3-yl]-2,3-dihydro-isoindol-1-one;
6-Chloro-2-[5-((S)-2-hydroxymethyl-pyrrolidin-1-yl)-pyridin-3-yl]-3,4-dihydro-2H-isoquinolin-1-one;
and pharmaceutically acceptable salts thereof.

31. The compound according to claim 1, selected from the group consisting of
5-Chloro-2-[5-((S)-2-hydroxymethyl-pyrrolidin-1-yl)-pyridin-3-yl]-2,3-dihydro-isoindol-1-one;
6-Chloro-2-[5-((R)-3-hydroxy-pyrrolidin-1-yl)-pyridin-3-yl]-3,4-dihydro-2H-isoquinolin-1-one;
5-Chloro-2-[5-((R)-3-hydroxy-pyrrolidin-1-yl)-pyridin-3-yl]-2,3-dihydro-isoindol-1-one;
2-Hydroxy-6-(5-methoxy-pyridin-3-yl)-7,8-dihydro-6H-[1,6]naphthyridin-5-one;
6-Chloro-2-(5-imidazol-1-ylmethyl-pyridin-3-yl)-3,4-dihydro-2H-isoquinolin-1-one;
6-Chloro-2-[5-(2-isopropyl-imidazol-1-ylmethyl)-pyridin-3-yl]-3,4-dihydro-2H-isoquinolin-1-one;
6-Chloro-2-[5-(2-methyl-imidazol-1-ylmethyl)-pyridin-3-yl]-3,4-dihydro-2H-isoquinolin-1-one;
6-Chloro-2-[5-(2-ethyl-4-methyl-imidazol-1-ylmethyl)-pyridin-3-yl]-3,4-dihydro-2H-isoquinolin-1-one;
6-Chloro-2-[5-(3-hydroxy-piperidin-1-ylmethyl)-pyridin-3-yl]-3,4-dihydro-2H-isoquinolin-1-one;
Propane-2-sulfonic acid [5-(6-chloro-1-oxo-3,4-dihydro-1H-isoquinolin-2-yl)-pyridin-3-ylmethyl]-amide
6-Chloro-2-[5-(3-hydroxy-pyrrolidin-1-ylmethyl)-pyridin-3-yl]-3,4-dihydro-2H-isoquinolin-1-one;
6-Chloro-2-[5-((R)-3-hydroxy-pyrrolidin-1-ylmethyl)-pyridin-3-yl]-3,4-dihydro-2H-isoquinolin-1-one;
6-Chloro-2-[5-((S)-3-hydroxy-pyrrolidin-1-ylmethyl)-pyridin-3-yl]-3,4-dihydro-2H-isoquinolin-1-one;
6-Chloro-2-[5-((S)-2-hydroxymethyl-pyrrolidin-1-ylmethyl)-pyridin-3-yl]-3,4-dihydro-2H-isoquinolin-1-one;
6-Chloro-2-[5-((R)-2-hydroxymethyl-pyrrolidin-1-ylmethyl)-pyridin-3-yl]-3,4-dihydro-2H-isoquinolin-1-one;
and pharmaceutically acceptable salts thereof.

32. The compound according to claim 1, selected from the group consisting of
6-Chloro-2-[5-(3,5-dimethyl-pyrazol-1-ylmethyl)-pyridin-3-yl]-3,4-dihydro-2H-isoquinolin-1-one;
N-[5-(6-Chloro-1-oxo-3,4-dihydro-1H-isoquinolin-2-yl)-pyridin-3-ylmethyl]-methanesulfonamide
N-[5-(6-Chloro-1-oxo-3,4-dihydro-1H-isoquinolin-2-yl)-pyridin-3-ylmethyl]-acetamide
6-Chloro-2-(5-morpholin-4-ylmethyl-pyridin-3-yl)-3,4-dihydro-2H-isoquinolin-1-one;
6-Chloro-2-[5-(2-oxo-pyrrolidin-1-ylmethyl)-pyridin-3-yl]-3,4-dihydro-2H-isoquinolin-1-one;
6-Chloro-2-[5-(1,1-dioxo-1λ6-thiomorpholin-4-ylmethyl)-pyridin-3-yl]-3,4-dihydro-2H-isoquinolin-1-one;
6-Chloro-2-[5-(2-oxo-oxazolidin-3-ylmethyl)-pyridin-3-yl]-3,4-dihydro-2H-isoquinolin-1-one;
6-Chloro-2-[5-(2-oxo-imidazolidin-1-ylmethyl)-pyridin-3-yl]-3,4-dihydro-2H-isoquinolin-1-one;
6-Chloro-2-[5-(3-methyl-2-oxo-imidazolidin-1-ylmethyl)-pyridin-3-yl]-3,4-dihydro-2H-isoquinolin-1-one;
6-Chloro-2-(5-pyrazol-1-ylmethyl-pyridin-3-yl)-3,4-dihydro-2H-isoquinolin-1-one;
6-Chloro-2-[5-(2-propyl-imidazol-1-ylmethyl)-pyridin-3-yl]-3,4-dihydro-2H-isoquinolin-1-one;
1-[5-(6-Chloro-1-oxo-3,4-dihydro-1H-isoquinolin-2-yl)-pyridin-3-ylmethyl]-1H-imidazole-2-carboxylic acid ethyl ester;
6-Chloro-2-[5-(2-hydroxymethyl-imidazol-1-ylmethyl)-pyridin-3-yl]-3,4-dihydro-2H-isoquinolin-1-one;
6-Chloro-2-[5-(oxetan-3-ylaminomethyl)-pyridin-3-yl]-3,4-dihydro-2H-isoquinolin-1-one;
6-Chloro-2-{5-[4-(2-hydroxy-ethyl)-piperazin-1-ylmethyl]-pyridin-3-yl}-3,4-dihydro-2H-isoquinolin-1-one;
and pharmaceutically acceptable salts thereof.

33. The compound according to claim 1, selected from the group consisting of
6-Chloro-2-[5-(4-isopropyl-piperazin-1-ylmethyl)-pyridin-3-yl]-3,4-dihydro-2H-isoquinolin-1-one;
6-Chloro-2-[5-(4-methyl-piperazin-1-ylmethyl)-pyridin-3-yl]-3,4-dihydro-2H-isoquinolin-1-one;
6-Chloro-2-[5-(4,4-difluoro-piperidin-1-ylmethyl)-pyridin-3-yl]-3,4-dihydro-2H-isoquinolin-1-one;
6-Chloro-2-[5-(3,3-difluoro-pyrrolidin-1-ylmethyl)-pyridin-3-yl]-3,4-dihydro-2H-isoquinolin-1-one;
6-Chloro-2-[5-(2-oxa-6-aza-spiro[3.4]oct-6-ylmethyl)-pyridin-3-yl]-3,4-dihydro-2H-isoquinolin-1-one;

6-Chloro-2-[5-(2-oxa-6-aza-spiro[3.3]hept-6-ylmethyl)-pyridin-3-yl]-3,4-dihydro-2H-isoquinolin-1-one;
6-Chloro-2-[5-(3,3-difluoro-piperidin-1-ylmethyl)-pyridin-3-yl]-3,4-dihydro-2H-isoquinolin-1-one;
6-Chloro-2-[5-(2-oxo-piperidin-1-ylmethyl)-pyridin-3-yl]-3,4-dihydro-2H-isoquinolin-1-one;
6-Chloro-2-(5-[1,2,3]triazol-2-ylmethyl-pyridin-3-yl)-3,4-dihydro-2H-isoquinolin-1-one;
6-Chloro-2-(5-[1,2,3]triazol-1-ylmethyl-pyridin-3-yl)-3,4-dihydro-2H-isoquinolin-1-one;
6-Chloro-2-[5-(2-chloro-imidazol-1-ylmethyl)-pyridin-3-yl]-3,4-dihydro-2H-isoquinolin-1-one;
6-Chloro-2-[5-(3-methyl-[1,2,4]triazol-4-ylmethyl)-pyridin-3-yl]-3,4-dihydro-2H-isoquinolin-1-one;
6-Chloro-2-[5-(5-methyl-[1,2,4]triazol-1-ylmethyl)-pyridin-3-yl]-3,4-dihydro-2H-isoquinolin-1-one;
6-chloro-2-[5-(3-methyl-[1,2,4]triazol-1-ylmethyl)-pyridin-3-yl]-3,4-dihydro-2H-isoquinolin-1-one;
6-Chloro-2-(5-[1,2,4]triazol-4-ylmethyl-pyridin-3-yl)-3,4-dihydro-2H-isoquinolin-1-one;
and pharmaceutically acceptable salts thereof.

34. The compound according to claim 1, selected from the group consisting of
6-Chloro-2-(5-[1,2,4]triazol-1-ylmethyl-pyridin-3-yl)-3,4-dihydro-2H-isoquinolin-1-one;
6-Chloro-2-[5-(2-methyl-benzoimidazol-1-ylmethyl)-pyridin-3-yl]-3,4-dihydro-2H-isoquinolin-1-one;
6-Chloro-2-(5-indazol-1-ylmethyl-pyridin-3-yl)-3,4-dihydro-2H-isoquinolin-1-one;
6-Chloro-2-(5-indazol-2-ylmethyl-pyridin-3-yl)-3,4-dihydro-2H-isoquinolin-1-one;
6-Chloro-2-[5-(6-fluoro-indol-1-ylmethyl)-pyridin-3-yl]-3,4-dihydro-2H-isoquinolin-1-one;
6-Chloro-2-[5-(7-fluoro-indol-1-ylmethyl)-pyridin-3-yl]-3,4-dihydro-2H-isoquinolin-1-one;
6-Chloro-2-[5-(4-fluoro-indol-1-ylmethyl)-pyridin-3-yl]-3,4-dihydro-2H-isoquinolin-1-one;
6-Chloro-2-[5-(4-methyl-pyrazol-1-ylmethyl)-pyridin-3-yl]-3,4-dihydro-2H-isoquinolin-1-one;
6-Chloro-2-[5-(2-cyclopropyl-imidazol-1-ylmethyl)-pyridin-3-yl]-3,4-dihydro-2H-isoquinolin-1-one;
6-Chloro-2-[5-(2-trifluoromethyl-imidazol-1-ylmethyl)-pyridin-3-yl]-3,4-dihydro-2H-isoquinolin-1-one;
6-Chloro-2-[5-(3-methyl-pyrazol-1-ylmethyl)-pyridin-3-yl]-3,4-dihydro-2H-isoquinolin-1-one;
6-Chloro-2-[5-(2-ethyl-imidazol-1-ylmethyl)-pyridin-3-yl]-3,4-dihydro-2H-isoquinolin-1-one;
2-(5-Aminomethyl-pyridin-3-yl)-6-chloro-3,4-dihydro-2H-isoquinolin-1-one;
6-Chloro-2-(5-methoxymethyl-pyridin-3-yl)-3,4-dihydro-2H-isoquinolin-1-one;
6-Chloro-2-(5-isopropoxymethyl-pyridin-3-yl)-3,4-dihydro-2H-isoquinolin-1-one;
and pharmaceutically acceptable salts thereof.

35. The compound according to claim 1, selected from the group consisting of
6-Chloro-2-[5-(2,2,2-trifluoro-1-methyl-ethoxymethyl)-pyridin-3-yl]-3,4-dihydro-2H-isoquinolin-1-one;
6-Chloro-2-{5-[2-(1-methyl-pyrrolidin-2-yl)-ethoxymethyl]-pyridin-3-yl}-3,4-dihydro-2H-isoquinolin-1-one;
6-Chloro-2-(5-cyclopentyloxymethyl-pyridin-3-yl)-3,4-dihydro-2H-isoquinolin-1-one;
6-Chloro-2-(5-cyclopropylmethoxymethyl-pyridin-3-yl)-3,4-dihydro-2H-isoquinolin-1-one;
6-Chloro-2-[5-(2-fluoro-phenoxymethyl)-pyridin-3-yl]-3,4-dihydro-2H-isoquinolin-1-one;
6-Chloro-2-[5-(1-methyl-cyclopropylmethoxymethyl)-pyridin-3-yl]-3,4-dihydro-2H-isoquinolin-1-one;
6-Chloro-2-[5-(tetrahydro-furan-2-ylmethoxymethyl)-pyridin-3-yl]-3,4-dihydro-2H-isoquinolin-1-one;
6-Chloro-2-[5-(2,2,2-trifluoro-ethoxymethyl)-pyridin-3-yl]-3,4-dihydro-2H-isoquinolin-1-one;
6-Chloro-2-(5-cyclobutoxymethyl-pyridin-3-yl)-3,4-dihydro-2H-isoquinolin-1-one;
6-Chloro-2-[5-(3,5-dimethyl-isoxazol-4-ylmethyl)-pyridin-3-yl]-3,4-dihydro-2H-isoquinolin-1-one;
6-Chloro-2-[5-(4-methanesulfonyl-benzyl)-pyridin-3-yl]-3,4-dihydro-2H-isoquinolin-1-one;
6-Chloro-2-[5-(6-methyl-pyridin-3-ylmethyl)-pyridin-3-yl]-3,4-dihydro-2H-isoquinolin-1-one;
6-Chloro-2-[5-(6-morpholin-4-yl-pyridin-3-ylmethyl)-pyridin-3-yl]-3,4-dihydro-2H-isoquinolin-1-one;
6-Chloro-2-[5-(2-methyl-2H-pyrazol-3-ylmethyl)-pyridin-3-yl]-3,4-dihydro-2H-isoquinolin-1-one;
6-Chloro-2-[5-(1-methyl-1H-pyrazol-4-ylmethyl)-pyridin-3-yl]-3,4-dihydro-2H-isoquinolin-1-one;
and pharmaceutically acceptable salts thereof.

36. The compound according to claim 1, selected from the group consisting of
6-Chloro-2-[5-(2,3-difluoro-benzyl)-pyridin-3-yl]-3,4-dihydro-2H-isoquinolin-1-one;
6-Chloro-2-[5-(3,5-difluoro-benzyl)-pyridin-3-yl]-3,4-dihydro-2H-isoquinolin-1-one;
6-Chloro-2-[5-(2,5-difluoro-benzyl)-pyridin-3-yl]-3,4-dihydro-2H-isoquinolin-1-one;
6-Chloro-2-[5-(2-trifluoromethyl-benzyl)-pyridin-3-yl]-3,4-dihydro-2H-isoquinolin-1-one;
6-Chloro-2-[5-(2,6-dichloro-benzyl)-pyridin-3-yl]-3,4-dihydro-2H-isoquinolin-1-one;
6-Chloro-2-[5-(2-chloro-6-fluoro-benzyl)-pyridin-3-yl]-3,4-dihydro-2H-isoquinolin-1-one;
6-Chloro-2-[5-(3,4-dichloro-benzyl)-pyridin-3-yl]-3,4-dihydro-2H-isoquinolin-1-one;
6-Chloro-2-[5-(2,5-dichloro-benzyl)-pyridin-3-yl]-3,4-dihydro-2H-isoquinolin-1-one;
Ethanesulfonic acid [5-(6-chloro-1-oxo-3,4-dihydro-1H-isoquinolin-2-yl)-pyridin-3-yl]-amide;
N-[5-(6-Chloro-1-oxo-3,4-dihydro-1H-isoquinolin-2-yl)-pyridin-3-yl]-benzenesulfonamide;
N-[5-(6-Chloro-1-oxo-3,4-dihydro-1H-isoquinolin-2-yl)-pyridin-3-yl]-methanesulfonamide;
Cyclopropanesulfonic acid [5-(6-chloro-1-oxo-3,4-dihydro-1H-isoquinolin-2-yl)-pyridin-3-yl]-amide;
6-Chloro-2-[5-(4-fluoro-benzylamino)-pyridin-3-yl]-3,4-dihydro-2H-isoquinolin-1-one;
6-Chloro-2-[5-(2,2,2-trifluoro-ethylamino)-pyridin-3-yl]-3,4-dihydro-2H-isoquinolin-1-one;
6-Chloro-2-(5-morpholin-4-yl-pyridin-3-yl)-3,4-dihydro-2H-isoquinolin-1-one;
and pharmaceutically acceptable salts thereof.

37. The compound according to claim 1, selected from the group consisting of
N-[5-(6-Chloro-1-oxo-3,4-dihydro-1H-isoquinolin-2-yl)-pyridin-3-yl]-propionamide;
6-Chloro-2-{5-[(2-methyl-2H-pyrazol-3-ylmethyl)-amino]-pyridin-3-yl}-3,4-dihydro-2H-isoquinolin-1-one;
2-[5-(6-Chloro-1-oxo-3,4-dihydro-1H-isoquinolin-2-yl)-pyridin-3-ylamino]-2-methyl-propionic acid;
6-Chloro-2-{5-[(1-methyl-1H-imidazol-4-ylmethyl)-amino]-pyridin-3-yl}-3,4-dihydro-2H-isoquinolin-1-one;

6-Chloro-2-[5-(1H-pyrazol-4-yl)-pyridin-3-yl]-3,4-dihydro-2H-isoquinolin-1-one;
6-Chloro-2-[5-(3,5-dimethyl-isoxazol-4-yl)-pyridin-3-yl]-3,4-dihydro-2H-isoquinolin-1-one;
6-Chloro-2-[5-(3-fluoro-phenyl)-pyridin-3-yl]-3,4-dihydro-2H-isoquinolin-1-one;
6-Chloro-2-[5-(3,4-difluoro-phenyl)-pyridin-3-yl]-3,4-dihydro-2H-isoquinolin-1-one;
6-Chloro-2-[5-(3,5-difluoro-phenyl)-pyridin-3-yl]-3,4-dihydro-2H-isoquinolin-1-one;
6-Chloro-2-[5-(3-chloro-phenyl)-pyridin-3-yl]-3,4-dihydro-2H-isoquinolin-1-one;
6-Chloro-2-[5-(2,5-difluoro-phenyl)-pyridin-3-yl]-3,4-dihydro-2H-isoquinolin-1-one;
6-Chloro-2-[5-(3-trifluoromethyl-phenyl)-pyridin-3-yl]-3,4-dihydro-2H-isoquinolin-1-one;
6-Chloro-2-[5-(3-trifluoromethoxy-phenyl)-pyridin-3-yl]-3,4-dihydro-2H-isoquinolin-1-one;
6-Chloro-2-[5-(2-methyl-2H-pyrazol-3-yl)-pyridin-3-yl]-3,4-dihydro-2H-isoquinolin-1-one;
6-Chloro-2-[5-(1-methyl-1H-pyrazol-4-yl)-pyridin-3-yl]-3,4-dihydro-2H-isoquinolin-1-one;
and pharmaceutically acceptable salts thereof.

38. The compound according to claim 1, selected from the group consisting of
6-Chloro-2-[5-(4-chloro-3-fluoro-phenyl)-pyridin-3-yl]-3,4-dihydro-2H-isoquinolin-1-one;
6-Chloro-2-[5-(3,4-dichloro-phenyl)-pyridin-3-yl]-3,4-dihydro-2H-isoquinolin-1-one;
6-Chloro-2-[5-(2-trifluoromethyl-phenyl)-pyridin-3-yl]-3,4-dihydro-2H-isoquinolin-1-one;
6-Chloro-2-(5-isoxazol-4-yl-pyridin-3-yl)-3,4-dihydro-2H-isoquinolin-1-one;
6-Chloro-2-[5-(1-methyl-1H-imidazol-2-yl)-pyridin-3-yl]-3,4-dihydro-2H-isoquinolin-1-one;
6-Chloro-2-[5-(2,4-dimethyl-2H-pyrazol-3-yl)-pyridin-3-yl]-3,4-dihydro-2H-isoquinolin-1-one;
5-[5-(6-Chloro-1-oxo-3,4-dihydro-1H-isoquinolin-2-yl)-pyridin-3-yl]-1-methyl-1H-pyrazole-4-carbonitrile
N-[5-(6-Chloro-1-oxo-3,4-dihydro-1H-isoquinolin-2-yl)-pyridin-3-yl]-isobutyramide
Cyclopropanecarboxylic acid [5-(6-chloro-1-oxo-3,4-dihydro-1H-isoquinolin-2-yl)-pyridin-3-yl]-amide
N-[5-(6-Chloro-1-oxo-3,4-dihydro-1H-isoquinolin-2-yl)-pyridin-3-yl]-4-fluoro-benzamide
1-[5-(6-Chloro-1-oxo-3,4-dihydro-1H-isoquinolin-2-yl)-pyridin-3-yl]-3-cyclohexyl-urea
1-[5-(6-Chloro-1-oxo-3,4-dihydro-1H-isoquinolin-2-yl)-pyridin-3-yl]-3-(3-trifluoromethyl-phenyl)-urea
6-Chloro-2-(5-hydroxy-pyridin-3-yl)-3,4-dihydro-2H-isoquinolin-1-one;
2-[5-(6-Chloro-1-oxo-3,4-dihydro-1H-isoquinolin-2-yl)-pyridin-3-yloxy]-acetamide;
2-[5-(6-Chloro-1-oxo-3,4-dihydro-1H-isoquinolin-2-yl)-pyridin-3-yloxy]-N-methyl-acetamide;
and pharmaceutically acceptable salts thereof.

39. The compound according to claim 1, selected from the group consisting of
[5-(6-Chloro-1-oxo-3,4-dihydro-1H-isoquinolin-2-yl)-pyridin-3-yloxy]-acetic acid methyl ester;
2-[5-(6-Chloro-1-oxo-3,4-dihydro-1H-isoquinolin-2-yl)-pyridin-3-yloxy]-N,N-dimethyl-acetamide;
6-Chloro-2-(5-phenylaminomethyl-pyridin-3-yl)-3,4-dihydro-2H-isoquinolin-1-one;
6-Chloro-2-{5-[(4-fluoro-phenylamino)-methyl]-pyridin-3-yl}-3,4-dihydro-2H-isoquinolin-1-one;
6-Chloro-2-{5-[3-fluoro-phenylamino)-methyl]-pyridin-3-yl}-3,4-dihydro-2H-isoquinolin-1-one;
6-Chloro-2-{5-[(4-chloro-phenylamino)-methyl]-pyridin-3-yl}-3,4-dihydro-2H-isoquinolin-1-one;
6-Chloro-2-{5-[(3-chloro-phenylamino)-methyl]-pyridin-3-yl}-3,4-dihydro-2H-isoquinolin-1-one;
6-Chloro-2-{5-[(1H-pyrazol-3-ylamino)-methyl]-pyridin-3-yl}-3,4-dihydro-2H-isoquinolin-1-one;
6-Chloro-2-[5-(2-morpholin-4-yl-2-oxo-ethyl)-pyridin-3-yl]-3,4-dihydro-2H-isoquinolin-1-one;
2-[5-(6-Chloro-1-oxo-3,4-dihydro-1H-isoquinolin-2-yl)-pyridin-3-yl]-N-(2-hydroxy-ethyl)-acetamide;
6-Chloro-2-[5-(1-methylamino-ethyl)-pyridin-3-yl]-3,4-dihydro-2H-isoquinolin-1-one;
6-Chloro-2-[5-(1-dimethylamino-ethyl)-pyridin-3-yl]-3,4-dihydro-2H-isoquinolin-1-one;
6-Chloro-2-[5-(1-methyl-1H-imidazole-2-carbonyl)-pyridin-3-yl]-3,4-dihydro-2H-isoquinolin-1-one;
6-Chloro-2-[5-(4-methyl-4H-[1,2,4]triazol-3-ylmethyl)-pyridin-3-yl]-3,4-dihydro-2H-isoquinolin-1-one;
6-Chloro-2-[5-(1-[1,2,3]triazol-2-yl-ethyl)-pyridin-3-yl]-3,4-dihydro-2H-isoquinolin-1-one;
and pharmaceutically acceptable salts thereof.

40. The compound according to claim 1, selected from the group consisting of
6-Chloro-2-[5-(1-imidazol-1-yl-ethyl)-pyridin-3-yl]-3,4-dihydro-2H-isoquinolin-1-one;
6-Chloro-2-[5-(1-pyrazol-1-yl-ethyl)-pyridin-3-yl]-3,4-dihydro-2H-isoquinolin-1-one;
6-Chloro-2-{5-[1-(oxazol-2-ylamino)-ethyl]-pyridin-3-yl}-3,4-dihydro-2H-isoquinolin-1-one;
6-Chloro-2-[5-(1-[1,2,4]triazol-1-yl-ethyl)-pyridin-3-yl]-3,4-dihydro-2H-isoquinolin-1-one;
6-Chloro-2-{5-[1-(2-oxo-pyrrolidin-1-yl)-ethyl]-pyridin-3-yl}-3,4-dihydro-2H-isoquinolin-1-one;
6-Chloro-2-{5-[1-(2-oxo-oxazolidin-3-yl)-ethyl]-pyridin-3-yl}-3,4-dihydro-2H-isoquinolin-1-one;
N-{1-[5-(6-Chloro-1-oxo-3,4-dihydro-1H-isoquinolin-2-yl)-pyridin-3-yl]-ethyl}-methanesulfonamide;
6-Chloro-2-{5-[1-(3-fluoro-phenylamino)-ethyl]-pyridin-3-yl}-3,4-dihydro-2H-isoquinolin-1-one;
6-Chloro-2-[5-(1-phenylamino-ethyl)-pyridin-3-yl]-3,4-dihydro-2H-isoquinolin-1-one;
6-Chloro-2-(5-methanesulfinyl-pyridin-3-yl)-3,4-dihydro-2H-isoquinolin-1-one;
6-Chloro-2-[4-(4-methyl-piperazin-1-ylmethyl)-pyridin-3-yl]-3,4-dihydro-2H-isoquinolin-1-one;
and pharmaceutically acceptable salts thereof.

41. The compound according to claim 1, selected from the group consisting of
5-Chloro-3,3-dimethyl-2-[5-(1-methyl-1H-pyrazol-4-ylmethyl)-pyridin-3-yl]-2,3-dihydro-isoindol-1-one;
5-Chloro-2-(5-difluoromethoxy-pyridin-3-yl)-3-ethyl-2,3-dihydro-isoindol-1-one;
5-Chloro-3-ethyl-2-[5-(1-hydroxy-ethyl)-pyridin-3-yl]-2,3-dihydro-isoindol-1-one;
5-Chloro-2-(4-chloro-pyridin-3-yl)-3-ethyl-2,3-dihydro-isoindol-1-one;
5-Chloro-2-(4-chloro-pyridin-3-yl)-3,3-dimethyl-2,3-dihydro-isoindol-1-one;
6-Chloro-5'-nitro-3,4-dihydro-[2,4']biisoquinolinyl-1-one;
6-Chloro-8'-nitro-3,4-dihydro-[2,4']biisoquinolinyl-1-one;
8'-Amino-6-chloro-3,4-dihydro-[2,4']biisoquinolinyl-1-one;

Ethanesulfonic acid (6-chloro-1-oxo-3,4-dihydro-1H-[2, 4']biisoquinolinyl-8'-yl)-amide;
6'-Chloro-2'-(5-fluoropyridin-3-yl)spiro[cyclopropane-1, 1'-isoindol]-3'(2'H)-one;
6'-Chloro-2'-[5-(difluoromethoxy)pyridin-3-yl]spiro[cyclopropane-1,1'-isoindol]-3'(2'H)-one;
2-Chloro-6-(5-fluoro-pyridin-3-yl)-7,7-dimethyl-6,7-dihydro-pyrrolo[3,4-b]pyridin-5-one;
2-Chloro-6-(5-difluoromethoxy-pyridin-3-yl)-7,7-dimethyl-6,7-dihydro-pyrrolo[3,4-b]pyridin-5-one;
6-(5-Fluoro-pyridin-3-yl)-2-methoxy-7,7-dimethyl-6,7-dihydro-pyrrolo[3,4-b]pyridin-5-one;
6-(5-Difluoromethoxy-pyridin-3-yl)-2-methoxy-7,7-dimethyl-6,7-dihydro-pyrrolo[3,4-b]pyridin-5-one;
and pharmaceutically acceptable salts thereof.

42. The compound according to claim 1, selected from the group consisting of
6'-Chloro-2'-(pyridin-3-yl)spiro[cyclopropane-1,1'-isoindol]-3'(2'H)-one;
5-Chloro-3-cyclopropyl-2-(5-fluoro-pyridin-3-yl)-2,3-dihydro-isoindol-1-one;
2-Chloro-7,7-dimethyl-6-pyridin-3-yl-6,7-dihydro-pyrrolo[3,4-b]pyridin-5-one;
2-Ethoxy-6-(5-fluoro-pyridin-3-yl)-7,7-dimethyl-6,7-dihydro-pyrrolo[3,4-b]pyridin-5-one;
2-Methoxy-7,7-dimethyl-6-pyridin-3-yl-6,7-dihydro-pyrrolo[3,4-b]pyridin-5-one;
5-Chloro-3-cyclopropyl-2-pyridin-3-yl-2,3-dihydro-isoindol-1-one;
5-Chloro-3-cyclopropyl-2-(5-difluoromethoxy-pyridin-3-yl)-2,3-dihydro-isoindol-1-one;
6-(5-Difluoromethoxy-pyridin-3-yl)-2-ethoxy-7,7-dimethyl-6,7-dihydro-pyrrolo[3,4-b]pyridin-5-one;
5-Chloro-2-(5-isopropoxy-pyridin-3-yl)-3,3-dimethyl-2,3-dihydro-isoindol-1-one;
6'-Chloro-2'-(4-chloropyridin-3-yl)spiro[cyclopropane-1, 1'-isoindol]-3'(2'H)-one;
5-Chloro-2-(5-cyclopropoxy-pyridin-3-yl)-3,3-dimethyl-2,3-dihydro-isoindol-1-one;
(S or R)-6-Chloro-3-ethyl-2-(5-fluoro-pyridin-3-yl)-2,3-dihydro-isoindol-1-one;
(R or S)-6-Chloro-3-ethyl-2-(5-fluoro-pyridin-3-yl)-2,3-dihydro-isoindol-1-one;
(R or S)-5-Chloro-3-ethyl-2-(5-fluoro-pyridin-3-yl)-2,3-dihydro-isoindol-1-one;
(S or R)-5-Chloro-3-ethyl-2-(5-fluoro-pyridin-3-yl)-2,3-dihydro-isoindol-1-one;
and pharmaceutically acceptable salts thereof.

43. The compound according to claim 1, selected from the group consisting of
2-(8-Amino-5,6,7,8-tetrahydro-isoquinolin-4-yl)-5-chloro-2,3-dihydro-isoindol-1-one;
N—[(R or S)-4-((R or S)-5-Chloro-1-ethyl-3-oxo-1,3-dihydro-isoindol-2-yl)-5,6,7,8-tetrahydro-isoquinolin-8-yl]-propionamide;
N—[(R or S)-4-((S or R)-5-Chloro-1-ethyl-3-oxo-1,3-dihydro-isoindol-2-yl)-5,6,7,8-tetrahydro-isoquinolin-8-yl]-propionamide;
N—[(R or S)-4-(5-Chloro-1-oxo-1,3-dihydro-isoindol-2-yl)-5,6,7,8-tetrahydro-isoquinolin-8-yl]-propionamide;
Ethanesulfonic acid [4-(5-chloro-1-oxo-1,3-dihydro-isoindol-2-yl)-5,6,7,8-tetrahydro-isoquinolin-8-yl]-amide;
Ethanesulfonic acid [(R or S)-4-(5-chloro-1-oxo-1,3-dihydro-isoindol-2-yl)-5,6,7,8-tetrahydro-isoquinolin-8-yl]-amide;
Ethanesulfonic acid [(S or R)-4-(5-chloro-1-oxo-1,3-dihydro-isoindol-2-yl)-5,6,7,8-tetrahydro-isoquinolin-8-yl]-amide;
N—[(S or R)-4-(5-Chloro-1-oxo-1,3-dihydro-isoindol-2-yl)-6,7-dihydro-5H-[2]pyrindin-7-yl]-acetamide;
N—[(R or S)-4-(5-Chloro-1-oxo-1,3-dihydro-isoindol-2-yl)-6,7-dihydro-5H-[2]pyrindin-7-yl]-acetamide;
N—((R or S)-6-Chloro-1-oxo-3,4,5',6',7',8'-hexahydro-1H-[2,4']biisoquinolinyl-8'-yl)-acetamide;
N—((S or R)-6-Chloro-1-oxo-3,4,5',6',7',8'-hexahydro-1H-[2,4']biisoquinolinyl-8'-yl)-acetamide;
N—[(S or R)-4-(5-Chloro-1-oxo-1,3-dihydro-isoindol-2-yl)-5,6,7,8-tetrahydro-isoquinolin-8-yl]-acetamide;
N—[(R or S)-4-(5-Chloro-1-oxo-1,3-dihydro-isoindol-2-yl)-5,6,7,8-tetrahydro-isoquinolin-8-yl]-acetamide;
N—((S or R)-6-Chloro-1-oxo-3,4,5',6',7',8'-hexahydro-1H-[2,4']biisoquinolinyl-8'-yl)-methanesulfonamide;
N—((R or S)-6-Chloro-1-oxo-3,4,5',6',7',8'-hexahydro-1H-[2,4']biisoquinolinyl-8'-yl)-methanesulfonamide;
and pharmaceutically acceptable salts thereof.

44. The compound according to claim 1, selected from the group consisting of
N—[(S or R)-4-(5-Chloro-1-oxo-1,3-dihydro-isoindol-2-yl)-5,6,7,8-tetrahydro-isoquinolin-8-yl]-methanesulfonamide;
N—[(R or S)-4-(5-Chloro-1-oxo-1,3-dihydro-isoindol-2-yl)-5,6,7,8-tetrahydro-isoquinolin-8-yl]-methanesulfonamide;
N—((R or S)-6-Chloro-1-oxo-3,4,5',6',7',8'-hexahydro-1H-[2,4']biisoquinolinyl-8'-yl)-propionamide;
N—((S or R)-6-Chloro-1-oxo-3,4,5',6',7',8'-hexahydro-1H-[2,4']biisoquinolinyl-8'-yl)-propionamide;
N—[(S or R)-4-(6-Chloro-1-oxo-3,4-dihydro-1H-isoquinolin-2-yl)-6,7-dihydro-5H-[2]pyrindin-7-yl]-methanesulfonamide;
N—[(R or S)-4-(6-Chloro-1-oxo-3,4-dihydro-1H-isoquinolin-2-yl)-6,7-dihydro-5H-[2]pyrindin-7-yl]-methanesulfonamide;
N—[(R or S)-4-(6-Chloro-1-oxo-3,4-dihydro-1H-isoquinolin-2-yl)-6,7-dihydro-5H-[2]pyrindin-7-yl]-acetamide;
N—[(S or R)-4-(6-Chloro-1-oxo-3,4-dihydro-1H-isoquinolin-2-yl)-6,7-dihydro-5H-[2]pyrindin-7-yl]-acetamide;
N—[(R or S)-4-(5-Chloro-1-oxo-1,3-dihydro-isoindol-2-yl)-6,7-dihydro-5H-[2]pyrindin-7-yl]-methanesulfonamide;
N—[(S or R)-4-(5-Chloro-1-oxo-1,3-dihydro-isoindol-2-yl)-6,7-dihydro-5H-[2]pyrindin-7-yl]-methanesulfonamide;
Ethanesulfonic acid [(R or S)-4-(5-chloro-1-oxo-1,3-dihydro-isoindol-2-yl)-6,7-dihydro-5H-[2]pyrindin-7-yl]-amide;
Ethanesulfonic acid [(S or R)-4-(5-chloro-1-oxo-1,3-dihydro-isoindol-2-yl)-6,7-dihydro-5H-[2]pyrindin-7-yl]-amide;
N—[(S or R)-4-(5-Chloro-1-oxo-1,3-dihydro-isoindol-2-yl)-6,7-dihydro-5H-[2]pyrindin-7-yl]-propionamide;
N—[(R or S)-4-(5-Chloro-1-oxo-1,3-dihydro-isoindol-2-yl)-6,7-dihydro-5H-[2]pyrindin-7-yl]-propionamide;
5-Chloro-2-((S or R)-8-hydroxy-5,6,7,8-tetrahydro-isoquinolin-4-yl)-2,3-dihydro-isoindol-1-one;
and pharmaceutically acceptable salts thereof.

45. The compound according to claim 1, selected from the group consisting of
5-Chloro-2-((R or S)-8-hydroxy-5,6,7,8-tetrahydro-isoquinolin-4-yl)-2,3-dihydro-isoindol-1-one;

N—[(S or R)-4-((R or S)-5-Chloro-3-ethyl-1-oxo-1,3-dihydro-isoindol-2-yl)-6,7-dihydro-5H-[2]pyrindin-7-yl]-acetamide;
N—[(R or S)-4-((S or R)-5-Chloro-3-ethyl-1-oxo-1,3-dihydro-isoindol-2-yl)-6,7-dihydro-5H-[2]pyrindin-7-yl]-acetamide;
N—[(R or S)-4-((S or R)-5-Chloro-3-ethyl-1-oxo-1,3-dihydro-isoindol-2-yl)-6,7-dihydro-5H-[2]pyrindin-7-yl]-acetamide;
N—[(S or R)-4-((S or R)-5-Chloro-3-ethyl-1-oxo-1,3-dihydro-isoindol-2-yl)-6,7-dihydro-5H-[2]pyrindin-7-yl]-acetamide;
N-[4-(5-Chloro-3-ethyl-1-oxo-1,3-dihydro-isoindol-2-yl)-5,6,7,8-tetrahydro-isoquinolin-8-yl]-methanesulfonamide;
N—[(R or S)-4-((R or S)-5-Chloro-3-ethyl-1-oxo-1,3-dihydro-isoindol-2-yl)-5,6,7,8-tetrahydro-isoquinolin-8-yl]-methanesulfonamide;
N—[(S or R)-4-((S or R)-5-Chloro-3-ethyl-1-oxo-1,3-dihydro-isoindol-2-yl)-5,6,7,8-tetrahydro-isoquinolin-8-yl]-methanesulfonamide;
N—[(S or R)-4-((R or S)-5-Chloro-3-ethyl-1-oxo-1,3-dihydro-isoindol-2-yl)-5,6,7,8-tetrahydro-isoquinolin-8-yl]-methanesulfonamide;
N—[(R or S)-4-((S or R)-5-Chloro-3-ethyl-1-oxo-1,3-dihydro-isoindol-2-yl)-5,6,7,8-tetrahydro-isoquinolin-8-yl]-methanesulfonamide;
N—[(S or R)-4-((S or R)-5-Chloro-3-ethyl-1-oxo-1,3-dihydro-isoindol-2-yl)-5,6,7,8-tetrahydro-isoquinolin-8-yl]-propionamide;
N—[(S or R)-4-((R or S)-5-Chloro-3-ethyl-1-oxo-1,3-dihydro-isoindol-2-yl)-5,6,7,8-tetrahydro-isoquinolin-8-yl]-propionamide;
N—[(R or S)-4-((S or R)-5-Chloro-3-ethyl-1-oxo-1,3-dihydro-isoindol-2-yl)-5,6,7,8-tetrahydro-isoquinolin-8-yl]-propionamide;
N—[(R or S)-4-((R or S)-5-Chloro-3-ethyl-1-oxo-1,3-dihydro-isoindol-2-yl)-5,6,7,8-tetrahydro-isoquinolin-8-yl]-propionamide;
N—[(S or R)-4-((R or S)-5-Chloro-3-ethyl-1-oxo-1,3-dihydro-isoindol-2-yl)-5,6,7,8-tetrahydro-isoquinolin-8-yl]-acetamide;
and pharmaceutically acceptable salts thereof.

46. The compound according to claim 1, selected from the group consisting of
N—[(S or R)-4-((S or R)-5-Chloro-3-ethyl-1-oxo-1,3-dihydro-isoindol-2-yl)-5,6,7,8-tetrahydro-isoquinolin-8-yl]-acetamide;
N—[(R or S)-4-((S or R)-5-Chloro-3-ethyl-1-oxo-1,3-dihydro-isoindol-2-yl)-5,6,7,8-tetrahydro-isoquinolin-8-yl]-acetamide;
N—[(R or S)-4-((R or S)-5-Chloro-3-ethyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-5,6,7,8-tetrahydro-isoquinolin-8-yl]-propionamide;
N—[(S or R)-4-((R or S)-5-Chloro-3-methyl-1-oxo-1,3-dihydro-isoindol-2-yl)-5,6,7,8-tetrahydro-isoquinolin-8-yl]-propionamide;
N—[(R or S)-4-((R or S)-5-Chloro-3-methyl-1-oxo-1,3-dihydro-isoindol-2-yl)-5,6,7,8-tetrahydro-isoquinolin-8-yl]-propionamide;
N—[(S or R)-4-((S or R)-5-Chloro-3-methyl-1-oxo-1,3-dihydro-isoindol-2-yl)-5,6,7,8-tetrahydro-isoquinolin-8-yl]-propionamide;
N—[(S or R)-4-((R or S)-5-Chloro-3-methyl-1-oxo-1,3-dihydro-isoindol-2-yl)-5,6,7,8-tetrahydro-isoquinolin-8-yl]-acetamide;
N—[(R or S)-4-((R or S)-5-Chloro-3-methyl-1-oxo-1,3-dihydro-isoindol-2-yl)-5,6,7,8-tetrahydro-isoquinolin-8-yl]-acetamide;
N—[(S or R)-4-((S or R)-5-Chloro-3-methyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-5,6,7,8-tetrahydro-isoquinolin-8-yl]-acetamide;
N—[(S or R)-4-((R or S)-5-Chloro-3-ethyl-1-oxo-1,3-dihydro-isoindol-2-yl)-6,7-dihydro-5H-[2]pyrindin-7-yl]-methanesulfonamide;
N—[(R or S)-4-((S or R)-5-Chloro-3-ethyl-1-oxo-1,3-dihydro-isoindol-2-yl)-6,7-dihydro-5H-[2]pyrindin-7-yl]-methanesulfonamide;
N—[(R or S)-4-((R or S)-5-Chloro-3-ethyl-1-oxo-1,3-dihydro-isoindol-2-yl)-6,7-dihydro-5H-[2]pyrindin-7-yl]-methanesulfonamide;
N—[(S or R)-4-((S or R)-5-Chloro-3-ethyl-1-oxo-1,3-dihydro-isoindol-2-yl)-6,7-dihydro-5H-[2]pyrindin-7-yl]-methanesulfonamide;
and pharmaceutically acceptable salts thereof.

47. The compound according to claim 1, selected from the group consisting of
N—[(S or R)-4-((S or R)-5-Chloro-3-cyclopropyl-1-oxo-1,3-dihydro-isoindol-2-yl)-5,6,7,8-tetrahydro-isoquinolin-8-yl]-acetamide;
N—[(R or S)-4-((R or S)-5-Chloro-3-cyclopropyl-1-oxo-1,3-dihydro-isoindol-2-yl)-5,6,7,8-tetrahydro-isoquinolin-8-yl]-acetamide;
N—[(S or R)-4-((R or S)-5-Chloro-3-cyclopropyl-1-oxo-1,3-dihydro-isoindol-2-yl)-5,6,7,8-tetrahydro-isoquinolin-8-yl]-acetamide;
N—[(R or S)-4-((S or R)-5-Chloro-3-cyclopropyl-1-oxo-1,3-dihydro-isoindol-2-yl)-5,6,7,8-tetrahydro-isoquinolin-8-yl]-acetamide;
N—[(R or S)-4-((S or R)-5-Chloro-3-methyl-1-oxo-1,3-dihydro-isoindol-2-yl)-6,7-dihydro-5H-[2]pyrindin-7-yl]-propionamide;
N—[(R or S)-4-((R or S)-5-Chloro-3-methyl-1-oxo-1,3-dihydro-isoindol-2-yl)-6,7-dihydro-5H-[2]pyrindin-7-yl]-propionamide;
N—[(S or R)-4-((R or S)-5-Chloro-3-methyl-1-oxo-1,3-dihydro-isoindol-2-yl)-6,7-dihydro-5H-[2]pyrindin-7-yl]-propionamide;
N—[(S or R)-4-((S or R)-5-Chloro-3-methyl-1-oxo-1,3-dihydro-isoindol-2-yl)-6,7-dihydro-5H-[2]pyrindin-7-yl]-propionamide;
5-Chloro-3,3-dimethyl-2-(5-pyrazol-1-ylmethyl-pyridin-3-yl)-2,3-dihydro-isoindol-1-one;
2-[5-(3-Amino-pyrazol-1-ylmethyl)-pyridin-3-yl]-5-chloro-3,3-dimethyl-2,3-dihydro-isoindol-1-one;
5-Chloro-3,3-dimethyl-2-{5-[(1H-pyrazol-3-ylamino)-methyl]-pyridin-3-yl}-2,3-dihydro-isoindol-1-one;
2-[5-(3-Amino-pyrazol-1-ylmethyl)-pyridin-3-yl]-6-chloro-3,4-dihydro-2H-isoquinolin-1-one;
2-Chloro-7,7-dimethyl-6-{5-[(1H-pyrazol-3-ylamino)-methyl]-pyridin-3-yl}-6,7-dihydro-pyrrolo[3,4-b]pyridin-5-one;
2-Methoxy-7,7-dimethyl-6-{5-[(1H-pyrazol-3-ylamino)-methyl]-pyridin-3-yl}-6,7-dihydro-pyrrolo[3,4-b]pyridin-5-one;

2-Ethoxy-7,7-dimethyl-6-{5-[(1H-pyrazol-3-ylamino)-methyl]-pyridin-3-yl}-6,7-dihydro-pyrrolo[3,4-b]pyridin-5-one;

and pharmaceutically acceptable salts thereof.

48. The compound according to claim 1, selected from the group consisting of 6'-Chloro-2'-{5-[(1H-pyrazol-3-ylamino)methyl]pyridin-3-yl}spiro[cyclopropane-1,1'-isoindol]-3'(2'H)-one;

Ethanesulfonic acid [5-(6-chloro-1,1-dimethyl-3-oxo-1,3-dihydro-isoindol-2-yl)-pyridin-3-ylmethyl]-amide;

Ethanesulfonic acid [5-(6-fluoro-1,1-dimethyl-3-oxo-1,3-dihydro-isoindol-2-yl)-pyridin-3-ylmethyl]-amide;

Ethanesulfonic acid [5-(6-cyano-1,1-dimethyl-3-oxo-1,3-dihydro-isoindol-2-yl)-pyridin-3-ylmethyl]-amide;

Ethanesulfonic acid [5-((S or R)-5-chloro-3-ethyl-1-oxo-1,3-dihydro-isoindol-2-yl)-pyridin-3-ylmethyl]-amide;

N-[5-(6-Chloro-1,1-dimethyl-3-oxo-1,3-dihydro-isoindol-2-yl)-pyridin-3-ylmethyl]-methanesulfonamide;

N-[5-(6-Chloro-1,1-dimethyl-3-oxo-1,3-dihydro-isoindol-2-yl)-pyridin-3-ylmethyl]-N-methyl-methanesulfonamide;

N-{[5-(6'-Fluoro-3'-oxospiro[cyclopropane-1,1'-isoindol]-2'(3'H)-yl)pyridin-3-yl]methyl}ethanesulfonamide;

N-{[5-(6'-Fluoro-3'-oxospiro[cyclopropane-1,1'-isoindol]-2'(3'H)-yl)pyridin-3-yl]methyl}-N-methylethanesulfonamide;

Ethanesulfonic acid [5-(6-chloro-1,1-dimethyl-3-oxo-1,3-dihydro-isoindol-2-yl)-pyridin-3-ylmethyl]-methylamide;

N-{[5-(6'-Chloro-3'-oxospiro[cyclopropane-1,1'-isoindol]-2'(3'H)-yl)pyridin-3-yl]methyl}propanamide;

N-[5-(6-Chloro-1,1-dimethyl-3-oxo-1,3-dihydro-isoindol-2-yl)-pyridin-3-ylmethyl]-propionamide;

N-[5-(6-Fluoro-1,1-dimethyl-3-oxo-1,3-dihydro-isoindol-2-yl)-pyridin-3-ylmethyl]-propionamide;

N-[5-((S or R)-5-Chloro-3-ethyl-1-oxo-1,3-dihydro-isoindol-2-yl)-pyridin-3-ylmethyl]-propionamide;

N-[5-(6-Chloro-1,1-dimethyl-3-oxo-1,3-dihydro-isoindol-2-yl)-pyridin-3-ylmethyl]-acetamide;

and pharmaceutically acceptable salts thereof.

49. The compound according to claim 1, selected from the group consisting of N-{[5-(5'-Fluoro-3'-oxospiro[cyclopropane-1,1'-isoindol]-2'(3'H)-yl)pyridin-3-yl]methyl}methanesulfonamide;

N-[5-(6-Cyano-1,1-dimethyl-3-oxo-1,3-dihydro-isoindol-2-yl)-pyridin-3-ylmethyl]-methanesulfonamide;

N-[5-(6-Fluoro-1,1-dimethyl-3-oxo-1,3-dihydro-isoindol-2-yl)-pyridin-3-ylmethyl]-methanesulfonamide;

N-{[5-(6'-Fluoro-3'-oxospiro[cyclopropane-1,1'-isoindol]-2'(3'H)-yl)pyridin-3-yl]methyl}methanesulfonamide;

N-[5-((S or R)-5-Chloro-1-ethyl-3-oxo-1,3-dihydro-isoindol-2-yl)-pyridin-3-ylmethyl]-methanesulfonamide;

N-[5-(5-Fluoro-1,1-dimethyl-3-oxo-1,3-dihydro-isoindol-2-yl)-pyridin-3-ylmethyl]-methanesulfonamide;

N-[5-((R or S)-5-Chloro-1-ethyl-3-oxo-1,3-dihydro-isoindol-2-yl)-pyridin-3-ylmethyl]-methanesulfonamide;

N-[5-(5-Chloro-1,1-dimethyl-3-oxo-1,3-dihydro-isoindol-2-yl)-pyridin-3-ylmethyl]-methanesulfonamide;

5-Chloro-2-[5-(1,1-dioxo-1λ6-isothiazolidin-2-ylmethyl)-pyridin-3-yl]-3,3-dimethyl-2,3-dihydro-isoindol-1-one;

5-Chloro-3,3-dimethyl-2-[5-(2-oxo-piperidin-1-ylmethyl)-pyridin-3-yl]-2,3-dihydro-isoindol-1-one;

5-Chloro-3,3-dimethyl-2-[5-(2-oxo-imidazolidin-1-ylmethyl)-pyridin-3-yl]-2,3-dihydro-isoindol-1-one;

5-Chloro-3,3-dimethyl-2-[5-(2-oxo-oxazolidin-3-ylmethyl)-pyridin-3-yl]-2,3-dihydro-isoindol-1-one;

5-Chloro-3,3-dimethyl-2-[5-(2-oxo-pyrrolidin-1-ylmethyl)-pyridin-3-yl]-2,3-dihydro-isoindol-1-one;

5-Chloro-3,3-dimethyl-2-[5-(3-methyl-2-oxo-imidazolidin-1-ylmethyl)-pyridin-3-yl]-2,3-dihydro-isoindol-1-one;

5-Chloro-2-[5-(1,1-dioxo-1λ6-[1,2]thiazinan-2-ylmethyl)-pyridin-3-yl]-3,3-dimethyl-2,3-dihydro-isoindol-1-one;

and pharmaceutically acceptable salts thereof.

50. The compound according to claim 1, selected from the group consisting of 5-Chloro-2-[5-(3-isopropyl-2-oxo-imidazolidin-1-ylmethyl)-pyridin-3-yl]-3,3-dimethyl-2,3-dihydro-isoindol-1-one;

6-Chloro-2-[5-(1,5-dimethyl-1H-imidazol-4-yl)-pyridin-3-yl]-3,4-dihydro-2H-isoquinolin-1-one;

5-Chloro-3,3-dimethyl-2-[5-(2-methyl-2H-pyrazol-3-yl)-pyridin-3-yl]-2,3-dihydro-isoindol-1-one;

6-Chloro-2-[5-(3-methyl-1H-pyrazol-4-yl)-pyridin-3-yl]-3,4-dihydro-2H-isoquinolin-1-one;

6-Chloro-2-[5-(4-methyl-2H-pyrazol-3-yl)-pyridin-3-yl]-3,4-dihydro-2H-isoquinolin-1-one;

6-Chloro-2-[5-(4-chloro-2-methyl-2H-pyrazol-3-yl)-pyridin-3-yl]-3,4-dihydro-2H-isoquinolin-1-one;

6-Chloro-2-[5-(2,5-dimethyl-2H-pyrazol-3-yl)-pyridin-3-yl]-3,4-dihydro-2H-isoquinolin-1-one;

6-Chloro-2-[5-(1,5-dimethyl-1H-pyrazol-4-yl)-pyridin-3-yl]-3,4-dihydro-2H-isoquinolin-1-one;

6-Chloro-2-[4-chloro-5-(2-methyl-2H-pyrazol-3-yl)-pyridin-3-yl]-3,4-dihydro-2H-isoquinolin-1-one;

2-Chloro-7,7-dimethyl-6-[5-(2-methyl-2H-pyrazol-3-yl)-pyridin-3-yl]-6,7-dihydro-pyrrolo[3,4-b]pyridin-5-one;

2-Methoxy-7,7-dimethyl-6-[5-(2-methyl-2H-pyrazol-3-yl)-pyridin-3-yl]-6,7-dihydro-pyrrolo[3,4-b]pyridin-5-one;

5-Chloro-2-[5-(4-chloro-2-methyl-2H-pyrazol-3-yl)-pyridin-3-yl]-3,3-dimethyl-2,3-dihydro-isoindol-1-one;

(R or S)-5-Chloro-3-ethyl-2-[5-(2-methyl-2H-pyrazol-3-yl)-pyridin-3-yl]-2,3-dihydro-isoindol-1-one;

(S or R)-5-Chloro-3-ethyl-2-[5-(2-methyl-2H-pyrazol-3-yl)-pyridin-3-yl]-2,3-dihydro-isoindol-1-one;

3-Methyl-pyridine-2-carboxylic acid [5-(6-chloro-1,1-dimethyl-3-oxo-1,3-dihydro-isoindol-2-yl)-pyridin-3-ylmethyl]-amide;

3-Chloro-pyridine-2-carboxylic acid [5-(6-chloro-1,1-dimethyl-3-oxo-1,3-dihydro-isoindol-2-yl)-pyridin-3-ylmethyl]-amide;

and pharmaceutically acceptable salts thereof.

51. The compound according to claim 1, selected from the group consisting of 1-Methyl-1H-imidazole-2-carboxylic acid [5-(6-chloro-1,1-dimethyl-3-oxo-1,3-dihydro-isoindol-2-yl)-pyridin-3-ylmethyl]-amide;

2-Chloro-N-[5-(6-chloro-1,1-dimethyl-3-oxo-1,3-dihydro-isoindol-2-yl)-pyridin-3-ylmethyl]-nicotinamide;

Pyridine-2-carboxylic acid [5-(6-chloro-1,1-dimethyl-3-oxo-1,3-dihydro-isoindol-2-yl)-pyridin-3-ylmethyl]-amide;

3-Methyl-3H-imidazole-4-carboxylic acid [5-(6-chloro-1,1-dimethyl-3-oxo-1,3-dihydro-isoindol-2-yl)-pyridin-3-ylmethyl]-amide;

N-[5-(6-Chloro-1,1-dimethyl-3-oxo-1,3-dihydro-isoindol-2-yl)-pyridin-3-ylmethyl]-6-methyl-nicotinamide;

3-Chloro-N-[5-(6-chloro-1,1-dimethyl-3-oxo-1,3-dihydro-isoindol-2-yl)-pyridin-3-ylmethyl]-isonicotinamide;

N-[5-(6-Chloro-1,1-dimethyl-3-oxo-1,3-dihydro-isoindol-2-yl)-pyridin-3-ylmethyl]-nicotinamide;

N-[5-(6-Chloro-1,1-dimethyl-3-oxo-1,3-dihydro-isoindol-2-yl)-pyridin-3-ylmethyl]-2-methyl-nicotinamide;

N-[5-(6-Chloro-1,1-dimethyl-3-oxo-1,3-dihydro-isoindol-2-yl)-pyridin-3-ylmethyl]-4-methyl-nicotinamide;

2-[5-(1-Acetyl-pyrrolidin-3-yloxy)-pyridin-3-yl]-5-chloro-3,3-dimethyl-2,3-dihydro-isoindol-1-one;

2-[5-((R)-1-Acetyl-pyrrolidin-3-yloxy)-pyridin-3-yl]-5-chloro-3,3-dimethyl-2,3-dihydro-isoindol-1-one;

2-[5-((S)-1-Acetyl-pyrrolidin-3-yloxy)-pyridin-3-yl]-5-chloro-3,3-dimethyl-2,3-dihydro-isoindol-1-one;

5-Chloro-3,3-dimethyl-2-[5-(1-propionyl-pyrrolidin-3-yloxy)-pyridin-3-yl]-2,3-dihydro-isoindol-1-one;

5-Chloro-2-[5-(1-methanesulfonyl-pyrrolidin-3-yloxy)-pyridin-3-yl]-3,3-dimethyl-2,3-dihydro-isoindol-1-one;

5-Chloro-2-[5-(1-ethanesulfonyl-pyrrolidin-3-yloxy)-pyridin-3-yl]-3,3-dimethyl-2,3-dihydro-isoindol-1-one;

and pharmaceutically acceptable salts thereof.

52. The compound according to claim 1, selected from the group consisting of

5-Chloro-2-[5-((R)-1-ethanesulfonyl-pyrrolidin-3-yloxy)-pyridin-3-yl]-3,3-dimethyl-2,3-dihydro-isoindol-1-one;

5-Chloro-2-[5-((S)-1-ethanesulfonyl-pyrrolidin-3-yloxy)-pyridin-3-yl]-3,3-dimethyl-2,3-dihydro-isoindol-1-one;

2-[5-(1-Acetyl-piperidin-4-yloxy)-pyridin-3-yl]-5-chloro-3,3-dimethyl-2,3-dihydro-isoindol-1-one;

2-[5-(1-Acetyl-azetidin-3-yloxy)-pyridin-3-yl]-5-chloro-3,3-dimethyl-2,3-dihydro-isoindol-1-one;

5-Chloro-3,3-dimethyl-2-[5-(1-propionyl-azetidin-3-yloxy)-pyridin-3-yl]-2,3-dihydro-isoindol-1-one;

5-Chloro-2-[5-(1-methanesulfonyl-azetidin-3-yloxy)-pyridin-3-yl]-3,3-dimethyl-2,3-dihydro-isoindol-1-one;

5-Chloro-2-[5-(1-ethanesulfonyl-azetidin-3-yloxy)-pyridin-3-yl]-3,3-dimethyl-2,3-dihydro-isoindol-1-one;

5-Chloro-2-[5-((S)-3-hydroxy-pyrrolidin-1-yl)-pyridin-3-yl]-3,3-dimethyl-2,3-dihydro-isoindol-1-one;

2-[5-(4-Acetyl-piperazin-1-yl)-pyridin-3-yl]-5-chloro-3,3-dimethyl-2,3-dihydro-isoindol-1-one;

5-Chloro-3,3-dimethyl-2-[5-(4-propionyl-piperazin-1-yl)-pyridin-3-yl]-2,3-dihydro-isoindol-1-one;

5-Chloro-2-[5-(4-methanesulfonyl-piperazin-1-yl)-pyridin-3-yl]-3,3-dimethyl-2,3-dihydro-isoindol-1-one;

5-Chloro-2-[5-(4-ethanesulfonyl-piperazin-1-yl)-pyridin-3-yl]-3,3-dimethyl-2,3-dihydro-isoindol-1-one;

5-Chloro-2-{5-[4-(3-chloro-pyridine-2-carbonyl)-piperazin-1-yl]-pyridin-3-yl}-3,3-dimethyl-2,3-dihydro-isoindol-1-one;

2-[5-(1-Acetyl-pyrrolidin-3-yl)-pyridin-3-yl]-5-chloro-3,3-dimethyl-2,3-dihydro-isoindol-1-one;

2-(1'-Acetyl-1',2',3',4',5',6'-hexahydro-[3,4']bipyridinyl-5-yl)-5-chloro-3,3-dimethyl-2,3-dihydro-isoindol-1-one;

and pharmaceutically acceptable salts thereof.

53. The compound according to claim 1, selected from the group consisting of

2-[6-(1-Acetyl-piperidin-3-yl)-pyrazin-2-yl]-5-chloro-3,3-dimethyl-2,3-dihydro-isoindol-1-one;

5-Chloro-3,3-dimethyl-2-[6-(1-propionyl-piperidin-3-yl)-pyrazin-2-yl]-2,3-dihydro-isoindol-1-one;

5-Chloro-2-[6-(1-ethanesulfonyl-piperidin-3-yl)-pyrazin-2-yl]-3,3-dimethyl-2,3-dihydro-isoindol-1-one;

5-Chloro-2-[6-(1-methanesulfonyl-piperidin-3-yl)-pyrazin-2-yl]-3,3-dimethyl-2,3-dihydro-isoindol-1-one;

N—[(S or R)-4-(6-Chloro-1,1-dimethyl-3-oxo-1,3-dihydro-isoindol-2-yl)-5,6,7,8-tetrahydro-isoquinolin-8-yl]-acetamide;

N—[(R or S)-4-(6-Chloro-1,1-dimethyl-3-oxo-1,3-dihydro-isoindol-2-yl)-5,6,7,8-tetrahydro-isoquinolin-8-yl]-acetamide;

N-[4-(6-Chloro-1,1-dimethyl-3-oxo-1,3-dihydro-isoindol-2-yl)-5,6,7,8-tetrahydro-isoquinolin-8-yl]-propionamide;

and pharmaceutically acceptable salts thereof.

54. The compound according to claim 1, selected from the group consisting of

6-Chloro-2-pyridin-3-yl-3,4-dihydro-2H-isoquinolin-1-one;

6-Chloro-2-(4-chloro-pyridin-3-yl)-3,4-dihydro-2H-isoquinolin-1-one;

6-Chloro-2-(5-isopropoxy-pyridin-3-yl)-3,4-dihydro-2H-isoquinolin-1-one;

6-Chloro-2-[5-((R)-1-hydroxy-ethyl)-pyridin-3-yl]-3,4-dihydro-2H-isoquinolin-1-one;

6-Chloro-2-(5-cyclopropoxy-pyridin-3-yl)-3,4-dihydro-2H-isoquinolin-1-one;

2-Methoxy-6-(5-methoxy-pyridin-3-yl)-7,8-dihydro-6H-[1,6]naphthyridin-5-one;

5-Chloro-3-ethyl-2-(5-fluoro-pyridin-3-yl)-2,3-dihydro-isoindol-1-one;

5-Chloro-2-(5-fluoro-pyridin-3-yl)-3,3-dimethyl-2,3-dihydro-isoindol-1-one;

5-Chloro-2-(5-difluoromethoxy-pyridin-3-yl)-3,3-dimethyl-2,3-dihydro-isoindol-1-one;

6-Chloro-2-[5-(2-oxa-6-aza-spiro[3.4]oct-6-ylmethyl)-pyridin-3-yl]-3,4-dihydro-2H-isoquinolin-1-one;

6-Chloro-2-(5-methoxymethyl-pyridin-3-yl)-3,4-dihydro-2H-isoquinolin-1-one;

6-Chloro-2-[5-(1-methyl-1H-pyrazol-4-ylmethyl)-pyridin-3-yl]-3,4-dihydro-2H-isoquinolin-1-one;

6-Chloro-2-{5-[(2-methyl-2H-pyrazol-3-ylmethyl)-amino]-pyridin-3-yl}-3,4-dihydro-2H-isoquinolin-1-one;

6-Chloro-2-[5-(2-methyl-2H-pyrazol-3-yl)-pyridin-3-yl]-3,4-dihydro-2H-isoquinolin-1-one;

6-Chloro-2-{5-[(1H-pyrazol-3-ylamino)-methyl]-pyridin-3-yl}-3,4-dihydro-2H-isoquinolin-1-one;

and pharmaceutically acceptable salts thereof.

55. The compound according to claim 1, selected from the group consisting of (R or S)-5-Chloro-3-ethyl-2-(5-fluoro-pyridin-3-yl)-2,3-dihydro-isoindol-1-one;

(S or R)-5-Chloro-3-ethyl-2-(5-fluoro-pyridin-3-yl)-2,3-dihydro-isoindol-1-one;

N—[(R or S)-4-((R or S)-5-Chloro-3-ethyl-1-oxo-1,3-dihydro-isoindol-2-yl)-5,6,7,8-tetrahydro-isoquinolin-8-yl]-acetamide;

N—[(R or S)-4-((S or R)-5-Chloro-3-methyl-1-oxo-1,3-dihydro-isoindol-2-yl)-5,6,7,8-tetrahydro-isoquinolin-8-yl]-propionamide;

N—[(R or S)-4-((S or R)-5-Chloro-3-methyl-1-oxo-1,3-dihydro-isoindol-2-yl)-5,6,7,8-tetrahydro-isoquinolin-8-yl]-acetamide;

N—[(R or S)-4-((S or R)-5-Chloro-3-ethyl-1-oxo-1,3-dihydro-isoindol-2-yl)-6,7-dihydro-5H-[2]pyrindin-7-yl]-methanesulfonamide;

N—[(R or S)-4-((R or S)-5-Chloro-3-methyl-1-oxo-1,3-dihydro-isoindol-2-yl)-6,7-dihydro-5H-[2]pyrindin-7-yl]-propionamide;

N—[(S or R)-4-((R or S)-5-Chloro-3-methyl-1-oxo-1,3-dihydro-isoindol-2-yl)-6,7-dihydro-5H-[2]pyrindin-7-yl]-propionamide;

5-Chloro-3,3-dimethyl-2-{5-[(1H-pyrazol-3-ylamino)-methyl]-pyridin-3-yl}-2,3-dihydro-isoindol-1-one;

6'-Chloro-2'-{5-[(1H-pyrazol-3-ylamino)methyl]pyridin-3-yl}spiro[cyclopropane-1,1'-isoindol]-3'(2'H)-one;

N-[5-(6-Chloro-1,1-dimethyl-3-oxo-1,3-dihydro-isoindol-2-yl)-pyridin-3-ylmethyl]-methanesulfonamide;

3-Methyl-pyridine-2-carboxylic acid [5-(6-chloro-1,1-dimethyl-3-oxo-1,3-dihydro-isoindol-2-yl)-pyridin-3-ylmethyl]-amide;

2-[5-((R)-1-Acetyl-pyrrolidin-3-yloxy)-pyridin-3-yl]-5-chloro-3,3-dimethyl-2,3-dihydro-isoindol-1-one;

2-[5-((S)-1-Acetyl-pyrrolidin-3-yloxy)-pyridin-3-yl]-5-chloro-3,3-dimethyl-2,3-dihydro-isoindol-1-one;

5-Chloro-2-[5-(1-methanesulfonyl-pyrrolidin-3-yloxy)-pyridin-3-yl]-3,3-dimethyl-2,3-dihydro-isoindol-1-one;

5-Chloro-2-[5-((R)-1-ethanesulfonyl-pyrrolidin-3-yloxy)-pyridin-3-yl]-3,3-dimethyl-2,3-dihydro-isoindol-1-one;

5-Chloro-2-[5-((S)-1-ethanesulfonyl-pyrrolidin-3-yloxy)-pyridin-3-yl]-3,3-dimethyl-2,3-dihydro-isoindol-1-one;

2-[5-(1-Acetyl-piperidin-4-yloxy)-pyridin-3-yl]-5-chloro-3,3-dimethyl-2,3-dihydro-isoindol-1-one;

5-Chloro-2-[5-(1-ethanesulfonyl-azetidin-3-yloxy)-pyridin-3-yl]-3,3-dimethyl-2,3-dihydro-isoindol-1-one;

2-[5-(4-Acetyl-piperazin-1-yl)-pyridin-3-yl]-5-chloro-3,3-dimethyl-2,3-dihydro-isoindol-1-one;

5-Chloro-2-[5-(4-methanesulfonyl-piperazin-1-yl)-pyridin-3-yl]-3,3-dimethyl-2,3-dihydro-isoindol-1-one;

5-Chloro-2-[5-(4-ethanesulfonyl-piperazin-1-yl)-pyridin-3-yl]-3,3-dimethyl-2,3-dihydro-isoindol-1-one;

2-(1'-Acetyl-1',2',3',4',5',6'-hexahydro-[3,4']bipyridinyl-5-yl)-5-chloro-3,3-dimethyl-2,3-dihydro-isoindol-1-one;

and pharmaceutically acceptable salts thereof.

56. A pharmaceutical composition comprising a compound according to claim 1 and a therapeutically inert carrier.

* * * * *

UNITED STATES PATENT AND TRADEMARK OFFICE
CERTIFICATE OF CORRECTION

| | | |
|---|---|---|
| PATENT NO. | : 9,133,158 B2 | Page 1 of 1 |
| APPLICATION NO. | : 13/688373 | |
| DATED | : September 15, 2015 | |
| INVENTOR(S) | : Johannes Aebi et al. | |

It is certified that error appears in the above-identified patent and that said Letters Patent is hereby corrected as shown below:

ON THE TITLE PAGE

Item (73) Assignees to read as follows:

-- HOFFMANN-LA ROCHE INC., Nutley, NJ (US) --

Signed and Sealed this
Twenty-sixth Day of January, 2016

Michelle K. Lee
*Director of the United States Patent and Trademark Office*